US007927613B2

(12) United States Patent
Almarsson et al.

(10) Patent No.: US 7,927,613 B2
(45) Date of Patent: *Apr. 19, 2011

(54) PHARMACEUTICAL CO-CRYSTAL COMPOSITIONS

(75) Inventors: Örn Almarsson, Shrewsbury, MA (US); Magali Bourghol Hickey, Medford, MA (US); Matthew L. Peterson, Framingham, MA (US); Michael J. Zaworotko, Tampa, FL (US); Brian Moulton, Providence, RI (US); Nair Rodriguez-Hornedo, Ann Arbor, MI (US)

(73) Assignees: University of South Florida, Tampa, FL (US); The Regents of the University of Michigan, Ann Arbor, MI (US); Transform Pharmaceuticals, Inc., Lexington, MA (US)

( * ) Notice: Subject to any disclaimer, the term of this patent is extended or adjusted under 35 U.S.C. 154(b) by 1101 days.
This patent is subject to a terminal disclaimer.

(21) Appl. No.: 10/660,202

(22) Filed: Sep. 11, 2003

(65) Prior Publication Data
US 2007/0026078 A1 Feb. 1, 2007

Related U.S. Application Data

(60) Continuation-in-part of application No. PCT/US03/27772, filed on Sep. 4, 2003, which is a continuation-in-part of application No. 10/378,956, filed on Mar. 1, 2003, application No. 10/660,022, which is a continuation-in-part of application No. 10/637,829, filed on Aug. 8, 2003, now abandoned, which is a division of application No. 10/295,995, filed on Nov. 18, 2002, now Pat. No. 6,699,840, which is a continuation of application No. 10/232,589, filed on Sep. 3, 2002, now Pat. No. 6,559,293, application No. 10/660,202, which is a continuation-in-part of application No. 10/601,092, filed on Jun. 20, 2003, now abandoned, and a continuation-in-part of application No. 10/449,307, filed on May 30, 2003, now Pat. No. 7,078,526.

(60) Provisional application No. 60/360,768, filed on Mar. 1, 2002, provisional application No. 60/451,213, filed on Feb. 28, 2003, provisional application No. 60/463,962, filed on Apr. 18, 2003, provisional application No. 60/487,064, filed on Jul. 11, 2003, provisional application No. 60/406,974, filed on Aug. 30, 2002, provisional application No. 60/380,288, filed on May 15, 2002, provisional application No. 60/356,764, filed on Feb. 15, 2002, provisional application No. 60/444,315, filed on Jan. 31, 2003, provisional application No. 60/439,282, filed on Jan. 10, 2003, provisional application No. 60/384,152, filed on May 31, 2002.

(51) Int. Cl.
*A61K 9/00* (2006.01)
*A01N 43/46* (2006.01)
*A01N 43/56* (2006.01)

(52) U.S. Cl. .................. 424/400; 514/217; 514/403

(58) Field of Classification Search .................. 424/400; 514/217, 403
See application file for complete search history.

(56) References Cited

U.S. PATENT DOCUMENTS

| 2,665,277 | A | 1/1954 | Homeyer et al. |
|---|---|---|---|
| 2,711,411 | A | 6/1955 | Holbert et al. |
| 3,028,420 | A | 4/1962 | Petrow et al. |
| 3,598,123 | A | 8/1971 | Zaffaroni |
| 3,845,770 | A | 11/1974 | Theeuwes et al. |
| 3,916,899 | A | 11/1975 | Theeuwes et al. |
| 3,970,651 | A | 7/1976 | Kaplan et al. |
| 4,008,321 | A | 2/1977 | Kamishita et al. |
| 4,008,719 | A | 2/1977 | Theeuwes et al. |
| 4,198,507 | A | 4/1980 | Barry et al. |
| 4,267,179 | A | 5/1981 | Heeres et al. |
| 4,368,197 | A | 1/1983 | Shefter et al. |
| 4,513,006 | A | 4/1985 | Maryanoff et al. |
| 4,764,604 | A | 8/1988 | Muller |
| 4,853,379 | A | 8/1989 | Shroot et al. |
| 4,916,134 | A | 4/1990 | Heeres et al. |
| 4,925,674 | A | 5/1990 | Giannini et al. |
| 4,927,855 | A | 5/1990 | Lafon |
| 4,994,604 | A | 2/1991 | Tung et al. |
| 3,536,809 | A | 4/1991 | Schaller et al. |

(Continued)

FOREIGN PATENT DOCUMENTS
EP 0310122 B1 4/1989
(Continued)

OTHER PUBLICATIONS

Angelo Gavezzotti, Are Crystal Structures Predictable?, 1994, Acc. Chem. Res., vol. 27, pp. 309-314.*

(Continued)

*Primary Examiner* — Sreeni Padmanabhan
*Assistant Examiner* — Renee Claytor
(74) *Attorney, Agent, or Firm* — Saliwanchik, Lloyd & Saliwanchik

(57) ABSTRACT

A pharmaceutical composition comprising a co-crystal of an API and a co-crystal former; wherein the API has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile diazo, organohalide, nitro, s-heterocyclic ring, thiophene, n-heterocyclic ring, pyrrole, o-heterocyclic ring, furan, epoxide, peroxide, hydroxamic acid, imidazole, pyridine and the co-crystal former has at least one functional group selected from amine, amide, pyridine, imidazole, indole, pyrrolidine, carbonyl, carboxyl, hydroxyl, phenol, sulfone, sulfonyl, mercapto and methyl thio, such that the API and co-crystal former are capable of co-crystallizing from a solution phase under crystallization conditions.

36 Claims, 66 Drawing Sheets

U.S. PATENT DOCUMENTS

| | | | |
|---|---|---|---|
| 5,006,513 A | 4/1991 | Hector et al. | |
| 5,023,092 A | 6/1991 | DuRoss | |
| 5,059,595 A | 10/1991 | Le Grazie | |
| 5,073,543 A | 12/1991 | Marshall et al. | |
| 5,120,548 A | 6/1992 | McClelland et al. | |
| 5,177,262 A | 1/1993 | Taylor et al. | |
| 5,242,942 A | 9/1993 | Costanzo et al. | |
| 5,273,760 A | 12/1993 | Oshlack et al. | |
| 5,286,493 A | 2/1994 | Oshlack et al. | |
| 5,324,351 A | 6/1994 | Oshlack et al. | |
| 5,332,834 A | 7/1994 | Bhattacharya et al. | |
| 5,338,644 A | 8/1994 | Taylor et al. | |
| 5,354,556 A | 10/1994 | Sparks et al. | |
| 5,356,467 A | 10/1994 | Oshlack et al. | |
| 5,366,738 A | 11/1994 | Rork et al. | |
| 5,380,867 A | 1/1995 | Bhattacharya et al. | |
| 5,384,327 A | 1/1995 | Costanzo et al. | |
| 5,412,094 A | 5/1995 | Amos et al. | |
| 5,414,997 A | 5/1995 | Tailer | |
| 5,466,823 A | 11/1995 | Talley et al. | |
| 5,472,712 A | 12/1995 | Oshlack et al. | |
| 5,474,997 A | 12/1995 | Gray et al. | |
| 5,510,496 A | 4/1996 | Talley et al. | |
| 5,521,207 A | 5/1996 | Graneto | |
| 5,523,090 A | 6/1996 | Znaiden et al. | |
| 5,563,165 A | 10/1996 | Talley et al. | |
| 5,591,767 A | 1/1997 | Mohr et al. | |
| 5,614,342 A | 3/1997 | Molaire et al. | |
| 5,631,250 A | 5/1997 | Bunnell et al. | |
| 5,633,015 A | 5/1997 | Gilis et al. | |
| 5,633,272 A | 5/1997 | Talley et al. | |
| 5,639,476 A | 6/1997 | Oshlack et al. | |
| 5,641,512 A | 6/1997 | Cimiluca | |
| 5,661,151 A | 8/1997 | Saksena et al. | |
| 5,674,533 A | 10/1997 | Santus et al. | |
| 5,703,232 A | 12/1997 | Bunnell et al. | |
| 5,707,975 A | 1/1998 | Francois et al. | |
| 5,733,566 A | 3/1998 | Lewis | |
| 5,736,541 A | 4/1998 | Bunnell et al. | |
| 5,753,688 A | 5/1998 | Talley et al. | |
| 5,753,693 A | 5/1998 | Shank | |
| 5,760,007 A | 6/1998 | Shank et al. | |
| 5,760,068 A | 6/1998 | Talley et al. | |
| 5,932,598 A | 8/1999 | Talley et al. | |
| 5,935,933 A | 8/1999 | Shank et al. | |
| 5,952,187 A | 9/1999 | Stenglein et al. | |
| 5,972,986 A | 10/1999 | Seibert et al. | |
| 5,985,902 A | 11/1999 | Talley et al. | |
| 5,994,365 A | 11/1999 | Zaworotko et al. | |
| 5,998,380 A | 12/1999 | Ehrenberg et al. | |
| 5,998,413 A | 12/1999 | Heeres et al. | |
| 6,001,996 A | 12/1999 | Amos et al. | |
| 6,054,136 A | 4/2000 | Farah et al. | |
| 6,071,537 A | 6/2000 | Shank | |
| 6,132,420 A | 10/2000 | Dionne et al. | |
| 6,156,781 A | 12/2000 | Talley et al. | |
| 6,191,117 B1 | 2/2001 | Kozachuk | |
| 6,201,010 B1 | 3/2001 | Cottrell | |
| 6,245,357 B1 | 6/2001 | Edgren et al. | |
| 6,268,385 B1 | 7/2001 | Whittle et al. | |
| 6,270,787 B1 | 8/2001 | Ayer | |
| 6,283,953 B1 | 9/2001 | Ayer et al. | |
| 6,287,295 B1 | 9/2001 | Chen et al. | |
| 6,294,192 B1 | 9/2001 | Patel et al. | |
| 6,319,903 B1 | 11/2001 | Carrazana et al. | |
| 6,323,266 B2 | 11/2001 | Phillips | |
| 6,333,050 B2 | 12/2001 | Wong et al. | |
| 6,342,249 B1 | 1/2002 | Wong et al. | |
| 6,348,458 B1 | 2/2002 | Hamied et al. | |
| 6,365,185 B1 | 4/2002 | Ritschel et al. | |
| 6,368,626 B1 | 4/2002 | Bhatt et al. | |
| 6,375,978 B1 | 4/2002 | Kleiner et al. | |
| 6,384,034 B2 | 5/2002 | Simitchieva et al. | |
| 6,403,640 B1 | 6/2002 | Stoner et al. | |
| 6,413,965 B1 | 7/2002 | Mylari | |
| 6,420,394 B1 | 7/2002 | Supersaxo | |
| 6,488,962 B1 | 12/2002 | Berner et al. | |
| 6,503,884 B1 | 1/2003 | Ehrenberg et al. | |
| 6,559,293 B1 * | 5/2003 | Almarsson et al. | 536/18.7 |
| 6,570,036 B1 | 5/2003 | Reuter | |
| 6,579,895 B2 | 6/2003 | Karim et al. | |
| 6,613,790 B2 | 9/2003 | Carter | |
| 6,699,840 B2 | 3/2004 | Almarsson et al. | |
| 7,078,526 B2 * | 7/2006 | Remenar et al. | 544/336 |
| 7,132,570 B2 | 11/2006 | Neckebrock et al. | |
| 7,172,769 B2 | 2/2007 | Kararli et al. | |
| 7,205,413 B2 | 4/2007 | Morissette et al. | |
| 7,446,107 B2 | 11/2008 | Remenar et al. | |
| 7,452,555 B2 | 11/2008 | Childs | |
| 7,459,449 B2 | 12/2008 | Keltjens | |
| 2002/0006951 A1 | 1/2002 | Hageman et al. | |
| 2002/0013357 A1 | 1/2002 | Nadkarni et al. | |
| 2002/0015735 A1 | 2/2002 | Hedden et al. | |
| 2002/0034542 A1 | 3/2002 | Thombre et al. | |
| 2002/0037925 A1 | 3/2002 | Dewey et al. | |
| 2002/0042446 A1 | 4/2002 | Dewey et al. | |
| 2002/0071857 A1 | 6/2002 | Kararli et al. | |
| 2002/0107250 A1 | 8/2002 | Hariharan et al. | |
| 2002/0119193 A1 | 8/2002 | Le et al. | |
| 2003/0069190 A1 | 4/2003 | Abdel-Magid et al. | |
| 2003/0072802 A1 | 4/2003 | Cutler | |
| 2003/0096014 A1 | 5/2003 | Sherman | |
| 2003/0162226 A1 | 8/2003 | Cima et al. | |
| 2003/0166581 A1 | 9/2003 | Almarsson et al. | |
| 2003/0224006 A1 | 12/2003 | Zaworotko et al. | |
| 2004/0019211 A1 | 1/2004 | Remenar et al. | |
| 2004/0029946 A1 | 2/2004 | Arora et al. | |
| 2004/0053853 A1 | 3/2004 | Almarsson et al. | |
| 2004/0106052 A1 | 6/2004 | Molaire | |
| 2004/0106053 A1 | 6/2004 | Molaire et al. | |
| 2004/0106055 A1 | 6/2004 | Molaire et al. | |
| 2004/0154890 A1 | 8/2004 | Liu | |
| 2004/0171062 A1 | 9/2004 | Hirth et al. | |
| 2004/0176335 A1 * | 9/2004 | Childs | 514/165 |
| 2004/0242640 A1 | 12/2004 | Desai et al. | |
| 2005/0070551 A1 * | 3/2005 | Remenar et al. | 514/254.07 |
| 2005/0169982 A1 | 8/2005 | Almarsson et al. | |
| 2005/0181041 A1 | 8/2005 | Goldman | |
| 2005/0252649 A1 | 11/2005 | Chiu et al. | |
| 2005/0256127 A1 | 11/2005 | Ku et al. | |
| 2006/0223794 A1 * | 10/2006 | Bourghol Hickey et al. | 514/220 |
| 2007/0015841 A1 | 1/2007 | Tawa et al. | |
| 2007/0021510 A1 * | 1/2007 | Hickey et al. | 514/618 |
| 2007/0059356 A1 * | 3/2007 | Almarsson et al. | 424/464 |
| 2007/0293674 A1 | 12/2007 | Scoppettuolo et al. | |

FOREIGN PATENT DOCUMENTS

| | | |
|---|---|---|
| EP | 0283992 B1 | 9/1992 |
| EP | 413528 B1 | 11/1995 |
| EP | 1167355 A1 | 1/2002 |
| EP | 1364649 A1 | 11/2003 |
| FR | 769586 | 6/1934 |
| FR | 2849029 | 6/2004 |
| GB | 1 297 261 A | 11/1972 |
| GB | 2 169 601 | 7/1986 |
| IN | 182620 | 12/1994 |
| IT | 01303251 | 11/2000 |
| JP | B 46-33588 | 10/1971 |
| JP | 54-16494 | 2/1979 |
| JP | 54-095589 | 7/1979 |
| WO | WO 94/16733 A1 | 8/1994 |
| WO | WO 95/17407 A1 | 6/1995 |
| WO | WO 95/23596 A1 | 9/1995 |
| WO | WO 96/07331 A1 | 3/1996 |
| WO | WO 96/33193 | 10/1996 |
| WO | WO 98/57967 A1 | 12/1998 |
| WO | WO 00/07583 A2 | 2/2000 |
| WO | WO 00/32189 A1 | 6/2000 |
| WO | WO 00/50020 A2 | 8/2000 |
| WO | WO 00/53283 A1 | 9/2000 |
| WO | WO 00/72841 A1 | 12/2000 |
| WO | WO 01/13904 A2 | 3/2001 |
| WO | WO 01/41536 A2 | 6/2001 |
| WO | WO 01/41760 A3 | 6/2001 |
| WO | WO 01/42221 A1 | 6/2001 |
| WO | WO 01 42222 A1 | 6/2001 |
| WO | WO 01/42222 A1 | 6/2001 |

| | | |
|---|---|---|
| WO | WO 01/45706 | 6/2001 |
| WO | WO 01/51919 A2 | 7/2001 |
| WO | WO 01 51919 A2 | 7/2001 |
| WO | WO 01/78724 A1 | 10/2001 |
| WO | WO 01/91750 A1 | 12/2001 |
| WO | WO 01/97853 A1 | 12/2001 |
| WO | WO 02/00627 A1 | 1/2002 |
| WO | WO 02/10125 | 2/2002 |
| WO | WO 02/056878 A2 | 7/2002 |
| WO | WO 02/056915 | 7/2002 |
| WO | WO 02/062318 A2 | 8/2002 |
| WO | WO 02/102376 | 12/2002 |
| WO | WO 03/033462 A2 | 4/2003 |
| WO | WO 03 033462 A2 | 4/2003 |
| WO | WO 03/070738 A2 | 8/2003 |
| WO | WO 03/074474 A2 | 9/2003 |
| WO | WO 03074474 A2 * | 9/2003 |
| WO | WO 03/101392 A2 | 12/2003 |
| WO | WO 2004/054571 A1 | 7/2004 |
| WO | WO 2004/078161 A1 | 9/2004 |
| WO | WO 2004/078163 A2 | 9/2004 |
| WO | WO 2004/089313 A2 | 10/2004 |
| WO | WO 2005/023198 A2 | 3/2005 |
| WO | WO 2005/037424 A1 | 4/2005 |
| WO | WO 2005/053612 | 6/2005 |
| WO | WO 2005/055983 A2 | 6/2005 |
| WO | WO 2005/060968 A1 | 7/2005 |
| WO | WO 2005/089375 A2 | 9/2005 |
| WO | WO 2005/094804 A1 | 10/2005 |
| WO | WO 2006/024930 A1 | 3/2006 |

OTHER PUBLICATIONS

Oswald et al, The Formation of Paracetamol (Acetaminophen) Adducts with Hydrogen-Bond Acceptors, 2002, Acta Crystallographica, vol. B58, pp. 1057-1066.*
Remenar et al, Crystal Engineering of Novel Cocrystals of a Triazole Drug with 1,4-Dicarboxylic Acids, 2003,JACS, vol. 125, pp. 8456-8457.*
Fleischman et al, Crystal Engineering of the Composition of Pharmaceutical Phases: Multiple-Component Crystalline Solids Involving Carbamazepine, 2003, Crystal Growth and Design, vol. 3, No. 6, pp. 909-919.*
Dvorkin et al, Crystal and Molecular Structure of a Complex of 18-crown-6 with 6-chloror-7-sulfamido-3,4-dihydro-1,2,4-benzothiadiazine-1,1-dioxide (hypothiazide) of 1:1 Composition, 1990, Kristallografiya, vol. 35, No. 3, pp. 682-686 (with English abstract.).*
Ammar et al. Effect of aromatic hydrotopes on the solubility of carbamazepine. Part II: Effect of nicotinamide, sodium salts of benzoic, naphthoic and nicotinic acids. Egypt J. Pharm. Sci. 35, No. 1-6, pp. 209-223.*
de Jong et al. et al. Dystrophic psoriatic fingernails treated with 1% 5-Fluorouracil in a nail penetration-enhancing vehicle: a double-blind study. Dermatology 1999; 199: 313-318.*
Brader, M.L. et al. *Nature Biotechnol.*, 2002, 20 :800-804.
El-Nahhas, S.A. *Pharmazie*, 1996, 51(12):960-963.
Fleischman, S.G. et al. *Crystal Growth & Design.*, 2003, 3(6): 909-919.
Oswald, I.D.H. et al. *Acta Cryst.*, 2002, B58:1057-1066.
Reynolds, J.E.F. (ed). Martindale, The Extra Pharmacopoeia, 1993, The Pharmaceutical Press, London, England, 13th Edition, pp. 1431 (e.g., Acetaminophen, Aspirin, and Caffeine Tablets), 1465 (e.g., Aspirin plus C), 1521 (Codafen Continus), 1610 (Gaboril Complex).
Walsh, R.D. Bailey et al. *Chem. Commun.*, 2003, 2003:186-187.
Weissbuch, I. et al., "Understanding and Control of Nucleation, Growth, Habit, Dissolution and Structure . . . ," Acta Cryst. (1995), pp. 115-148, vol. B51.
Aakeröy, C. et al. "Crystal engineering of hydrogen-bonded assemblies- a progress report" *Aust. J. Chem.*, 2001, pp. 409-421, vol. 54.
Bingham, A. et al. "Over one hundred solvates of sulfathiazole" *Chem. Commun.*, 2001, pp. 603-604.
Byriel, K., et al. "Molecular cocrystals of carboxylic acids. IX' Carboxylic acid interactions with organic heterocyclic bases. The crystal structures of the adducts of (2,4-dichlorophenoxy) acetic acid with 3-hydroxypyridine, 2,4,6,-trinitrobenzoic acid with 2-aminopyrimidine, and 4-nitrobenzoic acid with 3-amino-1,2,4-triazole" *Aust. J. Chem.*, 1992, pp. 969-981, vol. 45, No. 6.
Salmon, J. et al. "Supramolecular chemistry of boronic acids (Abstract)" 38th Midwest Regional Meeting of the American Chemical Society in Columbia, MO., Nov. 5-7, 2003, published by the American Chemical Society, Washington, D.C.
Urbina, J. et al. "Supramolecular design of inorganic/organic networks using flexible ligands with self-complementary hydrogen bonds (Abstract)" 38th Midwest Regional Meeting of the American Chemical Society in Columbia, MO., Nov. 5-7, 2003, published by the American Chemical Society, Washington, D.C.
Smith, D. et al. "Structure confirmation by single crystal X-ray diffraction of a series of new schiff bases and theoretical computations on 3-(N-2-α, α, α-triflourotoluylidene amino) tetrahydrothiophene-1, 1-dioxide (Abstract)" 216th ACS National Meeting in Boston, MA., Aug. 23-27, 1998, published by the American Chemical Society, Washington, D.C.
Desiraju, G. "Supramolecular synthons in crystal engineering- A new organic synthesis" *Angew. Chem. Int. Ed. Engl.*, 1995, pp. 2311-2327, vol. 34.
Fritchie, C. et al. "The configuration of phenothiazine in various molecular complexes" *Chem. Commun.*, 1968, pp. 833-834.
Huang, C.-M. et al. "Molecular packing modes. Part Xl. Crystal structures of the 2:1 complexes of benzamide with succinic acid and furamide with oxalic acid" *J. Chem. Soc. Perkins Trans. 2: Physical Organic Chemistry*, 1973, pp. 503-508, vol. 5.
Jackisch, M. et al. "Structures of three related biphenyl compounds: 4,4'-biphenyldiol, 3, 3',5,5'-tetra-*tert*-butyl-4,4'-biphenyldiol, and 3,3',5,5'- tetra-*tert*-butyl-1,1'-bicyclohexa-2,5-dienylidene-4,4'-dione" *Acta Cryst.*, 1990, pp. 919-922, vol. C46.
Kim, S. et al. "The structure of a crystalline complex containing one phenobarbital molecule and two adenine derivatives" *Proc. Natl. Acad. Sci. USA*, 1968, pp. 402-408, vol. 60.
Kobayashi, H. et al. "Sinusoidal structure of the 1:1 complex of phenothiazine and 7,7,8,8-tetracyanoquinodimethane, PTZ-TCNQ" *Acta Cryst.*, 1974, pp. 1010-1017, vol. B30.
Ermer, O. et al. "Molecular recognition among alcohols and amines: super-tetrahedral crystal architectures of linear diphenol-diamine complexes and aminophenols" *J. Chem. Soc. Perkins Trans. 2*, 1994, pp. 925-944.
Martin, R. et al. "Polyphenal-caffeine complexation" *J. Chem. Soc., Chem. Commun.*, 1986, pp. 105-106.
Lehn, J.-M. et al. "Molecular recognition directed self-assembly of ordered supramolecular strands by cocrystallization of complementary molecular components" *Chem. Soc., Chem. Commun.*, 1990, pp. 479-481.
Lynch, D. et al. "Molecular cocrystals of carboxylic acids. XV' Preparation and characterization of heterocyclic base adducts with a series of carboxylic acids, and the crystal structures of the adducts of 2-aminopyrimidine with 2,6-dihydroxybenzoic acid, 4-aminobenzoic acid, phenoxyacetic acid, (2,4-dichlorophenoxy) acetic acid, (3,4-dichlorophenoxy)- acetic acid and salicylic acid, and 2-aminopyridmine with 2,6- dihydroxybenzoic acid" *Aust. J. Chem.*, 1994, pp. 1097-1115, vol. 47.
McIntosh, J. et al. "Chemotherapeutic drugs in anaerobic infections of wounds" *The Lancet*, Jun. 26, 1943, pp. 793-795.
McIntosh, J. et al. "Zinc peroxide, proflavine and penicillin in experimental *cl. welchii* infections" *The Lancet*, Dec. 26, 1942, pp. 750-752.
Smith, G. et al. "Molecular cocrystals of carboxylic acids. XXI' The role of secondary group interactions in adduct formation between 2-aminopyramidine and substituted benzoic acids: the crystal structures of the adducts with *o*-phthalic acid, *o*-nitrobenzoic acid, *o*-aminobenzoic acid and *m*-aminobenzoic acid" *Aust. J. Chem.*, 1995, pp. 1151-1166, vol. 48.
Weissbuch, I. et al. "Crystal morphology control with tailor-made additives; a stereochemical approach" *Advances in Crystal Growth Research*, 2001, pp. 381-400.
McMahon, J. et al. "Crystal engineering of the composition of pharmaceutical phases. $3^1$. Primary amide supramolecular heterosynthons and their role in the design of pharmaceutical co-crystals" *Z. Kristallogr.*, 2005, pp. 340-350, vol. 220.

Meejoo, S. et al. "The interplay of aryl-perfluoroaryl stacking interactions and interstack hydrogen bonding in controlling the structure of a molecular cocrystal" *Chemphyschem*, 2003, pp. 766-769, vol. 4.

Mirmehrabi, M. et al. "Improving the filterability and solid density of ranitidine hydrochloride form 1" *Journal of Pharmaceutical Sciences*, Jul. 2004, pp. 1692-1700, vol. 93, No. 7.

Morris, K. et al. "Theoretical approaches to physical transformations of active pharmaceutical ingredients during manufacturing processes" *Advanced Drug Delivery Reviews*, 2001, pp. 91-114, vol. 48.

Nakanishi, I. et al. "X-ray structural studies on two forms of β-cyclodextrin barbital complexes" *Journal of Inclusion Phenomena*, 1984, pp. 689-699, vol. 2.

Nakao, S. et al. "The crystal and molecular structure of the 2:1 molecular complex of theophylline with phenobarbital" *Acta Cryst.*, 1977, pp. 1373-1378, vol. B33.

Natarajan, S. et al. "Reinvestigation of the crystal structure of diglycine hydrochloride" *Zeitschrift für Kristallographic*, 1992, pp. 265-270, vol. 198.

Olenik, B. et al. "Cooperative and anticooperative effects in the cocrystals of mono- and diazanaphthalenes with *meso*-1, 2-diphenyl-1,2-ethanediol" *Crystal Growth & Design*, 2003, pp. 175-181, vol. 3, No. 2.

Olenik, B. et al. "Supramolecular synthesis by cocrystallization of oxalic and fumaric acid with diazanaphthalenes" *Crystal Growth & Design*, 2003, pp. 183-188, vol. 3, No. 2.

Groth, P. "*d*-Glucose-sodium chloride-monohydrate (glucose-sodium chloride) = $2C_6H_{12}O_6.NaCl.H_2O$" *Chemische Krystallographie*, 1910, pp. 438-439.

Oswald, I. et al. "Rationalisation of co-crystal formation through knowledge-mining" *Crystallography Reviews*, 2004, pp. 57-66, vol. 10, No. 1.

Ouyang, X. et al. "Single-crystal-to-single-crystal topochemical polymerizations of a terminal diacetylene: two remarkable transformations give the same conjugated polymer" *J. Am. Chem. Soc.*, 2003, pp. 12400-12401, vol. 125.

Patel, U. et al. "Structure of the 1:1 complex between 4-amino-*N*-(4,6-dimethyl-2-pyrimidinyl)- benzenesulfonamide (sulfadimidine) and 2-hydroxybenzoic acid (salicylic acid)" *Acta Cryst.*, 1988, pp. 1264-1267, vol. C44.

Reddy, L. et al. "Phenyl-perfluorophenyl synthon mediated cocrystallization of carboxylic acids and amides" *Crystal Growth & Design*, 2004, pp. 89-94, vol. 4., No. 1.

Remenar, J. et al. "Crystal engineering of novel cocrystals of a triazole drug with 1,4-dicarboxylic acids" *J. Am. Chem. Soc.*, 2003, pp. 8456-8457, vol. 125.

Schmidt, G. "Photodimerization in the solid state" *Pure Appl. Chem.*, 1971, pp. 647-678, vol. 27.

Shan, N. et al. "Co-crystal of 4,7-phenanthroline and carboxylic acids: synthon competition and prediction" *Tetrahedron Letters*, 2002, pp. 8721-8725, vol. 43.

Shan, N. et al. "Crystal engineering using 4,4'-bipyridyl with di- and tricarboxylic acids" *Crystal Engineering*, 2002, pp. 9-24, vol. 5.

Shan, N. et al "Supramolecular synthons in the co-crystal structures of 2-aminopyrimdine with diols and carboxylic acids" *Tetrahedron Letters*, 2002, pp. 3101-3104, vol. 43.

McIntosh, J. et al. "Further observations on the chemotherapy of experimental gas gangrene: flavazole, marfanil, V187 and V335" *British Journal of Experimental Pathology*, 1946, pp. 46-54, vol. 27.

Shaviv, R. et al. "Magnetochemistry of the tetrahaloferrate (III) ions 6. Crystal structure and magnetic ordering in $[(pyH)_3Cl] [FeCl_4]_2$" *Inorganica Chimica Acta*, 1992, pp. 613-621, vol. 198-200.

Shefter, E. "Structural studies on complexes IV: Crystal structure of a 1:1 5-chlorosalicylic acid and theophylline complex" *Journal of Pharmaceutical Sciences*, 1969, pp. 710-714, vol. 58.

Shimizu, N. et al. "Structure of 2,4-diamino-5-(3,4,5-trimethoxybenzyl) pyrimidine-5,5-diethylbarbituric acid (1:1)" *Acta Cryst.*, 1982, pp. 2309-2311, vol. B38.

Singh, N. B. et al. "Solid state reaction between 8-hydroxyquinoline and *p*-nitrobenzoic acid" *Indian Journal of Chemistry*, May 1988, pp. 429-432, vol. 37B.

Smith, G. et al. "The 1:1 adduct of 4-aminobenzoic acid with 4-aminobenzonitrile" *Acta Cryst.*, 2000, pp. 1155-1156, vol. C56.

Steiner, T. "Donor and acceptor strengths in C-H•••O hydrogen bonds quantified from crystallographic data of small solvent molecules" *New. J. Chem.*, 1998, pp. 1099-1103.

Storey, R. et al. "Automation of solid form screening procedures in the pharmaceutical industry- how to avoid the bottlenecks" *Crystallography Reviews*, 2004, pp. 45-56, vol. 10, No. 1.

Szafran, M. et al. "Molecular structures and hydrogen bonding in the 1:1 and 1:2 complexes of pyridine betaine with 2,6-dichloro-4-nitrophenol; an example of strongly coupled hydrogen bonds, O-H•••O=C-O-H•••O-" *Journal of Molecular Structure*, 1997, pp. 145-160, vol. 416.

Takeuchi, M. et al. "Synchrotron radiation SAXS/WAXS study of polymorph-dependent phase behavior of binary mixtures of saturated monoacid triacylglycerols" *Crystal Growth & Design*, 2003, pp. 369-374, vol. 3, No. 3.

Tang, C. P. et al. "Reaction pathways in crystalline host-guest inclusion complexes: rotation by a net 180° of the acetyl group on photoaddition of guest- acetophenone and—*m*-Chloroacetophenone to the atom C5 of host deoxycholic acid" *J. Am. Chem. Soc.*, 1985, pp. 4058-4070, vol. 107.

Taylor, R. et al. "Rules governing the crystal packing of mono- and dialcohols" *Acta Crystallographica Section B, Structural Science*, 2001, pp. 815-827, vol. B57.

Thallapally, P. et al. "Polymorphism of 1,3,5-trinitrobenzene induced by a trisindane additive" *Angew. Chem. Int. Ed.*, 2004, pp. 1149-1155, vol. 43.

Timmerman, P. et al. "Noncovalent Assembly of functional groups on calix[4]arene molecular boxes" *Chem. Eur. J.*, 1997, pp. 1823-1832, vol. 3., No. 11.

Shan, N. et al. "Mechanochemistry and co-crystal formation: effect of solvent on reaction kinetics" *Chem. Commun.*, 2002, pp. 2372-2373.

Caira, M. et al. "X-ray structure and thermal analysis of a 1:1 complex between (S)-naproxen and heptakis (2,3,6-tri-*O*-methyl)-β-cyclodextrin" *Journal of Inclusion Phenomena and Molecular Recognition in Chemistry*, 1995, pp. 277-290, vol. 20.

Trask, A. et al. "Crystal engineering of organic cocrystals by the solid-state grinding approach" *Top Curr. Chem.*, 2005, pp. 41-70, vol. 254.

Trask, A. et al. "Pharmaceutical cocrystallization: engineering a remedy for caffeine hydration" *Crystal Growth & Design*, 2005, pp. 1013-1021, vol. 5, No. 3.

Trask, A. et al. "Solvent-drop grinding: green polymorph control of cocrystallisation" *Chem. Commun.*, 2004, pp. 890-891 in addition to supplemental materials.

Trowbridge, L. et al. "Composites for nonlinear optics: Crystal growth and polymorphism" *University of Sussex, Falmer Brighton UK, School of Chemistry and Molecular Sciences*, pp. 272, 1994.

Uno, T. et al. "Structure of 5,5-diphenylhydantoin-1-(4-bromophenyl)-4-dimethylamino-2,3-dimethyl-3-pyrazolin-5-one (1:1)" *Acta Cryst.*, 1980, pp. 2794-2796, vol. B36.

Van Roey, P. et al. "Structure-activity studies of non-steroidal aromatase inhibitors: the crystal and molecular structures of CGS 16949A and CGS 18320B" *J. Enzyme Inhibition*, 1991, pp. 119-132, vol. 5.

Van Roey, P. et al. "Structure of *cis*1-{[4-(1-imidazolylmethyl) cyclohexyl] methyl} imidazole- succinic acid complex" *Acta Cryst.*, 1991, pp. 1015-1018, vol. C47.

Vishweshwar, P. et al. "Crystal engineering of pharmaceutical co-crystals from polymorphic active pharmaceutical ingredients" *Chem. Commun.*, 2005, pp. 4601-4603.

Vishweshwar, P. et al. "Recurrence of carboxylic acid- pyridine supramolecular synthon in the crystal structures of some pyrazinecarboxylic acids" *J. Org. Chem.*, 2002, pp. 556-565, vol. 67.

Vishweshwar, P. et al. "Supramolecular synthons based on N-H•••N and C-H•••O hydrogen bonds. Crystal engineering of a helical structure with 5,5-diethylbarbituric acid" *Chem. Commun.*, 2002, pp. 1830-1831.

Vishweshwar, P. et al. "Supramolecular synthons in phenol-isonicotinamide adducts" *Cryst. Eng. Comm.* 2003, pp. 164-168, vol. 5, No. 31.

Voet, D. et al. "The crystal and molecular structure of the intermolecular complex 9-ethyladenine-5, 5-diethylbarbituric acid" *Journal of the American Chemical Society*, Nov. 15, 1972, pp. 8213-8222, vol. 94, No. 23.

Voet, D. et al. "The structure of an intermolecular complex between cytosine and 5-fluorouracil" *Journal of the American Chemical Society*, May 21, 1969, pp. 3069-3075, vol. 91, No. 11.

Stezowski, J. J. et al. "Characterization of a 1:1 complex of an unusual structure in the phenothiazine/phenazine binary phase diagram" *Zeitschrift fur Kristallographie* in *International Journal for Structural, Physical, Chemical Aspects of Crystalline Materials*, 1983, pp. 213-215, vol. 162, No. 1-4.

Wang, A. et al. "Crystal structure of 1:1 complex of barbital with 1-methylimidazole" *Journal of Pharmaceutical Sciences*, Mar. 1979, pp. 361-363, vol. 68, No. 3.

Alberola, S. et al. "Crystalline and Molecular Structure of Sulfanilimide-Antipyrine" *Acta Cryst*, 1977, pp. 3337-3341, vol. B33.

Wood, R. A. et al. "2,5-O-methylene-D-mannitol sodium-chloride, $C_7 H_{14} O_6$. NaCl" *Cryst. Struct. Comm.*, 1976, 207-210, vol. 5.

Xu, J. et al. "Effect of composition distribution on miscibility and co-crystallization phenomena in the blends of low density polyethylene with conventional and metallocene-based ethylene-butene copolymers" *Polymer*, 2001, pp. 3867-3874, vol. 42.

Yoo, J. et al. "Cocrystallization of a dinuclear platinum complex as a monomer and a one-dimensional polymer" *Polyhedron*, 2002, pp. 715-719, vol. 21.

Zaitu, S. et al. "A 2:1 molecular complex of theophylline and 5-fluorouracil as the monohydrate" *Acta Cryst.*, 1995, pp. 1857-1859, vol. C51.

Zaman, M. B. et al. "Linear hydrogen-bonded molecular tapes in the cocrystals of squaric acid with 4,4'-dipyridylacetylene and 1,2-bis(4-pyridyl) ethylene" *Acta Cryst.*, 2001, pp. 621-624, vol. C57.

Zerkowski, J. et al. "Design of organic structures in the solid state: hydrogen-bonded molecular "tapes"[1]" *J. Am. Chem. Soc.*, 1990, pp. 9025-9026, vol. 112.

Zerkowski, J. et al. "Investigations into the robustness of secondary and tertiary architecture of hydrogen-bonded crystalline tapes" *Chem. Mater.*, 1994, pp. 1250-1257, vol. 6.

Zerkowski, J. et al. "New varieties of crystalline architecture produced by small changes in molecular structure in tape complexes of melamines and barbiturates" *J. Am. Chem. Soc.*, 1994, pp. 4305-4315, vol. 116.

Zerkowski, J. et al. "Polymorphic packing arrangements in a class of engineered organic crystals" *Chem. Mater.*, 1997, pp. 1933-1941, vol. 9.

Zerkowski, J. et al. "Solid-state structures of "Rosette" and "Crinkled Tape" motifs derived from the cyanuric acid-melamine lattice" *J. Am. Chem. Soc.*, 1992, pp. 5473-5475, vol. 114.

Zhang, R. et al. "Atmospheric new particle formation enhanced by organic acids" *Science*, Jun. 4, 2004, pp. 1487-1490 with additional supporting online material, vol. 304.

Zhu, H. et al. "Influence of water activity in organic solvent + water mixtures on the nature of the crystallizing drug phase. 1. theophylline" *International Journal of Pharmaceutics*, 1996, pp. 151-160, vol. 135.

Aakeröy, C. et al. "Aromatic dicarboxylic acids as building blocks of extended hydrogen-bonded architectures" *Supramolecular Chemistry*, 1998, pp. 127-135, vol. 9.

Aakeröy, C. et al. "Assembly of 2-D inorganic/organic lamellar structures through a combination of copper (I) coordination polymers and self-complimentary hydrogen bonds" *J. Chem. Soc., Dalton Trans.*, 2000, pp. 3869-3872.

Aakeröy, C. et al. "Building organic assemblies with 2-pyridone and dicarboxylic acids: relating molecular conformation and synthon stability to crystal structure" *Crystal Engineering*, 1998, pp. 225-241, vol. 1, No. 3-4.

Aakeröy, C. et al. "The C-H•••Cl hydrogen bond: does it exist?" *New J. Chem.*, 1999, pp. 145-152.

Aakeröy, C. et al. "Crystal engineering of ionic solids" *Modular Chemistry* (ed. by Michl, J.), 1997, pp. 153-162, Kluwer Academic Publishers, The Netherlands.

Aakeröy, C. et al. "Crystal engineering: strategies and architectures" *Acta Cryst.*, 1997, pp. 569-586, vol. B53.

Aakeröy, C. et al. "Crystal engineering using intermolecular hydrogen-bonded connectors and classic coordination chemistry" *Transactions ACA*, 1998, pp. 97-103, vol. 33.

Aakeröy, C. et al. "The crystal structure of the molecular cocrystal L-malic acid L-tartaric acid (1/1)" *Supramolecular Chemistry*, 1996, pp. 153-156, vol. 7.

Aakeröy, C. et al. "Deliberate combination of coordination polymers and hydrogen bonds in a supramolecular design strategy for inorganic/organic hybrid networks" *Chem. Commun.*, 2000, pp. 935-936.

Aakeröy, C. et al. "Di-hydroxy malonic acid as a building block of hydrogen-bonded 3-dimensional architectures" *Journal of Chemical Crystallography*, 1998, pp. 111-117, vol. 28, No. 2.

Aakeröy, C. et al. "Do polymorphic compounds make good cocrystallizing agents? A structural case study that demonstrates the importance of synthon flexibility" *Crystal Growth & Design*, 2003, 159-165, vol. 3, No. 2.

Aakeröy, C. et al. "Heteromeric intermolecular interactions as synthetic tools for the formation of binary co-crystals" *Cryst. Eng. Comm.*, 2004, pp. 19-24, vol. 6, No. 5.

Aakeröy, C. et al. "A high-yielding supramolecular reaction" *J. Am. Chem. Soc.*, 2002, 14425-14432, vol. 124.

Aakeröy, C. et al. "The hydrogen bond and crystal engineering" *Chemical Society Reviews*, 1993, pp. 397-407.

Aakeröy, C. et al. "Hydrogen-bond assisted assembly of organic and organic-inorganic solids" *Crystal Engineering: From Molecules and Crystals to Materials*, 1999, pp. 89-106, Kluwer Academic Publishers, The Netherlands.

Aakeröy, C. et al. "Hydrogen-bonding in solids" *Crystal Engineering* (ed. by Seddon, K. R. et al.), 1999, pp. 303-324, Kluwer Academic Publishers, The Netherlands.

Aakeröy, C. et al. "Low-dimensional architectures of silver coordination compounds assembled via amide-amide hydrogen bonds" *Crystal Engineering*, 1998, pp. 39-49, vol. 1, No. 1.

Aakeröy, C. et al. "Molecular mechanics and crystal engineering" *Crystal Engineering* (ed. by Seddon, K. R. et al.), 1999, pp. 69-82, Kluwer Academic Publishers, The Netherlands.

Aakeröy, C. et al. "New building blocks for crystal engineering. Syntheses and crystal structures of oxime-substituted pyridines" *Cryst. Eng. Comm.*, 2000, pp. 1-6, vol. 27.

Aakeröy, C. et al. "Novel colorless composite materials for nonlinear optics" *Adv. Mater.*, 1993, pp. 364-367, vol. 5, No. 5.

Aakeröy, C. et al. "Organic assemblies of 2-pyridones with dicarboxylic acids" *Tetrahedron*, 2000, pp. 6693-6699, vol. 56.

Aakeröy, C. et al. "Pitfalls in the supramolecular assembly of silver(I) coordination compounds" *Journal of Molecular Structure*, 1999, pp. 91-101, vol. 474.

Aakeröy, C. et al. "A structural study of 2-amino-5-nitropyridine and 2-amino-3-nitropyridine: intermolecular forces and polymorphism" *J. Mater. Chem.*, 1998, pp. 1385-1389, vol. 8, No. 6.

Aakeröy, C. et al. "Supramolecular assembly of low-dimensional silver (I) architectures via amide-amide hydrogen bonds" *Chem. Commun.*, 1998, pp. 1067-1068.

Aakeröy, C. et al. "'Total synthesis' supramolecular style: design and hydrogen-bond-directed assembly of ternary supermolecules" *Angew. Chem. Int. Ed.*, 2001, pp. 3240-3242, vol. 40, No. 17.

Aakeröy, C. et al. "Two-fold interpenetration of 3-D nets assembled via three-co-ordinate silver(I) ions and amide-amide hydrogen bonds" *J. Chem. Soc., Dalton Trans.*, 1998, pp. 1943-1945.

Ahn, S. et al. "Polymorphs of a 1:1 cocrystal with tunnel and layer structures: p,p'-biphenol/dimethyl sulfoxide" *Crystal Growth & Design*, 2001, pp. 107-111, vol. 1, No. 2.

Akazome, M. et al. "Enantioselective inclusion of methyl phenyl sulfoxides and benzyl methyl sulfoxides by (R)-phenylglycyl-(R)-phenylglycine and the crystal structures of the inclusion cavities" *J. Org. Chem.*, 2000, pp. 68-76, vol. 65.

Akhtaruzzaman, M.D. et al. "One-dimensional hydrogen-bonded molecular tapes in 1,4-bis[(4-pyridinio) ethynyl]benzene chloranilate" *Acta. Cryst.*, 2001, pp. o353-o355, vol. E57.

Allen, F. et al. "Systematic analysis of structural data as a research technique in organic chemistry" *Acc. Chem. Res.*, 1983, pp. 146-153, vol. 16.

Almarsson, Ö. et al. "Crystal engineering of the composition of pharmaceutical phases. Do pharmaceutical co-crystals represent a new path to improved medicines?" *Chem. Commun.*, 2004, pp. 1889-1896.

Amai, M. et al. "1:1 complex of octadecanoic acid and 3-pyridinecarboxamide" *Acta Cryst.*, 1998, pp. 1367-1369, vol. C54.

Anderson, N. et al. "Sulfonation with inversion by mitsunobu reaction: an improvement on the original conditions" *J. Org. Chem.*, 1996, pp. 7955-7958, vol. 61.

Aoki, K. et al. "A 1:1 complex of theophylline and *p*-nitrophenol" *Acta Cryst.*, 1978, pp. 2333-2336, vol. B34.

Ashton, P. et al. "Combining different hydrogen-bonding motifs to self-assemble interwoven superstructures" *Chem. Eur. J.*, 1998, pp. 577-589, vol. 4, No. 4.

Barker, P. A. et al. "Effect of crystallization temperature on the cocrystallization temperature on the cocrystallization of hydroxybutyrate/ hydroxyvalerate copolymers" *Polymer*, pp. 913-919, vol. 38, No. 4.

Berkovitch-Yellin, Z. et al. "Electron density distribution in cumulenes: an x-ray study of the complex allenedicarboxylic acid-acetamide (1:1) at -150°C." *Acta Cryst.*, 1977, pp. 3670-3677, vol. B33.

Berkovitch-Yellin, Z. et al. "The role played by C-H•••O and C-H•••N interactions in determining molecular packing and conformation" *Acta Cryst.*, 1984, pp. 159-165, vol. B40.

Berl, V. et al. "Induced fit selection of a barbiturate receptor from a dynamic structural and conformational/configurational library" *Eur. J. Org. Chem.*, 1999, pp. 3089-3094.

Bertolasi, V. et al. "Competition between hydrogen bonding and donor-acceptor interactions in co-crystals of 1,3-dimethylbarbituric acid with aromatic amines" *New J. Chem.*, 2001, pp. 408-415, vol. 25.

Bertolasi, V. et al. "General rules for the packing of hydrogen-bonded crystals as derived from the analysis of squaric acid anions: aminoaromatic nitrogen base co-crystals" *Acta Cryst.*, 2001, pp. 591-598, vol. B57.

Bettinetti, G. et al. "Structure and solid-state chemistry of anhydrous and hydrated crystal forms of the trimethoprim-sulfamethoxypyridazine 1:1 molecular complex" *Journal of Pharmaceutical Sciences*, Apr. 2000, pp. 478-489, vol. 89, No. 4.

Bettinetti, G. et al. "Thermal analysis of binary systems of the pharmaceuticals trimethoprim and benzoic acid" *Journal of Thermal Analysis*, 1983, pp. 285-294, vol. 28.

Bettis, J. et al. "Biopharmaceutics and dosage form design" *Amer. J. Hosp. Pharm.*, Mar. 1973, pp. 240-243, vol. 30.

Bolton, S. et al. "Complexes formed in solution by homologs of caffeine" *Journal of the American Pharmaceutical Association*, Jan. 1957, pp. 38-41, vol. XLVI, No. 1.

Bond, A. "In situ co-crystallisation as a tool for low-temperature crystal engineering" *Chem. Commun.*, 2003, pp. 250-251, vol. 2.

Bonin, M. et al. "Urotropin azelate: a rather unwilling co-crystal" *Acta Cryst.*, 2003, pp. 72-86, vol. B59.

Bosshard, C. et al. "Microscopic nonlinearities of two-component organic crystals" *J. Opt. Soc. Am. B*, Nov. 2001, pp. 1620-1626, vol. 18, No. 11.

Gluzman, M. Kh. et al. "Investigation of Eutectic Melting in Systems Composed of Organic Salts and Acids" *Journal of Physical Chemistry*, 1960, pp. 2742-2747, vol. 34.

Braga, D. et al. "Hydrogen bonding interactions between ions: a powerful tool in molecular crystal engineering" *Structure and Bonding*, 2004, pp. 1-32, vol. 111.

Brierley, C. et al. "Preparation and structure of the 1:2 π-molecular complex of phenothiazine with pyromellitic dianhydride" *J. Chem. Phys.*, Feb. 1, 1985, pp. 1522-1528, vol. 82, No. 1.

Burgi, H. et al. "Crystallisation of supramolecular materials" *Current Opinion in Solid State & Materials Science*, 1998, pp. 425-430, vol. 3.

Byrn, S. R. et al. "Solid-state pharmaceutical chemistry" *Chem. Mater.*, 1994, pp. 1148-1158, vol. 6.

Caira, M. "Molecular complexes of sulfonamides. Part 1. 1:1 complexes between sulfadimidine [4-amino-N-(4,6-dimethyl-2-pyrimidinyl) benzenesulfonamide] and 2- and 4-aminobenzoic acids" *Journal of Crystallographic and Spectroscopic Research*, 1991, pp. 641-648, vol. 21, No. 5.

Caira, M. "Molecular complexes of sulfonamides. Part 2. 1:1 complexes between drug molecules: sulfadimidine -acetylsalicylic acid and sulfadimidine-4-aminosalicylic acid" *Journal of Crystallographic and Spectroscopic Research*, 1992, pp. 193-200, vol. 22, No. 2.

Caira, M. "Molecular complexes of sulfonamides. 3. Structure of 5-methoxysulfadiazine (Form II) and its 1:1 complex with acetylsalicylic acid" *Journal of Chemical Crystallography*, 1994, pp. 695-701, vol. 24, No. 10.

Caira, M. et al. "Order-disorder enantiotropy, monotropy, and isostructurality in a tetroxoprim-sulfametrole 1:1 molecular complex: crystallographic and thermal studies" *Journal of Pharmaceutical Sciences*, Nov. 2003, pp. 2164-2176, vol. 92, No. 11.

Caira, M. et al. "Selective formation of hydrogen bonded cocrystals between a sulfonamide and aromatic carboxylic acids in the solid state" *J. Chem. Soc. Perkin Trans. 2*, 1995, pp. 2213-2216.

Caira, M. et al. "Structure of a 1:1 complex between the anthelmintic drug mebendazole and propionic acid" *Journal of Chemical Crystallography*, 1998, vol. 28, No. 1.

Camerman, A. et al. "Hydrogen bonding interaction of diphenylbarbituric acid and 9-ethyladenine. Crystal structure of a 1:1 complex" *Can. J. Chem.*, 2000, pp. 1045-1051, vol. 78.

Camerman, A. et al. "Molecular structure of acetylacetone. A crystallographic determination" *J. Am. Chem. Soc.*, 1983, pp. 1584-1586, vol. 105, No. 6.

Cannon, A. et al. "Noncovalent derivatization: green chemistry applications of crystal engineering" *Crystal Growth & Design*, 2002, pp. 255-257, vol. 2. No. 4.

Chinnakali, K. et al. "2-aminopyrimidine and *p*-phenylene-diacetic acid (1:1) co-crystal" *Acta Cryst.*, 1999, pp. 399-401, vol. C55.

Choi, C. et al. "Cocrystallization of melaminium levulinate monohydrate" *Acta Cryst.*, 2004, pp. o295-o296, vol. C60.

Chow, Y. P. et al. "Complexation of acetaminophen with methyl xanthines" *Journal of Pharmaceutical Sciences*, 1972, pp. 1454-1458, vol. 61.

Christian, S. et al. "Activity coefficient effects in spectral and solubility studies of molecular complex equilibria" *Journal of the American Chemical Society*, Sep. 20, 1972, pp. 6861-6862, vol. 94, No. 19, Communications to the editor.

Coll, M. et al. "Molecular structure of the complex formed between the anticancer drug cisplatin and d(pGpG): C222$_1$ crystal form" *Journal of Biomolecular Structure & Dynamics*, 1990, pp. 315-330, vol. 8, No. 2.

Copp, S. et al. "Supramolecular chemistry of [Mn(CO)$_3$ (μ$_3$-OH)]$_4$: Assembly of a cubic hydrogen-bonded diamondoid network with 1,2-diamineothane" *J. Am. Chem. Soc.*, 1992, pp. 8719-8720, vol. 114.

Cordi, A. et al. "(S)-Spiro [(1, 3-diazacyclopent-1-ene)-5, 2' -(7'-methyl-1',2',3',4'-tetrahydronaphthalene)]: resolution, stereospecific synthesis, and preliminary pharmacological characterization as a partial α-adrenergic agonist" *J. Med. Chem.*, 1997, pp. 2931-2935, vol. 40.

Craven, M. et al. "The 2:1 crystal complex of 5, 5-diethylbarbituric acid (barbital) and caffeine" *Acta Cryst.*, 1974, pp. 1191-1195, vol. B30.

Craven, M. et al. "The crystal structures of two polymorphs of 5,5'-diethylbarbituric acid (barbital)" *Acta Cryst.*, 1969, pp. 1978-1993, vol. B25.

Cudney, B. et al. "Screening and optimization strategies for macromolecular crystal growth" *Acta Cryst.*, 1994, pp. 414-423, vol. D50.

Datta, S. et al. "Molecular complex formation between riboflavin and salicylate in an aqueous medium" *Bull. Chem. Soc. Jpn.*, 2003, pp. 1729-1734, vol. 76.

Davey, R. J. et al. "Crystal engineering- nucleation, the key step" *Cryst. Eng. Comm.*, 2002, pp. 257-264, vol. 4, No. 47.

Davey, R. J. et al. "Crystallisation in polymer films: control of morphology and kinetics of an organic dye in a polysilicone matrix" *J. Mater. Chem.*, 1997, pp. 237-241, vol. 7, No. 2.

Debernardis, J. et al. "Conformationally defined adrenergic agents. 5. Resolution, absolute configuration, and pharmacological characterization of the enantiomers of 2-(5,6-dihydroxy-1,2,3,4-tetrahydro-1-naphthyl) imidazoline: a potent agonist at $\alpha$-adrenoceptors" *J. Med. Chem.*, 1987, pp. 1011-1017, vol. 30.

Desiraju, G. et al. "Crystal and co-crystal" *Cryst. Eng. Comm.*, 2003, pp. 466-467, vol. 5, No. 82.

Desiraju, G. et al. "Crystal engineering: outlook and prospects" *Current Science*, Oct. 25, 2001, pp. 1038-1042, vol. 81, No. 8.

Duax, W. et al. "The structure of the crystalline complex estradiol. Urea (1:1)" *Acta Cryst.*, 1972, pp. 1864-1871, vol. B28.

Dunitz, J. "Crystal and co-crystal: a second opinion" *Cryst. Eng. Comm.*, 2003, pp. 506, vol. 5, No. 91.

Dunitz, J. "New light on an old story: the solid-state transformation on ammonium cyanate into urea" *J. Am. Chem. Soc.*, 1998, pp. 13274-13275, vol. 120.

Enright, G. et al. "Thermally programmable gas storage and release in single crystals of an organic van der Waals host" *J. Am. Chem. Soc.*, 2003, pp. 9896-9897, vol. 125.

Epstein, R. et al. "The x-ray crystal structure of the molecular complex 8-bromo-9-ethyladenine-5-allyl-5-isobutylbarbituric acid" *Acta Cryst.*, 1976, pp. 2180-2188, vol. B32.

Etter, M. "Encoding and decoding hydrogen-bond patterns of organic compounds" *Acc. Chem. Res.*, 1990, pp. 120-126, vol. 23.

Etter, M. et al. "Graph-set analysis of hydrogen-bond patterns in organic crystals" *Acta Cryst.*, 1990, pp. 256-262, vol. B46.

Etter, M. et al. "Hydrogen bond directed cocrystallization and molecular recognition properties of acyclic imides" *J. Am. Chem. Soc.*, 1991, pp. 2586-2598, vol. 113.

Etter, M. "Hydrogen bonds as design elements in organic chemistry" *J. Phys. Chem.*, 1991, pp. 4601-4610, vol. 95.

Fabian, L. et al. "Volumetric measure of isostructurality" *Acta Cryst.*, 1999, pp. 1099-1108, vol. B55.

Fallon III, L. "The crystal and molecular structure of 5-fluorouracil" *Acta Cryst.*, pp. 2549-2556, vol. B29, 1973.

Feibush, B. et al. "Chiral separation of heterocyclic drugs by HPLC: solute-stationary phase base-pair interactions" *J. Am. Chem. Soc.*, 1986, pp. 3310-3318, vol. 108.

Fifer, E. et al. "Fentanyl analogues 3. 2-(1,2,3,4-tetrahydro)-naphthyl substituted 4-anilidopiperidines" *Eur. J. Med. Chem.—Chim. Ther.*, 1984, pp. 519-524, vol. 19, No. 6.

Reck, G. et al. "Crystal structures of the carbamazepine/ammonium chloride and carbamazepine/ammonium bromide adducts and their transformation into carbamazepine dihydrate" *Pharmazie*, 1991, pp. 509-512, vol. 46, No. 7.

Foxman, B. M. et al. "Environmentally benign synthesis using crystal engineering: steric accommodation in non-covalent derivatives of hydroquinones" *Crystal Engineering*, 1998, pp. 109-118, vol. 1, No. 1.

Foxman, B. M. et al. "Noncovalent derivatives of hydroquinone: BIS-(N,N-dialkyl) bicyclo[2.2.2]octane-1,4-dicarboxamide complexes" *Crystal Engineering*, 1999, pp. 55-64, vol. 2. No. 1.

Fujii, S. et al. "Crystal and molecular structure of a 1:1 molecular complex of adenine and riboflavin" *Archives of Biochemistry and Biophysics*, 1977, pp. 363-370, vol. 181.

Gao, X. et al. "Supramolecular construction of molecular ladders in the solid state" *Angew. Chem. Int. Ed.*, 2004, pp. 232-236, vol. 43.

Gartland, G. L. et al. "Hydrogen bonding NH•••O=C of barbiturates: the (1:1) crystal complex of urea and 5,5-diethylbarbituric acid (barbital)" *Acta Cryst.*, 1974, pp. 980-987, vol. B30.

Ghosh, M. "Structure and conformation of the 1:1 molecular complex sulfaproxyline-caffeine" *Acta Cryst.*, 1991, pp. 577-580, vol. C47.

Giuseppetti, G. P. et al. "The crystal structure of a sulfamethoxazole-trimethoprim 1:1 molecular compound" *II Farmaco- Ed. Sc.*, pp. 138-151, vol. 35, 1980.

Goswami, S. et al. "2-aminopyrimidine-fumaric acid cocrystal" *Acta Cryst.*, 1999, pp. 583-585, vol. C55.

Haynes, D. "Supramolecular synthon competition in organic sulfonates: A CSD survey" *Cryst. Eng. Comm.*, 2004, pp. 584-588, vol. 6, No. 95.

Goswami, S. et al. "1:1 Hetero-assembly of 2-amino-pyramidine and (+)-camphoric acid" *Acta Cryst.*, 2000, pp. 477-478, vol. C56.

Goswami, S. et al. "Molecular recognition induced supramolecular array of 2-aminopyrimidine with terephthalic acid, 1,4-phenylenediacetic acid and furmaric acid in solid state via H-bonding and $\pi$-stacking interactions" *Supramolecular Chemistry*, 1999, pp. 25-33, vol. 11.

Graja, A. et al. "Interplay of acceptor molecule shape, crystal structure and physical properties of a new molecular complex $C_{70} \cdot 2[(Ph_3P) AuCl]$" *Chemical Physics Letters*, Nov. 19, 1999, pp. 725-732. vol. 313.

Haixin, L. et al. "Structure of the 1:1 complex of 6,6'-diquinolyl ether with 5,5-diethylbarbituric acid" *Acta Cryst.*, 1992, pp. 2096-2098, vol. C48.

Henck, J. et al. "Disappearing and reappearing polymorphs. The benzocaine:picric acid system" *J. Am. Chem. Soc.*, 2001, pp. 1834-1841, vol. 123.

Higuchi, T. et al. "Complexation of organic substances in aqueous solution by hydroxyaromatic acids and their salts" *J. Pharm. Sci.*, 1961, pp. 905-909, vol. 50.

Hino, T. et al. "Assessment of nicotinamide polymorphs by differential scanning calorimetry" *Thermochimica Acta*, 2001, pp. 85-92, vol. 374.

Högberg, T. et al. "Crystallographic, theoretical and molecular modelling studies on the conformations of the salicylamide, raclopride, a selective dopamine-$D_2$ antagonist" *J. Pharm. Pharmacol.*, 1987, pp. 787-796, vol. 39.

Hsu, I. et al. "The 2:1 crystal complex of 2-aminopyridine and 5,5-diethylbarbituric acid (barbital)" *Acta Cryst.*, 1974, pp. 994-997, vol. B30.

Hsu, I. et al. "The 1:1 crystal complex of N-methyl-2-pyridone and 5,5-diethylbarbituric acid (barbital)" *Acta Cryst.*, 1974, pp. 998-1001, vol. B30.

Hsu, I. et al. "The crystalline complex (1:1) of salicylamide and 5-ethyl-5-isoamylbarbituric acid (amobarbital)" *Acta Cryst.*, 1974, pp. 843-846, vol. B30.

Hsu, I. et al. "The crystal structure of the 1:1 complex of acetamide with 5,5-diethylbarbituric acid (barbital)" *Acta Cryst.*, 1974, pp. 974-979, vol. B30.

Hsu, I. et al. "The crystal structure of the triclinic 1:2 complex of hexamethylphosphoramide with 5,5-diethylbarbituric acid (barbital)" *Acta Cryst.*, 1974, pp. 1299-1304, vol. B30.

Hsu, I. et al. "Hydrogen bonding NH . . . N of barbiturates: The 1:1 crystal complex of imidazole and 5,5-diethylbarbituric acid (barbital)" *Acta Cryst.*, 1974, pp. 988-993, vol. B30.

Ibragimov, B. "A simple correlation between the structures of different crystal modifications of a given host-guest complex and their crystallization temperatures" *Journal of Inclusion of Phenomena and Macrocyclic Chemistry*, 1999, pp. 345-353, vol. 34.

Ishida, T. et al. "Structural study of histamine $H_2$-receptor antagonists. Five 3-[2-(diamino-methyleneamino)-4-thiazolymethylthio] propionamidine and -amide derivatives" *Acta Cryst.*, 1989, pp. 505-512, vol. B45.

Katakai, R. et al. "Stepwise synthesis of oligopeptides with N-carboxy-$\alpha$-amino acid anhydrides. IV. Glycine NCA" *J. Org. Chem.*, 1972, pp. 327-329, vol. 37, No. 2.

Kawakami, Y. et al. "The rationale for E2020 as a potent acetylcholinesterase inhibitor" *Bioorganic & Medicinal Chemistry*, 1996, pp. 1429-1446, vol. 4, No. 9.

Kelders, H. et al. "Automated protein crystallization and a new crystal form of a subtilisin: eglin complex" *Protein Engineering*, 1987, pp. 301-303, vol. 1, No. 4.

Khalil, R. M. "Complexation of paracetamol with xanthine derivatives" *Egypt. J. Pharm. Sci.*, 1992, pp. 757-769, vol. 33, No. 5-6.

Kim, S. "Crystal structure of the 1:1 complex of 5-fluorouracil and 9-ethylhypoxanthine" *Science*, Nov. 24, 1967, pp. 1046-1048, vol. 158, No. 3804.

Kiryu, S. et al. "Crystal structure of a 1:1 aminopyrine-barbital complex" *Journal of Pharmaceutical Sciences*, May 1971, pp. 699-703, vol. 60, No. 5.

Kiryu, S. et al. "Crystal structure of a 1:1 aminopyrine-cyclobarbital complex" *Chem. Pham. Bull.*, 1974, pp. 1588-1592, vol. 22.

Klein, C. et al. "Molecular structure of two conformationally restrained fentanyl analogues: cis- and trans-isomers of N-{3-methyl-1-[1,2,3,4-tetrahydro) naphthyl]-4-piperidinyl}-N-phenylpropanamide" *Journal of Pharmaceutical Sciences*, Nov. 1985, pp. 1147-1151, vol. 74, No. 11.

Koshima, H. et al. "Photoreactivities of two kinds of bimolecular crystals formed from acridine and phenothiazine" *J. Chem. Soc., Perkins Trans. 2*, 1997, pp. 2033-2038.

Koshima, H. et al. "Polymorphs of a cocrystal with achiral and chiral structures prepared by pseudoseeding: tryptamine/hydrocinnamic acid" *Crystal Growth & Design*, 2001, pp. 355-357, vol. 1, No. 5.

Krishnamohan Sharma, C. V. et al."X-ray crystal structure of $C_6H_3(CO_2H)_3$-1,3,5•1.5(4,4'-bipy): a 'super trimesic acid' chicken-wire grid" *Chem. Commun.*, 1996, pp. 2655-2656.

Kuroda, R. et al. "Generation of a co-crystal phase with coloristic properties via solid state grinding procedures" *Chem. Commun.*, 2002, pp. 2848-2849.

Leiserowitz, L. et al. "The molecular packing modes and hydrogen-bonding properties of amide: dicarboxylic acid complexes" *Acta Cryst.*, 1977, pp. 2719-2733, vol. B33.

Leiserowitz, L. "Molecular packing modes. Carboxylic acids" *Acta Cryst.*, 1976, pp. 775-802, vol. B32.

Lynch, D. et al. "Molecular cocrystals of carboxylic acids. XXXI' adducts of 2-aminopyrimidine and 3-amino-1,2,4-triazole with heterocyclic carboxylic acids" *Aust. J. Chem.*, 1998, pp. 403-408, vol. 51.

MacGillivray, L. et al. "Supramolecular control of reactivity in the solid state using linear molecular templates" *J. Am. Chem. Soc.*, 2000, pp. 7817-7818, vol. 122.

Mathias, J. et al. "Structural preferences of hydrogen-bonded networks in organic solution- the cyclic $CA_3 \cdot M_3$ 'rosette'" *J. Am. Chem. Soc.*, 1994, pp. 4316-4325, vol. 116.

Mastropaolo, D. et al. "Hydrogen bonding interaction of diphenylhydantoin and 9-ethyladenine" *Molecular Pharmacology*, 1983, pp. 273-277, vol. 23.

Maryanoff, B. "Stereochemistry in a medium-sized ring. Highly diastereoselective N-oxidation of a substituted 3-benzazonine. X-ray crystal structure of an unusual complex between an amine N-oxide and saccharin" *J. Org. Chem.*, 1990, pp. 760-764, vol. 55.

Martin, R. et al. "The caffeine-potassium chlorogenate molecular complex" *Phytochemistry*, 1987, pp. 273-279, vol. 26, No. 1.

Anderson, J. "Constitution of aurous compounds: Gold mirrors" *Nature*, Oct. 2, 1937, pp. 583-584, Letters to the Editor.

Robbins, A. H. et al. "The crystal structure of the 1:2 adduct of potassium triiodide and 5,5-diethylbarbituric acid (barbital)" *American Crystallographic Association- Series 2, Papers and Abstracts*, 1973, p. 87.

Beerges, P. et al. "Phenothiazine tetracyanoethylene" *Private Communication*, 1994.

Madarasz, J. et al. "Thermal, ftir and xrd study on some 1:1 molecular compounds of theophylline" *Journal of Thermal Analysis and Calorimetry*, 2002, pp. 281-290, vol. 69.

Caronna, T. et al. "Halogen bonding and π•••π stacking control reactivity in the solid state" *J. Am. Chem. Soc.*, 2004, pp. 4500-4501, vol. 126.

Zerkowski, J. et al. "Steric control of secondary, solid-state architecture in 1:1 complexes of melamines and barbiturates that crystallize as crinkled tapes" *J. Am. Chem. Soc.*, 1994, pp. 4298-4304, vol. 116.

Zaitu, S. et al. "1:1 Molecular complex of theophylline and p-nitroaniline" *Acta Cryst.*, 1995, pp. 2390-2392, vol. C51.

Kofler, L. et al., *Thermal micromethods for the study of organic compounds and their mixtures*, pp. 1-145, 148-351, 354-386, Innsbruck, Austria, 1980.

Quehenberger, H. "Concerning organic molecular compounds and their polymorphism" *Monatshefte für Chemie*, 1949, pp. 595-606, vol. 80, No. 5.

Wiedenfeld, H. et al. "The crystal structure of the theophylline-urea complex" *Arch. Pharm.*, 1986, pp. 654-659, vol. 319.

Bunick, G. et al. "The crystal and molecular structure of the complex 2,6-diamino-9-ethylpurine 5,5-diethylbarbituric acid" *American Crystallographic Association, Abstract Papers* Winter 1976, p. 30.

Buczak, G. et al. "Crystal structure and vibrational spectra of the 1:1 and 1:2 complexes of pyridine betaine with pentachlorophenol" *Journal of Molecular Structure*, 1997, pp. 143-151, vol. 436-437.

Tomura, M. et al. "One-dimensional zigzag chain structures with intermolecular C-H••• π and C-H•••O interactions consisted of phthalic acid and pyridine derivatives" *Chemistry Letters*, 2001, pp. 532-533.

Zerkowski, J. et al. "Design of organic structures in the solid state: molecular tapes based on the network of hydrogen bonds present in the cyanuric acid•melamine complex" *J. Am. Chem. Soc.*, 1994, pp. 2382-2391, vol. 116.

Harkema, S. et al. "The crystal structure of urea oxalic acid (2:1)" *Acta Cryst.*, 1972, pp. 1646-1648, vol. B28.

Krantz, J. et al. "Sodium theophylline glycinate" *Journal of the American Pharmaceutical Association*, 1946, pp. 248-250.

Datta, S. et al. "Crystal structures of drugs: advances in determination, prediction and engineering" *Nature*, Jan. 2004, pp. 42-57, vol. 3.

Aakeröy, C. et al. "Charge-assisted hydrogen bonds and halogen-halogen interactions in organic salts: benzylammonium benzoates and pentaflourobenzoates" *Structural Chemistry*, 1999, pp. 229-242, vol. 10, No. 3.

Childs, S. et al. "Crystal engineering approach to forming cocrystals of amine hydrochlorides with organic acids. Molecular complexes of fluoxetine hydrochloride with benzoic, succinic, and fumaric acids" *J. Am. Chem. Soc.*, 2004, pp. 13335-13342, vol. 126.

Aakeroy, C. et al. "Modular supramolecular synthesis based on a dominance hierarchy of intermolecular interactions (Abstract)" 223rd ACS National Meeting in Orlando, FL., Apr. 7-11, 2002, published by the American Chemical Society, Washington, D.C.

Helfrich, B. et al. "Polymorphism as an indication of structural versatility (Abstract)" 223rd ACS National Meeting in Orlando, FL., Apr. 7-11, 2002, published by the American Chemical Society, Washington, D.C.

Weber, E. et al. "Synthesis of new Schiff bases: reaction of monofluorobenzaldehydes with 3-aminosulfolane hydrochloride (Abstract)" 216th ACS National Meeting in Boston, MA., Aug. 23-27, 1998, published by the American Chemical Society, Washington, D.C.

Scarbrough, F. et al. "Crystal structure of a complex between lumiflavin and 2,6-diamino-9-ethylpurine: a flavin adenine dinucleotide model exhibiting charge-transfer interactions" *Proc. Natl. Acad. Sci. USA*, Nov. 1976, pp. 3807-3811, vol. 73, No. 11.

Munn, R. et al. "A Model for resonance-assisted hydrogen bonding in crystals and its graph set analysis" *J. Phys. Chem. A*, 2001, pp. 6938-6942, vol. 105.

Lynch, D. et al. "1:1 Molecular complexes of 4-amino-N-(4,6-dimethylpyrimidin-2-yl) benzene-sulfonamide (sulfamethazine) with indole-2-carboxylic acid and 2,4-dinitrobenzoic acid" *Aust. J. Chem.*, 2000, pp. 383-387, vol. 53.

Aakeroy, C. et al. "Solid state, crystal engineering and hydrogen bonds" *Comprehensive Coordination Chemistry II* (ed. by McCleverty, J. et al.), pp. 679-688, Elsevier Ltd., Oxford, UK., 2004.

Levin, B. et al. "The not-so-trivial synthesis and characterization of heterocyclic boronic acids (Abstract)" 38th Midwest Regional Meeting of the American Chemical Society in Columbia, MO., Nov. 5-7, 2003, published by the American Chemical Society, Washington, D.C.

Smith, G. et al. "Interactions of aromatic carboxylic acids with quinolin-8-ol (oxine): Synthesis and the crystal structures of the proton-transfer compounds with the nitro-substituted benzoic acids" *Aust. J. Chem.*, 2001, pp. 171-175, vol. 54.

Stalker, R. et al. "Asymmetric synthesis of two new conformationally constrained lysine derivatives" *Tetrahedron*, 2002, pp. 4837-4849, vol. 58.

Voet, D. et al. "Barbiturates and adenine derivatives. Molecular structure of a hydrogen-bonded complex" *Journal of the American Chemical Society*, Aug. 9, 1972, pp. 5888-5891, vol. 94, No. 16.

Vishweshwar, P. et al. "Molecular complexes of homologous alkanedicarboxylic acids with isonicotinamide: X-ray crystal structures, hydrogen bond synthons, and melting point alternation" *Crystal Growth & Design*, 2003, pp. 783-790, vol. 3, No. 5.

Le Jeunne, C. et al. "Comparative efficacy and safety of calcium carbasalate plus metoclopramide versus ergotamine tartrate plus caffeine in the treatment of acute migraine attacks" *Eur. Neurol.*, 1999, pp. 37-43, vol. 41.

Aakeröy, C. et al. "Hydrogen-bonded layers of hydrogentartrate anions: two-dimensional building blocks for crystal engineering" *J. Mater. Chem.*, 1993, 1129-1135, vol. 3, No. 11.

Hu, Z. et al. "Separation of 4-aminobenzoic acid by cocrystallization: Crystal structure of the complex of 4-aminobenzoic acid with (2R,3R)-tartaric acid" *Journal of Chemical Crystallography*, Dec. 2002, pp. 525-529, vol. 32, No. 12.

Guarrera, D. et al. "Molecular self-assembly in the solid state. The combined use of solid state NMR and differential scanning calorimetry for the determination of phase constitution" *Chem. Mater.*, 1994, pp. 1293-1296, vol. 6.

Doi, M. et al. "Conformational study of a potent human renin inhibitor: x-ray crystal structure of isopropyl (2R, 3S) -4-cyclohexyl-2-hydroxy-3-{N-[(2R)-2-morpholinocarbonylmethyl-3-(1-naphthyl)propionyl] -L-histidylamino}butyrate (KRI-1314), a pentapeptide analogue with amino acid sequence corresponding to the cleavage site of angiotensinogen" *J. Chem. Soc. Perkin Trans. 1*, 1991, pp. 1153-1158.

Crihfield, A. et al. "Crystal engineering through halogen bonding. 2. Complexes of diacetylene-linked heterocycles with organic iodides" *Crystal Growth & Design*, 2003, pp. 313-320, vol. 3, No. 3.

Aakeröy, C. et al. "A versatile route to porous solids: organic-inorganic hybrid materials assembled through hydrogen bonds" *Angew. Chem. Int. Ed.*, 1999, pp. 1815-1819, vol. 38, No. 12.

Shefter, E. et al., ACS, Abstr. Papers (Summer), 1970, 35, compound name: sulfathiazole-theophylline complex.

Shefter, E. et al., ACS, Abstr. Papers (Summer), 1970, 35, compound name: sulfathiazole-sulfanilamide complex.

Wiedenfeld, H. et al. "Solubilization of aminophenazone" *Arch. Pharm.*, 1982, pp. 633-641, vol. 315.

Cacciapuoti, A. et al. "In vitro and in vivo activities of SCH 56592 (Posaconazole), a new triazole antifungal agent, against *Aspergillus* and *Candida*" *Antimicrobial Agents and Chemotherapy*, Aug. 2000, pp. 2017-2022, vol. 44, No. 8.

Callahan, J.C. et al. "Equilibrium moisture content of pharmaceutical excipients" *Drug Development and Industrial Pharmacy*, 1982, pp. 355-369, vol. 8, No. 3.

Dannaoui, E. et al. "Acquired itraconazole resistance in *Aspergillus fumigatus*" *Journal of Antimicrobial Chemotherapy*, 2001, pp. 333-340, vol. 47.

Denning, D. W. et al. "In vitro activity of Saperconazole (R66 905) compared with Amphotericin B and Itraconazole against *Aspergillus* species" *Eur. J. Clin. Microbial. Infect. Dis.*, 1990, pp. 693-697, vol. 9.

Dressman, J. B. et al. "Dissolution testing as a prognostic tool for oral drug absorption: immediate release dosage forms" *Pharmaceutical Research*, 1998, pp. 11-22, vol. 15, No. 1.

Ebert, W. R. "Soft elastic gelatin capsules: a unique dosage form" *Pharmaceutical Technology*, Oct. 1977, pp. 44-50, vol. 1, No. 5.

Gascon, M. -P. et al. "In vitro forecasting of drugs which may interfere with the biotransformation of midazolam" *Eur. J. Clin. Pharmacol.*, 1991, pp. 573-578, vol. 41.

Heeres, J. et al. "Antimycotic azoles. 7. Synthesis and antifungal properties of a series of novel triazol-3-ones" *J. Med. Chem.*, 1984, pp. 894-900, vol. 27.

Honig, P. K. et al. "Itraconazole affects single-dose Terfenadine pharmacokinetics and cardiac repolarization pharmacodynamics" *J. Clin. Pharmacol.*, 1993, pp. 1201-1206, vol. 33.

Imai, T. et al. "Successful treatment of cerebral Aspergillosis with a high oral dose of Itraconazole after excisional surgery" *Internal Medicine*, Oct. 1999, pp. 829-832, vol. 38, No. 10.

Kovacs, J. et al. "New type of bridged monoamino-β-cyclodextrins" *Journal of Inclusion Phenomena and Molecular Recognition in Chemistry*, 1996, pp. 53-56, vol. 25.

Lavrijsen, A. P. M. et al. "Hepatic injury associated with itraconazole" *The Lancet*, Jul. 25, 1992, pp. 251-252, vol. 340.

Neuvonen, P. J. et al. "Itraconazole drastically increases plasma concentrations of lovastatin and lovastatin acid" *Clinical Pharmacology & Therapeutics*, 1996, pp. 54-61, vol. 60, No. 1.

Nomeir, A. A. et al. "Pharmacokinetics of SCH 56592, a new azole broad-spectrum antifungal agent, in mice, rats, rabbits, dogs, and cynomolgus monkeys" *Antimicrobial Agents and Chemotherapy*, Mar. 2000, pp. 727-731, vol. 44, No. 3.

Odds, F. C. "Antifungal activity of saperconazole (R 66 905) in vitro" *Journal of Antimicrobial Chemotherapy*, 1989, pp. 533-537, vol. 24.

Remenar, J. F. et al. "Crystal engineering of novel cocrystals of a triazole drug with 1,4-dicarboxylic acids" *J. Am. Chem. Soc.*, 2003, pp. 8456-8457, vol. 125.

Saksena, A. K. et al. "Advances in the chemistry of novel broad-spectrum orally active azole antifungals: recent studies leading to the discovery of SCH 56592" in *Advances in the Chemistry of Novel Broad-Spectrum Orally Active Azole Antifungals* (Royal Soc. Chem., Cambridge), 1997, pp. 180-199.

Saksena, A. K. et al. "Concise asymmetric routes to 2,2,4-trisubstituted tetrahydrofurans via chiral titanium imide enolates: key intermediates towards synthesis of highly active azole antifungals SCH 51048 and SCH 56592" *Tetrahedron Letters*, 1996, pp. 5657-5660, Vol. 37, No. 32.

Hepperle, M. et al. "Mono N-arylation of piperazine(III): metal-catalyzed N-arylation and its application to the novel preparations of the antifungal posaconazole and its advanced intermediate" *Tetrahedron Letters*, 2002, pp. 3359-3363, vol. 43.

Cutsem, J. V. et al. "Oral and parenteral therapy with saperconazole (R 66905) of invasive aspergillosis in normal and immunocompromised animals" *Antimicrobial Agents and Chemotheraphy*, Dec. 1989, pp. 2063-2068, vol. 33, No. 12.

Villa, L. A. et al. "Central nervous system paracoccidioidomycosis. Report of a case successfully treated with itraconazol" *Rev. Inst. Med. Trop. S. Paulo*, Jul.-Aug. 2000, pp. 231-234, vol. 42, No. 4.

West, A. R., "Solid Solutions" In: *Solid State Chemistry and its Applications*, 1988, p. 358, p. 365, Wiley, NY.

Aronhime, J. et al. "Crystalline forms of pharmaceuticals and characterization thereof", Oral Presentation, Mar. 8, 2005, USPTO, Alexandria, VA.

Desiraju, G. R. "Chemistry beyond the molecule" *Nature*, Jul. 26, 2001, pp. 397-400, vol. 412.

Gavezzotti, A. "Are crystal structures predictable?" *Acc. Chem. Res.*, 1994, pp. 309-314, vol. 27.

Physician's Desk Reference, 56th Ed., pp. 1800-1804, 2002.

Kim, H. et al. "High-performance liquid chromatographic analysis of the anti-fungal agent SCH 56592 in dog serum" *Journal of Chromatography B*, 2000, pp. 93-98, vol. 738.

Vippagunta, S. R. et al. "Crystalline solids" *Advanced Drug Delivery Reviews*, 2001, pp. 3-26, vol. 48.

McCrone, W. C. "Polymorphism", In: *The Physics and Chemistry of the Organic Solid State*, vol. II, Fox, D. et al. (eds.), 1965, pp. 725-767, Interscience, New York.

Leger, J.M. et al. "Crystal Structure of the 1:1 Sulfacetamide-Caffeine Complex" *Acta Cryst.*, 1977, pp. 1455-1459, vol. B33.

Simonov, Y. et al. "Structure of the caffeine-copper(II) acetate additional compound", *Izvestiya Akademii Nauk Moldavskoi SSR, Seriya Fiziko-Tekhnicheskikh i Matematicheskikh Nauk*, 1972, vol. 3, pp. 83-84, abstract only.

Weissbuch, I. et al. "Understanding and control of nucleation, growth, habit, dissolution and structure of two- and three-dimensional crystals using 'tailor-made' auxiliaries" *Acta Cryst.*, 1995, B51:115-148.

Faught, E. et al. "Topiramate Dose-Ranging Trial in Refractory Partial Epilepsy", *Amer. Epilepsy Soc. Proc.*, (1995), p. 33, vol. 36, Supp. 4.

Privitera, M. et al. "Dose-Ranging Trial with Higher Doses of Topiramate in Patients with Resistant Partial Seizures", *Amer. Epilepsy Soc. Proc.*, 1995, p. 33, vol. 36, Supp. 4.

Sachdeo, S. K. et al. "Topiramate: Double-Blind Trial as Monotherapy", *Amer. Epilepsy Soc. Proc.*, 1995, p. 33, vol. 36, Supp. 4.

Press Release. "Clinical Development of Topiramate for Obesity Extended to Simplify Dosing, Improve Tolerability". http://www.orthomcneil.com/news/article020402.html (Feb. 4, 2002), N.J.

Rosenfeld, W. E. "Topiramate: A Review of Preclinical, Pharmacokinetic, and Clinical Data", *Clinical Therapeutics*, 1997, pp. 1294-1308, vol. 19, No. 6.

Physician's Desk Reference, 56th Edition, 2002, pp. 2590-2595.
Database WPI, Section Ch, Week 197936, Derwent Publishing Ltd., London, Great Britain, AN 1979-65538B, XP002282989 and JP 54 095589A (Sumitomo) 1979 Abstract.
Fung et al., "Solvent Effects on Comparative Dissolution of Pharmaceutical Solvates," *Chem. Farm. Bull.*, 22(2), pp. 454-458 (1974).
Rubino et al., "Influence of Solvent Composition on the Solubilities and Solid-State Properties of the Sodium Salts of Some Drugs", *Int. J. of Pharma*, 65, pp. 141-145 (1990).
Fitzgerald, G. A. "The Coxibs, Selective Inhibitors of Cyclooxygenase-2", *New England Journal of Medicine*, vol. 345, No. 6, Aug. 9, 2001.
Wunderlich, H. F. et al. "The Derivatives of carbamazepine with ammonium halogenides and formahide" *Pharmazie*, 1991, pp. 507-509, vol. 46, No. 7, Not in English.
El-Nahhas, S. A. "Physico-chemical characteristics of carbamazepine-β-cyclodextrin inclusion compounds and carbamazepine-PEG solid dispersions" *Pharmazie*, 1996, pp. 960-963, vol. 51, No. 12.
Reynolds, J. E. F. (ed). Martindale, The Extra Pharmacopoeia, 1993, The Pharmaceutical Press, London, England, 13th edition, p. 1610.
Pedireddi, V. R. et al. "Layered Structures Formed by Dinitrobenzoic Acids" *Tetrahedron Letters*, 1998, pp. 9831-9834, vol. 39.
Zaman, M. B. et al. "Crystal Engineering Using Anilic Acids and Dipyridyl Compounds through a New Supramolecular Synthon" *J. Org. Chem.*, 2001, pp. 5987-5995, vol. 66.
Japanese Notice of Reasons for Rejection dated Oct. 8, 2009, Japanese Application No. 2003-572946.
Ball, P. "Scandal of crystal design . . ." *Nature*, Jun. 20, 1996, pp. 648-650, vol. 381.
Bastin, R. J. et al. "Salt Selection and Optimization Procedures for Pharmaceutical New Chemical Entities" *Organic Process Research & Development*, 2000, pp. 427-435, vol. 4, No. 5.
Bernstein, J. et al. "Concomitant Polymorphs" *Angew. Chem. Int. Ed.*, 1999, pp. 3440-3461, vol. 38.
Boucher, E. et al. "Use of Hydrogen Bonds to Control Molecular Aggregation. Behavior of Dipyridones and Pyridone-Pyrimidones Designed to Form Cyclic Triplexes" *J. Org. Chem.*, 1995, pp. 1408-1412, vol. 60.
Brittain, H. G., *Polymorphism in Pharmaceutical Solids*, Marcel Dekker, Inc., 1999, pp. 183, 202-208 and 219.
Chang, Y. et al. "An Approach to the Design of Molecular Solids. Strategies for Controlling the Assembly of Molecules into Two-Dimensional Layered Structures" *J. Am. Chem. Soc.*, 1993, pp. 5991-6000, vol. 115.
Cowan, J. A. et al. "Neutron diffraction studies of the 1:1 and 2:1 cocrystals of benzene-1,2,4,5-tetracarboxylic acid and 4,4'-bipyridine" Acta Cryst., 2006, pp. o157-o161, vol. C62.
Davidovich, M. et al. "Detection of Polymorphism by Powder X-Ray Diffraction: Interference by Preferred Orientation" *American Pharmaceutical Review*, 2004, pp. 10, 12, 14, 16, and 100, vol. 7, Issue 1.
Davies, N. M. et al. "Clinical Pharmacokinetics and Pharmacodynamics of Celecoxib. A Selective Cyclo-Oxygenase-2 Inhibitor" *Clin. Pharmacokinet.*, Mar. 2000, pp. 225-242, vol. 38, No. 3.
Dean, J A., *Analytical Chemistry Handbook*, McGraw-Hill, Inc., 1995, pp. 10.24-10.26.
Definition of solvate, The Free Dictionary, http://www.thefreedictionary.com/solvate, accessed online on Jul. 21, 2009, pp. 1-3.

Desiraju, G.R. "Solid-State Chemistry: Crystal Gazing: Structure Prediction and Polymorphism" *Science*, Oct. 17, 1997, pp. 404-405, vol. 278, No. 5337.
Doelker, E. "Physicochemical behavior of active substances. Consequences for the feasibility and stability of pharmaceutical forms" *STP Pharma Pratiques*, 1999, pp. 399-409, vol. 9, No. 5.
Doelker, E. "Cystalline modifications and polymorphism changes during drug manufacturing" *Annales Pharmaceutiques Francaises*, 2002, pp. 161-176, vol. 60, No. 3.
Dunitz, J. D. "Are crystal structures predictable?" *Chem Commun.*, 2003, pp. 545-548.
Feynman, R. P. "There's Plenty of Room at the Bottom" *Engineering and Science*, Feb. 1960, pp. 22-36.
Jain, N. K. et al. "Polymorphism in Pharmacy" *Indian Drugs*, 1986, pp. 315-329, vol. 23, No. 6.
Kirchner, M. T. et al., Co-crystals with Acetylene: Small is not Simple! *Chem. Eur. J.*, 2010, pp. 2131-2146, vol. 16.
Moulton, B. et al. "From Molecules to Crystal Engineering: Supramolecular Isomerism and Polymorphism in Network Solids" *Chem. Rev.*, 2001, pp. 1629-1658, vol. 101.
Muzaffar, N. A. et al. "Polymorphism and Drug Availability" *Journal of Pharmacy*, 1979, pp. 59-66, vol. 1, No. 1.
Osorio-Lozada, A. et al. "Synthesis and determination of the absolute stereochemistry of the enantiomers of adrafinil and modafinil" *Tetrahedron: Asymmetry*, 2004, pp. 3811-3815, vol. 15.
Otsuka, M. et al. "Effect of Polymorphic Forms of Bulk Powders on Pharmaceutical Properties of Carbamazepine Granules" *Chem. Pharm. Bull.*, 1999, pp. 852-856, vol. 47, No. 6.
Shattock, T. R, et al. "Hierarchy of Supramolecular Synthons: Persistent Carboxylic Acid•••Pyridine Hydrogen Bonds in Cocrystals That also Contain a Hydroxyl Moiety" *Cryst. Growth Des.*, 2008, pp. 4533-4545, vol. 8, No. 12.
Thayer, A. M. "Form and Function: The choice of pharmaceutical crystalline form can be used to optimize drug properties, and cocrystals are emergiing as new alternatives" *Chemical & Engineering News*, Jun. 18, 2007, pp. 17-30, vol. 85, No. 25.
U.S. Pharmacopia #23, 1995, p. 1843.
Villa, L. A. et al. "Central Nervous System Paracoccidioidomycosis. Report of a Case Successfully Treated with Itraconazol" *Rev. Inst. Med. Trop. S. Paulo*, Jul.-Aug. 2000, pp. 231-234, vol. 42, No. 4.
Zaworotko, M. J. "Crystal Engineering of Diamondoid Networks" *Chemical Society Reviews*, 1994, pp. 283-288, vol. 23.
Klein, C. L. et al. "Molecular Structure of Two Conformationally Restrained Fentanyl Analogues: cis- and trans-Isomers of N-{3-Methyl-1-[2-(1,2,3,4-tetrahydro)naphthyl]-4-piperidinyl}-N-phenylpropanamide" *Journal of Pharmaceutical Sciences*, Nov. 1985, pp. 1147-1151, vol. 74, No. 11.
Felthouse, T. R. et al. "Maleic Anhydride, Maleic Acid and Fumaric Acid", Apr. 26, 2001, submitted for *Kirk Online*, http://www.huntsman.com/performance_products/media/komaleic.pdf.
Salem, M.S. et al. "Preparation, characterisation and transformation of terfenadine polymorphic forms" *International Journal of Pharmacuetics*, 1996, pp. 257-259, vol. 141.
Office Action dated Feb. 2, 2010 in U.S. Appl. No. 10/546,963, filed Aug. 26, 2005.
Pending claims in U.S. Appl. No. 10/546,963, filed Aug. 26, 2005.
Heinrich Stahl P Ed-Wermuth C G: "The Practice of Medicinal Chemistry; 35 Preparation of water-soluble compounds through salt formation" Jan. 1, 2003, The Practice of Medicinal Chemistry, Elsevier, NL, pp. 601-615, XP002566271ISBN: 978-0-12-744481-9.

* cited by examiner

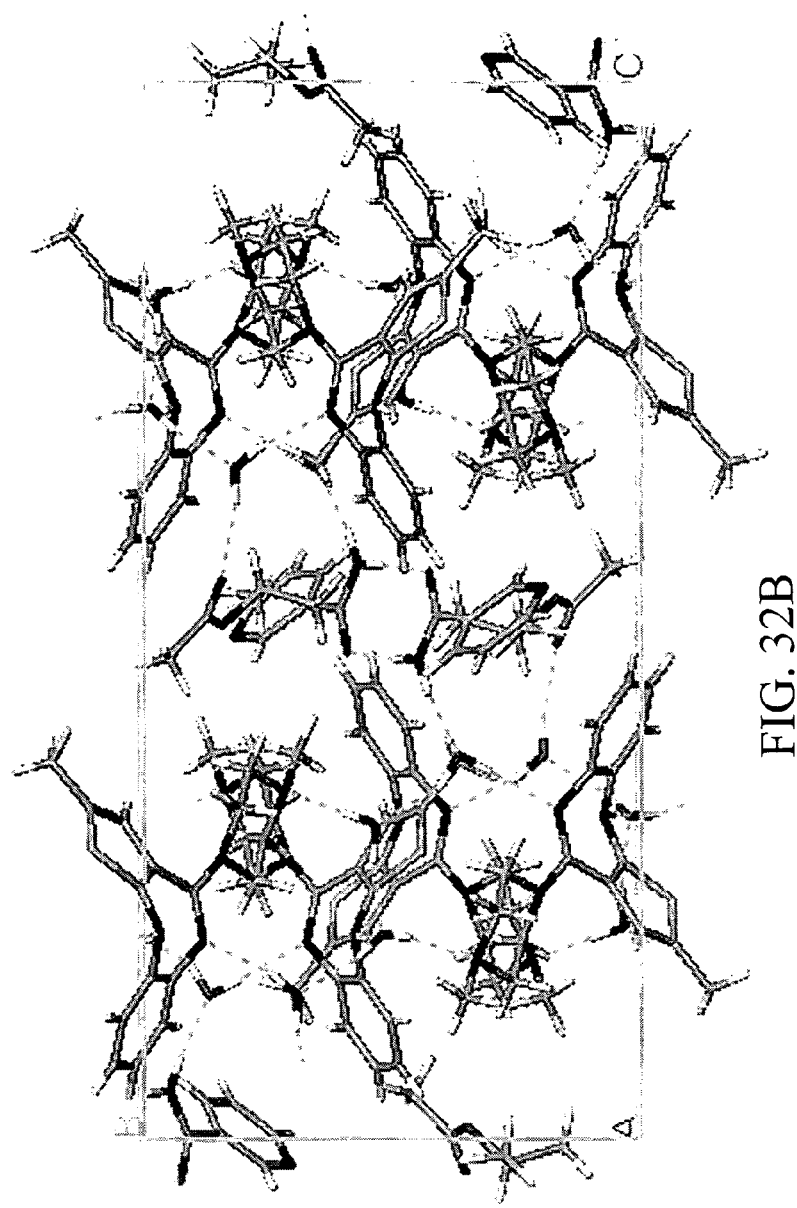
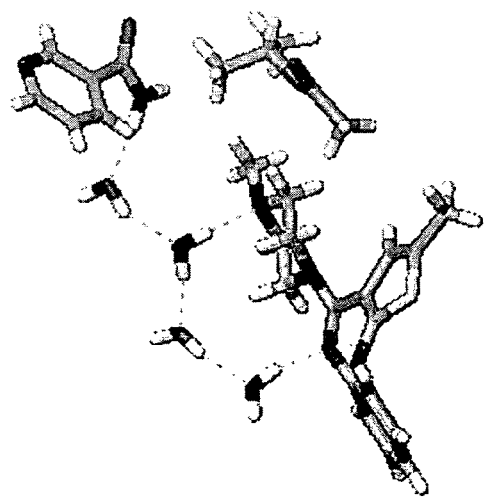
FIG. 32A
FIG. 32B

FIND PEAKS:
Spectrum: MO-157.72C_Modafinil-Malonic_
Region: 3432  200
Absolute threshold: 580.428
Sensitivity: 66
Peak list:
  Position: 1004   Intensity: 48530.113
  Position: 222    Intensity: 41031.178
  Position: 833    Intensity: 30431.455
  Position: 265    Intensity: 27032.348
  Position: 1032   Intensity: 25424.109
  Position: 1183   Intensity: 23455.441
  Position: 814    Intensity: 21886.129
  Position: 1601   Intensity: 20374.211
  Position: 490    Intensity: 19817.480
  Position: 718    Intensity: 18779.322
  Position: 767    Intensity: 16891.541
  Position: 361    Intensity: 15080.872
  Position: 917    Intensity: 12651.283
  Position: 1104   Intensity: 11708.740
  Position: 889    Intensity: 11172.833
  Position: 412    Intensity: 11137.415
  Position: 1225   Intensity: 9027.109
  Position: 1251   Intensity: 8844.833
  Position: 1368   Intensity: 8252.702
  Position: 1442   Intensity: 6738.694
  Position: 1731   Intensity: 5730.559
  Position: 1268   Intensity: 5700.056
  Position: 3065   Intensity: 1935.514
  Position: 2049   Intensity: 1912.835

FIG. 42B

1. One-dimentional (linear) hydrogen-bonded chains:

2. Isolated rings:

3. Extended Networks:

4. Isolated triads:

PHARMACEUTICAL CO-CRYSTAL COMPOSITIONS

INCORPORATION BY REFERENCE

This application claims the benefit of U.S. Provisional Patent Application No. 60/451,213 filed on Feb. 28, 2003; U.S. Provisional Patent Application No. 60/463,962, filed on Apr. 18, 2003; and U.S. Provisional Application No. 60/487,064, filed on Jul. 11, 2003 each of which incorporated herein by reference in its entirety. This application is also a continuation-in-part of PCT/US03/27772, filed on Sep. 4, 2003 which is a continuation-in-part of U.S. patent application Ser. No. 10/378,956, filed Mar. 3, 2003, which claims the benefit of U.S. Provisional Application No. 60/360,768, filed Mar. 1, 2002; said PCT/US03/27772 also claims the benefit of U.S. Provisional Patent Application No. 60/451,213 filed on Feb. 28, 2003; U.S. Provisional Patent Application No. 60/463,962, filed on Apr. 18, 2003; and U.S. Provisional Application No. 60/487,064, filed on Jul. 11, 2003. This application is also a continuation-in-part of U.S. patent application Ser. No. 10/601,092, filed Jun. 20, 2003. Each of these applications is hereby incorporated by reference in their entireties, including all figures, tables and formulae.

FIELD OF THE INVENTION

The present invention relates to co-crystal API-containing compositions, pharmaceutical compositions comprising such APIs, and methods for preparing the same.

BACKGROUND OF THE INVENTION

Active pharmaceutical ingredients (API or APIs (plural)) in pharmaceutical compositions can be prepared in a variety of different forms. Such APIs can be prepared so as to have a variety of different chemical forms including chemical derivatives or salts. Such APIs can also be prepared to have different physical forms. For example, the APIs may be amorphous, may have different crystalline polymorphs, or may exist in different solvation or hydration states. By varying the form of an API, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapour pressure, density, colour, and compressibility. Accordingly, variation of the crystalline state of an API is one of many ways in which to modulate the physical properties thereof.

It would be advantageous to have new forms of these APIs that have improved properties, in particular, as oral formulations. Specifically, it is desirable to identify improved forms of APIs that exhibit significantly improved properties including increased aqueous solubility and stability. Further, it is desirable to improve the processability, or preparation of pharmaceutical formulations. For example, needle-like crystal forms or habits of APIs can cause aggregation, even in compositions where the API is mixed with other substances, such that a non-uniform mixture is obtained. It is also desirable to increase the dissolution rate of API-containing pharmaceutical compositions in water, increase the bioavailability of orally-administered compositions, and provide a more rapid onset to therapeutic effect. It is also desirable to have a form of the API which, when administered to a subject, reaches a peak plasma level faster, has a longer lasting therapeutic plasma concentration, and higher overall exposure when compared to equivalent amounts of the API in its presently-known form.

SUMMARY OF THE INVENTION

It has now been found that new co-crystalline forms of APIs can be obtained which improve the properties of APIs as compared to such APIs in a non-co-crystalline state (free acid, free base, zwitter ions, salts, etc.).

Accordingly, in a first aspect, the present invention provides a co-crystal pharmaceutical composition comprising an API compound and a co-crystal former, such that the API and co-crystal former are capable of co-crystallizing from a solid or solution phase under crystallization conditions.

Another aspect of the present invention provides a process for the production of a pharmaceutical composition, which process comprises:

(1) providing an API which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, s-heterocyclic ring, thiophene, n-heterocyclic ring, pyrrole, o-heterocyclic ring, furan, epoxide, peroxide, hydroxamic acid, imidazole, and pyridine;

(2) providing a co-crystal former which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, s-heterocyclic ring, thiophene, n-heterocyclic ring, pyrrole, o-heterocyclic ring, furan, epoxide, peroxide, hydroxamic acid, imidazole, and pyridine;

(3) grinding, heating or contacting in solution the API with the co-crystal former under crystallization conditions;

(4) isolating co-crystals formed thereby; and (5) incorporating the co-crystals into a pharmaceutical composition.

A further aspect of the present invention provides a process for the production of a pharmaceutical composition, which comprises:

(1) grinding, heating or contacting in solution an API compound with a co-crystal former, under crystallization conditions, so as to form a solid phase;

(2) isolating co-crystals comprising the API and the co-crystal former; and (3) incorporating the co-crystals into a pharmaceutical composition.

In a further aspect, the present invention provides a process for the production of a pharmaceutical composition, which comprises:

(1) providing (i) an API or a plurality of different APIs, and (ii) a co-crystal former or a plurality of different co-crystal formers, wherein at least one of the APIs and the co-crystal formers is provided as a plurality thereof;

(2) isolating co-crystals comprising the API and the co-crystal former; and (3) incorporating the co-crystals into a pharmaceutical composition.

Solubility Modulation

In a further aspect, the present invention provides a process for modulating the solubility of an API, which process comprises:

(1) grinding, heating or contacting in solution the API with a co-crystal former under crystallization conditions, so as to form a co-crystal of the API and the co-crystal former; and (2) isolating co-crystals comprising the API and the co-crystal former.

Dissolution Modulation

In a further aspect, the present invention provides a process for modulating the dissolution of an API, whereby the aqueous dissolution rate or the dissolution rate in simulated gastric fluid or in simulated intestinal fluid, or in a solvent or plurality of solvents is increased or decreased, which process comprises:

(1) grinding, heating or contacting in solution the API with a co-crystal former under crystallization conditions, so as to form a co-crystal of the API and the co-crystal former; and (2) isolating co-crystals comprising the API and the co-crystal former.

In one embodiment, the dissolution of the API is increased.

Bioavailability Modulation

In a further aspect, the present invention provides a process for modulating the bioavailability of an API, whereby the AUC is increased, the time to $T_{max}$ is reduced, the length of time the concentration of the API is above ½ $T_{max}$ is increased, or $C_{max}$ is increased, which process comprises:

(1) grinding, heating or contacting in solution the API with a co-crystal former under crystallization conditions, so as to form a co-crystal of the API and the co-crystal former; and (2) isolating co-crystals comprising the API and the co-crystal former.

Dose Response Modulation

In a further aspect the present invention provides a process for improving the linearity of a dose response of an API, which process comprises:

(1) grinding, heating, or contacting in solution an API with a co-crystal former under crystallization conditions, so as to form a co-crystal of the API and the co-crystal former; and (2) isolating co-crystals comprising the API and the co-crystal former.

Increased Stability

In a still further aspect the present invention provides a process for improving the stability of a pharmaceutical salt, which process comprises:

(1) grinding, heating or contacting in solution the pharmaceutical salt with a co-crystal former under crystallization conditions, so as to form a co-crystal of the API and the co-crystal former; and (2) isolating co-crystals comprising the API and the co-crystal former.

Difficult to Salt or Unsaltable Compounds

In a still further aspect the present invention provides a process for making co-crystals of difficult to salt or unsaltable APIs, which process comprises:

(1) grinding, heating or contacting in solution the API with a co-crystal former under crystallization conditions, so as to form a co-crystal of the API and the co-crystal former; and (2) isolating co-crystals comprising the API and the co-crystal former.

Decreasing Hygroscopicity

In a still further aspect the present invention provides a method for decreasing the hygroscopicity of an API, which method comprises:

(1) grinding, heating or contacting in solution the API with a co-crystal former under crystallization conditions, so as to form a co-crystal of the API and the co-crystal former; and (2) isolating co-crystals comprising the API and the co-crystal former.

Crystallizing Amorphous Compounds

In a still further embodiment aspect the present invention provides a process for crystallizing an amorphous compound, which process comprises:

(1) grinding, heating or contacting in solution the API with a co-crystal former under crystallization conditions, so as to form a co-crystal of the API and the co-crystal former; and (2) isolating co-crystals comprising the API and the co-crystal former.

Decreasing Form Diversity

In a still further embodiment aspect the present invention provides a process for reducing the form diversity of an API, which process comprises:

(1) grinding, heating or contacting in solution the API with a co-crystal former under crystallization conditions, so as to form a co-crystal of the API and the co-crystal former; and (2) isolating co-crystals comprising the API and the co-crystal former.

Morphology Modulation

In a still further embodiment aspect the present invention provides a process for modifying the morphology of an API, which process comprises:

(1) grinding, heating or contacting in solution the API with a co-crystal former under crystallization conditions, so as to form a co-crystal of the API and the co-crystal former; and (2) isolating co-crystals comprising the API and the co-crystal former.

In a further aspect, the present invention provides a co-crystal composition comprising a co-crystal, wherein said co-crystal comprises an API compound and a co-crystal former. In further embodiments the co-crystal has an improved property as compared to the free form (including a free acid, free base, zwitter ion, hydrate, solvate, etc.) or a salt (which includes salt hydrates and solvates). In further embodiments, the improved property is selected from the group consisting of: increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, or other property described herein.

BRIEF DESCRIPTION OF THE DRAWINGS

FIG. 32A-D Packing diagrams and crystal structure of olanzapine and nicotinamide (Form III). FIG. 32A depicts the molecular structure of the olanzapine-nicotinamide-$H_2O$-IP-OAc crystal. In FIG. 32C, the olanzapine molecules occupy the spaces shown and are hydrogen bonded to the water molecules. The arrangement of the olanzapine molecules is similar to that observed from the methanol solvate and the published structures for the hydrates; the water molecules bridge the olanzapine moieties resulting in hydrogen-bonded zigzag sheets (see FIG. 32D).

FIGS. 46C and 46D show the supramolecular entity containing the synthon and corresponding co-crystal of aspirin and 4,4'-bipyridine, respectively.

FIGS. 7C and 7D show the supramolecular entity containing the synthon and corresponding co-crystal of ibuprofen and 4,4'-bipyridine, respectively.

FIGS. 5C and 5D show the supramolecular synthon and corresponding co-crystal of flurbiprofen and 4,4'-bipyridine, respectively.

DETAILED DESCRIPTION OF THE INVENTION

Figure 63:
FIG. 63 Hydrogen-bonding motifs observed in co-crystals.
Figure 63:
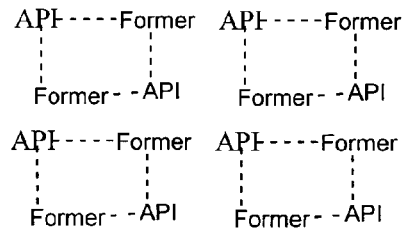
Figure 63:
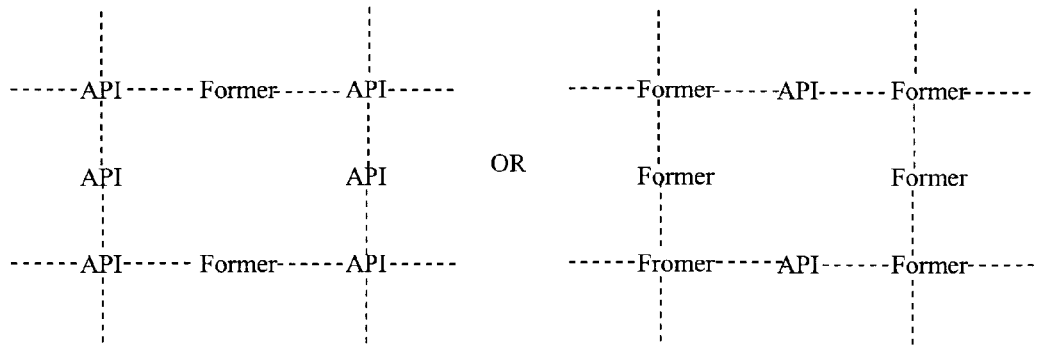
Figure 63:
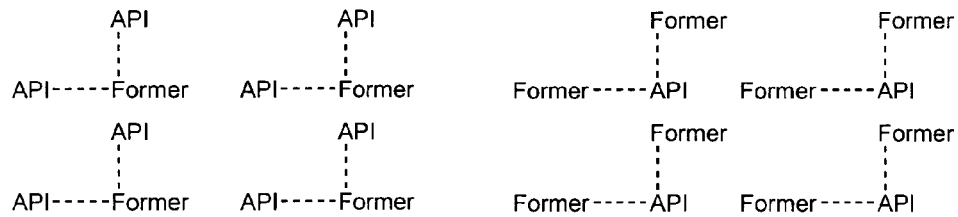

The term "co-crystal" as used herein means a crystalline material comprised of two or more unique solids at room temperature, each containing distinctive physical characteristics, such as structure, melting point and heats of fusion, with the exception that, if specifically stated, the API may be a liquid at room temperature. The co-crystals of the present invention comprise a co-crystal former H-bonded to an API. The co-crystal former may be H-bonded directly to the API or may be H-bonded to an additional molecule which is bound to the API. The additional molecule may be H-bonded to the API or bound ionically or covalently to the API. The additional molecule could also be a different API. Solvates of API compounds that do not further comprise a co-crystal former are not co-crystals according to the present invention. The co-crystals may however, include one or more solvate molecules in the crystalline lattice. That is, solvates of co-crystals, or a co-crystal further comprising a solvent or compound that is a liquid at room temperature, is included in the present invention, but crystalline material comprised of only one solid and one or more liquids (at room temperature) are not included in the present invention, with the previously noted exception of specifically stated liquid APIs. The co-crystals may also be a co-crystal between a co-crystal former and a salt of an API, but the API and the co-crystal former of the present invention are constructed or bonded together through hydrogen bonds. Other modes of molecular recognition may also be present including, pi-stacking, guest-host complexation and van der Waals interactions. Of the interactions listed above, hydrogen-bonding is the dominant interaction in the formation of the co-crystal, (and a required interaction according to the present invention) whereby a non-covalent bond is formed between a hydrogen bond donor of one of the moieties and a hydrogen bond acceptor of the other. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads (FIG. 63). An alternative embodiment provides for a co-crystal wherein the co-crystal former is a second API. In another embodiment, the co-crystal former is not an API. In another embodiment the co-crystal comprises two co-crystal formers. For purposes of the present invention, the chemical and physical properties of an API in the form of a co-crystal may be compared to a reference compound that is the same API in a different form. The reference compound may be specified as a free form, or more specifically, a free acid, free base, or zwitter ion; a salt, or more specifically for example, an inorganic base addition salt such as sodium, potassium, lithium, calcium, magnesium, ammonium, aluminum salts or organic base addition salts, or an inorganic acid addition salts such as HBr, HCl, sulfuric, nitric, or phosphoric acid addition salts or an organic acid addition salt such as acetic, proprionic, pyruvic, malanic, succinic, malic, maleic, fumaric, tartaric, citric, benzoic, methanesulfonic, ethanesulforic, stearic or lactic acid addition salt; an anhydrate or hydrate of a free form or salt, or more specifically, for example, a hemihydrate, monohydrate, dihydrate, trihydrate, quadrahydrate, pentahydrate; or a solvate of a free form or salt. For example, the reference compound for an API in salt form co-crystallized with a co-crystal former can be the API salt form. Similarly, the reference compound for a free acid API co-crystallized with a co-crystal former can be the free acid API. The reference compound may also be specified as crystalline or amorphous.

According to the present invention, the co-crystals can include an acid addition salt or base addition salt of an API. Acid addition salts include, but are not limited to, inorganic acids such as hydrochloric acid, hydrobromic acid, sulfuric acid, nitric acid, and phosphoric acid, and organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutaric acid, hydroxynaphthoic acid, salicylic acid, stearic acid, and muconic acid. Base addition salts include, but are not limited to, inorganic bases such as sodium, potassium, lithium, ammonium, calcium and magnesium salts, and organic bases such as primary, secondary and tertiary amines (e.g. isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, and N-ethylpiperidine).

The ratio of API to co-crystal former may be stoichiometric or non-stoichiometric according to the present invention. For example, 1:1, 1:1.5 and 1:2 ratios of API:co-crystal former are acceptable.

It has surprisingly been found that when an API and a selected co-crystal former are allowed to form co-crystals, the resulting co-crystals give rise to improved properties of the API, as compared to the API in a free form (including free acids, free bases, and zwitter ions, hydrates, solvates, etc.), or an acid or base salt thereof particularly with respect to: solubility, dissolution, bioavailability, stability, Cmax, Tmax, processability, longer lasting therapeutic plasma concentration, hygroscopicity, crystallization of amorphous compounds, decrease in form diversity (including polymorphism and crystal habit), change in morphology or crystal habit, etc. For example, a co-crystal form of an API is particularly advantageous where the original API is insoluble or sparingly soluble in water. Additionally, the co-crystal properties conferred upon the API are also useful because the bioavailability of the API can be improved and the plasma concentration and/or serum concentration of the API can be improved. This is particularly advantageous for orally-administrable formulations. Moreover, the dose response of the API can be improved, for example by increasing the maximum attainable response and/or increasing the potency of the API by increasing the biological activity per dosing equivalent.

Accordingly, in a first aspect, the present invention provides a pharmaceutical composition comprising a co-crystal of an API and a co-crystal former, such that the API and co-crystal former are capable of co-crystallizing from a solution phase under crystallization conditions or from the solid-state, for example, through grinding or heating. In another aspect, the API has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, s-heterocyclic ring, thiophene, n-heterocyclic ring, pyrrole, o-heterocyclic ring, furan, epoxide, peroxide, hydroxamic acid, imidazole, and pyridine and a co-crystal former which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, s-heterocyclic ring, thiophene, n-heterocyclic ring, pyrrole, o-heterocyclic ring, furan, epoxide, peroxide, hydroxamic acid, imidazole, and pyridine, or a functional group in a Table herein, such that the API and co-crystal former are capable of co-crystallizing from a solution phase under crystallization conditions.

The co-crystals of the present invention are formed where the API and co-crystal former are bonded together through hydrogen bonds. Other non-covalent interactions, including pi-stacking and van der Waals interactions, may also be present.

In one embodiment, the co-crystal former is selected from the co-crystal formers of Table I and Table II. In other embodiments, the co-crystal former of Table I is specified as a Class 1, Class 2, or Class 3 co-crystal former (see column labeled "class" Table I). In another embodiment, the difference in $pK_a$ value of the co-crystal former and the API is less than 2. In other embodiments, the difference in $pK_a$ values of the co-crystal former and API is less than 3, less than 4, less than 5, between 2 and 3, between 3 and –4, or between 4 and 5. Table I lists multiple $pK_a$ values for co-crystal formers having multiple functionalities. It is readily apparent to one skilled in the art the particular functional group corresponding to a particular $pK_a$ value.

In another embodiment the particular functional group of a co-crystal former interacting with the API is specified (see for example Table I, columns labeled "Functionality" and "Molecular Structure" and the column of Table II labeled "Co-Crystal Former Functional Group"). In a further embodiment the functional group of the API interacting with the co-crystal former functional group is specified (see, for example, Tables II and III).

In another embodiment, the co-crystal comprises more than one co-crystal former. For example, two, three, four, five, or more co-crystal formers can be incorporated in a co-crystal with an API. Co-crystals which comprise two or more co-crystal formers and an API are bound together via hydrogen bonds. In one embodiment, incorporated co-crystal formers are hydrogen bonded to the API molecules. In another embodiment, co-crystal formers are hydrogen bonded to either the API molecules or the incorporated co-crystal formers.

In a further embodiment, several co-crystal formers can be contained in a single compartment, or kit, for ease in screening an API for potential co-crystal species. The co-crystal kit can comprise 5, 10, 15, 20, 25, 30, 40, 50, 60, 70, 80, 90, 100, or more of the co-crystal formers in Tables I and II. The co-crystal formers are in solid form and in an array of individual reaction vials such that individual co-crystal formers can be tested with one or more APIs by one or more crystallization methods or multiple co-crystal formers can be easily tested against one or more compounds by one or more crystallization methods. The crystallization methods include, but are not limited to, melt recrystallization, grinding, milling, standing, co-crystal formation from solution by evaporation, thermally driven crystallization from solution, co-crystal formation from solution by addition of anti-solvent, co-crystal formation from solution by vapor-diffusion, co-crystal formation from solution by drown-out, co-crystal formation from solution by any combination of the above mentioned techniques, co-crystal formation by co-sublimation, co-crystal formation by sublimation using a Knudsen cell apparatus, co-crystal formation by standing the desired components of the co-crystal in the presence of solvent vapor, co-crystal formation by slurry conversion of the desired components of the co-crystal in a solvent or mixtures of solvents, or co-crystal formation by any combination of the above techniques in the presence of additives, nucleates, crystallization enhancers, precipitants, chemical stabilizers, or anti-oxidants. The co-crystallization kits can be used alone or as part of larger crystallization experiments. For example, kits can be constructed as single co-crystal former single well kits, single co-crystal former multi-well kits, multi-co-crystal former single well kits, or multi-co-crystal former multi-well kits.

In a further embodiment, the API is selected from an API of Table IV or elsewhere herein. For pharmaceuticals listed in Table IV, co-crystals can comprise such APIs in free form (i.e. free acid, free base, zwitter ion), salts, solvates, hydrates, or the like. For APIs in Table IV listed as salts, solvates, hydrates, and the like, the API can either be of the form listed in Table IV or its corresponding free form, or of another form that is not listed. Table IV includes the CAS number, chemical name, or a PCT or patent reference (each incorporated herein in their entireties). In further embodiments, the functional group of the particular API interacting with the co-crystal former is specified. A specific functional group of a co-crystal former, a specific co-crystal former, or a specified functional group or a specific co-crystal former interacting with the particular API may also be specified. It is noted that for Table II, the co-crystal former, and optionally the specific functionality, and each of the listed corresponding interacting groups are included as individual species of the present invention. Thus, each specific combination of a co-crystal former and one of the interacting groups in the same row may be specified as a species of the present invention. The same is true for other combinations as discussed in the Tables and elsewhere herein.

In each process according to the invention, there is a need to contact the API with the co-crystal former. This may involve grinding the two solids together or melting one or both components and allowing them to recrystallize. This may also involve either solubilizing the API and adding the co-crystal former, or solubilizing the co-crystal former and adding the API. Crystallization conditions are applied to the API and co-crystal former. This may entail altering a property of the solution, such as pH or temperature and may require concentration of the solute, usually by removal of the solvent, typically by drying the solution. Solvent removal results in the concentration of both API and co-crystal former increasing over time so as to facilitate crystallization. Once the solid phase comprising any crystals is formed, this may be tested as described herein.

The co-crystals obtained as a result of such process steps may be readily incorporated into a pharmaceutical composition by conventional means. Pharmaceutical compositions in general are discussed in further detail below and may further comprise a pharmaceutically-acceptable diluent, excipient or carrier.

In a further aspect, the present invention provides a process for the production of a pharmaceutical composition, which process comprises:

(1) providing an API which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile diazo, organohalide, nitro, s-heterocyclic ring, thiophene, n-heterocyclic ring, pyrrole, o-heterocyclic ring, furan, epoxide, peroxide, hydroxamic acid, imidazole, and pyridine or of Table II or III;

(2) providing a co-crystal former which has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile diazo, organohalide, nitro, s-heterocyclic ring, thiophene, n-heterocyclic ring, pyrrole, o-heterocyclic ring, furan, epoxide, peroxide, hydroxamic acid, imidazole, and pyridine or of Table I, II, or III;

(3) grinding, heating or contacting in solution the API with the co-crystal former under crystallization conditions;

(4) isolating co-crystals formed thereby; and (5) incorporating the co-crystals into a pharmaceutical composition.

In a still further aspect the present invention provides a process for the production of a pharmaceutical composition, which comprises:

(1) grinding, heating or contacting in solution an API with a co-crystal former, under crystallization conditions, so as to form a solid phase;

(2) isolating co-crystals comprising the API and the co-crystal former; and (3) incorporating the co-crystals into a pharmaceutical composition.

Assaying the solid phase for the presence of co-crystals of the API and the co-crystal former may be carried out by conventional methods known in the art. For example, it is convenient and routine to use powder X-ray diffraction techniques to assess the presence of co-crystals. This may be affected by comparing the spectra of the API, the crystal former and putative co-crystals in order to establish whether or not true co-crystals had been formed. Other techniques, used in an analogous fashion, include differential scanning calorimetry (DSC), thermogravimetric analysis (TGA) and Raman spectroscopy. Single crystal X-ray diffraction is especially useful in identifying co-crystal structures.

In a further aspect, the present invention therefore provides a process of screening for co-crystal compounds, which comprises:

(1) providing (i) an API compound, and (ii) a co-crystal former; and (2) screening for co-crystals of APIs with co-crystal formers by subjecting each combination of API and co-crystal former to a step comprising:

(a) grinding, heating or contacting in solution the API with the co-crystal former under crystallization conditions so as to form a solid phase; and (b) isolating co-crystals comprising the API and the co-crystal former.

An alternative embodiment is drawn to a process of screening for co-crystal compounds, which comprises:

(1) providing (i) an API or a plurality of different APIs, and (ii) a co-crystal former or a plurality of different co-crystal formers, wherein at least one of the API and the co-crystal former is provided as a plurality thereof; and (2) screening for co-crystals of APIs with co-crystal formers by subjecting each combination of API and co-crystal former to a step comprising (a) grinding, heating or contacting in solution the API with the co-crystal former under crystallization conditions so as to form a solid phase; and (b) isolating co-crystals comprising the API and the co-crystal former.

Solubility Modulation

In a further aspect, the present invention provides a process for modulating the solubility of an API, which process comprises:

(1) grinding, heating or contacting in solution the API with a co-crystal former under crystallization conditions, so as to form a co-crystal of the API and the co-crystal former; and (2) isolating co-crystals comprising the API and the co-crystal former.

In one embodiment, the solubility of the API is modulated such that the aqueous solubility is increased. Solubility of APIs may be measured by any conventional means such as chromatography (e.g., HPLC) or spectroscopic determination of the amount of API in a saturated solution of the API, such as UV-spectroscopy, IR-spectroscopy, Raman spectroscopy, quantitative mass spectroscopy, or gas chromatography.

In another aspect of the invention, the API may have low aqueous solubility. Typically, low aqueous solubility in the present application refers to a compound having a solubility in water which is less than or equal to 10 mg/mL, when measured at 37 degrees C., and preferably less than or equal to 5 mg/mL or 1 mg/mL. Low aqueous solubility can further be specifically defined as less than or equal to 900, 800, 700, 600, 500, 400, 300, 200 150 100, 90, 80, 70, 60, 50, 40, 30, 20 micrograms/mL, or further 10, 5 or 1 micrograms/mL, or further 900, 800, 700, 600, 500, 400, 300, 200 150, 100 90, 80, 70, 60, 50, 40, 30, 20, or 10 ng/mL, or less than 10 ng/mL when measured at 37 degrees C. Aqueous solubility can also be specified as less than 500, 400, 300, 200, 150, 100, 75, 50 or 25 mg/mL. As embodiments of the present invention, solubility can be increased 2, 3, 4, 5, 7, 10, 15, 20, 25, 50, 75, 100, 200, 300, 500, 750, 1000, 5000, or 10,000 times by making a co-crystal of the reference form (e.g., crystalline or amorphous free acid, free base or zwitter ion, hydrate or solvate), or a salt thereof. Further aqueous solubility can be measured in simulated gastric fluid (SGF) or simulated intestinal fluid (SIF) rather than water. SGF (non-diluted) of the present invention is made by combining 1 g/L Triton X-100 and 2 g/L NaCl in water and adjusting the pH with 20 mM HCl to obtain a solution with a final pH=1.7 (SIF is 0.68% monobasic potassium phosphate, 1% pancreatin, and sodium hydroxide where the pH of the final solution is 7.5). The pH of the solvent used may also be specified as 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 11.5, or 12, or any pH in between successive values.

Examples of embodiments includes: co-crystal compositions with an aqueous solubility, at 37 degrees C. and a pH of 7.0, that is increased at least 5 fold over the reference form, co-crystal compositions with a solubility in SGF that is increased at least 5 fold over the reference form, co-crystal compositions with a solubility in SIF that is increased at least 5 fold over the reference form.

Dissolution Modulation

In another aspect of the present invention, the dissolution profile of the API is modulated whereby the aqueous dissolution rate or the dissolution rate in simulated gastric fluid or in simulated intestinal fluid, or in a solvent or plurality of solvents is increased. Dissolution rate is the rate at which API solids dissolve in a dissolution medium. For APIs whose absorption rates are faster than the dissolution rates (e.g., steroids), the rate-limiting step in the absorption process is often the dissolution rate. Because of a limited residence time at the absorption site, APIs that are not dissolved before they are removed from intestinal absorption site are considered useless. Therefore, the rate of dissolution has a major impact on the performance of APIs that are poorly soluble. Because of this factor, the dissolution rate of APIs in solid dosage forms is an important, routine, quality control parameter used in the API manufacturing process.

$$\text{Dissolution rate} = K\,S(C_s - C)$$

where K is dissolution rate constant, S is the surface area, $C_s$ is the apparent solubility, and C is the concentration of API in the dissolution medium.

For rapid API absorption, $C_s - C$ is approximately equal to $C_s$

The dissolution rate of APIs may be measured by conventional means known in the art.

The increase in the dissolution rate of a co-crystal, as compared to the reference form (e.g., free form or salt), may be specified, such as by 10, 20, 30, 40, 50, 60, 70, 80, 90, or 100%, or by 2, 3, 4, 5, 6, 7, 8, 9, 10, 15, 20, 25, 30, 40, 50, 75, 100, 125, 150, 175, 200, 250, 300, 350, 400, 500, 1000, 10,000, or 100,000 fold greater than the reference form (e.g., free form or salt form) in the same solution. Conditions under which the dissolution rate is measured is the same as discussed above The increase in dissolution may be further specified by the time the composition remains supersaturated before reaching equilibrium solubility.

Examples of above embodiments include: co-crystal compositions with a dissolution rate in aqueous solution, at 37 degrees C. and a pH of 7.0, that is increased at least 5 fold over the reference form, co-crystal compositions with a dissolution rate in SGF that is increased at least 5 fold over the reference form, co-crystal compositions with a dissolution rate in SIF that is increased at least 5 fold over the reference form.

Bioavailability Modulation

The methods of the present invention are used to make a pharmaceutical API formulation with greater solubility, dissolution, and bioavailability. Bioavailability can be improved via an increase in AUC, reduced time to $T_{max}$, (the time to reach peak blood serum levels), or increased $C_{max}$. The present invention can result in higher plasma concentrations of API when compared to the neutral form or salt alone (reference form).

AUC is the area under the plot of plasma concentration of API (not logarithm of the concentration) against time after API administration. The area is conveniently determined by the "trapezoidal rule": The data points are connected by straight line segments, perpendiculars are erected from the abscissa to each data point, and the sum of the areas of the triangles and trapezoids so constructed is computed. When the last measured concentration ($C_n$, at time $t_n$) is not zero, the AUC from $t_n$ to infinite time is estimated by $C_n/k_{el}$.

The AUC is of particular use in estimating bioavailability of APIs, and in estimating total clearance of APIs ($Cl_T$). Following single intravenous doses, $AUC = D/Cl_T$, for single compartment systems obeying first-order elimination kinetics, where D is the dose; alternatively, $AUC = C_0/k_{el}$, where $k_{el}$ is the API elimination rate constant. With routes other than the intravenous, for such systems, $AUC = F \cdot D/Cl_T$, where F is the absolute bioavailability of the API.

Thus, in a further aspect, the present invention provides a process for modulating the bioavailability of an API when administered in its normal and effective dose range as a co-crystal, whereby the AUC is increased, the time to $T_{max}$ is reduced, or $C_{max}$ is increased, as compared to a reference form, which process comprises:

(1) grinding, heating or contacting in solution the API with a co-crystal former under crystallization conditions, so as to form a co-crystal of the API and the co-crystal former; and (2) isolating co-crystals comprising the API and the co-crystal former.

Examples of the above embodiments include: co-crystal compositions with a time to $T_{max}$ that is reduced by at least 10% as compared to the reference form, co-crystal compositions with a time to $T_{max}$ that is reduced by at least 20% over the reference form, co-crystal compositions with a time to $T_{max}$ that is reduced by at least 40% over the reference form, co-crystal compositions with a time to $T_{max}$ that is reduced by at least 50% over the reference form, co-crystal compositions with a $T_{max}$ that is reduced by at least 60% over the reference form, co-crystal compositions with a $T_{max}$ that is reduced by at least 70% over the reference form, co-crystal compositions with a $T_{max}$ that is reduced by at least 80% over the reference form, co-crystal compositions with a $T_{max}$ that is reduced by at least 90% over the reference form, co-crystal compositions with a $C_{max}$ that is increased by at least 20% over the reference form, co-crystal compositions with a $C_{max}$ that is increased by at least 30% over the reference form, co-crystal compositions with a $C_{max}$ that is increased by at least 40% over the reference form, co-crystal compositions with a $C_{max}$ that is increased by at least 50% over the reference form, co-crystal compositions with a $C_{max}$ that is increased by at least 60% over the reference form, co-crystal compositions with a $C_{max}$ that is increased by at least 70% over the reference form, co-crystal compositions with a $C_{max}$ that is increased by at least 80% over the reference form, co-crystal compositions with a Cmax that is increased by at least 2 fold, 3 fold, 5 fold, 7.5 fold, 10 fold, 25 fold, 50 fold or 100 fold, co-crystal compositions with an AUC that is increased by at least 10% over the reference form, co-crystal compositions with an AUC that is increased by at least 20% over the reference form, co-crystal compositions with an AUC that is increased by at least 30% over the reference form, co-crystal compositions with an AUC that is increased by at least 40% over the reference form, co-crystal compositions with an AUC that is increased by at least 50% over the reference form, co-crystal compositions with an AUC that is increased by at least 60% over the reference form, co-crystal compositions with an AUC that is increased by at least 70% over the reference form, co-crystal compositions with an AUC that is increased by at least 80% over the reference form or co-crystal compositions with an AUC that is increased by at least 2 fold, 3 fold, 4 fold, 5 fold, 6 fold, 7 fold, 8 fold, 9 fold, or 10 fold. Other examples include wherein the reference form is crystalline, wherein the reference form is amorphous, wherein the reference form is an anhydrous crystalline sodium salt, or wherein the reference form is an anhydrous crystalline HCl salt.

Dose Response Modulation

In a further aspect the present invention provides a process for improving the dose response of an API, which process comprises:

(1) contacting in solution an API with a co-crystal former under crystallization conditions, so as to form a co-crystal of the API and the co-crystal former; and (2) isolating co-crystals comprising the API and the co-crystal former.

Dose response is the quantitative relationship between the magnitude of response and the dose inducing the response and may be measured by conventional means known in the art. The curve relating effect (as the dependent variable) to dose (as the independent variable) for an API-cell system is the "dose-response curve". Typically, the dose-response curve is the measured response to an API plotted against the dose of the API (mg/kg) given. The dose response curve can also be a curve of AUC against the dose of the API given.

In an embodiment of the present invention, a co-crystal of the present invention has an increased dose response curve or a more linear dose response curve than the corresponding reference compound.

Increased Stability

In a still further aspect the present invention provides a process for improving the stability of an API (as compared to a reference form such as its free form or a salt thereof), which process comprises:

(1) grinding, heating or contacting in solution the pharmaceutical salt with a co-crystal former under crystallization conditions, so as to form a co-crystal of the API and the co-crystal former; and (2) isolating co-crystals comprising the API and the co-crystal former.

In a preferred embodiment, the compositions of the present invention, including the API or active pharmaceutical ingredient (API) and formulations comprising the API, are suitably stable for pharmaceutical use. Preferably, the API or formulations thereof of the present invention are stable such that when stored at 30 degrees C. for 2 years, less than 0.2% of any one degradant is formed. The term degradant refers herein to product(s) of a single type of chemical reaction. For example, if a hydrolysis event occurs that cleaves a molecule into two products, for the purpose of the present invention, it would be considered a single degradant. More preferably, when stored at 40 degrees C. for 2 years, less than 0.2% of any one degradant is formed. Alternatively, when stored at 30 degrees C. for 3 months, less than 0.2% or 0.15%, or 0.1% of any one degradant is formed, or when stored at 40 degrees C. for 3 months, less than 0.2% or 0.15%, or 0.1% of any one degradant is formed. Further alternatively, when stored at 60 degrees C. for 4 weeks, less than 0.2% or 0.15%, or 0.1% of any one degradant is formed. The relative humidity (RH) may be specified as ambient (RH), 75% (RH), or as any single integer between 1 to 99%.

Difficult to Salt or Unsaltable Compounds

In a still further aspect the present invention provides a process for making co-crystals of unsaltable or difficult to salt APIs which process comprises:

(1) grinding, heating or contacting in solution an API with a co-crystal former under crystallization conditions, so as to form a co-crystal of the API and the co-crystal former; and (2) isolating co-crystals comprising the API and the co-crystal former.

Difficult to salt compounds include bases with a pKa<3 or acids with a pKa>10. Zwitter ions are also difficult to salt or unsaltable compounds according to the present invention.

Decreasing Hygroscopicity

In a still further aspect, the present invention provides a method for decreasing the hygroscopicity of an API, which method comprises:

(1) grinding, heating or contacting in solution the API with a co-crystal former under crystallization conditions, so as to form a co-crystal of the API and the co-crystal former; and (2) isolating co-crystals comprising the API and the co-crystal former.

An aspect of the present invention provides a pharmaceutical composition comprising a co-crystal of an API that is less hygroscopic than amorphous or crystalline, free form or salt (including metal salts such as sodium, potassium, lithium, calcium, magnesium) or another reference compound.

Hygroscopicity can be assessed by dynamic vapor sorption analysis, in which 5-50 mg of the compound is suspended from a Cahn microbalance. The compound being analyzed should be placed in a non-hygroscopic pan and its weight should be measured relative to an empty pan composed of identical material and having nearly identical size, shape, and weight. Ideally, platinum pans should be used. The pans should be suspended in a chamber through which a gas, such as air or nitrogen, having a controlled and known percent relative humidity (% RH) is flowed until equilibrium criteria are met. Typical equilibrium criteria include weight changes of less than 0.01% over 3 minutes at constant humidity and temperature. The relative humidity should be measured for samples dried under dry nitrogen to constant weight (<0.01% change in 3 minutes) at 40 degrees C. unless doing so would de-solvate or otherwise convert the material to an amorphous compound. In one aspect, the hygroscopicity of a dried compound can be assessed by increasing the RH from 5 to 95% in increments of 5% RH and then decreasing the RH from 95 to 5% in 5% increments to generate a moisture sorption isotherm. The sample weight should be allowed to equilibrate between each change in % RH. If the compound deliquesces or becomes amorphous above 75% RH, but below 95% RH, the experiment should be repeated with a fresh sample and the relative humidity range for the cycling should be narrowed to 5-75% RH or 10-75% RH, instead of 5-95% RH. If the sample cannot be dried prior to testing due to lack of form stability, than the sample should be studied using two complete humidity cycles of either 10-75% RH or 5-95% RH, and the results of the second cycle should be used if there is significant weight loss at the end of the first cycle.

Hygroscopicity can be defined using various parameters. For purposes of the present invention, a non-hygroscopic molecule should not gain or lose more than 1.0%, or more preferably, 0.5% weight at 25 degrees C. when cycled between 10 and 75% RH (relative humidity at 25 degrees C.). The non-hygroscopic molecule more preferably should not gain or lose more than 1.0%, or more preferably, 0.5% weight when cycled between 5 and 95% RH at 25 degrees C., or more than 0.25% of its weight between 10 and 75% RH. Most preferably, a non-hygroscopic molecule will not gain or lose more than 0.25% of its weight when cycled between 5 and 95% RH.

Alternatively, for purposes of the present invention, hygroscopicity can be defined using the parameters of Callaghan et al., "Equilibrium moisture content of pharmaceutical excipients", in Api Dev. Ind. Pharm., Vol. 8, pp. 335-369 (1982). Callaghan et al. classified the degree of hygroscopicity into four classes.

Class 1: Non-hygroscopic Essentially no moisture increases occur at relative humidities below 90%.

Class 2: Slightly hygroscopic Essentially no moisture increases occur at relative humidities below 80%.

Class 3: Moderately hygroscopic Moisture content does not increase more than 5% after storage for 1 week at relative humidities below 60%.

Class 4: Very hygroscopic Moisture content increase may occur at relative humidities as low as 40 to 50%.

Alternatively, for purposes of the present invention, hygroscopicity can be defined using the parameters of the European Pharmacopoeia Technical Guide (1999, p. 86) which has defined hygrospocity, based on the static method, after storage at 25 degrees C. for 24 hours at 80% RH:

Slightly hygroscopic: Increase in mass is less than 2 percent m/m and equal to or greater than 0.2 percent m/m.

Hygroscopic: Increase in mass is less than 15 percent m/m and equal to or greater than 0.2 percent m/m.

Very Hygroscopic: Increase in mass is equal to or greater than 15 percent m/m.

Deliquescent: Sufficient water is absorbed to form a liquid.

Co-crystals of the present invention can be set forth as being in Class 1, Class 2, or Class 3, or as being Slightly hygroscopic, Hygroscopic, or Very Hygroscopic. Co-crystals of the present invention can also be set forth based on their ability to reduce hygroscopicity. Thus, preferred co-crystals of the present invention are less hygroscopic than a reference compound. The reference compound can be specified as the API in free form (free acid, free base, hydrate, solvate, etc.) or salt (e.g., especially metal salts such as sodium, potassium, lithium, calcium, or magnesium). Further included in the present invention are co-crystals that do not gain or lose more than 1.0% weight at 25 degrees C. when cycled between 10 and 75% RH, wherein the reference compound gains or loses more than 1.0% weight under the same conditions. Further included in the present invention are co-crystals that do not gain or lose more than 0.5% weight at 25 degrees C. when cycled between 10 and 75% RH, wherein the reference compound gains or loses more than 0.5% or more than 1.0% weight under the same conditions. Further included in the present invention are co-crystals that do not gain or lose more than 1.0% weight at 25 degrees C. when cycled between 5 and 95% RH, wherein the reference compound gains or loses more than 1.0% weight under the same conditions. Further included in the present invention are co-crystals that do not gain or lose more than 0.5% weight at 25 degrees C. when cycled between 5 and 95% RH, wherein the reference compound gains or loses more than 0.5% or more than 1.0% weight under the same conditions. Further included in the present invention are co-crystals that do not gain or lose more than 0.25% weight at 25 degrees C. when cycled between 5 and 95% RH, wherein the reference compound gains or loses more than 0.5% or more than 1.0% weight under the same conditions.

Further included in the present invention are co-crystals that have a hygroscopicity (according to Callaghan et al.) that is at least one class lower than the reference compound or at least two classes lower than the reference compound. Included are a Class 1 co-crystal of a Class 2 reference compound, a Class 2 co-crystal of a Class 3 reference compound, a Class 3 co-crystal of a Class 4 reference compound, a Class 1 co-crystal of a Class 3 reference compound, a Class 1 co-crystal of a Class 4 reference compound, or a Class 2 co-crystal of a Class 4 reference compound.

Further included in the present invention are co-crystals that have a hygroscopicity (according to the European Pharmacopoeia Technical Guide) that is at least one class lower than the reference compound or at least two classes lower than the reference compound. Non-limiting examples include; a slightly hygroscopic co-crystal of a hygroscopic reference compound, a hygroscopic co-crystal of a very hygroscopic reference compound, a very hygroscopic co-crystal of a deliquescent reference compound, a slightly hygroscopic co-crystal of a very hygroscopic reference compound, a slightly hygroscopic co-crystal of a deliquescent reference compound, and a hygroscopic co-crystal of a deliquescent reference compound.

Crystallizing Amorphous Compounds

In a further aspect, the present invention provides a process for crystallizing an amorphous compound, which process comprises:
(1) grinding, heating or contacting in solution the API with a co-crystal former under crystallization conditions, so as to form a co-crystal of the API and the co-crystal former; and
(2) isolating co-crystals comprising the API and the co-crystal former.

An amorphous compound includes compounds that do not crystallize using routine methods in the art.

Decreasing Form Diversity

In a still further embodiment aspect the present invention provides a process for reducing the form diversity of an API, which process comprises:
(1) grinding, heating or contacting in solution the API with a co-crystal former under crystallization conditions, so as to form a co-crystal of the API and the co-crystal former; and
(2) isolating co-crystals comprising the API and the co-crystal former.

For purposes of the present invention, the number of forms of a co-crystal is compared to the number of forms of a reference compound (e.g. the free form or a salt of the API) that can be made using routine methods in the art.

Morphology Modulation

In a still further aspect the present invention provides a process for modifying the morphology of an API, which process comprises:
(1) grinding, heating or contacting in solution the API with a co-crystal former under crystallization conditions, so as to form a co-crystal of the API and the co-crystal former; and
(2) isolating co-crystals comprising the API and the co-crystal former.

In an embodiment the co-crystal comprises or consists of a co-crystal former and a pharmaceutical wherein the interaction between the two, e.g., H-bonding, occurs between a functional group of Table III of an API with a corresponding interacting group of Table III. In a further embodiment, the co-crystal comprises a co-crystal former of Table I or II and an API with a corresponding interacting group of Table III. In a further embodiment the co-crystal comprises an API from Table IV and a co-crystal former with a functional group of Table III. In a further embodiment, the co-crystal is from Table I or II. In an aspect of the invention, only co-crystals having an H-bond acceptor on the first molecule and an H-bond donor on the second molecule, where the first and second molecules are either co-crystal former and API respectively or API and co-crystal former respectively, are included in the present invention. Table IV includes the CAS number, chemical name or a PCT or patent reference (each incorporated herein in their entireties). Thus, whether a particular API contains an H-bond donor, acceptor or both is readily apparent.

In another embodiment, the co-crystal former and API each have only one H-bond donor/acceptor. In another aspect, the molecular weight of the API is less than 2000, 1500, 1000, 750, 500, 350, 200, or 150 Daltons. In another embodiment, the molecular weight of the API is between 100-200, 200-300, 300-400, 400-500, 500-600, 600-700, 700-800, 800-900, 900-1000, 1000-1200, 1200-1400, 1400-1600, 1600-1800, or 1800-2000. APIs with the above molecular weights may also be specifically excluded from the present invention.

In another embodiment, peptides, proteins, nucleic acids or other biological APIs are excluded from the present invention. In another embodiment, all non-pharmaceutically acceptable co-crystal formers are excluded from the present invention. In another embodiment, organometalic APIs are excluded from the present invention. In another embodiment, a co-crystal former comprising any one or more of the functional groups of Table III may be specifically excluded from the present invention. In another embodiment, any one or more of the co-crystal formers of Table I or II may be specifically excluded from the present invention. Any APIs currently known in the art may also be specifically excluded from the present invention. For example, carbanazepine, itraconazole, nabumetone, fluoxetine, acetaminophen and theophylline can each be specifically excluded from the present invention. In another embodiment, the API is not a salt, is not a non-metal salt, or is not a metal salt, e.g., sodium, potassium, lithium, calcium or magnesium. In another embodiment, the API is a salt, is a non-metal salt, or is a metal salt, e.g., sodium, potassium, lithium, calcium, magnesium. In one embodiment, the API does not contain a halogen. In one embodiment, the API does contain a halogen.

In another embodiment, any one or more of the APIs of Table IV may be specifically excluded from the present invention. Any APIs currently known in the art may also be specifically excluded from the present invention. For example, nabumetone:2,3-naphthalenediol, fluoxetine HCl:benzoic acid, fluoxetine HCl:succinic acid, acetaminophen:piperazine, acetaminophen:theophylline, theophylline:salicylic acid, theophylline:p-hydroxybenzoic acid, theophylline:sorbic acid, theophylline:1-hydroxy-2-naphthoic acid, theophylline:glycolic acid, theophylline:2,5-dihydroxybenzoic acid, theophylline:chloroacetic acid, bis(diphenylhydantoin):9-ethyladenine acetylacetone solvate, bis(diphenylhydantoin):9-ethyladenine 2,4-pentanedione solvate, 5,5-diphenylbarbituric acid:9-ethyladenine, bis(diphenylhydantoin):9-ethyladenine, 4-aminobenzoic acid:4-aminobenzonitrile, sulfadimidine:salicylic acid, 8-hydroxyquinolinium 4-nitrobenzoate:4-nitrobenzoic acid, sulfaproxyline:caffeine, retro-inverso-isopropyl (2R,3S)-4-cyclohexyl-2-hydroxy-3-(N-((2R)-2-morpholinocarbonylmethyl-3-(1-naphthyl)propionyl)-L-histidylamino)butyrate: cinnamic acid monohydrate, benzoic acid:isonicotinamide, 3-(2-N',N'-(dimethylhydrazino)-4-thiazolylmethylthio)-N''-sulfamoylpropionamidine:maleic acid, diglycine hydrochloride ($C_2H_5NO_2$:$C_2H_6NO_2^+Cl^-$), octadecanoic acid:3-pyridinecarboxamide, cis-N-(3-methyl-1-(2-(1,2,3,4-tetrahydro) naphthyl)-piperidin-4-yl)-N-phenylpropanamide hydrochloride:oxalic acid, trans-N-(3-methyl-1-(2-(1,2,3,4-tetrahydro)naphthyl)-piperidin-4-ylium)-N-phenylpropanamide oxalate:oxalic acid dihydrate, bis(1-(3-((4-(2-isopropoxyphenyl)-1-piperazinyl)methyl)benzoyl)piperidine) succinate:succinic acid, bis(p-cyanophenyl)imidazolylmethane:succinic acid, cis-1-((4-(1-imidazolylmethyl)cyclohexyl)methyl)imidazole:succinic acid, (+)-2-(5,6-dimethoxy-1,2,3,4-tetrahydro-1-naphthyl)imidazoline:(+)-dibenzoyl-D-tartaric acid, raclopride:tartaric acid, 2,6-diamino-9-ethylpurine:5,5-diethylbarbituric acid, 5,5-diethylbarbituric acid:bis(2-aminopyridine), 5,5-diethylbarbituric acid:acetamide, 5,5-diethylbarbituric acid: $KI_3$, 5,5-diethylbarbituric acid:urea, bis(barbital): hexamethylphosphoramide, 5,5-diethylbarbituric acid: imidazole, barbital: 1-methylimidazole, 5,5-diethylbarbituric acid:N-methyl-2-pyridone, 2,4-diamino-5-(3,4,5-trimethoxybenzyl)-pyrimidine:5,5-diethylbarbituric acid, bis(barbital):caffeine, bis(barbital): 1-methylimidazole, bis(beta-cyclodextrin):bis(barbital) hydrate, tetrakis(beta-cyclodextrin):tetrakis(barbital), 9-ethyladenine:5,5-diethylbarbituric acid, barbital:N'-(p-cyanophenyl)-N-(p-iodophenyl)melamine, barbital:2-amino-4-(m-bromophenylamino)-6-chloro-1,3,5-triazine, 5,5-diethylbarbituric acid:N,N'-diphenylmelamine, 5,5-diethylbarbituric acid:N,N'-bis(p-chlorophenyl)melamine, N,N'-bis(p-bromophenyl)melamine:5,5-diethylbarbituric acid, 5,5-diethylbarbituric acid:N,N'-bis(p-iodophenyl)melamine, 5,5-diethylbarbituric acid:N,N'-bis(p-tolyl)melamine, 5,5-diethylbarbituric acid: N,N'-bis(m-tolyl)melamine, 5,5-diethylbarbituric acid:N,N'-bis(m-chlorophenyl)melamine, N,N'-Bis(m-methylphenyl) melamine:barbital, N,N'-bis(m-chlorophenyl)melamine: barbital tetrahydrofuran solvate, 5,5-diethylbarbituric acid: N,N'-bis(t-butyl)melamine, 5,5-diethylbarbituric acid:N,N'-di(t-butyl)melamine, 6,6'-diquinolyl ether:5,5-diethylbarbituric acid, 5-t-butyl-2,4,6-triaminopyrimidine: diethylbarbituric acid, N,N'-bis(4-carboxymethylphenyl) melamine:barbital ethanol solvate, N,N'-bis(4-t-butylphenyl) melamine:barbital, tris(5,17-N,N'-bis(4-amino-6-(butylamino)-1,3,5-triazin-2-yl)diamino-11,23-dinitro-25, 26,27,28-tetrapropoxycalix(4)arene):hexakis (diethylbarbituric acid) toluene solvate, N,N'-bis(m-fluorophenyl)melamine:barbital, N,N'-bis(m-bromophenyl) melamine:barbital acetone solvate, N,N'-bis(m-iodophenyl) melamine:barbital acetonitrile solvate, N,N'-bis(m-trifluoromethylphenyl)melamine:barbital acetonitrile solvate, aminopyrine:barbital, N,N'-bis(4-fluorophenyl) melamine:barbital, N,N'-bis(4-trifluoromethylphenyl) melamine:barbital, 2,4-diamino-5-(3,4,5-trimethoxybenzyl) pyrimidine:barbital, hydroxybutyrate:hydroxyvalerate, 2-aminopyrimidine:succinic acid, 1,3-bis(((6-methylpyrid-2-yl)amino)carbonyl)benzene:glutaric acid, 5-t-butyl-2,4,6-triaminopyrimidine:diethylbarbituric acid, bis(dithiobiuret-S,S')nickel(II):diuracil, platinum 3,3'-dihydroxymethyl-2,2'-bipyridine dichloride:$AgF_3$ $_{CSO_3}$, 4,4'-bipyridyl:isophthalic acid, 4,4'-bipyridyl:1,4-naphthalenedicarboxylic acid, 4,4'-bipyridyl:1,3,5-cyclohexane-tricarboxylic acid, 4,4'-bipyridyl:tricaballylic acid, urotropin:azelaic acid, insulin:C8-HI (octanoyl-$N^e$-LysB29-human insulin), isonicotinamide:cinnamic acid, isonicotinamide:3-hydroxybenzoic acid, isonicotinamide:3-N,N-dimethylaminobenzoic acid, isonicotinamide:3,5-bis(trifluoromethyl)-benzoic acid, isonicotinamide:d,1-mandelic acid, isonicotinamide:chloroacetic acid, isonicotinamide:fumaric acid monoethyl ester, isonicotinamide:12-bromododecanoic acid, isonicotinamide:fumaric acid, isonicotinamide:succinic acid, isonicotinamide:4-ketopimelic acid, isonicotinamide:thiodiglycolic acid, 1,3,5-cyclohexane-tricarboxylic acid:hexamethyltetramine, 1,3,5-cyclohexane-tricarboxylic acid:4,7-phenanthroline, 4,7-phenanthroline:oxalic acid, 4,7-phenanthroline: terephthalic acid, 4,7-phenanthroline: 1,3,5-cyclohexane-tricarboxylic acid, 4,7-phenanthroline: 1,4-naphthalenedicarboxylic acid, pyrazine:methanoic acid, pyrazine:ethanoic acid, pyrazine:propanoic acid, pyrazine: butanoic acid, pyrazine:pentanoic acid, pyrazine:hexanoic acid, pyrazine:heptanoic acid, pyrazine:octanoic acid, pyrazine:nonanoic acid, pyrazine:decanoic acid, diammine-(deoxy-quanyl-quanyl-$N^7$,$N^7$)-platinum:tris(glycine) hydrate, 2-aminopyrimidine:p-phenylenediacetic acid, bis(2-aminopyrimidin-1-ium)fumarate:fumaric acid, 2-aminopyrimidine:indole-3-acetic acid, 2-aminopyrimidine:N-methylpyrrole-2-carboxylic acid, 2-aminopyrimidine:thiophen-2-carboxylic acid, 2-aminopyrimidine:(+)-camphoric acid, 2,4, 6-Trinitrobenzoic acid: 2-aminopyrimidine, 2-aminopyrimidine:4-aminobenzoic acid, 2-aminopyrimidine:bis(phenoxyacetic acid), 2-aminopyrimidine:(2,4-dichlorophenoxy)acetic acid, 2-aminopyrimidine:(3,4-dichlorophenoxy)acetic acid, 2-aminopyrimidine:indole-2-carboxylic acid, 2-aminopyrimidine:terephthalic acid, 2-aminopyrimidine:bis(2-nitrobenzoic acid), 2-aminopyrimidine:bis(2-aminobenzoic acid), 2-aminopyrimidine:3-aminobenzoic acid, 2-hexeneoic acid:isonicotinamide, 4-nitrobenzoic acid:isonicotinamide, 3,5-dinitrobenzoic acid: isonicotinamide:4-methylbenzoic acid, 2-amino-5-nitropyridine:2-amino-3-nitropyridine, 3,5-dinitrobenzoic acid:4-chlorobenzamide, 3-dimethylaminobenzoic acid:4-chlorobenzamide, fumaric acid:4-chlorobenzamide, oxine:4-nitrobenzoic acid, oxine:3, 5-dinitrobenzoic acid, oxine:3,5-dinitrosalicylic acid, 3-[2-

(N',N'-dimethylhydrazino)-4-thiazolylmethylthio]-$N^2$-sulfamoylpropionamidine:maleic acid, 5-fluorouracil:9-ethylhypoxanthine, 5-fluorouracil:cytosine dihydrate, 5-fluorouracil:theophylline monohydrate, stearic acid:nicotinamide, cis-1-{[4-(1-imidazolylmethyl)cyclohexyl]methyl}imidazole:succinic acid, CGS18320B:succinic acid, sulfaproxyline:caffeine, 4-aminobenzoic acid:4-aminobenzonitrile, 3,5-dinitrobenzoic acid:isonicotinamide:3-methylbenzoic acid, 3,5-dinitrobenzoic acid:isonicotinamide:4-(dimethylamino)benzoic acid, 3,5-dinitrobenzoic acid: isonicotinamide:4-hydroxy-3-methoxycinnamic acid, isonicotinamide:oxalic acid, isonicotinamide:malonic acid, isonicotinamide:succinic acid, isonicotinamide:glutaric acid, isonicotinamide:adipic acid, benzoic acid:isonicotinamide, mazapertine:succinate, betaine:dichloronitrophenol, betainepyridine:dichloronitrophenol, betainepyridine:pentachlorophenol, 4-{2-[1-(2-hydroxyethyl)-4-pyridylidene]-ethylidene}-cyclo-hexa-2,5-dien-1-one:methyl 2,4-dihydroxybenzoate, 4-{2-[1-(2-hydroxyethyl)-4-pyridylidene]-ethylidene}-cyclo-hexa-2,5-dien-1-one:2,4-dihydroxypropiophenone, 4-{2-[1-(2-hydroxyethyl)-4-pyridylidene]-ethylidene}-cyclo-hexa-2,5-dien-1-one:2,4-dihydroxyacetophenone, squaric acid:4,4'-dipyridylacetylene, squaric acid: 1,2-bis(4-pyridyl)ethylene, chloranilic acid: 1,4-bis[(4-pyridyl)ethynyl]benzene, 4,4'-bipyridine:phthalic acid, 4,4'-dipyridylacetylene:phthalic acid, bis(pentamethylcyclopentadienyl)iron:bromanilic acid, bis(pentamethylcyclopentadienyl)iron:chloranilic acid, bis(pentamethylcyclopentadienyl)iron:cyananilic acid, pyrazinotetrathiafulvalene:chloranilic acid, phenol: pentafluorophenol, co-crystals of itraconazole, and co-crystals of topiramate are specifically excluded from the present invention.

Excipients employed in pharmaceutical compositions of the present invention can be solids, semi-solids, liquids or combinations thereof. Preferably, excipients are solids. Compositions of the invention containing excipients can be prepared by any known technique of pharmacy that comprises admixing an excipient with an API or therapeutic agent. A pharmaceutical composition of the invention contains a desired amount of API per dose unit and, if intended for oral administration, can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the API, such as tablets or capsules.

In another embodiment, APIs with an inappropriate pH for transdermal patches can be co-crystallized with an appropriate co-crystal former, thereby adjusting its pH to an appropriate level for use as a transdermal patch. In another embodiment, an APIs pH level can be optimized for use in a transdermal patch via co-crystallization with an appropriate co-crystal former.

Non-limiting examples follow of excipients that can be used to prepare pharmaceutical compositions of the invention.

Pharmaceutical compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Lactose, mannitol, dibasic sodium phosphate, and microcrystalline cellulose (particularly Avicel PH microcrystalline cellulose such as Avicel PH 101), either individually or in combination, are preferred diluents. These diluents are chemically compatible with many co-crystals described herein. The use of extragranular microcrystalline cellulose (that is, microcrystalline cellulose added to a granulated composition) can be used to improve hardness (for tablets) and/or disintegration time. Lactose, especially lactose monohydrate, is particularly preferred. Lactose typically provides compositions having suitable release rates of co-crystals, stability, pre-compression flowability, and/or drying properties at a relatively low diluent cost. It provides a high density substrate that aids densification during granulation (where wet granulation is employed) and therefore improves blend flow properties and tablet properties.

Pharmaceutical compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colorcon™ 1500), clays (e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated pharmaceutical compositions of the present invention.

Pharmaceutical compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a co-crsytal of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition.

Many of the binding agents are polymers comprising amide, ester, ether, alcohol or ketone groups and, as such, are preferably included in pharmaceutical compositions of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Pharmaceutical compositions of the invention optionally comprise one or more pharmaceutically acceptable wetting agents as excipients. Such wetting agents are preferably selected to maintain the co-crystal in close association with water, a condition that is believed to improve bioavailability of the composition. Such wetting agents can also be useful in solubilizing or increasing the solubility of co-crystals.

Non-limiting examples of surfactants that can be used as wetting agents in pharmaceutical compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and degrees Ctoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the pharmaceutical composition.

Pharmaceutical compositions of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the pharmaceutical composition.

Magnesium stearate is a preferred lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the pharmaceutical composition.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in pharmaceutical compositions of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of pharmaceutical compositions of the invention. When present in pharmaceutical compositions of the invention to promote dosage form disintegration, one or more effervescent agents are preferably present in a total amount of about 30% to about 75%, and preferably about 45% to about 70%, for example about 60%, by weight of the pharmaceutical composition.

According to a particularly preferred embodiment of the invention, an effervescent agent, present in a solid dosage form in an amount less than that effective to promote disintegration of the dosage form, provides improved dispersion of the API in an aqueous medium. Without being bound by theory, it is believed that the effervescent agent is effective to accelerate dispersion of the API from the dosage form in the gastrointestinal tract, thereby further enhancing absorption and rapid onset of therapeutic effect. When present in a pharmaceutical composition of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the pharmaceutical composition.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base.

Non-limiting examples of suitable acids as components of effervescent agents and/or solid organic acids useful in the invention include citric acid, tartaric acid (as D-, L-, or D/L-tartaric acid), malic acid (as D-, L-, or DL-malic acid), maleic acid, fumaric acid, adipic acid, succinic acid, acid anhydrides of such acids, acid salts of such acids, and mixtures thereof. Citric acid is a preferred acid.

In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Excipients which solubilize APIs typically have both hydrophilic and hydrophobic regions, or are preferably amphiphilic or have amphiphilic regions. One type of amphiphilic or partially-amphiphilic excipient comprises an amphiphilic polymer or is an amphiphilic polymer. A specific amphiphilic polymer is a polyalkylene glycol, which is commonly comprised of ethylene glycol and/or propylene glycol subunits. Such polyalkylene glycols can be esterified at their termini by a carboxylic acid, ester, acid anhyride or other suitable moiety. Examples of such excipients include poloxamers (symmetric block copolymers of ethylene glycol and propylene glycol; e.g., poloxamer 237), polyalkyene glycolated esters of tocopherol (including esters formed from a di- or multi-functional carboxylic acid; e.g., d-alpha-tocopherol polyethylene glycol-1000 succinate), and macrogolglycerides (formed by alcoholysis of an oil and esterification of a polyalkylene glycol to produce a mixture of mono-, di- and tri-glycerides and mono- and di-esters; e.g., stearoyl macrogol-32 glycerides). Such pharmaceutical compositions are advantageously administered orally.

Pharmaceutical compositions of the present invention can comprise about 10% to about 50%, about 25% to about 50%, about 30% to about 45%, or about 30% to about 35% by weight of a co-crystal; about 10% to about 50%, about 25% to about 50%, about 30% to about 45%, or about 30% to about 35% by weight of an excipient which inhibits crystallization in aqueous solution, in simulated gastric fluid, or in simulated intestinal fluid; and about 5% to about 50%, about 10% to about 40%, about 15% to about 35%, or about 30% to about 35% by weight of a binding agent. In one example, the weight ratio of the co-crystal to the excipient which inhibits crystallization to binding agent is about 1 to 1 to 1.

Solid dosage forms of the invention can be prepared by any suitable process, not limited to processes described herein.

An illustrative process comprises (a) a step of blending an API of the invention with one or more excipients to form a blend, and (b) a step of tableting or encapsulating the blend to form tablets or capsules, respectively.

In a preferred process, solid dosage forms are prepared by a process comprising (a) a step of blending a co-crystal of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a dry granulation step. A salt of the present invention is advantageously granulated to form particles of about 1 micrometer to about 100 micrometer, about 5 micrometer to about 50 micrometer, or about 10 micrometer to about 25 micrometer. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in API content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein an API is suspended with one or more excipients in one or more sprayable liquids, preferably a non-protic (e.g., non-aqueous or non-alcoholic) sprayable liquid, and then is rapidly spray dried over a current of warm air.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

Pharmaceutically acceptable co-crystals can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity;

and 10) improvement in speed of control of diseases or conditions. Kim, Cherng-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the co-crystals and compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS®) (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed co-crystals and thus effect controlled delivery of the drug. Examples of specific anion exchangers include, but are not limited to, Duolite® A568 and Duolite® AP143 (Rohm & Haas, Spring House, Pa. USA).

One embodiment of the invention encompasses a unit dosage form which comprises a pharmaceutically acceptable co-crystal, or a solvate, hydrate, dehydrate, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the invention include, but are not limited to, the OROS® Push-Pull™, Delayed Push-Pull™, Multi-Layer Push-Pull™, and Push-Stick™ Systems, all of which are well known. See, e.g., http://www.alza.com. Additional OROS® systems that can be used for the controlled oral delivery of compounds and compositions of the invention include OROS®-CT and L-OROS®. Id.; see also, Delivery Times, vol. II, issue II (Alza Corporation).

Conventional OROS® oral dosage forms are made by compressing a drug powder (e.g. co-crystal) into a hard tablet, coating the tablet with cellulose derivatives to form a semipermeable membrane, and then drilling an orifice in the coating (e.g., with a laser). Kim, Chemg-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively deliver drugs with low water solubility. Id. at 234. Because co-crystals of this invention can be far more soluble in water than the API itself, they are well suited for osmotic-based delivery to patients. This invention does, however, encompass the incorporation of conventional crystalline API (e.g. pure API without co-crystal former), and non-salt isomers and isomeric mixtures thereof, into OROS® dosage forms.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a co-crystal, or a solvate, hydrate, dehydrate, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a co-crystal, or a solvate, hydrate, dehydrate, anhydrous, or amorphous form thereof. See U.S. Pat. No. 6,342,249, the entirety of which is incorporated herein by reference.

The invention will now be described in further detail, by way of example, with reference to the accompanying drawings.

EXEMPLIFICATION

General Methods for the Preparation of Co-Crystals a) High Throughput Crystallization Using the CrystalMax Platform CrystalMax™ comprises a sequence of automated, integrated high throughput robotic stations capable of rapid generation, identification and characterization of polymorphs, salts, and co-crystals of APIs and API candidates. Worksheet generation and combinatorial mixture design is carried out using proprietary design software InForm™. Typically, an API or an API candidate is dispensed from an organic solvent into tubes and dried under a stream of nitrogen. Salts and/or co-crystal formers may also be dispensed and dried in the same fashion. Water and organic solvents may be combinatorially dispensed into the tubes using a multi-channel dispenser. Each tube in a 96-tube array is then sealed within 15 seconds of combinatorial dispensing to avoid solvent evaporation. The mixtures are then rendered supersaturated by heating to 70 degrees C. for 2 hours followed by a 1 degree C./minute cooling ramp to 5 degrees C. Optical checks are then conducted to detect crystals and/or solid material. Once a solid has been identified in a tube, it is isolated through aspiration and drying. Raman spectra are then obtained on the solids and cluster classification of the spectral patterns is performed using proprietary software (QForm™).

b) Crystallization from Solution

Co-crystals may be obtained by dissolving the separate components in a solvent and adding one to the other. The co-crystal may then precipitate or crystallize as the solvent mixture is evaporated slowly. The co-crystal may also be obtained by dissolving the two components in the same solvent or a mixture of solvents.

c) Crystallization from the Melt

A co-crystal may be obtained by melting the two components together and allowing recrystallization to occur. In some cases, an anti-solvent may be added to facilitate crystallization.

d) Thermal Microscopy

A co-crystal may be obtained by melting the higher melting component on a glass slide and allowing it to recrystallize. The second component is then melted and is also allowed to recrystallize. The co-crystal may form as a separated phase/band in between the eutectic bands of the two original components.

e) Mixing and/or Grinding

A co-crystal may be obtained by mixing or grinding two components together in the solid state.

Analytical Methods

Procedure for DSC Analysis

DSC analysis of the samples was performed using a Q1000 Differential Scanning Calorimeter (TA Instruments, New Castle, Del., U.S.A.), which uses Advantage for QW-Series, version 1.0.0.78, Thermal Advantage Release 2.0 ($^8$2001 TA Instruments-Water LLC). In addition, the analysis software used was Universal Analysis 2000 for Windows 95/95/2000/NT, version 3.1 E;Build 3.1.0.40 ($^8$2001 TA Instruments-Water LLC).

For the DSC analysis, the purge gas used was dry nitrogen, the reference material was an empty aluminum pan that was crimped, and the sample purge was 50 mL/minute.

DSC analysis of the sample was performed by placing $\leq 2$ mg of sample in an aluminum pan with a crimped pan closure. The starting temperature was typically 20 degrees C. with a heating rate of 10 degrees C./minute, and the ending temperature was 300 degrees C. Unless otherwise indicated, all reported transitions are as stated +/−10 degrees C.

Procedure for TGA Analysis

TGA analysis of samples was performed using a Q500 Thermogravimetric Analyzer (TA Instruments, New Castle, Del., U.S.A.), which uses Advantage for QW-Series, version 1.0.0.78, Thermal Advantage Release 2.0 (82001 TA Instruments-Water LLC). In addition, the analysis software used was Universal Analysis 2000 for Windows 95/95/2000/NT, version 3.1E;Build 3.1.0.40 ($^8$2001 TA Instruments-Water LLC).

For all of the TGA experiments, the purge gas used was dry nitrogen, the balance purge was 40 mL/minute $N_2$, and the sample purge was 60 mL/minute $N_2$.

TGA of the sample was performed by placing $\leq 2$ mg of sample in a platinum pan. The starting temperature was typically 20 degrees C. with a heating rate of 10 degrees C./minute, and the ending temperature was 300 degrees C.

Procedure for PXRD Analysis

A powder X-ray diffraction pattern for the samples was obtained using a D/Max Rapid, Contact (Rigaku/MSC, The Woodlands, Tex., U.S.A.), which uses as its control software RINT Rapid Control software, Rigaku Rapid/XRD, version 1.0.0 ($^8$1999 Rigaku Co.). In addition, the analysis software used were RINT Rapid display software, version 1.18 (Rigaku/MSC), and JADE XRD Pattern Processing, versions 5.0 and 6.0 (($^8$1995-2002, Materials Data, Inc.).

For the PXRD analysis, the acquisition parameters were as follows: source was Cu with a K line at 1.5406 Å; x-y stage was manual; collimator size was 0.3 or 0.8 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0-5 degrees at a speed of 1 degree/minute; the phi-axis was spinning at an angle of 360 degrees at a speed of 2 degrees/second; 0.3 or 0.8 mm collimator; the collection time was 60 minutes; the temperature was room temperature; and the heater was not used. The sample was presented to the X-ray source in a boron rich glass capillary.

In addition, the analysis parameters were as follows: the integration 2-theta range was 2-40 or 60 degrees; the integration chi range was 0-360 degrees; the number of chi segments was 1; the step size used was 0.02; the integration utility was cylint; normalization was used; dark counts were 8; omega offset was 180; and chi and phi offsets were 0.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, preferably +/−0.05. The entire pattern or most of the pattern peaks may also shift by about +/−0.1 degree due to differences in calibration, settings, and other variations from instrument to instrument and from operator to operator.

Procedure for Raman Acquisition Filtering and Binning Acquisition

The sample was either left in the glass vial in which it was processed or an aliquot of the sample was transferred to a glass slide. The glass vial or slide was positioned in the sample chamber. The measurement was made using an Almega™ Dispersive Raman (Almega™ Dispersive Raman, Thermo-Nicolet, 5225 Verona Road, Madison, Wis. 53711-

4495) system fitted with a 785 nm laser source. The sample was manually brought into focus using the microscope portion of the apparatus with a 10×power objective (unless otherwise noted), thus directing the laser onto the surface of the sample. The spectrum was acquired using the parameters outlined in Table A. (Exposure times and number of exposures may vary; changes to parameters will be indicated for each acquisition.)

Filtering and Binning

Each spectrum in a set was filtered using a matched filter of feature size 25 to remove background signals, including glass contributions and sample fluorescence. This is particularly important as large background signal or fluorescence limit the ability to accurately pick and assign peak positions in the subsequent steps of the binning process. Filtered spectra were binned using the peak pick and bin algorithm with the parameters given in Table B. The sorted cluster diagrams for each sample set and the corresponding cluster assignments for each spectral file were used to identify groups of samples with similar spectra, which was used to identify samples for secondary analyses.

TABLE A

Raman Spectral acquisition parameters

| Parameter | Setting Used |
| --- | --- |
| Exposure time (s) | 2.0 |
| Number of exposures | 10 |
| Laser source wavelength (nm) | 785 |
| Laser power (%) | 100 |
| Aperture shape | pin hole |
| Aperture size (um) | 100 |
| Spectral range | 104-3428 |
| Grating position | Single |
| Temperature at acquisition (degrees C.) | 24.0 |

TABLE B

Raman Filtering and Binning Parameters

| Parameter | Setting Used |
| --- | --- |
| Filtering Parameters | |
| Filter type | Matched |
| Filter size | 25 |
| QC Parameters | |
| Peak Height Threshold | 1000 |
| Region for noise test (cm$^{-1}$) | 0-10000 |
| RMS noise threshold | 10000 |
| Automatically eliminate failed spectra | Yes |
| Region of Interest | |
| Include (cm$^{-1}$) | 104-3428 |
| Exclude region I (cm$^{-1}$) | |
| Exclude region II (cm$^{-1}$) | |
| Exclude region III (cm$^{-1}$) | |
| Exclude region IV (cm$^{-1}$) | |
| Peak Pick Parameters | |
| Peak Pick Sensitivity | Variable |
| Peak Pick Threshold | 100 |
| Peak Comparison Parameters | |
| Peak Window (cm$^{-1}$) | 2 |
| Analysis Parameters | |
| Number of clusters | Variable |

Procedure for Single Crystal X-Ray Diffraction

Single crystal x-ray data were collected on a Bruker SMART-APEX CCD diffractometer (M. J. Zawarotko, Department of Chemistry, University of South Florida). Lattice parameters were determined from least squares analysis. Reflection data was integrated using the program SAINT. The structure was solved by direct methods and refined by full matrix least squares using the program SHELXTL (Sheldrick, G. M. SHELXTL, Release 5.03; Siemans Analytical X-ray Instruments Inc.: Madison, Wis.).

The co-crystals of the present invention can be characterized, e.g., by the TGA or DSC data or by any one, any two, any three, any four, any five, any six, any seven, any eight, any nine, any ten, or any single integer number of PXRD 2-theta angle peaks or Raman shift peaks listed herein or disclosed in a figure, or by single crystal x-ray diffraction data.

Example 1

Figure 1:
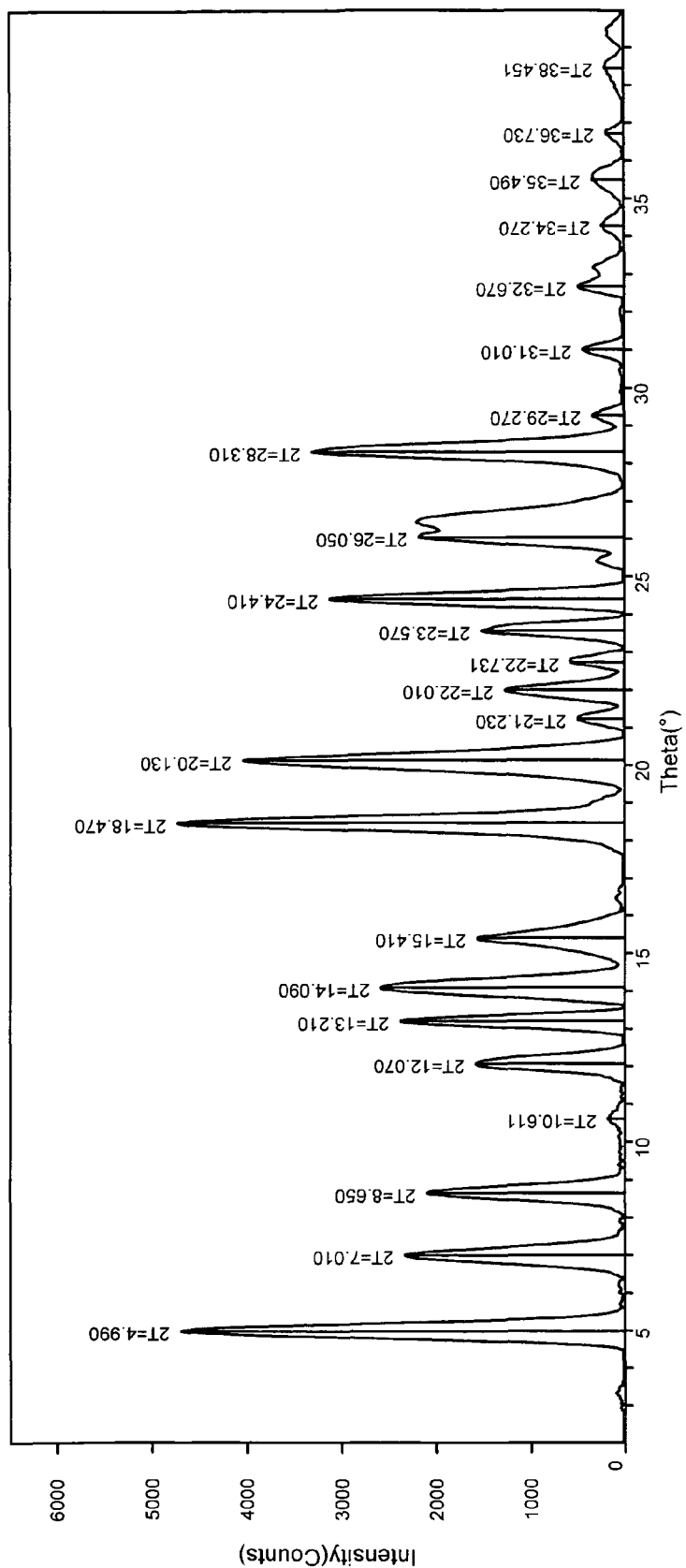
FIG. 1 PXRD pattern for a co-crystal of carbamazepine and saccharin (Form I).

1:1 carbamazepine:saccharin co-crystals (Form I) were prepared. A 12-block experiment was designed with 12 solvents. 1152 crystallization experiments were carried out using the CMAX platform. The co-crystal was obtained from a mixture of isopropyl acetate and heptane. Detailed characterization of the co-crystal is listed in Table V. (See FIGS. 1 and 2)

Example 2

Figure 3:
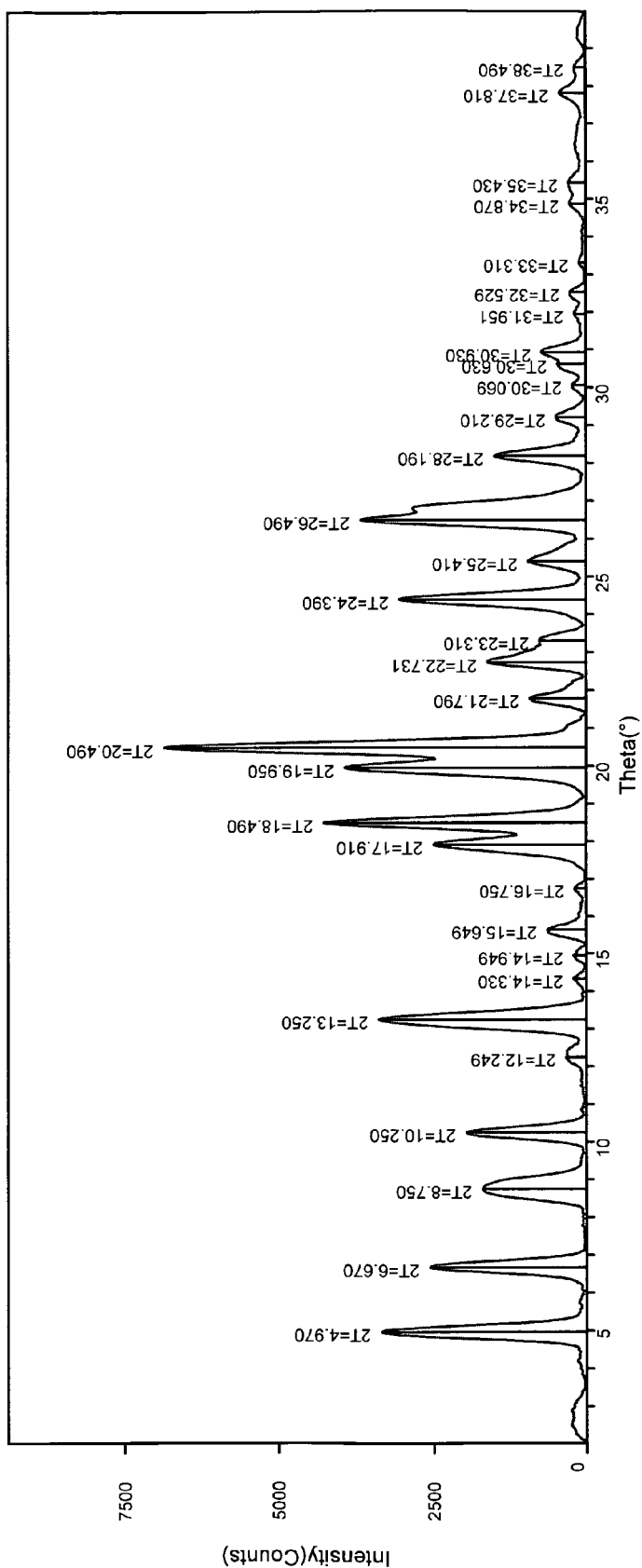
FIG. 3 PXRD pattern for a co-crystal of carbamazepine and nicotinamide (Form I).
Figure 4:
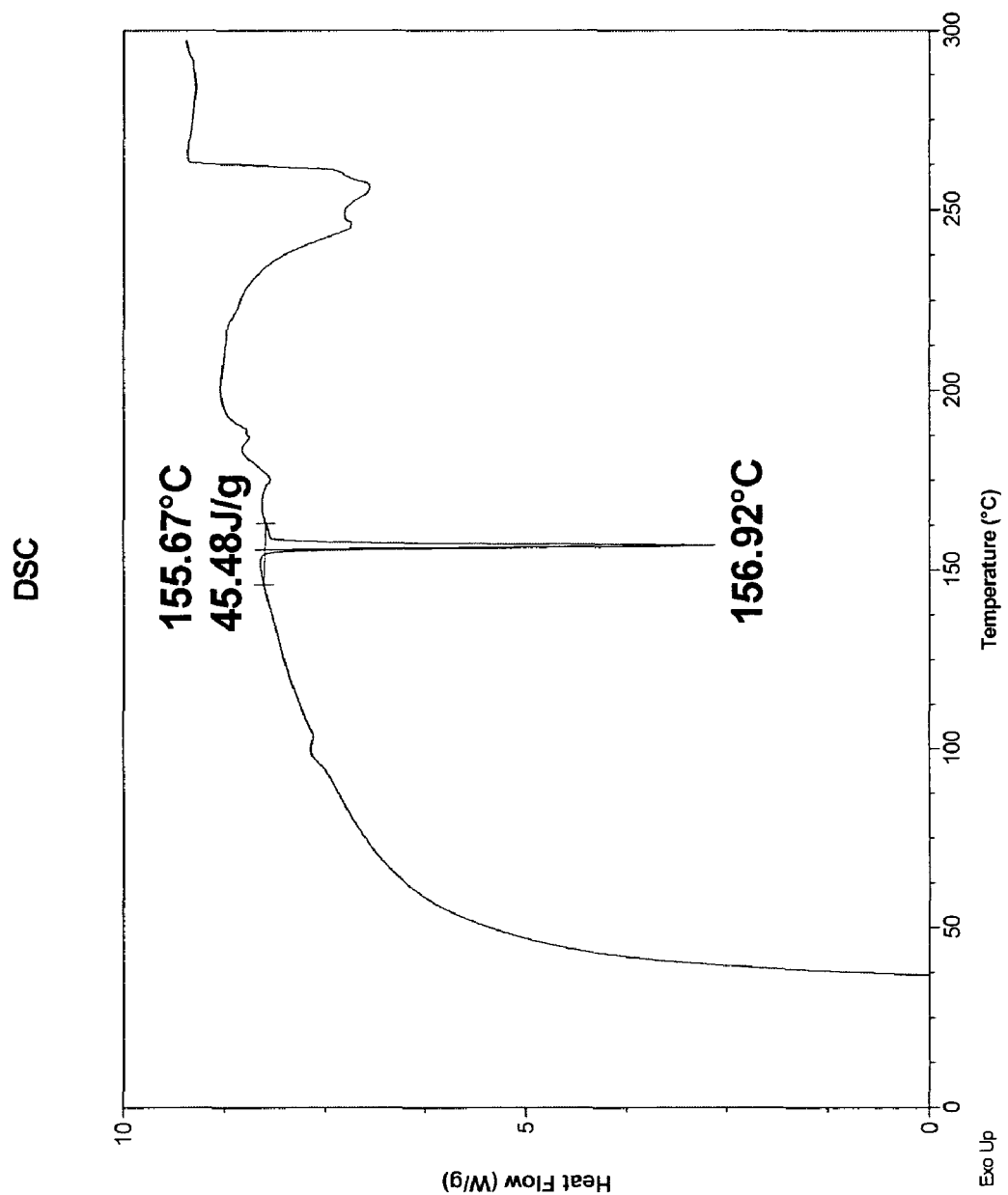
FIG. 4 DSC thermogram for a co-crystal of carbamazepine and nicotinamide (Form I).

1:1 carbamazepine:nicotinamide co-crystals (Form I) were prepared. A 12-block experiment was designed with 12 solvents. 1152 crystallization experiments were carried out using the CMAX platform. The co-crystal was obtained from samples containing toluene, acetone, or isopropyl acetate. Detailed characterization of the co-crystal is listed in Table V. (See FIGS. 3 and 4)

Example 3

Figure 5:
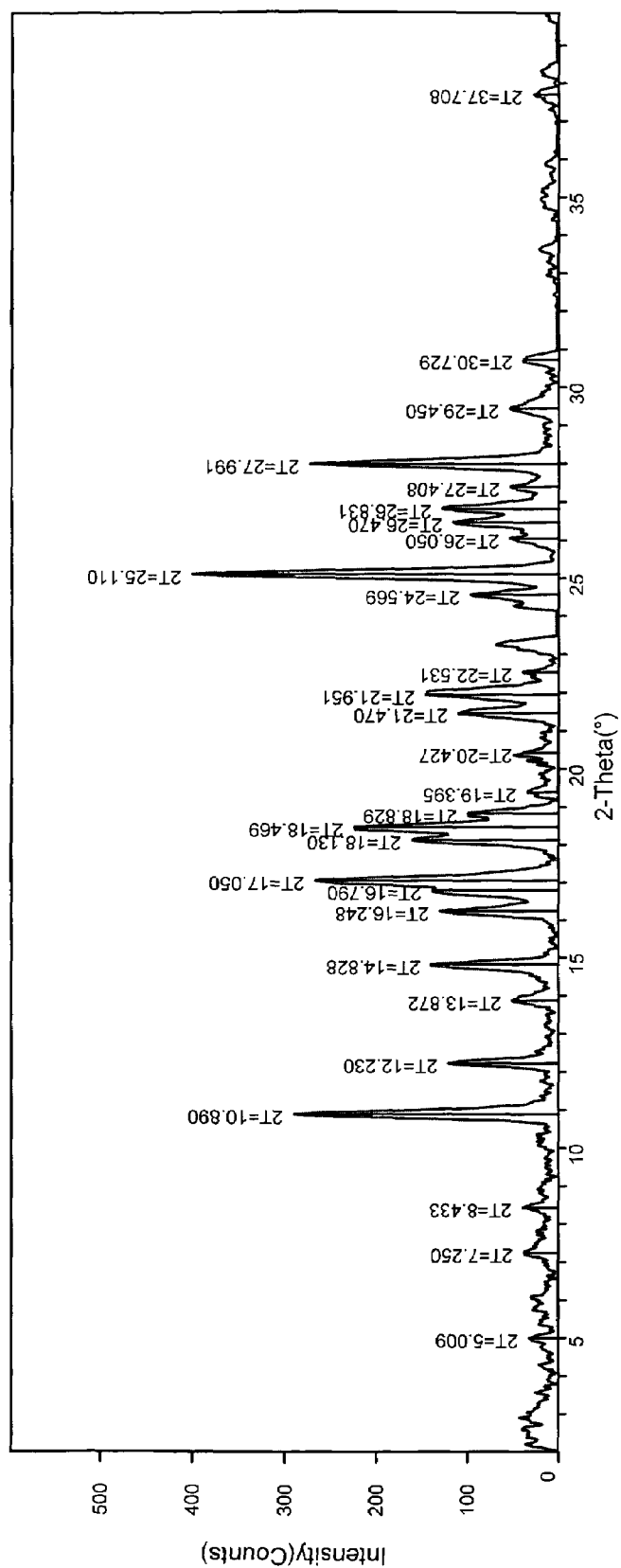
FIG. 5 PXRD pattern for a co-crystal of carbamazepine and trimesic acid (Form I).

1:1 carbamazepine:trimesic acid co-crystals (Form I) were prepared. A 9-block experiment was designed with 10 solvents. 864 crystallization experiments with 8 co-crystal formers and 3 concentrations were carried out using the CMAX platform. The co-crystal was obtained from samples containing methanol. Detailed characterization of the co-crystal is listed in Table V. (See FIG. 5)

Example 4

1:1 celecoxib:nicotinamide co-crystals were prepared. Celecoxib (100 mg, 0.26 mmol) and nicotinamide (32.0 mg, 0.26 mmol) were each dissolved in acetone (2 mL). The two solutions were mixed and the resulting mixture was allowed to evaporate slowly overnight. The precipitated solid was collected and characterized. Detailed characterization of the co-crystal is listed in Table V.

Example 5

Figure 6:
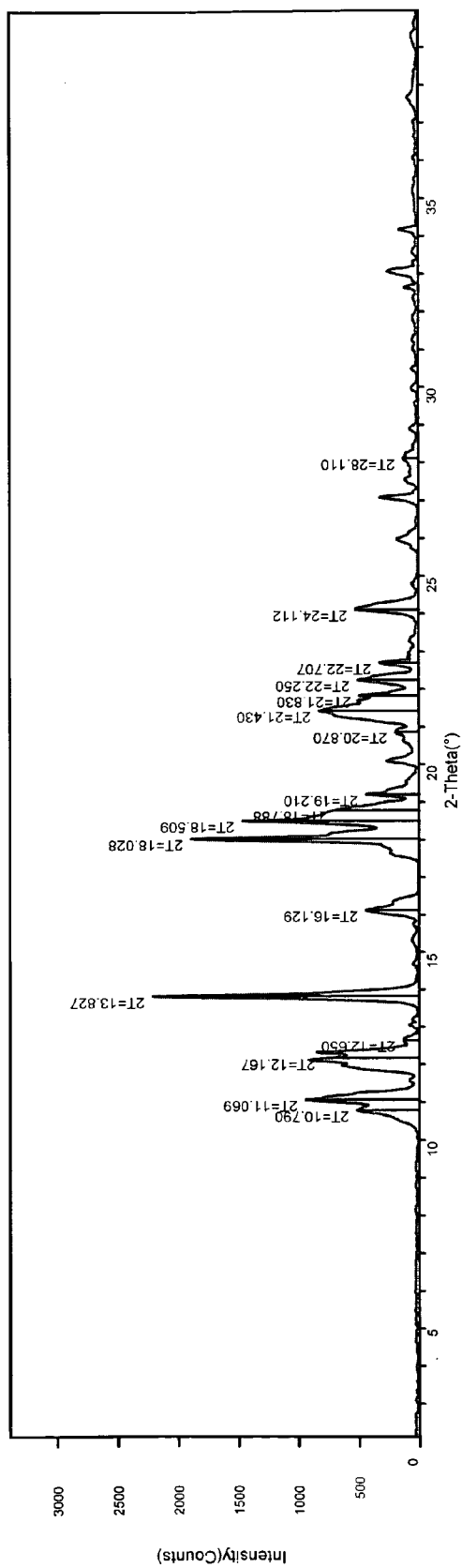
FIG. 6 PXRD pattern for a co-crystal of topiramate and 18-crown-6.
Figure 7:
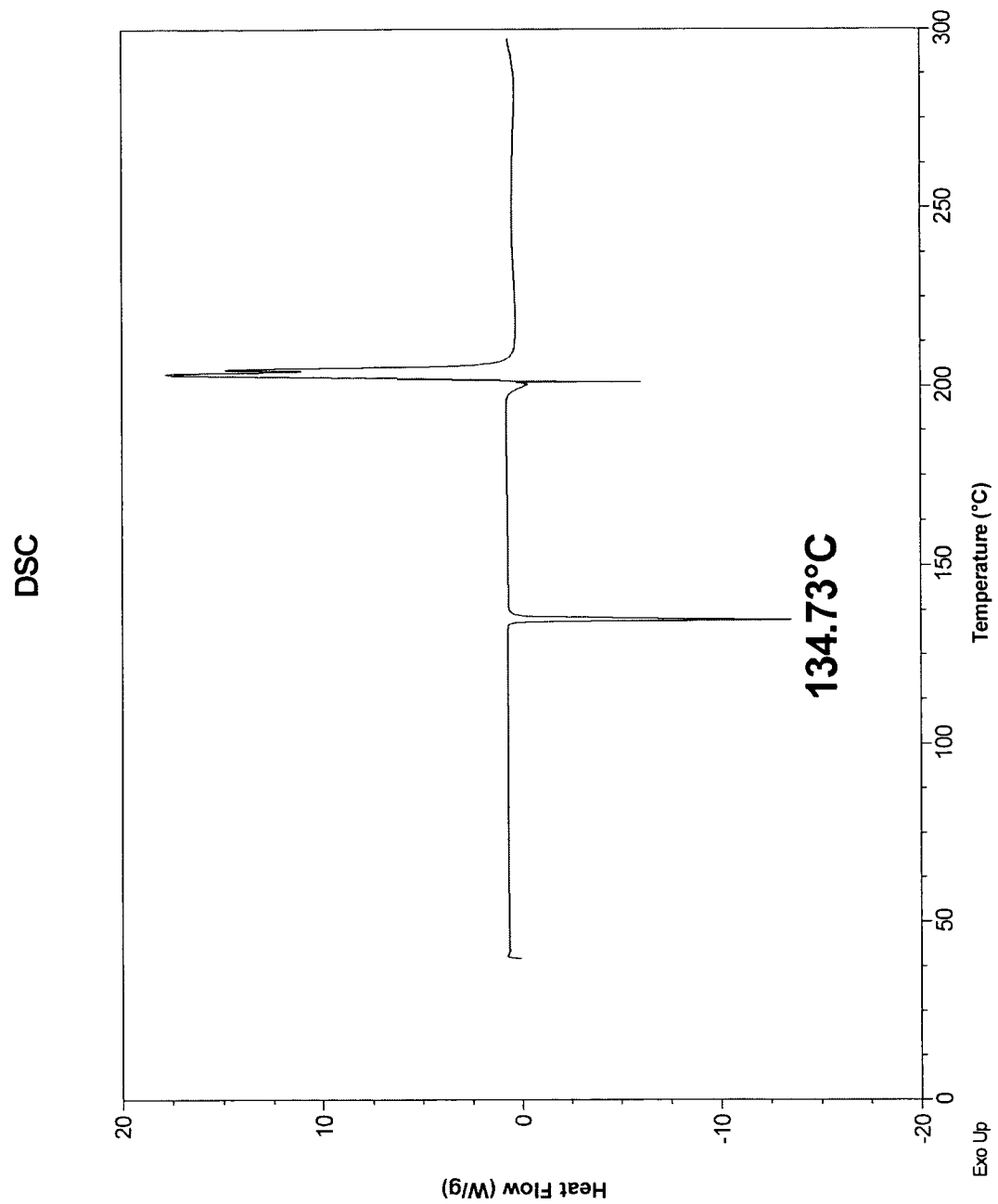
FIG. 7 DSC thermogram for a co-crystal of topiramate and 18-crown-6.

Co-crystals of topiramate and 18-crown-6 were prepared. An equimolar amount of topiramate and 18-crown-6 were dissolved in ether separately. The solution containing topiramate was then added to the solution containing 18-crown-6. A white solid precipitated after minor agitation and was collected and dried. Detailed characterization of the co-crystal is listed in Table V. (See FIGS. 6 and 7)

Example 6

Figure 8:
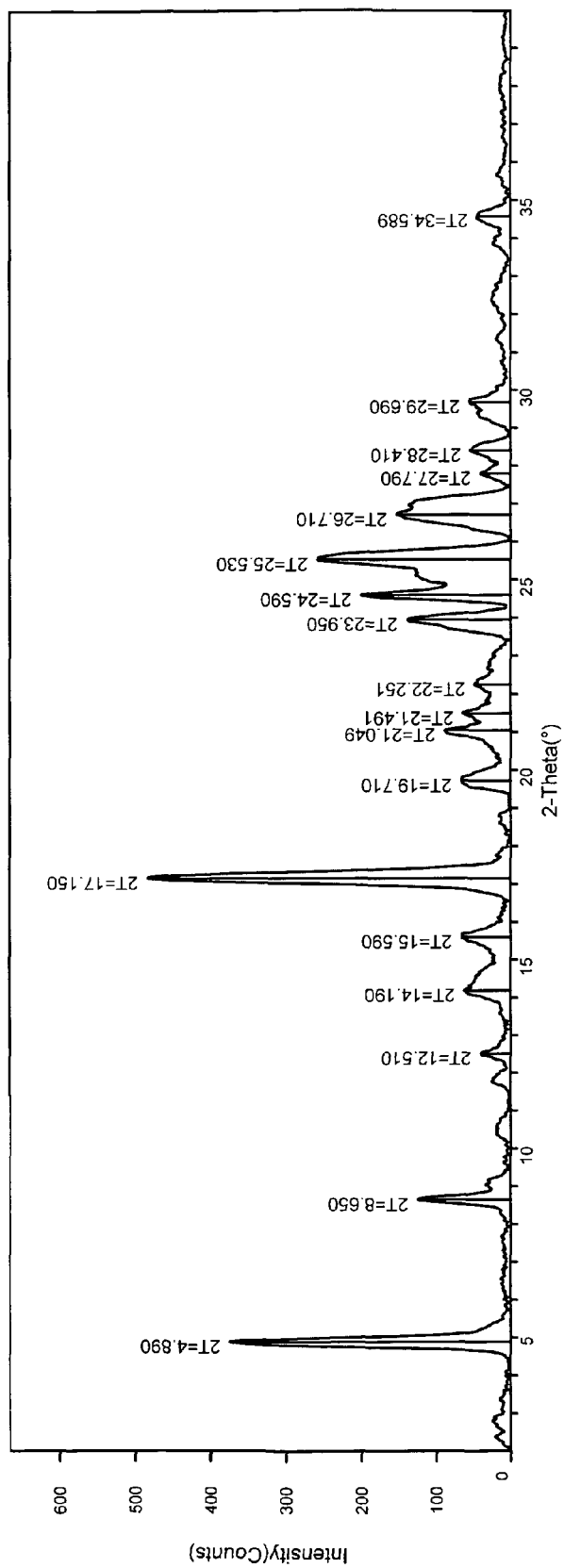
FIG. 8 PXRD pattern for a co-crystal of olanzapine and nicotinamide (Form I).
Figure 9:
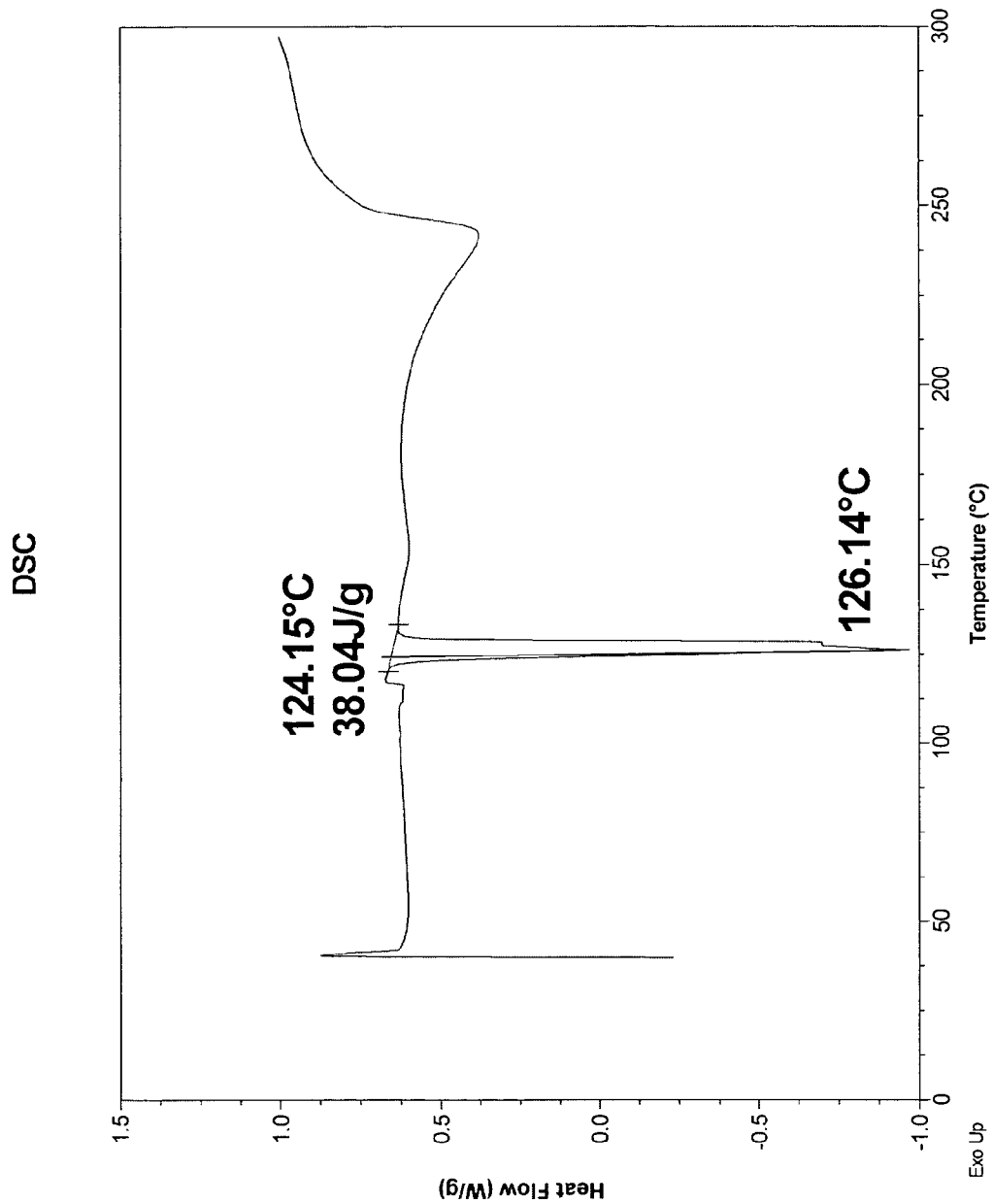
FIG. 9 DSC thermogram for a co-crystal of olanzapine and nicotinamide (Form I).
Figure 30:
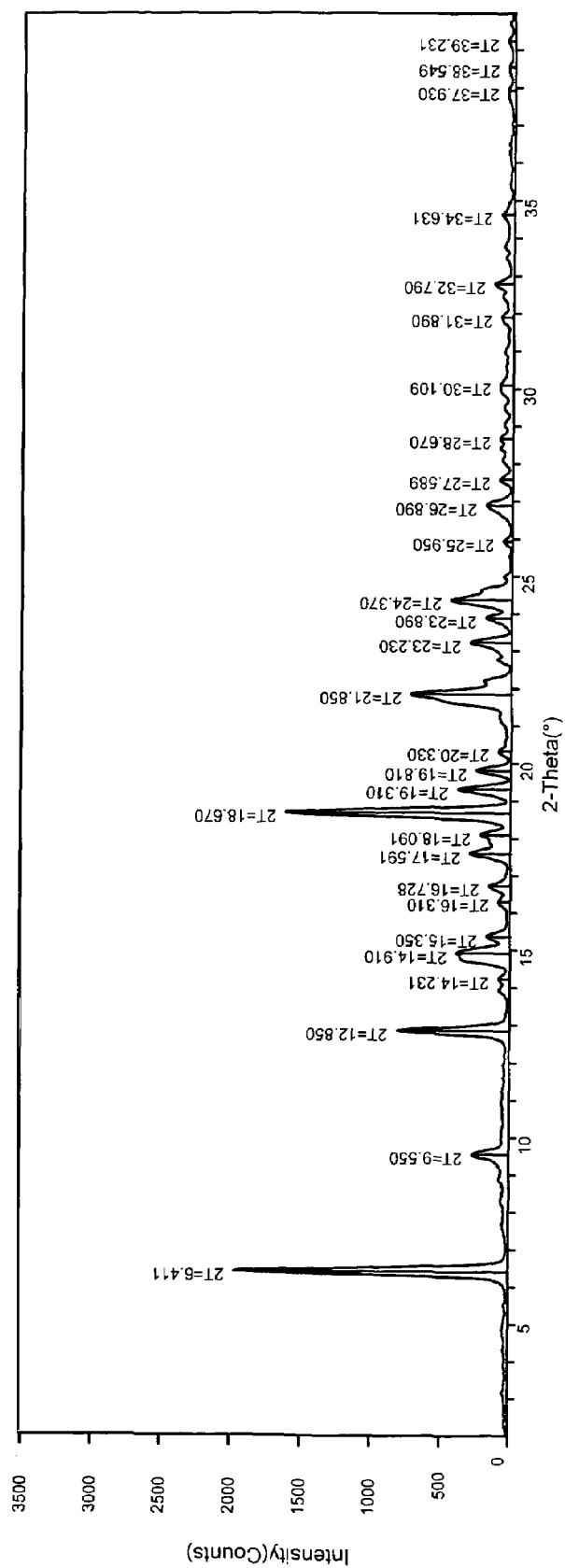
FIG. 30 PXRD pattern for a co-crystal of olanzapine and nicotinamide (Form II).
Figure 31:
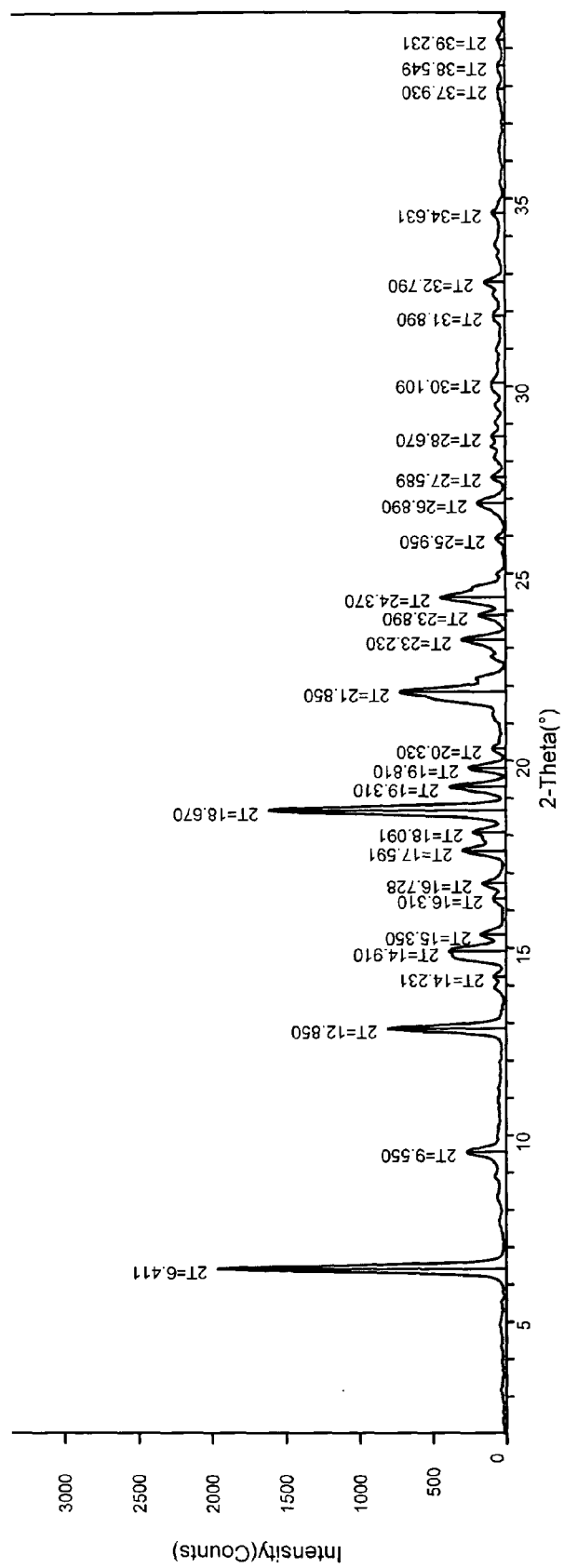
FIG. 31 PXRD pattern for a co-crystal of olanzapine and nicotinamide (Form III).

Co-crystals of olanzapine and nicotinamide (Form I and II) were prepared. A 9-block experiment was designed with 12 solvents. 864 crystallization experiments with 10 co-crystal formers and 3 concentrations were carried out using the CMAX platform. The co-crystal was obtained from tubes containing isopropyl acetate. PXRD and DSC characterization of the co-crystal (Form I and II) is listed in Table V. (See FIGS. 8, 9, and 30)

Example 7

Figure 10:
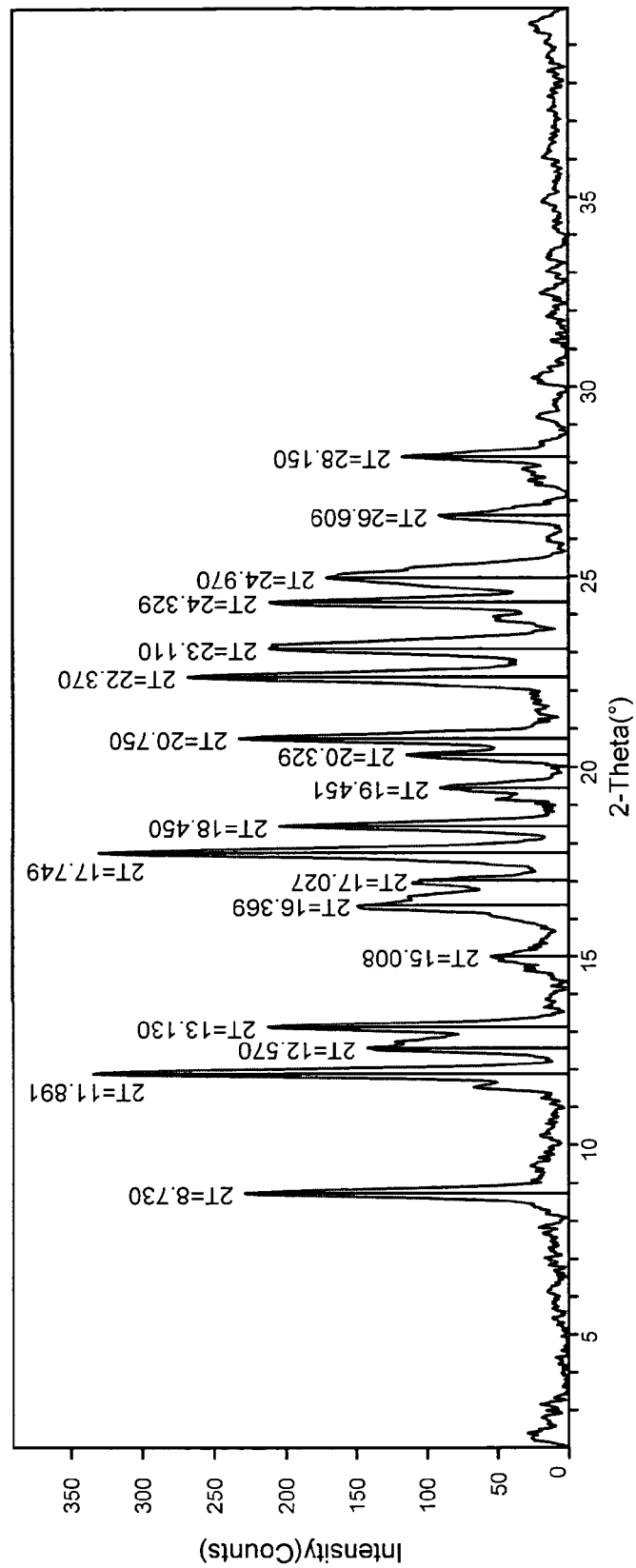
FIG. 10 PXRD pattern for a co-crystal of celecoxib and 18-crown-6.
Figure 11:
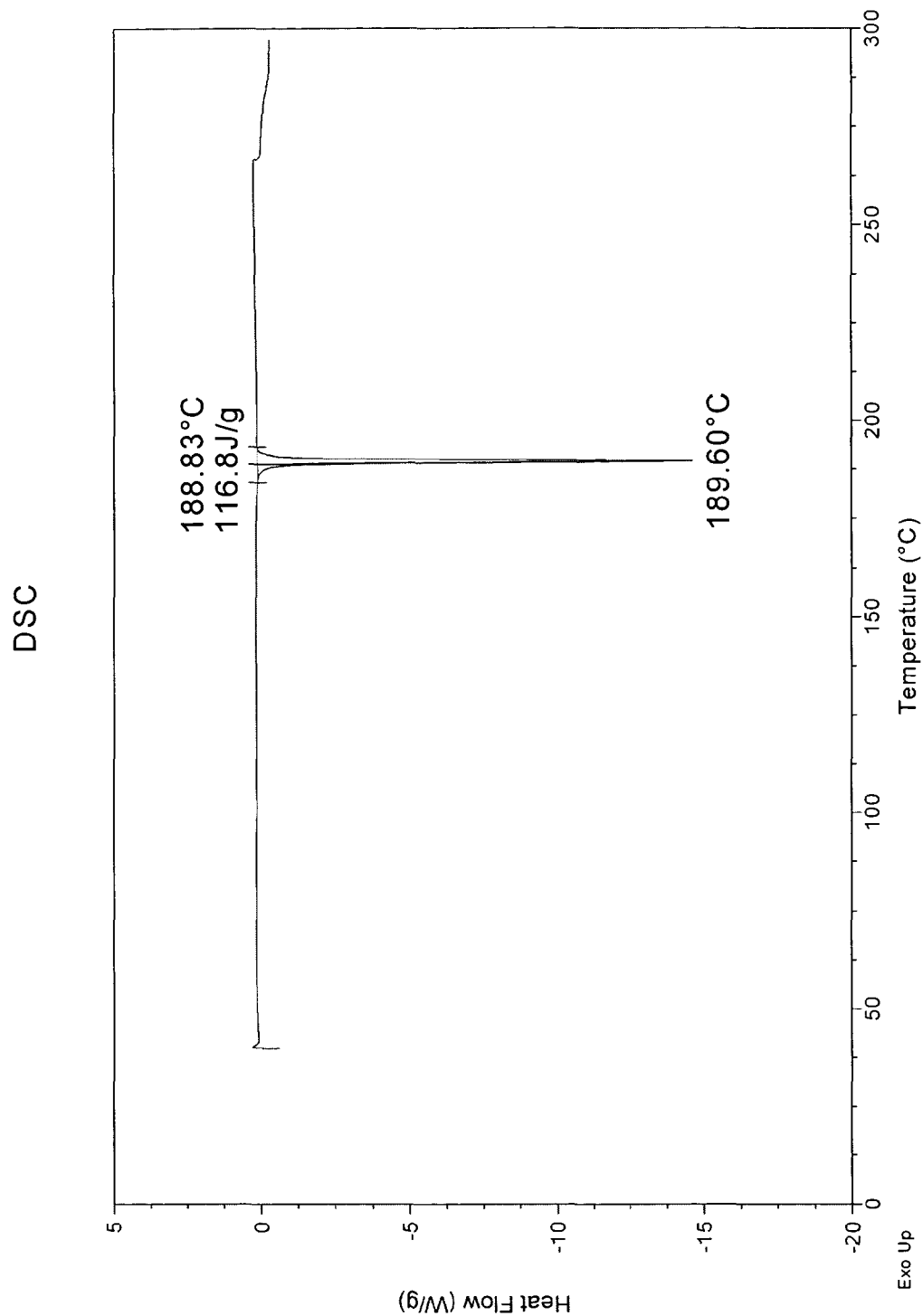
FIG. 11 DSC thermogram for a co-crystal of celecoxib and 18-crown-6.

Co-crystals of celecoxib and 18-crown-6 were prepared. A solution of celecoxib (157.8 mg, 0.4138 mmol) in $Et_2O$ (10.0 mL) was added to 18-crown-6 (118.1 mg, 0.447 mmol). The opaque solid dissolves immediately and a white solid subsequently began to crystallize very rapidly. The solid was collected via filtration and was washed with additional $Et_2O$ (5 mL). Detailed characterization of the co-crystal is listed in Table V. (See FIGS. 10 and 11)

Example 8

Figure 12:
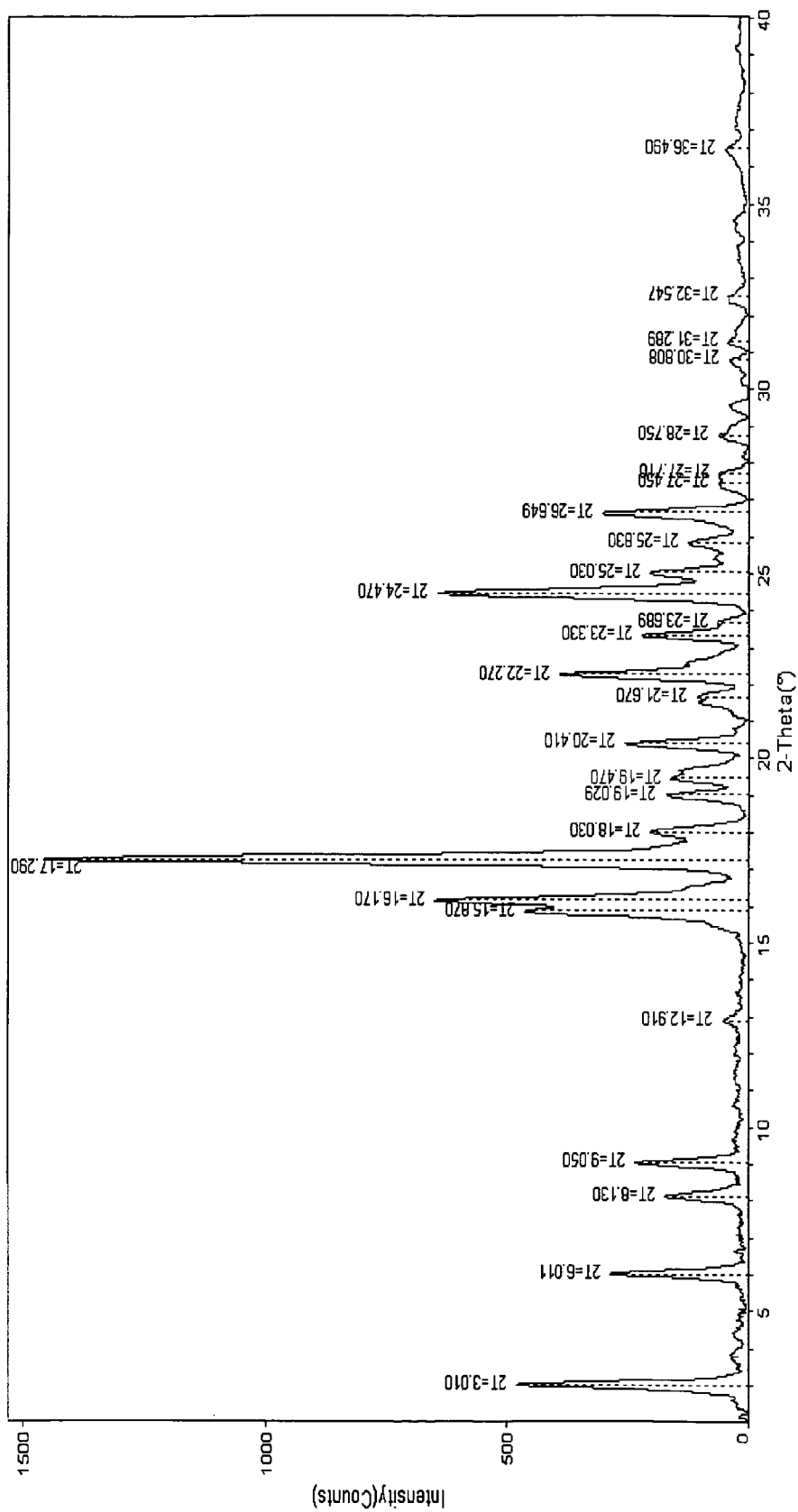
FIG. 12 PXRD pattern for a co-crystal of itraconazole and succinic acid.
Figure 13:
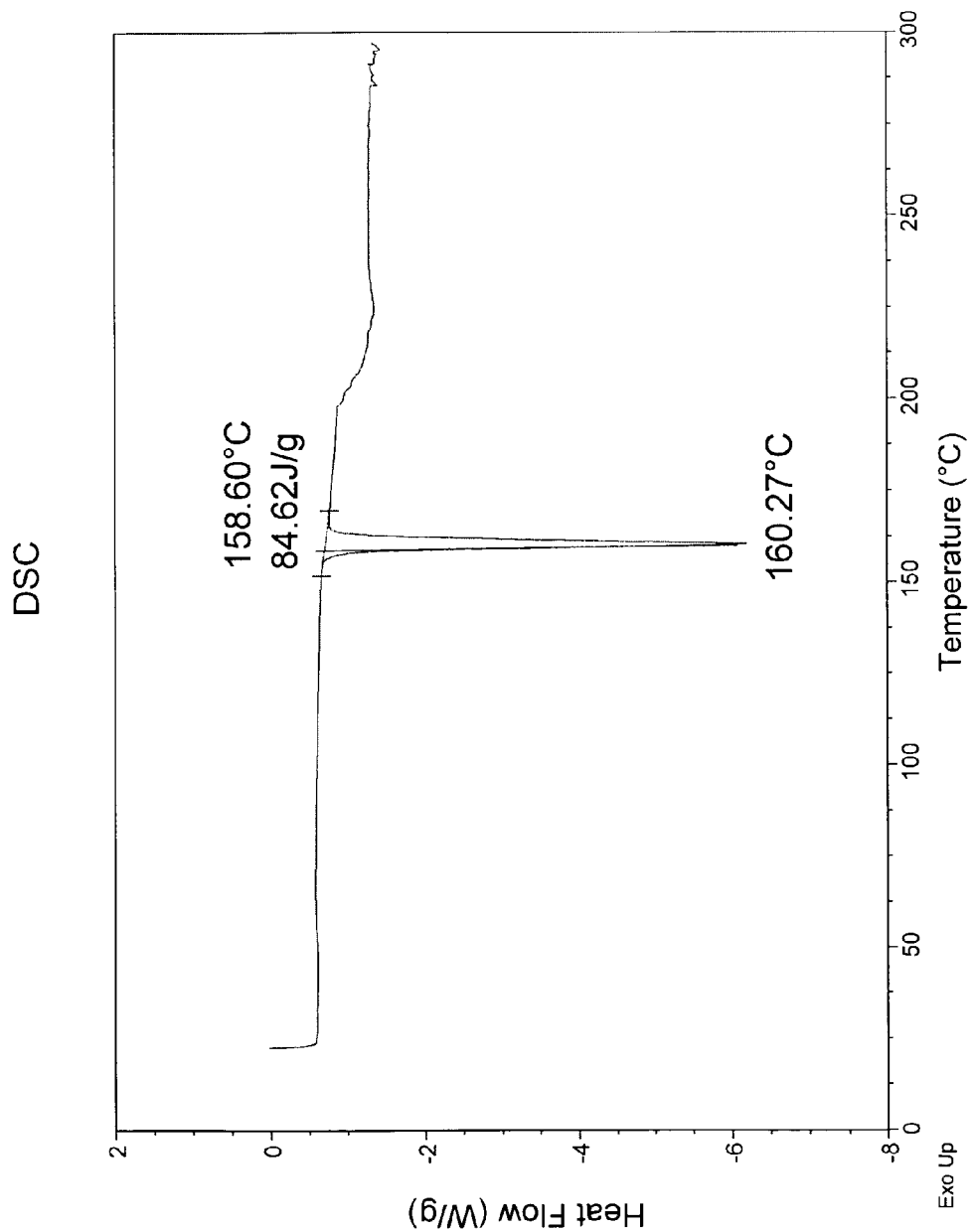
FIG. 13 DSC thermogram for a co-crystal of itraconazole and succinic acid.

Co-crystals of itraconazole and succinic acid were prepared. Approximately 51.1 mg of cis-itraconazole free base, 0.75 mL of THF, and a magnetic stir bar were charged into a screw cap vial, heated to reflux to dissolve, and then the vial was closed with the screw cap and placed on top of a hot plate maintained at a temperature between 60 and 75 degrees C. A solution of 77.7 mg of succinic acid in 1.58 mL of THF was prepared. 0.20 mL of the succinic acid solution was added to the cis-itraconazole solution and the solution remained clear. 0.75 mL of iso-propylacetate was added and the solution was seeded with <1 mg of the L-tartaric acid co-crystal salt from Example 10 below. The heat was turned off and the sample crystallized as it cooled to room temperature. The cooled sample was suction filtered. It was rinsed with 0.2-0.3 mL of THF. The filter cake was broken-up and allowed to air-dry for 1 hour prior to analysis. (See FIGS. 12 and 13)

Example 9

Figure 14:
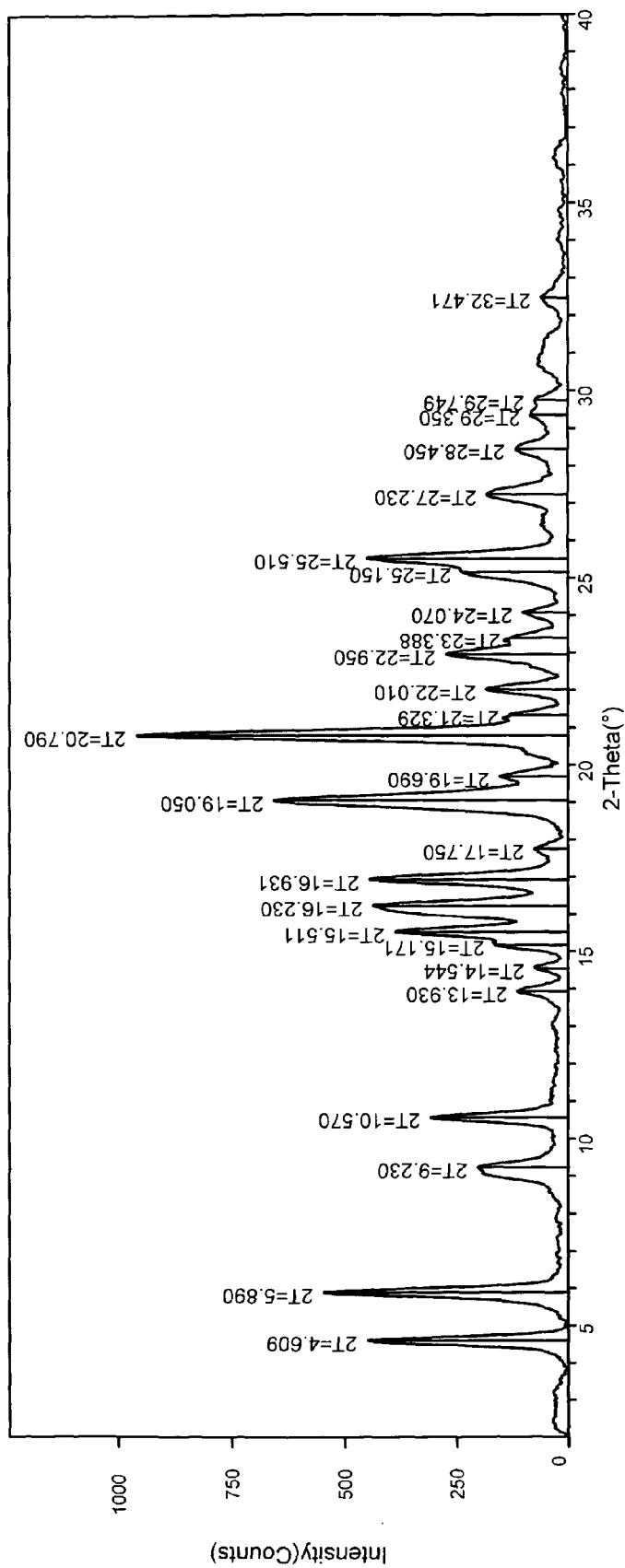
FIG. 14 PXRD pattern for a co-crystal of itraconazole and fumaric acid.
Figure 15:
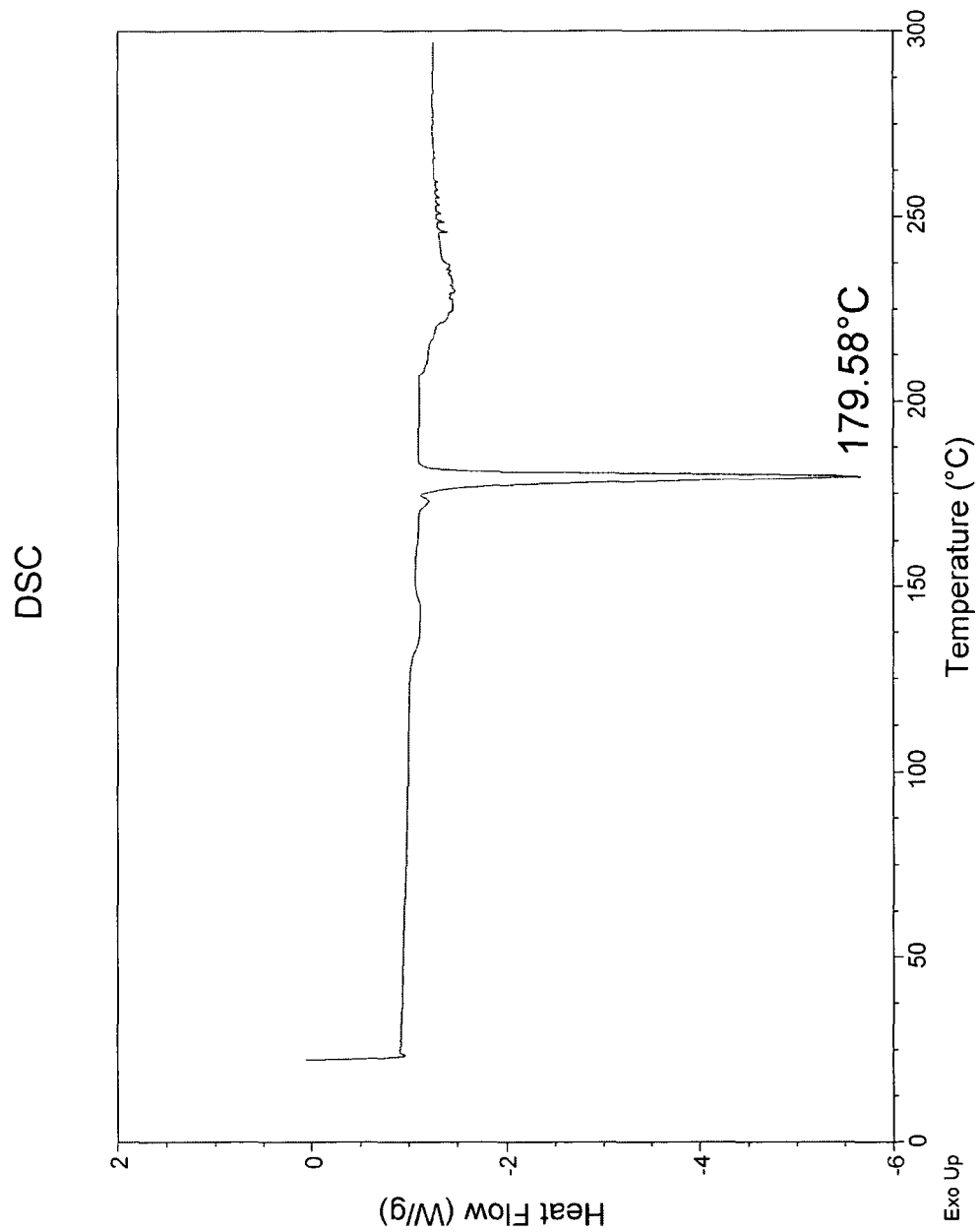
FIG. 15 DSC thermogram for a co-crystal of itraconazole and fumaric acid.

Co-crystals of itraconazole and fumaric acid were prepared. Approximately 500 mg of cis-itraconazole free base was placed in a 50 mL screw top bottle along with 33.33 mL of tetrahydrofuran (THF). 3.0887 mL of fumaric acid stock solution (prepared in Example 1) was then added to the beaker (resulting in a 1.05:1 ratio of salt former to free base). The cap was screwed on to seal the bottle and the bottle was placed in a 70 degrees C. oven (Model #1400E, VWR Scientific) and heated for approximately 1 hour. Thereafter, the bottle was removed from the oven, the cap from the bottle was removed, and the sample was allowed to evaporate under flowing air under ambient conditions. When all but about 5 mL of the solvent had evaporated, the remaining solvent was removed by decantation and the solid was isolated by filtering over a Whatman filter using suction. This solid was returned back into the 50 mL bottle with the remaining solid and the bottle was placed into the vacuum oven at approximately 25 mm Hg and the solid was allowed to dry for 4 days prior to analysis. (See FIGS. 14 and 15)

Example 10

Figure 16:
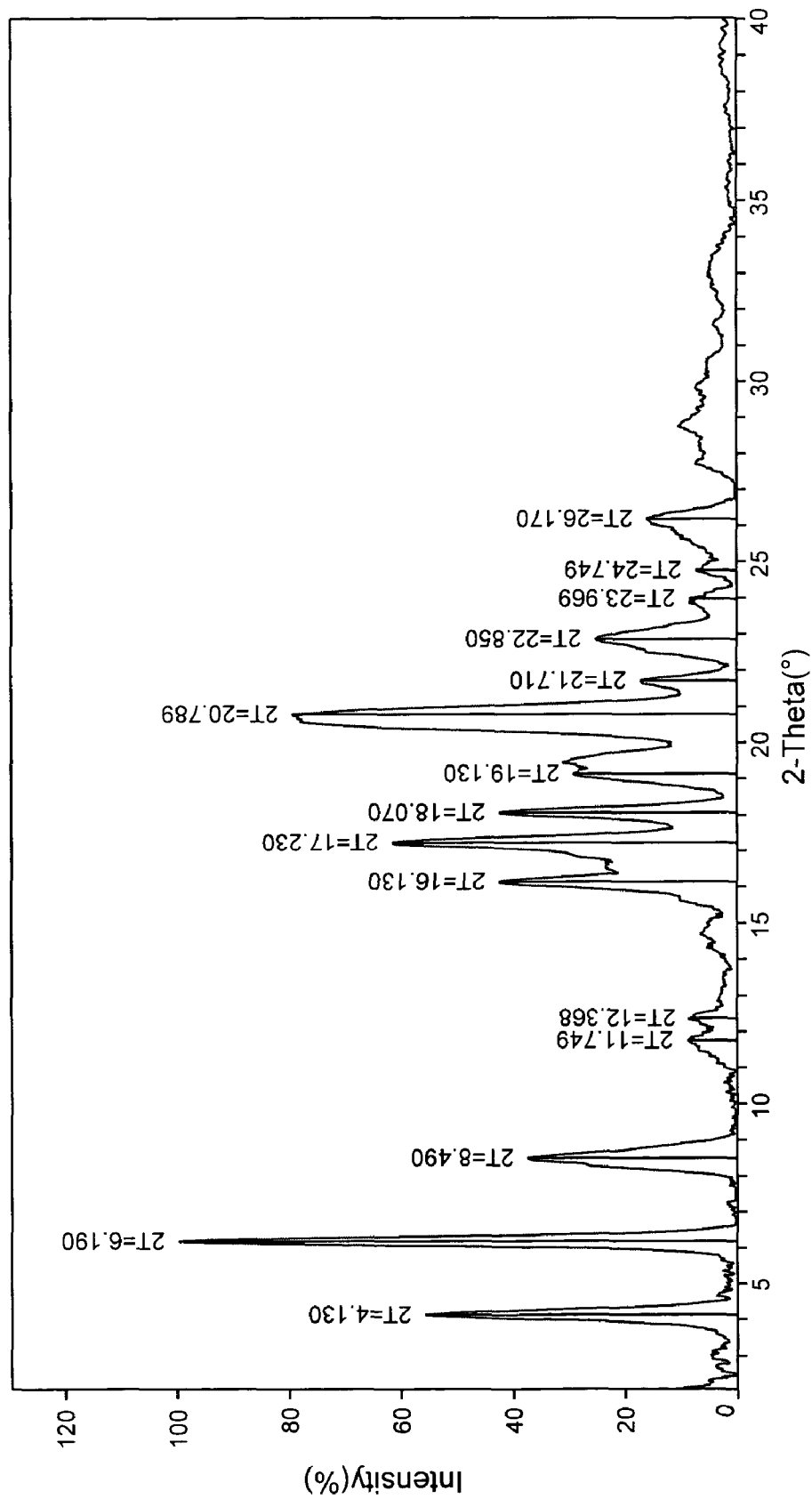
FIG. 16 PXRD pattern for a co-crystal of itraconazole and tartaric acid
Figure 17:
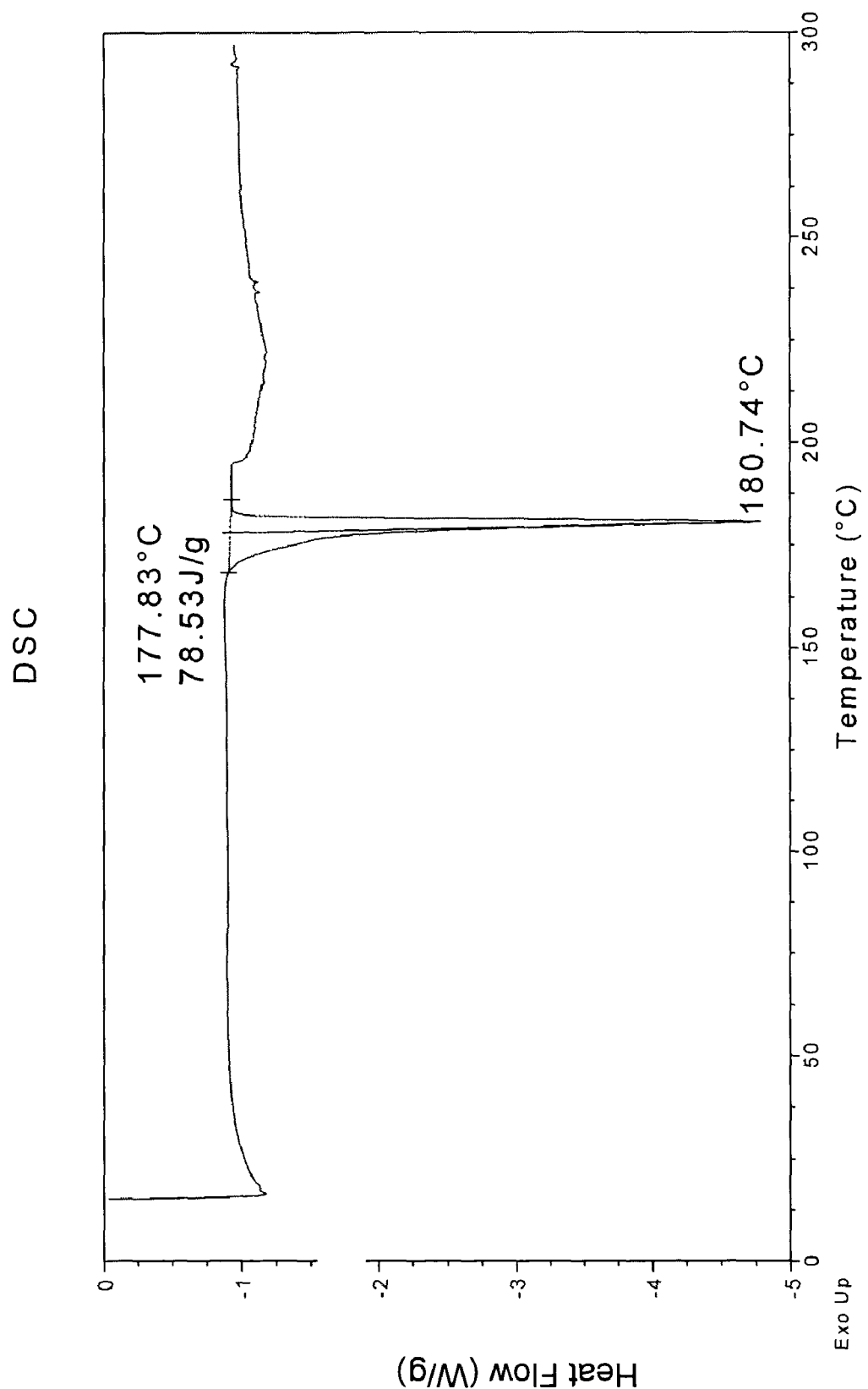
FIG. 17 DSC thermogram for a co-crystal of itraconazole and tartaric acid.

Co-crystals of itraconazole and tartaric acid were prepared. Approximately 100.4 mg of cis-itraconazole free base, 0.90 mL of THF, and a magnetic stir bar were charged into a screw cap vial, heated to reflux to dissolve, and then the vial was closed with the screw cap and placed in an oil bath maintained at 70 degrees C. A solution of 138.5 mg of L(+) tartaric acid in 1.15 mL of THF was prepared. 0.21 mL of the L(+)tartaric acid solution was added to the cis-itraconazole solution and the solution remained clear. 0.90 mL of iso-propylacetate was added and the solution was seeded with <1 mg of the salt from a preparation of DL-tartaric acid co-crystal. The sample was allowed to crystallize over about 5 minutes in the 70 degrees C. oil bath before it was removed and allowed to cool to room temperature. The cooled sample was suction filtered. It was rinsed with 0.2-0.3 mL of THF. The filter cake was broken-up and allowed to air-dry for 4 hours prior to analysis. (See FIGS. 16 and 17)

Example 11

Figure 18:
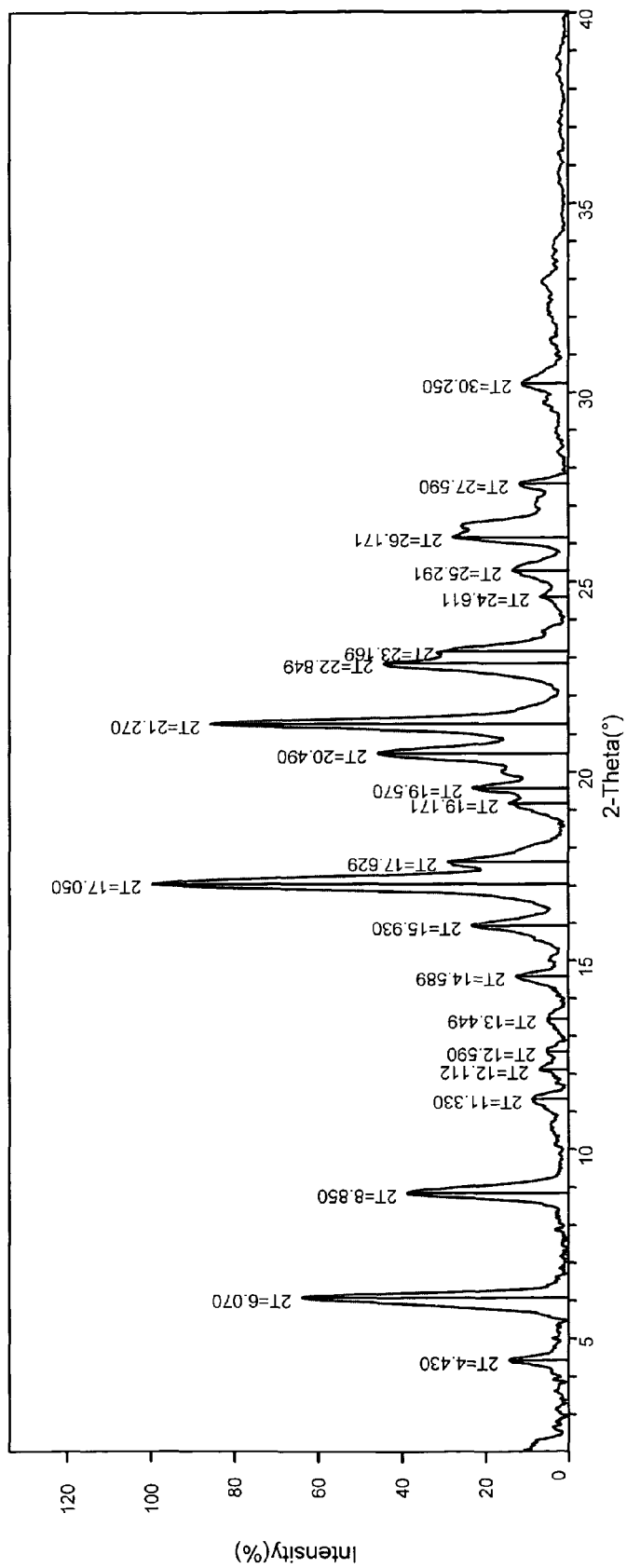
FIG. 18 PXRD pattern for a co-crystal of itraconazole and malic acid.
Figure 19:
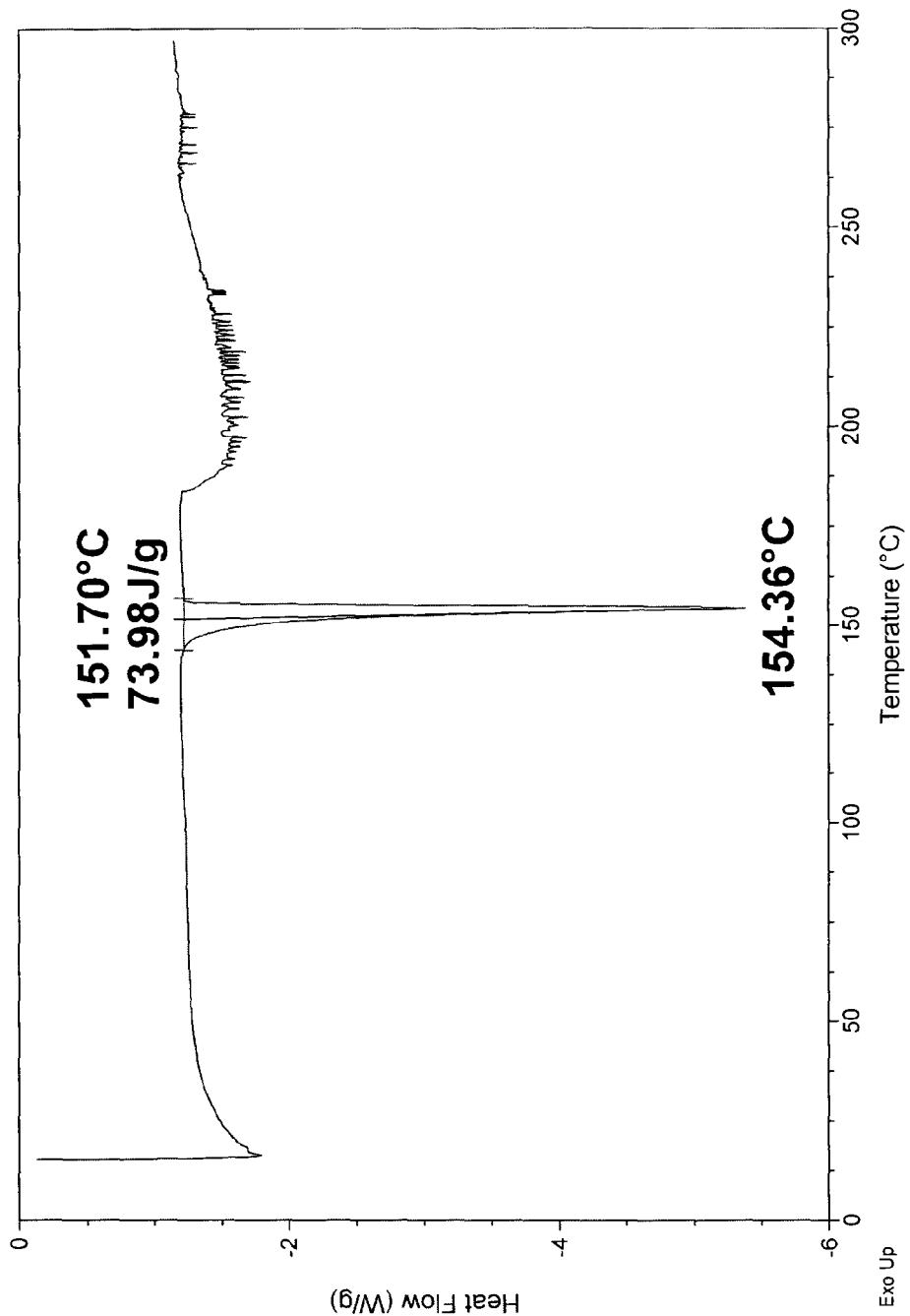
FIG. 19 DSC thermogram for a co-crystal of itraconazole and malic acid.

Co-crystals of itraconazole and malic acid were prepared. To prepare the L-malic acid co-crystal salt of cis-itraconazole, 100.4 mg of cis-itraconazole free base, 0.50 mL of THF, and a magnetic stir bar were charged into a screw cap vial. A solution of 191.3 mg of L(−)malic acid in 5.0 mL of THF was prepared. 0.50 mL of the L-malic acid solution was added to the vial containing cis-itraconazole and the solution was heated with a heat gun to dissolve. The solution was allowed to cool and was then seeded with <1 mg of the salt from cis-itraconazole-L-tartaric acid co-crystal. The cooled crystals were filtered in a centrifuge filter tube. The filter cake was broken-up and allowed to air-dry prior to analysis. (See FIGS. 18 and 19)

Example 12

Figure 20:
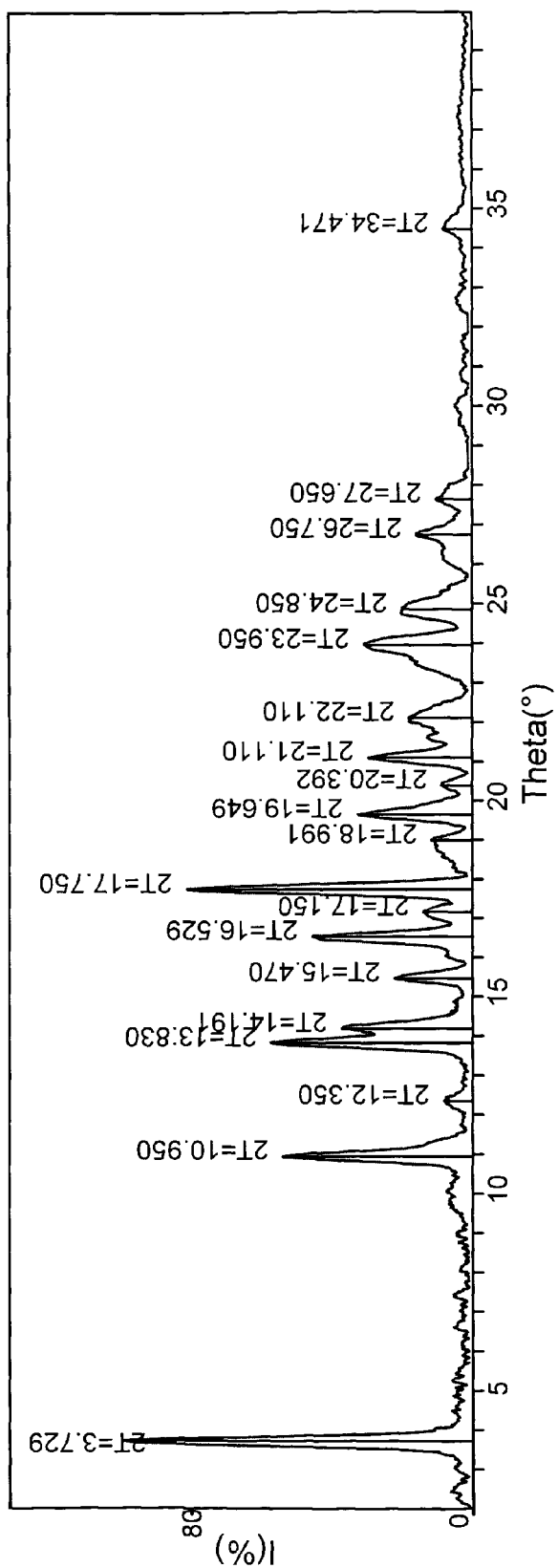
FIG. 20 PXRD pattern for a co-crystal of itraconazoleHCl and tartaric acid.
Figure 21:
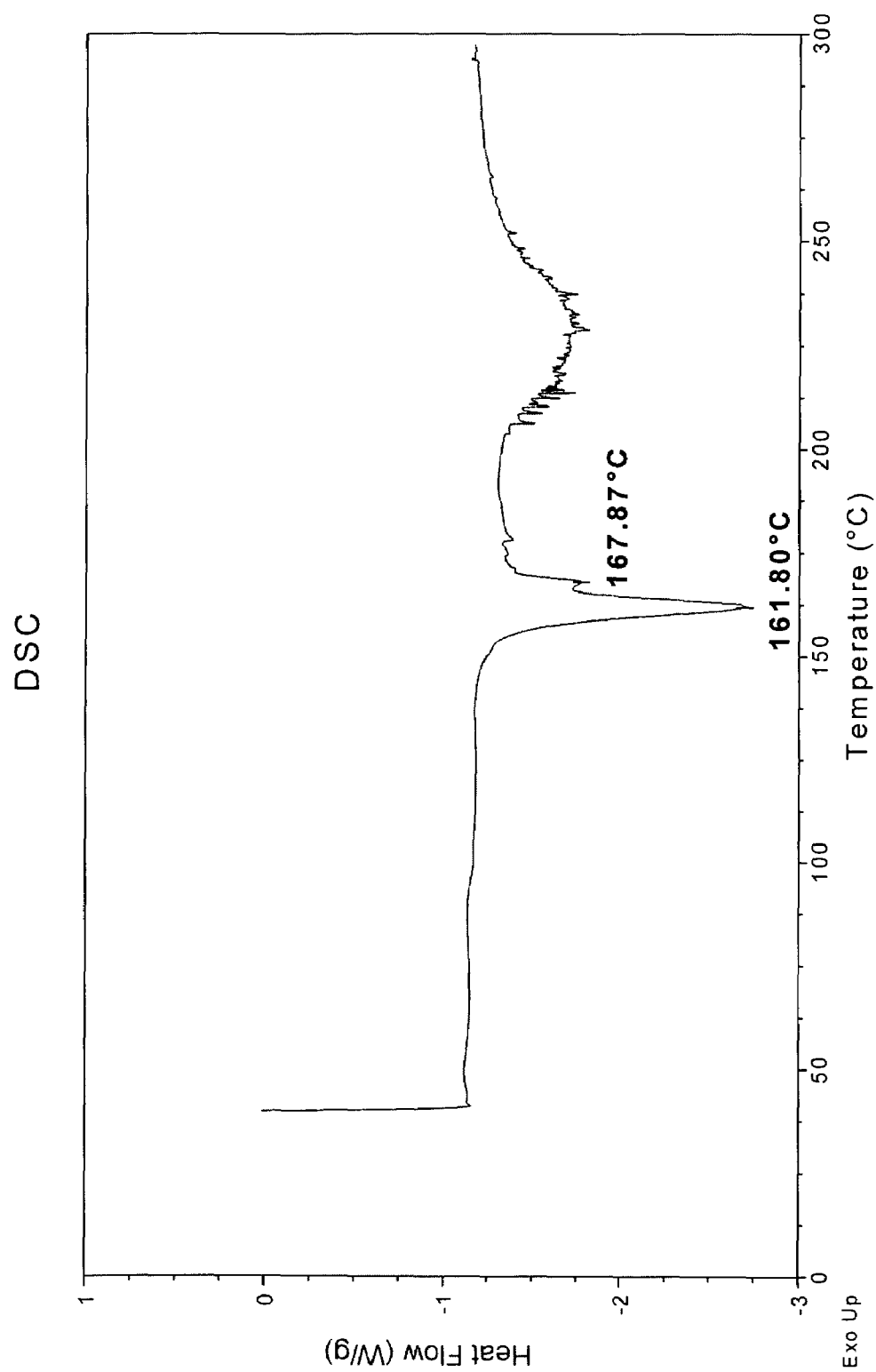
FIG. 21 DSC thermogram for a co-crystal of itraconazole-HCl and tartaric acid.

Co-crystals of itraconazole HCl and tartaric acid were prepared. Approximately 212.7 mg of L-tartaric acid and 118 microL of 37% HCl were dissolved in 25 mL of hot dioxane. This solution was added to 1.0 g of cis-itraconazole dissolved in 50 mL of hot dioxane with stirring. The mixture was heated until a clear solution formed and was then allowed to cool to room temperature. Upon cooling, 50 mL tert-butyl methyl ether was added and the crystals were harvested by vacuum filtration on a Buchner funnel with #4 Whatman filter paper. The crystals were washed 3 times with 5 mL aliquots of cold tert-butyl methyl ether and left to air dry. Approximately 573 mg of a crystalline form of cis-itraconazole HCl-tartaric acid (1:1:0.5) co-crystal were obtained. (See FIGS. 20 and 21)

Example 13

Figure 22:
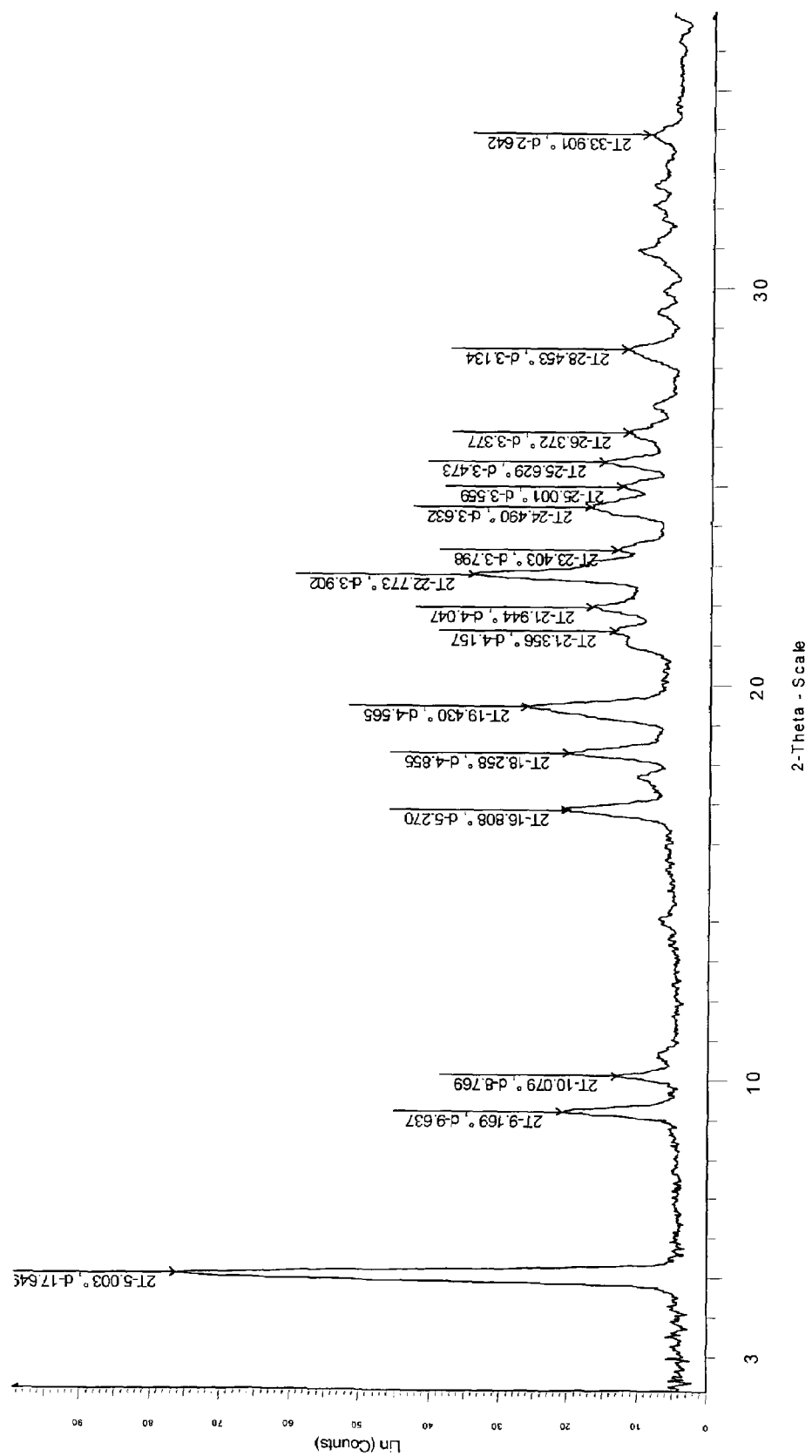
FIG. 22 PXRD pattern for a co-crystal of modafinil and malonic acid.

Co-crystals of modafinil and malonic acid were prepared. Using a 250 mg/ml modafinil-acetic acid solution, malonic acid was dissolved on a hotplate (about 67 degrees C.) at a 1:2 modafinil to malonic acid ratio. The mixture was dried under flowing nitrogen overnight. A powdery white solid was produced. After further drying for 1 day, acetic acid is removed (as determined by TGA) and the crystal structure, as determined by PXRD, remains the same. (See FIG. 22)

Example 14

Figure 23:
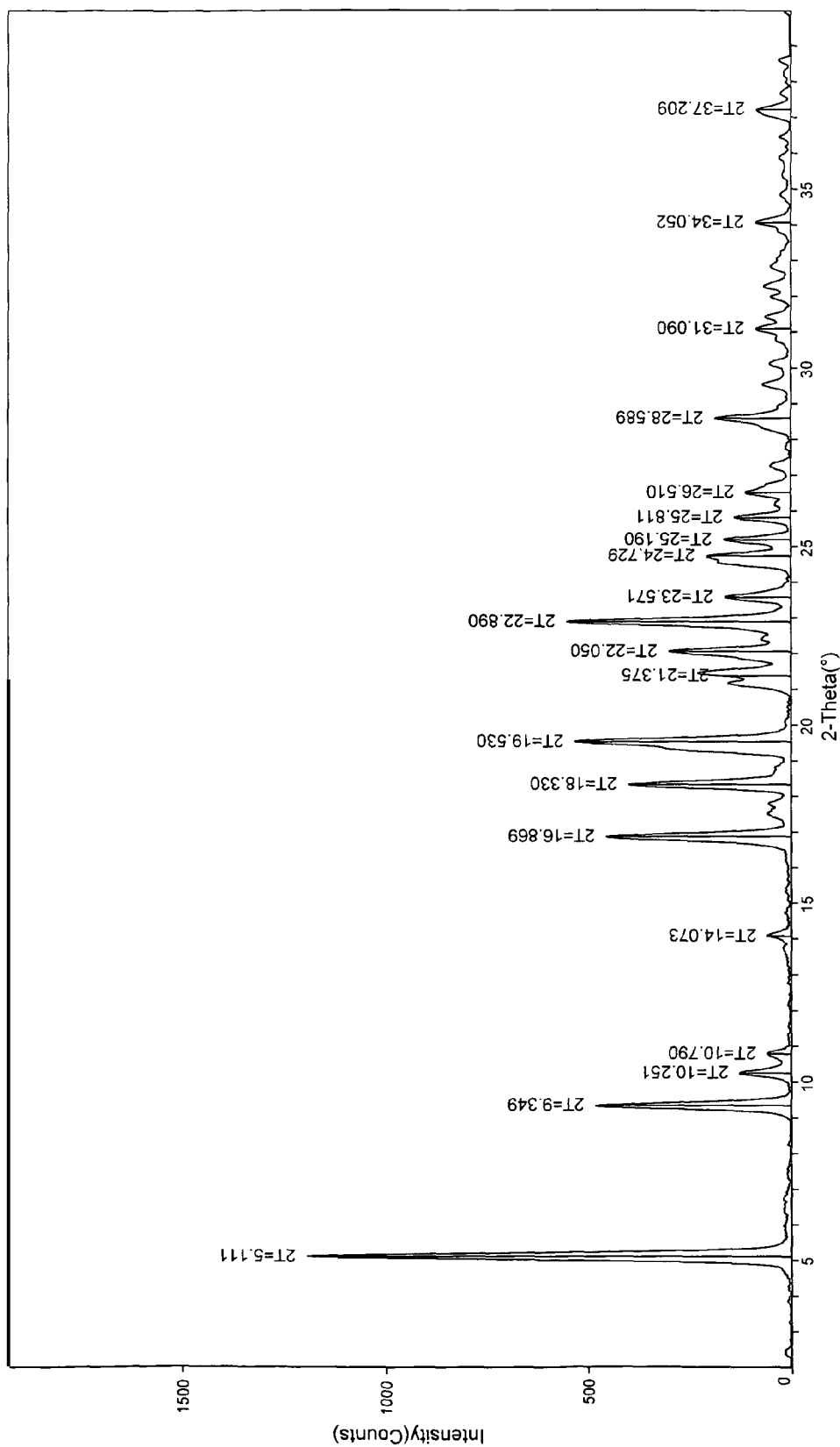
FIG. 23 PXRD pattern for a co-crystal of modafinil and benzamide.

Co-crystals of modafinil and benzamide were prepared. Modafinil (1 mg, 0.0037 mmol) and benzamide (0.45 mg, 0.0037 mmol) were dissolved in 1,2-dichloroethane (400 microL). The solution was allowed to evaporate to dryness and the resulting solid was characterized using PXRD. PXRD data for the co-crystal is listed in Table V. (See FIG. 23)

Example 15

Figure 24:
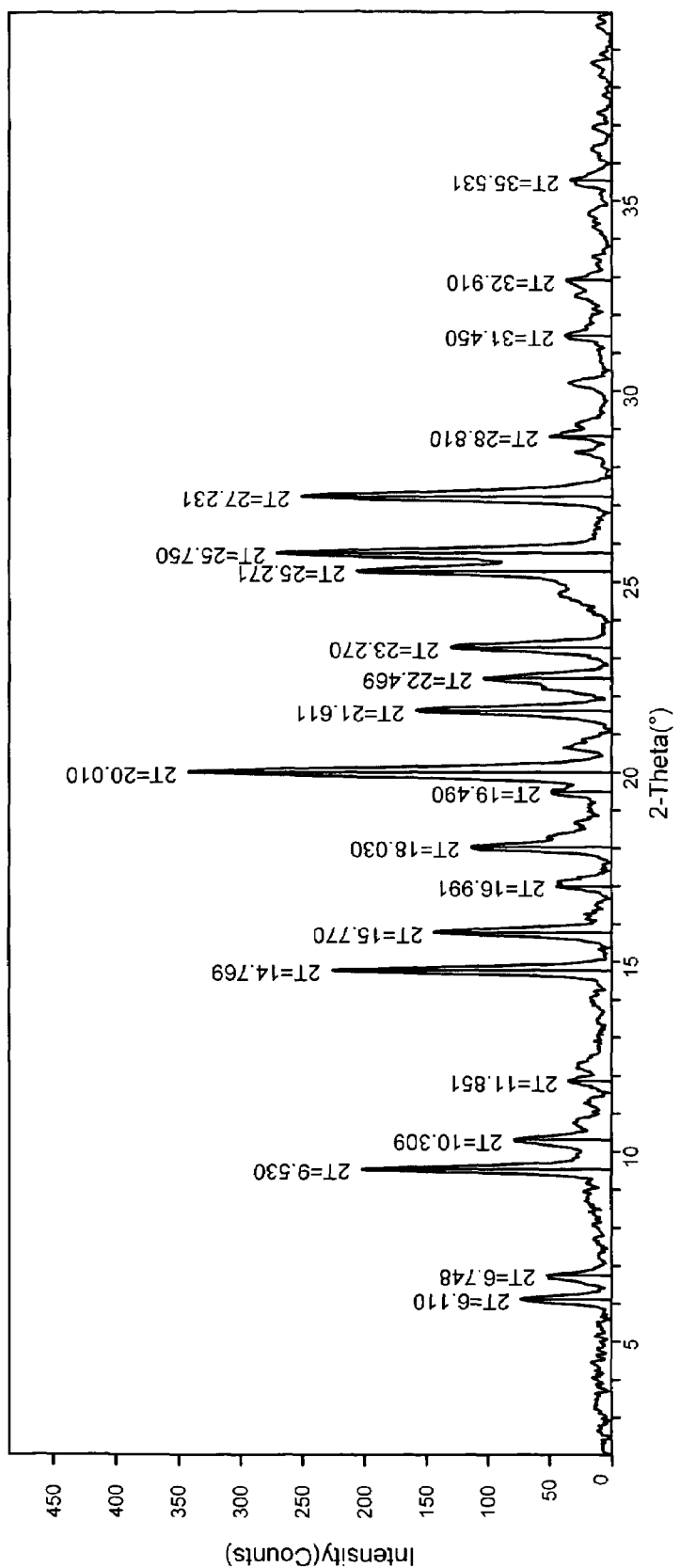
FIG. 24 PXRD pattern for a co-crystal of modafinil and mandelic acid.

Co-crystals of modafinil and mandelic acid were prepared. Modafinil (1 mg, 0.0037 mmol) and mandelic acid (0.55 mg, 0.0037 mmol) were dissolved in acetone (400 microL). The solution was allowed to evaporate to dryness and the resulting solid was characterized using PXRD. PXRD data for the co-crystal is listed in Table V. (See FIG. 24)

Example 16

Figure 25:
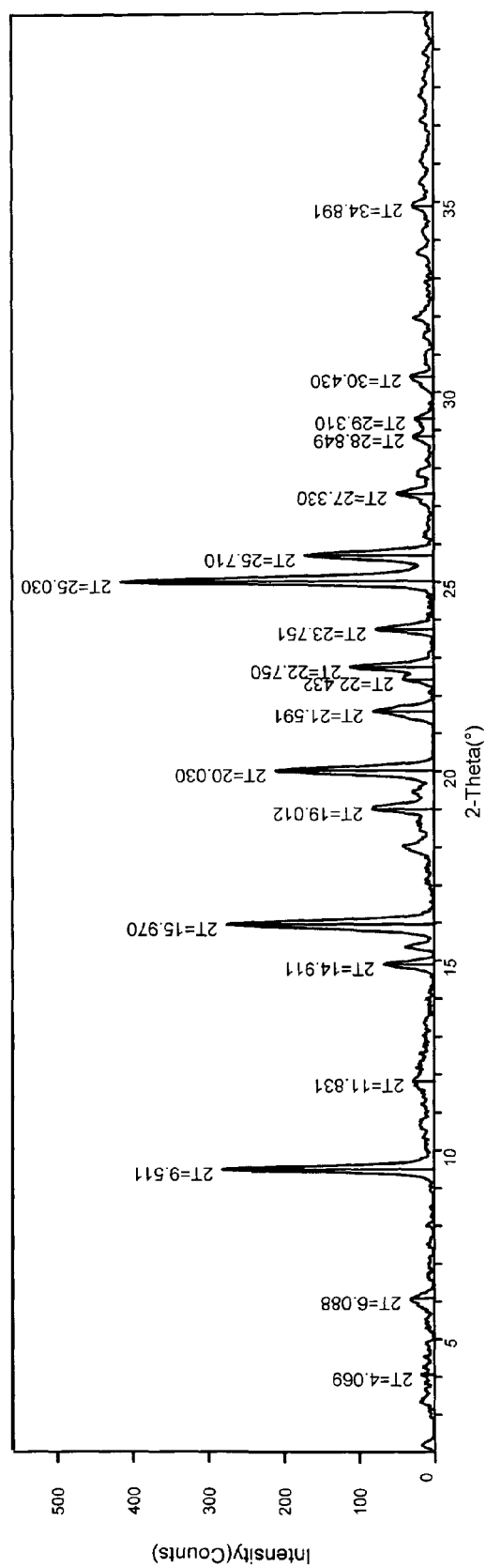
FIG. 25 PXRD pattern for a co-crystal of modafinil and glycolic acid.

Co-crystals of modafinil and glycolic acid were prepared. Modafinil (1 mg, 0.0037 mmol) and glycolic acid (0.30 mg, 0.0037 mmol) were dissolved in acetone (400 microL). The solution was allowed to evaporate to dryness and the resulting solid was characterized using PXRD. PXRD data for the co-crystal is listed in Table V. (See FIG. 25)

Example 17

Figure 26:
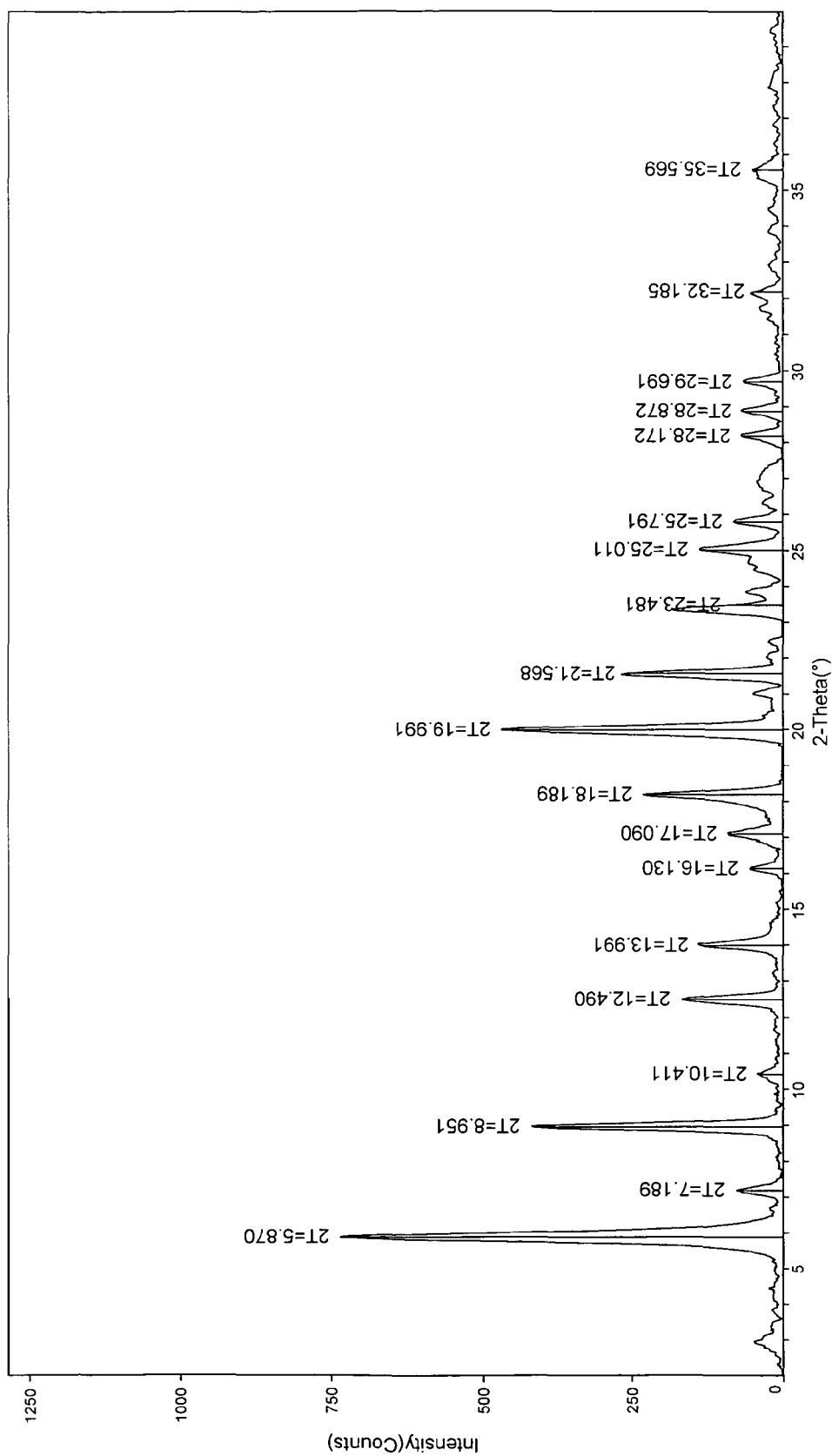
FIG. 26 PXRD pattern for a co-crystal of modafinil and fumaric acid.

Co-crystals of modafinil and fumaric acid were prepared. Modafinil (1 mg, 0.0037 mmol) and fumaric acid (0.42 mg, 0.0037 mmol) were dissolved in 1,2-dichloroethane (400 microL). The solution was allowed to evaporate to dryness and the resulting solid was characterized using PXRD. PXRD data for the co-crystal is listed in Table V. (See FIG. 26)

Example 18

Figure 43:
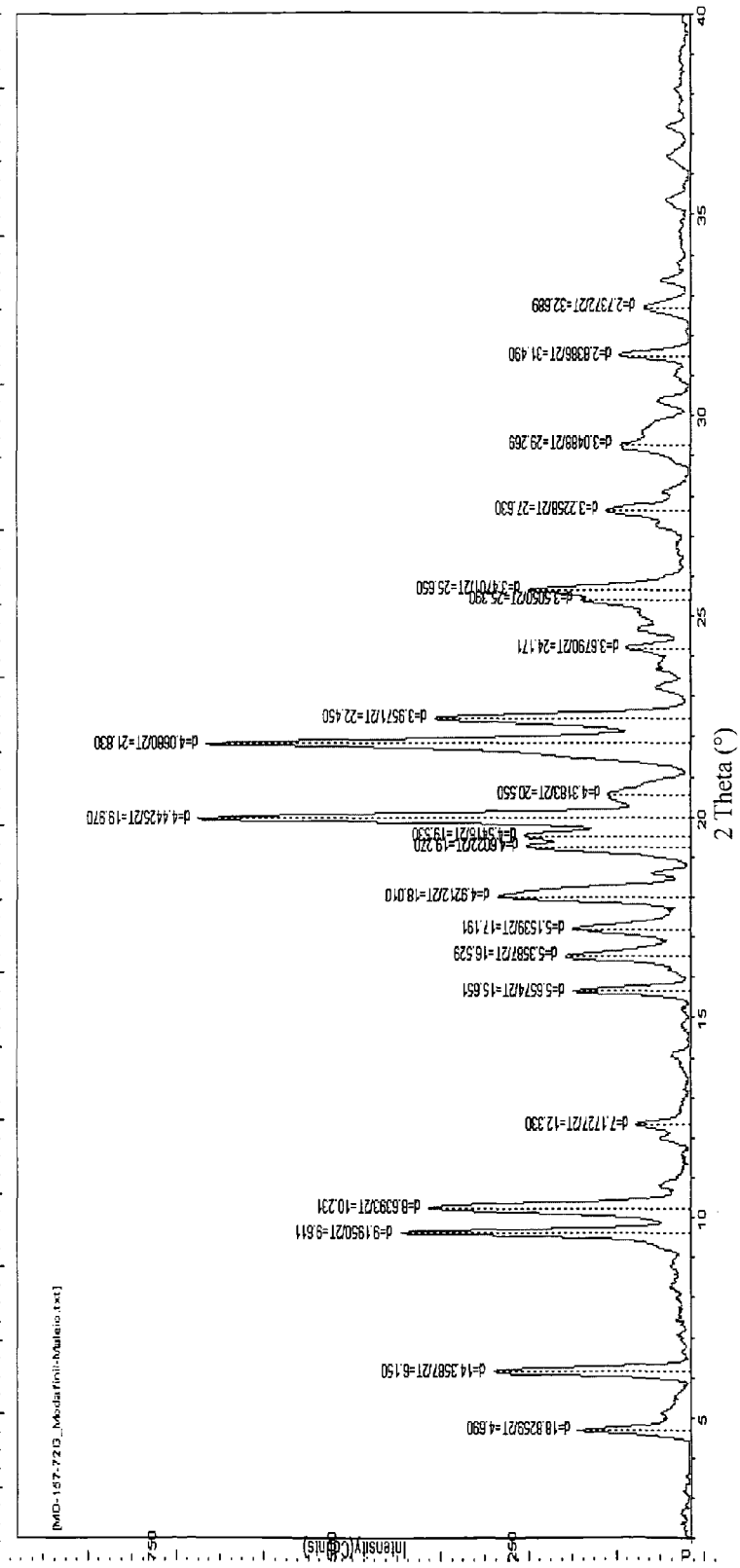
FIG. 43 PXRD pattern for a co-crystal of modafinil and maleic acid.

Co-crystals of modafinil and maleic acid were prepared. Using a 250 mg/ml modafinil-acetic acid solution, maleic acid was dissolved on a hotplate (about 67 degrees C.) at a 2:1 modafinil to maleic ratio. The mixture was dried under flowing nitrogen overnight. A clear amorphous material remained. Solids began to grow after 2 days stored in a sealed vial at room temperature. (See FIG. 43)

Example 19

Co-crystals of olanzapine and nicotinamide (Form III) were prepared. Olanzapine (40 µL of 25 mg/mL stock solution in tetrahydrofuran) and nicotinamide (37.6 µL of 20 mg/mL stock solution in methanol) were added to a glass vial and dried under a flow of nitrogen. To the solid mixture was added isopropyl acetate (100 µL) and the vial was sealed with an aluminum cap. The suspension was then heated at 70 degrees C. for two hours in order to dissolve all of the solid material. The solution was then cooled to 5 degrees C. and maintained at that temperature for 24 hours. After 24 hours the vial was uncapped and the mixture was concentrated to 50 µL of total volume. The vial was then resealed with an aluminum cap and was maintained at 5 degrees C. for an additional 24 hours. Large, yellow plates were observed and were collected (Form III). The solid was characterized with single crystal x-ray diffraction and powder x-ray diffraction. PXRD characterization of the co-crystal is listed in Table V. (See FIGS. 31 and 32A-D)

Figure 32C:
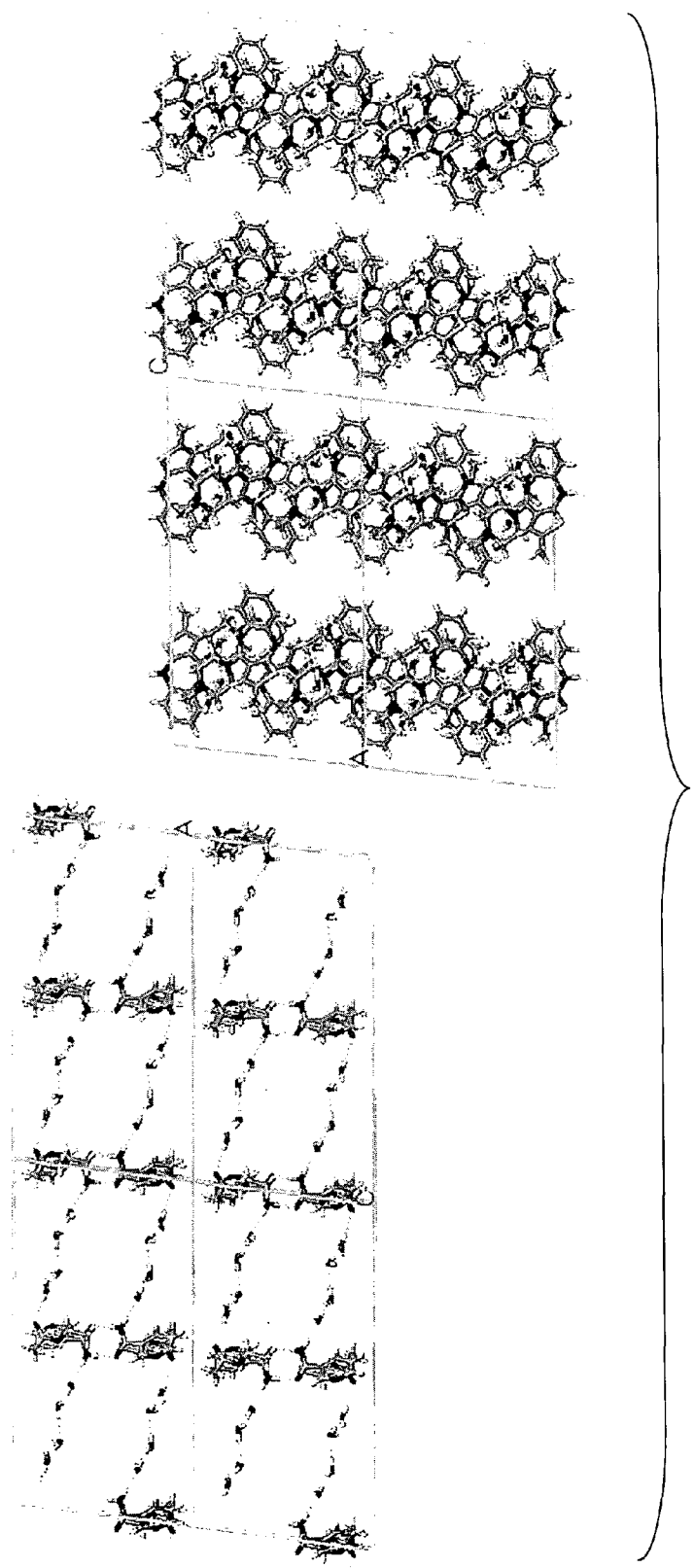
Figure 32D:
Figure 33:
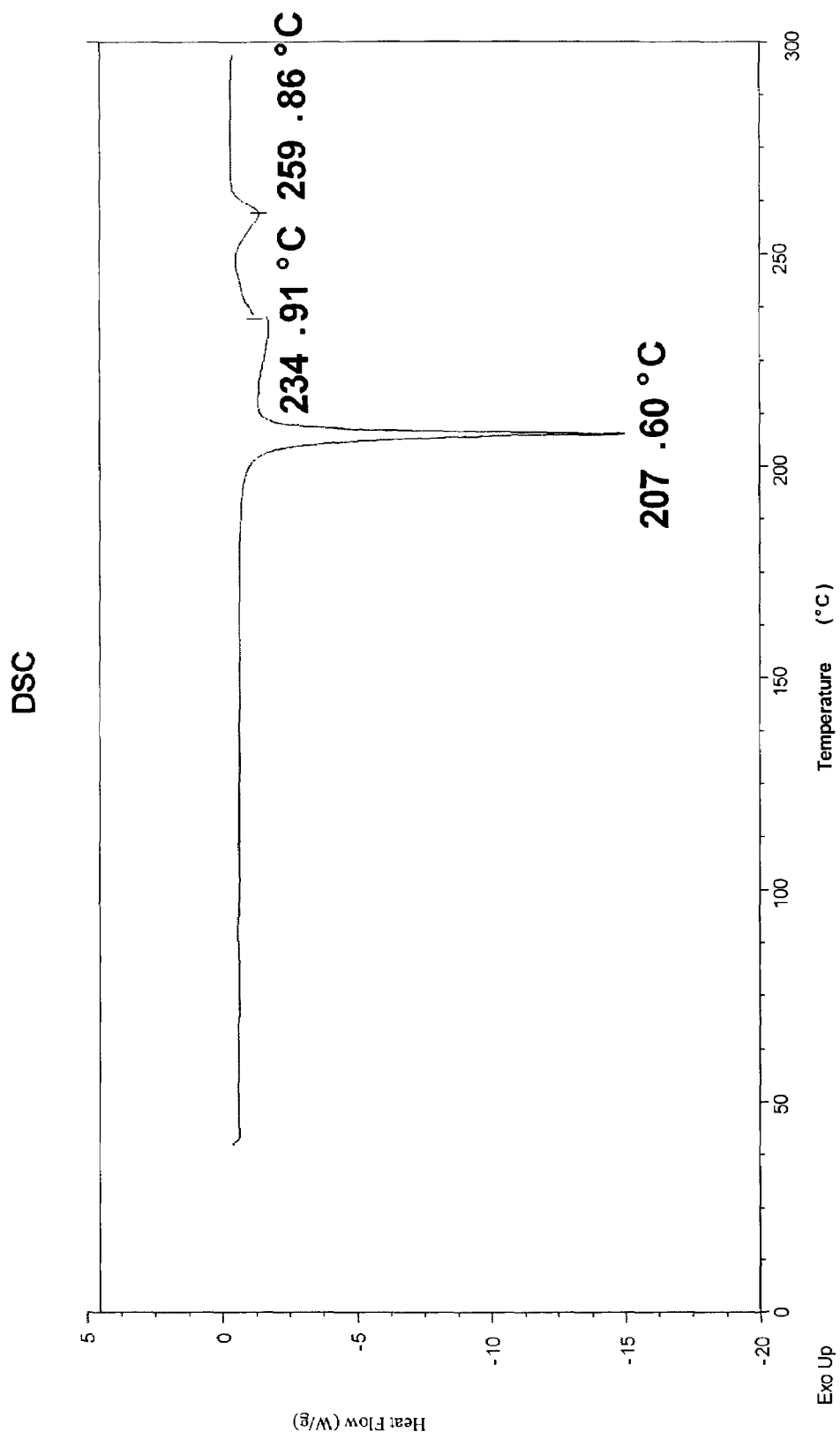
FIG. 33 DSC thermogram for a co-crystal of 5-fluorouracil and urea.
Figure 34:
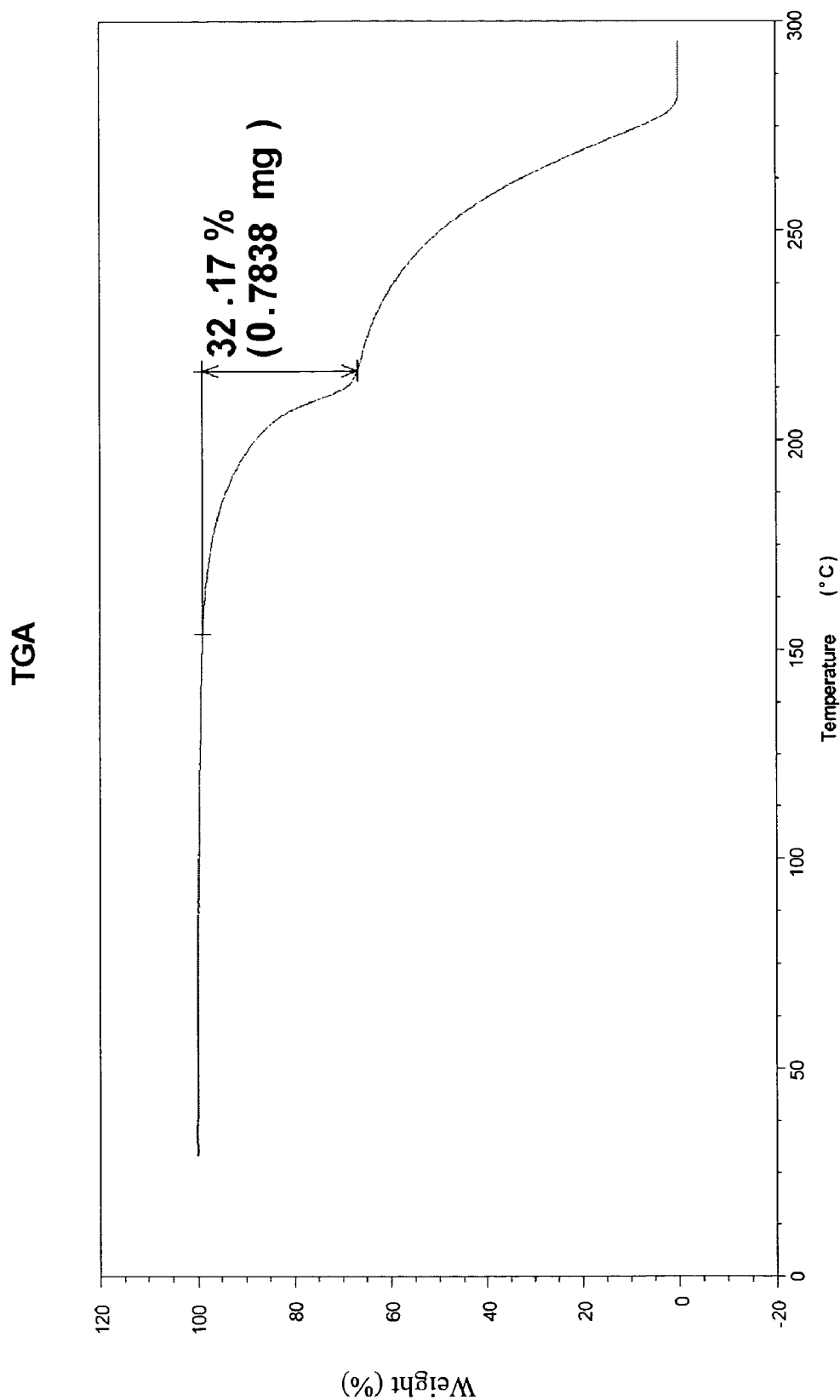
FIG. 34 TGA thermogram for a co-crystal of 5-fluorouracil and urea.
Figure 35:
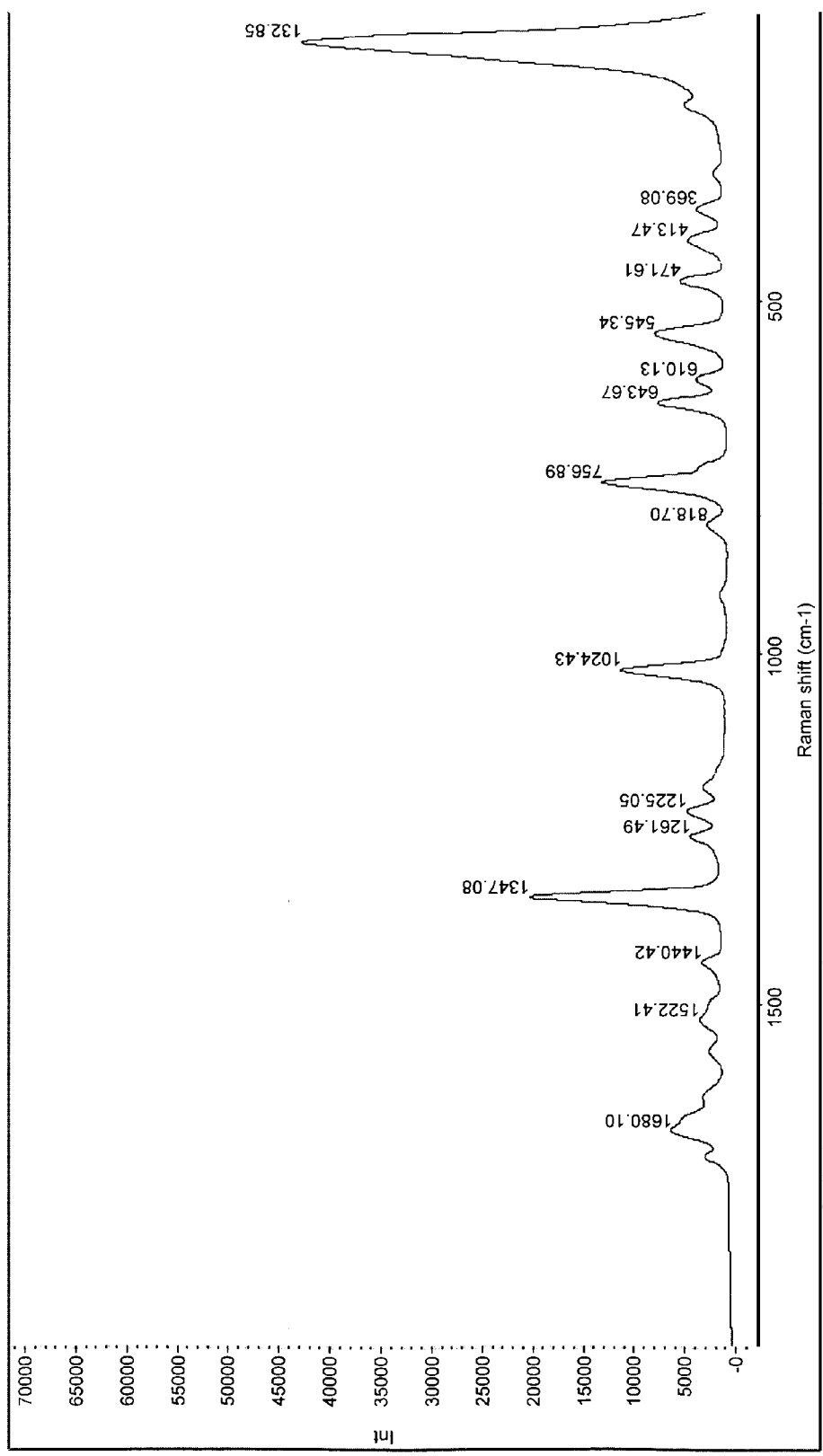
FIG. 35 Raman spectrum for a co-crystal of 5-fluorouracil and urea.
Figure 36:
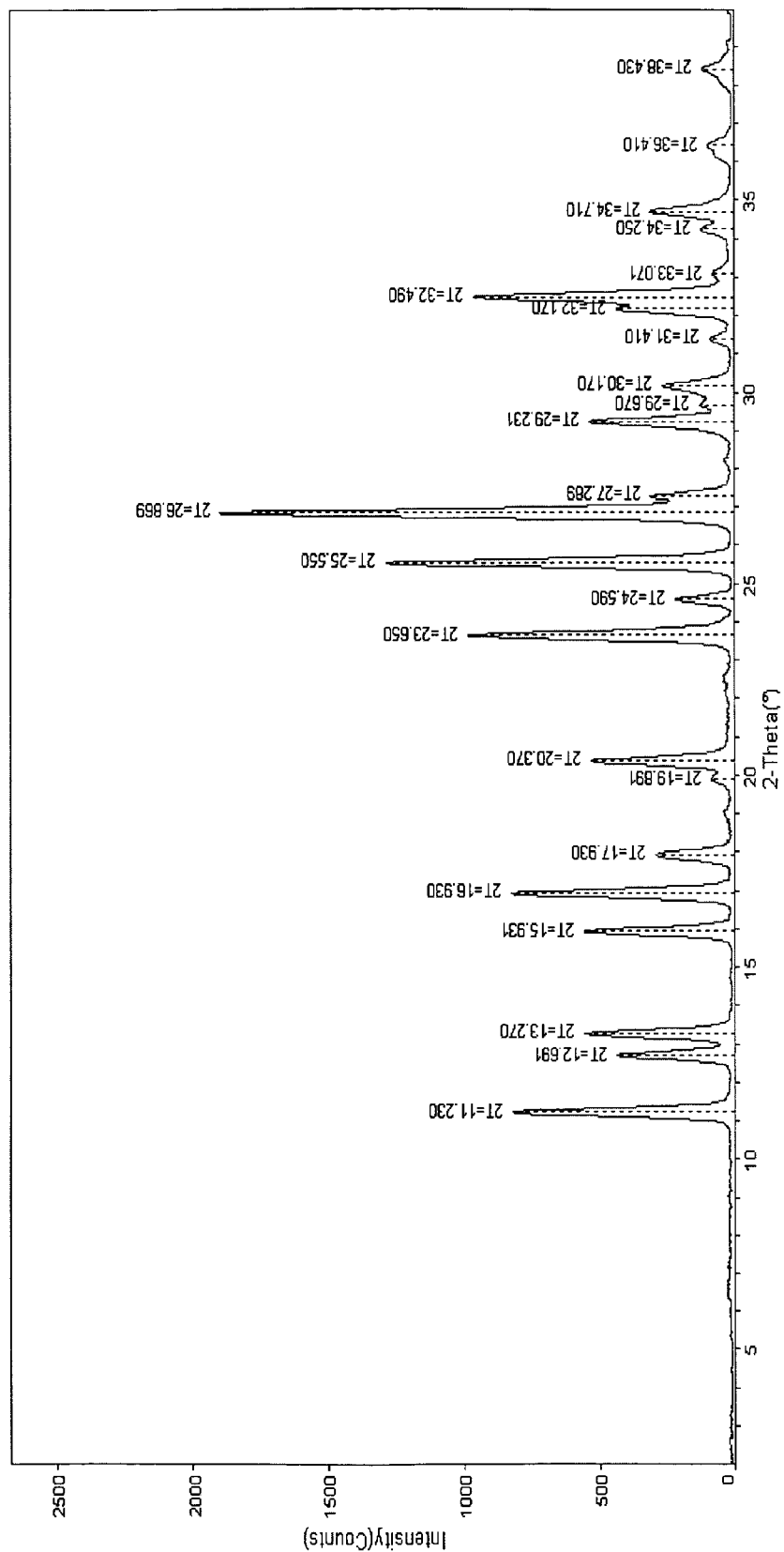
FIG. 36 PXRD pattern for a co-crystal of 5-fluorouracil and urea.

Single crystal x-ray analysis reveals that the olanzapine: nicotinamide (Form III) co-crystal is made up of a ternary system containing olanzapine, nicotinamide, water and isopropyl acetate in the unit cell. The co-crystal crystallizes in the monoclinic space group $P2_1/c$ and contains one olanzapine, one nicotinamide, 4 waters and one isopropyl acetate solvate in the asymmetric unit. The packing diagram is made up of a two-dimensional hydrogen-bonded network with the water molecules connecting the olanzapine and nicotinamide moieties. The packing diagram is also comprised of alternating olanzapine and nicotinamide layers connected through hydrogen bonding via the water and isopropyl acetate molecules, as shown in FIG. 32B. The olanzapine layer propagates along the b axis at c/4 and 3c/4. The nicotinamide layer propagates along the b axis at c/2. The top of FIG. 32C illustrates the nicotinamide superstructure. The nicotinamide molecules form dimers which hydrogen bond to chains of 4 water molecules. The water chains terminate with isopropyl acetate molecules on each side.

Crystal data: $C_{45}H_{64}N_{10}O_7S_2$, M=921.18, monoclinic P21/c; a=14.0961(12) Å, b=12.5984(10) Å, c=27.219(2) Å, α=90°, β=97.396(2)°, γ=90°, T=100(2) K, Z=4, $D_c$=1.276 Mg/m$^3$, U=4793.6(7) Å$^3$, λ=0.71073 Å; 24952 reflections measured, 8457 unique ($R_{int}$=0.0882). Final residuals were $R_1$=0.0676, $wR_2$=0.1461 for I>2σ(I), and $R_1$=0.1187, $wR_2$=0.1687 for all 8457 data.

Example 20

Co-crystals of 5-fluorouracil and urea were prepared. To 5-fluorouracil (1 g, 7.69 mmol) and urea (0.46 g, 7.69 mmol) was added methanol (100 mL). The solution was heated at 65 degrees C. and sonicated until all the material dissolved. The solution was then cooled to 5 degrees C. and maintained at that temperature overnight. After about 3 days a white precipitate was observed and collected. The solid was characterized by DSC, PXRD, Raman spectroscopy, and TGA. Characterization data are listed in Table V. (See FIGS. 33-36)

Example 21

Figure 37:
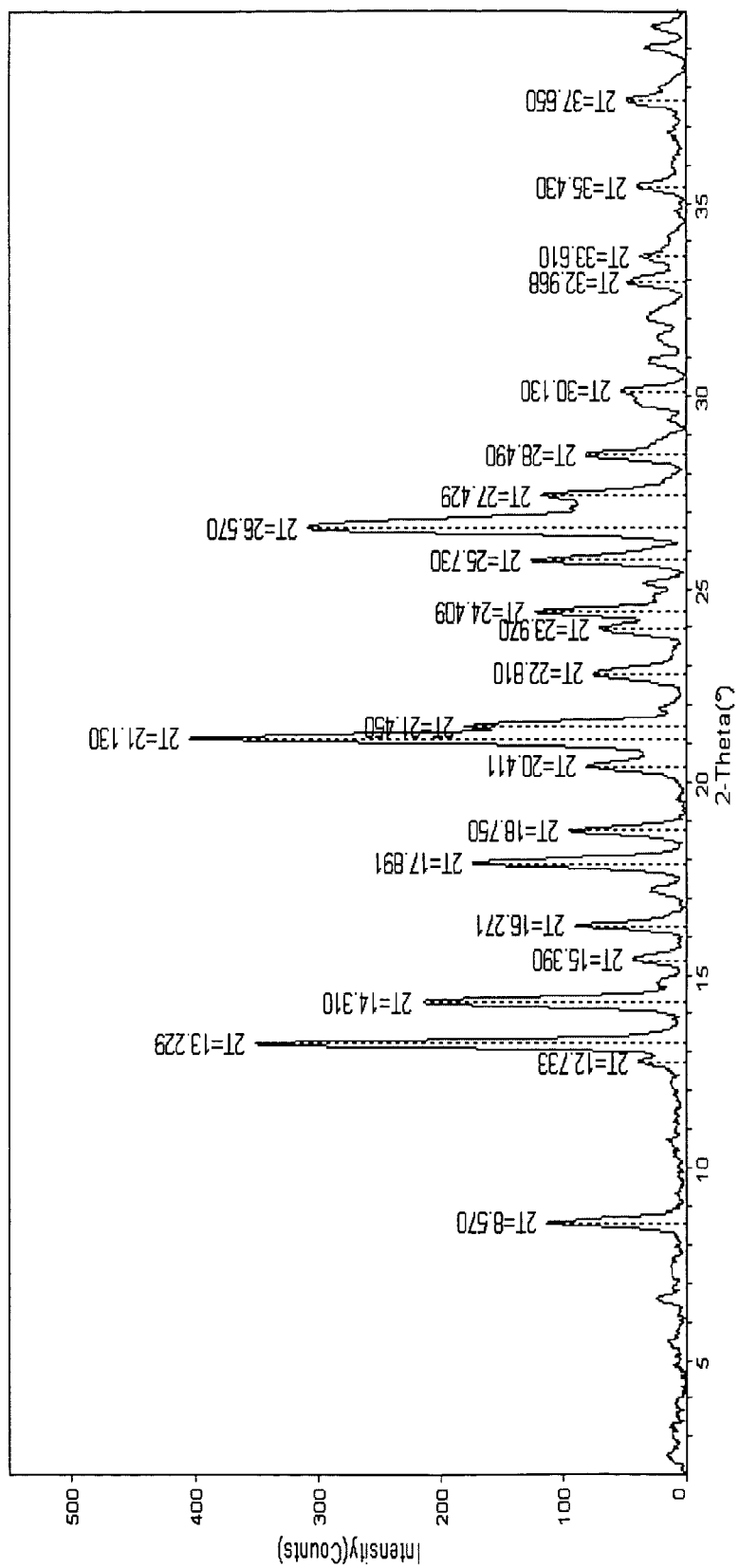
FIG. 37 PXRD pattern for a co-crystal of hydrochlorothiazide and nicotinic acid.

Co-crystals of hydrochlorothiazide and nicotinic acid were prepared. Hydrochlorothiazide (I2.2 mg, 0.041 mmol) and nicotinic acid (5 mg, 0.041 mmol) were dissolved in methanol (1 mL). The solution was then cooled to 5 degrees C. and maintained at that temperature for 12 hours. A white solid precipitated and was collected and characterized using PXRD. (See FIG. 37)

Example 22

Figure 38:
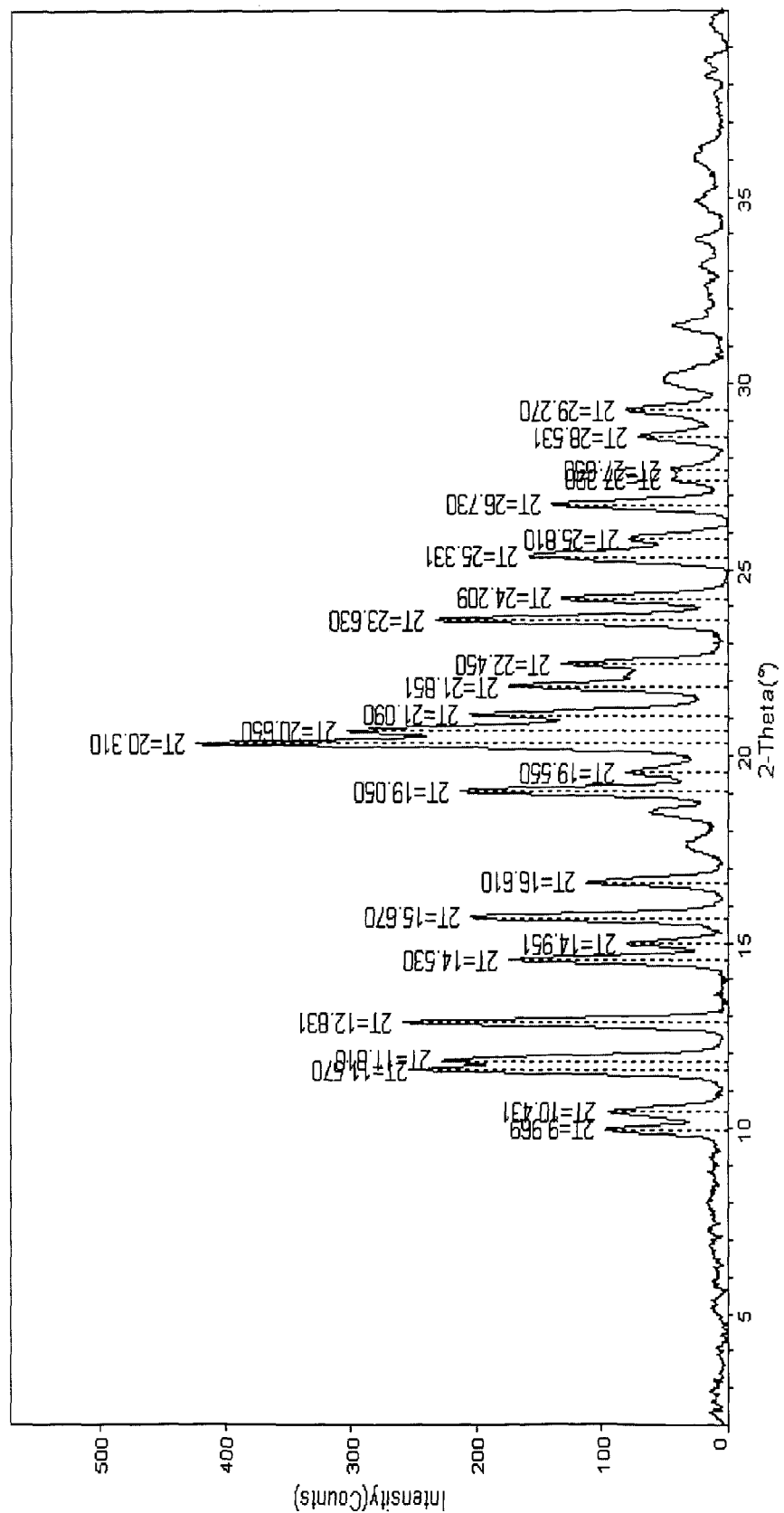
FIG. 38 PXRD pattern for a co-crystal of hydrochlorothiazide and 18-crown-6.

Co-crystals of hydrochlorothiazide and 18-crown-6 were prepared. Hydrochlorothiazide (100 mg, 0.33 mmol) was dissolved in diethyl ether (15 mL) and was added to a solution of 18-crown-6 (87.2 mg, 0.33 mmol) in diethyl ether (15 mL). A white precipitate immediately began to form and was collected and characterized as the hydrochlorothiazide: 18-crown-6 co-crystal using PXRD. (See FIG. 38)

Example 23

Figure 39:
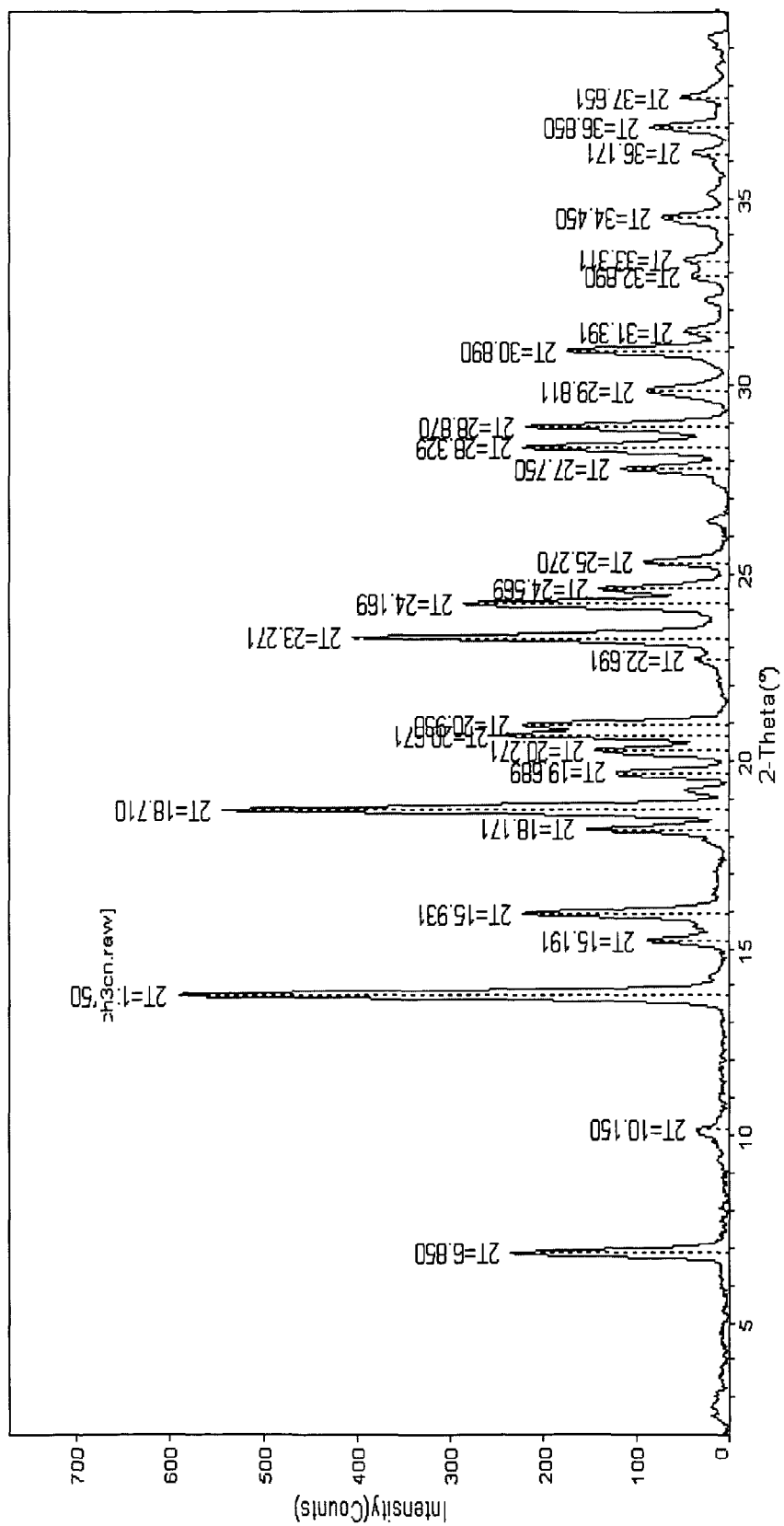
FIG. 39 PXRD pattern for a co-crystal of hydrochlorothiazide and piperazine.

Co-crystals of hydrochlorothiazide and piperazine were prepared. Hydrochlorothiazide (17.3 mg, 0.058 mmol) and piperazine (5 mg, 0.058 mmol) were dissolved in a 1:1 mixture of ethyl acetate and acetonitirle (1 mL). The solution was then cooled to 5 degrees C. and maintained at that temperature for 12 hours. A white solid precipitated and was collected and characterized using PXRD. (See FIG. 39)

Example 24

Figure 44A:
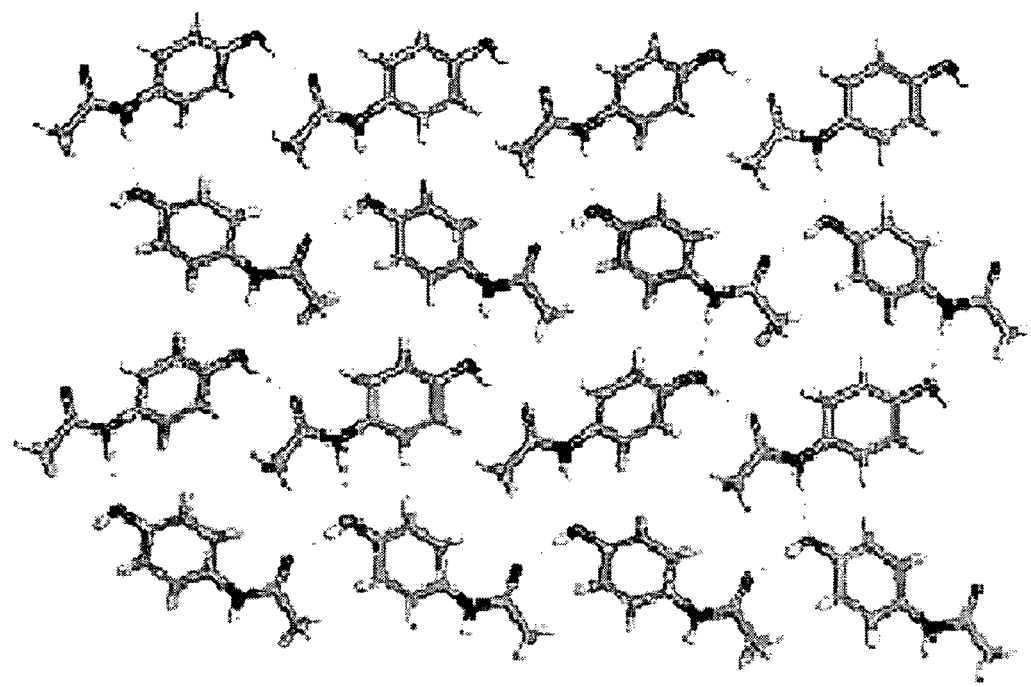
FIG. 44A-B An acetaminophen 1-D polymeric chain and a co-crystal of acetaminophen and 4,4'-bipyridine, respectively.
Figure 44B:
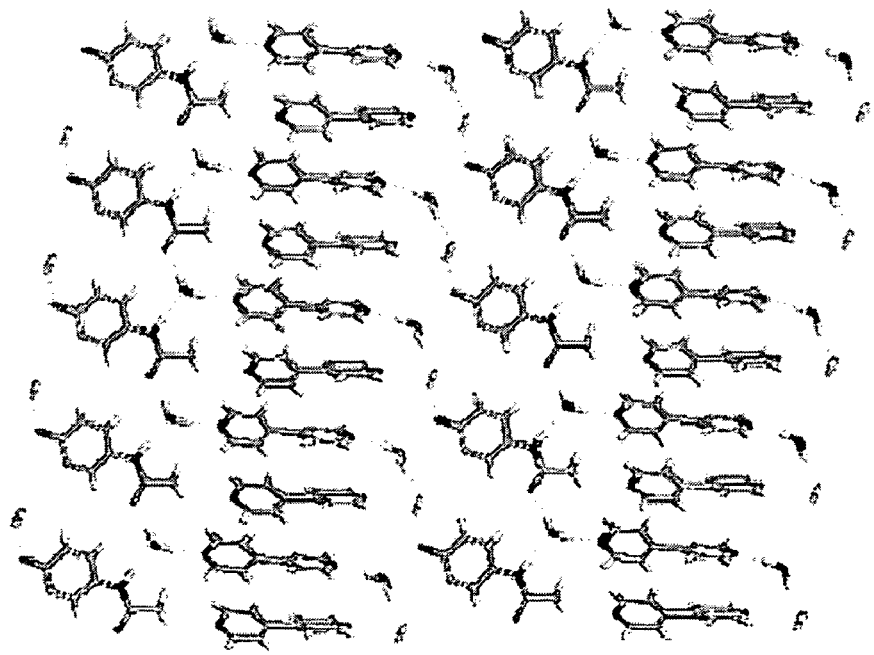

Acetaminophen:4,4'-bipyridine:water (1:1:1 stoichiometry)
50 mg (0.3307 mmol) acetaminophen and 52 mg (0.3329 mmol) 4,4'-bipyridine were dissolved in hot water and allowed to stand. Slow evaporation yielded colorless needles of a 1:1:1 acetaminophen/4,4'-bipyridine/water co-crystal, as shown in FIG. 44A-B.

Crystal data: (Bruker SMART-APEX CCD Diffractometer). $C_{36}H_{44}N_2O_4$, M=339.84, triclinic, space group P$\bar{1}$, a=7.0534(8), b=9.5955(12), c=19.3649(2) Å, α=86.326(2), β80.291(2), γ=88.880(2)°, U=1308.1(3) Å$^3$, T=200(2) K, Z=2, μ(Mo—Kα)=0.090 mm$^{-1}$, $D_c$=1.294 Mg/m$^3$, λ=0.71073 Å, F(000)=537, 2θ$_{max}$=25.02°; 6289 reflections measured, 4481 unique ($R_{int}$=0.0261). Final residuals for 344 parameters were $R_1$=0.0751, w$R_2$=0.2082 for I>2σ(I), and $R_1$=0.1119, w$R_2$=0.2377 for all 4481 data.

Crystal packing: The co-crystals contain bilayered sheets in which water molecules act as a hydrogen bonded bridge between the network bipyridine moieties and the acetaminophen. Bipyridine guests are sustained by π-υ stacking interactions between two network bipyridines. The layers stack via π-π interactions between the phenyl groups of the acetaminophen moieties.

Differential Scanning Calorimetry: (TA Instruments 2920 DSC), 57.77 degrees C. (endotherm); m.p.=58-60 degrees C. (MEL-TEMP); (acetaminophen m.p.=169 degrees C., 4,4'-bipyridine m.p.=111-114 degrees C.).

Example 25

Phenyloin:Pyridone (1:1 stoichiometry)

Figure 45A:
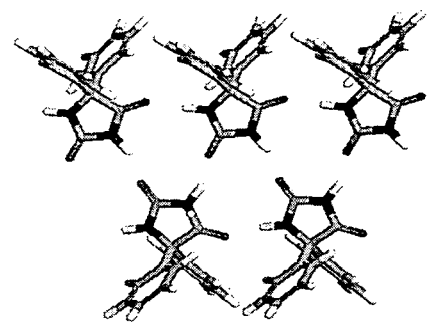
FIG. 45A-B Pure phenyloin and a co-crystal with phenyloin and pyridone, respectively.
Figure 45B:
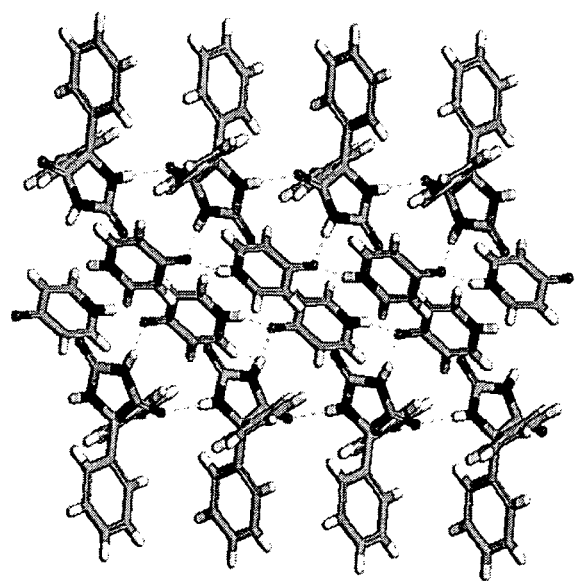
Figure 46A:
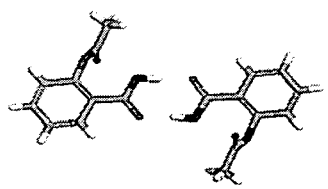
FIG. 46A-D Pure aspirin and the corresponding crystal structure are shown in FIGS. 46A and 46B, respectively.
Figure 46C:
Figure 46B:
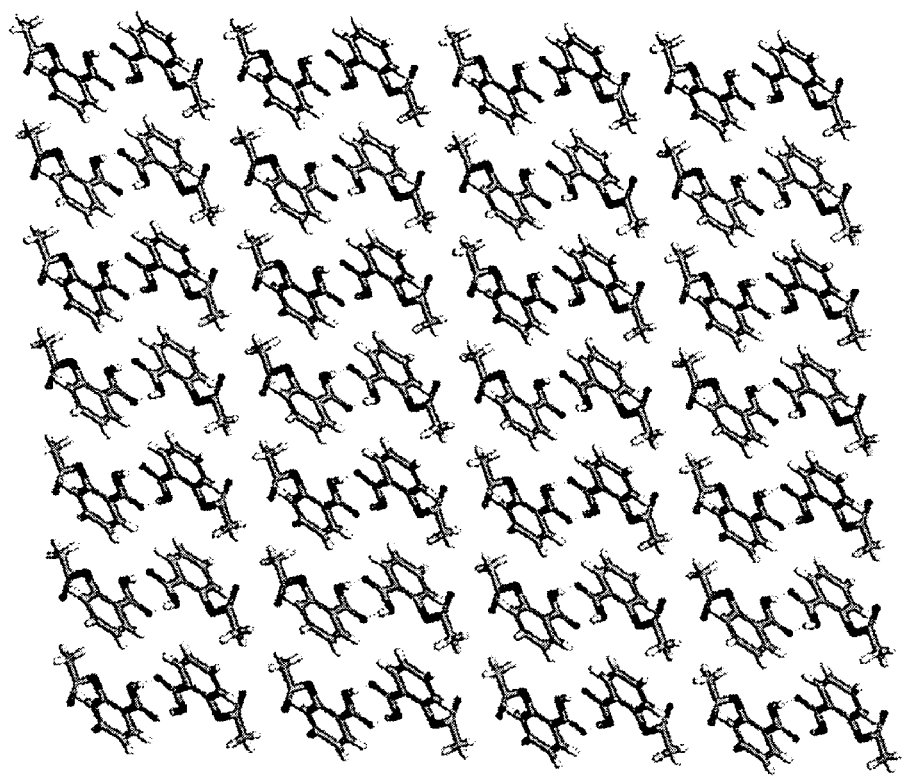
Figure 46D:
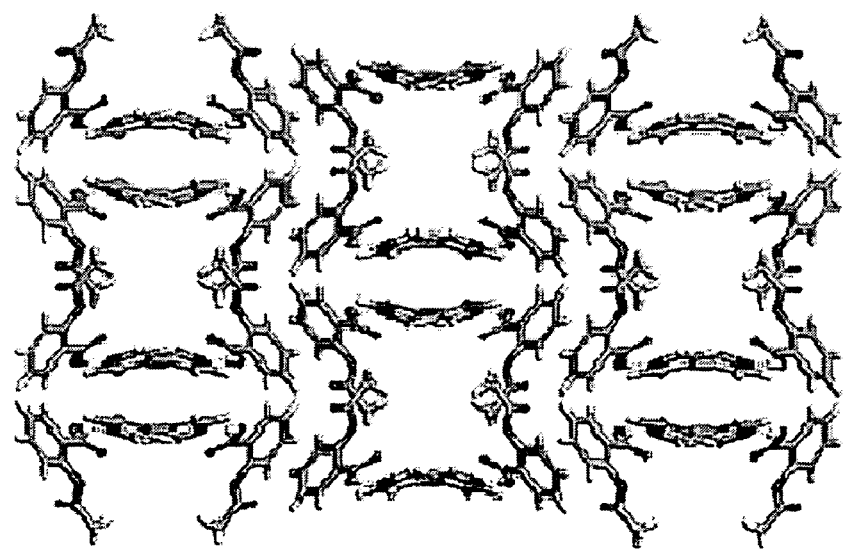
Figure 47A:
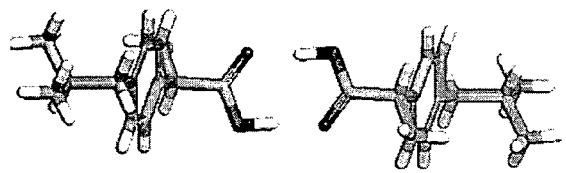
FIG. 47A-D Pure ibuprofen and the corresponding crystal structure are shown in FIGS. 7A and 7B, respectively.
Figure 47C:
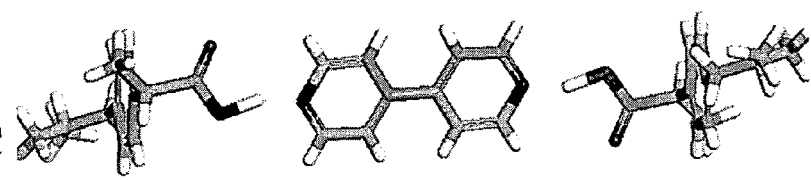
Figure 47B:
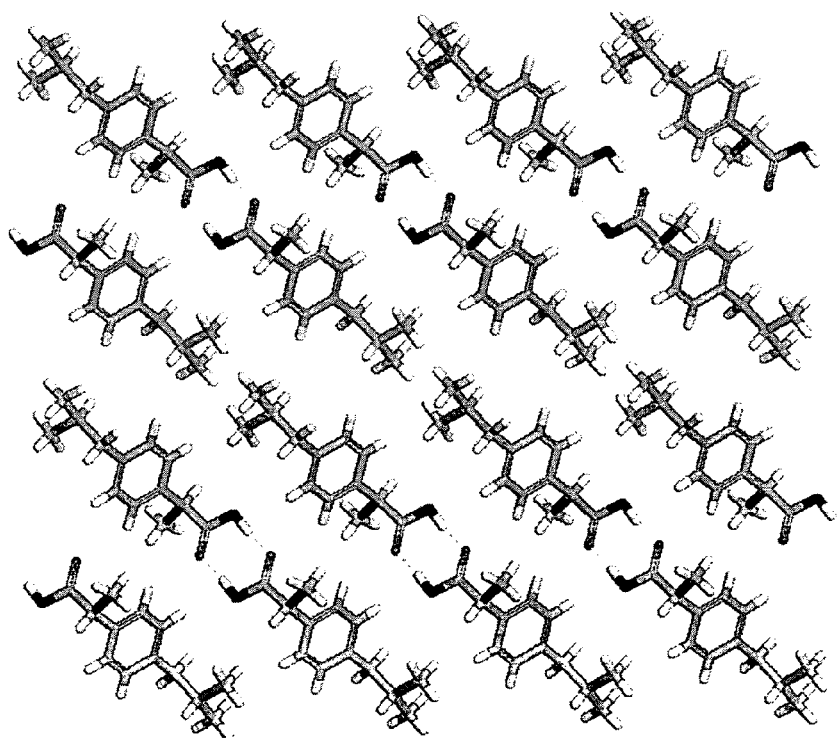
Figure 47D:
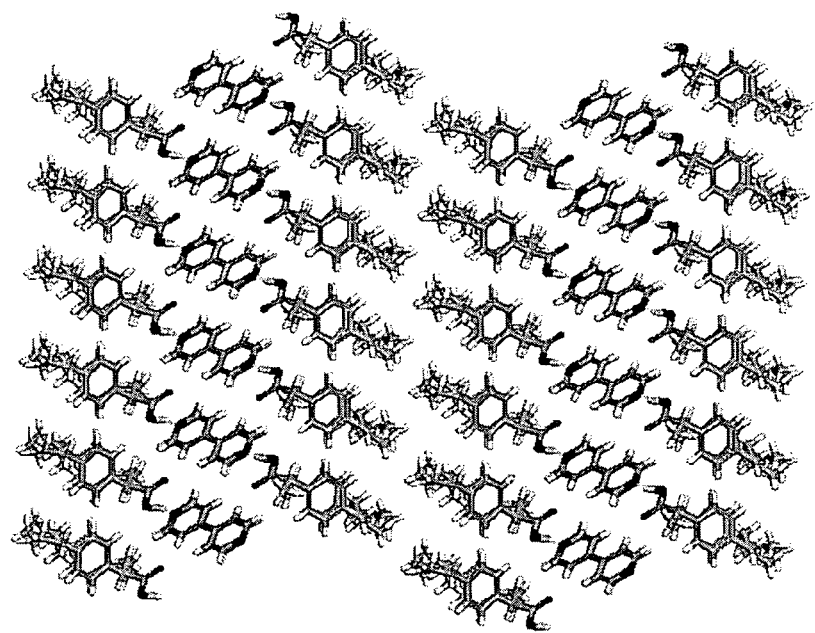
Figure 48A:
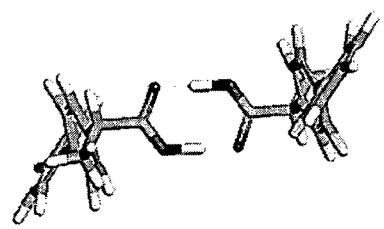
FIG. 48A-D Pure flurbiprofen and the corresponding crystal structure are shown in FIGS. 48A and 48B, respectively.
Figure 48C:
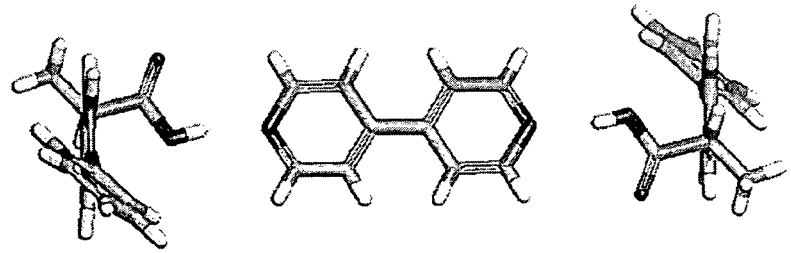
Figure 48B:
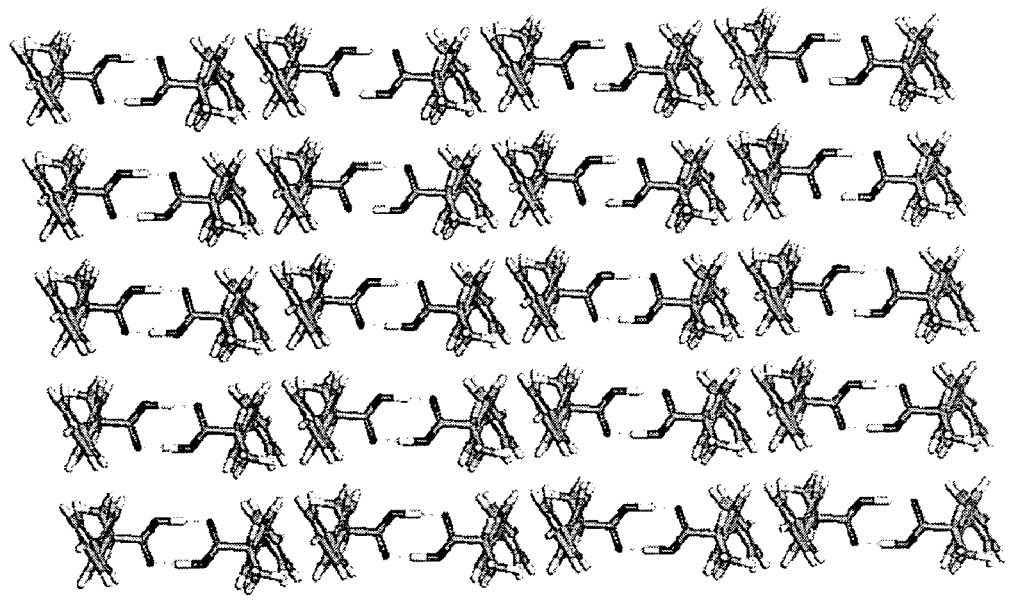
Figure 48D:
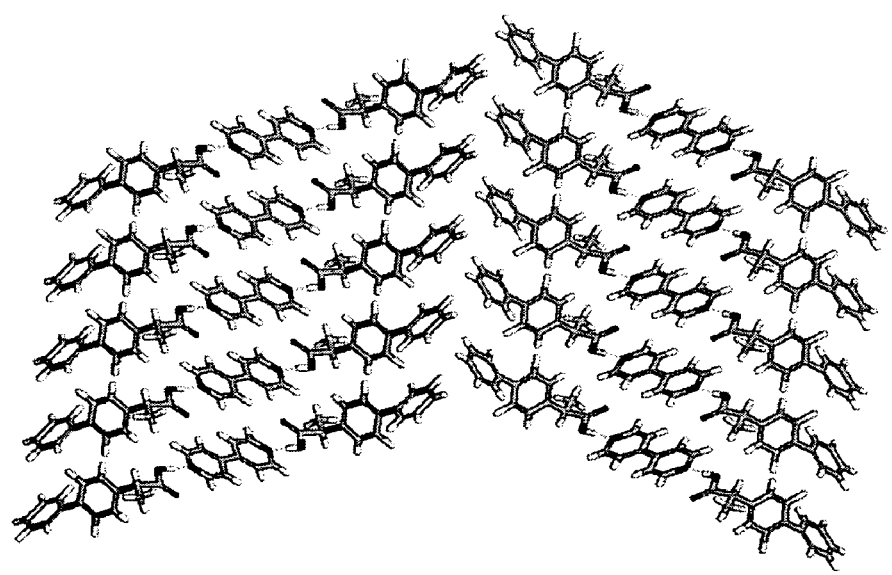

28 mg (0.1109 mmol) phenyloin and 11 mg (0.1156 mmol) 4-hydroxypyridone were dissolved in 2 mL acetone and 1 mL ethanol with heating and stirring. Slow evaporation yielded colorless needles of a 1:1 phenyloin/pyridone co-crystal, as shown in FIG. 45A-B.

Crystal data: (Bruker SMART-APEX CCD Diffractometer), $C_{20}H_{17}N_3O_3$, M=347.37, monoclinic P2$_1$/c; a=16.6583 (19), b=8.8478(10), c=11.9546(14) Å, β=96.618(2)°, U=1750.2(3) Å$^3$, T=200(2) K, Z=4, μ(Mo—Kα)=0.091 mm$^{-1}$, $D_c$=1.318 Mg/m$^3$, λ=0.71073 Å, F(000)=728, 2θ$_{max}$=56.60°; 10605 reflections measured, 4154 unique ($R_{int}$=0.0313). Final residuals for 247 parameters were $R_1$=0.0560, w$R_2$=0.1356 for I>2σ(I), and $R_1$=0.0816, w$R_2$=0.1559 for all 4154 data.

Crystal packing: The co-crystal is sustained by hydrogen bonding of adjacent phentoin molecules between the carbonyl and the amine closest to the tetrahedral carbon, and by hydrogen bonding between pyridone carbonyl functionalities and the amine not involved in phenyloin-phenyloin interactions. The pyridone carbonyl also hydrogen bonds with adjacent pyridone molecules forming a one-dimensional network.

Infrared Spectroscopy: (Nicolet Avatar 320 FTIR), characteristic peaks for the co-crystal were identified as: 2° amine found at 3311 cm$^{-1}$, carbonyl (ketone) found at 1711 cm$^{-1}$, olephin peak found at 1390 cm$^{-1}$.

Differential Scanning Calorimetry: (TA Instruments 2920 DSC), 233.39 degrees C. (endotherm) and 271.33 degrees C. (endotherm); m.p.=231-233 degrees C. (MEL-TEMP); (phenyloin m.p.=295 degrees C., pyridone m.p.=148 degrees C.).

Thermogravimetric Analysis: (TA Instruments 2950 Hi-Resolution TGA), a 29.09% weight loss starting at 192.80 degrees C., 48.72% weight loss starting at 238.27 degrees C., and 18.38% loss starting at 260.17 degrees C. followed by complete decomposition.

Powder x-ray diffraction: (Rigaku Miniflex Diffractometer using Cu Kα (λ=1.540562), 30 kV, 15 mA). The powder data were collected over an angular range of 3° to 40°2θ in continuous scan mode using a step size of 0.02= 2θ and a scan speed of 2.0°/minute. PXRD: Showed analogous peaks to the simulated PXRD derived from the single crystal data. In all cases of recrystallization and solid state reaction, experimental (calculated): 5.2 (5.3); 11.1 (11.3); 15.1 (15.2); 16.2 (16.4); 16.7 (17.0); 17.8 (17.9); 19.4 (19.4); 19.8 (19.7); 20.3 (20.1); 21.2 (21.4); 23.3 (23.7); 26.1 (26.4); 26.4 (26.6); 27.3 (27.6); 29.5 (29.9).

Example 26

Aspirin (acetylsalicylic acid):4,4'-bipyridine (2:1 stoichiometry)

50 mg (0.2775 mmol) aspirin and 22 mg (0.1388 mmol) 4,4'-bipyridine were dissolved in 4 mL hexane. 8 mL ether was added to the solution and allowed to stand for one hour, yielding colorless needles of a 2:1 aspirin/4,4'-bipyridine co-crystal, as shown in FIG. 46A-D. Alternatively, aspirin/4,4'-bipyridine (2:1 stoichiometry) can be made by grinding the solid ingredients in a pestle and mortar.

Crystal data: (Bruker SMART-APEX CCD Diffractometer), $C_{28}H_{24}N_2O_8$, M=516.49, orthorhombic Pbcn; a=28.831 (3), b=11.3861(12), c=8.4144(9) Å, U=2762.2(5) Å$^3$, T=173 (2) K, Z=4, μ(Mo—Kα)=0.092 mm$^{-1}$, $D_c$=1.242 Mg/m$^3$, λ=0.71073 Å, F(000)=1080, 2θ$_{max}$=25.02°; 12431 reflections measured, 2433 unique ($R_{int}$=0.0419). Final residuals for 202 parameters were $R_1$=0.0419, w$R_2$=0.1358 for I>2σ (I), and $R_1$=0.0541, w$R_2$=0.1482 for all 2433 data.

Crystal packing: The co-crystal contains the carboxylic acid-pyridine heterodimer that crystallizes in the Pbcn space group. The structure is an inclusion compound containing disordered solvent in the channels. In addition to the dominant hydrogen bonding interaction of the heterodimer, π-π stacking of the bipyridine and phenyl groups of the aspirin and hydrophobic interactions contribute to the overall packing interactions.

Infrared Spectroscopy: (Nicolet Avatar 320 FTIR), characteristic (—COOH) peak at 1679 cm$^{-1}$ was shifted up and less intense at 1694 cm$^{-1}$, where as the lactone peak is shifted down slightly from 1750 cm$^{-1}$ to 1744 cm$^{-1}$.

Differential Scanning Calorimetry: (TA Instruments 2920 DSC), 95.14 degrees C. (endotherm); m.p.=91-96 degrees C. (MEL-TEMP); (aspirin m.p.=1345 degrees C., 4,4'-bipyridine m.p.=111-114 degrees C.).

Thermogravimetric Analysis: (TA Instruments 2950 Hi-Resolution TGA), weight loss of 9% starting at 22.62 degrees C., 49.06% weight loss starting at 102.97 degrees C. followed by complete decomposition starting at 209.37 degrees C.

Example 27

Ibuprofen:4,4'-Bipyridine (2:1 stoichiometry)

50 mg (0.242 mmol) racemic ibuprofen and 18 mg (0.0960 mmol) 4,4'-bipyridine were dissolved in 5 mL acetone. Slow evaporation of the solvent yielded colorless needles of a 2:1 ibuprofen/4,4'-bipyridine co-crystal, as shown in FIG. 47A-D.

Crystal data: (Bruker SMART-APEX CCD Diffractometer), $C_{36}H_{44}N_2O_4$, M=568.73, triclinic, space group P-1; a=5.759(3), b=11.683(6), c=24.705(11) Å, α=93.674(11), β=90.880(10), γ=104.045(7)°, U=1608.3(13) Å$^3$, λ=200(2) K, Z=2, μ(Mo—Kα)=0.076 mm$^{-1}$, $D_c$=1.174 Mg/m$^3$, λ=0.71073 Å, F(000)=612, 2θ$_{max}$=23.29°; 5208 reflections measured, 3362 unique ($R_{int}$=0.0826). Final residuals for 399 parameters were $R_1$=0.0964, w$R_2$=0.2510 for I>2σ(I), and $R_1$=0.1775, w$R_2$=0.2987 for all 3362 data.

Crystal packing: The co-crystal contains ibuprofen/bipyridine heterodimers, sustained by two hydrogen bonded carboxylic acidpyridine supramolecular synthons, arranged in a herringbone motif that packs in the space group P-1. The heterodimer is an extended version of the homodimer and packs to form a two-dimensional network sustained by π-π stacking of the bipyridine and phenyl groups of the ibuprofen and hydrophobic interactions from the ibuprofen tails.

Infrared Spectroscopy: (Nicolet Avatar 320 FTIR). Analysis observed stretching of aromatic C—H at 2899 cm$^{-1}$; N—H bending and scissoring at 1886 cm$_{-1}$; C=O stretching at 1679 cm$^{-1}$; C—H out-of-plane bending for both 4,4'-bipyridine and ibuprofen at 808 cm$^{-1}$ and 628 cm$^{-1}$.

Differential Scanning Calorimetry: (TA Instruments 2920 DSC), 64.85 degrees C. (endotherm) and 118.79 degrees C. (endotherm); m.p.=113-120 degrees C. (MEL-TEMP); (ibuprofen m.p.=75-77 degrees C., 4,4'-bipyridine m.p.=111-114 degrees C.).

Thermogravimetric Analysis: (TA Instruments 2950 Hi-Resolution TGA), 13.28% weight loss between room temperature and 100.02 degrees C. immediately followed by complete decomposition.

Powder x-ray diffraction: (Rigaku Miniflex Diffractometer using Cu Kα (λ=1.540562), 30 kV, 15 mA). The powder data were collected over an angular range of 3° to 40° 2θ in continuous scan mode using a step size of 0.02° 2θ and a scan speed of 2.0°/minute. PXRD derived from the single crystal data, experimental (calculated): 3.4 (3.6); 6.9 (7.2); 10.4 (10.8); 17.3 (17.5); 19.1 (19.7).

Example 28

Flurbiprofen:4,4'-bipyridine (2:1 stoichiometry)

50 mg (0.2046 mmol) flurbiprofen and 15 mg (0.0960 mmol) 4,4'-bipyridine were dissolved in 3 mL acetone. Slow evaporation of the solvent yielded colorless needles of a 2:1 flurbiprofen/4,4'-bipyridine co-crystal, as shown in FIG. 48A-D.

Crystal data: (Bruker SMART-APEX CCD Diffractometer), $C_{40}H_{34}F_2N_2O_4$, M=644.69, monoclinic P2$_1$/n; a=5.860 (4), b=47.49(3), c=5.928(4) Å, β=107.382 (8)°, U=1574.3 (19) Å$^3$, T=200(2) K, Z=2, μ(Mo—Kα)=0.096 mm$^{-1}$, D$_c$=1.360 Mg/m$^3$, λ=0.71073 Å, F(000)=676, 2θ$_{max}$=21.69°; 4246 reflections measured, 1634 unique (R$_{int}$=0.0677). Final residuals for 226 parameters were R$_1$=0.0908, wR$_2$=0.2065 for I>2σ(I), and R$_1$=0.1084, wR$_2$=0.2209 for all 1634 data.

Crystal packing: The co-crystal contains flurbiprofen/bipyridine heterodimers, sustained by two hydrogen bonded carboxylic acidpyridine supramolecular synthon, arranged in a herringbone motif that packs in the space group P2$_1$/n. The heterodimer is an extended version of the homodimer and packs to form a two-dimensional network sustained by π-π stacking and hydrophobic interactions of the bipyridine and phenyl groups of the flurbiprofen.

Infrared Spectroscopy: (Nicolet Avatar 320 FTIR), aromatic C—H stretching at 3057 cm$^{-1}$ and 2981 cm$^-$; N—H bending and scissoring at 1886 cm$^{-1}$; C=O stretching at 1690 cm$^{-1}$; C=C and C=N ring stretching at 1418 cm$^{-1}$.

Differential Scanning Calorimetry: (TA Instruments 2920 DSC), 162.47 degrees C. (endotherm); m.p.=155-160 degrees C. (MEL-TEMP); (flurbiprofen m.p.=110-111 degrees C., 4,4'-bipyridine m.p.=111-114 degrees C.).

Thermogravimetric Analysis: (TA Instruments 2950 Hi-Resolution TGA), 30.93% weight loss starting at 31.13 degrees C. and a 46.26% weight loss starting at 168.74 degrees C. followed by complete decomposition.

Powder x-ray diffraction: (Rigaku Miniflex Diffractometer using Cu Kα (λ=1.540562), 30 kV, 15 mA), the powder data were collected over an angular range of 3° to 40° 2θin continuous scan mode using a step size of 0.02° 2θ and a scan speed of 2.0°/minute. PXRD derived from the single crystal data: experimental (calculated): 16.8 (16.8); 17.1 (17.5); 18.1 (18.4); 19.0 (19.0); 20.0 (20.4); 21.3 (21.7); 22.7 (23.0); 25.0 (25.6); 26.0 (26.1); 26.0 (26.6); 26.1 (27.5); 28.2 (28.7); 29.1 (29.7).

Example 29

Flurbiprofen:trans-1,2-bis(4-pyridyl) ethylene (2:1 stoichiometry)

Figure 49A:
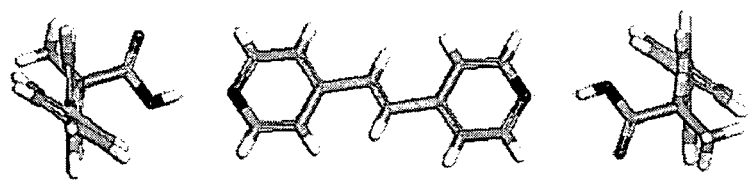
FIG. 49A-B The supramolecular entity containing the synthon and the corresponding co-crystal structure of flurbiprofen and trans-1,2-bis(4-pyridyl)ethylene, respectively.
Figure 49B:
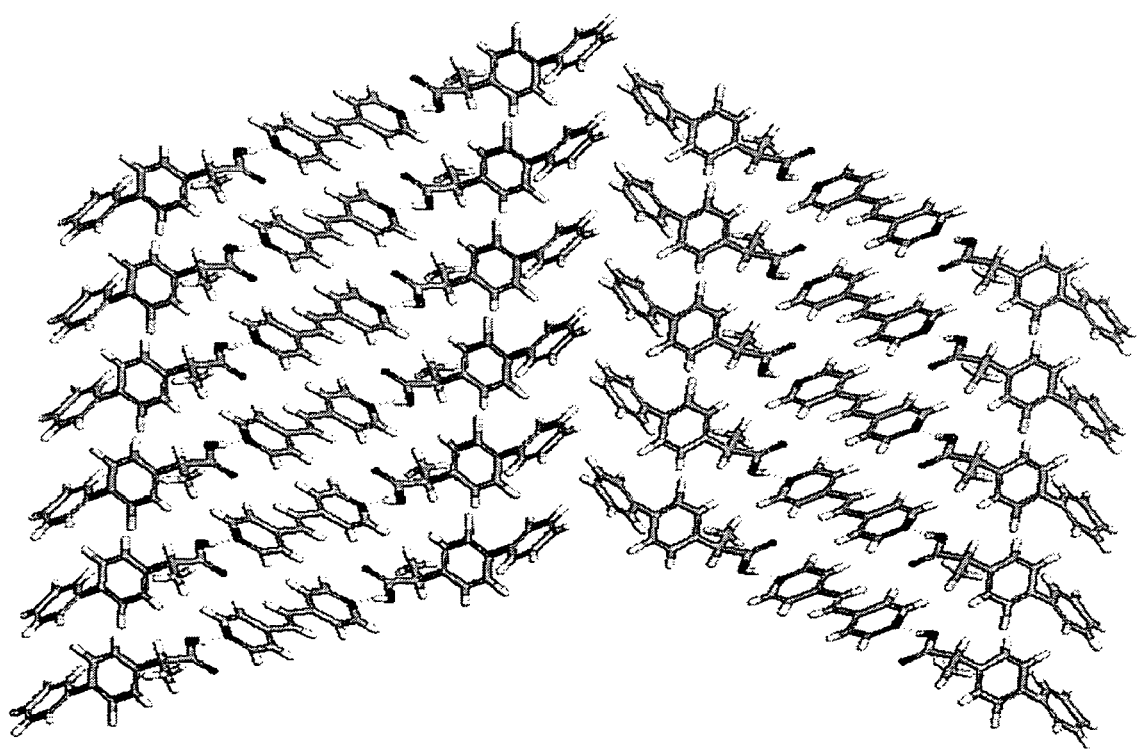

25 mg (0.1023 mmol) flurbiprofen and 10 mg (0.0548 mmol) trans-1,2-bis(4-pyridyl) ethylene were dissolved in 3 mL acetone. Slow evaporation of the solvent yielded colorless needles of a 2:1 flurbiprofen/1,2-bis(4-pyridyl) ethylene co-crystal, as shown in FIG. 49A-B.

Crystal data: (Bruker SMART-APEX CCD Diffractometer), $C_{42}H_{36}F_2N_2O_4$, M=670.73, monoclinic P2$_1$/n; a=5.8697 (9), b=47.357(7), c=6.3587(10) Å, β=109.492(3)°, U=1666.2(4) Å$^3$, T=200(2) K, Z=2, μ(Mo—Kα)=0.093 mm$^{-1}$, D$_c$=1.337 Mg/m$^3$, λ=0.71073 Å, F(000)=704, 2θ$_{max}$=21.69°, 6977 reflections measured, 2383 unique (R$_{int}$=0.0383). Final residuals for 238 parameters were R$_1$=0.0686, wR$_2$=0.1395 for I>2θ(I), and R$_1$=0.1403, wR$_2$=0.1709 for all 2383 data.

Crystal packing: The co-crystal contains flurbiprofen/1,2-bis(4-pyridyl) ethylene heterodimers, sustained by two hydrogen bonded carboxylic acid-pyridine supramolecular synthons, arranged in a herringbone motif that packs in the space group P2$_1$/n. The heterodimer from 1,2-bis(4-pyridyl) ethylene further extends the homodimer relative to example 28 and packs to form a two-dimensional network sustained by π-π stacking and hydrophobic interactions of the bipyridine and phenyl groups of the flurbiprofen.

Infrared Spectroscopy: (Nicolet Avatar 320 FTIR), aromatic C—H stretching at 2927 cm$^{-1}$ and 2850 cm$^{-1}$; N—H bending and scissoring at 1875 cm$^{-1}$; C=O stretching at 1707 cm$^{-1}$; C=C and C=N ring stretching at 1483 cm$^{-1}$.

Differential Scanning Calorimetry: (TA Instruments 2920 DSC), 100.01 degrees C., 125.59 degrees C. and 163.54 degrees C. (endotherms); m.p.=153-158 degrees C. (MEL-TEMP); (flurbiprofen m.p.=110-111 degrees C., trans-1,2-bis(4-pyridyl) ethylene m.p.=150-153 degrees C.).

Thermogravimetric Analysis: (TA Instruments 2950 Hi-Resolution TGA), 91.79% weight loss starting at 133.18 degrees C. followed by complete decomposition.

Powder x-ray diffraction: (Rigaku Miniflex Diffractometer using Cu Kα (λ=1.540562), 30 kV, 15 mA), the powder data were collected over an angular range of 3° to 40° 2θ in continuous scan mode using a step size of 0.02° 2θ and a scan speed of 2.0°/minute. PXRD derived from the single crystal data, experimental (calculated): 3.6 (3.7); 17.3 (17.7); 18.1 (18.6); 18.4 (18.6); 19.1 (19.3); 22.3 (22.5); 23.8 (23.9); 25.9 (26.4); 28.1 (28.5).

Example 30

Carbamazepine:p-Phthalaldehyde (1:1 stoichiometry)

Figure 50A:
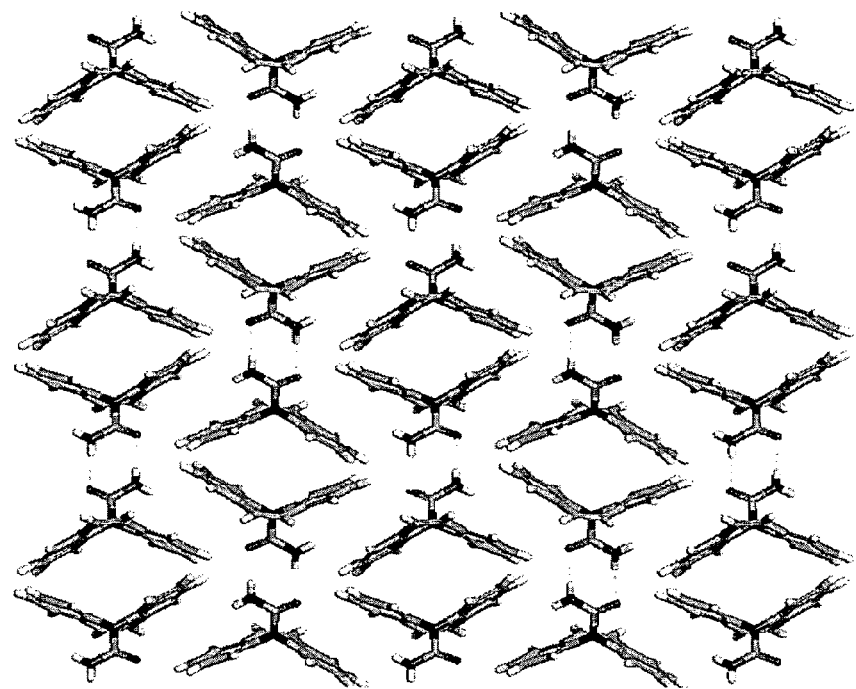
FIG. 50A-B The crystal structure of pure carbamazepine and the co-crystal structure of carbamazepine and p-phthalaldehyde, respectively.
Figure 50B:
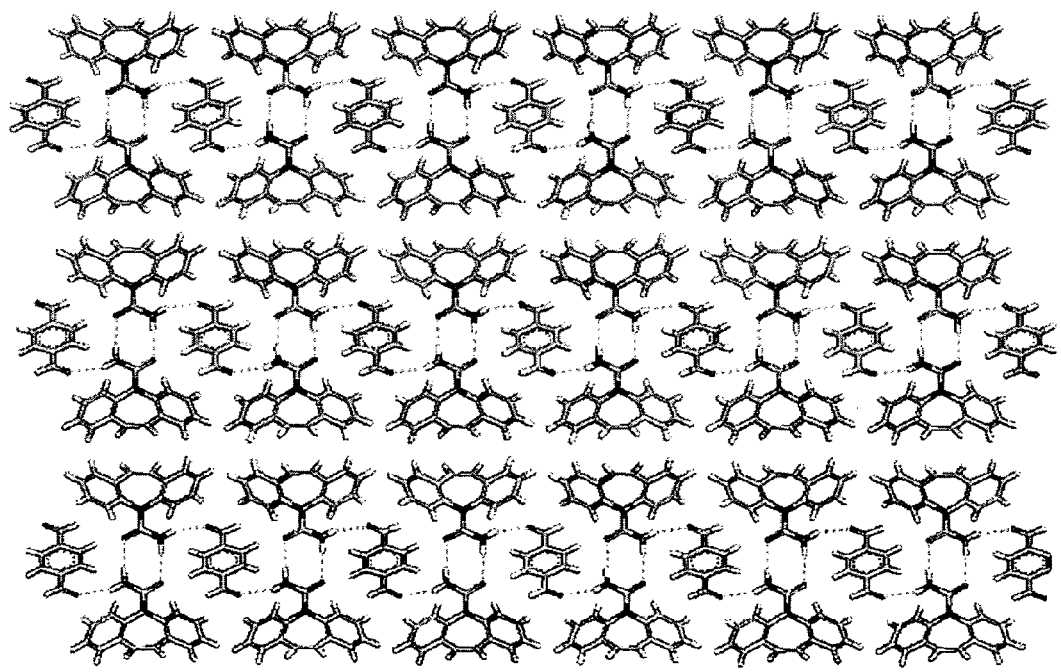

25 mg (0.1058 mmol) carbamazepine and 7 mg (0.0521 mmol) p-phthalaldehyde were dissolved in approximately 3 mL methanol. Slow evaporation of the solvent yielded colorless needles of a 1:1 carbamazepine/p-phthalaldehyde co-crystal, as shown in FIG. 50A-B.

Crystal data: (Bruker SMART-APEX CCD Diffractometer), $C_{38}H_{30}N_4O_4$, M=606.66, monoclinic C2/c; a=29.191 (16), b=4.962(3), c=20.316(11) Å, β=92.105(8)°, U=2941(3) Å$^3$, T=200(2) K, Z=4, μ(Mo—Kα)=0.090 mm$^{-1}$, D$_c$=1.370 Mg/m$^3$, λ=0.71073 Å, F(000)=1272, 2θ$_{max}$=43.66°, 3831 reflections measured, 1559 unique ($R_{int}$=0.0510). Final residuals for 268 parameters were $R_1$=0.0332, $wR_2$=0.0801 for I>2σ(I), and $R_1$=0.0403, $wR_2$=0.0831 for all 1559 data.

Crystal packing: The co-crystals contain hydrogen bonded carboxamide homodimers that crystallize in the space group C2/c. The 1° amines of the homodimer are bifurcated to the carbonyl of the p-phthalaldehyde forming a chain with an adjacent homodimer. The chains pack in a crinkled tape motif sustained by π-π interactions between phenyl rings of the CBZ.

Infrared Spectroscopy: (Nicolet Avatar 320 FTIR). The 1° amine unsymmetrical and symmetrical stretching was shifted down to 3418 cm$^{-1}$; aliphatic aldehyde and 1° amide C=O stretching was shifted up to 1690 cm$^{-1}$; N—H in-plane bending at 1669 cm$^{-1}$; C—H aldehyde stretching at 2861 cm$^{-1}$ and H—C=O bending at 1391 cm$^{-1}$.

Differential Scanning Calorimetry: (TA Instruments 2920 DSC), 128.46 degrees C. (endotherm), m.p.=121-124 degrees C. (MEL-TEMP), (carbamazepine m.p.=190.2 degrees C., p-phthalaldehyde m.p.=116 degrees C.).

Thermogravimetric Analysis: (TA Instruments 2950 Hi-Resolution TGA), 17.66% weight loss starting at 30.33 degrees C. then a 17.57% weight loss starting at 100.14 degrees C. followed by complete decomposition.

Powder x-ray diffraction: (Rigaku Miniflex Diffractometer using Cu Kα (λ=1.540562), 30 kV, 15 mA). The powder data were collected over an angular range of 3° to 40° 2θ in continuous scan mode using a step size of 0.02° 2θ and a scan speed of 2.0°/minute. PXRD derived from the single crystal data, experimental (calculated): 8.5 (8.7); 10.6 (10.8); 11.9 (12.1); 14.4 (14.7) 15.1 (15.2); 18.0 (18.1); 18.5 (18.2); 19.8 (18.7); 23.7 (24.0); 24.2 (24.2); 26.4 (26.7); 27.6 (27.9); 27.8 (28.2); 28.7 (29.1); 29.3 (29.6); 29.4 (29.8).

Example 31

Carbamazepine:nicotinamide (Form II) (1:1 stoichiometry)

Figure 51:
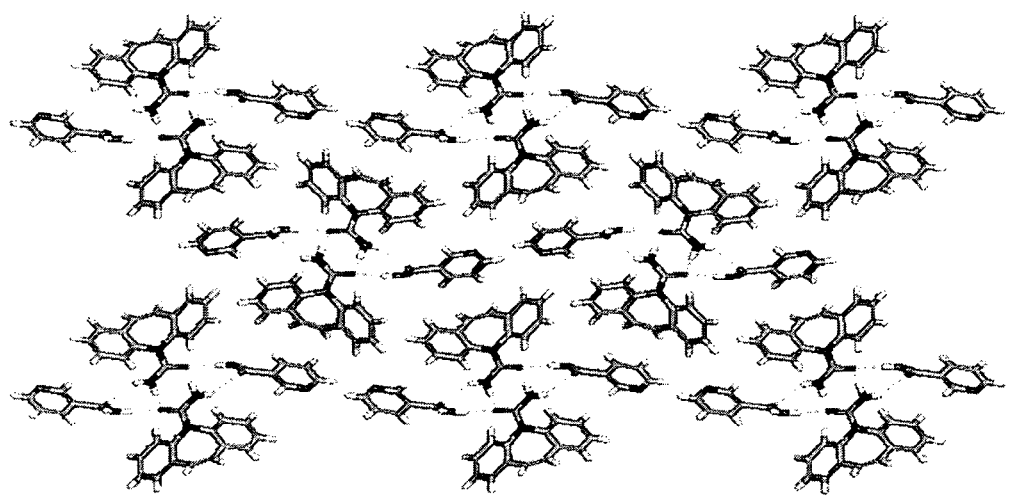
FIG. 51 The co-crystal structure of carbamazepine and nicotinamide (Form II).

25 mg (0.1058 mmol) carbamazepine and 12 mg (0.0982 mmol) nicotinamide were dissolved in 4 mL of DMSO, methanol or ethanol. Slow evaporation of the solvent yielded colorless needles of a 1:1 carbamazepine/nicotinamide co-crystal, as shown in FIG. 51.

Using a separate method, 25 mg (0.1058 mmol) carbamazepine and 12 mg (0.0982 mmol) nicotinamide were ground together with mortar and pestle. The solid was determined to be 1:1 carbamazepine/nicotinamide microcrystals (PXRD).

Crystal data: (Bruker SMART-APEX CCD Diffractometer), $C_{21}H_{18}N_4O_2$, M=358.39, monoclinic P2$_1$/n; a=5.0961 (8), b=17.595(3), c=19.647(3) Å, β=90.917(3)°, U=1761.5 (5) Å$^3$, T=200(2) K, Z=4, μ(Mo—Kα)=0.090 mm$^{-1}$, $D_c$=1.351 Mg/m$^3$, λ=0.71073 Å, F(000)=752, 2θ$_{max}$=56.600°, 10919 reflections measured, 4041 unique ($R_{int}$=0.0514). Final residuals for 248 parameters were $R_1$=0.0732, $wR_2$=0.1268 for I>2σ(I), and $R_1$=0.1161, $wR_2$=0.1430 for all 4041 data.

Crystal packing: The co-crystals contain hydrogen bonded carboxamide homodimers. The 1° amines are bifurcated to the carbonyl of the nicotinamide on each side of the dimer. The 1° amines of each nicotinamide are hydrogen bonded to the carbonyl of the adjoining dimer. The dimers form chains with π-π interactions from the phenyl groups of the CBZ.

Infrared Spectroscopy: (Nicolet Avatar 320 FTIR), unsymmetrical and symmetrical stretching shifts down to 3443 cm$^{-1}$ and 3388 cm$^{-1}$ accounting for 1° amines; 1° amide C=O stretching at 1690 cm$^{-1}$; N—H in-plane bending at 1614 cm$^{-1}$; C=C stretching shifted down to 1579 cm$^{-1}$; aromatic H's from 800 cm$^{-1}$ to 500 cm$^{-1}$ are present.

Differential Scanning Calorimetry: (TA Instruments 2920 DSC), 74.49 degrees C. (endotherm) and 159.05 degrees C. (endotherm), m.p.=153-158 degrees C. (MEL-TEMP), (carbamazepine m.p.=190.2 degrees C., nicotinamide m.p.=150-160 degrees C.).

Thermogravimetric Analysis: (TA Instruments 2950 Hi-Resolution TGA), 57.94% weight loss starting at 205.43 degrees C. followed by complete decomposition.

Powder x-ray diffraction: (Rigaku Miniflex Diffractometer using Cu Kα (λ=1.540562), 30 kV, 15 mA). The powder data were collected over an angular range of 3° to 40° 2θ in continuous scan mode using a step size of 0.02° 2θ and a scan speed of 2.0°/minute. PXRD: Showed analogous peaks to the simulated PXRD derived from the single crystal data. PXRD analysis experimental (calculated): 6.5 (6.7); 8.8 (9.0); 10.1 (10.3); 13.2 (13.5); 15.6 (15.8); 17.7 (17.9); 17.8 (18.1); 18.3 (18.6); 19.8 (20.1); 20.4 (20.7); 21.6 (22.); 22.6 (22.8); 22.9 (23.2); 26.4 (26.7); 26.7 (27.0); 28.0 (28.4).

Example 32

Carbamazepine:saccharin (Form II) (1:1 stoichiometry)

Figure 52:
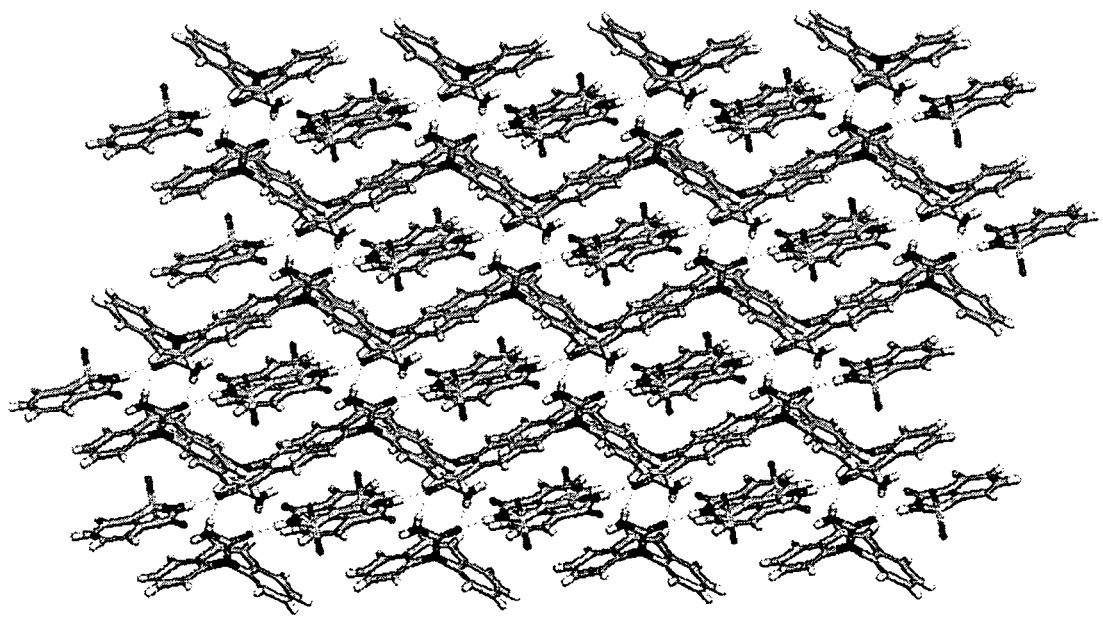
FIG. 52 The co-crystal structure of carbamazepine and saccharin (Form II).
Figure 53A:
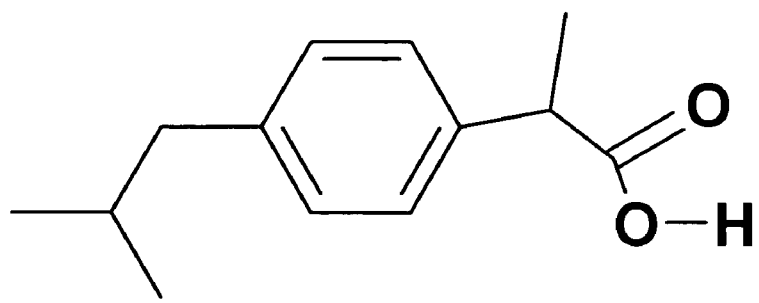
FIG. 53A-C The chemical structures of ibuprofen, flurbiprofen, and aspirin, respectively.
Figure 53B:
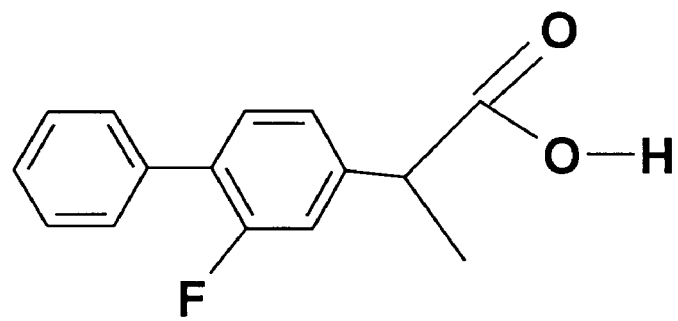
Figure 53C:
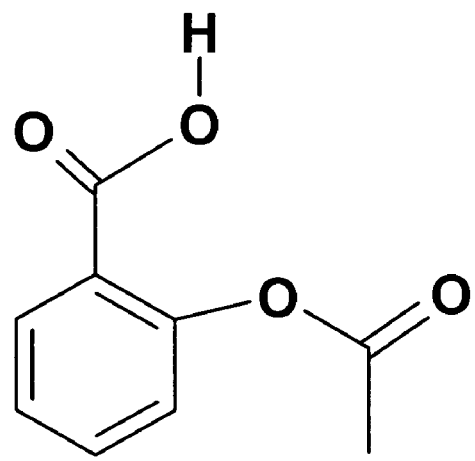

25 mg (0.1058 mmol) carbamazepine and 19 mg (0.1037 mmol) saccharin were dissolved in approximately 4 mL ethanol. Slow evaporation of the solvent yielded colorless needles of a 1:1 carbamazepine/saccharin cocrystal, as shown in FIG. 52. Solubility measurements indicate that this multiple-component crystal of carbamazepine has improved solubility over previously known forms of carbamazepine (e.g., increased molar solubility and longer solubility in aqueous solutions).

Crystal data: (Bruker SMART-APEX CCD Diffractometer), $C_{22}H_{17}N_3O_4S_1$, M=419.45, triclinic P-1; a=7.5140(11), b=10.4538(15), c=12.6826(18) Å, α=83.642(2)°, β=85.697 (2)°, γ=75.411(2)°, U=957.0(2) Å$^3$, T=200(2) K, Z=2, μ(Mo—Kα)=0.206 mm$^{-1}$, $D_c$=1.456 Mg/m$^3$, λ=0.71073 Å, F(000)=436, 2θ$_{max}$=56.20°; 8426 reflections measured, 4372 unique ($R_{int}$=0.0305). Final residuals for 283 parameters were $R_1$=0.0458, $wR_2$=0.1142 for I>2σ(I), and $R_1$=0.0562, $wR_2$=0.1204 for all 4372 data.

Crystal packing: The co-crystals contain hydrogen bonded carboxamide homodimers. The 2° amines of the saccharin are hydrogen bonded to the carbonyl of the CBZ on each side forming a tetramer. The crystal has a space group of P-1 with π-π interactions between the phenyl groups of the CBZ and the saccharin phenyl groups.

Infrared Spectroscopy: (Nicolet Avatar 320 FTIR), unsymmetrical and symmetrical stretching shifts up to 3495 cm$^{-1}$ accounting for 1° amines; C=O aliphatic stretching was shifted up to 1726 cm$^{-1}$ N—H in-plane bending at 1649 cm$^{-1}$; C=C stretching shifted down to 1561 cm$^{-1}$; (O=S=O) sulfonyl peak at 1330 cm$^{-1}$ C—N aliphatic stretching 1175 cm$^{-1}$.

Differential Scanning Calorimetry: (TA Instruments 2920 DSC), 75.31 degrees C. (endotherm) and 177.32 degrees C. (endotherm), m.p.=148-155 degrees C. (MEL-TEMP); (carbamazepine m.p.=190.2 degrees C., saccharin m.p.=228.8 degrees C.).

Thermogravimetric Analysis: (TA Instruments 2950 Hi-Resolution TGA), 3.342% weight loss starting at 67.03 degrees C. and a 55.09% weight loss starting at 118.71 degrees C. followed by complete decomposition.

Powder x-ray diffraction: (Rigaku Miniflex Diffractometer using Cu Kα (λ=1.540562), 30 kV, 15 mA). The powder data were collected over an angular range of 3° to 40° 2θ in continuous scan mode using a step size of 0.02° 2θ and a scan speed of 2.0°/minute. PXRD derived from the single crystal data, experimental (calculated): 6.9 (7.0); 12.2 (12.2); 13.6

(13.8); 14.0 (14.1); 14.1 (14.4); 15.3 (15.6); 15.9 (15.9); 18.1 (18.2); 18.7 (18.8); 20.2 (20.3); 21.3 (21.5); 23.7 (23.9); 26.3 (26.4); 28.3 (28.3).

Example 33

Carbamazepine:2,6-pyridinedicarboxylic acid (2:3 stoichiometry)

Figure 54A:
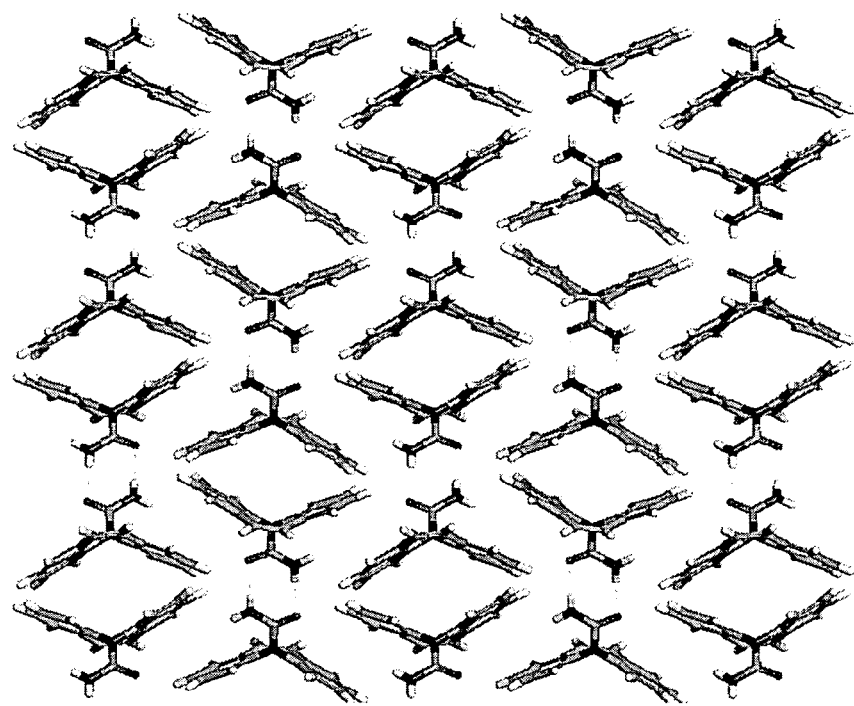
FIG. 54A-B The crystal structure of carbamazepine and the co-crystal structure of carbamazepine and 2,6-pyridinedicarboxylic acid, respectively.
Figure 54B:
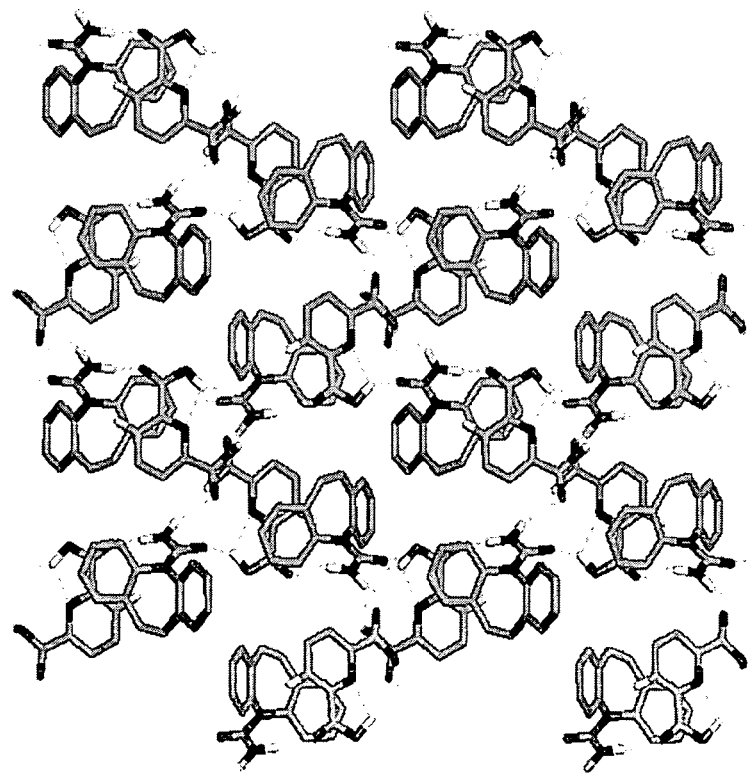

36 mg (0.1524 mmol) carbamazepine and 26 mg (0.1556 mmol) 2,6-pyridinedicarboxylic acid were dissolved in approximately 2 mL ethanol. Slow evaporation of the solvent yielded clear needles of a 1:1 carbamazepine/2,6-pyridinedicarboxylic acid co-crystal, as shown in FIG. 54A-B.

Crystal data: (Bruker SMART-APEX CCD Diffractometer). $C_{22}H_{17}N_3O_5$, M=403.39, orthorhombic P2(1)2(1)2(1); a=7.2122, b=14.6491, c=17.5864 Å, α=90°, β=90°, γ=90°, V=1858.0(2) Å$^3$, T=100 K, Z=4, μ(MO-Kα)=0.104 mm$^{-1}$, $D_c$=1.442 Mg/m$^3$, λ=0.71073 Å, F(000)840, $2θ_{max}$=28.3. 16641 reflections measured, 4466 unique ($R_{int}$=0.093). Final residuals for 271 parameters were $R_1$=0.0425 and $wR_2$=0.0944 for I>2σ(I).

Crystal packing: Each hydrogen on the CBZ 1° amine is hydrogen bonded to a carbonyl group of a different 2,6-pyridinedicarboxylic acid moiety. The carbonyl of the CBZ carboxamide is hydrogen bonded to two hydroxide groups of one 2,6-pyridinedicarboxylic acid moitey.

Infrared Spectroscopy: (Nicolet Avatar 320 FTIR). 3439 cm$^{-1}$, (N—H stretch, 1° amine, CBZ); 1734 cm$^{-1}$, (C=O); 1649 cm$^{-1}$, (C=C).

Melting Point: 214-216 degrees C. (MEL-TEMP). (carbamazepine m.p.=191-192 degrees C., 2,6-pyridinedicarboxylic acid m.p.=248-250 degrees C.).

Thermogravimetric Analysis: (TA Instruments 2950 Hi-Resolution TGA). 69% weight loss starting at 215 degrees C. and a 17% weight loss starting at 392 degrees C. followed by complete decomposition.

Example 34

Carbamazepine:5-nitroisophthalic acid (1:1 stoichiometry)

Figure 55A:
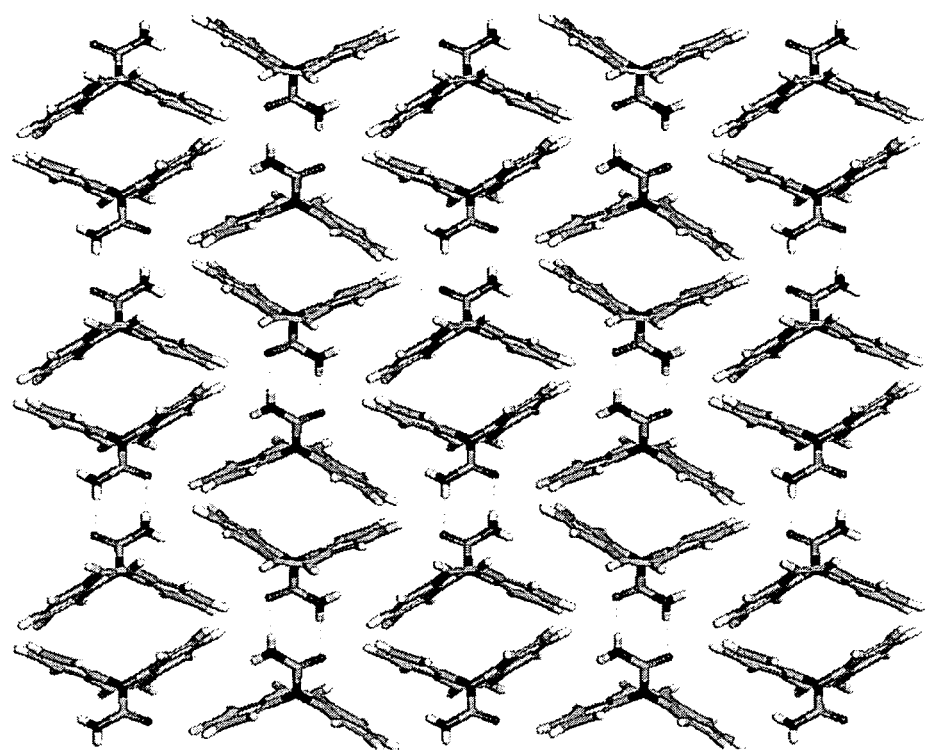
FIG. 55A-B The crystal structure of carbamazepine and the co-crystal structure of carbamazepine and 5-nitroisophthalic acid, respectively.
Figure 55B:
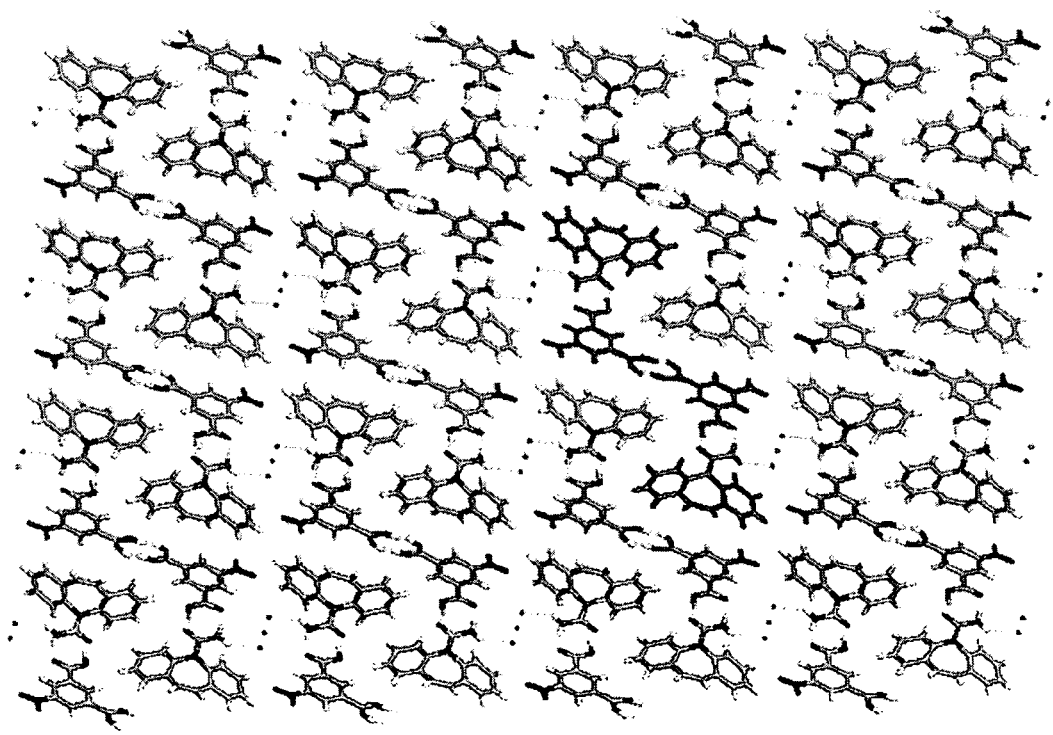

40 mg (0.1693 mmol) carbamazepine and 30 mg (0.1421 mmol) 5-nitroisophthalic acid were dissolved in approximately 3 mL methanol or ethanol. Slow evaporation of the solvent yielded yellow needles of a 1:1 carbamazepine/5-nitroisophthalic acid co-crystal, as shown in FIG. 55A-B.

Crystal data: (Bruker SMART-APEX CCD Diffractometer). $C_{47}H_{40}N_6O_{16}$, M=944.85, monoclinic C2/c; a=34.355 (8), b=5.3795(13), c=23.654(6) Å, α=90°, β=93.952(6)°, γ=90°, V=4361.2(18)Å$^3$, T=200(2) K, Z=4, μ(MO-Kα)= 0.110 mm$^{-1}$, $D_c$=1.439 Mg/m$^3$, λ=0.71073 Å, F(000)1968, $2θ_{max}$=26.43°. 11581 reflections measured, 4459 unique ($R_{int}$=0.0611). Final residuals for 311 parameters were $R_1$=0.0725, $wR_2$=0.1801 for I>2σ(I), and $R_1$=0.1441, $wR_2$=0.1204 for all 4459 data.

Crystal packing: The co-crystals are sustained by hydrogen bonded carboxylic acid homodimers between the two 5-nitroisophthalic acid moieties and hydrogen bonded carboxyamide heterodimers between the carbamazepine and 5-nitroisophthalic acid moiety. There is solvent hydrogen bonded to an additional N—H donor from the carbamazepine moiety.

Infrared Spectroscopy: (Nicolet Avatar 320 FTIR). 3470 cm$^{-1}$, (N—H stretch, 1° amine, CBZ); 3178 cm$^{-1}$, (C—H stretch, alkene); 1688 cm$^{-1}$, (C=O); 1602 cm$^{-1}$, (C=C).

Differential Scanning Calorimetry: (TA Instruments 2920 DSC). 190.51 degrees C. (endotherm). m.p.=NA (decomposes at 197-200 degrees C.) (MEL-TEMP). (carbamazepine m.p.=191-192 degrees C., 5-nitroisophthalic acid m.p.=260-261 degrees C.).

Thermogravimetric Analysis: (TA Instruments 2950 Hi-Resolution TGA). 32.02% weight loss starting at 202 degrees C., a 12.12% weight loss starting at 224 degrees C. and a 17.94% weight loss starting at 285 degrees C. followed by complete decomposition.

Powder x-ray diffraction: (Rigaku Miniflex Diffractometer using CuKα (λ=1.540562), 30 kV, 15 mA). The powder data were collected over an angular range of 3 to 40 2 in continuous scan mode using a step size of 0.02 2 and a scan speed of 2.0/min. PXRD: Showed analogous peaks to the simulated PXRD derived from the single crystal data. PXRD analysis experimental (calculated): 10.138 (10.283), 15.291 (15.607), 17.438 (17.791), 21.166 (21.685), 31.407 (31.738), 32.650 (32.729).

Example 35

Carbamazepine: 1,3,5,7-adamantane tetracarboxylic acid (1:1 stoichiometry)

Figure 56A:
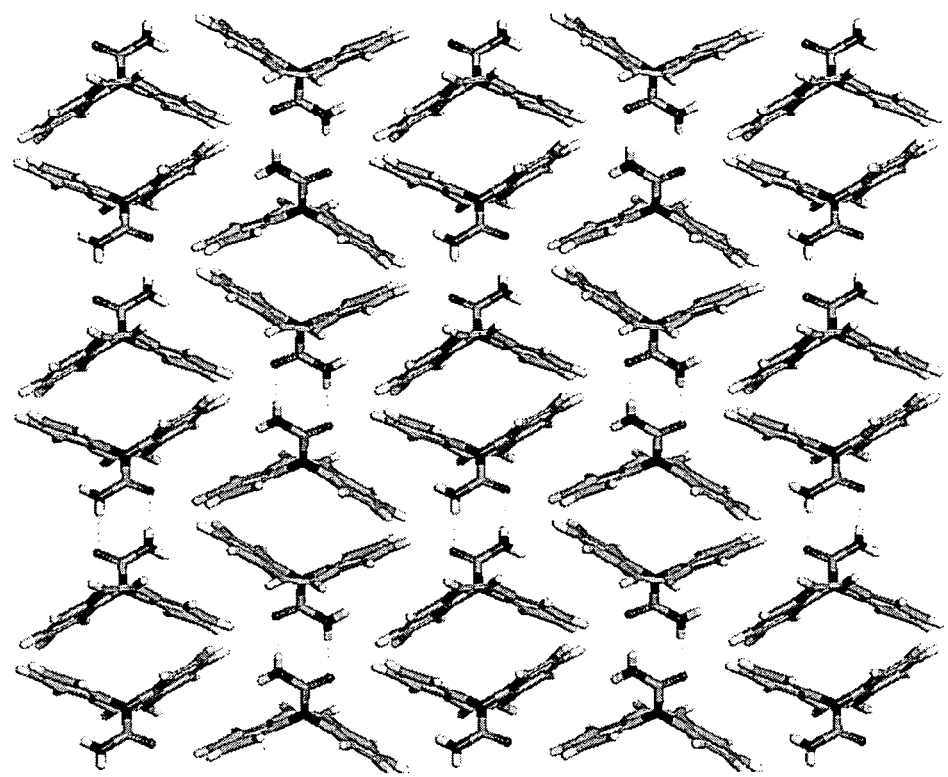
FIG. 56A-B The crystal structure of carbamazepine and the co-crystal structure of carbamazepine and 1,3,5,7-adamantanetetracarboxylic acid, respectively.
Figure 56B:
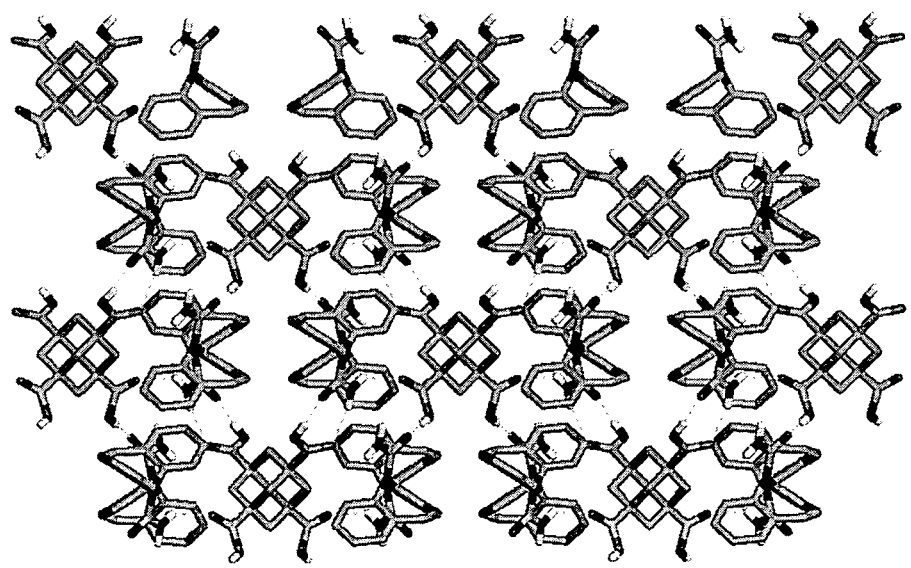

15 mg (0.1524 mmol) carbamazepine and 20 mg (0.1556 mmol) 1,3,5,7-adamantanetetracarboxylic acid were dissolved in approximately 1 mL methanol or 1 mL ethanol. Slow evaporation of the solvent yields clear plates of a 2:1 carbamazepine/1,3,5,7-adamantanetetracarboxylic acid co-crystal, as shown in FIG. 56A-B.

Crystal data: (Bruker SMART-APEX CCD Diffractometer). $C_{44}H_{40}N_2O_{10}$, M=784.80, monoclinicC2/c; a=18.388 (4), b=12.682(3), c=16.429(3) Å, β=100.491(6)°, V=3767.1 (14) Å$^3$, T=100(2) K, Z=4, μ(MO-Kα)=0.099 mm$^{-1}$, $D_c$=1.384 Mg/m$^3$, λ=0.71073 Å, F(000)1648, $2θ_{max}$=28.20°. 16499 reflections measured, 4481 unique ($R_{int}$=0.052). Final residuals for 263 parameters were $R_1$=0.0433 and $wR_2$=0.0913 for I>2σ(I).

Crystal packing: The co-crystals form a single 3D network of four tetrahedron, linked by square planes similar to the PtS topology. The crystals are sustained by hydrogen bonding.

Infrared Spectroscopy: (Nicolet Avatar 320 FTIR). 3431 cm$^{-1}$, (N—H stretch, 1° amine, CBZ); 3123 cm$^{-1}$, (C—H stretch, alkene); 1723 cm$^{-1}$, (C=O); 1649 cm$^{-1}$, (C=C).

Melting Point: (MEL-TEMP). 258-260 degrees C. (carbamazepine m.p.=191-192 degrees C., adamantanetetracarboxylic acid m.p.=>390 degrees C.).

Thermogravimetric Analysis: (TA Instruments 2950 Hi-Resolution TGA). 9% weight loss starting at 189 degrees C., a 52% weight loss starting at 251 degrees C. and a 31% weight loss starting at 374 degrees C. followed by complete decomposition.

Example 36

Carbamazepine:benzoquinone (1:1 stoichiometry)

Figure 57A:
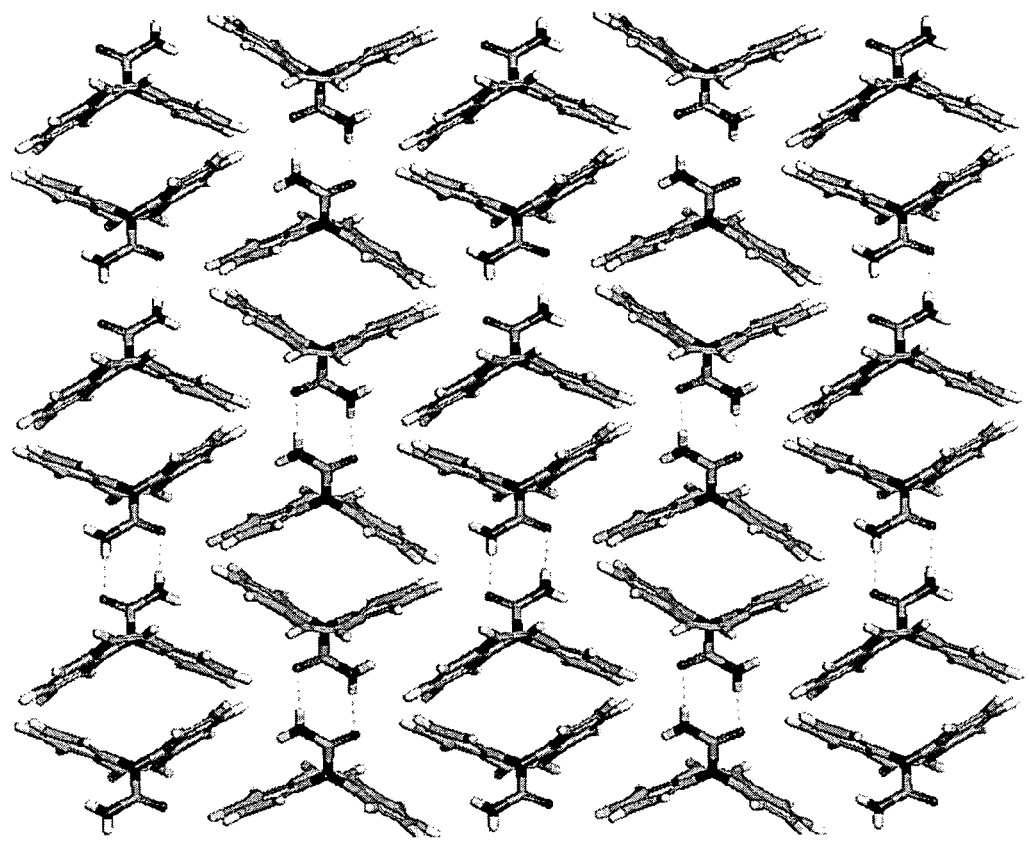
FIG. 57A-B The crystal structure of carbamazepine and the co-crystal structure of carbamazepine and benzoquinone, respectively.
Figure 57B:
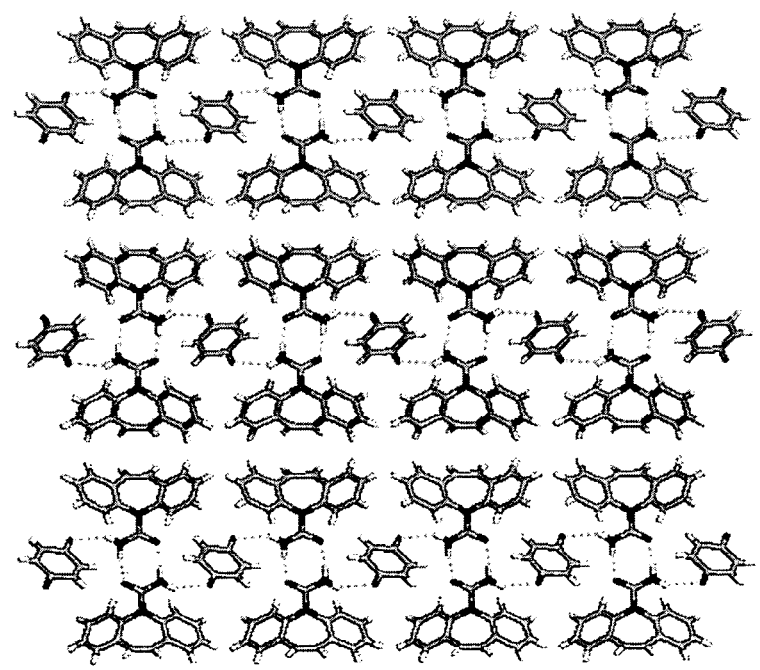

25 mg (0.1058 mmol) carbamazepine and 11 mg (0.1018 mmol) benzoquinone was dissolved in 2 mL methanol or THF. Slow evaporation of the solvent produced an average yield of yellow crystals of a 1:1 carbamazepine/benzoquinone co-crystal, as shown in FIG. 57A-B.

Crystal data: (Bruker SMART-APEX CCD Diffractometer). $C_{21}H_{16}N_2O_3$, M=344.36, monoclinic P2(1)/c; a=10.3335(18), b=27.611(5), c=4.9960(9) Å, β=102.275 (3)°, V=1392.9(4) Å$^3$, T=100(2) K, Z=3, $D_c$=1.232 Mg/m$^3$, μ(MO-Kα)=0.084 mm$^{-1}$, λ=0.71073 Å, F(000)540, $2θ_{max}$=28.24°. 8392 reflections measured, 3223 unique ($R_{int}$=0.1136). Final residuals for 199 parameters were $R_1=0.0545$ and $wR_2=0.1358$ for $I>2\sigma(I)$, and $R_1=0.0659$ and $wR_2=0.1427$ for all 3223 data.

Crystal packing: The co-crystals contain hydrogen bonded carboxamide homodimers. Each 1° amine on the CBZ is bifurcated to a carbonyl group of a benzoquinone moiety. The dimers form infinite chains.

Infrared Spectroscopy: (Nicolet Avatar 320 FTIR). 3420 cm$^{-1}$, (N—H stretch, 1° amine, CBZ); 2750 cm$^{-1}$, (aldehyde stretch); 1672 cm$^{-1}$, (C=O); 1637 cm$^{-1}$, (C=C, CBZ).

Melting Point: 170 degrees C. (MEL-TEMP). (carbamazepine m.p.=191-192 degrees C., benzoquinone m.p.=115.7 degrees C.).

Thermogravimetric Analysis: (TA Instruments 2950 Hi-Resolution TGA). 20.62% weight loss starting at 168 degrees C. and a 78% weight loss starting at 223 degrees C. followed by complete decomposition.

Example 37

Carbamazepine:trimesic Acid (Form II) (1:1 stoichiometry)

Figure 58A:
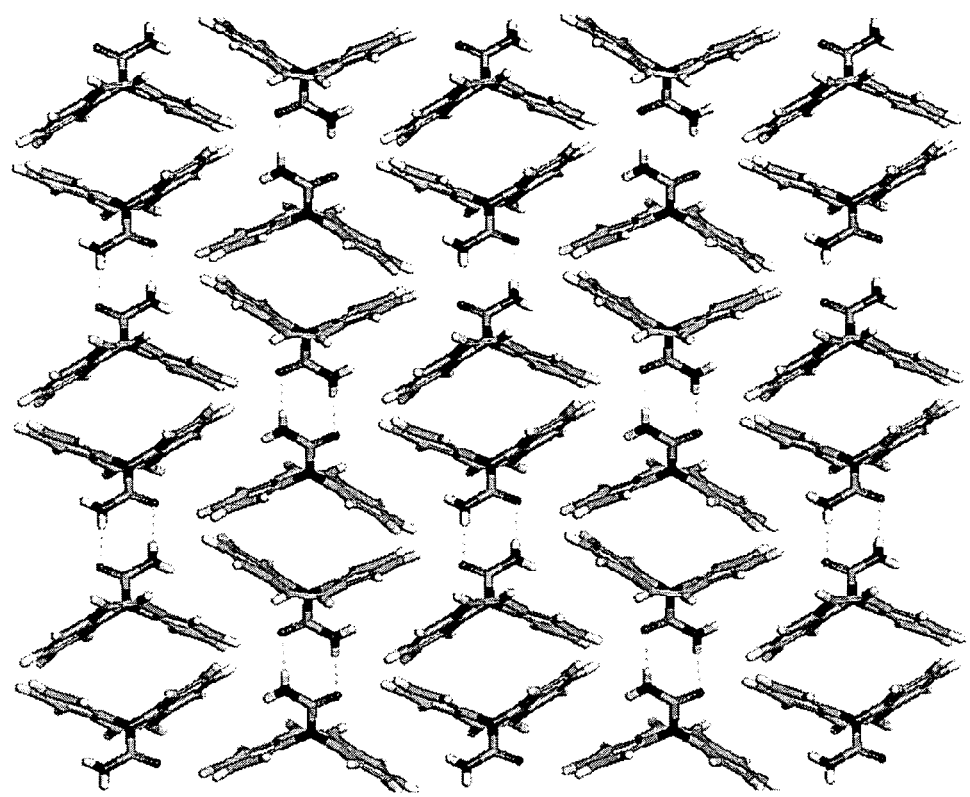
FIG. 58A-B The crystal structure of carbamazepine and the co-crystal structure of carbamazepine and trimesic acid (Form II), respectively.
Figure 58B:
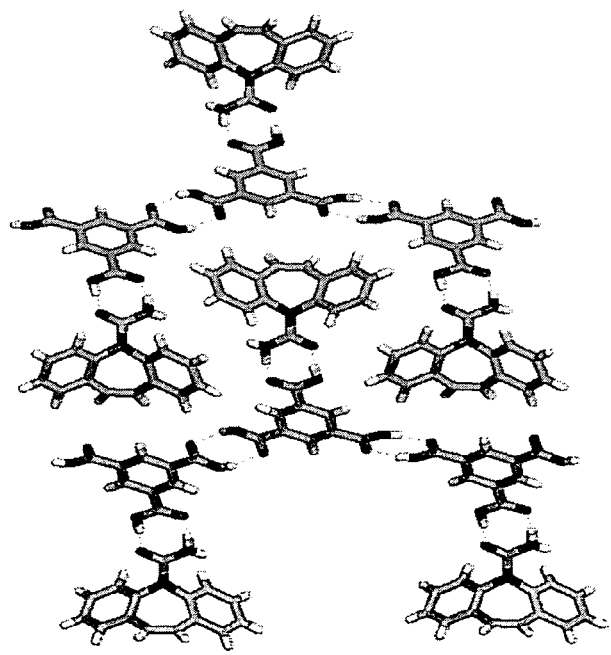
Figure 59:
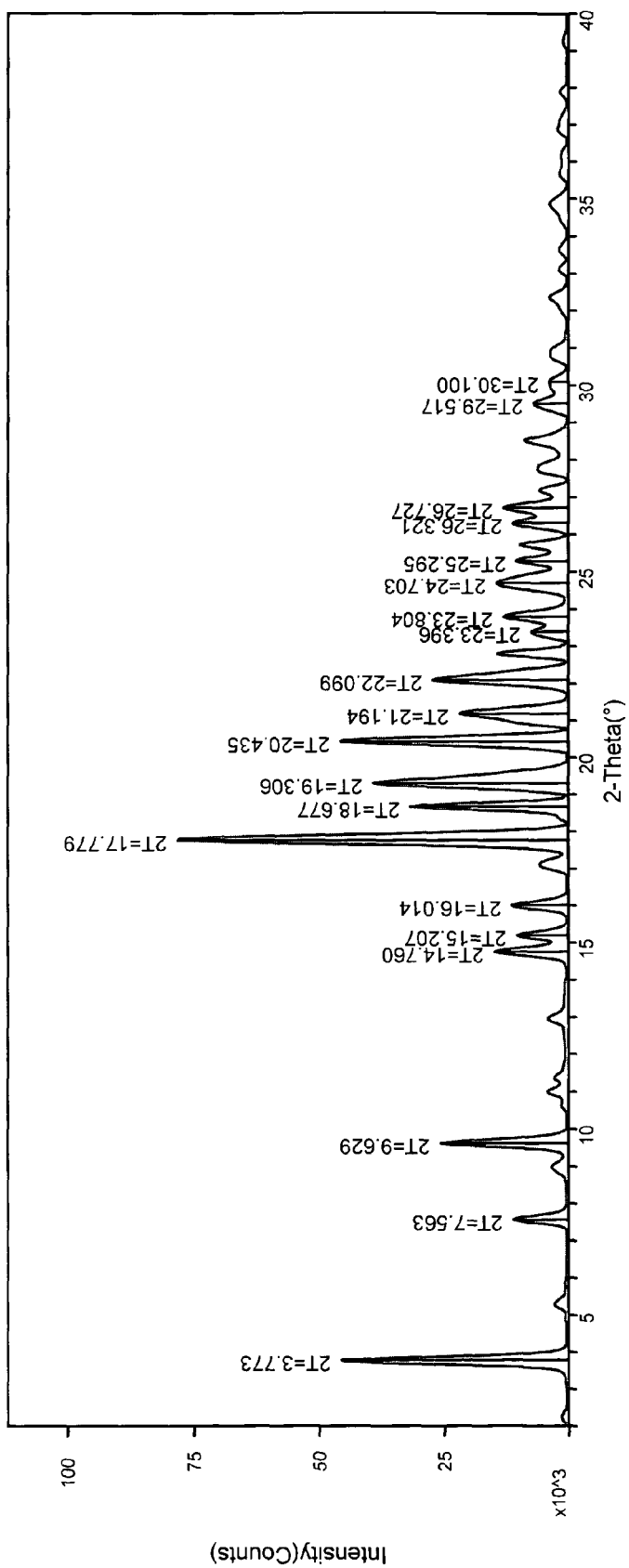
FIG. 59 PXRD diffractogram for a co-crystal of celecoxib and nicotinamide.
Figure 60:
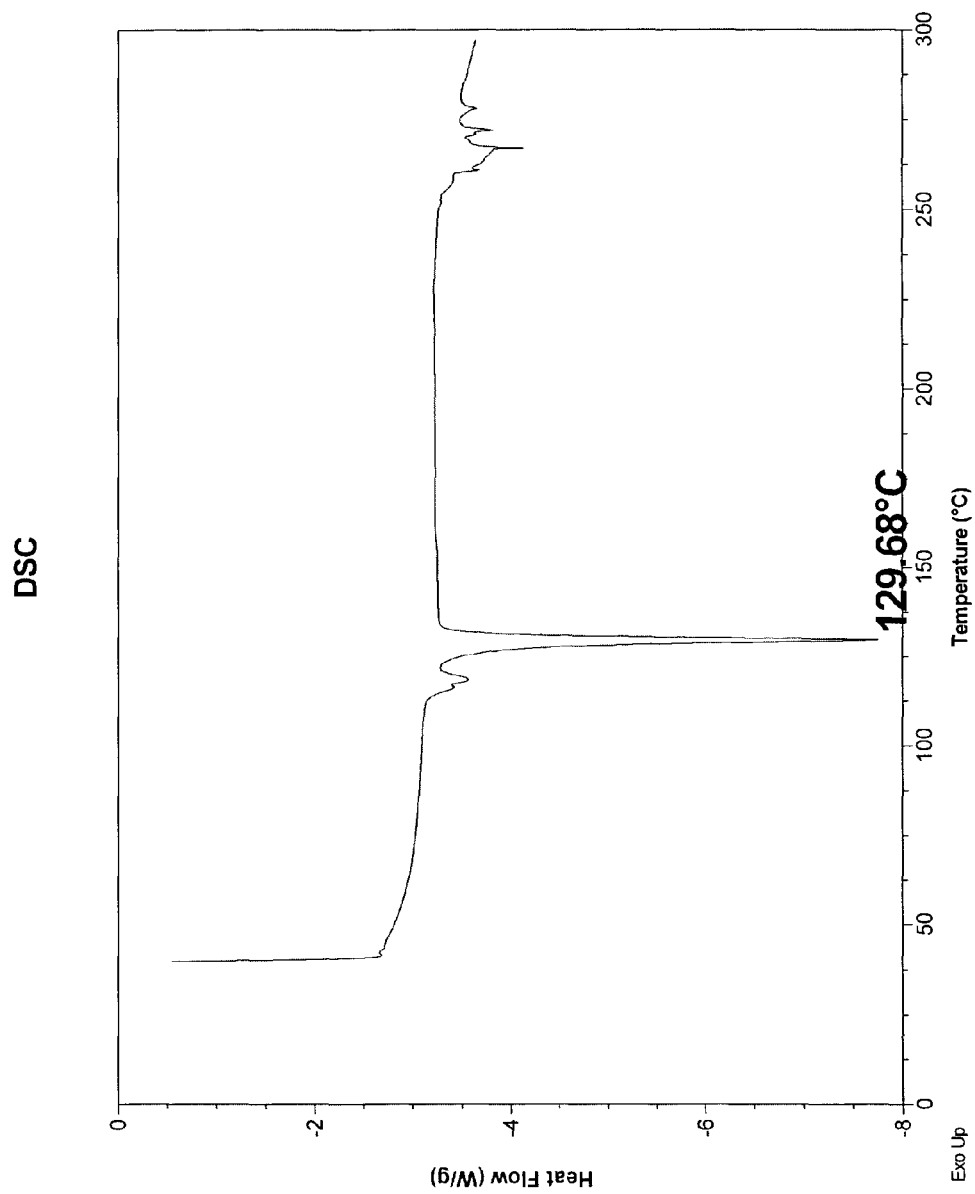
FIG. 60 DSC thermogram for a co-crystal of celecoxib and nicotinamide.
Figure 61:
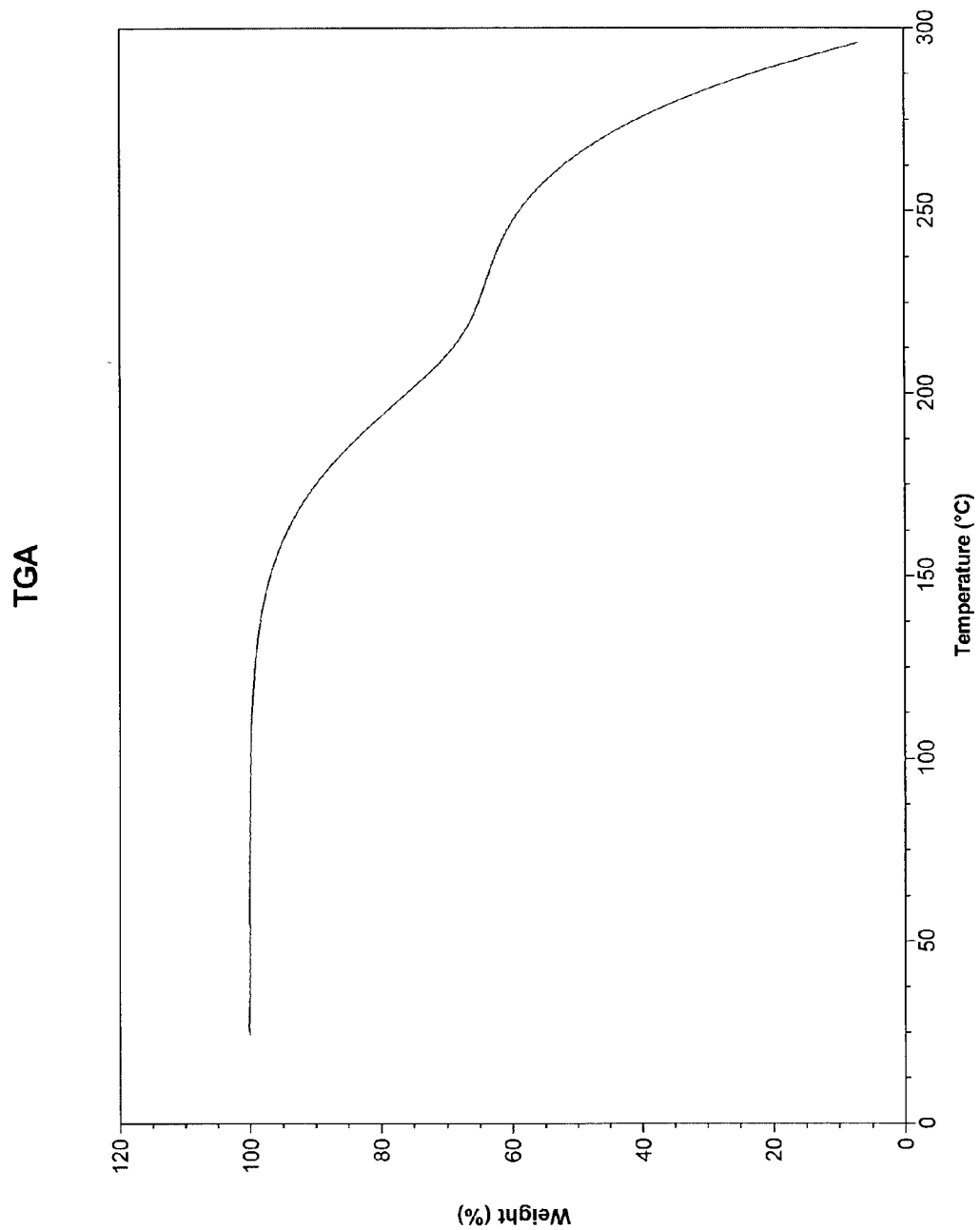
FIG. 61 TGA thermogram for a co-crystal of celecoxib and nicotinamide.
Figure 62:
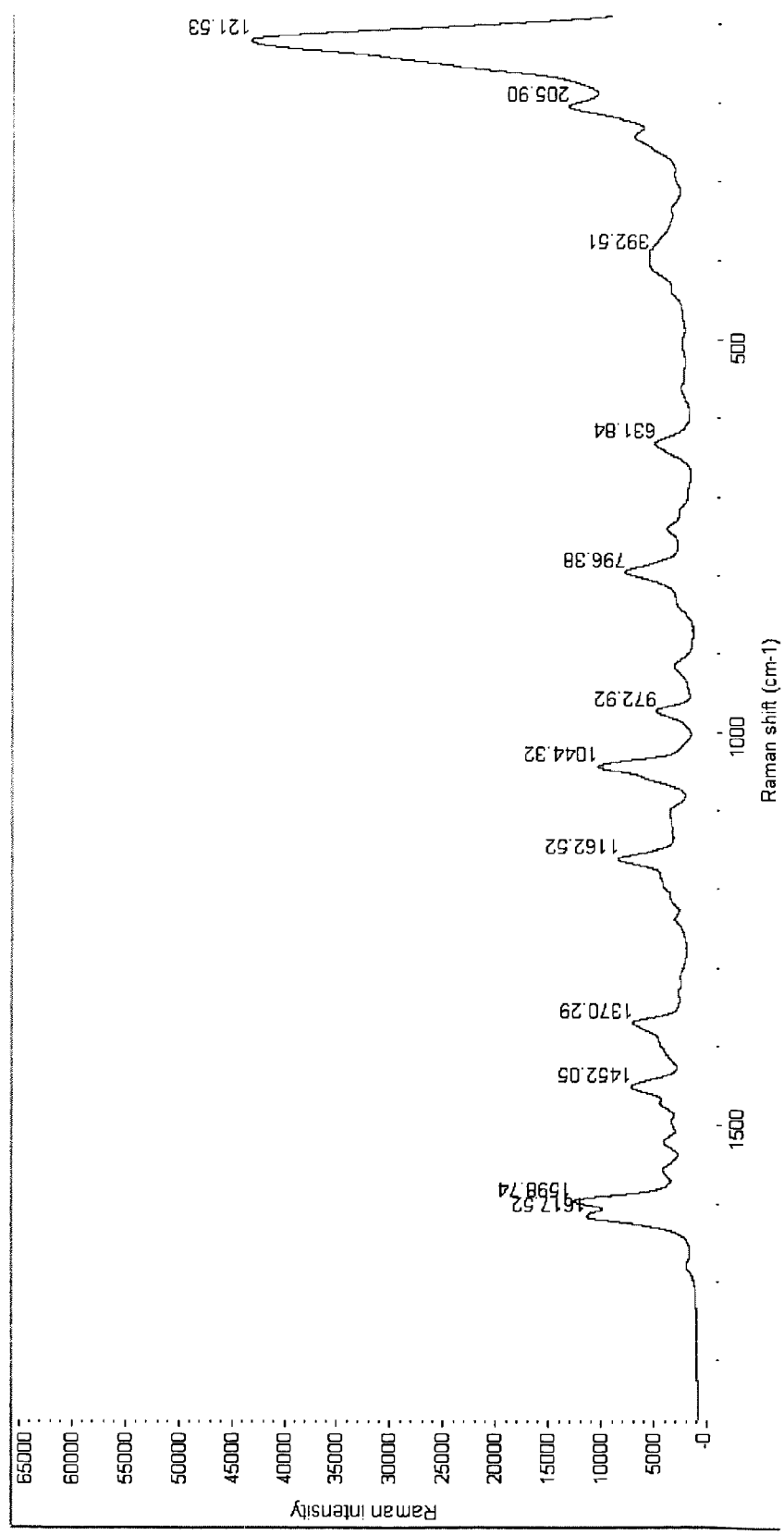
FIG. 62 Raman spectrum for a co-crystal of celecoxib and nicotinamide.

36 mg (0.1524 mmol) carbamazepine and 31 mg (0.1475 mmol) trimesic acid were dissolved in a solvent mixture of approximately 2 mL methanol and 2 mL dichloromethane. Slow evaporation of the solvent mixture yielded white starbursts of a 1:1 carbamazepine/trimesic acid co-crystal, as shown in FIG. 58A-B.

Crystal data: (Bruker SMART-APEX CCD Diffractometer). $C_{24}H_{18}N_2O_7$, M=446.26, monoclinic C2/c; a=32.5312 (50), b=5.2697(8), c=24.1594(37) Å, $\alpha$=90°, $\beta$=98.191(3)°, $\gamma$=90°, V=4099.39(37) Å$^3$, T=−173 K, Z=8, $\mu$(MO-K$\alpha$)= 0.110 mm$^{-1}$, $D_c$=1.439 Mg/m$^3$, $\lambda$=0.71073 Å, F(000)1968, $2\theta_{max}$=26.43°. 11581 reflections measured, 4459 unique ($R_{int}$=0.0611). Final residuals for 2777 parameters were $R_1$=0.1563, $wR_2$=0.1887 for $I>2\sigma(I)$, and $R_1$=0.1441, $wR_2$=0.1204 for all 3601 data.

Crystal packing: The co-crystals are sustained by hydrogen bonded carboxylic acid homodimers between carbamazepine and trimesic acid moieties and hydrogen bonded carboxylic acid-amine heterodimers between two trimesic acid moieties arranged in a stacked ladder formation.

Infrared Spectroscopy: (Nicolet Avatar 320 FTIR). 3486 cm$^{-1}$ (N—H stretch, 1° amine, CBZ); 1688 cm$^{-1}$ (C=O, 1° amide stretch, CBZ); 1602 cm$^{-1}$ (C=C, CBZ).

Differential Scanning Calorimetry: (TA Instruments 2920 DSC). 273 degrees C. (endotherm). m.p.=NA, decomposes at 278 degrees C. (MEL-TEMP). (carbamazepine m.p.=191-192 degrees C., trimesic acid m.p.=380 degrees C.)

Thermogravimetric Analysis: (TA Instruments 2950 Hi-Resolution TGA). 62.83% weight loss starting at 253 degrees C. and a 30.20% weight loss starting at 278 degrees C. followed by complete decomposition.

Powder x-ray diffraction: (Rigaku Miniflex Diffractometer using CuK$\alpha$ ($\lambda$=1.540562), 30 kV, 15 mA). The powder data were collected over an angular range of 3 to 40 2 in continuous scan mode using a step size of 0.02 2 and a scan speed of 2.0/min. PXRD analysis experimental: 10.736, 12.087, 16.857, 24.857, 27.857.

TABLE V

Detailed Characterization of Co-Crystals

Figure 2:
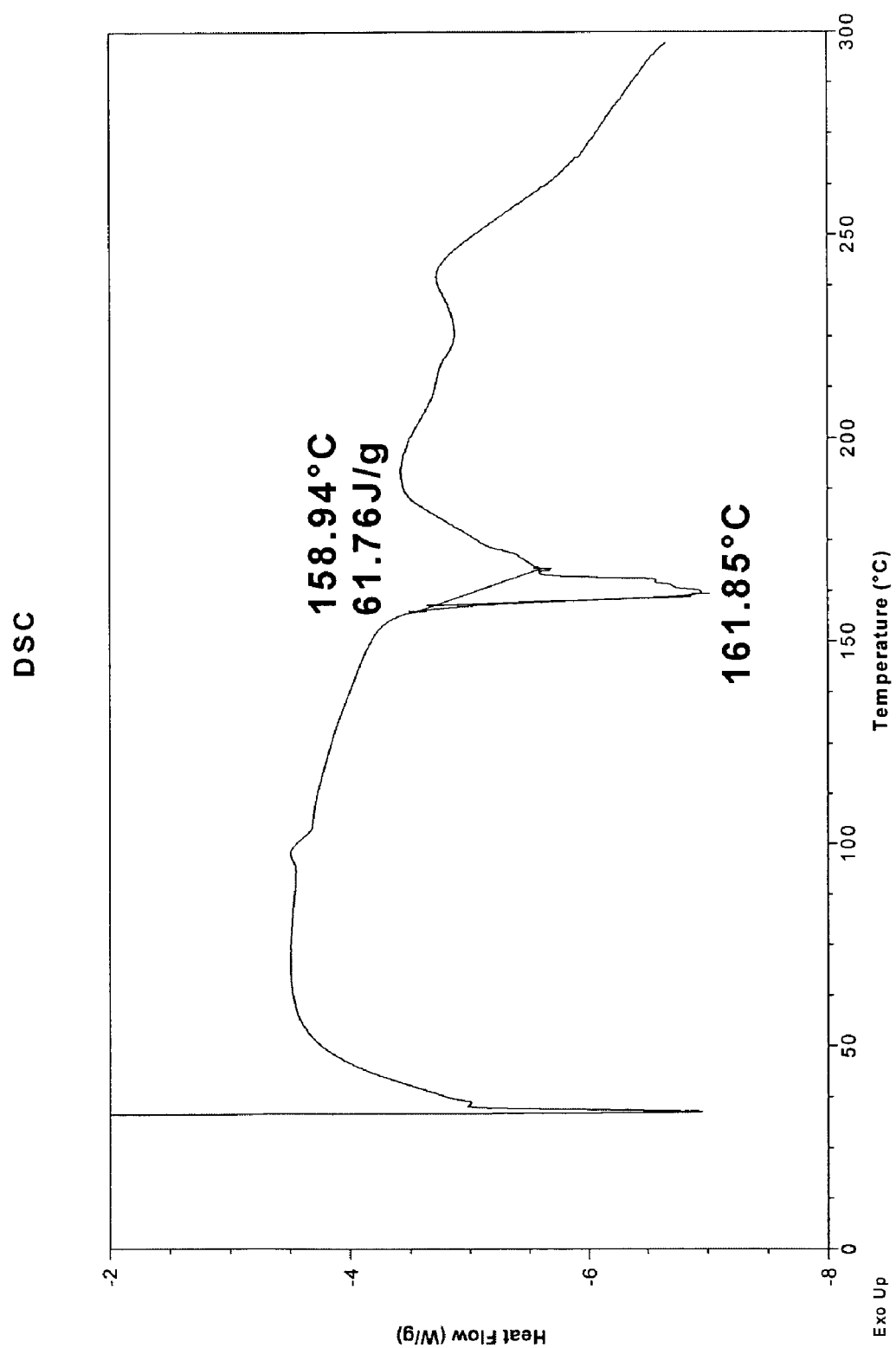
FIG. 2 DSC thermogram for a co-crystal of carbamazepine and saccharin (Form I).

All PXRD peaks are in units of degrees 2-theta
All Raman shifts are in units of cm$^{-1}$ Carbamazepine: Saccharin
PXRD (Form I): 7.01, 12.07, 14.09, 15.41, 18.47, 20.13, 22.01, 23.57, 24.41, 28.31 (FIG. 1)
PXRD (Form II): 6.9, 12.2, 13.6, 14.0, 14.1, 15.3, 15.9, 18.1, 18.7, 20.2, 21.3, 23.7, 26.3, 28.3
DSC (Form I): Broad endotherm at 161.9 degrees C. (FIG. 2)

TABLE V-continued

Detailed Characterization of Co-Crystals

TGA (Form I): Decomposition above 200 degrees CDSC (Form II): Endothermic transitions at 75.31 and 177.32 degrees C.
TGA (Form II): 3.342 percent weight loss starting at 67.03 degrees C., 55.09 percent weight loss starting at 118.71 degrees C., followed by decomposition
Method: CMAX Carbamazepine: Nicotinamide
PXRD (Form I): 4.97, 6.67, 8.75, 10.25, 13.25, 17.91, 18.49, 19.95, 20.49, 22.73, 24.39, 26.49 (FIG. 3)
PXRD (Form II): 6.5, 8.8, 10.1, 13.2, 15.6, 17.7, 17.8, 18.3, 19.8, 20.4, 21.6, 22.6, 22.9, 26.4, 26.7, 28.0
DSC (Form I): Sharp endotherm at 156.9 degrees C. (FIG. 4)
TGA (Form I): Decomposition beginning at ~150 degrees CDSC (Form II): Endothermic transitions at 74.49 and 159.05 degrees C.
TGA (Form II): 57.94 percent weight loss starting at 205.43 degrees C., followed by decomposition
Method: CMAX Carbamazepine: Trimesic acid
PXRD (Form I): 10.89, 12.23, 14.83, 16.25, 17.05, 18.13, 18.47, 21.47, 21.95, 24.57, 25.11, 27.99 (FIG. 5)
PXRD (Form II): 10.74, 12.09, 16.86, 24.86, 27.86
DSC (Form II): Endothermic transition at 273 degrees C.
TGA (Form II): 62.83 percent weight loss starting at 253 degrees C., 30.20 percent weight loss starting at 278 degrees C., followed by decomposition
Method: CMAX Celecoxib: Nicotinamide
PXRD: 3.77, 7.56, 9.63, 14.76, 15.21, 16.01, 17.78, 18.68, 19.31, 20.44, 21.19, 22.10
DSC: Two endothermic transitions at 117.2 and 118.8 degrees C. and a sharp endotherm at 129.7 degrees C.
TGA: Decomposition beginning at ~150 degrees C.
Raman: 1617.5, 1598.7, 1452.1, 1370.3, 1162.5, 1044.3, 972.9, 796.4, 631.8, 392.5, 205.9
Method: Slow evaporation of a 1:1 solution from acetone Topiramate: 18-Crown-6
PXRD: 10.79, 11.07, 12.17, 13.83, 16.13, 18.03, 18.51, 18.79, 19.21, 21.43, 22.25, 24.11 (FIG. 6)
DSC: Sharp endotherm at 134.7 degrees C., followed by an exotherm at 203 degrees C. (FIG. 7)
TGA: Rapid decomposition beginning at ~135 degrees C. and leveling off slightly after 200 degrees C.
Raman: 2994.5, 2942.7, 1471.6, 1427.4, 1261.7, 849.4, 804.5, 745.1, 629.2, 280.4, 225.9
Method: Addition of an ether solution containing 1 equivalent of topiramate to an ether solution containing 18-crown-6. Product precipitated following minor agitation of the combined mixture and was collected.

Olanzapine: Nicotinamide
PXRD (Form I): 4.89, 8.65, 12.51, 14.19, 15.59, 17.15, 19.71, 21.05, 23.95, 24.59, 25.53, 26.71 (FIG. 8)
PXRD (Form II): 6.41, 12.85, 18.67, 21.85, 24.37 (FIG. 30)
PXRD (Form III): 6.41, 12.85, 14.91, 18.67, 21.85, 24.37 (FIG. 31)
DSC (Form I): Slightly broad endotherm at 126.1 degrees C. (FIG. 9)
Method: See above Celecoxib: 18-Crown-6
PXRD: 8.73, 11.89, 12.57, 13.13, 15.01, 16.37, 17.03, 17.75, 18.45, 20.75, 22.37, 23.11, 24.33, 24.97, 26.61, 28.15 (FIG. 10)
DSC: Sharp endotherm at 189.6 degrees C. (FIG. 11)
TGA: Decomposition above 200 degrees C. with a 25% weight loss between ~190-210 degrees C.
Method: A solution containing one equivalent of celecoxib in ether was added to a solution containing 18-crown-6. A white solid formed immediately and was collected.

Itraconazole: Succinic Acid
PXRD: 3.0, 6.0, 8.1, 9.0, 17.1, 24.5 (FIG. 12)
DSC: Single endothermic transition at 160.1 degrees C. ± 1.0 degrees C. (FIG. 13)
TGA: Less than 0.1% volatile components by weight
Method: See above

TABLE V-continued

Detailed Characterization of Co-Crystals

Figure 40:
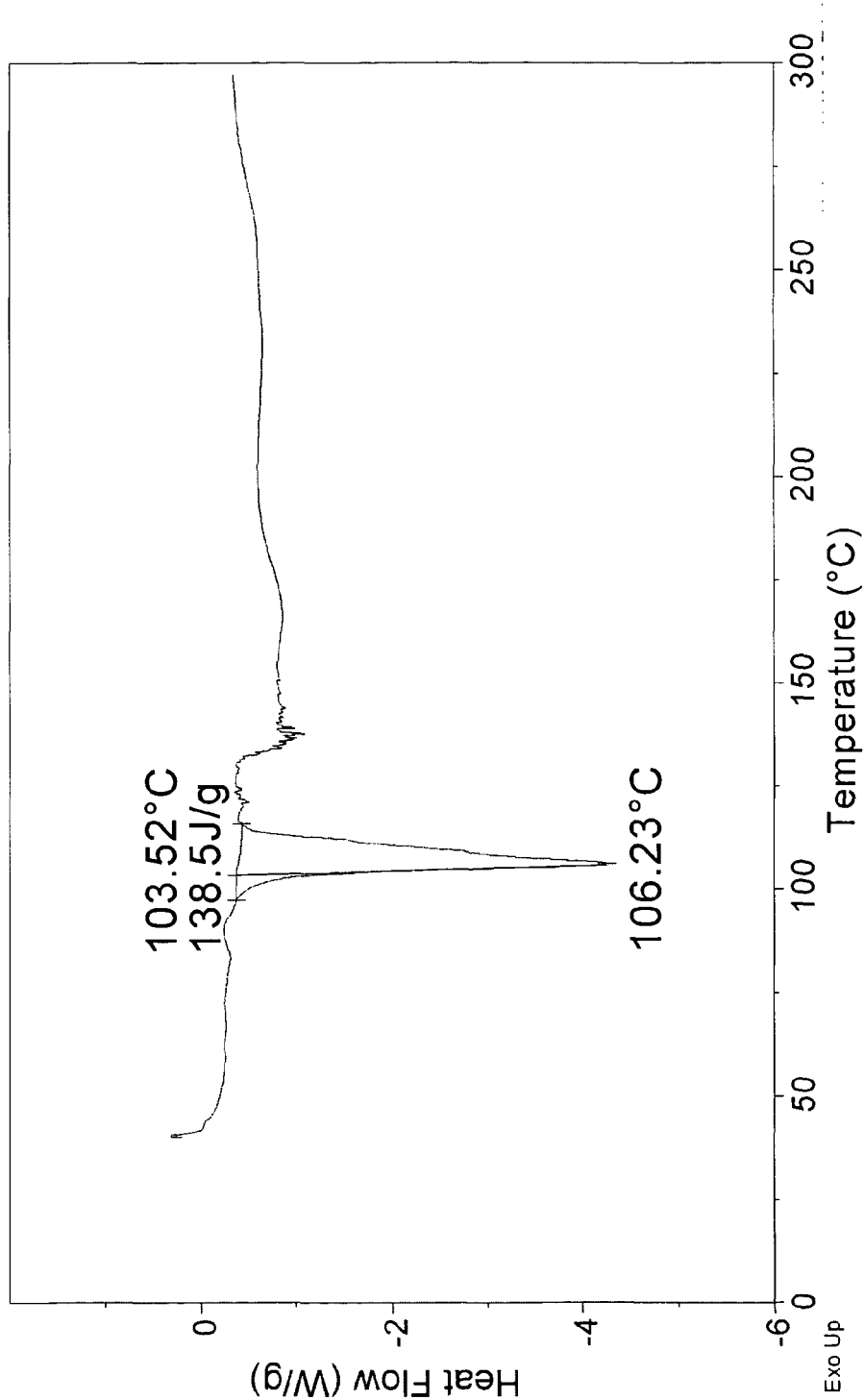
FIG. 40 DSC thermogram for a co-crystal of modafinil and malonic acid.
Figure 41:
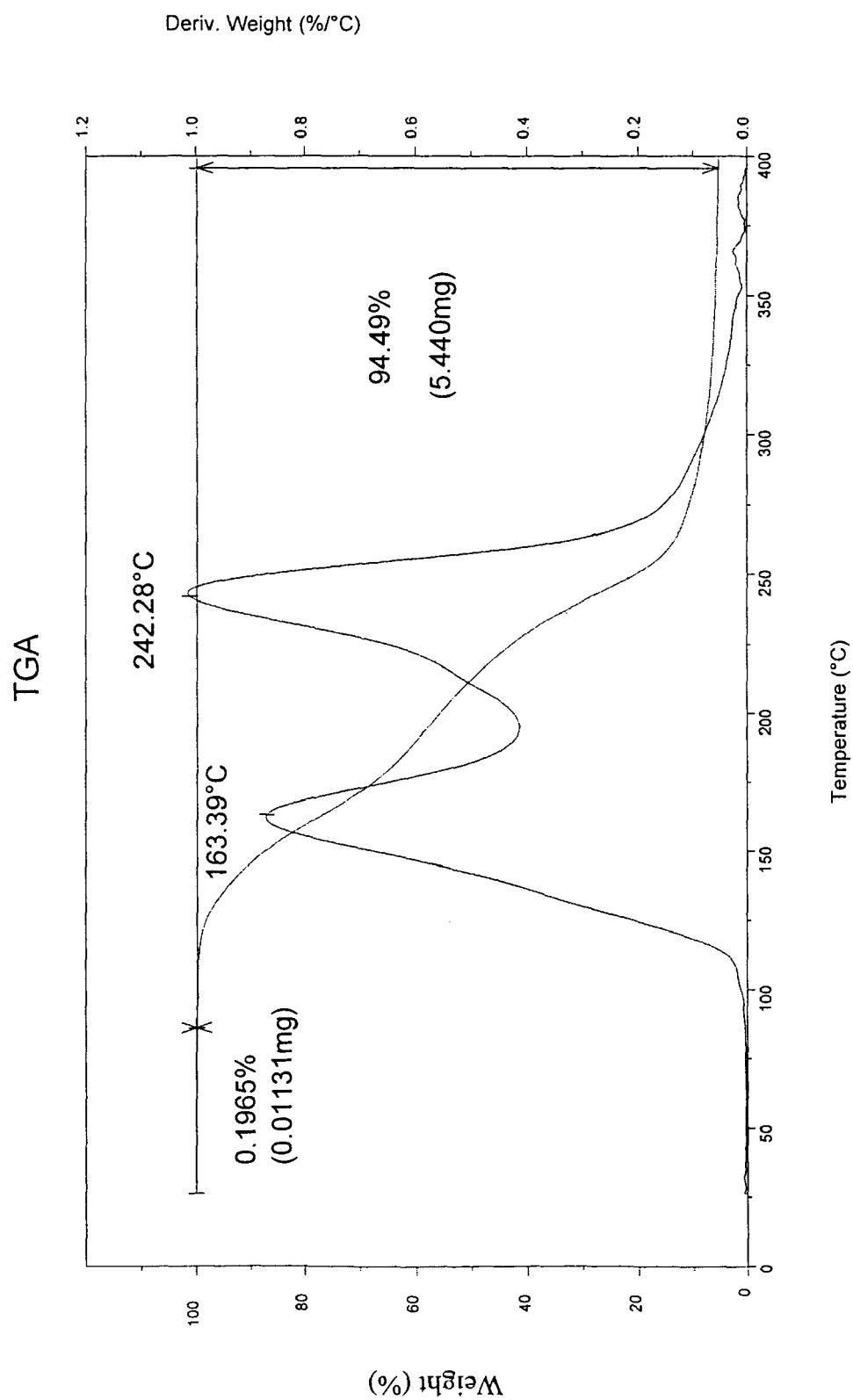
FIG. 41 TGA thermogram for a co-crystal of modafinil and malonic acid.
Figure 42A:
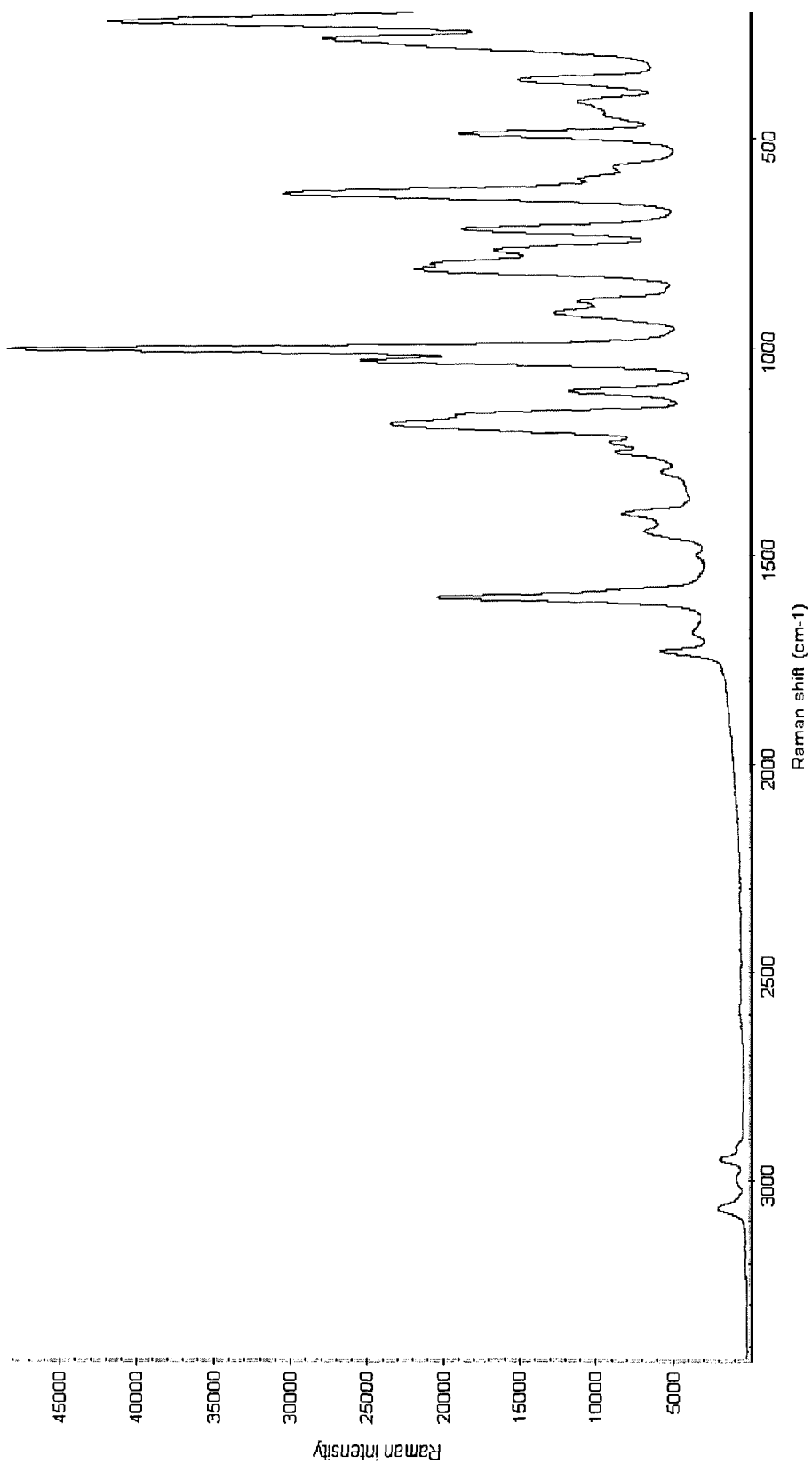
FIG. 42 Raman spectrum for a co-crystal of modafinil and malonic acid.

Itraconazole: Fumaric Acid
PXRD: 4.6, 5.9, 9.2, 10.6, 19.1, 20.8 (FIG. 14)
DSC: The material had a weak endothermic transition at 141.7 degrees C. and a strong endothermic transition at 179.58 degrees C. (FIG. 15)
TGA: The sample loses 0.5% of its weight on the TGA between room temperature and 100 degrees C.
Method:

Itraconazole: Tartaric Acid
PXRD: 4.1, 6.2, 8.3, 20.7, 25.6, 26.3 (FIG. 16)
DSC: An endothermic transition at 180.74 degrees C. (FIG. 17)
TGA: Less than 0.1% volatile components by weight by TGA.
Method: See above Itraconazole: Malic acid
PXRD: 4.4, 5.9, 8.8, 17.7, 20.0, 21.1, 22.6 (FIG. 18)
DSC: The sample has a strong endothermic transition at 154.36 degrees C. (FIG.19)
TGA: The sample contained less than 0.1% volatile components by weight
Method: See above ItraconazoleHCl: Tartaric acid
PXRD: 3.7, 11.0, 13.8, 16.5, 17.8 (FIG. 20)
DSC: The sample has a peak endothermic transition at 161degrees C. (FIG. 21)
TGA: The sample contained less than 0.1% volatile components by weight
Method: See above Modafinil: Malonic acid
PXRD: 5.00, 9.17, 16.81, 18.26, 19.43, 21.36, 21.94, 22.77, 24.49, 25.63, 28.45 (FIG. 22)
DSC: Endothermic transition at 106.23 degrees C. (FIG. 40)
Raman: 1601, 1183, 1032, 1004, 814, 633, 265, 222 (FIG. 42)
Method: See above Modafinil: Benzamide
PXRD: 5.11, 9.35, 10.25, 10.79, 14.07, 16.87, 18.33, 19.53, 21.38, 22.05, 22.89, 23.57, 24.73, 25.19, 25.81, 26.51, 28.60 (FIG. 23)
Method: Slow evaporation from a 1:1 solution in 1,2-dichoroethane Modafinil: Mandelic acid
PXRD: 6.11, 6.75, 9.53, 10.31, 14.77, 15.77, 16.99, 18.03, 20.01, 21.61, 22.47, 23.27, 25.27, 25.75, 27.23 (FIG. 24)
Method: Slow evaporation from a 1:1 solution in acetone Modafinil: Glycolic acid
PXRD: 6.09, 9.51, 14.91, 15.97, 19.01, 20.03, 21.59, 22.43, 22.75, 23.75, 25.03, 25.71 (FIG. 25)
Method: Slow evaporation from a 1:1 solution in acetone Modafinil: Fumaric acid
PXRD: 5.87, 7.19, 8.95, 12.49, 13.99, 16.13, 17.09, 18.19, 19.99, 21.57, 23.48, 25.01, 25.79, 28.17, 28.87, 29.69, 32.19 (FIG. 26)
Method: Slow evaporation from a 1:1 solution in 1,2-dichoroethane Modafinil: Maleic acid
PXRD: 4.69, 6.15, 9.61, 10.23, 15.65, 16.53, 17.19, 18.01, 19.27, 19.53, 19.97, 21.83, 22.45, 25.65 (FIG. 43)
Method: See above 5-fluorouracil: Urea
PXRD: 11.23, 12.69, 13.27, 15.93, 16.93, 20.37, 23.65, 25.55, 26.87, 32.49 (FIG. 36)
DSC: Sharp endotherm at 207.6 degrees C. (FIG. 33)
TGA: 32 percent weight loss between 150 and 220 degrees C. (FIG. 34)
Raman: 1347.1, 1024.4, 756.9, 643.7, 545.3 (FIG. 35)
Method: See above Hydroclorothiazide: Nicotinic acid
PXRD: 8.57, 13.23, 14.31, 16.27, 17.89, 18.75, 21.13, 21.45, 24.41, 25.73, 26.57, 27.43 (FIG. 37)
Method: See above Hydrochlorothiazide: 18-crown-6
PXRD: 9.97, 10.43, 11.57, 11.81, 12.83, 14.53, 15.67, 16.61, 19.05, 20.31, 20.65, 21.09, 21.85, 22.45, 23.63, 24.21, 25.33, 26.73 (FIG. 38)
Method: See above Hydrochlorothiazide: piperazine
PXRD: 6.85, 13.75, 15.93, 18.71, 20.67, 20.93, 23.27, 24.17, 28.33, 28.87, 30.89 (FIG. 39)
Method: See above Acetaminophen: 4,4'-bipyridine:water
DSC: Endothermic transition at 57.77 degrees C.
Method: See above Phenytoin: Pyridone
PXRD: 5.2, 11.1, 15.1, 16.2, 16.7, 17.8, 19.4, 19.8, 20.3, 21.2, 23.3, 26.1, 26.4, 27.3, 29.5
DSC: Endothermic transitions at 233.39 and 271.33 degrees C.
TGA: 29.09 percent weight loss starting at 192.8 degrees C., 48.72 percent weight loss starting at 238.27 degrees C., 18.38 percent weight loss starting at 260.17 degrees C., followed by decomposition
Method: See above Aspirin: 4,4'-bipyridine
DSC: Endothermic transition at 95.14 degrees C.
TGA: 9 percent weight loss starting at 22.62 degrees C., 49.06 percent weight loss starting at 102.97 degrees C., decomposition starting at 209.37 degrees C.
Method: See above Ibuprofen: 4,4'-bipyridine
PXRD: 3.4, 6.9, 10.4, 17.3, 19.1
DSC: Endothermic transitions at 64.85 and 118.79 degrees C.
TGA: 13.28 percent weight loss between room temperature and 100.02 degrees C. followed by decomposition
Method: See above Flurbiprofen: 4,4'-bipyridine
PXRD: 16.8, 17.1, 18.1, 19.0, 20.0, 21.3, 22.7, 25.0, 26.0, 26.0, 26.1, 28.2, 29.1
DSC: Endothermic transition at 162.47 degrees C.
TGA: 30.93 percent weight loss starting at 31.13 degrees C., 46.26 percent weight loss starting at 168.74 degrees C., followed by decomposition
Method: See above Flurbiprofen: trans-1,2-bis (4-pyridyl) ethylene
PXRD: 3.6, 17.3, 18.1, 18.4, 19.1, 22.3, 23.8, 25.9, 28.1
DSC: Endothermic transitions at 100.01, 125.59, and 163.54 degrees C.
TGA: 91.79 percent weight loss starting at 133.18 degrees C. followed by decomposition
Method: See above Carbamazepine: p-phthalaldehyde
PXRD: 8.5, 10.6, 11.9, 14.4, 15.1, 18.0, 18.5, 19.8, 23.7, 24.2, 26.4, 27.6, 27.8, 28.7, 29.3, 29.4
DSC: Endothermic transition at 128.46 degrees C.
TGA: 17.66 percent weight loss starting at 30.33 degrees C., 17.57 percent weight loss starting at 100.14 degrees C., followed by decomposition
Method: See above Carbamazepine: 2,6-pyridinecarboxylic acid
TGA: 69 percent weight loss starting at 215 degrees C., 17 percent weight loss starting at 392 degrees C., followed by decomposition
Method: See above Carbamazepine: 5-nitroisophthalic acid
PXRD: 10.14, 15.29, 17.44, 21.17, 31.41, 32.65
TGA: 32.02 percent weight loss starting at 202 degrees C., 12.12 percent weight loss starting at 224 degrees C., 17.94 percent weight loss starting at 285 degrees C., followed by decomposition
Method: See above Carbamazepine: 1,3,5,7-adamantane tetracarboxylic acid
TGA: 9 percent weight loss starting at 189 degrees C., 52 percent weight loss starting at 251 degrees C., 31 percent weight loss starting at 374 degrees C., followed by decomposition
Method: See above Carbamazepine: Benzoquinone
TGA: 20.62 percent weight loss starting at 168 degrees C., 78 percent weight loss starting at 223 degrees C., followed by decomposition
Method: See above

Example 38

Figure 27:
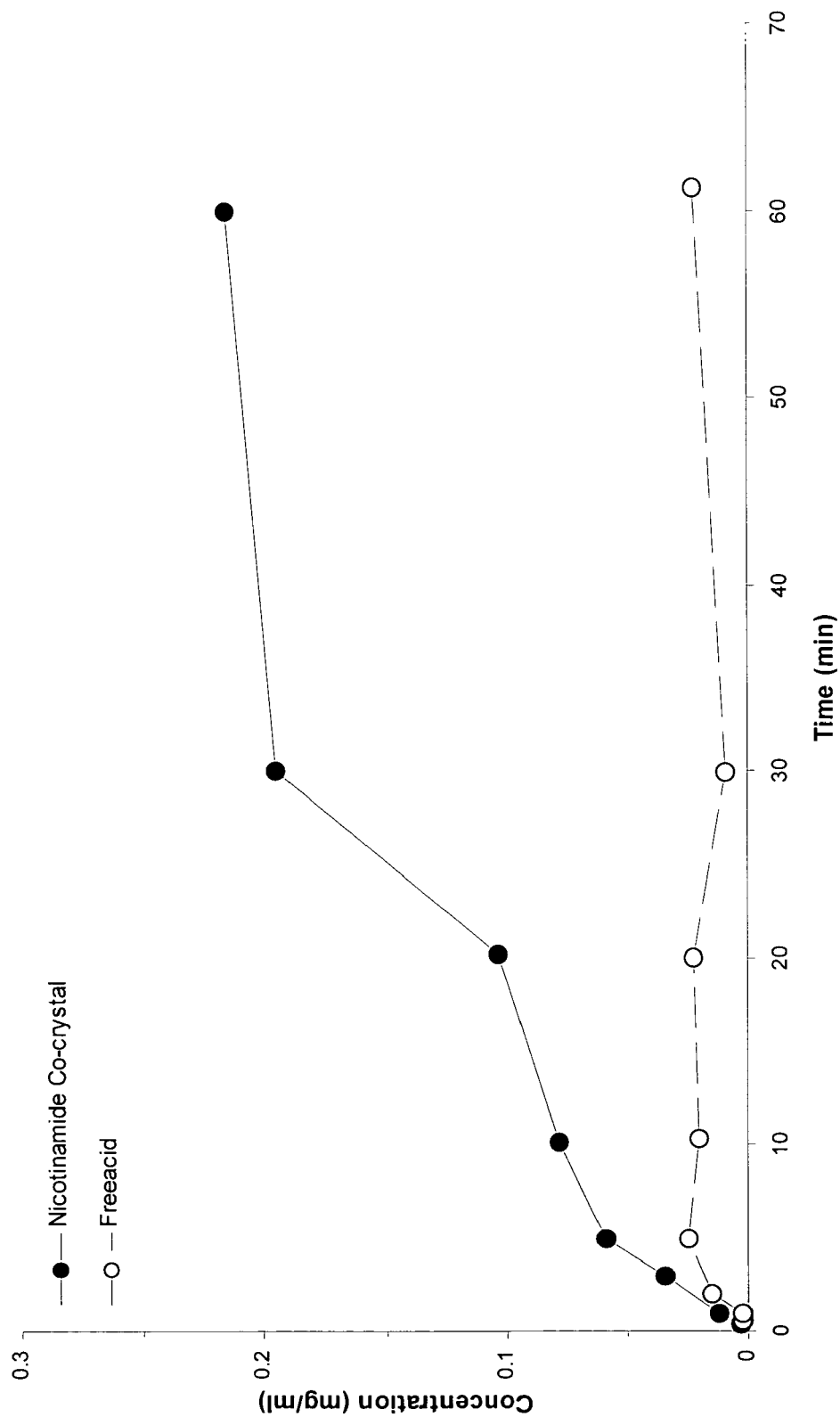
FIG. 27 Dissolution profile for a co-crystal of celecoxib: nicotinamide vs. celecoxib free acid.

A co-crystal with a modulated dissolution profile has been prepared. Celecoxib: nicotinamide co-crystals were prepared via methods shown in example 4. (See FIG. 27)

Example 39

Figure 28:
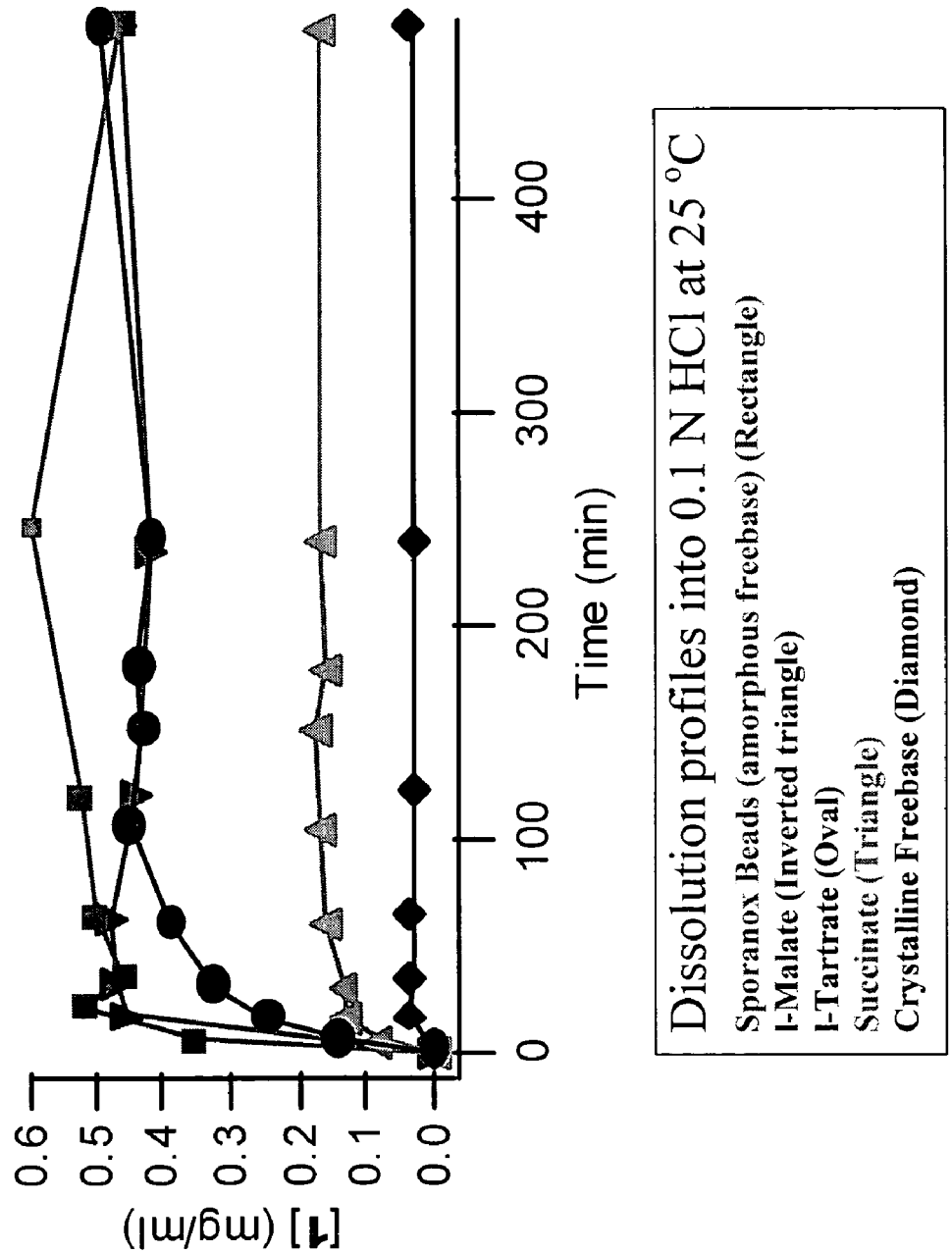
FIG. 28 Dissolution profile for co-crystals of itraconazole: succinic acid, itraconazle:tartaric acid and itraconazole:malic acid vs. itraconazole free base.

A co-crystal with a modulated dissolution profile has been prepared. Itraconazole: succinic acid, itraconazole:tartaric acid and itraconazole:malic acid co-crystals were prepared via methods shown in examples 8, 10 and 11. (See FIG. 28)

Example 40

A co-crystal of an unsaltable or difficult to salt API has been prepared. Celecoxib: nicotinamide co-crystals were prepared via methods shown in example 4.

Example 41

Figure 29:
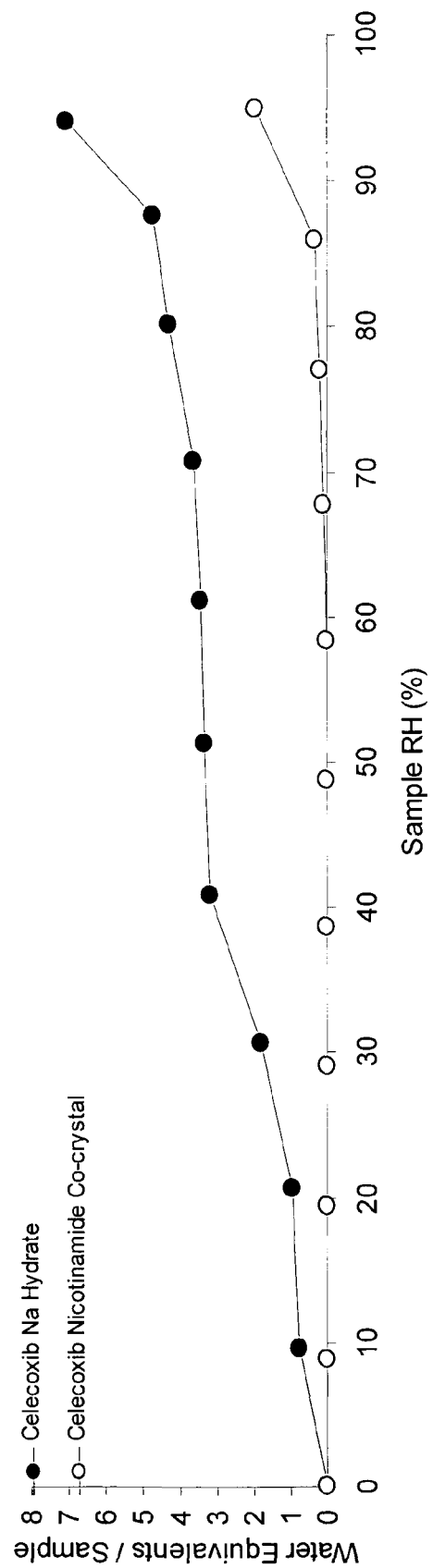
FIG. 29 Hygroscopicity profile for a co-crystal of celecoxib:nicotinamide vs. celecoxib sodium.

A co-crystal with an improved hygroscopicity profile has been prepared. Celecoxib: nicotinamide co-crystals were prepared via methods shown in example 4. (See FIG. 29)

Example 42

A co-crystal with reduced form diversity as compared to the API has been prepared. Co-crystals of carbamazepine and saccharin have been prepared via method shown in example 1.

| Co-Crystal Former | MW (g/mol) | MP (°C.) | Class | Functionalilty | # acceptors | # donors | Molecular Structure | pKa Values |
|---|---|---|---|---|---|---|---|---|
| 1-Hydroxy-2-naphthoic acid | 188.18 | 191-192 | 2 | Carboxylic acid, alcohol | 1 | 2 | 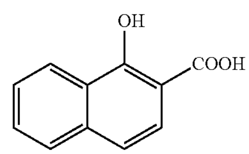 | 2.7,13.5 |
| 4-aminobenzoic acid | 137.14 | 187-188 | 2 | Amine, carboxylic acid | 1 | 3 | 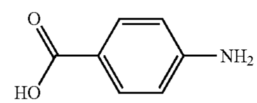 | 4.7,4.8 |
| 4-aminopyridine | 94.11 | 158-159 | 3 | Amine, pyridine | 1 | 2 | 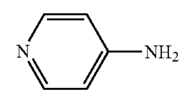 | 10 |
| 4-Chlorobenzene-sulfonic acid | 192.63 | 67 | 1 | $SO_3H$ | 3 | 1 | 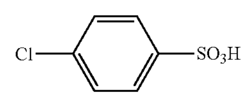 | 0-1 |
| 4-ethoxyphenyl urea | 180.2 | 173-174 | 3 | Amide, NH | 2 | 3 | 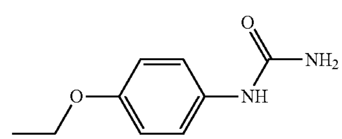 | ~7-9 |
| 7-oxo-DHEA | 303 | 190-192 | 1 | Alcohol, Ketone | 3 | 1 | 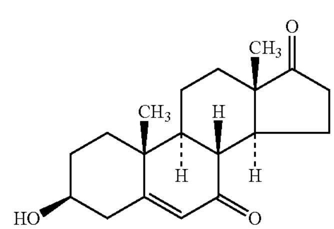 | |
| Acesulfame | 163.15 | 123-124 | 3 | $SO_2$, Amide | 4 | 1 | 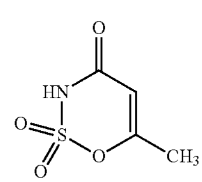 | ~5-7 |
| Acetohydroxamic acid | 75.07 | 89-92 | 3 | Amide, NH, OH | 2 | 2 | 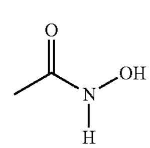 | 8.7 |

-continued

| Co-Crystal Former | MW (g/mol) | MP (° C.) | Class | Functionalilty | # acceptors | # donors | Molecular Structure | pKa Values |
|---|---|---|---|---|---|---|---|---|
| Adenine | 135.13 | 200 (sub.) | 1 | Amide, NH | 3 | 3 | 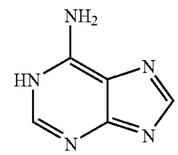 | 3.8 |
| Adipic Acid | 146.14 | 152 | 1 | Carboxylic acid | 2 | 2 | $HOOC(CH_2)_4COOH$ | 4.44, 5.44 |
| Alanine | 89.09 | 289-291 | 1 | Amine, carboxillic acid | 1 | 3 | 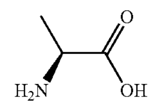 | 2.35, 9.87 |
| Allopurinaol | 136.11 | >350 | 3 | OH, NH | 4 | 2 | 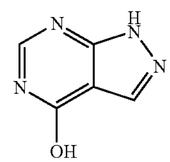 | 10.2 |
| Arginine | 174.2 | 244 (dec.) | 1 | Amine, COOH | 2 | 7 | 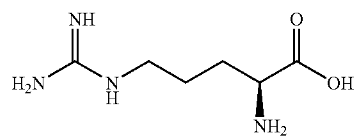 | 2.18, 9.09, 13.2 |
| Ascorbic acid | 176.12 | 190-192 | 1 | C=O, OH | 6 | 4 | 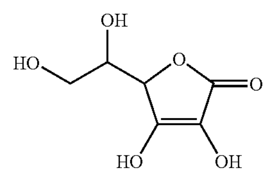 | 4.17, 11.57 |
| Asparagine | 132.12 | 234-235 | 1 | Amine, amide, COOH | 3 | 5 | 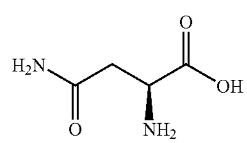 | 2.02, 8.5 |
| Aspartic acid | 133.1 | 270-271 | 1 | Amine, COOH | 2 | 4 | 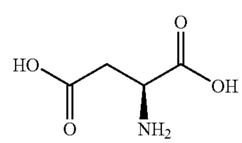 | 1.88, 3.65, 9.60 |
| Benzenesulfonic Acid | 158.18 | 43-44 | 1 | $SO_3H$ | 2 | 1 | 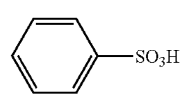 | 0.70, 1.58 |
| Benzoic acid* | 122.12 | 122-123 | 2 | COOH | 1 | 1 | 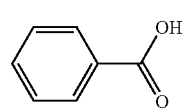 | 4.19 |
| Caffeine | 194.19 | 238 | 3 | C=O | 3 | 0 | 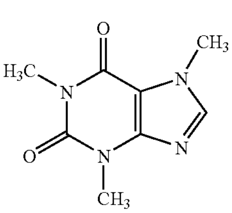 | |

-continued

| Co-Crystal Former | MW (g/mol) | MP (° C.) | Class | Functionalilty | # acceptors | # donors | Molecular Structure | pKa Values |
|---|---|---|---|---|---|---|---|---|
| Camphoric acid | 200.23 | 186-189 | 2 | Carboxylic acid | 2 | 2 | H₃C-COOH, CH₃, CH₃, COOH (cyclopentane) | 4.72, 5.83 |
| Capric acid | 172.27 | 31.4 | 1 | Carboxylic acid | 1 | 1 | CH₃(CH₂)₈COOH | 4.9 |
| Chrysin | 254.24 | 285 | 1 | Phenol, ether, ketone | 2 | 2 | (chrysin structure) | — |
| Cinnamic acid | 144.2 | 133 | 3 | Carboxylic acid | 1 | 1 | (cinnamic acid structure) | 4.4 |
| Citric Acid | 192.12 | 153 | 1 | OH, COOH | 4 | 4 | (citric acid structure) | 3.13, 4.76, 6.40 |
| Clemizole | 325.84 | 167 | 1 | Pyrrolidine | 3 | 0 | (clemizole structure) | — |
| Cyclamic acid | 179.24 | 169-170 | 3 | NH, SO₃H | 2 | 2 | (cyclohexyl-NH-SO₃H) | −2 |
| Cysteine | 121.15 | — | 1 | Amine, COOH, SH | 2 | 4 | (cysteine structure) | 1.71, 8.33, 10.78 |
| Dimethylglycine | 103.1 | 178-192 | 1 | Amine, Carboxylic acid | 2 | 1 | (dimethylglycine structure) | 2.5 |
| D-Ribose | 150.13 | 87 | 1 | Alcohol, ether | 1 | 4 | (D-ribose structure) | — |

-continued

| Co-Crystal Former | MW (g/mol) | MP (° C.) | Class | Functionalilty | # acceptors | # donors | Molecular Structure | pKa Values |
|---|---|---|---|---|---|---|---|---|
| Fumaric acid | 116.07 | 287 | 1 | COOH | 2 | 2 | 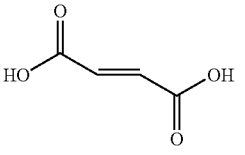 | 3.03, 4.38 |
| Galactaric acid | 210.14 | 255 (dec) | 1 | Carboxylic acid, alcohol | 2 | 6 | 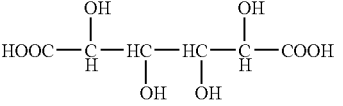 | 3.08, 3.63 |
| Genistein | 270.24 | 297-298 | 1 | Alcohol, Phenol, ether, ketone | 2 | 3 | 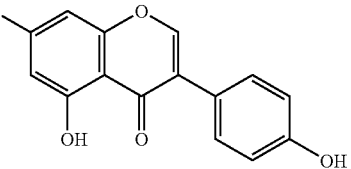 | |
| Gentisic acid | 154.12 | 199-200 form I, 205 form II | 2 | Carboxylic acid, alcohol, phenol | 1 | 3 | 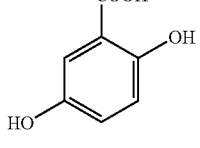 | 2.93 |
| Glucamine, N-Methyl | 195.22 | 128-129 | 1 | Alcohol, Amine | 5 | 6 | 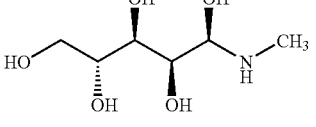 | 8.03(B) |
| Gluconic acid | 196.15 | 131 | 1 | OH, COOH | 6 | 6 | 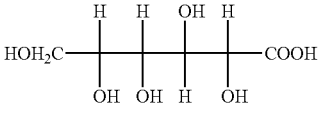 | 3.76 |
| Glucosamine | 179.17 | 88 | 1 | OH | 5 | 6 | 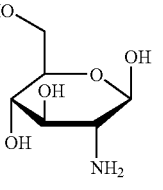 | 6.91 |
| Glucuronic acid | 194.14 | 165 | 1 | Carboxylic acid, alcohol, aldehyde | 2 | 5 | 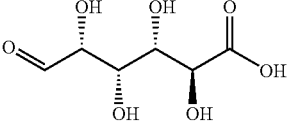 | 3.18 |
| Glutamic acid | 147.13 | 160 | 1 | Amine, COOH | 2 | 4 | 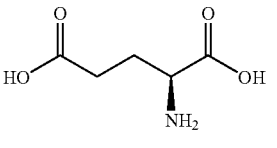 | 2.19, 4.25, 9.67 |
| Glutamine | 146.15 | 185-186 | 1 | Amine, Amide, COOH | 2 | 5 | 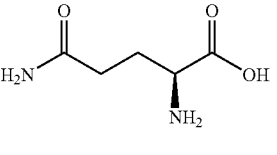 | 2.17, 9.13 |

-continued

| Co-Crystal Former | MW (g/mol) | MP (° C.) | Class | Functionalilty | # acceptors | # donors | Molecular Structure | pKa Values |
|---|---|---|---|---|---|---|---|---|
| Glutaric acid | 132.11 | 98-98 | 1 | COOH | 2 | 2 | 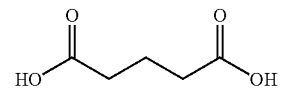 | 2.7, 4.5 |
| Glycine | 75.07 | 182 | 1 | Amine, COOH | 2 | 3 | 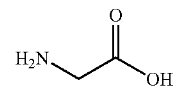 | 2.34, 9.6 |
| Glycolic acid | 76.05 | 80 | 1 | OH, COOH | 2 | 2 | 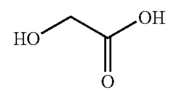 | 3.82 |
| Hippuric acid | 179.17 | 187-188 | 1 | Amide, NH, COOH | 2 | 2 | 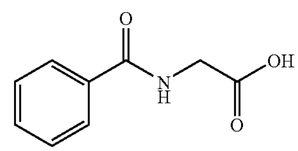 | 3.55 |
| Histidine | 155.16 | 287 (dec.) | 1 | Amine, COOH, Imidazole | 2 | 4 | 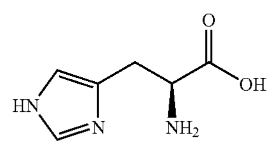 | 1.78, 5.97, 8.97 |
| Hydroquinone* | 110.11 | 170-171 | 2 | OH, Phenol | 2 | 2 | 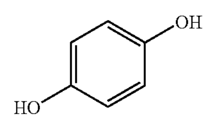 | ~10 |
| Imidazole | 68.08 | 90-91 | 1 | NH | 1 | 1 | 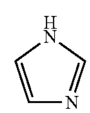 | 6.92 |
| Ipriflavone | 280.32 | 115-117 | 1 | Ketone, ether | 3 | 0 | 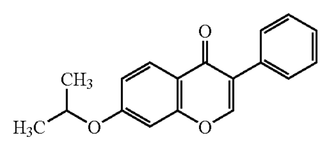 | |
| Isoleucine | 131.17 | 168-170 (sub.) | 1 | Amine, COOH | 1 | 3 | 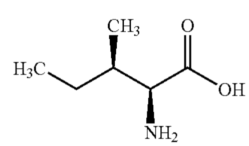 | 2.32, 9.76 |
| Lactobionic acid | 358.3 | 128-130 | 2 | Alcohol, carboxylic acid, ether | 1 | 9 | 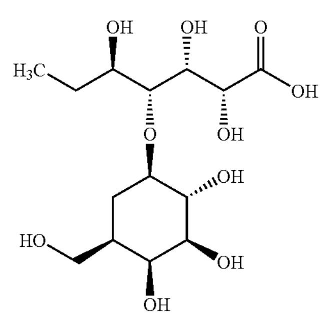 | 3.2 |
| Lauric acid | 200.32 | 44-48 | 1 | Carboxylic acid | 1 | 1 | $CH_3(CH_2)_{10}COOH$ | ~4.5 |

-continued

| Co-Crystal Former | MW (g/mol) | MP (° C.) | Class | Functionalility | # acceptors | # donors | Molecular Structure | pKa Values |
|---|---|---|---|---|---|---|---|---|
| Leucine | 131.17 | 145-148 (sub.) | 1 | Carboxylic acid, amine | 1 | 3 | 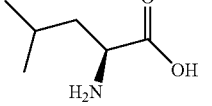 | 2.36, 9.6 |
| Lysine | 146.19 | 225 (dec.) | 1 | Amine, COOH | 1 | 5 | 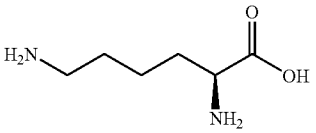 | 2.2, 8.9, 10.28 |
| Maleic | 116.07 | 138-139 | 1 | COOH | 2 | 2 | 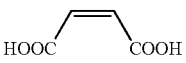 | 1.92, 6.23 |
| Malic acid | 134.09 | 131-132 | 1 | OH, COOH | 3 | 3 | 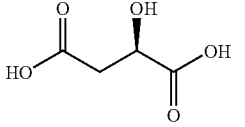 | 3.46, 5.1 |
| Malonic | 104.06 | 135 | 1 | COOH | 2 | 2 | 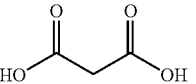 | 2.83, 5.70 |
| Mandelic acid | 152.15 | 119 | 1 | OH, COOH | 2 | 2 | 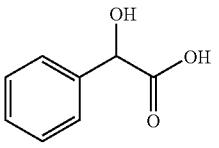 | 3.37 |
| Methionine | 149.21 | 280-282 (dec.) | 1 | Amine, COOH, S-Me | 2 | 3 | 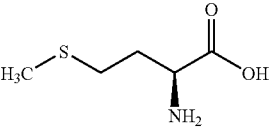 | 2-3, 9 |
| Nicotinamide | 122.12 | 128-131 | 1 | Pyridine, amide | 2 | 2 | 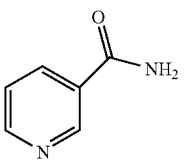 | 3.3 |
| Nicotinic acid | 123.11 | 236-237 | 2 | Carboxylic acid, pyridine | 2 | 1 | 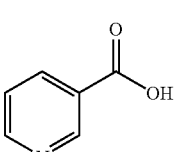 | 2.07(B), 4.85 |
| Orotic acid | 156.1 | 345-346 | 2 | Carboxilic acid, lactam | 3 | 3 | 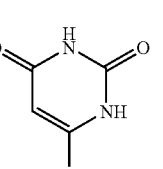 | 5.85, 8.95 |
| Oxalic acid | 90.04 | 189 (dec) | 2 | Carboxilic acid | 2 | 2 | 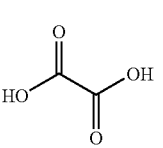 | 1.27, 4.27 |

-continued

| Co-Crystal Former | MW (g/mol) | MP (° C.) | Class | Functionality | # acceptors | # donors | Molecular Structure | pKa Values |
|---|---|---|---|---|---|---|---|---|
| Palmitic acid | 256.43 | 63-64 | 1 | Carboxylic acid | 1 | 1 | CH₃(CH₂)₁₄COOH | 4.9 |
| Pamoic | 388.38 | 280 (dec) | 2 | Carboxylic acid, phenol | 2 | 4 | 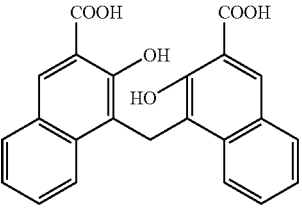 | 2.51, 3.1 |
| Phenylalanine | 165.19 | 283 (dec.) | 1 | Amine, COOH | 1 | 3 | 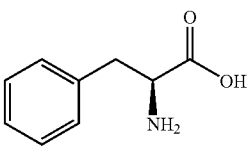 | ~2, ~9 |
| Piperazine | 86.14 | 106 | 1 | NH | 0 | 2 | 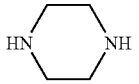 | 9.82(B) |
| Procaine | 236.31 | 61 | 1 | Amine, C=O | 2 | 2 | 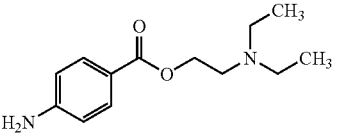 | 8.9(B) |
| Proline | 115.13 | 220-222 (dec.) | 1 | COOH, NH | 1 | 2 | 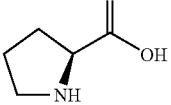 | 1.99, 10.6 |
| p-Toluenesulfonic acid | 172.2 | 106-107 | 2 | Sulfonic acid | 2 | 1 | 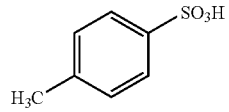 | −1.34 |
| Pyridoxamine | 168 | 193-194 | 2 | OH, Amine, Pyridine | 3 | 4 | 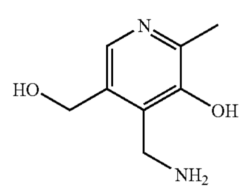 | ~9 |
| Pyridoxine | 170 | 160 | 2 | Alcohol, Pyridine | 3 | 3 | 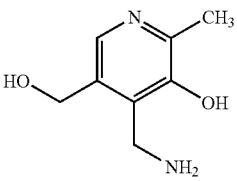 | ~9 |
| Pyroglutamic acid | 129.12 | 162 | 2 | Carboxylic acid, Lactam | 2 | 2 | 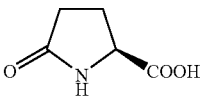 | 3.32 |

-continued

| Co-Crystal Former | MW (g/mol) | MP (° C.) | Class | Functionalilty | # acceptors | # donors | Molecular Structure | pKa Values |
|---|---|---|---|---|---|---|---|---|
| Quercetin | 302.24 | 314 dec. | 1 | Phenol, ether, ketone | 2 | 5 | 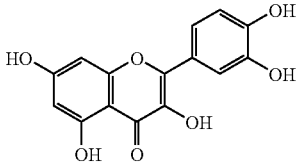 | |
| Resveratrol | 228.24 | 253-255 | 1 | Phenol | 0 | 3 | 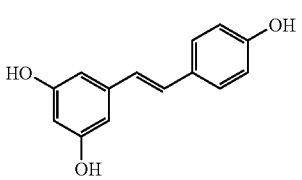 | |
| Saccharin | 183.19 | 228-230 | 1 | Amide, C=O, S=O, N—H | 3 | 1 | 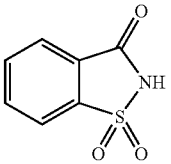 | 2 |
| Salicylic acid, 4-amino | 153.14 | 150-151 | 3 | COOH, OH, Analine | 1 | 4 | 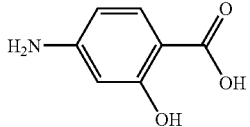 | 3.25,10, 3.5(B) |
| Salicylic acid | 138.12 | 159 | 3 | COOH, OH | 2 | 2 | 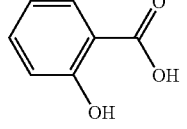 | 2.98, 13.82 |
| Sebacic acid | 202.25 | 134.5 | 1 | Carboxylic acid | 2 | 2 | HOOC(CH$_2$)$_8$COOH | 4.59, 5.59 |
| Serine | 105.09 | 228 (dec.) | 1 | Carboxylic acid, amine, OH | 2 | 3 | 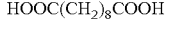 | 2.21, 9.15 |
| Stearic acid | 284.47 | 70-71 | 1 | Carboxylic acid | 1 | 1 | CH$_3$(CH$_2$)$_{16}$COOH | 4.9 |
| Succinic acid | 118.09 | 185-187 | 1 | Carboxylic acid | 2 | 2 | 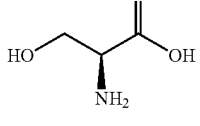 | 4.21, 5.64 |
| Tartaric acid | 150.09 | 205-206 | 1 | Carboxylic acid | 4 | 4 | 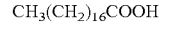 | 3.02, 4.36 |
| Threonine | 119.12 | 255-257 (dec.) | 1 | Amine, COOH, OH | 2 | 4 | 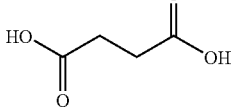 | 2.15, 9.12 |

-continued

| Co-Crystal Former | MW (g/mol) | MP (° C.) | Class | Functionalilty | # acceptors | # donors | Molecular Structure | pKa Values |
|---|---|---|---|---|---|---|---|---|
| TRIS | 121.13 | 171-172 | 2 | Amine, OH | 3 | 5 | 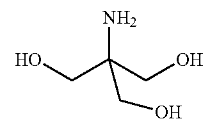 | 5.91, 8.3 |
| Tryptophan | 204.23 | 289 (dec.) | 1 | Amine, COOH, Indole | 1 | 4 | 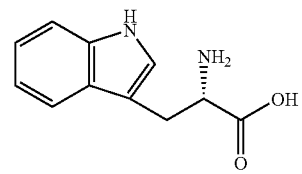 | 2.38, 9.39 |
| Tyrosine | 181.19 | 342-344 | 1 | Amine, COOH, OH | 2 | 3 | 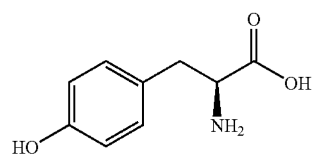 | 2.2, 9.11, 10.07 |
| Urea | 60.06 | Dec. | 1 | C=O, NH2 | 1 | 4 | 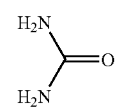 | ~8 |
| Valine | 117.15 | 315 | 1 | Amine, COOH | 1 | 3 | 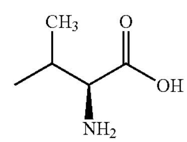 | ~4.5, ~9 |
| Vitamin K5 | 209.68 | 280-282 (dec.) | 3 | Amine, OH | 1 | 3 | 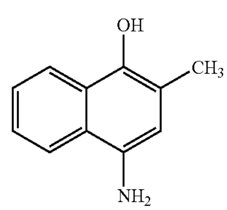 | ~9 |
| Xylitol | 152.15 | 93-95 (1) | 2 | OH | 5 | 5 | 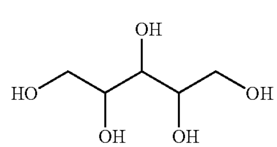 | ~9 |

TABLE II

| Co-crystal Former | Co-crystal Former Functional Group | Interacting Group | | | |
|---|---|---|---|---|---|
| 1,5-Napthalene-disulfonic Acid | Sulfonic Acid | pyridine | aldehyde | ether | amide | Carboxylic Acid |
| 1-Hydroxy-2-naphthoic acid | Carboxylic Acid | alcohol | thiol | amide | amine | phenol |
| 1-Hydroxy-2-naphthoic acid | alcohol | alcohol | thiol | amide | amine | phenol |
| 4-Aminobenzoic Acid | Amine | alcohol | thiol | amide | amine | phenol |
| 4-Aminobenzoic Acid | Carboxylic Acid | alcohol | thiol | amide | amine | phenol |
| 4-aminopyridine | Amine | *alcohol | * | *amide | *amine | *Carboxylic Acid |
| 4-aminopyridine | Pyridine | pyridinium | aldehyde | ether | nitro | Carboxylic Acid |
| 4-Chlorobenzene-Sulfonic Acid | Sulfonic Acid | pyridine | aldehyde | ether | amide | Carboxylic Acid |
| 4-ethoxyphenyl Urea | Amine | alcohol | thiol | amide | amine | phenol |
| 4-ethoxyphenyl Urea | Amine | alcohol | thiol | amide | amine | phenol |
| 7-oxo-DHEA | alcohol | alcohol | thiol | amide | amine | phenol |
| 7-oxo-DHEA | Ketone | alcohol | thiol | amide | ester | carboxilic acid |
| Acesulfame | Sulfone | pyridine | aldehyde | ether | ester | phenol |
| Acesulfame | Amide | alcohol | thiol | amide | amine | phenol |
| Acetohydroxamic Acid | Amide | alcohol | thiol | amide | amine | phenol |
| Acetohydroxamic Acid | Amine | alcohol | thiol | amide | amine | phenol |
| Acetohydroxamic Acid | Alcohol | alcohol | thiol | amide | amine | phenol |
| Adenine | Amine | alcohol | thiol | amide | amine | phenol |
| Adenine | N | *alcohol | * | *amide | *amine | *carboxilic acid |
| Adipic acid | Carboxylic Acid | alcohol | thiol | amide | amine | phenol |
| Alanine | Amine | alcohol | thiol | amide | amine | phenol |
| Alanine | Carboxylic Acid | alcohol | thiol | amide | amine | phenol |
| Allopurinaol | Alcohol | alcohol | thiol | amide | amine | phenol |
| Allopurinaol | Amine | alcohol | thiol | amide | amine | phenol |
| Arginine | Amine | alcohol | thiol | amide | amine | phenol |
| Arginine | Carboxylic Acid | alcohol | thiol | amide | amine | phenol |
| Ascorbic Acid | Ketone | alcohol | thiol | amide | amine | phenol |
| Ascorbic Acid | Alcohol | alcohol | thiol | amide | amine | phenol |
| Asparagine | Carboxylic Acid | alcohol | thiol | amide | amine | phenol |
| Asparagine | Amine | pyridine | aldehyde | ether | ester | Carboxylic Acid |
| Aspartic Acid | Amide | alcohol | thiol | amide | amine | phenol |
| Aspartic Acid | Carboxylic Acid | alcohol | thiol | amide | amine | phenol |
| Benzenesulfonic Acid | Sulfonic Acid | alcohol | aldehyde | ether | ester | Carboxylic Acid |
| Benzoic Acid | Carboxylic Acid | alcohol | thiol | amide | amine | phenol |
| Caffeine | Ketone | alcohol | thiol | amide | amine | phenol |
| Camphoric acid | Carboxylic Acid | alcohol | thiol | amide | amine | phenol |
| Capric acid | Carboxylic Acid | ketone | thiol | amide | amine | phenol |
| Genistein | Ketone | alcohol | sulfoxide | n | pyridine | aldehyde |
| Genistein | Phenol | amine | amine | aromatic_s | Sp2 amine | cyano |
| Cinnamic acid | Ether | aromatic-N | thiol | amide | amine | chlorate |
| Citric Acid | Carboxylic Acid | alcohol | thiol | amide | amine | phenol |
| Citric Acid | Alcohol | alcohol | thiol | amide | amine | phenol |
| Clemizole | Carboxylic Acid | *alcohol | * | *amide | *amine | *carboxilic acid |
| Cyclamic Acid | Pyrrolidine | alcohol | thiol | amide | amine | phenol |
| | Amine | | | | | |

TABLE II-continued

| | | | | | | | |
|---|---|---|---|---|---|---|---|
| Cyclamic Acid | Sulfonic Acid | pyridine | ketone | aldehyde | ether | ester | amide | Carboxylic Acid |
| Cysteine | Amine | alcohol | ketone | thiol | amide | amine | analine | phenol |
| Cysteine | Carboxylic Acid | alcohol | ketone | thiol | amide | amine | analine | phenol |
| Cysteine | Thiol | carboxylic acid | sodium | aldehyde | ketone | -N | cadmium | |
| Dimethylglycine | Carboxylic Acid | alcohol | ketone | thiol | amide | amine | analine | phenol |
| Dimethylglycine | Amine | alcohol | ketone | thiol | amide | amine | analine | phenol |
| D-ribose | Ether | aromatic-N | amide | amine | aromatic_s | Sp2 amine | sulfoxide | chlorate |
| D-ribose | Alcohol | alcohol | ketone | thiol | amide | amine | analine | phenol |
| Fumaric Acid | Carboxylic Acid | alcohol | ketone | thiol | amide | amine | analine | phenol |
| Galactaric acid | Carboxylic Acid | alcohol | ketone | thiol | amide | amine | analine | phenol |
| Galactaric acid | alcohol | alcohol | ketone | thiol | amide | amine | analine | phenol |
| Chrysin | Ketone | alcohol | | sulfoxide | n | pyridine | cyano | aldehyde |
| Chrysin | Phenol | amine | amide | amine | amide | Sp2 amine | sulfoxide | chlorate |
| Gentisic Acid | Ether | aromatic-N | ketone | thiol | amide | amine | analine | phenol |
| Gentisic acid | Phenol | amine | amide | sulfoxide | n | pyridine | cyano | aldehyde |
| Glucamine, N-methyl | alcohol | alcohol | ketone | thiol | amide | amine | analine | phenol |
| Glucamine, N-methyl | Amine | alcohol | ketone | thiol | amide | amine | analine | phenol |
| Gluconic Acid | Alcohol | alcohol | ketone | thiol | amide | amine | analine | phenol |
| Gluconic Acid | Carboxylic Acid | alcohol | ketone | thiol | amide | amine | analine | phenol |
| Glucosamine | alcohol | alcohol | ketone | thiol | amide | amine | analine | phenol |
| Glucuronic acid | Carboxylic Acid | alcohol | ketone | thiol | amide | amine | analine | phenol |
| Glucuronic acid | alcohol | alcohol | ketone | thiol | amide | amine | analine | phenol |
| Glucuronic acid | Aldehyde | alcohol | ketone | thiol | amide | amine | analine | phenol |
| Glutamic Acid | Amine | alcohol | ketone | thiol | amide | amine | analine | phenol |
| Glutamic Acid | Carboxylic Acid | alcohol | ketone | thiol | amide | amine | analine | phenol |
| Glutamine | Amine | alcohol | ketone | thiol | amide | amine | analine | phenol |
| Glutamine | Amide | alcohol | ketone | thiol | amide | amine | analine | phenol |
| Glutaric Acid | Carboxylic Acid | alcohol | ketone | thiol | amide | amine | analine | phenol |
| Glycine | Carboxylic Acid | alcohol | ketone | thiol | amide | amine | analine | phenol |
| Glycine | Amine | alcohol | ketone | thiol | amide | amine | analine | phenol |
| Glycolic Acid | Carboxylic Acid | alcohol | ketone | thiol | amide | amine | analine | phenol |
| Glycolic Acid | Alcohol | alcohol | ketone | thiol | amide | amine | analine | phenol |
| Hippuric Acid | Carboxylic Acid | alcohol | ketone | thiol | amide | amine | analine | phenol |
| Hippuric Acid | Amide | alcohol | ketone | thiol | amide | amine | analine | phenol |
| Hippuric Acid | Amine | alcohol | ketone | thiol | amide | amine | analine | phenol |
| Histidine | Carboxylic Acid | alcohol | ketone | thiol | amide | amine | analine | phenol |
| Histidine | Amine | alcohol | ketone | thiol | amide | amine | analine | phenol |
| Histidine | Carboxylic Acid | alcohol | ketone | thiol | amide | amine | analine | phenol |
| Imidazole | Imidazole | imidazole | chlorine | acetamide | carboxylate | | thione | nitro |
| Hydroquinone | Alcohol | alcohol | ketone | thiol | amide | amine | analine | phenol |
| Hydroquinone | Phenol | amine | amide | sulfoxide | n | pyridine | cyano | aldehyde |
| Imidazole | Amine | alcohol | ketone | thiol | amide | amine | analine | phenol |
| Ipriflavone | Ether | aromatic-N | amide | amine | aromatic_s | Sp2 amine | sulfoxide | chlorate |
| Ipriflavone | Ketone | alcohol | amide | thiol | amide | amine | analine | phenol |
| Isoleucine | Amine | alcohol | ketone | thiol | amide | amine | analine | phenol |
| lactobionic acid | Carboxylic Acid | alcohol | ketone | thiol | amide | amine | analine | phenol |
| Lactobionic acid | Carboxylic Acid | alcohol | ketone | thiol | amide | amine | analine | phenol |
| alcohol | alcohol | aromatic-N | amide | amine | aromatic_s | Sp2 amine | sulfoxide | chlorate |
| Lauric acid | Ether | alcohol | ketone | thiol | amide | amine | analine | phenol |
| Leucine | Carboxylic Acid | alcohol | ketone | thiol | amide | amine | analine | phenol |
| Leucine | Amine | alcohol | ketone | thiol | amide | amine | analine | phenol |

TABLE II-continued

| | | | | | | |
|---|---|---|---|---|---|---|
| Lysine | Amine | alcohol | ketone | thiol | amide | amine | analine | phenol |
| Lysine | Carboxylic Acid | alcohol | ketone | thiol | amide | amine | analine | phenol |
| Maleic | Carboxylic Acid | alcohol | ketone | thiol | amide | amine | analine | phenol |
| Malic Acid | Alcohol | alcohol | ketone | thiol | amide | amine | analine | phenol |
| Malic Acid | Carboxylic Acid | alcohol | ketone | thiol | amide | amine | analine | phenol |
| Malonic | Carboxylic Acid | alcohol | ketone | thiol | amide | amine | analine | phenol |
| Mandelic Acid | Alcohol | alcohol | ketone | thiol | amide | amine | analine | phenol |
| Mandelic Acid | Carboxylic Acid | alcohol | ketone | thiol | amide | amine | analine | phenol |
| Methionine | Amine | alcohol | ketone | thiol | amide | amine | analine | phenol |
| Methionine | Carboxylic Acid | alcohol | ketone | thiol | amide | amine | analine | phenol |
| Methionine | Thioether | -N | amide | amine | s | Sp2 amine | sulfoxide | chlorate |
| Nicotinamide | Pyridine | *alcohol | ketone | * | *amide | nitro | *amine | *Carboxylic Acid |
| Nicotinamide | Amide | alcohol | ketone | thiol | amide | amine | analine | phenol |
| Nicotinic Acid | Carboxylic Acid | alcohol | ketone | thiol | amide | nitro | *amine | *Carboxylic Acid |
| Nicotinic Acid | Pyridine | *alcohol | | * | *amide | amine | analine | phenol |
| Orotic acid | Carboxylic Acid | alcohol | ketone | thiol | amide | amine | analine | phenol |
| Orotic acid | Lactam | alcohol | ketone | thiol | amide | amine | analine | phenol |
| Oxalic acid | Carboxylic Acid | alcohol | ketone | thiol | amide | amine | analine | phenol |
| Palmitic Acid | Carboxylic Acid | alcohol | ketone | thiol | amide | amine | analine | phenol |
| Pamoic acid | Carboxylic Acid | alcohol | ketone | thiol | amide | amine | analine | phenol |
| Pamoic acid | alcohol | alcohol | ketone | thiol | amide | pyridine | cyano | aldehyde |
| Pamoic acid | Phenol | amine | amide | sulfoxide | n | amine | analine | phenol |
| Phenylalanine | Amine | alcohol | ketone | thiol | amide | amine | analine | phenol |
| Phenylalanine | Carboxylic Acid | alcohol | ketone | thiol | amide | amine | analine | phenol |
| Piperazine | Amine | alcohol | ketone | thiol | amide | amine | analine | phenol |
| Procaine | Ketone | alcohol | ketone | thiol | amide | amine | analine | phenol |
| Procaine | Carboxylic Acid | alcohol | ketone | thiol | amide | amine | analine | phenol |
| Proline | Amine | alcohol | ketone | thiol | amide | amine | analine | phenol |
| p-Toluenesulfonic acid | Sulfonic Acid | pyridine | ketone | aldehyde | ether | ester | amide | Carboxylic Acid |
| Pyridoxamine | Alcohol | alcohol | ketone | thiol | amide | amine | analine | phenol |
| Pyridoxamine | Amine | alcohol | ketone | thiol | amide | amine | analine | phenol |
| Pyridoxamine | Pyridine | *alcohol | ketone | * | *amide | *amine | *amine | *Carboxylic Acid |
| Pyridoxine (4-Pyridoxic Acid) | Pyridine | *alcohol | pyridinium | thiol | *amide | nitro | *amine | *Carboxylic Acid |
| Pyridoxine (4-Pyridoxic Acid) | Alcohol | alcohol | ketone | thiol | amide | amine | analine | phenol |
| Pyroglutamic acid | Carboxylic Acid | alcohol | ketone | thiol | amide | amine | analine | phenol |
| Pyroglutamic acid | Lactam | alcohol | ketone | thiol | amide | amine | analine | phenol |
| Quercetin | Ketone | alcohol | ketone | thiol | amide | amine | analine | phenol |
| Quercetin | Phenol | amine | amide | sulfoxide | n | pyridine | cyano | aldehyde |
| Resveratrol | Ether | aromatic-N | amide | amine | aromatic_s | Sp2 amine | sulfoxide | chlorate |
| Resveratrol | Ketone | alcohol | ketone | thiol | amide | amine | analine | phenol |
| Saccharin | Phenol | amine | amide | sulfoxide | n | pyridine | cyano | aldehyde |
| Saccharin | Amide | alcohol | ketone | thiol | amide | amine | analine | phenol |
| Saccharin | Ketone | alcohol | ketone | thiol | amide | amine | analine | phenol |
| Saccharin | Sulfoxide | pyridine | ketone | aldehyde | ether | ester | amide | Carboxylic Acid |
| Salicylic Acid | Amine | alcohol | ketone | thiol | amide | amine | analine | phenol |
| Salicylic Acid | Carboxylic Acid | alcohol | ketone | thiol | amide | amine | analine | phenol |
| Salicylic Acid | Alcohol | alcohol | ketone | thiol | amide | amine | analine | phenol |
| Salicylic Acid, 4-amino | Carboxylic Acid | alcohol | ketone | thiol | amide | amine | analine | phenol |
| Salicylic Acid, 4-amino | alcohol | alcohol | ketone | thiol | amide | amine | analine | phenol |
| Salicylic Acid, 4-amino | Amine | alcohol | ketone | thiol | amide | amine | analine | phenol |
| Sebacic acid | Carboxylic Acid | alcohol | ketone | thiol | amide | amine | analine | phenol |
| Serine | Carboxylic Acid | alcohol | ketone | thiol | amide | amine | analine | phenol |

TABLE II-continued

| | | | | | | |
|---|---|---|---|---|---|---|
| Serine | Amine | alcohol | ketone | thiol | amide | amine | analine | phenol |
| Serine | Alcohol | alcohol | ketone | thiol | amide | amine | analine | phenol |
| Stearic acid | Carboxylic Acid | alcohol | ketone | thiol | amide | amine | analine | phenol |
| Succinic Acid | Carboxylic Acid | alcohol | ketone | thiol | amide | amine | analine | phenol |
| Tartaric Acid | Carboxylic Acid | alcohol | ketone | thiol | amide | amine | analine | phenol |
| Threonine | Amine | alcohol | ketone | thiol | amide | amine | analine | phenol |
| Threonine | Carboxylic Acid | alcohol | ketone | thiol | amide | amine | analine | phenol |
| Threonine | alcohol | alcohol | ketone | thiol | amide | amine | analine | phenol |
| Tris | Amine | alcohol | ketone | thiol | amide | amine | analine | phenol |
| Tris | Alcohol | alcohol | ketone | thiol | amide | amine | analine | phenol |
| Tryptophan | Amine | alcohol | ketone | thiol | amide | amine | analine | phenol |
| Tryptophan | Carboxylic Acid | alcohol | ketone | thiol | amide | amine | analine | phenol |
| Tryptophan | Indole | *alcohol | pyridinium | * | *amide | nitro | *amine | *carboxilic acid |
| Tyrosine | Amine | alcohol | ketone | thiol | amide | amine | analine | phenol |
| Tyrosine | Carboxylic Acid | alcohol | ketone | thiol | amide | amine | analine | phenol |
| Tyrosine | Alcohol | alcohol | ketone | thiol | amide | amine | analine | phenol |
| Urea | Ketone | alcohol | ketone | thiol | amide | amine | analine | phenol |
| Urea | Amine | alcohol | ketone | thiol | amide | amine | analine | phenol |
| Urea | Amide | alcohol | ketone | thiol | amide | amine | analine | phenol |
| Valine | Amine | alcohol | ketone | thiol | amide | amine | analine | phenol |
| Valine | Carboxylic Acid | alcohol | ketone | thiol | amide | amine | analine | phenol |
| Vitamin K5 | Amine | alcohol | ketone | thiol | amide | amine | analine | phenol |
| Vitamin K5 | Alcohol | alcohol | ketone | thiol | amide | amine | analine | phenol |
| Xylitol | Alcohol | alcohol | ketone | thiol | amide | amine | analine | phenol |

| Co-crystal Former | | | | Interacting Group | | | |
|---|---|---|---|---|---|---|---|
| 1,5-Napthalene-disulfonic Acid | amine | metals | thioether | | sulfate | alcohol | metals | aldehyde |
| 1-Hydroxy-2-naphthoic acid | phosphate | sulfate | sulfone | nitrate | pyridine | carboxylic acid | metals | aldehyde |
| 1-Hydroxy-2-naphthoic acid | phosphate | sulfate | sulfone | nitrate | pyridine | carboxylic acid | carboxilic acid | metals |
| 4-Aminobenzoic Acid | phosphate | sulfate | sulfone | nitrate | pyridine | | Carboxilic Acid | metals |
| 4-Aminobenzoic Acid | phosphate | sulfate | sulfone | nitrate | pyridine | | carboxilic acid | metals |
| 4-aminopyridine | phosphate | sulfate | ether | triazole | | ammonium | oxime | *chlorine |
| 4-aminopyridine | *sulfonamide | *ketone | thioether | | | alcohol | | |
| 4-Chlorobenzene-Sulfonic Acid | amine | metals | | | sulfate | | | |
| 4-ethoxyphenyl Urea | phosphate | sulfate | sulfone | nitrate | pyridine | | Carboxylic Acid | metals |
| 4-ethoxyphenyl Urea | phosphate | sulfate | sulfone | nitrate | pyridine | | carboxilic acid | metals |
| 7-oxo-DHEA | phosphate | sulfate | sulfone | nitrate | pyridine | carboxylic acid | metals | aldehyde |
| 7-oxo-DHEA | phosphate | sulfate | sulfone | nitrate | pyridine | | Carboxilic Acid | metals |
| Acesulfame | amine | metals | thioether | | sulfate | alcohol | | |
| Acesulfame | phosphate | sulfate | sulfone | nitrate | pyridine | | Carboxylic Acid | metals |
| Acetohydroxamic Acid | phosphate | sulfate | sulfone | nitrate | pyridine | | carboxilic acid | metals |
| Acetohydroxamic Acid | phosphate | sulfate | sulfone | nitrate | pyridine | | Carboxilic Acid | metals |
| Acetohydroxamic Acid | phosphate | sulfate | sulfone | nitrate | pyridine | | carboxilic acid | metals |
| Adenine | phosphate | *ketone | ether | triazole | | ammonium | oxime | *chlorine |
| Adenine | *sulfonamide | | | | | | | |
| Adipic acid | phosphate | sulfate | sulfone | nitrate | pyridine | | carboxilic acid | metals |
| Alanine | phosphate | sulfate | sulfone | nitrate | pyridine | | carboxilic acid | metals |
| Alanine | phosphate | sulfate | sulfone | nitrate | pyridine | | carboxilic acid | metals |
| Allopurinaol | phosphate | sulfate | sulfone | nitrate | pyridine | | carboxilic acid | metals |
| Allopurinaol | phosphate | sulfate | sulfone | nitrate | pyridine | | carboxilic acid | metals |
| Arginine | phosphate | sulfate | sulfone | nitrate | pyridine | | carboxilic acid | metals |

TABLE II-continued

| | | | | | |
|---|---|---|---|---|---|
| Arginine | phosphate | sulfate | nitrate | pyridine | | carboxilic acid | metals |
| Ascorbic Acid | phosphate | sulfone | nitrate | pyridine | | Carboxylic Acid | metals |
| Ascorbic Acid | phosphate | sulfone | nitrate | pyridine | | Carboxylic Acid | metals |
| Asparagine | phosphate | sulfate | nitrate | pyridine | | carboxilic acid | metals |
| Asparagine | phosphate | sulfone | nitrate | pyridine | | Carboxylic Acid | metals |
| Aspartic Acid | phosphate | sulfate | nitrate | pyridine | | carboxilic acid | metals |
| Aspartic Acid | phosphate | sulfone | nitrate | pyridine | | carboxilic acid | metals |
| Benzenesulfonic Acid | amine | thioether | | sulfate | alcohol | carboxilic acid | metals |
| Benzoic Acid | phosphate | sulfone | nitrate | pyridine | | carboxilic acid | metals |
| Caffeine | phosphate | sulfone | nitrate | pyridine | | Carboxylic Acid | metals |
| Camphoric acid | phosphate | sulfone | nitrate | pyridine | | carboxilic acid | metals |
| Capric acid | phosphate | sulfate | nitrate | pyridine | | carboxilic acid | metals |
| Genistein | phosphate | sulfone | nitrate | pyridine | | Carboxylic Acid | fluorine |
| Genistein | alchohol | | ester | ether | n-oxide | chlorine | bromine |
| Genistein | chlorine | cyano | ester | amine | nitro | nitrate | metals |
| Cinnamic acid | phosphate | sulfone | nitrate | pyridine | | carboxilic acid | metals |
| Citric Acid | phosphate | sulfone | nitrate | pyridine | | Carboxylic Acid | metals |
| Citric Acid | phosphate | sulfone | nitrate | pyridine | | carboxilic acid | metals |
| Clemizole | *sulfonamide | *ketone | triazole | ether | ammonium | oxime | *chlorine |
| Cyclamic Acid | phosphate | sulfone | nitrate | pyridine | | carboxilic acid | metals |
| Cyclamic Acid | amine | thioether | | sulfate | alcohol | | Sb |
| Cysteine | phosphate | sulfone | nitrate | pyridine | | carboxilic acid | metals |
| Cysteine | phosphate | sulfone | nitrate | Ru | | carboxilic acid | metals |
| Cysteine | arsenic | alcohol | potassium | pyridine | | Rb | |
| Dimethylglycine | phosphate | sulfone | nitrate | pyridine | | carboxilic acid | metals |
| Dimethylglycine | phosphate | sulfone | nitrate | pyridine | | carboxilic acid | bromine |
| D-ribose | chlorine | cyano | ester | amine | nitro | nitrate | metals |
| Fumaric Acid | phosphate | sulfone | nitrate | pyridine | | Carboxylic Acid | metals |
| Galactaric acid | phosphate | sulfone | nitrate | pyridine | | carboxilic acid | metals |
| Galacturic acid | phosphate | sulfone | nitrate | pyridine | carboxilic acid | metals | aldehyde |
| Chrysin | phosphate | sulfone | nitrate | pyridine | n-oxide | Carboxylic Acid | metals |
| Chrysin | chlorine | cyano | ester | ether | nitro | chlorine | fluorine |
| Gentisic acid | phosphate | sulfone | nitrate | pyridine | | carboxilic acid | bromine |
| Gentisic acid | | alchohol | ester | ether | n-oxide | chlorine | metals |
| Glucamine, N-methyl | phosphate | sulfate | nitrate | pyridine | carboxilic acid | metals | fluorine |
| Glucamine, N-methyl | phosphate | sulfone | nitrate | pyridine | | carboxilic acid | aldehyde |
| Gluconic Acid | phosphate | sulfone | nitrate | pyridine | | Carboxylic Acid | metals |
| Gluconic Acid | phosphate | sulfone | nitrate | pyridine | | carboxilic acid | metals |
| Glucosamine | phosphate | sulfone | nitrate | pyridine | | Carboxylic Acid | metals |
| Glucuronic acid | phosphate | sulfone | nitrate | pyridine | | carboxilic acid | metals |
| Glucuronic acid | phosphate | sulfone | nitrate | pyridine | carboxilic acid | metals | aldehyde |
| Glutamic Acid | phosphate | sulfone | nitrate | pyridine | | carboxilic acid | metals |
| Glutamic Acid | phosphate | sulfone | nitrate | pyridine | aromatic | carboxilic acid | metals |
| Glutamine | phosphate | sulfone | nitrate | pyridine | | carboxilic acid | metals |
| Glutamine | phosphate | sulfone | nitrate | pyridine | | Carboxylic Acid | metals |
| Glutaric Acid | phosphate | sulfone | nitrate | pyridine | | carboxilic acid | metals |
| Glycine | phosphate | sulfone | nitrate | pyridine | | carboxilic acid | metals |

TABLE II-continued

| | | | | | |
|---|---|---|---|---|---|
| Glycine | phosphate | sulfate | nitrate | pyridine | | carboxilic acid | metals |
| Glycolic Acid | phosphate | sulfate | nitrate | pyridine | | Carboxylic Acid | metals |
| Glycolic Acid | phosphate | sulfate | nitrate | pyridine | | carboxilic acid | metals |
| Hippuric Acid | phosphate | sulfate | nitrate | pyridine | | carboxilic acid | metals |
| Hippuric Acid | phosphate | sulfate | nitrate | pyridine | | carboxilic acid | metals |
| Histidine | phosphate | sulfate | nitrate | pyridine | | carboxilic acid | metals |
| Histidine | cyanamide | ketone | Carboxylic Acid | alcohol | | thiol | amine |
| Hydroquinone | phosphate | sulfate | nitrate | pyridine | n-oxide | Carboxylic Acid | metals |
| Hydroquinone | chlorine | alchohol | ester | ether | | chlorine | fluorine |
| Imidazole | phosphate | sulfate | nitrate | pyridine | nitro | carboxilic acid | bromine |
| Ipriflavone | | cyano | cyano | amine | | nitrate | metals |
| Ipriflavone | phosphate | sulfate | nitrate | pyridine | | Carboxylic Acid | metals |
| Isoleucine | phosphate | sulfate | nitrate | pyridine | | carboxilic acid | metals |
| lactobionic acid | phosphate | sulfate | nitrate | pyridine | | carboxilic acid | metals |
| Lactobionic acid | phosphate | sulfate | nitrate | pyridine | carboxilic acid | metals | aldehyde |
| Lactobionic acid | chlorine | cyano | ester | amine | nitro | nitrate | bromine |
| Lauric acid | phosphate | sulfate | nitrate | pyridine | | carboxilic acid | metals |
| Leucine | phosphate | sulfate | nitrate | pyridine | | Carboxylic Acid | metals |
| Leucine | phosphate | sulfate | nitrate | pyridine | | carboxilic acid | metals |
| Lysine | phosphate | sulfate | nitrate | pyridine | | carboxilic acid | metals |
| Lysine | phosphate | sulfate | nitrate | pyridine | | carboxilic acid | metals |
| Maleic | phosphate | sulfate | nitrate | pyridine | | carboxilic acid | metals |
| Malic Acid | phosphate | sulfate | nitrate | pyridine | | Carboxylic Acid | metals |
| Malic Acid | phosphate | sulfate | nitrate | pyridine | | carboxilic acid | metals |
| Malonic | phosphate | sulfate | nitrate | pyridine | | carboxilic acid | metals |
| Mandelic Acid | phosphate | sulfate | nitrate | pyridine | | Carboxylic Acid | metals |
| Mandelic Acid | phosphate | sulfate | nitrate | pyridine | | carboxilic acid | metals |
| Methionine | phosphate | sulfate | nitrate | pyridine | | carboxilic acid | metals |
| Methionine | phosphate | sulfate | nitrate | pyridine | | carboxilic acid | metals |
| Nicotinamide | chlorine | cyano | ester | amine | nitro | nitrate | bromine |
| Nicotinamide | *sulfonamide | ether | triazole | pyridine | ammonium | oxime | *chlorine |
| Nicotinic Acid | phosphate | sulfonate | nitrate | pyridine | | Carboxylic Acid | metals |
| Nicotinic Acid | phosphate | sulfone | nitrate | pyridine | | Carboxylic Acid | metals |
| Nicotinic Acid | *sulfonamide | ether | triazole | pyridine | ammonium | oxime | *chlorine |
| Orotic acid | phosphate | sulfate | nitrate | pyridine | | carboxilic acid | metals |
| Orotic acid | phosphate | sulfate | nitrate | pyridine | | Carboxylic Acid | metals |
| Oxalic acid | phosphate | sulfate | nitrate | pyridine | | carboxilic acid | |
| Palmitic acid | phosphate | sulfate | nitrate | pyridine | | carboxilic acid | |
| Pamoic acid | phosphate | sulfate | nitrate | pyridine | | carboxilic acid | |
| Pamoic acid | phosphate | sulfate | nitrate | pyridine | carboxilic acid | metals | |
| Pamoic acid | alchohol | | ester | ether | n-oxide | chlorine | aldehyde |
| Phenylalanine | phosphate | sulfate | nitrate | pyridine | | carboxilic acid | fluorine |
| Phenylalanine | phosphate | sulfate | nitrate | pyridine | | carboxilic acid | metals |
| Piperazine | phosphate | sulfate | nitrate | pyridine | | carboxilic acid | metals |
| Procaine | phosphate | sulfate | nitrate | pyridine | | carboxilic acid | metals |
| Procaine | phosphate | sulfate | nitrate | pyridine | | Carboxylic Acid | metals |
| Proline | phosphate | sulfate | nitrate | pyridine | | carboxilic acid | metals |
| Proline | phosphate | sulfate | nitrate | pyridine | | carboxilic acid | metals |
| p-Toluenesulfonic acid | amine | metals | thioether | sulfate | alcohol | | |

TABLE II-continued

| Co-crystal Former | | | | | | |
|---|---|---|---|---|---|---|
| Pyridoxamine | phosphate | sulfate | sulfone | nitrate | pyridine | Carboxylic Acid | metals |
| Pyridoxamine | phosphate | sulfate | sulfone | nitrate | pyridine | carboxilic acid | metals |
| Pyridoxamine | *sulfonamide | *ketone | ether | triazole | | oxime | *chlorine |
| Pyridoxine (4-Pyridoxic Acid) | *sulfonamide | *ketone | ether | triazole | | oxime | *chlorine |
| Pyridoxine (4-Pyridoxic Acid) | phosphate | sulfate | sulfone | nitrate | pyridine | Carboxylic Acid | metals |
| Pyroglutamic acid | phosphate | sulfate | sulfone | nitrate | pyridine | carboxilic acid | metals |
| Pyroglutamic acid | phosphate | sulfate | sulfone | nitrate | pyridine | Carboxylic Acid | metals |
| Quercetin | phosphate | alchohol | | nitrate | ether | chlorine | fluorine |
| Quercetin | chlorine | | cyano | ester | amine | nitrate | bromine |
| Resveratrol | phosphate | alchohol | sulfone | nitrate | pyridine | Carboxylic Acid | metals |
| Resveratrol | | | | ester | ether | chlorine | fluorine |
| Saccharin | phosphate | sulfate | sulfone | nitrate | pyridine | Carboxylic Acid | metals |
| Saccharin | phosphate | sulfate | sulfone | nitrate | pyridine | Carboxylic Acid | metals |
| Saccharin | amine | metals | thioether | | sulfate | | |
| Salicylic Acid | phosphate | sulfate | sulfone | nitrate | pyridine | Carboxylic Acid | metals |
| Salicylic Acid | phosphate | sulfate | sulfone | nitrate | pyridine | carboxilic acid | metals |
| Salicylic Acid, 4-amino | phosphate | sulfate | sulfone | nitrate | pyridine | Carboxylic Acid | metals |
| Salicylic Acid, 4-amino | phosphate | sulfate | sulfone | nitrate | pyridine | carboxilic acid | metals |
| Sebacic acid | phosphate | sulfate | sulfone | nitrate | pyridine | metals | aldehyde |
| Serine | phosphate | sulfate | sulfone | nitrate | pyridine | carboxilic acid | metals |
| Serine | phosphate | sulfate | sulfone | nitrate | pyridine | Carboxylic Acid | metals |
| Serine | phosphate | sulfate | sulfone | nitrate | pyridine | carboxilic acid | metals |
| Stearic acid | phosphate | sulfate | sulfone | nitrate | pyridine | Carboxylic Acid | metals |
| Succinic Acid | phosphate | sulfate | sulfone | nitrate | pyridine | carboxilic acid | metals |
| Tartaric Acid | phosphate | sulfate | sulfone | nitrate | pyridine | Carboxylic Acid | metals |
| Threonine | phosphate | sulfate | sulfone | nitrate | pyridine | Carboxylic Acid | metals |
| Threonine | phosphate | sulfate | sulfone | nitrate | pyridine | carboxilic acid | metals |
| Threonine | phosphate | sulfate | sulfone | nitrate | pyridine | carboxilic acid | metals |
| Tris | phosphate | sulfate | sulfone | nitrate | pyridine | Carboxylic Acid | metals |
| Tris | phosphate | sulfate | sulfone | nitrate | pyridine | carboxilic acid | metals |
| Tryptophan | phosphate | sulfate | sulfone | nitrate | pyridine | Carboxylic Acid | metals |
| Tryptophan | phosphate | sulfate | sulfone | nitrate | pyridine | carboxilic acid | metals |
| Tryptophan | *sulfonamide | *ketone | ether | triazole | | oxime | *chlorine |
| Tyrosine | phosphate | sulfate | sulfone | nitrate | pyridine | carboxilic acid | metals |
| Tyrosine | phosphate | sulfate | sulfone | nitrate | pyridine | carboxilic acid | metals |
| Urea | phosphate | sulfate | sulfone | nitrate | pyridine | Carboxylic Acid | metals |
| Urea | phosphate | sulfate | sulfone | nitrate | pyridine | carboxilic acid | metals |
| Valine | phosphate | sulfate | sulfone | nitrate | pyridine | Carboxylic Acid | metals |
| Valine | phosphate | sulfate | sulfone | nitrate | pyridine | carboxilic acid | metals |
| Vitamin K5 | phosphate | sulfate | sulfone | nitrate | pyridine | carboxilic acid | metals |
| Vitamin K5 | phosphate | sulfate | sulfone | nitrate | pyridine | Carboxylic Acid | metals |
| Xylitol | phosphate | sulfate | sulfone | nitrate | pyridine | Carboxylic Acid | metals |

| Co-crystal Former | | | | Interacting Group | | | |
|---|---|---|---|---|---|---|---|
| 1,5-Napthalene-disulfonic Acid | | | | | | | |

TABLE II-continued

| Compound | Col1 | Col2 | Col3 | Col4 | Col5 | Col6 | Col7 |
|---|---|---|---|---|---|---|---|
| 1-Hydroxy-2-naphthoic acid | ester | ether | cyano | furan | bromine | chlorine | s-heterocyclic |
| 1-Hydroxy-2-naphthoic acid | ester | ether | cyano | furan | bromine | chlorine | s-heterocyclic |
| 4-Aminobenzoic Acid | aldehyde | ester | ether | | furan | bromine | chlorine |
| 4-Aminobenzoic Acid | aldehyde | ester | ether | cyano | furan | bromine | chlorine |
| 4-aminopyridine | aldehyde | ester | ether | cyano | furan | bromine | chlorine |
| 4-Chlorobenzene-Sulfonic Acid | aldehyde | thiol | n-heterocyclic ring | thionedisulfide | pyrrolidindione | iodine | hydrazone | thiocyanate |
| 4-ethoxyphenyl Urea | aldehyde | ester | ether | cyano | | furan | bromine | chlorine |
| 4-ethoxyphenyl Urea | aldehyde | ester | ether | cyano | | furan | bromine | chlorine |
| 7-oxo-DHEA | | ester | ether | cyano | furan | chlorine | s-heterocyclic |
| 7-oxo-DHEA | aldehyde | ester | ether | | | bromine | chlorine |
| Acesulfame | | | | | | | |
| Acesulfame | aldehyde | ester | ether | cyano | | furan | bromine | chlorine |
| Acetohydroxamic Acid | aldehyde | ester | ether | cyano | | furan | bromine | chlorine |
| Acetohydroxamic Acid | aldehyde | ester | ether | cyano | | furan | bromine | chlorine |
| Acetohydroxamic Acid | aldehyde | ester | ether | cyano | | furan | bromine | chlorine |
| Adenine | aldehyde | ester | ether | cyano | | furan | bromine | chlorine |
| Adenine | aldehyde | thiol | n-heterocyclic ring | thionedisulfide | pyrrolidindione | iodine | hydrazone | thiocyanate |
| Adipic acid | aldehyde | ester | ether | cyano | | furan | bromine | chlorine |
| Alanine | aldehyde | ester | ether | cyano | | furan | bromine | chlorine |
| Alanine | aldehyde | ester | ether | cyano | | furan | bromine | chlorine |
| Allopurinaol | aldehyde | ester | ether | cyano | | furan | bromine | chlorine |
| Allopurinaol | aldehyde | ester | ether | cyano | | furan | bromine | chlorine |
| Arginine | aldehyde | ester | ether | cyano | | furan | bromine | chlorine |
| Arginine | aldehyde | ester | ether | cyano | | furan | bromine | chlorine |
| Ascorbic Acid | aldehyde | ester | ether | cyano | | furan | bromine | chlorine |
| Ascorbic Acid | aldehyde | ester | ether | cyano | | furan | bromine | chlorine |
| Ascorbic Acid | aldehyde | ester | ether | cyano | | furan | bromine | chlorine |
| Asparagine | aldehyde | ester | ether | cyano | | furan | bromine | chlorine |
| Asparagine | aldehyde | ester | ether | cyano | | furan | bromine | chlorine |
| Asparagine | aldehyde | ester | ether | cyano | | furan | bromine | chlorine |
| Aspartic Acid | aldehyde | ester | ether | cyano | | furan | bromine | chlorine |
| Aspartic Acid | aldehyde | ester | ether | cyano | | furan | bromine | chlorine |
| Benzenesulfonic Acid | | | | | | | | |
| Benzoic Acid | aldehyde | ester | ether | cyano | | furan | bromine | chlorine |
| Caffeine | aldehyde | ester | ether | cyano | | furan | bromine | chlorine |
| Camphoric acid | aldehyde | ester | ether | cyano | | furan | bromine | chlorine |
| Capric acid | aldehyde | ester | ether | cyano | | furan | bromine | chlorine |
| Genistein | aldehyde | ester | ether | cyano | | furan | bromine | chlorine |
| Genistein | bromine | iodine | ketone | sulfonic acid | sulfate | phosphate | phosphonic acid | carboxylic acid |
| Genistein | aldehyde | ketone | peroxide | epoxide | | | | iodine |
| Cinnamic acid | aldehyde | ester | ether | cyano | | furan | bromine | heterocyclic-S |
| Citric Acid | aldehyde | ester | ether | cyano | | furan | bromine | chlorine |
| Citric Acid | aldehyde | ester | ether | cyano | | furan | bromine | chlorine |
| Clemizole | aldehyde | ester | n-heterocyclic ring | thionedisulfide | pyrrolidindione | iodine | hydrazone | thiocyanate |
| Cyclamic Acid | aldehyde | thiol | ether | cyano | | furan | bromine | chlorine |
| Cyclamic Acid | | | | | | | | |
| Cysteine | aldehyde | ester | ether | cyano | | furan | bromine | chlorine |
| Cysteine | aldehyde | ester | ether | cyano | | furan | bromine | chlorine |
| Cysteine | | | | | | | | |
| Dimethylglycine | aldehyde | ester | ether | cyano | | furan | bromine | chlorine |
| Dimethylglycine | aldehyde | ester | ether | cyano | | furan | bromine | chlorine |

TABLE II-continued

| | | | | | | |
|---|---|---|---|---|---|---|
| D-ribose | aldehyde | ketone | epoxide | | furan | heterocyclic-S | iodine |
| D-ribose | aldehyde | ester | cyano | | furan | bromine | chlorine |
| Fumaric Acid | aldehyde | ester | cyano | | furan | bromine | chlorine |
| Galactaric acid | aldehyde | ester | cyano | | furan | bromine | chlorine |
| Galactaric acid | ester | ether | cyano | furan | bromine | chlorine | s-heterocyclic |
| Chrysin | aldehyde | ester | ether | | bromine | chlorine | chlorine |
| Chrysin | bromine | iodine | sulfonic acid | sulfate | furan | bromine | carboxylic acid |
| Chrysin | aldehyde | ketone | epoxide | | phosphate | phosphonic acid | iodine |
| Gentisic acid | aldehyde | ester | cyano | | furan | heterocyclic-S | chlorine |
| Gentisic acid | bromine | iodine | sulfonic acid | sulfate | | bromine | bromine |
| Glucamine, N-methyl | ester | ether | ketone | furan | phosphate | phosphonic acid | carboxylic acid |
| Glucamine, N-methyl | aldehyde | ether | cyano | | bromine | chlorine | s-heterocyclic |
| Gluconic Acid | aldehyde | ester | cyano | | furan | bromine | chlorine |
| Gluconic Acid | aldehyde | ester | cyano | | furan | bromine | chlorine |
| Glucosamine | aldehyde | ester | cyano | | furan | bromine | chlorine |
| Glucuronic acid | aldehyde | ester | cyano | | furan | bromine | chlorine |
| Glucuronic acid | ester | ether | cyano | furan | bromine | chlorine | s-heterocyclic |
| Glutamic Acid | aldehyde | ester | ether | | furan | bromine | chlorine |
| Glutamic Acid | aldehyde | ester | ether | | furan | bromine | chlorine |
| Glutaric Acid | aldehyde | ester | ether | | furan | bromine | chlorine |
| Glutamine | aldehyde | ester | ether | | furan | bromine | chlorine |
| Glutamine | aldehyde | ester | ether | | furan | bromine | chlorine |
| Glutaric Acid | aldehyde | ester | ether | | furan | bromine | chlorine |
| Glycine | aldehyde | ester | ether | | furan | bromine | chlorine |
| Glycine | aldehyde | ester | ether | | furan | bromine | chlorine |
| Glycolic Acid | aldehyde | ester | ether | | furan | bromine | chlorine |
| Glycolic Acid | aldehyde | ester | ether | | furan | bromine | chlorine |
| Hippuric Acid | aldehyde | ester | ether | | furan | bromine | chlorine |
| Hippuric Acid | aldehyde | ester | ether | | furan | bromine | chlorine |
| Histidine | aldehyde | ester | ether | | furan | bromine | chlorine |
| Histidine | aldehyde | ester | ether | | furan | bromine | chlorine |
| Histidine | phosphinic acid hemihydrate | chlorine | sulfoxide | amide | fluorine | sulfonate ester | chlorine |
| Hydroquinone | aldehyde | ester | cyano | | furan | bromine | chlorine |
| Hydroquinone | bromine | iodine | sulfonic acid | sulfate | phosphate | phosphonic acid | carboxylic acid |
| Imidazole | aldehyde | ester | cyano | | furan | bromine | chlorine |
| Ipriflavone | aldehyde | ketone | epoxide | | heterocyclic-S | iodine |
| Ipriflavone | aldehyde | ester | peroxide | | furan | bromine | chlorine |
| Isoleucine | aldehyde | ester | ether | | furan | bromine | chlorine |
| Isoleucine | aldehyde | ester | ether | | furan | bromine | chlorine |
| lactobionic acid | ester | ether | cyano | furan | bromine | chlorine | s-heterocyclic |
| Lactobionic acid | aldehyde | ketone | peroxide | | bromine | heterocyclic-S | iodine |
| Lauric acid | aldehyde | ester | epoxide | | furan | bromine | chlorine |
| Leucine | aldehyde | ester | cyano | | furan | bromine | chlorine |
| Leucine | aldehyde | ester | cyano | | furan | bromine | chlorine |
| Lysine | aldehyde | ester | cyano | | furan | bromine | chlorine |
| Lysine | aldehyde | ester | cyano | | furan | bromine | chlorine |
| Maleic | aldehyde | ester | cyano | | furan | bromine | chlorine |
| Malic Acid | aldehyde | ester | cyano | | furan | bromine | chlorine |
| Malic Acid | aldehyde | ester | cyano | | furan | bromine | chlorine |
| Malonic | aldehyde | ester | cyano | | furan | bromine | chlorine |

TABLE II-continued

| | | | | | | |
|---|---|---|---|---|---|---|
| Mandelic Acid | aldehyde | ester | ether | cyano | | furan | bromine | chlorine |
| Mandelic Acid | aldehyde | ester | ether | cyano | | furan | bromine | chlorine |
| Methionine | aldehyde | ester | ether | cyano | | furan | bromine | chlorine |
| Methionine | aldehyde | ester | ether | cyano | | furan | bromine | chlorine |
| Methionine | aldehyde | ketone | ether | epoxide | Ag | Se | heterocyclic-S | iodine |
| Nicotinamide | | thiol | peroxide | thionedisulfide | pyrrolidindione | iodine | hydrazone | thiocyanate |
| Nicotinamide | aldehyde | ester | n-heterocyclic ring | cyano | | furan | bromine | chlorine |
| Nicotinic Acid | aldehyde | ester | ether | cyano | | furan | bromine | chlorine |
| Nicotinic Acid | | thiol | n-heterocyclic ring | thionedisulfide | pyrrolidindione | iodine | hydrazone | thiocyanate |
| Orotic acid | aldehyde | ester | ether | cyano | | furan | bromine | chlorine |
| Orotic acid | aldehyde | ester | ether | cyano | | furan | bromine | chlorine |
| Oxalic acid | aldehyde | ester | ether | cyano | | furan | bromine | chlorine |
| Palmitic acid | aldehyde | ester | ether | cyano | | furan | bromine | chlorine |
| Pamoic acid | aldehyde | ester | ether | cyano | | furan | bromine | chlorine |
| Pamoic acid | ester | | cyano | | furan | chlorine | bromine | s-heterocyclic |
| Pamoic acid | bromine | iodine | ketone | sulfonic acid | sulfate | phosphate | phosphonic acid | carboxylic acid |
| Phenylalanine | aldehyde | ester | ether | cyano | | furan | bromine | chlorine |
| Phenylalanine | aldehyde | ester | ether | cyano | | furan | bromine | chlorine |
| Piperazine | aldehyde | ester | ether | cyano | | furan | bromine | chlorine |
| Procaine | aldehyde | ester | ether | cyano | | furan | bromine | chlorine |
| Procaine | aldehyde | ester | ether | cyano | | furan | bromine | chlorine |
| Proline | aldehyde | ester | ether | cyano | | furan | bromine | chlorine |
| Proline | aldehyde | ester | ether | cyano | | furan | bromine | chlorine |
| p-Toluenesulfonic acid | | | | | | | | |
| Pyridoxamine | aldehyde | ester | ether | cyano | | furan | bromine | chlorine |
| Pyridoxamine | aldehyde | ester | ether | cyano | | furan | bromine | chlorine |
| Pyridoxamine | | thiol | n-heterocyclic ring | thionedisulfide | | iodine | hydrazone | thiocyanate |
| Pyridoxine | | thiol | n-heterocyclic ring | thionedisulfide | pyrrolidindione | iodine | hydrazone | thiocyanate |
| Pyridoxine (4-Pyridoxic Acid) | aldehyde | ester | ether | cyano | | furan | bromine | chlorine |
| Pyridoxine (4-Pyridoxic Acid) | aldehyde | ester | ether | cyano | | furan | bromine | chlorine |
| Pyroglutamic acid | aldehyde | ester | ether | cyano | | furan | bromine | chlorine |
| Pyroglutamic acid | aldehyde | ester | ether | cyano | | furan | bromine | chlorine |
| Quercetin | bromine | iodine | ketone | sulfonic acid | sulfate | phosphate | phosphonic acid | carboxylic acid |
| Quercetin | aldehyde | ketone | peroxide | epoxide | | heterocyclic-S | bromine | iodine |
| Resveratrol | aldehyde | ester | ether | cyano | | furan | bromine | chlorine |
| Resveratrol | bromine | iodine | ketone | sulfonic acid | sulfate | phosphate | phosphonic acid | carboxylic acid |
| Saccharin | aldehyde | ester | ether | cyano | | furan | bromine | chlorine |
| Saccharin | aldehyde | ester | ether | cyano | | furan | bromine | chlorine |
| Saccharin | | | | | | | | |
| Salicylic Acid | aldehyde | ester | ether | cyano | | furan | bromine | chlorine |
| Salicylic Acid | aldehyde | ester | ether | cyano | | furan | bromine | chlorine |
| Salicylic Acid, 4-amino | aldehyde | ester | ether | cyano | | furan | bromine | chlorine |
| Salicylic Acid, 4-amino | aldehyde | ester | ether | cyano | | furan | chlorine | s-heterocyclic |
| Sebacic acid | ester | ether | cyano | | furan | bromine | chlorine |
| Serine | aldehyde | ester | ether | cyano | furan | | bromine | chlorine |
| Serine | aldehyde | ester | ether | cyano | | furan | bromine | chlorine |
| Serine | aldehyde | ester | ether | cyano | | furan | bromine | chlorine |
| Stearic acid | aldehyde | ester | ether | cyano | | furan | bromine | chlorine |
| Succinic Acid | aldehyde | ester | ether | cyano | | furan | bromine | chlorine |

TABLE II-continued

| Co-crystal Former | | | | | |
|---|---|---|---|---|---|
| Tartaric Acid | aldehyde | ester | ether | cyano | furan | bromine | chlorine |
| Threonine | aldehyde | ester | ether | cyano | furan | bromine | chlorine |
| Threonine | aldehyde | ester | ether | cyano | furan | bromine | chlorine |
| Threonine | aldehyde | ester | ether | cyano | furan | bromine | chlorine |
| Tris | aldehyde | ester | ether | cyano | furan | bromine | chlorine |
| Tris | aldehyde | ester | ether | cyano | furan | bromine | chlorine |
| Tryptophan | aldehyde | ester | ether | cyano | furan | bromine | chlorine |
| Tryptophan | aldehyde | ester | ether | cyano | furan | bromine | chlorine |
| Tryptophan | aldehyde | thiol | n-heterocyclic ring | thionedisulfide | iodine | hydrazone | thiocyanate |
| Tyrosine | aldehyde | ester | ether | pyrrolidindione | furan | bromine | chlorine |
| Tyrosine | aldehyde | ester | ether | cyano | furan | bromine | chlorine |
| Tyrosine | aldehyde | ester | ether | cyano | furan | bromine | chlorine |
| Urea | aldehyde | ester | ether | cyano | furan | bromine | chlorine |
| Urea | aldehyde | ester | ether | cyano | furan | bromine | chlorine |
| Valine | aldehyde | ester | ether | cyano | furan | bromine | chlorine |
| Valine | aldehyde | ester | ether | cyano | furan | bromine | chlorine |
| Vitamin K5 | aldehyde | ester | ether | cyano | furan | bromine | chlorine |
| Vitamin K5 | aldehyde | ester | ether | cyano | furan | bromine | chlorine |
| Xylitol | aldehyde | ester | ether | cyano | furan | bromine | chlorine |

| Co-crystal Former | | Interacting Group | | | | |
|---|---|---|---|---|---|---|
| 1,5-Napthalene-disulfonic Acid | pyridine | cyano | n-heterocyclic | ketone | phosphate ester | fluorine | carbamate |
| 1-Hydroxy-2-naphthoic acid | pyridine | cyano | n-heterocyclic | ketone | phosphate ester | fluorine | carbamate |
| 1-Hydroxy-2-naphthoic acid | s-heterocyclic | pyridine | cyano | n-heterocyclic | phosphate ester | | fluorine |
| 4-Aminobenzoic Acid | s-heterocyclic | pyridine | cyano | n-heterocyclic | phosphate ester | | fluorine |
| 4-Aminobenzoic Acid | s-heterocyclic | pyridine | cyano | n-heterocyclic | *sulfonic acid | | fluorine |
| 4-aminopyridine | s-heterocyclic | pyridine | hydroxamic acid | carboxamide | | *phosphoric acid | N-oxide |
| 4-aminopyridine | *bromine | | | | | | |
| 4-Chlorobenzene-Sulfonic Acid | | | | | | | |
| 4-ethoxyphenyl Urea | s-heterocyclic | pyridine | cyano | n-heterocyclic | ketone | | fluorine |
| 4-ethoxyphenyl Urea | s-heterocyclic | pyridine | cyano | n-heterocyclic | ketone | | fluorine |
| 7-oxo-DHEA | pyridine | cyano | n-heterocyclic | phosphate ester | fluorine | | carbamate |
| 7-oxo-DHEA | s-heterocyclic | pyridine | cyano | n-heterocyclic | ketone | phosphate ester | fluorine |
| Acesulfame | | | | | | | |
| Acetohydroxamic Acid | s-heterocyclic | pyridine | cyano | n-heterocyclic | ketone | phosphate ester | fluorine |
| Acetohydroxamic Acid | s-heterocyclic | pyridine | cyano | n-heterocyclic | ketone | phosphate ester | fluorine |
| Acetohydroxamic Acid | s-heterocyclic | pyridine | cyano | n-heterocyclic | ketone | phosphate ester | fluorine |
| Adenine | s-heterocyclic | pyridine | cyano | n-heterocyclic | ketone | phosphate ester | fluorine |
| Adenine | s-heterocyclic | pyridine | hydroxamic acid | cyano | carboxamide | *sulfonic acid | *phosphoric acid | N-oxide |
| Adipic acid | s-heterocyclic | pyridine | cyano | n-heterocyclic | ketone | phosphate ester | fluorine |
| Alanine | s-heterocyclic | pyridine | cyano | n-heterocyclic | ketone | phosphate ester | fluorine |
| Alanine | s-heterocyclic | pyridine | cyano | n-heterocyclic | ketone | phosphate ester | fluorine |
| Allopurinaol | s-heterocyclic | pyridine | cyano | n-heterocyclic | ketone | phosphate ester | fluorine |
| Allopurinaol | s-heterocyclic | pyridine | cyano | n-heterocyclic | ketone | phosphate ester | fluorine |
| Arginine | s-heterocyclic | pyridine | cyano | n-heterocyclic | ketone | phosphate ester | fluorine |
| Arginine | s-heterocyclic | pyridine | cyano | n-heterocyclic | ketone | phosphate ester | fluorine |
| Ascorbic Acid | s-heterocyclic | pyridine | cyano | n-heterocyclic | ketone | phosphate ester | fluorine |
| Ascorbic Acid | s-heterocyclic | pyridine | cyano | n-heterocyclic | ketone | phosphate ester | fluorine |
| Ascorbic Acid | s-heterocyclic | pyridine | cyano | n-heterocyclic | ketone | phosphate ester | fluorine |

TABLE II-continued

| | | | | | | |
|---|---|---|---|---|---|---|
| Asparagine | s-heterocyclic | pyridine | cyano | n-heterocyclic | ketone | | phosphate ester | fluorine |
| Asparagine | s-heterocyclic | pyridine | cyano | n-heterocyclic | ketone | | phosphate ester | fluorine |
| Asparagine | s-heterocyclic | pyridine | cyano | n-heterocyclic | ketone | | phosphate ester | fluorine |
| Aspartic Acid | s-heterocyclic | pyridine | cyano | n-heterocyclic | ketone | | phosphate ester | fluorine |
| Aspartic Acid | s-heterocyclic | pyridine | cyano | n-heterocyclic | ketone | | phosphate ester | fluorine |
| Benzenesulfonic Acid | | | | | | | | |
| Benzoic Acid | s-heterocyclic | pyridine | cyano | n-heterocyclic | ketone | | phosphate ester | fluorine |
| Caffeine | s-heterocyclic | pyridine | cyano | n-heterocyclic | ketone | | phosphate ester | fluorine |
| Camphoric acid | s-heterocyclic | pyridine | cyano | n-heterocyclic | ketone | | phosphate ester | fluorine |
| Capric acid | s-heterocyclic | pyridine | cyano | n-heterocyclic | ketone | | phosphate ester | fluorine |
| Genistein | s-heterocyclic | pyridine | cyano | n-heterocyclic | ketone | | phosphate ester | fluorine |
| Genistein | nitro | sulfone | analine | sulfate | sulfone | alcohol | | |
| Genistein | ester | ether | carboxylic acid | n-heterocyclic | ketone | | phosphate ester | |
| Cinnamic acid | s-heterocyclic | pyridine | cyano | n-heterocyclic | ketone | | phosphate ester | fluorine |
| Citric Acid | s-heterocyclic | pyridine | cyano | n-heterocyclic | ketone | | phosphate ester | fluorine |
| Citric Acid | *bromine | pyridine | hydroxamic acid | n-heterocyclic | carboxamide | *phosphoric acid | *sulfonic acid | N-oxide |
| Clemizole | s-heterocyclic | pyridine | cyano | n-heterocyclic | ketone | | phosphate ester | fluorine |
| Cyclamic Acid | | | | | | | | |
| Cyclamic Acid | s-heterocyclic | pyridine | cyano | n-heterocyclic | ketone | | phosphate ester | fluorine |
| Cysteine | s-heterocyclic | pyridine | cyano | n-heterocyclic | ketone | | phosphate ester | fluorine |
| Cysteine | | | | | | | | |
| Cysteine | s-heterocyclic | pyridine | cyano | n-heterocyclic | ketone | | phosphate ester | fluorine |
| Dimethylglycine | s-heterocyclic | pyridine | cyano | n-heterocyclic | ketone | | phosphate ester | fluorine |
| Dimethylglycine | ester | ether | carboxylic acid | sulfate | sulfone | alcohol | | |
| D-ribose | s-heterocyclic | pyridine | cyano | n-heterocyclic | ketone | | phosphate ester | fluorine |
| Fumaric Acid | s-heterocyclic | pyridine | cyano | n-heterocyclic | ketone | | phosphate ester | fluorine |
| Galactaric acid | s-heterocyclic | pyridine | cyano | n-heterocyclic | ketone | | phosphate ester | fluorine |
| Galactaric acid | pyridine | cyano | n-heterocyclic | ketone | phosphate ester | fluorine | | carbamate |
| Chrysin | s-heterocyclic | pyridine | cyano | n-heterocyclic | ketone | | phosphate ester | fluorine |
| Chrysin | nitro | sulfone | analine | sulfate | sulfone | alcohol | | |
| Gentisic acid | ester | ether | carboxylic acid | n-heterocyclic | ketone | | phosphate ester | fluorine |
| Gentisic acid | nitro | sulfone | analine | | | | | |
| Glucamine, N-methyl | pyridine | cyano | n-heterocyclic | ketone | phosphate ester | fluorine | | carbamate |
| Glucamine, N-methyl | s-heterocyclic | pyridine | cyano | n-heterocyclic | ketone | | phosphate ester | fluorine |
| Gluconic Acid | s-heterocyclic | pyridine | cyano | n-heterocyclic | ketone | | phosphate ester | fluorine |
| Gluconic Acid | s-heterocyclic | pyridine | cyano | n-heterocyclic | ketone | | phosphate ester | fluorine |
| Gluosamine | s-heterocyclic | pyridine | cyano | n-heterocyclic | ketone | | phosphate ester | fluorine |
| Glucuronic acid | s-heterocyclic | pyridine | cyano | n-heterocyclic | ketone | | phosphate ester | fluorine |
| Glucuronic acid | pyridine | cyano | n-heterocyclic | ketone | phosphate ester | fluorine | | carbamate |
| Glutamic Acid | s-heterocyclic | pyridine | cyano | n-heterocyclic | ketone | | phosphate ester | fluorine |
| Glutamic Acid | s-heterocyclic | pyridine | cyano | n-heterocyclic | ketone | | phosphate ester | fluorine |
| Glutamic Acid | s-heterocyclic | pyridine | cyano | n-heterocyclic | ketone | | phosphate ester | fluorine |
| Glutamine | s-heterocyclic | pyridine | cyano | n-heterocyclic | ketone | | phosphate ester | fluorine |
| Glutamine | s-heterocyclic | pyridine | cyano | n-heterocyclic | ketone | | phosphate ester | fluorine |
| Glutaric Acid | s-heterocyclic | pyridine | cyano | n-heterocyclic | ketone | | phosphate ester | fluorine |
| Glycine | s-heterocyclic | pyridine | cyano | n-heterocyclic | ketone | | phosphate ester | fluorine |
| Glycine | s-heterocyclic | pyridine | cyano | n-heterocyclic | ketone | | phosphate ester | fluorine |
| Glycolic Acid | s-heterocyclic | pyridine | cyano | n-heterocyclic | ketone | | phosphate ester | fluorine |
| Glycolic Acid | s-heterocyclic | pyridine | cyano | n-heterocyclic | ketone | | phosphate ester | fluorine |
| Hippuric Acid | s-heterocyclic | pyridine | cyano | n-heterocyclic | ketone | | phosphate ester | fluorine |

TABLE II-continued

| | | | | | | |
|---|---|---|---|---|---|---|
| Hippuric Acid | s-heterocyclic | pyridine | cyano | n-heterocyclic | ketone | phosphate ester | fluorine |
| Hippuric Acid | s-heterocyclic | pyridine | cyano | n-heterocyclic | ketone | phosphate ester | fluorine |
| Histidine | s-heterocyclic | pyridine | cyano | n-heterocyclic | ketone | phosphate ester | fluorine |
| Histidine | s-heterocyclic | pyridine | cyano | n-heterocyclic | ketone | phosphate ester | fluorine |
| Hydroquinone | s-heterocyclic | pyridine | cyano | n-heterocyclic | ketone | phosphate ester | fluorine |
| Hydroquinone | nitro | sulfone | analine | | | | |
| Imidazole | s-heterocyclic | pyridine | cyano | n-heterocyclic | ketone | phosphate ester | fluorine |
| Ipriflavone | ester | ether | carboxylic acid | sulfone | | alcohol | |
| Isoleucine | s-heterocyclic | pyridine | cyano | n-heterocyclic | ketone | phosphate ester | fluorine |
| Isoleucine | s-heterocyclic | pyridine | cyano | n-heterocyclic | ketone | phosphate ester | fluorine |
| Lysine | s-heterocyclic | pyridine | cyano | n-heterocyclic | ketone | phosphate ester | fluorine |
| lactobionic acid | s-heterocyclic | pyridine | n-heterocyclic | n-heterocyclic | ketone | phosphate ester | carbamate |
| Lactobionic acid | pyridine | cyano | carboxylic acid | ketone | phosphate ester | fluorine | |
| Lactobionic acid | ester | ether | carboxylic acid | sulfate | | alcohol | |
| Lauric acid | s-heterocyclic | pyridine | cyano | n-heterocyclic | ketone | phosphate ester | fluorine |
| Leucine | s-heterocyclic | pyridine | cyano | n-heterocyclic | ketone | phosphate ester | fluorine |
| Leucine | s-heterocyclic | pyridine | cyano | n-heterocyclic | ketone | phosphate ester | fluorine |
| Lysine | s-heterocyclic | pyridine | cyano | n-heterocyclic | ketone | phosphate ester | fluorine |
| Lysine | s-heterocyclic | pyridine | cyano | n-heterocyclic | ketone | phosphate ester | fluorine |
| Maleic | s-heterocyclic | pyridine | cyano | n-heterocyclic | ketone | phosphate ester | fluorine |
| Malic Acid | s-heterocyclic | pyridine | cyano | n-heterocyclic | ketone | phosphate ester | fluorine |
| Malic Acid | s-heterocyclic | pyridine | cyano | n-heterocyclic | ketone | phosphate ester | fluorine |
| Malonic | s-heterocyclic | pyridine | cyano | n-heterocyclic | ketone | phosphate ester | fluorine |
| Mandelic Acid | s-heterocyclic | pyridine | cyano | n-heterocyclic | ketone | phosphate ester | fluorine |
| Mandelic Acid | s-heterocyclic | pyridine | cyano | n-heterocyclic | ketone | phosphate ester | fluorine |
| Methionine | s-heterocyclic | pyridine | cyano | n-heterocyclic | ketone | phosphate ester | fluorine |
| Methionine | s-heterocyclic | pyridine | cyano | n-heterocyclic | sulfone | phosphate ester | fluorine |
| Methionine | ester | ether | carboxylic acid | sulfate | | alcohol | |
| Nicotinamide | *bromine | pyridine | hydroxamic acid | cyano | carboxamide | *sulfonic acid | N-oxide |
| Nicotinamide | s-heterocyclic | pyridine | cyano | n-heterocyclic | ketone | phosphate ester | fluorine |
| Nicotinic Acid | s-heterocyclic | pyridine | cyano | n-heterocyclic | ketone | phosphate ester | fluorine |
| Nicotinic Acid | *bromine | | hydroxamic acid | cyano | carboxamide | *sulfonic acid | N-oxide |
| Orotic acid | s-heterocyclic | pyridine | cyano | n-heterocyclic | ketone | phosphate ester | fluorine |
| Orotic acid | s-heterocyclic | pyridine | cyano | n-heterocyclic | ketone | phosphate ester | fluorine |
| Oxalic acid | s-heterocyclic | pyridine | cyano | n-heterocyclic | ketone | phosphate ester | fluorine |
| Palmitic acid | s-heterocyclic | pyridine | cyano | n-heterocyclic | ketone | phosphate ester | fluorine |
| Pamoic acid | s-heterocyclic | pyridine | cyano | n-heterocyclic | ketone | phosphate ester | fluorine |
| Pamoic acid | s-heterocyclic | pyridine | n-heterocyclic | ketone | phosphate ester | fluorine | |
| Pamoic acid | pyridine | cyano | analine | | | | carbamate |
| Phenylalanine | nitro | sulfone | | | | | |
| Phenylalanine | s-heterocyclic | pyridine | cyano | n-heterocyclic | ketone | phosphate ester | fluorine |
| Piperazine | s-heterocyclic | pyridine | cyano | n-heterocyclic | ketone | phosphate ester | fluorine |
| Procaine | s-heterocyclic | pyridine | cyano | n-heterocyclic | ketone | phosphate ester | fluorine |
| Procaine | s-heterocyclic | pyridine | cyano | n-heterocyclic | ketone | phosphate ester | fluorine |
| Proline | s-heterocyclic | pyridine | cyano | n-heterocyclic | ketone | phosphate ester | fluorine |
| Proline | s-heterocyclic | pyridine | cyano | n-heterocyclic | ketone | phosphate ester | fluorine |
| p-Toluenesulfonic acid | | | | | | | |
| Pyridoxamine | s-heterocyclic | pyridine | cyano | n-heterocyclic | ketone | phosphate ester | fluorine |
| Pyridoxamine | s-heterocyclic | pyridine | cyano | n-heterocyclic | ketone | phosphate ester | fluorine |
| Pyridoxamine | *bromine | | hydroxamic acid | cyano | carboxamide | *sulfonic acid | N-oxide |
| Pyridoxine (4-Pyridoxic Acid) | *bromine | | hydroxamic acid | cyano | carboxamide | *phosphoric acid | N-oxide |

TABLE II-continued

| | | | | | |
|---|---|---|---|---|---|
| Pyridoxine (4-Pyridoxic Acid) | s-heterocyclic | pyridine | cyano | n-heterocyclic | ketone | phosphate ester | | fluorine |
| Pyroglutamic acid | s-heterocyclic | pyridine | cyano | n-heterocyclic | ketone | phosphate ester | | fluorine |
| Pyroglutamic acid | s-heterocyclic | pyridine | cyano | n-heterocyclic | ketone | phosphate ester | | fluorine |
| Quercetin | nitro | sulfone | analine | | | | | |
| Quercetin | ester | ether | carboxylic acid | sulfate | sulfone | | alcohol | |
| Resveratrol | s-heterocyclic | pyridine | cyano | n-heterocyclic | ketone | phosphate ester | | fluorine |
| Resveratrol | nitro | sulfone | analine | | | | | |
| Saccharin | s-heterocyclic | pyridine | cyano | n-heterocyclic | ketone | phosphate ester | | fluorine |
| Saccharin | s-heterocyclic | pyridine | cyano | n-heterocyclic | ketone | phosphate ester | | fluorine |
| Saccharin | | | | | | | | |
| Salicylic Acid | s-heterocyclic | pyridine | cyano | n-heterocyclic | ketone | phosphate ester | | fluorine |
| Salicylic Acid | s-heterocyclic | pyridine | cyano | n-heterocyclic | ketone | phosphate ester | | fluorine |
| Salicylic Acid, 4-amino | s-heterocyclic | pyridine | cyano | n-heterocyclic | ketone | phosphate ester | | fluorine |
| Salicylic Acid, 4-amino | pyridine | cyano | n-heterocyclic | ketone | phosphate ester | fluorine | | carbamate |
| Sebacic acid | s-heterocyclic | pyridine | cyano | n-heterocyclic | ketone | phosphate ester | | fluorine |
| Serine | s-heterocyclic | pyridine | cyano | n-heterocyclic | ketone | phosphate ester | | fluorine |
| Serine | s-heterocyclic | pyridine | cyano | n-heterocyclic | ketone | phosphate ester | | fluorine |
| Stearic acid | s-heterocyclic | pyridine | cyano | n-heterocyclic | ketone | phosphate ester | | fluorine |
| Succinic Acid | s-heterocyclic | pyridine | cyano | n-heterocyclic | ketone | phosphate ester | | fluorine |
| Tartaric Acid | s-heterocyclic | pyridine | cyano | n-heterocyclic | ketone | phosphate ester | | fluorine |
| Threonine | s-heterocyclic | pyridine | cyano | n-heterocyclic | ketone | phosphate ester | | fluorine |
| Threonine | s-heterocyclic | pyridine | cyano | n-heterocyclic | ketone | phosphate ester | | fluorine |
| Tris | s-heterocyclic | pyridine | cyano | n-heterocyclic | ketone | phosphate ester | | fluorine |
| Tris | s-heterocyclic | pyridine | cyano | n-heterocyclic | ketone | phosphate ester | | fluorine |
| Tryptophan | s-heterocyclic | pyridine | cyano | n-heterocyclic | ketone | *sulfonic acid | *phosphoric acid | fluorine |
| Tryptophan | s-heterocyclic | pyridine | cyano | n-heterocyclic | ketone | phosphate ester | | fluorine |
| Tryptophan | *bromine | pyridine | hydroxamic acid | cyano | carboxamide | | | N-oxide |
| Tyrosine | s-heterocyclic | pyridine | cyano | n-heterocyclic | ketone | phosphate ester | | fluorine |
| Tyrosine | s-heterocyclic | pyridine | cyano | n-heterocyclic | ketone | phosphate ester | | fluorine |
| Tyrosine | s-heterocyclic | pyridine | cyano | n-heterocyclic | ketone | phosphate ester | | fluorine |
| Urea | s-heterocyclic | pyridine | cyano | n-heterocyclic | ketone | phosphate ester | | fluorine |
| Urea | s-heterocyclic | pyridine | cyano | n-heterocyclic | ketone | phosphate ester | | fluorine |
| Valine | s-heterocyclic | pyridine | cyano | n-heterocyclic | ketone | phosphate ester | | fluorine |
| Valine | s-heterocyclic | pyridine | cyano | n-heterocyclic | ketone | phosphate ester | | fluorine |
| Vitamin K5 | s-heterocyclic | pyridine | cyano | n-heterocyclic | ketone | phosphate ester | | fluorine |
| Vitamin K5 | s-heterocyclic | pyridine | cyano | n-heterocyclic | ketone | phosphate ester | | fluorine |
| Xylitol | s-heterocyclic | pyridine | cyano | n-heterocyclic | ketone | phosphate ester | | fluorine |

TABLE II-continued

| Co-crystal Former | Interacting Group | | | | | | | | |
|---|---|---|---|---|---|---|---|---|---|
| 1,5-Napthalene-disulfonic Acid | imidazole | | | | | | | | |
| 1-Hydroxy-2-naphthoic acid | imidazole | | BF4 | | | | | | |
| 1-Hydroxy-2-naphthoic acid | imidazole | | BF4 | | | | | | |
| 4-Aminobenzoic Acid | carbamate | imidazole | BF4 | | N-SO2 | thiourea | iodine | | |
| 4-Aminobenzoic Acid | carbamate | imidazole | BF4 | | N-SO2 | thiourea | iodine | | |
| 4-aminopyridine | carbamate | imidazole | BF4 | | N-SO2 | thiourea | iodine | | |
| 4-aminopyridine | carbamate | ester | fluorine | acetate | dithiadiazocyclopentadienyl | | | | |
| 4-Chlorobenzene-Sulfonic Acid | | | | | | | | | |
| 4-ethoxyphenyl Urea | carbamate | imidazole | BF4 | | N-SO2 | thiourea | iodine | epoxide | peroxide |
| 4-ethoxyphenyl Urea | carbamate | imidazole | BF4 | | N-SO2 | thiourea | iodine | epoxide | |
| 7-oxo-DHEA | imidazole | | BF4 | | | | | | |
| 7-oxo-DHEA | carbamate | imidazole | BF4 | | N-SO2 | thiourea | iodine | | |
| Acesulfame | | | | | | | | | |
| Acetohydroxamic Acid | carbamate | imidazole | BF4 | | N-SO2 | thiourea | iodine | epoxide | peroxide |
| Acetohydroxamic Acid | carbamate | imidazole | BF4 | | N-SO2 | thiourea | iodine | epoxide | peroxide |
| Acetohydroxamic Acid | carbamate | imidazole | BF4 | | N-SO2 | thiourea | iodine | epoxide | |
| Adenine | carbamate | ester | fluorine | acetate | dithiadiazocyclopentadienyl | | | | |
| Adenine | carbamate | imidazole | BF4 | | N-SO2 | thiourea | iodine | | |
| Adipic acid | carbamate | imidazole | BF4 | | N-SO2 | thiourea | iodine | | |
| Alanine | carbamate | imidazole | BF4 | | N-SO2 | thiourea | iodine | | |
| Allopurinaol | carbamate | imidazole | BF4 | | N-SO2 | thiourea | iodine | epoxide | |
| Allopurinaol | carbamate | imidazole | BF4 | | N-SO2 | thiourea | iodine | | |
| Arginine | carbamate | imidazole | BF4 | | N-SO2 | thiourea | iodine | | |
| Arginine | carbamate | imidazole | BF4 | | N-SO2 | thiourea | iodine | | |
| Ascorbic Acid | carbamate | imidazole | BF4 | | N-SO2 | thiourea | iodine | epoxide | |
| Ascorbic Acid | carbamate | imidazole | BF4 | | N-SO2 | thiourea | iodine | | |
| Ascorbic Acid | carbamate | imidazole | BF4 | | N-SO2 | thiourea | iodine | | |
| Asparagine | carbamate | imidazole | BF4 | | N-SO2 | thiourea | iodine | epoxide | peroxide |
| Asparagine | carbamate | imidazole | BF4 | | N-SO2 | thiourea | iodine | | |
| Asparagine | carbamate | imidazole | BF4 | | N-SO2 | thiourea | iodine | | |
| Aspartic Acid | carbamate | imidazole | BF4 | | N-SO2 | thiourea | iodine | | |
| Aspartic Acid | carbamate | imidazole | BF4 | | N-SO2 | thiourea | iodine | | |
| Benzenesulfonic Acid | | | | | | | | | |
| Benzoic Acid | carbamate | imidazole | BF4 | | N-SO2 | thiourea | iodine | | |
| Caffeine | carbamate | imidazole | BF4 | | N-SO2 | thiourea | iodine | | |
| Camphoric acid | carbamate | imidazole | BF4 | | N-SO2 | thiourea | iodine | | |
| Capric acid | carbamate | ester | fluorine | acetate | dithiadiazocyclopentadienyl | | | | |
| Genistein | carbamate | imidazole | BF4 | | N-SO2 | thiourea | iodine | | |
| Genistein | phosphate | cyanamide | | | | | | | |
| Cinnamic acid | carbamate | imidazole | BF4 | | N-SO2 | thiourea | iodine | | |
| Citric Acid | carbamate | imidazole | BF4 | | N-SO2 | thiourea | iodine | epoxide | |
| Citric Acid | carbamate | imidazole | BF4 | | N-SO2 | thiourea | | | |
| Clemizole | carbamate | ester | fluorine | acetate | dithiadiazocyclopentadienyl | | | | |
| Cyclamic Acid | carbamate | imidazole | BF4 | | N-SO2 | thiourea | iodine | | |
| Cyclamic Acid | | | | | | | | | |
| Cysteine | carbamate | imidazole | BF4 | | N-SO2 | thiourea | iodine | | |
| Cysteine | carbamate | imidazole | BF4 | | N-SO2 | thiourea | iodine | | |

TABLE II-continued

| | | | | | |
|---|---|---|---|---|---|
| Cysteine | carbamate | imidazole | BF4 | N-SO2 | thiourea | iodine |
| Dimethylglycine | carbamate | imidazole | BF4 | N-SO2 | thiourea | iodine |
| Dimethylglycine | phospphate | cyanamide | | | | |
| D-ribose | carbamate | imidazole | BF4 | N-SO2 | thiourea | iodine |
| Fumaric Acid | carbamate | imidazole | BF4 | N-SO2 | thiourea | iodine |
| Galactaric acid | carbamate | imidazole | BF4 | N-SO2 | thiourea | iodine | epoxide |
| Galactaric acid | imidazole | BF4 | | | | |
| Chrysin | carbamate | imidazole | BF4 | N-SO2 | thiourea | iodine |
| Chrysin | phospphate | cyanamide | | | | |
| Gentisic acid | carbamate | imidazole | BF4 | N-SO2 | thiourea | iodine |
| Gentisic acid | | | | | | |
| Glucamine, N-methyl | imidazole | BF4 | | | | |
| Glucamine, N-methyl | carbamate | imidazole | BF4 | N-SO2 | thiourea | iodine | epoxide |
| Gluconic Acid | carbamate | imidazole | BF4 | N-SO2 | thiourea | iodine |
| Gluconic Acid | carbamate | imidazole | BF4 | N-SO2 | thiourea | iodine | epoxide |
| Glucosamine | carbamate | imidazole | BF4 | N-SO2 | thiourea | iodine |
| Glucuronic acid | carbamate | imidazole | BF4 | N-SO2 | thiourea | iodine |
| Glucuronic acid | imidazole | BF4 | | | | |
| Glucuronic acid | carbamate | imidazole | BF4 | N-SO2 | thiourea | iodine | epoxide |
| Glutamic Acid | carbamate | imidazole | BF4 | alkane | N-SO2 | thiourea | iodine |
| Glutamic Acid | carbamate | imidazole | BF4 | aromatic | N-SO2 | thiourea | iodine |
| Glutamine | carbamate | imidazole | BF4 | N-SO2 | thiourea | iodine |
| Glutamine | carbamate | imidazole | BF4 | N-SO2 | thiourea | iodine | epoxide |
| Glutaric Acid | carbamate | imidazole | BF4 | N-SO2 | thiourea | iodine |
| Glycine | carbamate | imidazole | BF4 | N-SO2 | thiourea | iodine |
| Glycine | carbamate | imidazole | BF4 | N-SO2 | thiourea | iodine |
| Glycolic Acid | carbamate | imidazole | BF4 | N-SO2 | thiourea | iodine | epoxide |
| Glycolic Acid | carbamate | imidazole | BF4 | N-SO2 | thiourea | iodine |
| Hippuric Acid | carbamate | imidazole | BF4 | N-SO2 | thiourea | iodine | epoxide | peroxide |
| Hippuric Acid | carbamate | imidazole | BF4 | N-SO2 | thiourea | iodine |
| Histidine | carbamate | imidazole | BF4 | N-SO2 | thiourea | iodine |
| Histidine | carbamate | imidazole | BF4 | N-SO2 | thiourea | iodine |
| Histidine | carbamate | imidazole | BF4 | N-SO2 | thiourea | iodine |
| Hydroquinone | carbamate | imidazole | BF4 | N-SO2 | thiourea | iodine | epoxide | peroxide |
| Hydroquinone | carbamate | imidazole | BF4 | N-SO2 | thiourea | iodine |
| Imidazole | | | | | | |
| Ipriflavone | carbamate | phospphate | cyanamide | | | |
| Ipriflavone | carbamate | imidazole | BF4 | N-SO2 | thiourea | iodine |
| Isoleucine | carbamate | imidazole | BF4 | N-SO2 | thiourea | iodine |
| Isoleucine | carbamate | imidazole | BF4 | N-SO2 | thiourea | iodine |
| lactobionic acid | imidazole | BF4 | | | | |
| Lactobionic acid | carbamate | phospphate | cyanamide | | | |
| Lauric acid | carbamate | imidazole | BF4 | N-SO2 | thiourea | iodine |
| Leucine | carbamate | imidazole | BF4 | N-SO2 | thiourea | iodine |
| Leucine | carbamate | imidazole | BF4 | N-SO2 | thiourea | iodine |
| Lysine | carbamate | imidazole | BF4 | N-SO2 | thiourea | iodine |

TABLE II-continued

| | | | | | | | |
|---|---|---|---|---|---|---|---|
| Lysine | carbamate | imidazole | BF4 | | N-SO2 | thiourea | iodine |
| Maleic | carbamate | imidazole | BF4 | | N-SO2 | thiourea | iodine |
| Malic Acid | carbamate | imidazole | BF4 | | N-SO2 | thiourea | iodine |
| Malic Acid | carbamate | imidazole | BF4 | | N-SO2 | thiourea | iodine |
| Malonic | carbamate | imidazole | BF4 | | N-SO2 | thiourea | iodine |
| Mandelic Acid | carbamate | imidazole | BF4 | | N-SO2 | thiourea | iodine |
| Mandelic Acid | carbamate | imidazole | BF4 | | N-SO2 | thiourea | iodine |
| Methionine | carbamate | imidazole | BF4 | | N-SO2 | thiourea | iodine |
| Methionine | carbamate | imidazole | BF4 | | N-SO2 | | |
| Methionine | phosphate | | | | | | |
| Nicotinamide | ester | ether | fluorine | acetate | dithiadiazocyclopentadienyl | | |
| Nicotinamide | carbamate | imidazole | BF4 | | N-SO2 | thiourea | iodine | epoxide |
| Nicotinic Acid | carbamate | imidazole | BF4 | | N-SO2 | thiourea | iodine |
| Nicotinic Acid | ester | ether | fluorine | acetate | dithiadiazocyclopentadienyl | | |
| Orotic acid | carbamate | imidazole | BF4 | | N-SO2 | thiourea | iodine | epoxide |
| Orotic acid | carbamate | imidazole | BF4 | | N-SO2 | thiourea | iodine |
| Oxalic acid | carbamate | imidazole | BF4 | | N-SO2 | thiourea | iodine |
| Palmitic acid | carbamate | imidazole | BF4 | | N-SO2 | thiourea | iodine |
| Pamoic acid | carbamate | imidazole | BF4 | | N-SO2 | thiourea | iodine |
| Pamoic acid | imidazole | BF4 | | | | | |
| Phenylalanine | carbamate | imidazole | BF4 | | N-SO2 | thiourea | iodine | epoxide |
| Phenylalanine | carbamate | imidazole | BF4 | | N-SO2 | thiourea | iodine |
| Piperazine | carbamate | imidazole | BF4 | | N-SO2 | thiourea | iodine |
| Procaine | carbamate | imidazole | BF4 | | N-SO2 | thiourea | iodine |
| Procaine | carbamate | imidazole | BF4 | | N-SO2 | thiourea | iodine |
| Proline | carbamate | imidazole | BF4 | | N-SO2 | thiourea | iodine |
| Proline | carbamate | imidazole | BF4 | | N-SO2 | thiourea | iodine |
| p-Toluenesulfonic acid | carbamate | imidazole | BF4 | | N-SO2 | thiourea | iodine | epoxide |
| Pyridoxamine | carbamate | imidazole | BF4 | | N-SO2 | thiourea | iodine |
| Pyridoxamine | ester | ether | fluorine | acetate | dithiadiazocyclopentadienyl | | |
| Pyridoxamine | ester | ether | fluorine | acetate | dithiadiazocyclopentadienyl | | |
| Pyridoxine (4-Pyridoxic Acid) | carbamate | imidazole | BF4 | | N-SO2 | thiourea | iodine | epoxide |
| Pyridoxine (4-Pyridoxic Acid) | carbamate | imidazole | BF4 | | N-SO2 | thiourea | iodine |
| Pyroglutamic acid | carbamate | imidazole | BF4 | | N-SO2 | thiourea | iodine | epoxide | peroxide |
| Pyroglutamic acid | carbamate | imidazole | BF4 | | N-SO2 | thiourea | iodine |
| Quercetin | phosphate | cyanamide | | | | | |
| Quercetin | carbamate | imidazole | BF4 | | N-SO2 | thiourea | iodine |
| Resveratrol | carbamate | imidazole | BF4 | | N-SO2 | thiourea | iodine | epoxide | peroxide |
| Resveratrol | | | | | | | |
| Saccharin | carbamate | imidazole | BF4 | | N-SO2 | thiourea | iodine |
| Saccharin | carbamate | imidazole | BF4 | | N-SO2 | thiourea | iodine |
| Saccharin | | | | | | | |
| Salicylic Acid | carbamate | imidazole | BF4 | | N-SO2 | thiourea | iodine |
| Salicylic Acid | carbamate | imidazole | BF4 | | N-SO2 | thiourea | iodine |
| Salicylic Acid, 4-amino | carbamate | imidazole | BF4 | | N-SO2 | thiourea | iodine |
| Salicylic Acid, 4-amino | imidazole | BF4 | | | | | |

TABLE II-continued

| | | | | | |
|---|---|---|---|---|---|
| Salicylic Acid, 4-amino | carbamate | imidazole | BF4 | | N-SO2 | thiourea | iodine | |
| Sebacic acid | carbamate | imidazole | BF4 | | N-SO2 | thiourea | iodine | |
| Serine | carbamate | imidazole | BF4 | | N-SO2 | thiourea | iodine | |
| Serine | carbamate | imidazole | BF4 | | N-SO2 | thiourea | iodine | epoxide |
| Stearic acid | carbamate | imidazole | BF4 | | N-SO2 | thiourea | iodine | |
| Succinic Acid | carbamate | imidazole | BF4 | | N-SO2 | thiourea | iodine | |
| Tartaric Acid | carbamate | imidazole | BF4 | | N-SO2 | thiourea | iodine | |
| Threonine | carbamate | imidazole | BF4 | | N-SO2 | thiourea | iodine | |
| Threonine | carbamate | imidazole | BF4 | | N-SO2 | thiourea | iodine | epoxide |
| Tris | carbamate | imidazole | BF4 | | N-SO2 | thiourea | iodine | |
| Tris | carbamate | imidazole | BF4 | | N-SO2 | thiourea | iodine | epoxide |
| Tryptophan | carbamate | imidazole | BF4 | | N-SO2 | thiourea | iodine | |
| Tryptophan | carbamate | imidazole | BF4 | | N-SO2 | thiourea | iodine | |
| Tryptophan | ester | ether | fluorine | acetate | thione | dithiadiazocyclopentadienyl | thiourea | iodine | |
| Tyrosine | carbamate | imidazole | BF4 | | N-SO2 | thiourea | iodine | |
| Tyrosine | carbamate | imidazole | BF4 | | N-SO2 | thiourea | iodine | |
| Tyrosine | carbamate | imidazole | BF4 | | N-SO2 | thiourea | iodine | epoxide |
| Urea | carbamate | imidazole | BF4 | | N-SO2 | thiourea | iodine | |
| Urea | carbamate | imidazole | BF4 | | N-SO2 | thiourea | iodine | epoxide |
| Valine | carbamate | imidazole | BF4 | | N-SO2 | thiourea | iodine | |
| Valine | carbamate | imidazole | BF4 | | N-SO2 | thiourea | iodine | peroxide |
| Vitamin K5 | carbamate | imidazole | BF4 | | N-SO2 | thiourea | iodine | |
| Vitamin K5 | carbamate | imidazole | BF4 | | N-S02 | thiourea | iodine | epoxide |
| Xylitol | carbamate | imidazole | BF4 | | N-SO2 | thiourea | iodine | epoxide |

TABLE III

| Functional Group | Functional Group Structure | Interacting Group | | | | |
|---|---|---|---|---|---|---|
| pyridine | (pyridine ring structure) | *alcohol | pyridinium | *amide | nitro | *amine | *carboxilic acid |
| imidazol | (imidazole ring structure) | imidazole | chlorine | acetamide | carboxylate | thione | nitro |
| Hydroxamic acid | O=C(R)N(H)OH | hydroxamic acid | alcohol | phosphinic ester | | pyridine | amide |
| peroxide | R—O—OH | ester | peroxide | amide | ether | alkane | N-heterocycle |
| epoxide | (epoxide structure) | alkane | bromine | alcohol | ester | epoxide | amide |
| thioester | S=C(R)OR | aromatic | thioester | alkane | sulfamide | hydroxy | bromine |
| thioketone | S=C(R)R | alkane | thioketone | ketone | SULFAMIDE | AMINE | thiol |

| Functional Group | | | | | | | |
|---|---|---|---|---|---|---|---|
| pyridine | *sulfonamide | *ketone | triazole | alkane | ammonium | oxime | *chlorine | alkyne |
| imidazole | cyanamide | ketone | carboxilic acid | alcohol | alkane | thiol | amine | phosphinic acid hemihydrate |
| Hydroxamic acid | sulfonamide | carboxylate | amine | aromatic | peroxy acid | ketone | carboxilic acid | azide |
| peroxide | aromatic | alcohol | analine | thiazole | aldehyde | chlorine | carboxilic acid | alkyne |
| epoxide | alkene | hydrazone | thioether | ketone | | chlorine | nitro | |
| thioester | iodine | amine | thioketone | amide | alkene | sulfone | iodine | AZOXY |
| thioketone | sulfoxide | oxo | bromine | AROMATIC | hydrazone | thiocyanate | *bromine | aromatic |
| pyridin | thiol | n-heterocyclic ring | pyrrolidindione | iodine | sulfonate ester | | | |
| imidazole | chlorine | sulfonyl | amide | fluorine | | | | |
| Hydroxamic acid peroxide | phosphine oxide | sulfonamide | analine | | | | | |

TABLE III-continued

| epoxide thio ster thioketone pyridine imidazole Hydroxamic acid peroxide epoxide thioester thioketone pyridine imidazole Hydroxamic acid peroxide epoxide thioester thioketone | potassium hydroxamic acid dithiadiazocyclop entadienyl | ammonium epoxide cyano | fluorine n-oxide carboxamide | nitro cyano *sulfonic acid | amine iron *phosphoric acid | cyano cobalt N-oxide | amine ester | sulfate ether | fluorine acetate | thione |

| Functional Group | Functional Group Structure | Interacting Group | | | | | | |
|---|---|---|---|---|---|---|---|---|
| nitrate ester | —O—NO$_2$ | aromatic | amide | alkane | chlorine | nitrate ester | bromine | |
| Thiophosphate ester-O | (S=P with O—, O—, OH) | amine | imidazole | cyclic amide | | | | |
| Phosphate ester | (O=P with O—, O—, OH) | aromatic | alcohol | phosphate ester | aromatic N-ring | pyridine | analine | |
| Ketone | R—C(=O)—R | alcohol | ketone | thiol | amide | amine | analine | |
| Aldehyde | R—C(=O)—H | alcohol | ketone | thiol | amide | amine | analine | |
| Thiol Alcohol | R—SH R—OH | carboxylic acid alcohol | sodium ketone | aldehyde thiol | ketone amide | aromatic-N amine | cadmium analine | |

TABLE III-continued

| Functional Group | | | | | | | | | |
|---|---|---|---|---|---|---|---|---|---|
| nitrate est r Thiophosphate ester-O Phosphate ester | alcohol | ether | acetate | | | | amide | | |
| | amine | | sodium | potassium | lithium | carboxylic acid | | | alkane |
| Ketone Aldehyde Thiol Alcohol nitrate ester Thiophosphate ester-O Phosphate ester | phenol phenol alkane phenol | phosphate phosphate arsenic phosphate | sulfate sulfate chlorine sulfate | sulfone sulfone alcohol sulfone | nitrate nitrate potassium nitrate | pyridine pyridine Ru pyridine | aromatic aromatic aromatic | carboxilic acid carboxilic acid Rb carboxilic acid | metals metals Sb metals |
| Ketone Aldehyde Thiol Alcohol nitrate ester Thiophosphate ester-O Phosphate ester | aldehyde aldehyde aldehyde | ester ester ester | ether ether ether | cyano cyano cyano | | furan furan furan | bromine bromine bromine | chlorine chlorine chlorine | s-heterocyclic s-heterocyclic s-heterocyclic |
| Ketone Aldehyde Thiol Alcohol nitrate ester Thiophosphate st r-O Phosphate ester | pyridine pyridine pyridine | cyano cyano cyano | n-heterocyclic n-heterocyclic n-heterocyclic | ketone ketone ketone | phosphate ester phosphate ester phosphate ester | | fluorine fluorine fluorine | carbamate carbamate carbamate | imidazole imidazole imidazole | BF4 BF4 BF4 | alkane alkane alkane |
| Ketone Aldehyde Thiol Alcohol | aromatic aromatic aromatic | N-SO2 N-SO2 N-SO2 | thiourea thiourea thiourea | iodine iodine iodine | epoxide epoxide | | | | |

| Functional Group | Functional Group Structure | Interacting Group | | | | | | |
|---|---|---|---|---|---|---|---|---|
| Thioether | R—S—R | aromatic-N | amide | amine | | aromatic_s | Sp2 amine | sulfoxide |
| Ether | R—O—R | aromatic-N | amide | amine | | aromatic_s | Sp2 amine | sulfoxide |
| Cyanamide | N—C≡N | cyano | amine | potassium | | aromatic-N | bromine | sodium |
| Thiocyanate | —S—C≡N | aromatic-S | ester | ether | | | | |

TABLE III-continued

| Functional Group | sP2 amine | NH  | thioether | ether | metals | MoOCl4 | BF4 | bromine |
|---|---|---|---|---|---|---|---|---|
| Amine primary | chlorate | R—NH2 | alcohol | ketone | thiol | amide | amine | analine |
| Amine secondary | chlorate | R2—NH | alcohol | ketone | thiol | amide | amine | analine |
| Functional Group | | | | | | | | |
| Thioether | chlorate | chlorine | | alkyne | ester | amine | nitro | nitrate | bromine |
| Ether | chlorate | chlorine | | alkyne | ester | amine | nitro | nitrate | bromine |
| Cyanamide | imidazole | ether | | n-heterocyclic | cesium | Ag | | | |
| Thiocyanate | | | | | | | | | |
| sP2 amine | | | | | | | | | |
| Amin primary | chlorine | phosphate | | Sp2 amine | sulfate | Osmium | aromatic | carboxilic acid | metals |
| Amine secondary | phenol | phosphate | | sulfate | sulfone | nitrate | aromatic | carboxilic acid | metals |
| Thioether | phenol | ketone | | sulfate | sulfone | pyridine | hetero-cyclic-S | iodine | ester |
|  | aldehyde | | | peroxide | epoxide | Se | | | |
| Ether | aldehyde | ketone | | peroxide | epoxide | Se | hetero-cyclic-S | iodine | ester |
| Cyanamide | | | | | | | | | |
| Thiocyanate | | | | | | | | | |
| sP2 amine | | | | | | | | | |
| Amine primary | aldehyde | ester | | ether | cyano | | furan | bromine | s-heterocyclic |
| Amine secondary | aldehyde | ester | | ether | cyano | | furan | bromine | s-heterocyclic |
| Thioether | ether | carboxylic acid | | sulfate | sulfone | alkane | alcohol | phospphate | |
| Ether | ether | carboxylic acid | | sulfate | | alkane | alcohol | | |
| Cyanamide | | | | | | | | phospphate | cyanamide |
| Thiocyanate | | | | | | | | | |
| sP2 amine | | | | | | | | | |
| Amine primary | pyridine | cyano | | n-heterocyclic | ketone | phosphate ester | | fluorine | carbamate | imidazole | BF4 |
| Amine secondary | pyridine | cyano | | n-heterocyclic | ketone | phosphate ester | | fluorine | carbamate | imidazole | BF4 |
| Thioether | | | | | | | | | | | |
| Ether | | | | | | | | | | | |
| Cyanamide | | | | | | | | | | | |
| Thiocyanate | | | | | | | | | | | |
| sP2 amine | | | | | | | | | | | |
| Amine primary | aromatic | N-SO2 | | thiourea | iodine | | | | | | alkane |
| Amine secondary | aromatic | N-SO2 | | thiourea | iodine | | | | | | alkane |

| Functional Group | Functional Group Structure | Interacting Group | | | | | | |
|---|---|---|---|---|---|---|---|---|
| Amin tertiary | $R_3\text{—}N$ | alcohol | ketone | thiol | amide | amine | analine |
| Amide |  | alcohol | ketone | thiol | amide | amine | analine |

TABLE III-continued

| | | | | | | | | |
|---|---|---|---|---|---|---|---|---|
| Sulfonic acid | ![R-S(=O)2-O-] | pyridine | phenol<br>phenol<br>carboxilic acid | sulfate<br>sulfate<br>metals | ketone | aldehyde | nitrate<br>nitrate | ether | amide |
| Phosphinic acid | ![R-P(=O)(R)-O-] | alkane | phenol<br>phenol | amine<br>aromatic<br>aromatic | potassium | lithium | | n-heterocyclic | ester | amide |
| Phosphonic acid | ![R-P(=O)(OH)-O-] | alkane | phenol<br>aldehyde<br>aldehyde | sulfate<br>ether<br>ether | potassium | lithium | | n-heterocyclic | oxime | amide |
| Carboxylic acid | ![R-C(=O)-OH] | alcohol | | | ketone | thiol | | amide | | |
| Functional Group | | | | | | | | | | |
| Amine tertiary<br>Amide<br>Sulfonic acid<br>Phosphinic acid<br>Phosphonic acid | | | phosphate<br>phosphate<br>amine<br>aromatic<br>aromatic | sulfate<br>sulfate<br>metals<br>amine<br>amine | sulfone<br>sulfone<br>thioether<br>alcohol<br>alcohol | aldehyde | nitrate<br>nitrate | pyridine<br>pyridine<br>sulfate<br>metals<br>metals | aromatic<br>aromatic<br>alcohol<br>carboxylic acid | ester | carboxilic acid<br>carboxilic acid<br>Sp2 amine | metals<br>metals<br>analine |
| Carboxilic acid<br>Amine tertiary<br>Amide<br>Sulfonic acid<br>Phosphinic acid | | | phosphate<br>ester<br>ester | sulfate<br>ether<br>ether | sulfone<br>cyano<br>cyano | | nitrate | pyridine<br>furan<br>furan | aromatic<br>bromine<br>bromine | oxime | carboxylic acid<br>chlorine<br>chlorine | metals<br>s-heterocyclic<br>s-heterocyclic |
| Phosphonic acid | | ether | phosphonic acid | aromatic-N | ketone | aldehyde | | imidazole | | | | |
| Carboxilic acid<br>Amine tertiary | | aldehyde<br>pyridine | ester<br>cyano | ether<br>n-heterocyclic | cyano<br>ketone | | phosphate ester | furan | bromine<br>fluorine | amine | chlorine<br>carbamate | s-heterocyclic<br>imidazole BF4 alkane |
| Amide | | pyridine | cyano | n-heterocyclic | ketone | | phosphate ester | | fluorine | | carbamate | imidazole BF4 alkane |
| Sulfonic acid<br>Phosphinic acid<br>Carboxilic acid | | pyridine | cyano | n-heterocyclic | ketone | | phosphate ester | | fluorine | | carbamate | imidazole BF4 alkane |
| Amine tertiary | | aromatic | N-SO2 | thiourea | iodine | | | | | | | analine |

TABLE III-continued

| Functional Group | Structure | Interacting Group | | | | | | | |
|---|---|---|---|---|---|---|---|---|---|
| Amide | aromatic | | thiourea | iodine | epoxide | peroxide | | | |
| Sulfonic acid | | | | | | | | | |
| Phosphinic acid | | | | | | | | | |
| Phosphoric acid | | | | | | | | | |
| Carboxylic acid | aromatic | N-SO2 | thiourea | iodine | | | | | |

| Functional Group | Structure | Interacting Group | | | | | | | |
|---|---|---|---|---|---|---|---|---|---|
| Sulfate ester |  | pyridine | ketone | aldehyde | ether | | ester | amide |
| Oxime | C=N—OH | alcohol | alkane | amine | amide | ether | ester |
| Nitrile | —C≡N | metal | ketone | phenol | alcohol | | cyano |
| Diazo | RH2C—N=N—CH2R | Oxime | | | | | |
| Nitro | NO2 | pyridine | ketone | aldehyde | ether | ester | amide |
| S-heterocyclic ring | 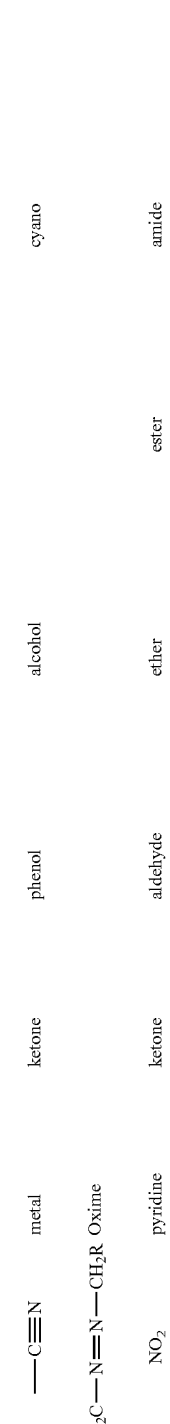 | alcohol | thioketone | thioether | s-heterocyclic | ketone | aromatic |
| Thiophene |  | chlorine | fluorine | amide | ketone | NO | SO |

| Functional Group | | | | | | | |
|---|---|---|---|---|---|---|---|
| Sulfate ester | carboxilic acid | amine | metals | thioether | sulfate | alcohol | thioketone | n-oxide |
| Oxime | pyridine | n-aromatic | chlorate | chlorine | Sp2-N | diazo | chlorine | aromatic |
| Nitrile | amine | analine | bromine | amide | alkane | carboxylic acid | | |
| Diazo | | | | | | | | |
| Nitro | carboxilic acid | amine | metals | thioether | sulfate | alcohol | | |
| S-heterocyclic ring | alkene | amine | chlorine | BF4 | sulfate | ester | NO | cyano n-heterocyclic |
| Thiophene | CO | | | | | | | |
| Sulfate ester | | | | | | | | |
| Oxime | ketone | aldehyde | carboxylic acid | bromine | aromatic | pyridine | BF4 | ether |
| Nitrile | potassium | aldehyde | thioether | pyridine | n-aromatic | bromine | ether | amide |
| Diazo | | | | | | | | |
| Nitro | | | | | | | | s-aromatic | thiophene |

TABLE III-continued

| S-heterocyclic ring | iodine | carboxylic acid | sodium | cyano | chloride | furan | | | |
|---|---|---|---|---|---|---|---|---|---|
| Thiophene | | | | | | | | | |
| Sulfate ester | | | | | | | | | |
| Oxime | | | | | | | | | |
| Nitrile | | | | | | | | | |
| Diazo | | | | | | | | | |
| Nitro | | | | | | | | | |
| S-heterocyclic ring | | | | | | | | | |
| Thiophene | | | | | | | | | |
| Sulfate ester | | | | | | | | | |
| Oxime | | | | | | | | | |
| Nitrile | | | | | | | | | |
| Diazo | | | | | | | | | |
| Nitro | | | | | | | | | |
| S-heterocyclic ring | | | | | | | | | |
| Thiophene | | | | | | | | | |

| Functional Group | Functional Group Structure | Interacting Group | | | | | | | |
|---|---|---|---|---|---|---|---|---|---|
| N-heterocyclic ring |  | alcohol | thioketone | thioether | s-heterocyclic | ketone | aromatic | | |
| O-heterocyclic ring |  | alcohol | thioketone | thioether | s-heterocyclic | ketone | aromatic | | |
| Pyrrole |  | chlorine | fluorine | amide | ketone | NO | SO | | |
| Furan |  | s-heterocyclic | | | | | | | |

| Functional Group | | | | | | | | | |
|---|---|---|---|---|---|---|---|---|---|
| N-heterocyclic ring | alkene | amine | chlorine | BF4 | sulfate | ester | NO | ether | amide |
| O-heterocyclic ring | alkene | amine | chlorine | BF4 | sulfate | ester | NO | ether | amide |

TABLE III-continued

| Pyrrole | CO | imidazole | pyridine | n-aromatic | aldehyde | carboxylic acid | sulfate | chlorine | bromine |
|---|---|---|---|---|---|---|---|---|---|
| Furan | | | | | | | | | |
| N-heterocyclic ring | iodine | carboxylic acid | sodium | cyano | chloride | aldehyde | | | |
| O-heterocyclic ring | iodine | carboxylic acid | sodium | cyano | chloride | aldehyde | | | |
| Pyrrole | oxime | alcohol | phenol | ester | ether | | | | |
| Furan | | | | | | | | | |
| N-heterocyclic ring | | | | | | | | | |
| O-heterocyclic ring | | | | | | | | | |
| Pyrrole | | | | | | | | | |
| Furan | | | | | | | | | |
| N-heterocyclic ring | | | | | | | | | |
| O-heterocyclic ring | | | | | | | | | |
| Pyrrol | | | | | | | | | |
| Furan | | | | | | | | | |

TABLE IV

| API Generic Name | API Chemical Name | CAS No. | Patent Reference | Example of Therapeutic Use | Example of Indication |
|---|---|---|---|---|---|
| (−)-amlodipine | 3,5-Pyridinedicarboxylic acid, 2-((2-aminoethoxy)methyl)-4-(2-chlorophenyl)-1,4-dihydro-6-methyl-, 3-ethyl-5-methyl ester, (S)-[CAS] | 103129-82-4 | WO 9310779 | Antihypertensive, other | Hypertension, general |
| (−)-halofenate | (−)-Benzeneacetic acid, 4-chloro-Alpha-[3-(trifluoromethyl)-phenoxy]-, 2-(acetylamino)ethyl ester | | U.S. 6,262,118 | Antidiabetic | Diabetes, Type II |
| (R)-salbutamol | 1,3-Benzenedimethanol, Alpha1-(((1,1-dimethylethyl)amino)methyl)-4-hydroxy-[CAS] | | | Formulation, modified-release, <=24 hr | Asthma |
| (R)-salbutamol | 1,3-Benzenedimethanol, Alpha1-(((1,1-dimethylethyl)amino)methyl)-4-hydroxy-[CAS] | 34391-04-3 | U.S. 5,547,994 | Antiasthma | Asthma |
| (R,R)-formoterol | Formamide, N-(2-hydroxy-5-(1-hydroxy-2-((2-(4-methoxyphenyl)-1-methylethyl)amino)ethyl)phenyl)-(R-(R*,R*))-[CAS] | 67346-49-0 | U.S. 5,795,564 | Antiasthma | Asthma |
| (S)-doxazosin | (S)-1-(4-amino-6,7-dimethoxy-2-quinazolinyl)-4-(1,4-benzodioxan-2-yl carbonyl)piperazine | 70918-18-2 | WO 9409785 | Prostate disorders | Benign prostatic hyperplasia |
| (S)-fluoxetine | Benzenepropanamide, N-methyl-Gamma-(4-(trifluoromethyl)phenoxy)-(S) | | | Antimigraine | Migraine |
| (S)-oxybutynin | Benzeneacetic acid, Alpha-cyclohexyl-Alpha-hydroxy-, 4-(diethylamino)-2-butynyl ester, (S)-[CAS] | 119618-22-3 | | Urological | Incontinence |
| 1,2-Naphthoquinone | | 524-42-5 | | | |
| 17α-Hydroxyprogesterone | | 68-96-2 | | | |
| 17-Methyltestosterone | | 58-18-4 | | | |
| 195mPt-cisplatin | Platinum-195m, diamminedichloro, (SP-4-2)- | | U.S. 6,074,626 | Anticancer, alkylating | Cancer, liver |
| 1α-Hydroxycholecalciferol | | 41294-56-8 | | | |
| 1-Naphthyl Salicylate | | 550-97-0 | | | |
| 1-Naphthylamine-4-sulfonic Acid | | 84-86-6 | | | |
| 1-Theobromineacetic Acid | | 5614-56-2 | | | |
| 2,4,6-Tribromo-m-cresol | | 4619-74-3 | | | |
| 2,6-Diamino-2′-butyloxy-3,5′-azopyridine | | 617-19-6 | | | |
| 21-Acetoxypregnenolone | | 566-78-9 | | | |
| 2-Amino-4-picoline | | 695-34-1 | | | |
| 2-Aminothiazole | | 96-50-4 | | | |
| 2-ethoxybenzoic acid | 2-Ethoxybenzoic acid | | DE 5134001 | Analgesic, NSAID | Pain, general |
| 2-Naphthol | | 135-19-3 | | | |
| 2-Naphthyl Benzoate | | 93-44-7 | | | |
| 2-Naphthyl Lactate | | 93-43-6 | | | |
| 2-Naphthyl Salicylate | | 613-78-5 | | | |

TABLE IV-continued

| API Generic Name | API Chemical Name | CAS No. | Patent Reference | Example of Therapeutic Use | Example of Indication |
|---|---|---|---|---|---|
| 2-p-Sulfanilylaminoethanol | | 80-02-4 | | | |
| 2-Thiouracil | | 141-90-2 | | | |
| 3,3",5,5"-Tetra-bromophenolphthalein | | 76-62-0 | | | |
| 3-Amino-4-hydroxybutyric Acid | | 589-44-6 | | | |
| 3-Bromo-d-camphor | | 76-29-9 | | | |
| 3-Hydroxycamphor | | 10373-81-6 | | | |
| 3-O-Lauroylpyridoxol Diacetate | | 1562-13-6 | | | |
| 3-Pentadecylcatechol | | 492-89-7 | | | |
| 3-Quinuclidinol | | 1619-34-7 | | | |
| 4,4-Oxydi-2-butanol | | 821-33-0 | | | |
| 4,4-Sulfinyldianiline | | 119-59-5 | | | |
| 4-Amino-3-hydroxybutyric Acid | | 352-21-6 | | | |
| 4-Amino-3-phenylbutyric Acid | | 1078-21-3 | | | |
| 4-aminosalicylic acid | Benzoic acid, 4-amino-2-hydroxy-[CAS] | 65-49-6 | | GI inflammatory/bowel disorders | Inflammatory bowel disease |
| 4-Chloro-m-cresol | | 59-50-7 | | | |
| 4-Hexylresorcinol | | 136-77-6 | | | |
| 4-Salicyloylmorpholine | | 3202-84-4 | | | |
| 5-Nitro-2'-propoxyacetanilide | | 553-20-8 | | | |
| 5-aminolevulinic acid, | Pentanoic acid, 5-amino-4-oxo- [CAS] | 106-60-5 | | Dermatological | Keratosis |
| 5-azacitidine | 1,3,5-Triaxin-2(1H)-one, 4-amino-1-β-D-ribofuransyl- [CAS] | 320-67-2 | | Anticancer, antimetabolite | Myelodysplastic syndrome |
| 5-Bromosalicyl-hydroxamic Acid | | 5798-94-7 | | | |
| 5F-DF-203 | | | | Anticancer, other | Cancer, breast |
| 5-FU | 2-(4-Amino-3-methylphenyl)-6-hydroxybenzothiazole 2,4(1H,3H)-Pyrimidinedione, 5-fluoro [CAS] | 51-21-8 | U.S. 6,037,360 | Formulation, parenteral, targeted | Cancer, general |
| 5-HT3 antagonists | | | | Male sexual dysfunction | Premature ejaculation |
| 6-Azauridine | | 54-25-1 | | | |
| 6-Mercaptopurine | | 50-44-2 | | | |
| 8-Hydroxyquinoline | | 148-24-3 | | | |
| 9-Aminocamptothecin | | 91421-43-1 | | | |
| A-151892 | N[2-(2,2,2-Trifluoro-1-hydroxy-1-trifluoromethyl-ethyl)-naphthalen-1-yl] amide | | | Urological | Overactive bladder |

TABLE IV-continued

| API Generic Name | API Chemical Name | CAS No. | Patent Reference | | Example of Therapeutic Use | Example of Indication |
|---|---|---|---|---|---|---|
| α₁-Antitrypsin A-5021 | 6H-Purin-6-one, 2-amino-9-(((1S,2R)-1,2-bis(hydroxymethyl)cyclopropyl)methyl)1,9-dihydro-[CAS] | 9041-92-3 145512-85-2 | | | Antiviral, other | Infection, varicella zoster virus |
| abacavir | 2-Cyclopentene-1-methanol, 4-(2-amino-6-(cyclopropylamino)-9H-purin-9-yl)-, (1S-cis)-[CAS] | 136470-78-5 188062-50-2 | EP | 434450 | Antiviral, anti-HIV | Infection, HIV/AIDS |
| abaperidone | 7-[3-[4-(6-Fluoro-1,2-benzisoxazol-3-yl)piperidin-1-yl]propoxy]-3-(hydroxymethyl)chromen-4-one | 183849-43-6 | WO | 9632389 | Neuroleptic | Schizophrenia |
| abarelix | D-Alaninamide, N-acetyl-3-(2-naphthalenyl)-D-alanyl-4-chloro-D-phenylalanyl-3-(3-pyridinyl)-D-alanyl-L-seryl-N-methyl-L-tyrosyl-D-asparaginyl-L-leucyl-N6-(1-methylethyl)-L-lysyl-L-prolyl-[CAS] | 183552-38-7 | U.S. | 5,843,902 | Anticancer, hormonal | Cancer, prostate |
| Abciximab Abecarnil abetimus | | 143653-53-6 111841-85-1 169147-32-4 | U.S. | 5,552,391 | Immunosuppressant | *Lupus erythematosus*, systemic |
| abiraterone | Androsta-5,16-dien-3-ol, 17-(3-pyridinyl)-, acetate (ester), (3β)-[CAS] | 154229-18-2 | GB | 2265624 | Anticancer, hormonal | Cancer, prostate |
| α-Bisabolol ABLC | Amphotericin B [CAS] | 515-69-5 1397-89-3 30652-87-0 | | | Formulation, conjugate, carbohydrate | Infection, Candida, general |
| ABT-751 | Benzenesulfonamide, N-[2-[(4-hydroxyphenyl)amino]-3-pyridinyl]-4-methoxy-[CAS] | 141430-65-1 | EP | 472053 | Anticancer, other | Cancer, general |
| AC-5216 | N-benzyl-N-ethyl-2-(7,8-dihydro-7-methyl-8-oxo-2-phenyl-9H-purin-9-yl)acetamide | | | | Anxiolytic | Anxiety, general |
| Acadesine acamprosate | 1-Propanesulfonic acid, 3-(acetylamino)-[CAS] | 2627-69-2 77337-76-9 | GB | 2051789 | Dependence treatment | Addiction, alcohol |
| Acarprosate Acarbose | | 77337-73-6 56180-94-0 | | | | |
| acebrophylline | 7H-Purine-7-acetic acid, 1,2,3,6-tetrahydro-1,3-dimethyl-2,6-dioxo-,compd. with trans-4-[[(2-amino-3,5-dibromophenyl)methyl]amino]cyclohexanol (1:1)[CAS] | 96989-76-3 | DE | 3425007 | Antiasthma | Asthma |
| acebutolol | Butanamide, N-[3-acetyl-4-[2-hydroxy-3-[(1-methylethyl)amino]propoxy]phenyl]-, (+/−)-[CAS] | 34381-68-5 37517-30-9 | U.S. | 3,726,919 | Antihypertensive, adrenergic | |
| Acecainide Acecarbromal | | 32795-44-1 77-66-7 | | | | |

TABLE IV-continued

| API Generic Name | API Chemical Name | CAS No. | Patent Reference | Example of Therapeutic Use | Example of Indication |
|---|---|---|---|---|---|
| aceclofenac | Benzeneacetic acid, 2-[(2,6-dichlorophenyl)amino]-, carboxymethyl ester[CAS] | 89796-99-6 | EP 119932 | Anti-inflammatory | Pain, musculoskeletal |
| Acedapsone | | 77-46-3 | | | |
| Acediasulfone | | 80-03-5 | | | |
| Acefylline | | 652-37-9 | | | |
| Aceglutamide | | 2490-97-3 | | | |
| aceglutamide | Aluminum, pentakis(N2-acetyl-L-glutaminoato)tetrahydroxytri-[CAS] | 12607-92-0 | DE 2127176 | Antiulcer | Ulcer, GI, general |
| acemetacin | 1H-Indole-3-acetic acid, 1-(4-chlorobenzoyl)-5-methoxy-2-methyl-, carboxymethyl ester [CAS] | 53164-05-9 | U.S. 3,910,952 | Anti-inflammatory | |
| Acenocoumarol | | 152-72-7 | | | |
| Acetal | | 105-57-7 | | | |
| Acetamidoeugenol | | 305-13-5 | | | |
| Acetaminophen | | 103-90-2 | | | |
| Acetaminosalol | | 118-57-0 | | | |
| Acetanilide | | 103-84-4 | | | |
| Acetarsone | | 97-44-9 | | | |
| Acetazolamide | | 59-66-5 | | | |
| Acetiamine | | 299-89-8 | | | |
| Acetohexamide | | 968-81-0 | | | |
| Acetohydroxamic Acid | | 546-88-3 | | | |
| Acetophenazine | | 2751-68-0 | | | |
| Acetophenone | | 98-86-2 | | | |
| Acetosulfone | | 128-12-1 | | | |
| acetoxolone | Olean-12-en-30-oic acid, 3β-hydroxy-11-oxo-acetate, aluminium salt [CAS] | 29728-34-5 6277-14-1 | U.S. 3,764,618 | Antiulcer | |
| Acetrizoat | | 129-63-5 | | | |
| Acetyl Sulfamethoxypyrazine | | 3590-05-4 | | | |
| Acetylcarnitine | | 14992-62-2 | | | |
| Acetylcholine | | 66-23-9 | | | |
| Acetylcholine | | 60-31-1 | | | |
| Acetylcysteine | | 616-91-1 | | | |
| Acetylleucine Monoethanolamine | | 149-90-6 | | | |
| Acetylpheneturide | | 13402-08-9 | | | |
| acetylsalicylic acid | Benzoic acid, 2-(acetyloxy)-[CAS] | 50-78-2 53075-6 | | Formulation, optimized, microencapsulate | Pain, general |
| α-Chloralose | | 15879-93-3 | | | |
| aciclovir | 6H-Purin-6-one, 2-amino-1,9-dihydro-9-[(2-hydroxyethoxy)methyl]-[CAS] | 59277-89-3 | | Formulation, dermal,topical | Infection, herpes simplex virus |
| Acifran | | 72420-38-3 | | | |
| acipimox | Pyrazinecarboxylic acid, 5-methyl-, 4-oxide [CAS] | 51037-30-0 | GB 1361967 | Hypolipidaemic/Antiatherosclerosis | Hyper-lipidaemia, general |
| acitazanolast | Acetic acid, oxo[[3-(1H-tetrazol-5-yl)phenyl]amino]-[CAS] | 114607-46-4 | EP 256507 | Ophthalmological | Conjunctivitis |

TABLE IV-continued

| API Generic Name | API Chemical Name | CAS No. | Patent Reference | Example of Therapeutic Use | Example of Indication |
|---|---|---|---|---|---|
| acitretin | 2,4,6,8-Nonatetraenoic acid, 9-(4-methoxy-2,3,6-trimethylphenyl)-3,7-dimethyl-, (all-E) [CAS] | 55079-83-9 | SB 1468401 | Antipsoriasis | Psoriasis |
| aclarubicin | | 57576-44-0 | U.S. 3,988,315 | Anticancer, antibiotic | |
| Aclatonium Napadisilate | | 75443-99-1 | | | |
| Aconitine | | 55077-30-0 | | | |
| Acranil ® | | 302-27-2 | | | |
| Acriflavine | | 1684-42-0 | | | |
| Acrisorcin | | 8048-52-0 | | | |
| | | 7527-91-5 | | | |
| acrivastine | 2-Propenoic acid, 3-[6-[1-(4-methylphenyl)-3-(1-pyrrolidinyl)-1-propenyl]-2-pyridinyl]-, (E,E)-[CAS] | 87848-99-5 | EP 85959 | Antipruritic/inflamm, allergic | Rhinitis, allergic, general |
| acrivastine + pseudoephedrine | Benzenemethanol, Alpha-[1-(methyl)aminoethyl]-, hydrochloride, [S-(R*,R*)]-, mixt.with 2-Propenoic acid, 3-[6-[1-(4-methylphenyl)-3-(1-pyrrolidinyl)-1-propenyl]-2-pyridinyl]-, (E,E)-3,3-dimethyl-1-propylamide HCl | | | Antiallergic, non-asthma | Rhinitis, allergic, seasonal |
| actagardine derivative | monocarboxamide actagardine | | | Peptide antibiotic | Infection, general |
| Actarit | | 18699-02-0 | | | |
| ACTH | | 900-60-2 | | | |
| Acyclovir | | 59277-89-3 | | | |
| adapalene | 2-Naphthalenecarboxylic acid, 6-(4-methoxy-3-tricyclo[3.3.1.13,7]dec-1-yl)phenyl)-[CAS] | 106685-40-9 | EP 199636 | Antiacne | Acne |
| ADCON-L | GL 402 [CAS] | 137802-74-5 | | Formulation, other | Fibrosis, epidural |
| Adefovir | | 106941-25-7 | | Antiviral, other | Infection, hepatitis-B virus |
| adefovir dipivoxil | Propanoic acid, 2,2-dimethyl-, (((2-(-6-amino-9H-purin-9-yl)ethoxy)methyl)phosphinylidene)bis(oxymethylene)ester-[CAS] | 142340-99-6 | EP 205826 | | |
| Adenoscan | 6-Amino-9-β-D-ribofuranosyl-9H-purine [CAS] | 58-61-7 | | Imaging agent | Diagnosis, coronary |
| Adenosine Triphosphate | | 56-65-5 | | | |
| ADEPT | | 156079-88-8 | | Immunoconjugate, other | Cancer, colorectal |
| Adinazolam | | 37115-32-5 | | | |
| Adiphenine | | 64-95-9 | | | |
| ADL-10-0101 | | 63547-13-7 | WO 9732857 | Analgesic, other | Pain, general |
| Adrafinil | | 99-45-6 | | | |
| Adrenalone | | 54-06-8 | | | |
| Adrenochrome | | | | | |
| adrogolide | Benzo(f)thieno(2,3-c)quinoline-9,10-diol, 4,5,5a,6,7,11b-hexahydro-2-propyl-, diacetate (ester), hydrochloride (5aR-trans)-[CAS] | 166591-11-3 171752-56-0 | U.S. 5,597,832 | Dependence treatment | Addiction, cocaine |
| AEOL-10150 | | | U.S. 6,103,714 | Neuroprotective | Unspecified |

TABLE IV-continued

| API Generic Name | API Chemical Name | CAS No. | Patent Reference | Example of Therapeutic Use | Example of Indication |
|---|---|---|---|---|---|
| AET | | 56-10-0 | | | |
| α-Ethylbenzyl Alcohol | | 93-54-9 | | | |
| AF-2259 | Benzeneacetic acid, Alpha-methyl-4-(2-methylpropyl)-, 2-methoxyphenyl ester [CAS] | 66332-77-2 | DE 2726435 | Anti-inflammatory | Inflammation, general |
| Afloqualone | | 56287-74-2 | | | |
| AG-041R | 1H-Indole-3-acetamide, 1-(2,2-diethoxyethyl)-2,3-dihydro-N-(4-methylphenyl)-3-(((4-methylphenyl)amino)carbonyl)amino-2-oxo-, (3R)-[CAS] | 199800-49-2 | WO 9419322 | Alimentary/Metaboloc, other | Unspecified |
| AG-2037 | N-(5-[2-(2-amino-4(3H)-oxo-5,6,7,8-tetrahydropyrido[2,3-d]pyrimidin-6-yl)ethyl]-4-methylthieno-2-yl)glutamic acid | | | Anticancer, antimetabolite | Cancer, general |
| α-Glucose-1-phosphate | | 59-56-3 | | | |
| AGN-194310 | Benzoic acid, 4-((4-(4-ethylphenyl)-2,2-dimethyl-2H-1-benzothiopyran-6-yl)ethynyl)-[CAS] | 229961-45-9 | WO 9709297 | Dermatological | Psoriasis |
| agomelatine | Acetamide, N-(2-(7-methoxy-1-naphthalenyl)ethyl)-[CAS] | 138112-76-2 | EP 447285 | Antidepressant | Sleep disorder, general |
| Ahistan | | 518-61-6 | | | |
| AHL-157 | 9H-Purine-9-propanamide, 1,6-dihydro-6-oxo-N-(3-(2-oxo-1-pyrrolidinyl)propyl)-[CAS] | | U.S. 5,411,972 | Hypolipaemic/Antiatherosclerosis | Atherosclerosis |
| AIT-034 | N-[2-(5-Hydroxy-1H-indol-3-yl)ethyl]-3-(6-oxo-6,9-dihydro-1H-purin-9-yl)propionamide | 138117-48-3 | U.S. 5,447,939 | Cognition enhancer | Dementia, senile, general |
| AIT-202 | Acetic acid, ((3-((2R)-2-(((2R)-2-(3-chlorophenyl)-2-hydroxyethyl)aminopropyl)-1H-indol-7-yl)oxy)-[CAS] | 244081-42-3 | WO 9957120 | Antidepressant | Unspecified |
| AJ-9677 | | | | Antidiabetic | Diabetes, Type II |
| AJG-049 | | | WO 9733885 | Gastroprokinetic | Motility dysfunction, GI, general |
| Ajmaline | | 12/07/4360 | | | |
| Alacepril | | 74258-86-9 | | | |
| albaconazole | 4(3H)-Quinazolinone, 7-chloro-3-[(1R,2R)-2-(2,4-difluorophenyl)-2-hydroxy-1-methyl-3-(1H01,2,4-triazol-1-yl)propyl]-[CAS] | 187949-02-6 | WO 9705131 | Antifungal | Infection, Candida, general |
| albendazole | Carbamic acid, [5-(propylthio)-1H-benzimidazol-2-yl]-, methyl ester [CAS] | 54029-12-8 | GB 1454326 | Anthelmintic | Infection, helminth, general |
| Albuterol | | 54965-21-8 | | | |
| Albutoin | | 18559-94-9 | | | |
| | | 830-89-7 | | | |
| alclofenac | Benzeneacetic acid, 3-chloro-4-(2-propenyloxy)-[CAS] | 22131-79-9 | GB 1174535 | Anti-inflammatory | |

TABLE IV-continued

| API Generic Name | API Chemical Name | CAS No. | Patent Reference | Example of Therapeutic Use | Example of Indication |
|---|---|---|---|---|---|
| alclometasone | Pregna-1,4-diene-3,20-dione, 7-chloro-11-hydroxy-16-methyl-17,21-bis(1-oxopropoxy)-, (7Alpha, 11β, 16Alpha)-[CAS] | 66734-13-2 67452-97-5 | U.S. 4,124,707 | Antipruritic/ inflamm, allergic | Inflammation, dermal |
| Alcuronium | | 23214-96-2 | | | |
| Aldioxa | | 5579-81-7 | | | |
| Aldol | | 107-89-1 | | | |
| Aldosterone | | 52-39-1 | | | |
| alendronate | Phosphonic acid, (4-amino-1-hydroxybutylidene)bis-[CAS] | 121268-17-5 129318-43-0 66376-36-1 | GB 2118042 | Osteoporosis treatment | Osteoporosis |
| Alendronic Acid | | | | | |
| Alexidine | | 22573-93-9 | | | |
| alfacalcidol | 9,10-Secocholesta-5,7,10(19)-triene-1,3-diol, (1Alpha,3β,5Z,7E)-[CAS] | 41294-56-8 | | Osteoporosis treatment | Osteodystrophy |
| Alfadolone | | 23930-37-2 | | | |
| Alfaxalone | | 23930-19-0 | | | |
| Alfentanil | | 71195-58-9 | | | |
| alfimeprase | | 259074-76-5 | | Fibrinolytic | Peripheral vascular disease |
| alfuzosin | 2-Furancarboxamide, N-[3-[(4-amino-6,7-dimethoxy-2-quinazolinyl)methylamino]-tetrahydro-[CAS] | 81403-68-1 81403-80-7 | GB 2013679 | Prostate disorders | Benign prostatic hyperplasia |
| alfuzosin | 2-Furancarboxamide, N-[3-[(4-amino-6,7-dimethoxy-2-quinazolinyl)methylamino]-propyl]tetrahydro-[CAS] | 81403-68-1 81403-80-7 | | Formulation, modified-release, other | Benign prostatic hyperplasia |
| Algestone | | 595-77-7 | | | |
| Algestone Acetophenide | | 24356-94-3 | | | |
| Algin | | 9005-38-3 | | | |
| Alglucerase | | 143003-46-7 | | | |
| Alibendol | | 26750-81-2 | | | |
| aliskiren | (2S,4S,5S,7S)-5-Amino-N-(2-carbamoyl-2-methylpropyl)-4-hydroxy-2-isopropyl-7-[4-methoxy-3-(3-methoxypropoxy)benzyl]-8-methylnonanamide | 173334-57-1 | | Antihypertensive, renin system | Hypertension, general |
| alitertinoin | 9-cis retinoic acid | 03/08/5300 | | Antipruritic/ inflamm, allergic | Eczema, general |
| alizapride | 1H-Benzotriazole-5-carboxamide, 6-methoxy-N-[[1-(2-propenyl)-2-pyrrolidinyl]methyl]-[CAS] | 59338-93-1 | GB 1475234 | Antiemetic | Nausea and vomiting, general |
| Alkannin | | 517-88-4 | | | |
| Alkofanone | | 7527-94-8 | | | |
| Allantoin | | 97-59-6 | | | |
| Allobarbital | | 52-43-7 | | | |
| Allopurinol | | 315-30-0 | | | |
| Allyl Isothiocyanate | | 57-06-7 | | | |
| Allylestrenol | | 432-60-0 | | | |

TABLE IV-continued

| API Generic Name | API Chemical Name | CAS No. | Patent Reference | | Example of Therapeutic Use | Example of Indication |
|---|---|---|---|---|---|---|
| almagate | Magnesium, [carbonato(2-)]heptahydroxy-(aluminum)tri-, dihydrate [CAS] | 66827-12-1 72526-11-5 | U.S. | 4,447,417 | Antacid/ Antiflatulent | |
| alminoprofen | Benzeneacetic acid, Alpha-methyl-4[(2-methyl-2-propenyl)amino]-[CAS] | 39718-89-3 | U.S. | 3,957,850 | Analgesic, NSAID | |
| almitrine | 1,3,5-Triazine-2,4-diamine, 6-[4-[bis(4-fluorophenyl)methyl]-1-piperazinyl]-N,N′-di-2-propenyl-, dimethanesulfonate [CAS] | 27469-53-0 29608-49-9 | GB | 1256513 | Respiratory | Bronchitis, chronic |
| almotriptan | Pyrrolidine, 1-(((3-(2-(dimethylamino)ethyl)-1H-indol-5-yl)methyl)sulfonyl)-[CAS] | 154323-57-6 | WO | 9402460 | Antimigraine | Migraine |
| Aloe-Emodin | | 481-72-1 | | | | |
| Aloin | | 5133-19-7 | | | | |
| alosetron | 2,3,4,5-Tetrahydro-5-methyl-2-[(5-methyl-1H-imidazol-4-yl)methyl]-1H-pyrido[4,3-b]indol-1-one [CAS] | 122852-42-0 122852-69-1 132414-02-9 | EP | 306323 | GI inflammatory/ bowel disorders | Irritable bowel syndrome |
| alovudine | Thymidine, 3′-deoxy-3′-fluoro-[CAS] | 25526-93-6 | EP | 470355 | Antiviral, anti-HIV | Infection, HIV/AIDS |
| Aloxiprin | | 9014-67-9 | | | | |
| Alpha-1 protease inhibitor | | | U.S. | 5,780,014 | Formulation, inhalable, topical | Emphysema, alpha-1 antitrypsin deficiency |
| Alpha-dihydroergocryptine | Ergocryptine, 9,10-dihydro-methanesulfonate (salt)-[CAS] | 29261-93-6 | | | Formulation, other | Parkinson's disease |
| Alphaprodine | | 77-20-3 | | | | |
| Alpidem | | 82626-01-5 | | | | |
| Alpiropride | | 81982-32-3 | | | | |
| alprazolam | 4H-[1,2,4]Triazolo[4,3-a][1,4]-benzodiazepine, 8-chloro-1-methyl-6-phenyl-[CAS] | 28981-97-7 | U.S. | 3,987,052 | Anxiolytic | Anxiety, general |
| Alprenolol | | 13655-52-2 | | | | |
| alsactide | Alpha-1-17-Carticotropin, 1-β-alanine-17-[N-(4-aminobutyl)-L-lysinamide]-[CAS] | 34765-96-3 | U.S. | 3,749,704 | ACTH | Arthritis, rheumatoid |
| ALT-711 | Thiazolium, 4,5-dimethyl-3-(2-oxo-2-phenylethyl)-, bromide [CAS] | 181069-80-7 | WO | 9622095 | Symptomatic antidiabetic | Hypertension, general |
| Althiazid | | 5588-16-9 | | | | |
| altinicline | Pyridine, 3-ethynyl-5-((2S)-1-methyl-2-pyrrolidinyl)-[CAS] | 179120-92-4 | U.S. | 5,594,011 | Antiparkinsonian | Parkinson's disease |
| altretamine | 1,3,5-Triazine-2,4,6-triamine, N,N,N′,N′,N″,N″-hexamethyl-[CAS] | 645-05-6 | U.S. | 3,424,752 | Anticancer, alkylating | Cancer, ovarian |
| aluminium chloride hexahydrate | Aluminium chloride, hexahydrate | 7446-70-0 7784-13-6 569-58-4 8006-13-1 | | | Dermatological | Hyperhidrosis |
| Aluminon | | | | | | |
| Aluminum Acetate Solution | | | | | | |
| Aluminum Chlorate | | 15477-33-5 | | | | |
| Aluminum Hydroxychloride | | 1327-41-9 | | | | |
| Aluminum Potassium Sulfate | | 10043-67-1 | | | | |

TABLE IV-continued

| API Generic Name | API Chemical Name | CAS No. | Patent Reference | Example of Therapeutic Use | Example of Indication |
|---|---|---|---|---|---|
| Aluminum Sodium Sulfate | | 10102-71-3 | | | |
| alusulf | Aluminum hydroxide sulfate (Al7(OH)17(SO4)2), dodecahydrate [CAS] | 61115-28-4 | DE 2510663 | Urological | Hyperphosphataemia |
| Alverine | | 150-59-4 | | | |
| alvimopan | Glycine, N-[(2S)-2-[[(3R,4R)-4-(3-hydroxyphenyl)-3,4-dimethyl-1-piperidinyl]methyl]-1-oxo-3-phenylpropyl]- [CAS] | 156053-89-3 | EP 657428 | GI inflammatory/bowel disorders | Ileus |
| alvocidib | 4H-1-Benzopyran-4-one, 2-(2-chlorophenyl)-5,7-dihydroxy-8-(3-hydroxy-1-methyl-4-piperidinyl)-, cis-(−)-[CAS] | 131740-09-5 146426-40-6 | | Anticancer, other | Cancer, renal |
| ALX-0646 | | | | | Migraine |
| AM-24 | 2,4,6-Triiodophenol | 609-23-4 | WO 9506638 | Antimigraine GI inflammatory/bowel disorders | Crohn's disease |
| AM-36 | 1-Piperazineethanol, 4-[[3,5-bis(1,1-dimethylrlthy)-4-hydroxyphenyl]methyl]-Alpha-(4-chlorophenyl)-[CAS] | 199467-52-2 | | Neuroprotective | Unspecified |
| AM-477 | 2-Methoxyoestradiol | 768-94-5 | | Antiasthma | Asthma |
| Amantadine | | | | | |
| amantanium | 1-Decanaminium, N,N-dimethyl-N-[2-[[tricyclo[3.3.1.13,7]dec-1-yl)carbonyl]oxy]ethyl]-, bromide [CAS] | 58158-77-3 | U.S. 4,288,609 | Antifungal | Infection, general |
| Ambazon | | 539-21-9 | | | |
| Ambenonium | | 115-79-7 | | | |
| ambrisentan | (+)(2S)-2-[(4,6-dimethylpyrimidin-2-yl)oxy]-3-methoxy-3,3-diphenylpropanoic acid | 177036-94-1 | | Vasodilator, peripheral | Heart failure |
| ambroxol | Cyclohexanol, 4-[[(2-amino-3,5-dibromophenyl)methyl]amino]-, trans- [CAS] | 18683-91-5 23828-92-4 | GB 1178034 | COPD treatment | Bronchitis, chronic |
| Ambucaine | | 119-29-9 | | | |
| Ambuphylline | | 5634-34-4 | | | |
| Ambusid | | 3754-19-6 | | | |
| Ambutonium Bromide | | 115-51-5 | | | |
| amcinonide | Pregna-1,4-diene-3,20-dione, 21-(acetyloxy)-16,17-[cyclopentylidenebis(oxy)]-9-fluoro-11-hydroxy-, (11β, 16Alpha)-[CAS] | 51022-69-6 | DE 2437847 | Antipsoriasis | |
| AMD-3100 | 1,4,8,11-Tetraazacyclotetradecane, 1,11-(1,4-phenylenebis(methylene))bis-, octahydrochloride [CAS] | 155148-31-5 | U.S. 5,612,478 | Haematological | Chemotherapy-induced injury, bone marrow, leucopenia |
| Andinocillin | | 32887-01-7 | | | |
| Andinocillin Pivoxil | | 32886-97-8 | | | |
| andoxovir | | 145514-04-1 | EP 656778 | Antiviral, anti-HIV | Infection, HIV/AIDS |
| amelubant | 1,3-Dioxolane-2-methanol, 4-(2,6-diamino-9H-purin-9-yl)-(2R-cis)-[CAS] Carbamic acid, ((4-((3-((4-(1-(4-hydroxyphenyl)-1-methylethyl)phenoxy)methyl)phenyl)methyl)phenyl)iminomethyl)-ethyl ester [CAS] | 346735-24-8 | DE 10000907 | COPD treatment | Chronic obstructive pulmonary disease |

TABLE IV-continued

| API Generic Name | API Chemical Name | CAS No. | Patent Reference | Example of Therapeutic Use | Example of Indication |
|---|---|---|---|---|---|
| Americaine | Benzenemethanaminium, N,N-dimethyl-N-[2-[2-[4-(1,1,3,3-tetramethylbutyl)phenoxy]ethoxy]ethyl]-, chloride, mixt. with ethyl 4-aminobenzoate [CAS] | 129128-13-8 | | Formulation, inhalable, other | Pain, general |
| Amezinium | | 30578-37-1 | | | |
| Amfenac | | 51579-82-9 | | | |
| Amidephrine | | 3354-67-4 | | | |
| Amidinomycin | | 3572-60-9 | | | |
| amifostine | Ethanethiol, 2-[(3-aminopropyl)amino]-, dihydrogen phosphate (ester)-[CAS] | 20537-88-6 63717-27-1 | EP 131500 | Radio/chemoprotective | Chemotherapy-induced injury, renal |
| amiglumide | Pentanoic acid, 5-(dipentylamino)-4-((2-naphthalenylcarbonyl)amino)-5-oxo-(R)-[CAS] | 119363-62-1 | WO 8805774 | GI inflammatory/bowel disorders | Pancreatitis |
| amikacin | | 37517-28-5 39831-55-5 | | Formulation, optimized, microencapsulate | Infection, general |
| Amiloride | | 2609-46-3 | | | |
| Aminacrine | | 90-45-9 | | | |
| amineptine | Heptanoic acid, 7-[(10,11-dihydro-5H-dibenzo[a,d]cyclohepten-5-yl)amino]-[CAS] | 30272-08-3 57574-09-1 | U.S. 3,758,528 | Antidepressant | |
| Aminitrozole | | 140-40-9 | | | |
| Amino Acid Preparations | | | | | |
| Aminocaproic Acid | | | | | |
| aminoglutethimide | 2,6-Piperidinedione, 3-(4-aminophenyl)-3-ethyl-[CAS] | 125-84-8 | U.S. 3,944,671 | Anticancer, hormonal | Cancer, breast |
| Aminoguanidine | | 79-17-4 | | | |
| Aminohippurate | | 642-44-4 | | | |
| Aminometradine | | 60-46-8 | | | |
| Aminopentamide | | | | | |
| aminophylline | 1H-Purine-2,6-dione, 3,7-dihydro-1,3-dimethyl-, compd. with 1,2-ethanediamine (2:1) [CAS] | 317-34-0 | | Formulation, modified-release, other | Asthma |
| Aminopromazine | | 58-37-7 | | | |
| Aminopyrine | | 58-15-1 | | | |
| Aminoquinuride | | 3811-56-1 | | | |
| Aminorex | | 2207-50-3 | | | |
| amiodarone | Methanone, (2-butyl-3-benzofuranyl)[4-[2-(diethylamino)ethoxy]-3,5-diiodophenyl]-[CAS] | 1951-25-3 19774-82-4 | U.S. 3,248,401 | Antiarrhythmic | Arrhythmia, general |
| Amiphenazole | | 490-55-1 | | | |
| Amiprilose | | 56824-20-5 | | | |
| amisulpride | Benzamide, 4-amino-N-[(1-ethyl-2-pyrrolidinyl)methyl]-5-(ethylsulfonyl)-2-methoxy-[CAS] | 71675-85-9 | U.S. 4,401,822 | Neuroleptic | Schizophrenia |
| Amitriptyline | | | | | |
| amitriptyline + | 1-Propanamine,3-(10,11-dihydro-5H- | 50-48-6 | | Formulation, | Pain, |

TABLE IV-continued

| API Generic Name | API Chemical Name | CAS No. | Patent Reference | | Example of Therapeutic Use | Example of Indication |
|---|---|---|---|---|---|---|
| ketamine | dibenzo[a,d]cyclohepten-5-ylidene)-N,N-dimethyl + cyclohexanone,2-(2-chlorophenyl)-2-(methylamino) | 4317-14-0 | | | fixed-dose combinations | neuropathic |
| Amitriptylinoxide amlexanox | 5H-[1]Benzopyrano[2,3-b]pyridine-3-carboxylic acid, 2-amino-7-(1-methylethyl)-5-oxo-[CAS] | 68302-57-8 | U.S. | 4,299,963 | Antiasthma | Asthma |
| amiodipine | 3,5-Pyridinedicarboxylic acid, 2-[(2-aminoethoxy)methyl]-4-(2-chlorophenyl)-1,4-dihydro-6-methyl-, 3-ethyl 5-methyl ester [CAS] | 111470-99-6 88150-42-9 88150-47-4 | EP | 89167 | Antianginal | Hypertension, general |
| Ammoniacum | | 03/07/9000 | | | | |
| Ammonium Benzoate | | 1863-63-4 | | | | |
| Ammonium Mandelate | | 530-31-4 | | | | |
| Ammonium Salicylate | | 528-94-9 | | | | |
| Ammonium Valerate | | 42739-38-8 | | | | |
| Amobarbital | | 57-43-2 | | | | |
| Amocarzine | | 36590-19-9 | | | | |
| Amodiaquin | | 86-42-0 | | | | |
| amorolfine | Morpholine, 4-[3-[4-(1,1-dimethylpropyl)phenyl]-2-methylpropyl]-2,6-dimethyl-, cis-[CAS] | 78613-35-1 78613-38-4 | EP | 24334 | Antifungal | Infection, fungal, general |
| Amoscanat amosulalol | Benzenesulfonamide, 5-[1-hydroxy-2-[[2-(2-methoxyphenoxy)ethyl]amino]ethyl]-2-methyl-, (+/−)-[CAS] | 26328-53-0 70958-86-0 85320-68-9 | EP | 136103 | Antihypertensive, adrenergic | Hypertension, general |
| Amotriphene amoxapine | Dibenz[b,f][1,4]oxazepine, 2-chloro-11-(1-piperazinyl)-[CAS] | 5585-64-8 14028-44-5 | GB | 1192812 | Antidepressant | Depression, general |
| amoxicillin | 4-Thia-1-azobicyclo[3,2,0]heptane-2-carboxylic acid, 6-[[amino(4-hydroxyphenyl)acetyl]amino]-3,3-dimethyl-7-oxo-,[2S-[2Alpha,5Alpha,6β(S*)]][CAS] | 26787-78-0 61336-70-7 | | | Formulation, modified-release, other | Infection, general |
| amoxicillin + potassium clavulan | | 74469-00-4 | GB | 1508977 | Formulation, fixed-dose combinations | Infection, respiratory tract, general |
| AMPAlex | Piperidine, 1-(6-quinoxalinylcarbonyl)-[CAS] | 154235-83-3 | U.S. | 5,650,409 | Psychostimulant | Attention deficit disorder |
| Amphetamine Amphetaminil | | 300-62-9 17590-01-1 | | | | |
| amphotericin B | Amphotericin B compd. with (3β)-cholest-5-en-3-yl hydrogen sulfate (1:1) [CAS] | 120895-52-5 1397-89-3 | U.S. | 4,822,777 | Formulation, optimized, liposomes | Infection, general |
| ampicillin | 4-Thia-1-azabicyclo[3.2.0]heptane-2-carboxylic acid, 6-[[(aminophenyl)acetyl]amino]-3,3-dimethyl-7-oxo-, [2S-[2Alpha,5Alpha,6β(S*)]] | 69-53-4 7177-48-2 | | | Formulation, fixed-dose combinations | Infection, general |
| Ampiroxicam Ampligen | | 99464-64-9 38640-92-5 | | | | |

TABLE IV-continued

| API Generic Name | API Chemical Name | CAS No. | Patent Reference | | Example of Therapeutic Use | Example of Indication |
|---|---|---|---|---|---|---|
| amprenavir | Carbamic acid, (3-(((4-aminophenyl)sulfonyl)(2-methylpropyl)amino)-2-hydroxy-1-(phenylmethyl)propyl)-, tetrahydro-3-furanyl ester, (3S-(3R*(1R*,2S*))-[CAS] [3,4'-Bipyridin]-6(1H)-one, 5-amino-[CAS] | 161814-49-9 | U.S. | 5,783,701 | Antiviral, anti-HIV | Infection, HIV/AIDS |
| amrinose | | 60719-84-8 75898-90-7 | U.S. | 4,004,012 | Cardiostimulant | |
| amrubicin | 5,12-Naphthacenedione, 9-acetyl-9-amino-7-[(2-deoxy-β-D-erythro-pentopyranosyl)oxy]-7,8,9,10-tetrahydro-6,11-dihydro-, hydrochloride, (7S,cis)-[CAS] | 92395-36-3 | EP | 107486 | Anticancer, antibiotic | Cancer, lung, non-small cell |
| amsacrine | Methanesulfonamide, N-[4-(9-acridinylamino)-3-methoxyphenyl]-[CAS] | 51264-14-3 | | | Anticancer, other | Cancer, leukaemia, acute lymphocytic |
| amtolmetin guacil | Glycine, N-[[1-methyl-5-(4-methylbenzoyl)-1H-pyrrol-2-yl]acetyl]-, 2-methoxyphenyl ester [CAS] | 87344-06-7 | GB | 2115417 | Analgesic, NSAID | Arthritis, rheumatiod |
| Amylocaine | | 532-59-2 | | | | |
| AN-152 | | | WO | 9719954 | Anticancer, antibiotic | Cancer, prostate |
| anabolic steroids | | | WO | 9848812 | Cardiovascular | Heart failure |
| Anagestone | | 2740-52-5 | | | | |
| anagrelide | Imidazo[2,1-b]quinazolin-2(3H)-one, 6,7-dichloro-1,5-dihydro-, monohydrochloride [CAS] | 58579-51-4 68475-42-3 | GB | 1418822 | Haematological | Thrombocytosis |
| anastrozole | 1,3-benzenediacetonitrile, Alpha,Alpha,Alpha,Alpha'-tetramethyl-5-(1H-1,2,4-triazol-1-ylmethyl)-[CAS] | 120511-73-1 | EP | 296749 | Anticancer, hormonal | Cancer, breast |
| Anazolene | | 3861-73-2 31698-14-3 9046-56-4 | | | | |
| Ancitabine | | | | | | |
| Ancrod | | | | | | |
| andolast | N-4'-[5-Tetrazolyl]-phenyl-4-(5-tetrazolyl)-benzamide | 132640-22-3 | EP | 460083 | Antiasthma | Asthma |
| Androisoxazole | | 360-66-7 | | | | |
| Androstenediol | | 521-17-5 | | | | |
| anecortave | 21-(Acetyloxy)-17-hydroxypregna-4,9(11)-diene-3,20-dione | 7753-60-8 | | | Ophthalmological | Macular degeneration |
| Anethole | | 4180-23-8; 104-46-1 (unspecified) | | | | |
| Anethole Trithione | | 532-11-6 | | | | |
| Angiogenix | | | U.S. | 6,417,205 | Cardiovascular | Cardio-myopathy, ischaemic |
| Angiotensin | | 1407-47-2 | | | | |
| anhydrovinblastine | Vincaleukoblastine, 3',4'-didehydro-4'-deoxy-[CAS] | 38390-45-3 | U.S. | 6,011,041 | Anticancer, other | Cancer, general |

TABLE IV-continued

| API Generic Name | API Chemical Name | CAS No. | Patent Reference | Example of Therapeutic Use | Example of Indication |
|---|---|---|---|---|---|
| anidulafungin | Echinocandin B, 1-((4R,5R)-4,5-dihydroxy-N2-((4''-(pentyloxy)(1,1':4',1''-terphenyl)-4-yl)carbonyl)-L-ornithine)-[CAS] | 166663-25-8 | U.S. 6,384,013 | Antifungal | Infection, Candida, general |
| Anilerdine | | 144-14-9 | | | |
| Aniracetam | | 72432-10-1 | | | |
| Anisindione | | 117-37-3 | | | |
| Anisomycin | | 22862-76-6 | | | |
| Anisotropine Methylbromide | | 80-50-2 | | | |
| anistreplase | Anistreplase [CAS] | 81669-57-0 | EP 28489 | Fibrinolytic | Infarction, myocardial |
| Antazoline | | 91-75-8 | | | |
| Anthiolimine | | 305-97-5 | | | |
| Anthralin | | 1143-38-0 | | | |
| Anthramycin | | 4803-27-4 | | | |
| Anthrarobin | | 577-33-3 | | | |
| Anthrax inhibitor | | | U.S. 6,436,933 | Anti-infective, other | Infection, anthrax |
| antiangiogenic dendrimers | | | U.S. 6,426,067 | Anticancer, other | Cancer, general |
| Anticort | L-Ascorbic acid, mixt with 2-(diethylamino)ethyl 4-aminobenzoate monohydrochloride, disodium hydrogen phosphate, potassium benzoate and zinc sulfate (1:1) [CAS] | 186646-39-9 | WO 9640038 | Anabolic | Cachexia |
| antidepressants | | | U.S. 5,898,036 | Antidepressant | Depression, general |
| anti-invasins | | | U.S. 6,303,302 | Antifungal | Infection, fungal, general |
| Antimony Potassium Tartrate | | 28300-74-5 | | | |
| Antimony Sodium Thioglycollate | | 539-54-8 | | | |
| Antimony Thioglycollamide | | 6533-78-4 | | | |
| Antiprogestin | 19-Norpregna-4,9-dien-3-one,(acetylphenyl)-20,20,21,21,21-pentafluoro-17-hydroxy-(11β, 17Alpha) [CAS] | 211254-73-8 | DE 19703061 | Anticancer, hormonal | Cancer, breast |
| Antipyrine | | 60-80-0 | | | |
| Antipyrine Salicylate | | 520-07-0 | | | |
| antithrombin III | Antithrombin, III [CAS] | 9000-94-6 | | Blood fraction | Antithrombin III deficiency |
| AR-116081 | | 90170-80-2 | | | Unspecified |
| AR-A2 | (R)-N-[5-methyl-8-(4-methylpiperazin-1-yl)-1,2,3,4-tetrahydro-2-naphthyl]-4-morpholinobenzamide | | U.S. 6,107,324 | Neuroleptic Anxiolytic | Anxiety, general |
| Arachidonic Acid | | 506-32-1 | | | |

TABLE IV-continued

| API Generic Name | API Chemical Name | CAS No. | Patent Reference | | Example of Therapeutic Use | Example of Indication |
|---|---|---|---|---|---|---|
| aranidipine | 3,5-Pyridinedicarboxylic acid, 1,4-dihydro-2,6-dimethyl-4-(2-nitrophenyl)-, methyl 2-oxopropyl ester-[CAS] | 86780-90-7 | GB | 2111978 | Antihypertensive, other | Hypertension, general |
| arbekacin | D-Streptamine, O-3-amino-3-deoxy-Alpha-D-glucopyranosyl-(1-6)-O-[2,6-diamino-2,3,4,6-tetradeoxy-Alpha-D-erythro-hexopyranosyl-(1-4)]-N1-(4-amino-2-hydroxy-1-oxobutyl)-2-deoxy-, (S)-[CAS] | 51025-85-5 75282-65-4 | U.S. | 4,001,208 | Aminoglycoside antibiotic | Infection, general |
| Arbidol | 1H-indole-3-carboxylic acid, 6-bromo-4-((dimethylamino)methyl)-5-hydroxy-1-methyl-2-((phenylthio)methyl)-, ethylester, monohydrochloride [CAS] | 131707-23-8 | WO | 9008135 | Immunostimulant, other | Infection, influenza virus |
| arbutamine | 1,2-Benzenediol, 4-[1-hydroxy-2-[[4-(4-hydroxyphenyl)butyl]amino]ethyl]-, (R)-[CAS] | 128470-16-6 | WO | 9220324 | Diagnostic | Diagnosis, coronary |
| Arcitumomab ardeparin | Heparin [CAS] | 154361-48-5 9005-49-6 | | | Anticoagulant | Thrombosis, venous |
| arecoline | 1,2,5,6-Tetrahydro-1-methyl-3-pyridine carboxylic acid methyl ester | | | | | Alzheimer's disease |
| argatroban | 2-Piperidinecarboxylic acid, 1-[5-[(aminoiminomethyl)amino]-1-oxo-2-[[(1,2,3,4-tetrahydro-3-methyl-8-quinolinyl)sulfonyl]amino]pentyl]-4-methyl-[CAS] | 74863-84-6 | EP | 8746 | Formulation, transdermal, patch Anticoagulant | Thrombosis, arterial |
| Arginine Ariflo ® | | 74-79-3 153259-65-5 | | | | |
| aripiprazole | 2(1H)-Quinolinone, 7-[4-[4-(2,3-dichlorophenyl)-1-piperazinyl]butoxy]-3,4-dihydro-[CAS] | 129722-12-9 | EP | 367141 | Neuroleptic | Schizophrenia |
| anxiolytics | | | U.S. | 5,756,538 | Anxiolytic | Anxiety, general |
| AP-521 | N-Piperonyl-2-amino-1,2,3,4-tetrahydrobenzo(b)thieno(2,3-c)pyridine-3-carbamide | 151227-08-6 | WO | 9321189 | Anxiolytic | Anxiety, general |
| AP-5280 | | | U.S. | 5,965,118 | Anticancer, alkylating | Cancer, general |
| Apalcillin apaziquone | 1H-indole-4,7-dione, 5-(1-aziridinyl)-3-(hydroxymethyl)-2-(3-hydroxy-1-propenyl)-1-methyl-, (E)-[CAS] | 63469-19-2 114560-48-4 | WO | 8706227 | Anticancer, alkylating | Cancer, breast |
| Apazone α-Phenylbutyramide Apocodeine apomine | Phosphonic acid, (2-(3,5-bis(1,1-dimethylethyl)-4-hydroxyphenyl)ethylidene)bis-tetrakis(1-methylethyl) ester [CAS] | 13539-59-8 90-26-6 641-36-1 126411-13-0 | | | Anticancer, other | Cancer, prostate |

TABLE IV-continued

| API Generic Name | API Chemical Name | CAS No. | Patent Reference | | Example of Therapeutic Use | Example of Indication |
|---|---|---|---|---|---|---|
| apomorphine | 4H-Dibenzo[de,g]quinoline-10,11-diol, 5,6,6a,7-tetrahydro-6-methyl-, hydrochloride | 314-19-2 58-00-4 | | | Formulation, transmucosal, nasal | Impotence |
| apraclonidine | 1,4-Benzenediamine, 2,6-dichloro-N1-(4,5-dihydro-1H-imidazol-2-yl)-[CAS] | 66711-21-5 73218-79-8 | U.S. | 4,517,199 | Antiglaucoma | Glaucoma |
| aprepitant | 3H-1,2,4-Triazol-3-one, 5-[[(2R,3S)-2-[(1R)-1-[3,5-bis(trifluoromethyl)phenyl]ethoxy]-3-(4-fluorophenyl)-4-morpholinyl]methyl]-1,2-dihydro-[CAS] | 170729-80-3 | U.S. | 5,719,147 | Antiemetic | Chemotherapy-induced nausea and vomiting |
| aprindine | 1,3-Propanediamine, N-(2,3-dihydro-1H-inden-2-yl)-N',N'-diethyl-N-phenyl-[CAS] | 33237-74-0 37640-71-4 | GB | 1321424 | Antiarrhythmic | |
| Aprobarbital | | 77-02-1 | | | | |
| Apronalide | | 528-92-7 | | | | |
| Aprotinin | | 9087-70-1 | | | | |
| Aptiganel | | 137159-92-3 | | | | |
| AQ4N | 9,10-Anthracenedione, 1,4-bis(2-(dimethyloxidoamino)ethyl)amino)-5,8-dihydroxy-[CAS] | 136470-65-0 | U.S. | 5,132,327 | Anticancer, other | Cancer, general |
| Aquavan | | | U.S. | 6,204,257 | Anaesthetic, injectable | Anaesthesia |
| arofylline | 1H-Purine-2,6-dione, 3-(4-chlorophenyl)-3,7-dihydro-1-propyl-[CAS] | 136145-07-8 | EP | 435811 | COPD treatment | Chronic obstructive pulmonary disease |
| arotinolol | 2-Thiophenecarboxamide, 5-[2-[[3-[(1,1-dimethylethyl)amino]-2-hydroxypropyl]thio]-4-thiazolyl]-, (±)-[CAS] | 104766-23-6 68377-92-4 | U.S. | 3,932,400 | Antihypertensive, adrenergic | Hypertension, general |
| Arsacetin | | 618-22-4 | | | | |
| arsenic trioxide | Arsenic oxide (As2O3) [CAS] | 1327-53-3 | | | Anticancer, other | Cancer, leukemia, acute myelogenous |
| Arsphenamine | | 139-93-5 | | | | |
| Aesthinol | | 119-96-0 | | | | |
| Arteether | | 75887-54-6 | | | | |
| Arteflene | | 123407-36-3 (Z-form) | | | | |
| Artemether | | 71963-77-4 | | | | |
| Artemisinin | | 63968-64-9 | | | | |
| artemotil | | 75887-54-6 | | | Antimalarial | Infection, malaria |
| artesunate | 3,12-Epoxy-12H-pyrano[4,3-j]-1,2-benzodioxepin, 10-ethoxydecahydro-3,6,9-trimethyl-, [3R-(3Alpha,5aβ,6β,8aβ,9aAlpha,10Alpha,12β,12aR*)]-[CAS] Butanedioic acid mono-[(3R,5aS,6R,8aS,9R,10R,12R,12aR)-decahydro-3,6,9-trimethyl-3,12-epoxy-12H-pyrano[4,3-j]-1,2-benzodioxepin-10-yl]ester | 88495-63-0 | | | Formulation, transmucosal, systemic | Infection, malaria |
| arzoxifene | Benzo(b)thiophene-6-ol, 2-(4-methoxyphenyl)-3-(4-(2-(1-piperidinyl)ethoxy)phenoxy)-[CAS] | 182133-27-3 | WO | 9609041 | Anticancer, hormonal | Cancer, breast |

TABLE IV-continued

| API Generic Name | API Chemical Name | CAS No. | Patent Reference | Example of Therapeutic Use | Example of Indication |
|---|---|---|---|---|---|
| AS-3201 | Spiro(pyrrolidine-3,4'(1H)-pyrrolo(1,2-a]pyrazine)-1',2',3',5(2'H)-tetrone, 2'-((4-bromo-2-fluorophenyl)methyl)-, (3'R)-[CAS] | 147254-64-6 | EP 520320 | Symptomatic antidiabetic | Diabetic complication, general |
| ASA | Benzoic acid, 2-(acetyloxy)-[CAS] | 50-78-2 56449-07-1 | | Formulation, modified-release, other | Pain, general |
| α-Santonin | | 481-06-1 | | | |
| Ascaridole | | 512-85-6 | | | |
| Ascorbic Acid | | 50-81-7 | | | |
| asenapine | 1H-Dibenz[2,3:6,7]oxepino[4,5-c]pyrrole, 5-chloro-2,3,3a,12b-tetrahydro-2-methyl-, trans-, (Z)-2-butenedioate (1:1) [CAS] | 85650-56-2 | WO 9523600 | Neuroleptic | Psychosis, general |
| asimadoline | Benzeneacetamide, N-[2-(3-hydroxy-1-pyrrolidinyl)-1-phenylethyl]-N-methyl-Alpha-phenyl-, [S-(R*,R*)]-[CAS] | 153205-46-0 | DE 4215213 | GI inflammatory/bowel disorders | Irritable bowel syndrome |
| asoprisnil | 11β-[4-(Hydroxyiminomethyl)phenyl]-17β-methoxy-17Alpha-(methoxymethyl)estra-4,9-dien-3-one | 199396-76-1 | EP 0648778 | Mensturation disorders | Endometriosis |
| Asoxime | | 34433-31-3 | | | |
| Aspartic Acid | | 56-84-8 | | | |
| Aspidin | | 584-28-1 | | | |
| Aspidinol | | 519-40-4 | | | |
| Aspirin, Dipyridamole | | 50-78-2 | | | |
| aspoxicillin | Glycinamide, N-methyl-D-asparaginyl-N-(2-carboxy-3,3-dimethyl-7-oxo-4-thia-1-azabicyclo[3.2.0]hept-6-yl)-D-2-(4-hydroxyphenyl)-, [2S-(2Alpha,5Alpha,6β)]-[CAS] | 63358-49-6 | GB 1533413 | Penicillin, injectable | Infection, respiratory tract, general |
| AST-120 | AST 120 [CAS] | 90597-58-3 68844-77-9 | | Urological | Renal failure |
| Astemizole | | | | | |
| asulacrine | 4-Acridinecarboxamide, 9-[[2-methoxy-4-[(methylsulfonyl)amino]phenyl]amino]-N,5-dimethyl-[CAS] | 80841-47-0 80841-48-1 | EP 39224 | Anticancer, other | Cancer, general |
| AT-1015 | (N-[2-[4-(5H-Dibenzo[a,d]cyclohepten-5-ylidene)-piperdino]ethyl]-1-formyl-4-piperidinecarboxamide monohydrochloride monohydrate | | | Antithrombotic | Thrombosis, general |
| atamestane | Androsta-1,4-diene-3,17-dione, 1-methyl-[CAS] | 96301-34-7 | DE 3338212 | Anticancer, hormonal | Cancer, breast |
| atazanavir | 2,5,6,10,13-Pentaazatetradecanedioic acid, 3,12-bis(1,1-dimethylethyl)-8-hydroxy-4,11-dioxo-9-(phenylmethyl)-6-((4-(2-pyridinyl)phenyl)methyl)-dimethyl ester, (3S,8S,9S,12S)-, sulfate (1:1) (salt) [CAS] | 229975-97-7 | | Antiviral, anti-HIV | Infection, HIV/AIDS |
| atenolol | Benzeneacetamide, 4-[2-hydroxy-3-[(1-methylethyl)amino]propoxy]-[CAS] | 29122-68-7 73677-19-7 | GB 1285038 | Antihypertensive, adrenergic | Hypertension, general |
| atenolol + | Benzeneacetamide, 4-[2-hydroxy-3-[(1- | 73677-19-7 | U.S. 3,836,671 | Formulation, | Hypertension, |

TABLE IV-continued

| API Generic Name | API Chemical Name | CAS No. | Patent Reference | Example of Therapeutic Use | Example of Indication |
|---|---|---|---|---|---|
| chlorthalidone | methylethyl)amino]propoxy]-, mixt. with 2-chloro-5-(2,3-dihydro-1-hydroxy-3-oxo-1H-isoindol-1-yl)benzenesulfonamide [CAS] | | | fixed-dose combinations | general |
| atenolol + nifedipine | Benzeneacetamide, 4-[2-hydroxy-3-[(1-methylethyl)amino]propoxy]-, + 4-(2'-nitrophenyl)-2,6-dimethyl-3,5-dicarbomethoxy-1,4-dihydropyridine | | | Formulation, fixed-dose combinations | Hypertension, general |
| α-Terpineol | | 98-55-5 | | | |
| Atevirdine | | 136816-75-6 | | | |
| atipamezole | 1H-Imidazole, 4-(2-ethyl-2,3-dihydro-1H-inden-2-yl)-[CAS] | 104054-27-5 | EP 183492 | Reproductive/ gonadal, general | Sexual dysfunction, female |
| atiprimod dimaleate | 2-Azaspivo[4.5]decane-2-propanamine, N,N-diethyl-8,8-dipropyl, dimaleate | 130065-61-1 | U.S. 5,744,495 | Antiarthritic, immunological | Arthritis, rheumatoid |
| ATL-146e | | | U.S. 6,232,297 | Imaging agent | Unspecified |
| α-Tocopherol | | 59-02-9 | | | |
| atomoxetine | Benzenepropanamine, N-methyl-Gamma-(2-methylphenoxy)-, (R)-[CAS] | 82248-59-7 83015-36-3 | EP 52492 | Neurological | Attention deficit disorder |
| atorvastatin | 1H-Pyrrole-1-heptanoic acid, 2-(4-fluorophenyl)-β,delta-dihydroxy-5-(1-methylethyl)-3-phenyl-4-[(phenylamino)carbonyl]-[CAS] | 134523-03-8 134523-00-5 | EP 409281 | Hypolipaemic/ Antiatherosclerosis | Hyper-cholesterolaemia |
| atosiban | Oxytocin, 1-(3-mercaptopropanoin acid)-2-(O-ethyl-D-tyrosine)-4-L-threonine-8-L-ornithine-[CAS] | 90779-69-4 | EP 112809 | Labour inhibitor | Labour, preterm |
| atovaquone | 1,4-Naphthalenedione, 2-[4-(4-chlorophenyl)cyclohexyl]-3-hydroxy-, trans-[CAS] | 95233-18-4 | EP 123238 | Antifungal | Infection, *Pneumocystis jiroveci* |
| atovaquone + proguanil | 1,4-Naphthalenedione, 2-[4-(4-chlorophenyl)cyclohexyl]-3-hydroxy-, trans + N-(4-chloro-phenyl)-N-(1-methylethyl)imidiodicarbonimidic diamide | | | Antimalarial | Infection, malaria |
| atracurium | Isoquinolinium, 2,2'-[1,5-pentanediylbis[oxy(3-oxo-3,1-propanediyl)]]bis[1-[(3,4-dimethoxyphenyl)methyl]-1,2,3,4-tetrahydro-6,7-dimethoxy-2-methyl-[CAS]] | 64228-81-5 | U.S. 4,179,557 | Muscle relaxant | Surgery adjunct |
| atrasentan | 3-Pyrrolidenecarboxylic acid, 4-(1,3-benzodioxol-5-yl)-1-[2-(dibutylamino)-2-oxoethyl]-2-(4-methoxyphenyl)-, (2R,3R,4S)-[CAS] | 173937-91-2 | WO 9730045 | Anticancer, other | Cancer, prostate |
| Atrial Natriuretic Peptide | | 85637-73-6 | | | |
| Atrolactamide | | 2019-68-3 | | | |
| Atropine | | 51-55-8 | | | |
| Augmentin | | 74469-00-4 | | Formulation, modified-release, other | Infection, respiratory tract, general |
| auranofin | Gold, (1-thio-β-D-glucopyranose 2,3,4,6-tetraacetato-S)(triethylphosphine)-[CAS] | 34031-32-8 | U.S. 3,708,579 | Antiarthritic, other | Arthritis, rheumatoid |

TABLE IV-continued

| API Generic Name | API Chemical Name | CAS No. | Patent Reference | | Example of Therapeutic Use | Example of Indication |
|---|---|---|---|---|---|---|
| Aurothioglucose avasimibe | Sulfamic acid, [[2,4,6-tris(1-methylethyl)phenyl]acetyl]-, 2,6-bis(1-methylethyl)phenyl ester [CAS] | 12192-57-3 166518-60-1 | U.S. | 5,491,172 | Hypolipaemic/ Antiatherosclerosis | Atherosclerosis |
| Avobenzone AWD-12-281 | AWD 12-281 [CAS] | 70356-09-1 257892-33-4 | | | Antiallergic, non-asthma | Rhinitis, allergic, general |
| Azacitidine Azacyclonol azanidazole | 2-Pyrimidinamine, 4-[2-(1-methyl-5-nitro-1H-imidazol-2-yl)ethenyl]-,(E)-[CAS] | 320-67-2 115-46-8 62973-76-6 | U.S. | 3,882,105 | Antibacterial, other | Infection, trichomoniasis |
| azapropazone | 1H-Pyrazolo[1,2-a][1,2,4]benzotriazine-1,3(2H)-dione, 5-(dimethylamino)-9-methyl-2-propyl-[CAS] | 13539-59-8 | FR | 1440629 | Anti-inflammatory | |
| Azaserine azasetron | 2H-1,4-Benzoxazine-8-carboxamide, N-1-azabicyclo[2.2.2]oct-3-yl-6-chloro-3,4-dihydro-4-methyl-3-oxo-, monohydrochloride-[CAS] | 115-02-6 123040-16-4 123040-94-8 123040-96-0 123040-69-7 | EP | 313393 | Antiemetic | Nausea and vomiting, general |
| Azatadine azathipprine | 6-[(1-Methyl-4-nitro-1H-imidazol-5-yl)thio]-1H-purine | 3964-81-6 446-86-6 | | | Formulation, oral, other | Transplant rejection, bone marrow |
| AZD-4282 | glycine | | | | Analgesic, other | Pain, neuropathic |
| AZD-6140 | 3,4-Difluorophenylcyclopropylamine | | | | Antithrombotic | Thrombosis, arterial |
| azelaic acid azelastine | Nonanedioic acid [CAS] 1(2H)-Phthalazinone, 4-[(4-chlorophenyl)methyl]-2-(hexahydro-1-methyl-1H-azepin-4-yl)-, monohydrochloride [CAS] | 123-99-9 58581-89-8 79307-93-0 | GB | 1377231 | Antiacne Antiasthma | Acne Asthma |
| azelnidipine | 3,5-Pyridinedicarboxylic acid, 2-amino-1,4-dihydro-6-methyl-4-(3-nitrophenyl)-, 3-[1-(diphenylmethyl)-3-azetidinyl] 5-(1-methylethyl)ester, (+/−)-[CAS] | 123524-52-7 | EP | 266922 | Antihypertensive, other | Hypertension, general |
| Azidamfenicol Azidocillin Azimilide Azintamide | | 13838-08-9 17243-38-8 149908-53-2 1830-32-6 | | | | |
| azithromycin | 9-deoxo-9a-aza-9a-methyl-9a-homoerythromycin-A | 76801-85-9 83905-01-5 92395-24-9 | U.S. | 4,328,334 | Macrolide antibiotic | Infection, respiratory tract, lower |
| azlocillin | 4-Thia-1-azabicyclo[3.2.0]heptane-2-carboxylic acid, 3,3-dimethyl-7-oxo-6-[[[[(2-oxo-1-imidazolidinyl)carbonyl]amino]-phenylacetyl]amino]-, [2S-[2 alpha.,5Alpha., 6β(S*)]]-[CAS] | 37091-65-9 37091-66-0 | GB | 1392849 | Penicillin, injectable | Infection, general |

TABLE IV-continued

| API Generic Name | API Chemical Name | CAS No. | Patent Reference | | Example of Therapeutic Use | Example of Indication |
|---|---|---|---|---|---|---|
| Azosemide | | 27589-33-9 | | | | |
| aztreonam | Propanoic acid, 2-[[[1-(2-amino-4-thiazolyl)-2-[(2-methyl-4-oxo-1-sulfo-3-azetidinyl)amino]-2-oxoethylidene]amino]oxy]-2-methyl-, [2S-[2Alpha,3β(Z)]]-[CAS] | 104184-69-2 78110-38-0 | GB | 2071650 | Beta-lactam antibiotic | Infection, general |
| azulene | Sodium 5-isopropyl-3,8-dimethyl-1-azulene sulfonate | 6223-35-4 | EP | 88958 | Formulation, modified-release, other | Inflammation, general |
| bacampicillin | 4-Thia-1-azabicyclo[3.2.0]heptane-2-carboxylic acid, 6-[[(aminophenylacetyl)amino]-3,3-dimethyl-7-oxo-, 1-[(ethoxycarbonyl)oxy]ethyl ester, [2S-[2Alpha,5Alpha,6β(S*)]]-[CAS] | 37661-08-8 50972-17-3 | GB | 1363506 | Penicillin, oral | Infection, general |
| Bacitracin | | 1405-87-4 | | | | |
| baclofen | β-(Aminomethyl)-4-chlorobenzenepropanoic acid [CAS] | 1134-47-0 | | | Formulation, implant | Spastic paralysis |
| Baicalein | | 491-67-8 | | | | |
| balofloxacin | 3-Quinolinecarboxylic acid, 1-cyclopropyl-6-fluoro-1,4-dihydro-8-methoxy-7-[3-(methylamino)-1-piperidinyl]-4-oxo-[CAS] | 127294-70-6 | EP | 342675 | Quinolone antibacterial | Infection, urinary tract |
| balsalazide | Benzoic acid, 5-[[4-[[(2-carboxyethyl)amino]carbonyl]phenyl]azo]-2-hydroxy-, (E)-[CAS] | 80573-04-2 | U.S. | 4,412,992 | GI inflammatory/bowel disorders | Colitis, ulcerative |
| bambuterol | Carbamic acid, dimethyl-, 5-[2-[(1,1-dimethylethyl)amino]-1-hydroxyethyl]-1,3-phenylene ester, monohydrochloride [CAS] | 81732-46-9 81732-65-5 | EP | 43807 | Antiasthma | Asthma |
| Bamethan | | 3703-79-5 | | | | |
| Bamifylline | | 2016-63-9 | | | | |
| Bamipine | | 4945-47-5 | | | | |
| Barbital | | 57-44-3 | | | | |
| bamidipine | 3,5-Pyridinedicarboxylic acid, 1,4-dihydro-2,6-dimethyl-4-(3-nitrophenyl)-, methyl-1-(phenylmethyl)-3-pyrrolidinyl ester, [S-(R*,R*)]- | 104713-75-9 104757-53-1 71863-56-4 | U.S. | 4,220,649 | Antihypertensive, other | Hypertension, general |
| BAS-118 | N-Methyl-3-[2-(2-napthyl)acetylamino]benzamide | | | | Antibacterial, other | Infection, Helicobacter pylori |
| Basic Aluminum Carbonate Gel | | 1339-92-0 | | | | |
| Basiliximab | | | | | | |
| Batimastat | | 179045-86-4 | | | | |
| Batroxobin | | 130370-60-4 | | | | |
| Bay-41-2272 | 5-cyclopropyl-2-[1(2-fluoro-benzyl)-1H-pyrazolo[3,4-b]pyridine-3-yl]pyrimidin-4ylamine | 9039-61-6 | | | Male sexual dysfunction | Sexual dysfunction, male, general |
| Bay-41-8543 | 2-[1-(2-Fluorobenzyl)-1H-pyrazolo[3,4-b]pyridin-3-yl]-5-(4-morpholinyl)pyrimidine-4,6-diamine | | | | Cardiovascular | Unspecified |

TABLE IV-continued

| API Generic Name | API Chemical Name | CAS No. | Patent Reference | | Example of Therapeutic Use | Example of Indication |
|---|---|---|---|---|---|---|
| BAY-43-9006 | N-(4-chloro-3-(trifluoromethyl)phenyl)-N'-(4-(2-(N-methylcarbamoyl)-4-pyridyloxy)phenyl)urea | | | | Anticancer, other | Cancer, liver |
| BAY-57-1293 | N-[5(aminosulfonyl)-4-methyl-1,3-thiazol-2-yl]-N-methyl-2-[4-(2-pyridinyl)phenyl]acetamide | | | | Antiviral, other | Infection, herpes simplex virus |
| bazedoxifen | TSE 424 [CAS] | 198481-33-3 | EP | 802183 | Osteoporosis treatment | Osteoporosis |
| β-Benzalbutyramide | | 7236-47-7 | | | | |
| BBR-3464 | Platinum(4+), hexaaminedichlorobis(μ-(1,6-hexanediamine-N:N')tri-stereoisomer, tetranitrate [CAS] | 172903-00-3 | U.S. | 5,744,497 | Anticancer, alkylating | Cancer, lung, non-small cell |
| BBR-3576 | | | U.S. | 5,519,029 | Anticancer, antibiotic | Cancer, prostate |
| BBR-3610 | | | U.S. | 6,060,616 | Anticancer, alkylating | Cancer, general |
| β-Carotene | | 7235-40-7 | | | | |
| BCH-1868 | (−)-2-R-dihydroxyphosphinyl-5-(S)-(guanin-9'-yl-methyl)tetrahydrofuran | | | | Anticancer, antimetabolite | Cancer, general |
| Bebeerine | | 477-60-1 | | | | |
| Beclamide | | 501-68-8 | | | | |
| beclometasone | Pregna-1,4-diene-3,20-dione, 9-chloro-11β,17,21-trihydroxy-16β-methyl, [CAS] | 5534-09-8 4419-39-0 | | | | |
| Befloxatone | | 134564-82-2 | | | | |
| befunolol | Ethanone, 1-[7-[2-hydroxy-3-[(1-methylethyl)amino]propoxy]-2-benzofuranyl]-[CAS] | 39543-79-8 39552-01-7 | | | | |
| Bemegride | | 64-65-3 | | | | |
| Benactyzine | | 302-40-9 | | | | |
| benazepril | 1H-1-Benzazepine-1-acetic acid, 3-[[1-(ethoxycarbonyl)-3-phenylpropyl]amino]-2,3,4,5-tetrahydro-2-oxo-, [S-(R*,R*)]-[CAS] | 86541-74-4 86541-75-5 86541-78-8 | EP | 72352 | Antihypertensive, renin system | Hypertension, general |
| bencyclane | 1-Propanamine, N,N-dimethyl-3-[[1-(phenylmethyl)cycloheptyl]oxy]-, (E)-2-butenedioate (1:1) [CAS] | 14286-84-1 2179-37-5 | WO | 9829409 | Vasodilator, peripheral | |
| bendazac | L-Lysine, mono[[1-(phenylmethyl)1H-indazol-3-yl]oxy]acetate][CAS] | 81919-14-4 20187-55-7 73-48-3 | GB | 2081708 | Ophthalmological | |
| Bendroflumethiazide | | | | | | |
| Benexate | Ethanol, 2-[[1-methyl-2-[3-(trifluoromethyl)phenyl]ethyl]amino]-, benzoate (ester) [CAS] | 78718-25-9 23602-78-0 23642-66-2 | GB | 1175516 | Hypolipaemic/Antiatherosclerosis | |
| benfluorex | | | | | | |
| Benfotiamine | | 22457-89-2 3447-95-8 | | | | |
| Benfurodil | | | | | | |
| benidipine | 3,5-Pyridinedicarboxylic acid, 1,4-dihydro-2,6-dimethyl-4-(3-nitrophenyl)-, methyl 1-(phenylmethyl)-3-piperidinyl ester, monohydrochloride (R*,R*)-(+/−)-[CAS] | 105979-17-7 91599-74-5 | EP | 63365 | Antihypertensive, other | Hypertension, general |
| Benorylate | | 5003-48-5 | | | | |
| Benoxaprofen | | 67434-14-4 | | | | |
| Benoxinate | | 99-43-4 | | | | |

TABLE IV-continued

| API Generic Name | API Chemical Name | CAS No. | Patent Reference | | Example of Therapeutic Use | Example of Indication |
|---|---|---|---|---|---|---|
| Benperidol | | 2062-84-2 | | | | |
| Benproperine | | 2156-27-6 | | | | |
| Benserazide | | 322-35-0 | | | | |
| bentazepam | 2H-[1]Benzothieno[2,3-e]-1,4-diazepin-2-one, 1,3,6,7,8,9-hexahydro-5-phenyl-[CAS] | 29462-18-8 | DE | 2005276 | Anxiolytic | |
| Bentiromide | | 37106-97-1 | | | | |
| Bentoquatam | | 1340-69-8 | | | | |
| Benzalkonium | | 8001-54-5 | | | | |
| Benzarone | | 1477-19-6 | | | | |
| benzbromarone | Methanone, (3,5-dibromo-4-hydroxyphenyl)(2-ethyl-3-benzofuranyl)-[CAS] | 3562-84-3 | U.S. | 3,012,042 | Antigout | |
| Benzethonium | | 121-54-0 | | | | |
| Benzetimide | | 14051-33-3 | | | | |
| Benzilonium | | 1050-48-2 | | | | |
| Benziodarone | | 68-90-6 | | | | |
| benzindazole | N-benzyl-2-nitroimidazole-1-acetamide | 22994-85-0 | GB | 1138529 | Protozoacide Formulation, fixed-dose combinations | Pain, musculoskeletal |
| benzocaine | Benzoic acid, 4-amino-, ethyl ester | 94-09-7 | | | | |
| Benzoctamine | | 17243-39-9 | | | | |
| Benzonatate | | 104-31-4 | | | | |
| Benzoxonium Chloride | | 19379-90-9 | | | | |
| benzoyl peroxide | Peroxide, dibenzoyl [CAS] | 94-36-0 | | | Formulation, other | Acne |
| Benzoylpas | | 13898-58-3 | | | | |
| Benzphetamine | | 156-08-1 | | | | |
| Benzpiperylon | | 53-89-4 | | | | |
| Benzquinamide | | 63-12-7 | | | | |
| Benzthiazide | | 91-33-8 | | | | |
| Benztropine | | 132-17-2 | | | | |
| benzydamine | 1-Propanamine, N,N-dimethyl-3-[[1-(phenylmethyl)-1H-indazol-3-yl]oxy]-[CAS] | 132-69-4 642-72-8 | | | Stomatological, reproductive/gonadal, anti-inflammatory | |
| Benzyl Benzoate | | 120-51-4 | | | | |
| Benzylhydrochlorothiazide | | 1824-50-6 | | | | |
| Benzylmorphine | | 14297-87-1 | | | | |
| Bephenium Hydroxynaphthoate | | 3818-50-6 | | | | |
| bepotastine | 1-Piperidinebutanoic acid, 4-((4-chlorophenyl)-2-pyridinylmethoxy)-, (S)-, monobenzenesulfonate [CAS] | 190786-44-8 190786-43-7 | WO | 9829409 | Antiallergic, non-asthma | Allergy, general |
| bepridil | 1-Pyrrolidineethanamine, β-[(2-methylpropoxy)methyl]-N-phenyl-N-(phenylmethyl)-[CAS] | 64706-54-3 74764-40-2 74764-75-3 | EP | 146155 | Antianginal | Angina, general |
| beraprost | 1H-Cyclopenta[b]benzofuran-5-butanoic acid, 2,3,3a,8b-tetrahydro-2-hydroxy-1-(3-hydroxy-4-methyl-1-octen-6-ynyl)-[CAS] | 88475-69-8 88430-50-6 | U.S. | 4,474,802 | Prostaglandin | Peripheral vascular disease |
| Berberine | | 2086-83-1 | | | | |
| Bergapten | | 484-20-8 | | | | |

TABLE IV-continued

| API Generic Name | API Chemical Name | CAS No. | Patent Reference | Example of Therapeutic Use | Example of Indication |
|---|---|---|---|---|---|
| Bermoprofen | | | | | |
| Besipirdine | 2-Pyridineethanamine, N-methyl-, dihydrochloride | 78499-27-1 119257-34-0 5579-84-0 5638-76-6 | | | Meniere's disease |
| betahistine | | | | | |
| betaine | Betaine-[CAS] | 107-43-7 | | Formulation, modified-release, <=24 hr Metabolic and enzyme disorders | Homocystinuria |
| betamethasone | Pregna-1,4-diene-3,20-dione, 9-fluoro-11,17,21-trihydroxy-16-methyl-, (11β,16β)-[CAS] | 378-44-9 | | Formulation, dermal, topical | Psoriasis |
| Betamipron | | 3440-28-6 3734-24-5 | | | |
| Betasine | | | | | |
| betaxolol | 2-Propanol, 1-[4-[2-(cyclopropylmethoxy)ethyl]phenoxy]-3-[(1-methylethyl)amino]-[CAS] | 63659-18-7 63659-19-8 | U.S. 4,252,984 | Antihypertensive, adrenergic | Hypertension, general, glaucoma |
| Betazole | | 105-20-4 | | | |
| Bethanechol | | 590-63-6 | | | |
| Bethanidine | | 55-73-2 | | | |
| Betoxycaine | | 3818-62-0 | | | |
| β-Eucaine | | 500-34-5 | | | |
| bevantolol | 2-Propanol, 1-[[2-(3,4-dimethoxyphenyl)ethyl]amino]-3-(3-methylphenoxy)-[CAS] | 42864-78-8 59170-23-9 | U.S. 3,857,891 | Antihypertensive, adrenergic | Hypertension, general |
| Bevonium | | 5205-82-3 | | | |
| bexarotene | Benzoic acid 4-(1-(5,6,7,8-tetrahydro-3,5,5,8,8-pentamethyl-2-naphthalenyl)-[CAS] | 153559-49-0 | WO 9321146 | Anticancer, other | Cancer, lymphoma, T-cell |
| benzafibrate | Propanoic acid, 2-[4-[2-[(4-chlorobenzoyl)amino]ethyl]phenoxy]-2-methyl-[CAS] | 41859-67-0 | GB 1359264 | Hypolipaemic/Antiatherosclerosis | |
| Bezitramide | | 15301-48-1 | | | |
| BG-9928 | | 166374-48-7 | | Cardiostimulant | Heart failure |
| BIA-2-024 | 10,11-dihydro-10-hydroxyimino-5H-dibenz/b,f/azepine-5-carboxamide | 199997-15-4 | WO 9745416 | Antiepileptic | Epilepsy, general |
| BIA-2-093 | (S)-(−)-10-acetoxy-10,11-dihydro-5H-dibenzo/b,f/azepine-5-carboxamide-[CAS] | 236395-14-5 | | Antiepileptic | Epilepsy, general |
| BIA-3-202 | 1-(3,4-dihydroxy-5-nitrophenyl)-2-phenyl-ethanone | 274925-86-9 | EP 1010688 | Antiparkinsonian | Parkinson's disease |
| Bialamicol | | 493-75-4 | | | |
| biapenem | 5H-Pyrazolo[1,2-a][1,2,4]triazol-4-ium, 6-[[2-carboxy-6-(1-hydroxyethyl)-4-methyl-7-oxo-1-azabicyclo[3.2.0]hept-2-en-3-yl]thio]-6,7-dihydro-, hydroxide, inner salt, [4R-[4Alpha,5β,6β(R*)]]-[CAS] | 120410-24-4 | EP 289801 | Beta-lactam antibiotic | Infection, beta-lactamase resistant |
| Bibenzonium | | 15585-70-3 | | | |
| Bibrocathol | | 6915-57-7 | | | |
| bicalutamide | Propanamide, N-[4-cyano-3-(trifluoromethyl)phenyl]-3-[(4-fluorophenyl)sulfonyl]-2-hydroxy-2-methyl-, (+/−)-[CAS] | 90357-06-5 | EP 100172 | Anticancer, hormonal | Cancer, prostate |

TABLE IV-continued

| API Generic Name | API Chemical Name | CAS No. | Patent Reference | Example of Therapeutic Use | Example of Indication |
|---|---|---|---|---|---|
| bicifadine | 3-Azabicyclo[3.1.0]hexane, 1-(4-methylphenyl)-, (+/−)-[CAS] | 66504-75-4<br>71195-57-8 | DE 2740562 | Analgesic, other | Pain, general |
| bicyclic monoterpene diols | | | U.S. 6,294,585 | Dermatological | Unspecified |
| Bidisomide | | 116078-65-0 | | | |
| Bietamiverine | | 479-81-2 | | | |
| Bietanautine | | 6888-11-5 | | | |
| Bietaserpine | | 53-18-9 | | | |
| bifermelane | 1-Butanamine, N-methyl-4-[2-(phenylmethyl)phenoxy]-, hydrochloride [CAS] | 62232-46-6<br>90293-01-9 | GB 1512880 | Cognition enhancer | Attention deficit disorder |
| Bifluranol | | 34633-34-6 | | | |
| bifonazole | 1H-Imidazole, 1-([1,1'-biphenyl]-4-ylphenylmethyl)-[CAS] | 60628-96-8<br>60629-08-5<br>60629-09-6 | U.S. 4,118,487 | Antifungal | Infection, fungal, general |
| bimatoprost | 5-Heptenamide, 7-(3,5-dihydroxy-2-(3-hydroxy-5-phenyl-1-pentenyl)cyclopentyl)-N-ethyl(1R-(1Alpha(Z)2β(1E,3S,3Alpha,5Alpha))[CAS] | 155206-00-1 | U.S. 5,688,819 | Prostaglandin | Glaucoma |
| bimoclomol | N-[2-hydroxy-3-(1-piperidinyl)propoxy]-3-pyridinecarboximidoyl chloride, (Z)-2-butanedioate (1:1) | 130493-04-8 | U.S. 5,147,874 | Symptomatic antidiabetic | Neuropathy, diabetic |
| bimosiamose | (1,1'-Biphenyl)-3-acetic acid, 3',3'''-(1,6-hexanediyl)bis(6-Alpha-D-mannopyranosyloxy)-, [CAS] | 187269-40-5 | U.S. 5,444,050 | Antiasthma | Asthma |
| Binifibrate | | 69047-39-8 | | | |
| binodenoson | Adenosine, 2-((cyclohexylmethylene)hydrazino)-[CAS] | 144348-08-3 | | Vasodilator, coronary | Diagnosis, coronary |
| Biomed-101 | | 58-85-5 | U.S. 6,423,744 | Anticancer, other | Cancer, renal |
| Biotin | | 514-65-8 | | | |
| Biperiden | | | | | |
| birlcodar | 2-Piperidinecarboxylic acid, 1-(oxo(3,4,5-trimethoxyphenyl)acetyl)-,4-(3-pyridinyl)-1-(3-(3-pyridinyl)propyl)butyl ester, (S)-, 2-hydroxy-1,2,3-propanetricarboxylate (1:2) [CAS] | 174254-13-8<br>159997-94-1 | | Radio/ chemosensitizer | Cancer, breast |
| biriperone | 1-Butanone, 1-(4-fluorophenyl)-4-(3,4,6,7,12,12a-hexahydropyrazino[1',2':1,6]pyrido[3,4-b]indol-2(1H)-yl)-[CAS] | 42021-34-1 | DE 2333922 | Neuroleptic | |
| Bisacodyl | | 603-50-9 | | | |
| Bisantrene | | 78186-34-2 | | | |
| Bisbentiamine | | 2667-89-2 | | | |
| Bisdequalinium | | 52951-36-7 | | | |
| Bismuth Aluminate | | 12284-76-3 | | | |
| Bismuth Butylthiolaurate | | 53897-25-9 | | | |
| Bismuth Ethyl Camphorate | | 52951-37-8 | | | |

TABLE IV-continued

| API Generic Name | API Chemical Name | CAS No. | Patent Reference | | Example of Therapeutic Use | Example of Indication |
|---|---|---|---|---|---|---|
| Bismuth Iodosubgallate | | 138-58-9 | | | | |
| Bismuth Sodium Iodide | | 53778-50-0 | | | | |
| Bismuth Sodium Triglycollamate | | 5798-43-6 | | | | |
| Bismuth Subcarbonate | | 5892-10-4 | | | | |
| Bismuth Subgallate | | 22650-86-8 | | | | |
| Bismuth Subnitrate | | 1304-85-4 | | | | |
| Bismuth Subsalicylate | | 14882-18-9 | | | | |
| Bismuth Tribromophenate | | 5175-83-7 | | | | |
| bisoprolol | 2-Propanol, 1-[4-[[2-(1-methylethoxy)ethoxy]methyl]phenoxy]-3-[(1-methylethyl)amino]-[CAS] | 104344-23-2 66722-44-9 | GB | 1532380 | Antihypertensive, adrenergic | Heart failure |
| bisoprolol + HCTZ | 2-Propanol, 1-[4-[[2-(1-methylethoxy)ethoxy]methyl]phenoxy]-3-[(1-methylethyl)amino] mixt. with 6-chloro-3,4-dihydro-2H-1,2,4-benzothiadiazine-7-sulfonamide 1,1-dioxide | | | | Formulation, fixed-dose combinations | Hypertension, general |
| bisoprolol + trichloromethiazide | 2-Propanol, 1-[4-[[2-(1-methylethoxy)ethoxy]methyl]phenoxy]-3-[(1-methylethyl)amino] mixt. with 6-chloro-3-(dichloromethyl)-3,4-dihydro-2H-1,2,4-benzothiadiazine-7-sulfonamide 1,1-dioxide | | | | Formulation, fixed-dose combinations | Hypertension, general |
| Bisoxatin | | 14008-48-1 | | | | |
| Bithionol | | 97-18-7 | | | | |
| Bitolterol | | 30392-40-6 | | | | |
| Bitoscanat | | 4044-65-9 | | | | |
| BL-3875 | | | | | | |
| bleomycin | Bleomycin [CAS] | 11056-06-7 9041-93-4 | WO | 0218378 | Anti-inflammatory Formulation, transdermal, enhanced | Unspecified Cancer, head and neck |
| blonanserin | Cycloocta[b]pyridine, 2-(4-ethyl-1-piperazinyl)-4-(4-fluorophenyl)-5,6,7,8,9,10-hexahydro-[CAS] | 132810-10-7 | EP | 385237 | Neuroleptic | Schizophrenia |
| BMS-184476 | | | EP | 639577 | Anticancer, other | Cancer, breast |
| BMS-387032 | cis-(+/-)-2-(Ethylthio)-5,7-dihydroxy-8-(3-hydroxy-1-methyl-4-piperidinyl)-4H-1-benzopyran-4-one | | WO | 9742949 | Anticancer, other | Cancer, general |
| BN-82451 | 4-[2-(aminomethyl)-1,3-thiazol-4-yl]-2,6-di-tert-butylphenol, dihydrochloride | | | | Neuroprotective | Unspecified |
| BNP-7787 | Ethanesulfonic acid, 2,2'-dithiobis-, disodium salt [CAS] | 16208-51-8 | | | Radio/chemoprotective | Chemotherapy-induced nausea and vomiting |
| BO-653 | 5-Benzofuranol, 4,6-bis(1,1-dimethylethyl)-2,3-dihydro-2,2-dipentyl-[CAS] | 157360-23-1 | WO | 9408930 | Hypolipaemic/Antiatherosclerosis | Atherosclerosis |
| Bolandiol | | 19793-20-5 | | | | |

TABLE IV-continued

| API Generic Name | API Chemical Name | CAS No. | Patent Reference | | Example of Therapeutic Use | Example of Indication |
|---|---|---|---|---|---|---|
| Bolasterone | | 1605-89-6 | | | | |
| Boldenone | | 846-48-0 | | | | |
| bopindolol | 2-Propanol, 1-[(1,1-dimethylethyl)amino]-3-[(2-methyl-1H-indol-4-yl)oxy]-, benzoate (ester), (+/−)-[CAS] | 62658-63-3 82857-38-3 | U.S. | 4,340,541 | Antihypertensive, adrenergic | Hypertension, general |
| Bornyl Chloride | | 464-41-5 | | | | |
| Bornyl Salicylate | | 560-88-3 | | | | |
| bortezomib | Boronic acid, [(1R)-3-methyl-1-[[(2S)-1-oxo-3-phenyl-2-[(pyrazinylcarbonyl)amino]propyl]amino]butyl]-[CAS] | 179324-69-7 | U.S. | 6,271,199 | Anticancer, other | Cancer, myeloma |
| Bromocriptine | | 25614-03-3 | | | | |
| Bromo-diphenhydramine | | 118-23-0 | | | | |
| Bromoform | | 75-25-2 | | | | |
| Bromopride | | 4093-35-0 | | | | |
| Bromo-salicychloranilide | | 3679-64-9 | | | | |
| bromperidol | 1-Butanone, 4-[4-(4-bromophenyl)-4-hydroxy-1-piperidinyl]-1-(4-fluorophenyl)-[CAS] | 10457-90-6 | U.S. | 3,438,991 | Neuroleptic | Psychosis, general |
| Brompheniramine | | 86-22-6 | | | | |
| Broparoestrol | | 479-68-5 | | | | |
| Bropirimine | | 56741-95-8 | | | | |
| brostallicin | 4-(2-Bromoacrylamido)-N'''-(2-guanidinoethyl)-1-1',1'',1'''-tetramethyl-N,4':N',4'':N'',4'''-quarter-[pyrrole-2-carboxamide][CAS] | | | | Anticancer, other | Cancer, general |
| brotizolam | 6H-Thieno[3,2-f][1,2,4]triazolo[4,3-a][1,4]diazepine, 2-bromo-4-(2-chlorophenyl)-9-methyl-[CAS] | 57801-81-7 | U.S. | 4,094,984 | Hypnotic/Sedative | |
| Brovincamine | | 57475-17-9 | | | | |
| Brozuridine | | 59-14-3 | | | | |
| Broxyquinoline | | 521-74-4 | | | | |
| Brucine | | 357-57-3 | | | | |
| β-Sitosterol | | 83-46-5 | | | | |
| Bucetin | | 1083-57-4 | | | | |
| Bucillamine | | 65002-17-7 | | | | |
| Bucindolol | | 71119-11-4 | | | | |
| bucladesine | Adenosine, N-(1-oxobutyl)-, cyclic 3',5'-(hydrogen phosphate) 2'-butanoate [CAS] | 362-74-3 | JP | 51113896 | Cardiostimulant | Wound healing |
| Buclizine | | 82-95-1 | | | | |
| Buclosamide | | 575-74-6 | | | | |
| Bucolome | | 841-73-6 | | | | |
| bucricaine | 9-Acridinamine, N-butyl-1,2,3,4-tetrahydro-, monohydrochloride [CAS] | 82636-28-0 | | | Anaesthetic, local | |
| bosentan | Benzenesulfonamide, 4-(1,1-dimethylethyl)-N-[6-(2-hydroxyethoxy)-5-(2-methoxyphenoxy)[2,2'-bipyrimidin]-4-yl]-[CAS] | 147536-97-8 | EP | 633259 | Vasodilator, peripheral | Hypertension, pulmonary |

TABLE IV-continued

| API Generic Name | API Chemical Name | CAS No. | Patent Reference | Example of Therapeutic Use | Example of Indication |
|---|---|---|---|---|---|
| BP2.94 | Phenol, 2-[[[(1R)-2-(1H-imidazol-4-yl)-1-methylethyl]imino]phenylmethyl]-[CAS] | 139191-80-3 | WO 9117146 | Respiratory | Rhinitis, general |
| BP4.897 | N-[4-(2-methoxyphenyl)-1-piperazinyl]butyl]naphthalene-2-carboxamide | | EP 779284 | Dependence treatment | Addiction, cocaine |
| β-Propiolactone | | 57-57-8 | | | |
| Bradycor | | 140661-97-8 | | | |
| Brain Natriuretic Peptide | | 114471-18-0 | | | |
| Brallobarbital | | 561-86-4 | | | |
| brasofensine | 8-Azabicyclo(3.2.1)octane-2-carboxaldehyde, 3-(3,4-dichlorophenyl)-8-methyl-, O-methyloxime, (1R-(1Alpha,2β(E),3Alpha,5Alpha)-[CAS] | 171655-91-7 | WO 9528401 | Antiparkinsonian | Parkinson's disease |
| Brequinar | | 96187-53-0 | | | |
| Bretylium | | 61-75-6 | | | |
| Brilliant Green | | 633-03-4 | | | |
| brimonidine | 6-Quinoxalinamine, 5-bromo-N-(4,5-dihydro-1H-imidazol-2-yl)-[CAS] | 59803-98-4 | DE 2538620 | Antiglaucoma | Glaucoma |
| brinzolamide | 2H-Thieno(3,2-e)-1,2-thiazine-6-sulfonamide, 4-(ethylamino)-3,4-dihydro-2-(3-methoxypropyl)-, 1,1-dioxide, (R)-[CAS] | 138890-62-7 | U.S. 5,378,703 | Antiglaucoma | Glaucoma |
| brivudin | Uridine, 5-(2-bromoethenyl)-2'-deoxy, (E)-[CAS] | 69304-47-8 | | Antiviral, other | Infection, varicella zoster virus |
| Brodimoprin | | 56518-41-3 | | | |
| Bromazepam | | 1812-30-2 | | | |
| bromfenac | Benzeneacetic acid, 2-amino-3-(4-bromobenzoyl)-[CAS] | 91714-93-1 91714-94-2 | | Formulation, mucosal, topical | Inflammation, ocular |
| Bromhexine | | 3572-43-8 | | | |
| Bromindione | | 1146-98-1 | | | |
| Bromisovalum | | 496-67-3 | | | |
| Bucumolol | | 58409-59-9 | | | |
| budesonide | Pregna-1,4-diene-3,20-dione, 16,17-[butylidenebis(oxy)]-11,21-dihydroxy-, (11β,16Alpha)-[CAS] | 51333-22-3 | GB 1429922 | Antiasthma | Asthma |
| budesonide + formoterol | Pregna-1,4-diene-3,20-dione, 16,17-[butylidenebis(oxy)]-11,21-dihydroxy-, (11β,1bAlpha) + formamide, N-[2-hydroxy-5-[1-hydroxy-2-[[2-(4-methoxyphenol)-1-methylethyl]amino]ethyl]phenyl]-(R*,R*)-(±) | | | Formulation, fixed-dose combinations | Asthma |
| budipine | Piperidine, 1-(1,1-dimethylethyl)-4,4-diphenyl-[CAS] | 57982-78-2 | DE 2825322 | Antiparkinsonian | Parkinson's disease |
| Budralazine | | 63661-61-0 | | | |
| Bufeniode | | 36798-79-5 | | | |
| Bufetolol | | 22103-14-6 53684-49-4 | | | |

TABLE IV-continued

| API Generic Name | API Chemical Name | CAS No. | Patent Reference | | Example of Therapeutic Use | Example of Indication |
|---|---|---|---|---|---|---|
| bufexamac | p-butoxyacetohydroxamic acid | 2438-72-4 | U.S. | 3,479,396 | Anti-inflammatory | |
| buflomedil | 1-Butanone, 4-(1-pyrrolidinyl)-1-(2,4,6-trimethoxyphenyl)-[CAS] | 35543-24-9 55837-25-7 | GB | 1325192 | Vasodilator, peripheral | |
| Buformin | | 692-13-7 | | | | |
| Bufuralol | | 54340-62-4 | | | | |
| Bumadizon | | 3583-64-0 | | | | |
| bumetanide | Benzoic acid, 3-(aminosulfonyl)-5-(butylamino)-4-phenoxy-[CAS] | 28395-03-1 | U.S. | 3,806,534 | Antihypertensive, diuretic | Hypertension, general |
| bunaftine | 1-Naphthalenecarboxamide, N-butyl-N-[2-(diethylamino)ethyl]-[CAS] | 32421-46-8 | DE | 2009894 | Antiarrhythmic | |
| Bunamiodyl Sodium | | | | | | |
| bunazosin | 1H-1,4-Diazepine, 1-(4-amino-6,7-dimethoxy-2-quinazolinyl)hexahydro-4-(1-oxobutyl)-[CAS] | 1923-76-8 52712-76-2 80755-51-7 | GB | 1398455 | Antihypertensive, adrenergic | Hypertension, general |
| bunitrolol | Benzonitrile, 2-[3-[(1,1-dimethylethyl)amino]-2-hydroxypropoxy]-[CAS] | 34915-68-9 | U.S. | 3,940,489 | Antihypertensive, adrenergic | |
| bupivacaine | 2-Piperidinecarboxamide, 1-butyl-N-(2,6-dimethylphenyl)-[CAS] | 38396-39-3 2180-92-9 | | | Formulation, modified-release, >24 hr | Anaesthesia |
| Bupranolol | | 14556-46-8 | | | | |
| buprenorphine | 6,14-Ethenomorphinan-7-methanol, 17-(cyclopropylmethyl)-Alpha-(1,1-dimethylethyl)-4,5-epoxy-18,19-dihydro-3-hydroxy-6-methoxy-Alpha-methyl-,[5Alpha,7Alpha(S)]-[CAS] | 52485-79-7 53152-21-9 | U.S. | 3,433,791 | Analgesic, other | |
| bupropion | 1-Propanone, 1-(3-chlorophenyl)-2-[(1,1-dimethylethyl)amino]-, (+/−)-[CAS] | 31677-93-7 34911-55-2 4663-83-6 | U.S. | 4,425,363 | Antidepressant | Depression, general |
| Buramate | | | | | | |
| buserelin | Luteinizing hormone-releasing factor (pig), 6-[O-(1,1-dimethylethyl)-D-serine]-9-(N-ethyl-L-prolinamide)-10-deglycinamide-[CAS] | 57982-77-1 68630-75-1 | GB | 1523623 | Releasing hormones | Cancer, prostate |
| buspirone | 8-Azaspiro[4.5]decane-7,9-dione, 8-[4-[4-(2-pyrimidinyl)-1-piperazinyl]butyl]-[CAS] | 36505-84-7 | EP | 276536 | Anxiolytic | Anxiety, general |
| busulfan | 1,4-Butanediol, dimethanesulfonate [CAS] | 55-98-1 | | | Formulation, optimized, microparticles | Cancer, general |
| busulfan | 1,4-Butanediol, dimethanesulfonate [CAS] | 55-98-1 | | | Formulation, parenteral, other | Cancer, leukaemia, acute myeolgenous |
| Butabarbital | | 143-81-7 | | | | |
| Butacaine | | 149-16-6 | | | | |
| Butacetin | | 2109-73-1 | | | | |
| Butalamine | | 22131-35-7 | | | | |
| Butalbital | | 77-26-9 | | | | |
| Butallylonal | | 1142-70-7 | | | | |

TABLE IV-continued

| API Generic Name | API Chemical Name | CAS No. | Patent Reference | | Example of Therapeutic Use | Example of Indication |
|---|---|---|---|---|---|---|
| butamben | 4-Aminobenzoic acid butyl ester [CAS] | 94-25-7 | | | Formulation, modified-release, other | Pain, cancer |
| butamirate | Benzeneacetic acid, Alpha-ethyl-, 2-[2-(diethylamino)ethoxy]ethylester, 2-hydroxy-1,2,3-propanetricarboxylate (1:1) [CAS] | 18109-80-3<br>18109-81-4 | | | Antitussive | Cough |
| Butanilicaine | | 3785-21-5 | | | | |
| Butaperazine | | 653-03-2 | | | | |
| Butaverine | | 55837-14-4 | | | | |
| Butazolamide | | 16790-49-1 | | | | |
| Butedronic Acid | | 51395-42-7 | | | | |
| butenafine | 1-Naphthalenemethanamine, N-(4-(1,1-dimethylethyl)phenyl)methyl)-N-methyl- [CAS] | 101827-46-7<br>101828-21-1 | EP | 164697 | Antifungal | Infection, dermatological |
| Butethal | | 77-28-1 | | | | |
| Butethamate | | 14007-64-8 | | | | |
| Butethamine | | 2090-89-3 | | | | |
| Buthalital | | 510-90-7 | | | | |
| Buthiazide | | 2043-38-1 | | | | |
| Butibufen | | 55837-18-8 | | | | |
| Butidrine | | 1506-12-3 | | | | |
| butobendine | benzoic acid, 3,4,5-trimethoxy-, 1,2-ethanediylbis[(methylimino)(2-ethyl-2,1-ethanediyl)]ester, [S-(R*,R*)]-[CAS] | 55769-64-7<br>55769-65-8 | U.S. | 4,012,473 | Antiarrhythmic | Arrhythmia, general |
| butoconazole | 1H-Imidazole, 1-[4-(4-chlorophenyl)-2-[(2,6-dichlorophenyl)thio]butyl]-, (+/-)- [CAS] | 64872-76-0<br>64872-77-1 | GB | 1567431 | Antifungal | Infection, Candida, general |
| Butoctamide | | 32838-26-9 | | | | |
| Butofilolol | | 64552-17-6 | | | | |
| butorphanol | Morphinan-3,14-diol, 17-(cyclobutylmethyl)-, [S-(R*,R*)]-2,3-dihydroxybutanedioate (1:1) (salt) [CAS] | 42408-82-2<br>58786-99-5 | GB | 1412129 | Analgesic, other | |
| Butoxycaine | | 3772-43-8 | | | | |
| Butriptyline | | 35941-65-2 | | | | |
| Butropium | | 29025-14-7 | | | | |
| Buzepide | | 3691-21-2 | | | | |
| BVT-5182 | | | WO | 0208178 | Anorectic/Antiobesity | Obesity |
| BXT-51072 | 2H-1,2-Benzoselenazine, 3,4-dihydro-4,4-dimethyl-[CAS] | 173026-17-0 | | | GI inflammatory/bowel disorders | Colitis, ulcerative |
| C-1311 | 6H-Imidazo[4,5,1-de]acridin-6-one, 5-[[2-(diethylamino)ethyl]amino]-8-hydroxy-, 2HCl, 2H2O | | | | Anticancer, other | Cancer, general |
| cabergoline | Ergoline-8-carboxamide, N-[3-(dimethylamino)propyl]-N-[(ethylamino)carbonyl]-6-(2-propenyl)-, (8β)-[CAS] | 81409-90-7<br>85329-89-1 | GB | 2103603 | Antiprolactin | Galactorrhoea |
| Cabergoline | | 81409-90-7 | | | | |
| Cacodylic Acid | | 75-60-5 | | | | |
| Cactinomycin | | 8052-16-2 | | | | |

TABLE IV-continued

| API Generic Name | API Chemical Name | CAS No. | Patent Reference | Example of Therapeutic Use | Example of Indication |
|---|---|---|---|---|---|
| cadexomer iodine | Cadexomer iodine [CAS] | 94820-09-4 | | Anti-infective, other | Ulcer, venostasis |
| Cadmium Salicylate | | 19010-79-8 | | | |
| Cadralazine | | 64241-34-5 | | | |
| Cafaminol | | 30924-31-3 | | | |
| caffeine | 1,2,3,-Propanetricarboxylic acid, 2-hydroxy mixt. with 3,7-dihydro-1,4,7-trimethyl-1H-purine-2,6-dione [CAS] | 69-22-7 58-08-2 | | Respiratory | Apnoea |
| Calcifediol | | 19356-17-3 | | | |
| Calcipotriene | | 112965-21-6 | | | |
| calcipotriol | 9,10-Secochola-5,7,10(19),22-tetraene-1,3,24-triol, 24-cyclopropyl-, (1Alpha,3β,5Z,7E,22E)-[CAS] | 112965-21-6 | WO 8700834 | Antipsoriasis | Psoriasis |
| calcipotriol + beclometasone | 9,10-Secochola-5,7,10(19),22-tetraene-1,3,24-triol, 24-cyclopropyl-, (1Alpha,3β,5Z,7E,22E) + Pregna-1,4-diene-3,20-dione, 9-chloro-11β,17,21-trihydroxy-16β-methyl, 17,21-dipropionate | | | Formulation, fixed-dose combinations | Psoriasis |
| calcitriol | 9,10-Secocholesta-5,7,10(19)-triene-1,3,25-triol, (1Alpha,3β,5Z,7E)-[CAS] | 32222-06-3 | | Antipsoriasis | Psoriasis |
| Calcium 3-Aurothio-2-propanol-1-sulfonate | | 5743-29-3 | | | |
| Calcium Acetylsalicylate | | 69-46-5 | | | |
| Calcium Bromolactobionate | | 33659-28-8 | | | |
| Calcium Carbonate | | 471-34-1 | | | |
| Calcium Gluconate | | 299-28-5 | | | |
| Calcium N-Carbamoylaspartate | | 27214-00-2 | | | |
| Calcium Glycerophosphate | | | | | |
| calcium hopantothenate | Calcium D-(+)-4-(2,4-dihydroxy-3,3-dimethylbutyramido)butyrate (hemihydrate) [CAS] | 17097-76-6 | EP 117260 | Neurological | Attention deficit disorder |
| Calcium Iodobehenate | | 1319-91-1 | | | |
| Calcium Iodosterate | | 1301-16-2 | | | |
| Calcium Lactate | | 814-80-2 | | | |
| Calcium Levulinate | | 591-64-0 | | | |
| Calcium Mesoxalate | | 21085-60-9 | | | |
| Calcium N-Carbamoylaspartate | | 16649-79-9 | | | |
| calcium polycarbophil | Polycarbophil, calcium salt-[CAS] | 126040-58-2 9003-97-9 | | GI inflammatory/bowel disorders | Irritable bowel syndrome |
| Calcium Propionate | | 4075-81-4 | | | |
| Calcium Succinate | | 140-99-8 | | | |
| caldaret | 5-methyl-2-(1-piperazinyl)-benzenesulfonic acid monohydrate | 133804-44-1 | | Cardiostimulant | Heart failure |
| Calusterone | | 17021-26-0 | | | |
| Camazepam | | 36104-80-0 | | | |

TABLE IV-continued

| API Generic Name | API Chemical Name | CAS No. | Patent Reference | | Example of Therapeutic Use | Example of Indication |
|---|---|---|---|---|---|---|
| camostat | Benzeneacetic acid, 4-[[(aminoiminomethyl)amino]benzoyl]oxy]-, 2-(diethylamino)-2-oxoethyl ester, monomethanesulfonate [CAS] | 59721-28-7 59721-29-8 71079-09-9 | U.S. | 4,021,472 | GI inflammatory/ bowel disorders | Pancreatitis |
| Camphor | | 76-22-2 | | | | |
| Camphotamide | | 4876-45-3 | | | | |
| camptothecin | 4-Ethyl-4-hydroxy-1H-pyrano[3'4':6,7]indolizino[1,2-b]quinoline-3,14(4H,12H)-dione | | | | Formulation, optimized, microemulsion | Cancer, general |
| Candesartan candesartan cilexetil | 1H-Benzimidazole-7-carboxylic acid, 2-ethoxy-1-[[2'-(1H-tetrazol-5-yl)[1,1'-biphenyl]-4-yl]methyl]-, 1-[[(cyclohexyloxy)carbonyl]oxy]ethyl ester, (+/-)-[CAS] | 139481-59-7 145040-37-5 | EP | 520423 | Antihypertensive, renin system | Hypertension, general |
| Candoxatril canertinib | N-[4-(3-Chloro-4-fluoro-phenylamino)-7-(3-morpholin-4-yl-propoxy)-quinazolin-6-yl]-acrylamide | 123122-55-4 289499-45-2 | | | Anticancer, other | Cancer, lung, non-small cell |
| Canrenone | | 976-71-6 | | | | |
| Cantharidin | | 56-25-7 | | | | |
| cantuzumab mertansine | Maytansine, N2-deacetyl-N2-(3-mercapto-1-oxopropyl)-, conjugated humanized C242 monoclonal antibody | 139504-50-0 | | | Immunotoxin | Cancer, colorectal |
| capecitabine | Cytidine, 5'-deoxy-5-fluoro-N-[(pentyloxy)carbonyl]-[CAS] | 154361-50-9 | EP | 602454 | Anticancer, antimetabolite | Cancer, breast |
| Capobenic Acid | | 21434-91-3 | | | | |
| capravirine | 1H-imidazole-2-methanol, 5-(3,5-dichlorophenyl)thio-4-(1-methylethyl)-1-(4-pyridinyl)methyl carbamate (ester) [CAS] | 178979-85-6 | | | Antiviral, anti-HIV | Infection, HIV/AIDS |
| Capromab capsaicin cream | N-[(4-hydroxy-3-methoxyphenyl)methyl]-8-methyl-, (E)-[CAS] | 151763-64-3 404-86-4 | | | Formulation, dermal, topical | Pain, postherpetic |
| Captodiamine | | 486-17-9 | | | | |
| captopril | L-Proline, 1-(3-mercapto-2-methyl-1-oxopropyl)-, (S)-[CAS] | 62571-86-2 | U.S. | 4,105,776 | Antihypertensive, renin system | Hypertension, general |
| captopril + HCTZ | L-Proline, 1-(3-mercapto-2-methyl-1-oxopropyl)-, (S)-, mixt. with 6-chloro-3,4-dihydro-2H-1,2,4-benzothiadiazine-7-sulfonamide 1,1-dioxide [CAS] | 110075-07-5 | U.S. | 4,217,347 | Antihypertensive, renin system | |
| Capuride carabersat | Benzamide, N-(6-acetyl-3,4-dihydro-3-hydroxy-2,2-dimethyl-2H-1-benzopyran-4-yl)-4-fluoro, (3R-trans)-[CAS] | 5579-13-5 184653-84-7 | | | Antiepileptic | Epilepsy, general |
| Caramiphen | | 77-22-5 | | | | |
| carazolol | 2-Propanol, 1-(9H-carbazol-4-yloxy)-3-[(1-methylethyl)amino]-[CAS] | 57775-29-8 | DE | 2240599 | Antihypertensive, adrenergic | |
| Carbachol | | 51-83-2 | | | | |

TABLE IV-continued

| API Generic Name | API Chemical Name | CAS No. | Patent Reference | Example of Therapeutic Use | Example of Indication |
|---|---|---|---|---|---|
| carbamazepine | 5H-Dibenz[b.f]azepine-5-carboxamide [CAS] | 298-46-4 | | Formulation, modified-release, other | Epilepsy, general |
| Carbamide Peroxide | | 124-43-6 | | | |
| Carbarsone | | 121-59-5 | | | |
| Carbaryl | | 63-25-2 | | | |
| Carbazochrome | | 13051-01-9 | | | |
| carbendazim | Methyl-2-benzimidazolecarbamate | 51460-26-5 | | Anticancer, other | Cancer, general |
| Carbenicillin | | 4697-36-3 | | | |
| Carbenoxolone | | 5697-56-3 | | | |
| Carbetapentane | | 77-23-6 | | | |
| Carbicarb | Carbonic acid disodium salt, mixt. with monosodium salt-[CAS] | 72227-05-5 | | Alimentary/Metabolic, other | Acidosis |
| Carbidopa carbidopa + levodopa-1 | S-Alpha Hydrazino-3,4-dihydroxy-Alpha methyl benzene propanoic acid monohydrate + 3-hydroxy-L-tyrosine | 28860-95-9 | | Formulation, fixed-dose combinations | Parkinson's disease |
| Carbimazole | | 22232-54-8 | | | |
| Carbinoxamine | | 486-16-8 | | | |
| Carbocloral | | 541-79-7 | | | |
| carbocysteine | | 151756-26-2 638-23-3 | EP 546272 | Cystic fibrosis treatment | Cystic fibrosis |
| Carbon Tetrachloride | | 56-23-5 | | | |
| carboplatin | Platinum, diammine[1,1-cyclobutanedicarboxylate(2-)]-, (SP-4-2)-[CAS] | 41575-94-4 | | Anticancer, alkylating | Cancer, ovarian |
| Carboprost | Prosta-5,13-dien-1-oic acid, 9,11,15-trihydroxy-15-methyl-, (5Z,9.alpha.,11Alpha,13E,15S)-, compd. with 2-amino-2-(hydroxymethyl)-1,3-propanediol(1:1) [CAS] | 35700-23-3 58551-69-2 74849-93-7 | U.S. 3,728,382 | Prostaglandin | Abortion |
| carboprost trometamol | | | | | |
| Carboquone | 2,5-Cyclohexadiene-1,4-dione, 2-[2-[(aminocarbonyl)oxy]-1-methoxyethyl]-3,6-bis(1-aziridinyl)-5-methyl-[CAS] | 24279-91-2 | DE 1905224 | Anticancer, antibiotic | |
| Carbromal | | 77-65-6 | | | |
| Carbubarb | | 960-05-4 | | | |
| Carbutamide | | 339-43-5 | | | |
| Carbuterol | | 34866-47-2 | | | |
| Carfimate | | 3567-38-2 | | | |
| carglumic acid | N-Carbamoyl-L-glutamic acid | 1188-38-1 | | Metabolic and enzyme disorders | Hyper-ammonaemia |
| Cargutocin | | 33605-67-3 | | | |
| Carindacillin | | 35531-88-5 | | | |
| cariporide | Benzamide, N-(aminoiminomethyl)-4-(1-methylethyl)-3-(methylsulfonyl)-[CAS] | 159138-80-4 159138-81-5 | EP 589336 | Antianginal | Angina, general |
| Cariporide | | 159138-80-4 | | | |
| Carisoprodol | | 78-44-4 | | | |

TABLE IV-continued

| API Generic Name | API Chemical Name | CAS No. | Patent Reference | Example of Therapeutic Use | Example of Indication |
|---|---|---|---|---|---|
| carmofur | 1(2H)-Pyrimidinecarboxamide, 5-fluoro-N-hexyl-3,4-dihydro-2,4-dioxo-[CAS] | 61422-45-5 | U.S. 4,071,519 | Anticancer, antimetabolite | |
| Carmoxirole | | 98323-83-2 | | | |
| carmustine | Urea, N,N'-bis(2-chloroethyl)-N-nitroso-[CAS] | 154-93-8 | | Formulation, implant | Cancer, brain |
| Carnitine | | 461-06-3 | | | |
| Caroverine | | 23465-76-1 | | | |
| Caroxazone | | 18464-39-6 | | | |
| Carphenazine | | 2622-30-2 | | | |
| Carpipramine | | 5942-95-0 | | | |
| carprofen | 9H-Carbazole-2-acetic acid, 6-chloro-Alpha-methyl-, (+/−)-[CAS] | 53716-49-7 | U.S. 3,896,145 | Anti-inflammatory | |
| Carsalam | | 2037-95-8 | | | |
| carteolol | 2(1H)-Quinolinone, 5-[3-[(1,1-dimethylethyl)amino]-2-hydroxypropoxy]-3,4-dihydro-, monohydrochloride [CAS] | 51781-06-7 51781-21-6 | U.S. 3,910,924 | Antihypertensive, adrenergic | Glaucoma |
| Carticaine | | 23964-58-1 | | | |
| Carubicin | | 50935-04-1 | | | |
| Carumonam | | 87638-04-8 | | | |
| Carvacrol | | 499-75-2 | | | |
| carvedilol | 2-Propanol, 1-(9H-carbazol-4-yloxy)-3-[[2-(2-methoxyphenoxy)ethyl]amino]-[CAS] | 72956-09-3 | EP 4920 | Antihypertensive, adrenergic | Hypertension, general |
| Carvone | | 99-49-0 | | | |
| Cascarillin | | 10118-56-6 | | | |
| caspofungin | Pneumocandin B0, 1-((4R,5S)-5-((2-aminoethyl)amino)-N2-(10,12-dimethyl-1-oxotetradecyl)-4-hydroxy-L-ornithine)-5-(threo-3-hydroxy-L-ornithine)-, diacetate (salt) [CAS] | 162808-62-0 179463-17-3 | WO 9421677 | Antifungal | Infection, Aspergillus |
| Catechin | | 154-23-4 | | | |
| cathepsin K inhibitors | N-(1-benzothien-2-ylcarbonyl)-N-[2-(2-fluorophenyl)-4-oxo-1,2,3,4-tetrahydropyrimidin-5-yl]-L-leucinamide | | WO 9613523 | Osteoporosis treatment | Osteoporosis |
| cathepsin S inhibitors | N-(1-benzothien-2-ylcarbonyl)-N-[2-(2-fluorophenyl)-4-oxo-1,2,3,4-tetrahydropyrimidin-5-yl]-L-leucinamide | | | Antiasthma | Asthma |
| CC-401 | | | U.S. 6,342,595 | Immunosuppressant | Arthritis, rheumatoid |
| CCI-779 | Rapamycin 42-(3-hydroxy-2-(hydroxymethyl)-2-methylpropanoate) [CAS] | 162635-04-3 | | Anticancer, antibiotic | Cancer, renal |
| CCR5 antagonists | | | WO 9732019 | Antiviral, anti-HIV | Infection, HIV/AIDS |
| CDC-394 | | | U.S. 634061 | Anticancer, other | Cancer, myeloma |
| CDC-801 | | | U.S. 5,605,914 | GI inflammatory/ bowel disorders | Crohn's disease |
| CEE-03-310 | 1H-3-Benzazepin-7-ol, 5-(2,3-dihydro-7-benzofuranyl)-2,3,4,5,-tetrahydro-3-methyl-8-nitro, (5S)-[CAS] | 128022-68-4 | EP 347672 | Dependence treatment | Addiction, alcohol |

TABLE IV-continued

| API Generic Name | API Chemical Name | CAS No. | Patent Reference | | Example of Therapeutic Use | Example of Indication |
|---|---|---|---|---|---|---|
| cefaclor | 5-Thia-1-azabicyclo[4.2.0]oct-2-ene-2-carboxylic acid, 7-[(aminophenylacetyl)amino]-3-chloro-8-oxo-, [6R-[6Alpha,7β(R*)]]-[CAS] | 53994-73-3 70356-03-5 | GB | 1461323 | Cephalosporin, oral | Infection, *Haemophilus influenzae prophylaxis* |
| cefadroxil | 5-Thia-1-azabicyclo[4.2.0]oct-2-ene-2-carboxylic acid, 7-[[amino(4-hydroxyphenyl)acetyl]amino]-3-methyl-8-oxo-, [6R-[6Alpha,7β(R*)]]-[CAS] | 50370-12-2 66592-87-8 | GB | 1240687 | Cephalosporin, oral | Infection, general |
| cefalexin | 5-Thia-1-azabicyclo[4.2.0]oct-2-ene-2-carboxylic acid, 7-[(aminophenylacetyl)amino]-3-methyl-8-oxo-, [CAS] | 105879-42-3 15686-71-2 | U.S. | 4,775,751 | Cephalosporin, oral | Infection, respiratory tract, upper |
| cefalexin pivoxil | 5-Thia-1-azabicyclo[4.2.0]oct-2-ene-2-carboxylic acid, 7-[(aminophenylacetyl)amino]-3-methyl-8-oxo-, (2,2-dimethyl-1-oxopropoxy)methyl ester, monohydrochloride, [6R-[6Alpha,7β(R*)]]-[CAS] | 27726-31-4 | | | Cephalosporin, oral | Infection, general |
| cefamandole | 7-D-mandelamido-3[[(1-methyl-1H-tetrazol-5-yl)thio]methyl]-3-cephem-4-carboxylic acid | 34444-01-4 | U.S. | 3,641,021 | Cephalosporin, injectable | Infection, general |
| cefatrizine | 5-Thia-1-azabicyclo[4.2.0]oct-2-ene-2-carboxylic acid, 7-[[amino(4-hydroxyphenyl)acetyl]amino]-8-oxo-3-[(1H-1,2,3-triazol-4-yl)thio]methyl]-, [6R-[6Alpha,7β(R*)]]-[CAS] | 51627-14-6 | GB | 1460914 | Cephalosporin, oral | Infection, general |
| Cefazedone Cefazolin Cefbuperazone | | 56187-47-4 25953-19-9 76610-84-9 | | | | |
| cefcapene pivoxil | 7β-[(Z)-2-(2-amino-4-thiazolyl)-2-pentenoyl)amino]-3-carbamoyloxymethyl-3-cephem-4-carboxylic acid, pivaloyloxymethyl ester HCl-[CAS] | 105889-45-0 105889-46-1 | GB | 2173194 | Cephalosporin, oral | Infection, respiratory tract, general |
| Cefclidin cefdinir | 5-Thia-1-azabicyclo[4.2.0]oct-2-ene-2-carboxylic acid, 7-[[(2-amino-4-thiazolyl)(hydroxyimino)acetyl]amino]-3-ethenyl-8-oxo-, [6R-[6Alpha,7β(Z)]]-[CAS] | 105239-91-6 91832-40-5 | EP | 105459 | Cephalosporin, oral | Infection, dermatological |
| cefditoren pivoxil | 5-Thia-1-azabicyclo[4.2.0]oct-2-ene-2-carboxylic acid, 7-[[(2-amino-4-thiazolyl)(methoxyimino)acetyl]amino]-3-[(4-methyl-5-thiazolyl)ethenyl]-8-oxo-, (2,2-dimethyl-1-oxopropoxy)methyl ester, [6R-[3(Z),6Alpha,7β(Z)]]-[CAS] | 104145-95-1 104146-53-4 117467-28-4 | JP | 61178991 | Cephalosporin, oral | Infection, general |
| cefepime | Pyrrolidinium, 1-[[7-[[(2-amino-4-thiazolyl)(methoxyimino)acetyl]amino]-2-carboxy-8-oxo-5-thia-1-azabicyclo[4.2.0]oct-2-en-3-yl]methyl]-1-methyl-, hydroxide, inner salt, [6R-[6Alpha,7β(Z)]]-[CAS] | 107648-80-6 123171-59-5 88040-23-7 | EP | 531981 | Cephalosporin, injectable | Infection, respiratory tract, lower |

TABLE IV-continued

| API Generic Name | API Chemical Name | CAS No. | Patent Reference | | Example of Therapeutic Use | Example of Indication |
|---|---|---|---|---|---|---|
| Cefetamet cefetamet pivoxil | 5-Thia-1-azabicyclo[4.2.0]oct-2-ene-2-carboxylic acid, 7-[[(2-amino-4-thiazolyl)(methoxyimino)acetyl]amino]-3-methyl-8-oxo-, (2,2-dimethyl-1-oxopropoxy)methyl ester, monohydrochloride, [6R-[6Alpha,7β(Z)]]-[CAS] | 65052-63-3 111696-23-2 | GB | 1581854 | Cephalosporin, oral | Infection, general |
| cefixime | 5-Thia-1-azabicyclo[4.2.0]oct-2-ene-2-carboxylic acid, 7-[[(2-amino-4-thiazolyl)[(carboxymethoxy)imino]acetyl]-amino]-3-ethenyl-8-oxo-, [6R-[6Alpha,7β(Z)]]-[CAS] | 79350-37-1 | EP | 30630 | Cephalosporin, oral | Infection, general |
| cefmenoxime | 5-Thia-1-azabicyclo[4.2.0]oct-2-ene-2-carboxylic acid, 7-[[(2-amino-4-thiazolyl)(methoxyimino)acetyl]amino]-3-[[(1-methyl-1H-tetrazol-5-yl)thio]methyl]-8-oxo-, [6R-[6Alpha,7β(Z)]]-[CAS] | 65085-01-0 75738-58-8 | GB | 1536281 | Cephalosporin, injectable | Infection, ocular |
| cefmetazole | 5-Thia-1-azabicyclo[4.2.0]oct-2-ene-2-carboxylic acid, 7-[[[(cyanomethyl)thio]acetyl]amino]-7-methoxy-3-[[(1-methyl-1H-tetrazol-5-yl)thio]methyl]-8-oxo-, (6R-cis)-[CAS] | 56796-20-4 56796-39-5 | GB | 1449420 | Cephalosporin, injectable | Infection, general |
| cefminox | 5-Thia-1-azabicyclo[4.2.0]oct-2-ene-2-carboxylic acid, 7-[[[(2-amino-2-carboxyethyl)thio]acetyl]amino]-7-methoxy-3-[[(1-methyl-1H-tetrazol-5-yl)thio]methyl]-8-oxo-, [6R-[6Alpha,7Alpha,7(S*)]]-[CAS] | 84305-41-9 | EP | 24879 | Cephalosporin, injectable | Infection, urinary tract |
| cefodizime | 5-Thia-1-azabicyclo[4.2.0]oct-2-ene-2-carboxylic acid, 7-[[(2-amino-4-thiazoyl)(methoxyimino)acetyl]amino]-3-[[[5-(carboxymethyl)-4-methyl-2-thiazolyl]thio]methyl]-8-oxo-, [6R-[6Alpha,7β(Z)]]-[CAS] | 69739-16-8 86329-79-5 | U.S. | 4,590,267 | Cephalosporin, injectable | Infection, respiratory tract, lower |
| cefonicid | 5-Thia-1-azabicyclo[4.2.0]oct-2-ene-2-carboxylic acid, 7-[(hydroxyphenyl)acetyl)-amino]-8-oxo-3-[[[1-(sulfomethyl)-1H-tetrazol-5-yl]thio]methyl]-, disodium salt, [6R-[6Alpha,7β(R*)]]-[CAS] | 61270-78-8 61270-58-4 | GB | 1547473 | Cephalosporin, injectable | Infection, general |
| cefoperazone | 5-Thia-1-azabicyclo[4.2.0]oct-2-ene-2-carboxylic acid, 7-[[[(4-ethyl-2,3-dioxo-1-piperazinyl)carbonyl]amino](4-hydroxyphenyl)acetyl]amino]-3-[[[(1-methyl-1H-tetrazol-5-yl)thio]methyl]-8-oxo-, [6R-[6Alpha,7β(R*)]]-[CAS] | 62893-19-0 | GB | 1508071 | Cephalosporin, injectable | Infection, general |
| cefoperazone + sulbactam Ceforanide | | 92739-15-6 60925-61-3 | U.S. | 4,234,579 | Antibiotic, other | Infection, general |

TABLE IV-continued

| API Generic Name | API Chemical Name | CAS No. | Patent Reference | Example of Therapeutic Use | Example of Indication |
|---|---|---|---|---|---|
| cefoselis | 5-Thia-1-azabicyclo[4.2.0]oct-2-ene-2-carboxylic acid, 7-[[(2-amino-4-thiazolyl)(methoxyimino)acetyl]amino]-3-[[2,3-dihydro-2-(2-hydroxyethyl)-3-amino-1H-pyrazol-1-yl]methyl]-8-oxo-, [6R-[6Alpha,7Beta(Z)]] | 122841-12-7 122841-10-5 | EP 307804 | Cephalosporin, injectable | Infection, general |
| cefotaxime | (6R,7R)-7-[[(2-amino-4-thiazolyl)(methoxyimino)acetyl]amino]cephalsporanic acidsodium salt | 64485-93-4 63527-52-6 | GB 1580621 | Cephalosporin, injectable | Infection, general |
| Cefotetan | | 69712-56-7 | | | |
| cefotiam | 5-Thia-1-azabicyclo[4.2.0]oct-2-ene-2-carboxylic acid, 7-[[(2-amino-4-thiazolyl)acetyl]amino]-3-[[[1-[2-(dimethylamino)ethyl]-1H-tetrazol-5-yl]thio]methyl]-8-oxo-, (6R-trans)-[CAS] | 61622-34-2 66309-69-1 | U.S. 4,080,498 | Cephalosporin, injectable | Infection, general |
| cefotiam hexetil | 1-(cyclohexloxycarbonyloxy)ethyl 7B-[2-(2-aminothiazol-4-yl)acetamido]-3-[[[1-(2-dimethylaminoethyl)-1H-tetrazol-5-yl]thio]methyl]ceph-3-em-4-carboxylate 2HCl [CAS] | 95789-30-3 | EP 128029 | Cephalosporin, oral | Infection, respiratory tract, lower |
| cefoxitin | 5-Thia-1-azabicyclo(4.2.0)oct-2-ene-2-carboxylic acid, 3-(((aminocarbonyl)oxy)methyl)-7-methoxy-8-oxo-7-((2-thienylacetyl)amino)-, monosodium salt, (6R-cis)-[CAS] | 33564-30-5 35607-66-0 | GB 1348984 | Cephalosporin, oral | Infection, general |
| cefozopran | Imidazo[1,2-b]pyridazinium, 1-[[7-[[(5-amino-1,2,4-thiadiazol-3-yl)(methoxyimino)acetyl]amino]-2-carboxy-8-oxo-5-thia-1-azabicyclo[4.2.0]oct-2-en-3-yl]methyl]-, hydroxide, inner salt, [6R-[6Alpha,7Beta(Z)]]-[CAS] | 113359-04-9 | EP 203271 | Cephalosporin, injectable | Infection, general |
| cefpimizole | Pyridinium, 1-[[2-carboxy-7-[[[[(5-carboxy-1H-imidazol-4-yl)carbonyl]amino]phenylacetyl]amino]-8-oxo-5-thia-1-azabicyclo[4.2.0]oct-2-en-3-yl]methyl]-4-(2-sulfoethyl)-, hydroxide, inner salt, [6R-[6Alpha,7Beta(R*)]]-[CAS] | 84880-03-5 85287-61-2 | EP 60028 | Cephalosporin, injectable | Infection, respiratory tract, general |
| cefpiramide | 5-Thia-1-azabicyclo[4.2.0]oct-2-ene-2-carboxylic acid, 7-[[[(4-hydroxy-6-methyl-3-pyridinyl)carbonyl]amino](4-hydroxyphenyl)acetyl]amino]-3-[[[(1-methyl-1H-tetrazol-5-yl)thio]methyl]-8-oxo-, [6R-[6Alpha,7Beta(R*)]]-[CAS] | 70797-11-4 | U.S. 4,156,724 | Cephalosporin, injectable | Infection, general |
| cefpirone | 5H-1-Pyrindinium, 1-[[7-[[[(2-amino-4-thiazolyl)(methoxyimino)acetyl]amino]-2-carboxy-8-oxo-5-thia-1-azabicyclo[4.2.0]oct-2-en-3-yl]methyl]-6,7-dihydro-,hydroxide, inner salt, [6R-[6Alpha,7Beta(Z)]]-[CAS] | 84957-29-9 98753-19-6 | EP 64740 | Cephalosporin, injectable | Infection, respiratory tract, lower |

TABLE IV-continued

| API Generic Name | API Chemical Name | CAS No. | Patent Reference | | Example of Therapeutic Use | Example of Indication |
|---|---|---|---|---|---|---|
| Cefpodoxime Proxetil | | 87239-81-4 | | | | |
| cefprozil | 5-Thio-1-azabicyclo[4.2.0]oct-2-ene-2-carboxylic acid, 7-[[amino(4-hydroxyphenyl)acetyl]amino]-8-oxo-3-(1-propenyl)-, [6R-[6Alpha,7β(R*)]]-[CAS] | 92665-29-7 | GB | 2173798 | Cephalosporin, oral | Infection, dermatological |
| cefroxadine | 5-Thia-1-azabicyclo[4.2.0]oct-2-ene-2-carboxylic acid, 7-[(amino-1,4-cyclohexadien-1-ylacetyl)amino]-3-methoxy-8-oxo-, [6R-[6Alpha,7β(R*)]]-[CAS] | 51762-05-1 | GB | 1435111 | Cephalosporin, oral | Infection, general |
| cefsulodin | Pyridinium, 4-(aminocarbonyl)-1-[[2-carboxy-8-oxo-7-[(phenylsulfoacetyl)amino]-5-thia-1-azabicyclo[4.2.0]oct-2-en-3-yl]methyl]-, hydroxide, inner salt, [6R-[6Alpha,7β(R*)]]-[CAS] | 52152-93-9 62587-73-9 | GB | | Cephalosporin, injectable | Infection, pseudomonal |
| ceftazidime | Pyridinium, 1-[[7-[[(2-amino-4-thiazolyl)[(1-carboxy-1-methylethoxy)imino]acetyl]amino]-2-carboxy-8-oxo-5-thia-1-azabicyclo[4.2.0]oct-2-en-3-yl]methyl]-, hydroxide, inner salt, [6R-[6Alpha,7β(Z)]]-[CAS] | 72558-82-8 | GB | 2025398 | Cephalosporin, injectable | Infection, respiratory tract, upper |
| Cefteram Ceftezole | | 82547-58-8 26973-24-0 | | | | |
| ceftibuten | 5-Thia-1-azabicyclo[4.2.0]oct-2-ene-2-carboxylic acid, 7-[[2-(2-amino-4-thiazolyl)-4-carboxy-1-oxo-2-butenyl]amino]-8-oxo-, [6R-[6Alpha,7β(Z)]]-[CAS] | 97519-39-6 | EP | | Cephalosporin, oral | Infection, respiratory tract, lower |
| ceftizoxime | 5-Thia-1-azabicyclo[4.2.0]oct-2-ene-2-carboxylic acid, 7-[[2-(2-amino-4-thiazolyl)-(methoxyimino)acetyl]amino]-8-oxo-, [6R-[6Alpha,7β(Z)]]-[CAS] | 68401-81-0 68401-82-1 | GB | 1600735 | Cephalosporin, injectable | Infection, general |
| ceftizoxime alapivoxil | 5-Thia-1-azabicyclo[4.2.0]oct-2-ene-2-carboxylic acid, 7-[[2-(2-amino-1-oxopropyl)amino]-4-thiazolyl](methoxyimino)acetyl]amino]-8-oxo-, (2,2-dimethyl-1-oxopropoxy)methyl ester, monohydrochloride, [6R-[6Alpha,7β(Z(S*)]]-[CAS] | 113812-94-5 135767-36-1 | JP | 62209112 | Cephalosporin, oral | Infection, general |
| ceftriaxone | 5-Thia-1-azabicyclo[4.2.0]oct-2-ene-2-carboxylic acid, 7-[[2-(2-amino-4-thiazolyl)(methoxyimino)acetyl]amino]-8-oxo-3-[[(1,2,5,6-tetrahydro-2-methyl-5,6-dioxo-1,2,4-triazin-3-yl)thio]methyl]-, [6R-[6Alpha,7β(Z)]]-[CAS] | 73384-59-5 74578-69-1 | GB | 2022090 | Cephalosporin, injectable | Infection, respiratory tract, lower |

TABLE IV-continued

| API Generic Name | API Chemical Name | CAS No. | Patent Reference | | Example of Therapeutic Use | Example of Indication |
|---|---|---|---|---|---|---|
| cefuroxime axetil | 5-Thia-1-azabicyclo[4.2.0]oct-2-ene-2-carboxylic acid, 3-[[(aminocarbonyl)oxy]methyl]-7-[[(2-furanyl(methoxyimino)acetyl]amino]-8-oxo-, 1-(acetyloxy)ethyl ester, [6R-[6Alpha,7β(Z)]]-[CAS] | 15686-71-2 64544-07-6 | GB | 1571683 | Cephalosporin, oral | Infection, respiratory tract, upper |
| cefuroxime | 5-Thia-1-azabicyclo[4.2.0]oct-2-ene-2-carboxylic acid, 3-[[(aminocarbonyl)oxy]methyl]-7-[[(2-furanyl(methoxyimino)acetyl]amino]-8-oxo-, 1-(acetyloxy)ethyl ester, [6R-[6Alpha,7β(Z)]]-[CAS] | 55268-75-2 56238-63-2 | GB | 1453049 | Cephalosporin, injectable | Infection, general |
| Cefuzonam | | 82219-78-1 | | | | |
| celecoxib | Benzenesulfonamide, 4-(5-(4-methylphenyl)-3-(trifluoromethyl)-1H-pyrazol-1-yl)-[CAS] | 169590-42-5 | U.S. | 5,760,068 | Antiarthritic, other | Arthritis, rheumatoid |
| celgosivir | Butanoic acid, octahydro-1,7,8-trihydroxy-6-indolizinyl ester, [1S-(1Alpha,6β,7Alpha,8β,8aβ)]-[CAS] | 121104-96-9 | U.S. | 5,017,563 | Antiviral, other | Infection, hepatitis virus, general |
| celiprolol | Urea, N'-[3-acetyl-4-[3-[(1,1-dimethylethyl)amino]-2-hydroxypropoxy]phenyl]-N,N-diethyl-[CAS] | 56980-93-9 57470-78-7 | GB | 1441359 | Antihypertensive, adrenergic | Angina, unstable |
| Cellulose Ethyl Hydroxyethyl Ether | | | | | | |
| CEP-1347 | 9,12-Epoxy-1H-diindolo[1,2,3-fg:3',2',1'-kl]pyrrolo[3,4-i][1,6]benzodiazocine-10-carboxylic acid, 5,16-bis((ethylthio)methyl)-2,3,9,10,11,12-hexahydro-10-hydroxy-9-methyl-1-oxo-, methyl ester, (9S,10R,12R)-[CAS] | 156177-65-0 | WO | 9731002 | Antiparkinsonian | Parkinson's disease |
| CEP-701 | 9,12-Epoxy-1H-diindolo[1,2,3-fg:3',2',1'-kl]pyrrolo[3,4-i][1,6]benzodiazocin-1-one, 2,3,9,10,11,12-hexahydro-10-hydroxy-10-(hydroxymethyl)-9-methyl-, (9S,10S,12R)-[CAS] | 111358-88-4 | | | Anticancer, antimetabolite | Cancer, prostate |
| Cephacetrile | | 23239-41-0 | | | | |
| Cephaeline | | 493-17-0 | | | | |
| Cephalexin | | 15686-71-2 | | | | |
| Cephaloglycin | | 3577-1-3 | | | | |
| Cephaloridine | | 50-59-9 | | | | |
| Cephalosporin C | | 61-24-5 | | | | |
| Cephalothin | | 153-61-7 | | | | |
| Cephapirin | | 24356-60-3 | | | | |
| Cephradine | | 38821-53-3 | | | | |
| Cerivastatin | | 145599-86-6 | | | | |
| Ceronapril | | 111223-26-8 | | | | |
| certoparin | Heparin [CAS] | 9005-49-6 | | | Anticoagulant | Thrombosis, venous |
| Ceruletide | | 17650-98-5 | | | | |

TABLE IV-continued

| API Generic Name | API Chemical Name | CAS No. | Patent Reference | Example of Therapeutic Use | Example of Indication |
|---|---|---|---|---|---|
| Cerviprost | Prosta-5,13-dien-1-oic acid, 11,15-dihydroxy-9-oxo-, (5Z,11Alpha,13E,-15S)-[CAS] | 363-24-6 | | Formulation, dermal, topical | |
| Cetalkonium | | 122-18-9 | | | |
| Cetamolol | | 34919-98-7 | | | |
| Cethexonium | | 1794-74-7 | | | |
| cethromycin | 2H-Oxacyclotetradecino(4,3-d)oxazole-2,6,8,14(1H,7H,9H)-tetrone 4-ethyloctahydro-3a,7,9,11,13,15-hexamethyl-11-((3-(3-quinolinyl)-2-propenyl)oxy)-10-((3S,4,6-trideoxy-3-(dimethylamino)-β-D-xylo-hexapyranosyl)oxy)-,(3aS,4R,7R,9R,10R,11R,13R,15R,15aR)-[CAS] | 205110-48-1 | EP 929563 | Macrolide antibiotic | Infection, respiratory tract, general |
| Cetiedil | | 14176-10-4 | | | |
| Cetirizine | | 83881-51-0 | | | |
| cetirizine | Acetic acid, [2-[4-[(4-chlorophenyl)phenylmethyl]-1-piperazinyl]-, [CAS] | 83881-51-0 83881-52-1 | EP 58146 | Antiallergic, non-asthma | Allergy, general |
| cetirizine + pseudoephedrine | Acetic acid, [2-[4-[(4-chlorophenyl)phenylmethyl]-1-piperazinyl]ethoxy]-, dihydrochloride, Benzenemethanol, Alpha-[1-(methylamino)ethyl]-, hydrochloride, [S-(R*,R*)]- | 83881-52-1 90-82-4 | | Formulation, optimized, microencapsulate | Allergy, general |
| Cetotiamine | | 137-76-/8 | | | |
| Cetoxime | | 25394-78-9 | | | |
| cetraxate | Benzenepropanoic acid, 4-[[[4-(aminomethyl)cyclohexyl]carbonyl]oxy]-, trans-[CAS] | 27724-96-5 34675-84-8 | JP 48075547 | Antiulcer | |
| Cetrimonium | | 57-09-0 | | | |
| Cetrorelix | | 120287-85-6 | | | |
| Cetyldimethylethyl-ammonium | | 124-03-8 | | | |
| Cetylpyridinium | | 123-03-5 | | | |
| cevimeline | Spiro[1-azabicyco[2.2.2]octane-3,5'-[1,3]oxathiolane], 2'-methyl-, cis-[CAS] | 107220-27-9 107233-08-9 | EP 205247 | Stromatological | Sjogran's syndrome |
| CG-1521 | 7-phenyl-2,4,6-heptatrienoylhydroxamic acid | | | Anticancer, other | Cancer, general |
| Chaulmoogric Acid | | 29106-32-9 | | | |
| Chenodiol | | 474-25-9 | | | |
| CHF-3381 | | | EP 951465 | Analgesic, other | Pain, neuropathic |
| Chlophedianol | | 791-35-5 | | | |
| Chloracizine | | 800-22-6 | | | |
| chloral | 1,1-Ethanediol, 2,2,2-trichloro-[CAS] | 302-17-0 2218-68-0 | | Formulation, transmucosal, systemic | Insomnia |
| Chlorambucil | | 515-82-2 305-03-3 | | | |
| Chloramine-B | | 127-52-6 | | | |

TABLE IV-continued

| API Generic Name | API Chemical Name | CAS No. | Patent Reference | Example of Therapeutic Use | Example of Indication |
|---|---|---|---|---|---|
| Chloramine-T | | 127-65-1 | | | |
| Chloramino-phenamide | | 121-30-2 | | | |
| Chloramphenicol | | 56-75-7 | | | |
| Chlorazanil | | 500-42-5 | | | |
| Chlorbenzoxamine | | 522-18-9 | | | |
| Chlorbetamide | | 97-27-8 | | | |
| Chlorcyclizine | | 82-93-9 | | | |
| Chlordantoin | | 5588-20-5 | | | |
| Chloriazepoxide | | 58-25-3 | | | |
| Chlorguanide | | 500-92-5 | | | |
| Chlorhexadol | | 3563-58-4 | | | |
| chlorhexidine | 2,4,11,13-Tetraazatetradecanediimidamide, N,N'''-bis(4-chlorophenyl)-3,12-diimino-[CAS] | 55-56-1 | | Formulation, other | Xerostomia, Periodontitis |
| Chlorisondamine | | 69-27-2 | | | |
| Chlormadinone | | 302-22-7 | | | |
| Chlormerodrin | | 62-37-3 | | | |
| Chlormezanone | | 80-77-3 | | | |
| Chlormidazole | | 3689-76-7 | | | |
| Chlornaphazine | | 494-03-1 | | | |
| Chloroazodin | | 502-98-7 | | | |
| Chlorophyll | | 1406-65-1 | | | |
| Chloroprednisone | | 52080-57-6 | | | |
| Chloroprocaine | | 3858-89-7 | | | |
| Chloropyramine | | 59-32-5 | | | |
| Chloroquine | | 54-05-7 | | | |
| Chlorothen | | 148-65-2 | | | |
| Chlorothiazide | | 58-94-6 | | | |
| Chlorotrianisene | | 569-57-3 | | | |
| Chloroxine | | 773-76-2 | | | |
| Chloroxylenol | | 88-04-0 | | | |
| Chlorozotocin | | 54749-90-5 | | | |
| chlorphenamine | 2-Pyridinepropanamine, Gamma-(4-chlorophenyl)-N,N-dimethyl-[CAS] | 132-22-9 | | Formulation, modified-release, other | Allergy, general |
| Chlorphenesin | | 104-29-0 | | | |
| Chlorpheniramine | | 886-74-8 | | | |
| Chlorphenoxamide | | 132-22-9 | | | |
| Chlorphenoxamine | | 3576-64-5 | | | |
| Chlorphentermine | | 77-38-3 | | | |
| Chlorproethazine | | 461-78-9 | | | |
| Chlorproguanil | | 84-01-5 | | | |
| chlorproguanil + dapsone | 4,4'-Sulfonyldianiline + 1-(3,4-Dichlorophenyl)5-isopropylbiguanide | 537-21-3 537-21-3 | | Antimalarial | Infection, malaria |
| Chlorpromazine | | 80-08-0 | | | |
| Chlorpropamide | | 50-53-3 | | | |
| Chloroprothixene | | 94-20-2 | | | |
| Chlorquinaldol | | 113-59-7 | | | |
| | | 72-80-0 | | | |

TABLE IV-continued

| API Generic Name | API Chemical Name | CAS No. | Patent Reference | Example of Therapeutic Use | Example of Indication |
|---|---|---|---|---|---|
| Chlortetracycline | | 57-62-5 | | | |
| Chlorthalidone | | 77-36-1 | | | |
| Chlorthenoxazine(e) | | 132-89-8 | | | |
| Chlorzoxazone | | 95-25-0 | | | |
| Cholic Acid | | 81-25-4 | | | |
| Choline | | 67-48-1 | | | |
| | | 2016-36-6 | | | |
| choline theophyllinate | Ethanaminium, 2-hydroxy-N,N,N-trimethyl-, salt with 3,7-dihydro-1,3-dimethyl-1H-purine-2,6-dione (1:1) [CAS] | 28319-77-9 4499-40-5 | | Formulation, modified-release, other | |
| choline-L-alfoscerate | Ethanaminium, 2-[[2,3-dihydroxypropoxy)hydroxyphosphinyl]oxy]-N,N,N-trimethyl-, hydroxide, inner salt, (R)-[CAS] | 28319-77-9 | JP 55028955 | Cognition enhancer | Amnesia |
| Chromocarb | | 4940-39-0 | | | |
| Chromonar | | 804-10-4 | | | |
| Chrysoidine | | 532-82-1 | | | |
| CHS-828 | Guanidine, N-[6-(4-chlorophenoxy)hexyl]-N'-cyano-N''-4-pyridinyl-[CAS] | 200484-11-3 | U.S. 5,696,140 | Anticancer, other | Cancer, general |
| CI-1031 | Glycine, N-[2-[5-(aminoiminomethyl)-2-hydroxyphenoxy]-6-[3-(4,5-dihydro-1-methyl-1H-imidazol-2-yl)phenoxy]-3,5-difluoro-4-pyridinyl]-N-methyl-[CAS] | 183305-24-0 | WO 9638421 | Antianginal | Angina, unstable |
| CI-1040 | Benzamide, 2-[(2-chloro-4-iodophenyl)amino]-N-(cyclopropylmethoxy)-3,4-difluoro-[CAS] | 212631-79-3 | WO 9837881 | Anticancer, other | Cancer, general |
| cibenzoline | 1H-Imidazole, 2-(2,2-diphenylcyclopropyl)-4,5-dihydro-[CAS] | 53267-01-9 | GB 1417174 | Antiarrhythmic | Arrhythmia, general |
| ciclesonide | Pregna-1,4-diene-3,20-dione 16,17-((cyclohexylmethylene)bis(oxy))-11-hydroxy-21-(2-methyl-1-oxopropoxy) (11β,16Alpha) [CAS] | 126544-47-6 | DE 4129535 | Antiasthma | Asthma |
| cicletanine | Furo[3,4-c]pyridin-7-ol, 3-(4-chlorophenyl)-1,3-dihydro-6-methyl-, (+/−)-[CAS] | 82747-56-6 89943-82-8 | U.S. 4,383,998 | Antihypertensive, other | |
| ciclonicate | 3-Pyridinecarboxylic acid, 3,3,5-trimethylcyclohexyl ester, trans-[CAS] | 53449-58-4 | DE 1910481 | Vasodilator, peripheral | |
| ciclopirox | 2(1H)-Pyridinone, 6-cyclohexyl-1-hydroxy-4-methyl-, [CAS] | 41621-49-2 29342-05-0 | U.S. 3,883,545 | Antifungal | Cancer, lung, small cell Infection, fungal, general |
| Ciclosidomine | | 66564-16-7 | | | |
| ciclosporin A | Cyclosporin A-[CAS] | 59865-13-3 | | Formulation, optimized, microemulsion | Transplant rejection, general |
| cidofovir | Phosphonic acid, [[2-(4-amino-2-oxo-1(2H)-pyrimidinyl)-1-(hydroxymethyl)ethoxy]methyl]-, (S)-[CAS] | 113852-37-2 | EP 253412 | Antiviral, other | Infection, cytomegalovirus |
| Cifenline | | 53267-01-9 | | | |
| cilansetron | 4H-Pyrido[3,2,1-jk]carbazol-11(8H)-one, 5,6,9,10-tetrahydro-10-[(2-methyl-1H-imidazol-1-yl)methyl]-, (R)-[CAS] | 120635-74-7 | EP 297651 | GI inflammatory/bowel disorders | Irritable bowel syndrome |

TABLE IV-continued

| API Generic Name | API Chemical Name | CAS No. | Patent Reference | | Example of Therapeutic Use | Example of Indication |
|---|---|---|---|---|---|---|
| Cilastatin | | 82009-34-5 | | | | |
| cilazapril | 6H-Pyridazino[1,2-a][1,2]diazepine-1-carboxylic acid, 9-[[1-(ethoxycarbonyl)-3-phenylpropyl]amino]octahydro-10-oxo-, [1S-[1Alpha,9Alpha(R*)]]-[CAS] | 88768-40-5 90139-06-3 | GB | 2128984 | Antihypertensive, renin system | Hypertension, general |
| cilengitide | Cyclo(L-arginylglycyl-L-Alpha-aspartyl-D-phenylalanyl-N-methyl-L-valyl) [CAS] | 188968-51-6 | EP | 770622 | Anticancer, other | Cancer, lung, non-small cell |
| cilnidipine | 3,5-Pyridinedicarboxylic acid, 1,4-dihydro-2,6-dimethyl-4-(3-nitrophenyl)-, 2-methoxyethyl 3-phenyl-2-propenyl ester [CAS] | 102106-21-8 132203-70-4 | EP | 161877 | Antihypertensive, other | Hypertension, general |
| cilomilast | Cis-4-cyano-4-[3-(cyclopentyloxy)-4-methoxyphenyl]cyclohexane-1-carboxylic acid | 153259-65-5 | U.S. | 5,602,157 | COPD treatment | Chronic obstructive pulmonary disease |
| cilostazol | 2(1H)-Quinolinone, 6-[4-(1-cyclohexyl-1H-tetrazol-5-yl)butoxy]-3,4-dihydro-[CAS] | 73963-72-1 | GB | 2033893 | Antithrombotic | Peripheral vascular disease |
| Cimetidine | | 51481-61-9 | | | | |
| cimetropium | 3-Oxa-9-azoniatricyclo[3.3.1.02,4]nonane, 9-(cyclopropylmethyl)-7-(3-hydroxy-1-oxo-2-phenylpropoxy)-9-methyl-, [7(S)-(1Alpha,2β,4β,5Alpha,7β)]-[CAS] | 51598-60-8 | U.S. | 3,853,886 | Antispasmodic | Muscle spasm, general |
| cinacalcet | 1-naphthalenemethanamine,Alpha-methyl-N-[3-(trifluoromethyl)phenyl]propyl]-, (AlphaR)- | 364782-34-3 | | | Hormone | Hyperparathyroidsm |
| Cinchonidine Cinchonine Cinchophen Cinepazet Cinepazide | | 485-71-2 118-10-5 132-60-5 23887-41-4 23887-46-9 | | | | |
| cinepazide | Piperazine, 1-[2-oxo-2-(1-pyrrolidinyl)ethyl]-4-[1-oxo-3-(3,4,5-trimethoxyphenyl)-2-propenyl]-, (Z)-2-butenedioate (1:1) [CAS] | 26328-04-1 | GB | 1218591 | Vasodilator, peripheral | Peripheral vascular disease |
| Cinitapride Cinmetacin Cinnamedrine Cinnarizine | | 66564-14-5 20168-99-4 90-86-8 298-57-7 | | | | |
| cinolazepam | 1H-1,4-Benzodiazepine-1-propanenitrile, 7-chloro-5-[2-fluorophenyl)-2,3-dihydro-3-hydroxy-2-oxo-[CAS] | 75696-02-5 | DE | 2950235 | Hypnotic/Sedative | Insomnia |
| cinoxacin | [1,3]Dioxolo[4,5-g]cinnoline-3-carboxylic acid, 1-ethyl-1,4-dihydro-4-oxo-[CAS] | 28657-80-9 | GB | 1296753 | Quinolone antibacterial | Infection, urinary tract |
| Cinoxate Cinromide Cioteronel | | 104-28-9 58473-74-8 89672-11-7 | | | | |
| cipamfylline | 1H-Purine-2,6-dione, 8-amino-1,3-bis(cyclopropylmethyl)-3,7-dihydro-[CAS] | 132210-43-6 | EP | 389282 | Antipruritic/inflamm, allergic | Eczema, atopic |

TABLE IV-continued

| API Generic Name | API Chemical Name | CAS No. | Patent Reference | | Example of Therapeutic Use | Example of Indication |
|---|---|---|---|---|---|---|
| cipralisant | 1H-Imidazole, 4-[(1R,2R)-2-(5,5-dimethyl-1-hexynyl)cyclopropyl]-[CAS] | 213027-19-1 | U.S. | 6,008,240 | Psychostimulant | Attention deficit disorder |
| ciprofibrate | Propanoic acid, 2-[4-(2,2-dichlorocyclopropyl)phenoxy]-2-methyl-[CAS] | 52214-84-3 | GB | 1385828 | Hypolipaemic/ Antiatherosclerosis | Hyper-lipidaemia, general |
| ciprofloxacin | 3-Quinolinecarboxylic acid, 1-cyclopropyl-6-fluoro-1,4-dihydro-4-oxo-7-(1-piperazinyl)-[CAS] | 85721-33-1 | U.S. | 4,670,444 | Quinolone antibacterial | Infection, general |
| ciprofloxacin + fluocinolone, SAL | 3-Quinolinecarboxylic acid, 1-Cyclopropyl-6 fluoro-1,4-dihydro-4-oxo-7-(1-piperazinyl) + (6Alpha, 11β, 16Alpha)-6,9-Difluoro-11,21-dihydroxy-16,17-[(1-methylethylidene)bis-(oxy)]-pregna-1,4-diene-3,20-dione | | | | Formulation, fixed-dose combinations | Otitis |
| Ciramadol cisapride | Benzamide, 4-amino-5-chloro-N-[1-[3-(4-fluorophenoxy)propyl]-3-methoxy-4-piperidinyl]-2-methoxy-, cis-[CAS] | 63269-31-8 81098-60-4 | EP | 76530 | Gastroprokinetic | |
| cisatracurium | Isoquinolinium, 2,2'-[1,5-pentanediylbis[oxy(3-oxo-3,1-propanediyl)]]bis[1-[(3,4-dimethoxyphenyl)methyl]]-1,2,3,4-tetrahydro-6,7-dimethoxy-2-methyl-, [1R-[1Alpha,2Alpha(1R*,2R*)]]-, [CAS] | 96946-42-8 | U.S. | 5,453,510 | Muscle relaxant | Surgery adjunct |
| cisplatin | Platinum, diamminedichloro-, (SP-4-2)-[CAS] | 15663-27-1 | U.S. | 4,177,263 | Anticancer, alkylating | |
| citalopram | 5-Isobenzofurancarbonitrile, 1-[3-(dimethylamino)propyl]-1-(4-fluorophenyl)-1,3-dihydro-[CAS] | 59729-32-7 59729-33-8 | GB | 1526331 | Antidepressant | Depression, general |
| citicoline | Cytidine 5'-(trihydrogen diphosphate), P'-[2(trimethylammonio)ethyl]ester, hydroxide, inner salt [CAS] | 987-78-0 | JP | 39006541 | Cognition enhancer | Infarction, cerebral |
| Citiolone Citric Acid Citrulline | | 1195-16-0 77-92-9 372-75-8 | | | | |
| cizolirtine | Ethanamine, N,N-dimethyl-2-[(1-methyl-1H pyrazol-5-yl)phenylmethoxy]-, 2-hydroxy-1,2,3-propanetricarboxylate [CAS] | 142155-44-0 | | | Urological | Incontinence |
| CJ-13610 | 4-(3-[4-(2-Methyl-imidazol-1-yl)-phenylsulfanyl]-phenyl)-tetrahydro-pyran-4-carboxylic acid amide | | | | COPD treatment | Chronic obstructive pulmonary disease |
| CKD-602 | 1H-Pyrano[3',4':6,7]indolizino[1,2-b]quinoline-3,15(4H,12H)-dione, 4-ethyl-4-hydroxy-11-[2-[(1-methylethyl)amino]ethyl]-, monohydrochloride, (4S)- [CAS]] | 213819-48-8 | WO | 9902530 | Anticancer, other | Cancer, ovarian |
| cladribine | Adenosine, 2-chloro-2'-deoxy-[CAS] | 4291-63-8 | EP | 173059 | Anticancer, antimetabolite | Cancer, leukaemia, hairy cell |

TABLE IV-continued

| API Generic Name | API Chemical Name | CAS No. | Patent Reference | Example of Therapeutic Use | Example of Indication |
|---|---|---|---|---|---|
| Clanobutin | | 30544-61-7 | | | |
| clarithromycin | Erythromycin, 6-O-methyl-[CAS] | 81103-11-9 | EP 41355 | Macrolide antibiotic | Infection, respiratory tract, lower |
| Clavulanate, Disodium | | | | | |
| Clavulanic Acid | | 58001-44-8 | | | |
| Clebopride | | 55905-53-8 | | | |
| Clemastine | | 15686-51-8 | | | |
| Clemizol | | 442-52-4 | | | |
| Clenbuterol | | 37148-27-9 | | | |
| Clentiazem | | 96125-53-0 | | | |
| clevidipine | 3,5-Pyridinedicarboxylic acid, 4-(2,3-dichlorophenyl)-1,4-dihydro-2,6-dimethyl-, methyl (1-oxobutoxy)methyl ester (±) [CAS] | 167221-71-8 | WO 9512578 | Antihypertensive, other | Hypertension, general |
| clevudine | 2,4(1H,3H)-Pyrimidinedione, 1-(2-deoxy-2-fluoro-β-L-arabinofuranosyl)-5-methyl-[CAS] | 163252-36-6 | | Antiviral, other | Infection, hepatitis-B virus |
| Clidanac | | 28968-07-2 | | | |
| Clidinium | | 3485-62-9 | | | |
| Clinafloxacin | | 105956-97-6 | | | |
| Clindamycin | | 18323-44-9 | | | |
| clindamycin + tretinoin | L-threo-Alpha-D-galacto-Octopyranoside, methyl 7-chloro-6,7,8-trideoxy-6-[[(1-methyl-4-propyl-2-pyrrolidinyl)carbonyl]amino]-1-thio, (2S-trans)- + retinoic acid | | | Formulation, fixed-dose combinations | Acne |
| clindamycin | L-Threo-Alpha-D-galacto-octopyranoside, methyl 7-chloro-6,7,8-trideoxy-6-[[(1-methyl-4-propyl-2-pyrrolidinyl)carbonyl]amino]-1-thio-, 2-(dihydrogen phosphate), (2S-trans)- | 18323-44-9 24729-96-2 | | Formulation, parenteral, other | Infection, gynaecological |
| Clinofibrate | | 30299-08-2 | | | |
| Cliprost | | 88931-51-5 | | | |
| clobazam | 1H-1,5-Benzodiazepine-2,4(3H,5H)-dione, 7-chloro-1-methyl-5-phenyl-[CAS] | 22316-47-8 | GB 1214662 | Anxiolytic | |
| Clobenfurol | | 3611-72-1 | | | |
| Clobenoside | | 29899-95-4 | | | |
| Clobenzepam | | 1159-93-9 | | | |
| Clobenzorex | | 13364-32-4 | | | |
| Clobenztropine | | 5627-46-3 | | | |
| clobetasol | Pregna-1,4-diene-3,20-dione, 21-chloro-9-fluoro-11,17-dihydroxy-16-methyl-, (11β,16β)-[CAS] | 25122-41-2 | | Formulation, dermal, topical | Psoriasis |
| clobetasone | Pregna-1,4-diene-3,11,20-trione, 21-chloro-9-fluoro-16-methyl-17-(1-oxobutoxy)-, (16β)-[CAS] | 25122-57-0 54063-32-0 | GB 1253831 | Antipruritic/inflamm, allergic | |
| Clobutinol | | 14860-49-2 | | | |
| Clocapramine | | 47739-98-0 | | | |

TABLE IV-continued

| API Generic Name | API Chemical Name | CAS No. | Patent Reference | | Example of Therapeutic Use | Example of Indication |
|---|---|---|---|---|---|---|
| Clocinizine | | 298-55-5 | | | | |
| Cloconazole | | 77175-51-0 | | | | |
| Clocortolone | | 4828-27-7 | | | | |
| clodronate | Phosphonic acid, (dichloromethylene)bis-[CAS] | 22560-50-5 | | | Osteoporosis treatment, Anticancer, hormonal | Pain, cancer, Hyper-calcaemia of malignancy |
| Clodronic Acid | | | | | | |
| clofarabine | 2-chloro-9-(2-deoxy-2-fluoro-β-D-arabinofurasonyl)adenine | 10596-23-3 | | | Anticancer, antimetabolite | Cancer, leukaemia, chronic lymphocytic |
| clofazimine | 3-(p-chloroanilo)-10-(p-chlorophenyl)-2,10-dihydro-2-(isopropylimino)-phenazine | 2030-63-9 | | | Formulation, optimized, microencapsulate | Infection, tuberculosis |
| Clofenamide | | 671-95-4 | | | | |
| Clofibrat | | 637-07-0 | | | | |
| Clofibric Acid | | 882-09-7 | | | | |
| Cloflucarban | | 369-77-7 | | | | |
| Clofoctol | | 37693-01-9 | | | | |
| Cloforex | | 14261-75-7 | | | | |
| Clomacran | | 5310-55-4 | | | | |
| Clomestrone | | 4091-75-2 | | | | |
| Clometacin | | 25803-14-9 | | | | |
| Clomethiazole | | 533-45-9 | | | | |
| Clometocillin | | 1926-49-4 | | | | |
| Clomiphene | | 911-45-5 | | | | |
| Clomipramine | | 303-49-1 | | | | |
| Clomocycline | | 1181-54-0 | | | | |
| clonazepam | 2H-1,4-Benzodiazepin-2-one, 5-(2-chlorophenyl)-1,3-dihydro-7-nitro-[CAS] | 1622-61-3 | U.S. | 4,316,897 | Antiepileptic | Epilepsy, general |
| clonidine | 1H-Imidazol-2-amine, N-(2,6-dichlorophenyl)-4,5-dihydro-[CAS] | 4205-90-7 | U.S. | 4,060,084 | Formulation, transdermal, patch | Hypertension, general |
| Clonitazene | | 3861-76-5 | | | | |
| Clonitrate | | 2612-33-1 | | | | |
| Clonixin | | 17737-65-4 | | | | |
| Clopamid | | 636-54-4 | | | | |
| Clopenthixol | | 982-24-1 | | | | |
| Cloperastine | | 3703-76-2 | | | | |
| clopidogrel | Thieno[3,2-c]pyridine-5(4H)-acetic acid, Alpha-(2-chlorophenyl)-6,7-dihydro-, methyl ester, (S)-[CAS] | 120202-48-4 90055-48-4 113665-84-2 | EP | 99802 | Antithrombotic | Infarction, myocardial |
| Clopirac | | 42779-82-8 | | | | |
| Cloprednol | | 5251-34-3 | | | | |
| cloranolol | 2-Propanol, 1-(2,5-dichlorophenoxy)-3-[(1,1-dimethylethyl)amino]-[CAS] | 39563-28-5 54247-25-5 | U.S. | 4,310,549 | Antihypertensive, adrenergic | |
| Clorazepic Acid | | 23887-31-2 | | | | |
| Clorexolone | | 2127-1-7 | | | | |

TABLE IV-continued

| API Generic Name | API Chemical Name | CAS No. | Patent Reference | | Example of Therapeutic Use | Example of Indication |
|---|---|---|---|---|---|---|
| cloricromene | Acetic acid, [[8-chloro-3-[2-(diethylamino)ethyl]-4-methyl-2-oxo-2H-1-benzopyran-7-yl]oxy]-, ethyl ester [CAS] | 68206-94-0 | U.S. | 4,349,566 | Vasodilator, coronary | Peripheral vascular disease |
| Clorindione | | 1146-99-2 | | | | |
| Clorprenaline | | 3811-25-4 | | | | |
| Clortermine | | 10389-73-8 | | | | |
| Clospirazine | | 24527-27-3 | | | | |
| Clostebol | | 1093-58-9 | | | | |
| Clothiapine | | 2058-52-8 | | | | |
| clotiazepam | 2H-Thieno[2,3-e]-1,4-diazepin-2-one, 5(2-chlorophenyl)-7-ethyl-1,3-dihydro-1-methyl-[CAS] | 33671-46-4 | U.S. | 3,849,405 | Anxiolytic | Anxiety, general |
| clotrimazole | 1-[(2-chlorophenyl)diphenylmethyl]-1H-imidazole | 23593-75-1 | U.S. | 3,705,172 | Antifungal | |
| clotrimazole + betamethasone | Pregna-1,4-diene-3,20-dione, 9-fluoro-11-hydroxy-16-methyl-17,21-bis(1-oxopropoxy)-, (11β,16β)-, mixt. with 1-[(2-chlorophenyl)diphenylmethyl]-1H-imidazole [CAS] | 92522-91-3 | | | Formulation, fixed-dose combinations | Infection, fungal, general |
| Cloxacillin | | 61-72-3 | | | | |
| cloxazolam | Oxazolo[3,2-d][1,4]benzodiazepin-6(5H)-one, 10-chloro-11b-(2-chlorophenyl)-2,3,7,11b-tetrahydro-[CAS] | 24166-13-0 | U.S. | 3,442,371 | Anxiolytic | |
| Cloxotestosterone | | 53608-96-1 | | | | |
| Cloxyquin | | 130-16-5 | | | | |
| clozapine | 5H-Dibenzo[b,e][1,4]diazepine, 8-chloro-11-(4-methyl-1-piperazinyl)-[CAS] | 5786-21-0 | U.S. | 3,539,573 | Neuroleptic | Schizophrenia |
| CMI-392 | Trans-2-[3-methoxy-4-(2-p-chlorophenylthio)ethoxy-5-(N'-methyl-N'-hydroxyureidyl)methylphenyl]-5-(3,4,5-trimethoxyphenyl)tetrahydrofuran | 193739-23-0 | U.S. | 5,648,486 | Antipsoriasis | Psoriasis |
| CMT-3 | 2-Naphthacenecarboxamide, 1,4,4a,5,5a,6,11,12a-octahydro-3,10,12,12a-tetrahydroxy-1,11-dioxo-, (4aS,5aR,12aS)-[CAS] | 15866-90-7 | U.S. | 5,837,696 | Anticancer, other | Cancer, sarcoma, Kaposi's |
| CNI-1493 | Decanediamide, N,N'-bis[3,5-bis[1-[(aminoiminomethyl)hydrazono]ethyl]-phenyl]-, tetrahydrochloride [CAS] | 164301-51-3 | U.S. | 5,750,573 | Anti-inflammatory | Psoriasis |
| CNS-5161 | N'-[2-chloro-5-(methylthio)phenyl]-N-methyl-N-[3-(methylthio)phenyl]guanide [CAS] | 160754-76-7 | WO | 9427591 | Analgesic, other | Pain, neuropathic |
| Cobamamide | | 13870-90-1 | | | | |
| Cocaethylene | | 529-38-4 | | | | |
| Cocaine | | 50-36-2 | | | | |
| Codeine | | 76-57-3 | | | | |
| | | 52-28-8 | | | | |
| CoFactor | 5,10 methylene-tetrahydrofolate | | | | Anticancer, antimetavolite | Cancer, colorectal |
| Colchicine | | 64-86-8 | | | | |

TABLE IV-continued

| API Generic Name | API Chemical Name | CAS No. | Patent Reference | | Example of Therapeutic Use | Example of Indication |
|---|---|---|---|---|---|---|
| colesevelam | 1-Hexanaminium, N,N,N-trimethyl-6-(2-propenylamino)-, polymer with (chloromethyl)oxirane, 2-propen-1-amine and N-2-propenyl-1-decanamine, hydrochloride [CAS] | 182815-44-7 | U.S. | 5,607,669 | Hypolipaemic/Antiatherosclerosis | Hyper-lipidaemia, general |
| colestilan | 1H-Imidazole, 2-methyl-, polymer with (chloromethyl)oxirane [CAS] | 95522-45-5 | JP | 59155421 | Hypolipaemic/Antiatherosclerosis | Hyper-cholesterol-aemia |
| Colestipol | | 26658-42-4 | | | | |
| colforsin daropate | 6-(3-dimethylaminopropionyl)forkolin- [CAS] | 138605-00-2 | EP | 222413 | Cardiostimulant | Heart failure |
| colfosceril | 3,5,9-Trioxa-4-phosphapentacosan-1-aminium, 4-hydroxy-N,N,N-trimethyl-10-oxo-7-[(1-oxohexadecyl)oxy]-, hydroxide, inner salt, 4-oxide, (R)-[CAS] | 63-89-8 99732-49-7 | U.S. | 4,826,821 | Lung Surfactant | Respiratory distress syndrome, infant |
| Collagraft | | 138331-02-9 | | | Formulation, implant | Regeneration, bone |
| Colocynthin | | 1398-78-3 | | | | |
| Colpormon | | 1247-71-8 | | | | |
| coluracetam | 1-Pyrrolidineacetamide, 2-oxo-N-(5,6,7,8-tetrahydro-2,3-dimethylfuro[2,3-b]quinolin-4-yl)-[CAS] | 135463-81-9 | EP | 427636 | Cognition enhancer | Alzheimer's disease |
| combretastatin A-4 prodrug | disodium combretastatin-A-4-3-O-phosphate | | | | Anticancer, other | Cancer, thyroid |
| compound B, Pharmacor | | | U.S. | 6,362,165 | Antiviral, anti-HIV | Infection, HIV/AIDS |
| conivaptin | [1,1'-Biphenyl]-2-carboxamide, N-[4-[(4,5-dihydro-2-methylimidazo[4,5-d][1-benzazepin-6(1H)-yl)carbonyl]phenyl]-, [CAS] | 168626-94-6 | WO | 9503305 | GI inflammatory/bowel disorders | Hyponatraemia |
| Connettivina | Hyaluronic acid [CAS] | 9004-61-9 | | | Vulnerary | |
| Convallatoxin | | 508-75-8 | | | | |
| Coparaffinate | | 8001-60-3 | | | | |
| Corticorelin Ovine Triflutate | | | | | | |
| Corticosterone | | 50-22-6 | | | | |
| Cortisone | | 53-06-5 | | | | |
| Cortivazol | | 1110-40-3 | | | | |
| Cosyntropin | | 16960-16-0 | | | | |
| Cotarnine | | 82-54-2 | | | | |
| Cotinine | | 486-56-6 | | | | |
| co-trimazine | Benzenesulfonamide, 4-amino-N-2-pyrimidinyl-, mixt. with 5-[(3,4,5-trimethoxyphenyl)methyl]-2,4-pyrimidinediamine [CAS] | 39474-58-3 | | | Trimethoprim and analogues | Infection, urinary tract |
| Coumetarol | | 4366-18-1 | | | | |
| CP-248 | 1H-Indene-3-acetamide, 5-fluoro-2-methyl-N-(phenylmethyl)-1-[(3,4,5-trimethoxyphenyl)methylene]-, (1Z)- [CAS] | 200803-37-8 | WO | 9747303 | Anticancer, other | Barrett's oesophagus |

TABLE IV-continued

| API Generic Name | API Chemical Name | CAS No. | Patent Reference | | Example of Therapeutic Use | Example of Indication |
|---|---|---|---|---|---|---|
| CP-461 | Acetic acid, dichloro-, sodium salt [CAS] | 2156-56-1 | U.S. | 5,948,779 | Anticancer, other | Cancer, prostate |
| CPC-211 | | | | | Neuroprotective | Acidosis, lactic |
| CPI-1189 | CPI 1189 [CAS] | 210475-67-5 | WO | 9631462 | Congnition enhancer | Dementia, AIDS-related |
| CRA-0450 | | | WO | 0202549 | Anxiolytic | Unspecified |
| creatinol-O-phosphate | Guanidine, N-methyl-N-[2-(phosphonooxy)ethyl]-[CAS] | 6903-79-3 | | | Antianginal | |
| CRL-5861 | Oxirane, methyl-, polymer with oxirane, block [CAS] | 106392-12-5 | U.S. | 4,837,014 | Antisickling | Anaemia, sickle cell |
| crobenetine | (2R,6S)-3-[2(S)-Benzyloxypropyl]-6,11,11-trimethyl-1,2,3,4,5,6,-hexahydro-2,6-methano-3-benzazocin-10-ol | | WO | 9914199 | Neuroprotective | Ischaemia, cerebral |
| croconazole | 1H-Imidazole, 1-[1-[2-[(3-chlorophenyl)methoxy]phenyl]ethenyl]-[CAS] | 77175-51-0 | DE | 3021467 | Antifungal | Infection, fungal, general |
| cromoglicic acid | 4H-1-Benzopyran-2-carboxylic acid, 5,5'-[(2-hydroxy-1,3-propanediyl)bis(oxy)]bs4-oxo-[CAS] | 53736-52-0 | | | Formulation, mucosal, topical | Conjunctivitis |
| cromolyn | 4H-1-Benzopyran-2-carboxylic acid, 5,5'-[(2-hydroxy-1,3-propanediyl)bis(oxy)]bis4-oxo-[CAS] | 15826-37-6 16110-51-3 | | | Formulation, inhalable, solution | Asthma |
| Cropropamide | | 633-47-6 | | | | |
| Crotamiton | | 483-63-6 | | | | |
| Crotethamide | | 6168-76-9 | | | | |
| Crystacide | | | U.S. | 4,557,935 | Formulation, dermal, topical | Infection, dermatological |
| CS-502 | □ | | EP | 799823 | Analgesic, other | Pain, general |
| CS-758 | 4-[(1E,3E)-4-[trans-5-[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile | | | | Antifungal | Infection, fungal, general |
| CS-834 | 1-Azabicyclo[3.2.0]hept-2-ene-2-carboxylic acid, 6-[(1R)-1-hydroxyethyl]-4-methyl-7-oxo-3-[[(3R)-5-oxo-3-pyrrolidinyl]thio]-, (2,2-dimethyl-1-oxopropoxy)methyl ester, (4R,5S,6S)-[CAS] | 157542-49-9 | EP | 599512 | Beta-lactam antibiotic | Infection, general |
| CT-052923 | [2H-benzo[d][1,3-dioxalan-5-methyl]amino][4-(6,7-dimethoxyquinazolin-4-yl)piperazinyl]methane-1-thione | | | | Cardiovascular | Restenosis |
| CT-32228 | N-(4-bromophenyl)-6-(5-chloro-2-methylphenyl)-[1,3,5]triazine-2,4-diamine | | | | Anticancer, other | Cancer, general |
| Cupric Citrate | | 866-82-0 | | | | |
| Cuproxoline | | 13007-93-7 | | | | |
| CVT-2584 | Ethanol, 2,2'-[[6-[[(4-methoxyphenyl)methyl]amino]-9-(1-methylethyl)-9H-purin-2-yl]imino]bis-[CAS] | 199986-75-9 | WO | 9805335 | Cardiovascular | Restenosis |

TABLE IV-continued

| API Generic Name | API Chemical Name | CAS No. | Patent Reference | Example of Therapeutic Use | Example of Indication |
|---|---|---|---|---|---|
| CX-659S | ((S)-6-amino-5-(6-hydroxy-2,5,7,8-tetramethylchroman-2-carboxamido)-3-methyl-1-phenyl-2,4-(1H,3H)-pyrimidinedione | | | Dermatological | Eczema, general |
| Cyacetacide | | 140-87-4 | | | |
| Cyamemazine | | 3546-03-0 | | | |
| Cyanidin | | 528-58-5 | | | |
| CYC400 | | | WO 00172745 | Anticancer, other | Cancer, general |
| Cyclacillin | | 3485-14-1 | | | |
| Cyclandelate | | 456-59-7 | | | |
| Cyclazocine | | 3572-80-3 | | | |
| Cyclexanone | | 15301-52-7 | | | |
| Cyclexedrine | | 532-52-5 | | | |
| cyclidrol | | 498-71-5 | | COPD treatment, Respiratory | Bronchitis, chronic |
| cyclin D1 inhibitors | 3-Cyclohexene-1-methanol, 5-hydroxy-Alpha,Alpha,4-trimethyl-[CAS] | | U.S. 6,033,843 | Anticancer, hormonal | Cancer, breast |
| Cyclizine | | 82-92-8 | | | |
| Cyclobarbital | | 52-31-3 | | | |
| Cyclobendazole | | 31431-43-3 | | | |
| cyclobenzaprine | 1-Propanamine, 3-(5H-dibenzo[a,d]cyclohepten-5-ylidene)-N,N-dimethyl-[CAS] | 303-53-7 | | Formulation, modified-release, other | Muscle spasm, general |
| Cyclobutyrol | | 512-16-3 | | | |
| Cyclocumarol | | 518-20-7 | | | |
| Cyclodrine | | 52109-93-0 | | | |
| Cyclofenil | | 2624-43-3 | | | |
| Cycloguanil | | 516-21-2 | | | |
| Cyclomethycaine | | 139-62-8 | | | |
| Cycloniumelodide | | 6677-41-9 | | | |
| Cyclopentamine | | 102-45-4 | | | |
| Cyclopenthiazide | | 742-20-1 | | | |
| Cyclopentobarbital | | 76-68-6 | | | |
| Cyclopentolate | | 512-15-2 | | | |
| cyclophosphamide | N,N-Bis(2-chloroethyl)tetrahydro-2H-1,3,2-oxazaphosphorin-2-amine-2-oxide monohydrate | 50-18-0 6055-19-2 | | Formulation, parenteral, targeted | Cancer, general |
| cyclopiroxolamine | 2(1H)-Pyridinone, 6-cyclohexyl-1-hydroxy-4-methyl-, cmpd with 2-aminoethanol(1:1) [CAS] | 41621-49-2 | | Formulation, transdermal, other | Vaginitis |
| Cycloserine | | 68-41-7 | | | |
| Cyclothiazide | | 2259-96-3 | | | |
| Cyclovalone | | 579-23-7 | | | |
| Cymarin | | 508-77-0 | | | |
| cymserine | Carbamic acid, [4-(1-methylethyl)phenyl]-, (3aS,8aR)-1,2,3,3a,8,8a-hexahydro-1,3a,8-trimethylpyrrolo[2,3-b]indol-5-yl ester [CAS] | 145209-39-8 | WO 9902154 | Cognition enhancer | Alzheimer's disease |
| Cynarin(e) | | 30964-13-7 | | | |

TABLE IV-continued

| API Generic Name | API Chemical Name | CAS No. | Patent Reference | Example of Therapeutic Use | Example of Indication |
|---|---|---|---|---|---|
| CYP26 inhibitors | | | | | Unspecified |
| Cyproheptadine | | 129-03-3 | | | |
| cyproterone | (1β,2β)-6-Chloro-1,2-dihydro-17-hydroxy-3H-cyclopropa[1,2]pregna-1,4,6-triene-3,20-dione [CAS] | 2098-66-0 | U.S. 6,063,606 | Dermatological | Chemotherapy-induced injury, general |
| Cysteamine | | 60-23-1 | | Radio/chemoprotective | |
| cystic fibrosis ther | | | | Cystic fibrosis treatment | Cystic fibrosis |
| cytarabine | [[4-[[3-[[4-[1-(4-hydroxyphenyl)-1-methyl-ethyl]phenoxy]methyl]phenyl]methoxy]-phenyl]iminomethyl]-, ethyl ester 2(1H)-Pyrimidinone, 4-amino-1-[5-O-[hydroxy(octadecyloxy)phosphinyl]-β-D-arabinofuranosyl]-, [CAS] | 65093-40-5 147-94-4 | EP 239015 | Anticancer, antimetabolite | Myelodysplastic syndrome |
| D-24851 | N-(Pyridin-4-yl)-(1-(4-chlorobenzyl)-indol-3-yl)-glyoxyl-amide) | | | Anticancer, other | Cancer, general |
| D-4418 | 8-Methoxyquinoline-5-[N-(2,5-dichloropyridin-3-yl)]carboxamide | | | Antiasthma | Asthma |
| DA-5018 | Benzeneacetamide, 4-(2-aminoethoxy)-N-(3-(3,4-dimethylphenyl)propyl)-3-methoxy-, monohydrochloride [CAS] | 174661-97-3 | U.S. 5,242,944 | Analgesic, other | Pain, musculoskeletal |
| DA-6034 | | | U.S. 6,025,387 | GI inflammatory/bowel disorders | Crohn's disease |
| DA-7867 | | | KR 9957803 | Antibacterial, other | Infection, general |
| DA-7911 | | | KR 56034 | Antiarthritic, other | Arthritis, rheumatiod |
| DA-8159 | 3-(1-Methyl-7-oxo-3-propyl-6,7-dihydro-1H-pyrazolo-[4,3-d]pyrimidin-5-yl)-N-[2-(1-methylpyrrolidin-2-yl)ethyl]-4-propoxybenzenesulfonamide | | KR 353014 | Male sexual dysfunction | Sexual dysfunction, male, general |
| Dacarbazine | | 4342-3-4 | | | |
| Daclizumab | | 152923-56-3 | | | |
| Dactinomycin | | 50-76-0 | | | |
| dalbavancin | 5,31-Dichloro-38-de(methoxycarbonyl)-7-demethyl-19-deoxy-56-O-[2-deoxy-2-(10-methylundecanamido)-β-D-glucopyranosyl]-38-[N-[3-(dimethylamino)propyl]carbamoyl]-42-O-Alpha-D-mannopyranosyl-N15-methylristomycin A aglycone | 171500-79-1 | | Peptide antibiotic | Infection, dermatological |
| Dalfopristin | | 112362-50-2 | | | |
| dalfopristin + quinupristin | Virginiamycin M1, 26-((2-(diethylamino)ethyl)sulfonyl)-26,27-dihydro-, (26R,27S)-, mixt with 4-(4-(dimethylamino)-N-methyl-L-phenylalanine)-5-(5-((1-azabicyclo(2.2.2)oct-3-ylthio)methyl)-4-oxo-L-2-piperidinecarboxylic acid) virginiamycin S1-[CAS] | 126602-89-9 | EP 248703 | Antibiotic, other | Infection, respiratory tract, general |
| dalteparin | Heparin-, [CAS] | 9041-08-1 | U.S. 4,303,651 | Anticoagulant | Thromboprophylaxis |

TABLE IV-continued

| API Generic Name | API Chemical Name | CAS No. | Patent Reference | | Example of Therapeutic Use | Example of Indication |
|---|---|---|---|---|---|---|
| Daltroban | | 79094-20-5 | | | | |
| δ-Aminolevulinic Acid | | 106-60-5 | | | | |
| danaparoid | | | EP | 66908 | Anticoagulant | Thrombosis, venous |
| danazol | Pregna-2,4-dien-20-yno[2,3-d]isoxazol-17-ol, (17Alpha)-[CAS] | 17230-88-5 | GB | 905844 | Menstruation disorders | |
| Danthron | | 117-10-2 | | | | |
| Dantrolene | | 7261-97-4 | | | | |
| dapiprazole | 1,2,4-Triazolo[4,3-a]pyridine, 5,6,7,8-tetrahydro-3-[2-[4-(2-methylphenyl)-1-piperazinyl]ethyl]-[CAS] | 72822-12-9 72822-13-0 | U.S. | 4,252,721 | Ophthalmological | Glaucoma |
| dapivirine | 4-[[4-(2,4,6-trimethylphenyl)amino]pyrimidin-2-yl]amino]benzonitrile | 244767-67-7 | | | Antiviral, anti-HIV | Infection, HIV/AIDS |
| dapoxetine | (+)-(S)-N,N-dimethyl-Alpha-[2-(1-naphthyl-oxy)ethyl]benzylamine HCl | 119356-77-3 | EP | 288188 | Male sexual dysfunction | Premature ejaculation |
| dapsone | 4,4'-Sulfonyldianiline | 80-08-0 | | | Formulation, dermal, topical | Acne |
| daptomycin | Daptomycin [CAS] | 103060-53-3 | EP | 178152 | Peptide antibiotic | Infection, dermatological |
| Darbepoetin Alfa | | | | | | |
| darifenacin | 3-Pyrrolidineacetamide, 1-[2-(2,3-dihydro-5-benzofuranyl)ethyl]-Alpha,Alpha-diphenyl-, (S)-[CAS] | 133099-04-4 | EP | 388054 | Urological | Overactive bladder |
| daunorubicin | 5,12-Naphthacenedione, 8-acetyl-10-[(3-amino-2,3,6-trideoxy-Alpha-L-lyxo-hexopyranosyl)oxy]-7,8,9,10-tetrahydro-6,8,11-trihydroxy-1-methoxy-, (8S-cis)-[CAS] | 20830-81-3 | U.S. | 5,441,745 | Formulation, optimized, liposomes | Cancer, sarcoma, Kaposi's |
| DAX< SciClone | | | | | Cystic fibrosis treatment | Cystic fibrosis |
| DB-67 | 3-diallyl-8-cyclohexylxanthine | | | | Anticancer, other | Cancer, general |
| d-Camphocarboxylic | 7-tert-Butyldimethylsilyl-10-hydroxycamptothecin | | | | | |
| DCF-987 | Dextran | 18530-30-8 | U.S. | 5,514,665 | Formulation, other | Cystic fibrosis |
| DDT | | 50-29-3 | | | | |
| Deaminooxytocin | | 113-78-0 | | | | |
| Deanol | | 108-01-0 | | | | |
| Debrisoquin | | 1131-64-2 | | | | |
| Decamethonium | | 541-22-0 | | | | |
| Decimemide | | 14817-09-5 | | | | |
| decitabine | 1,3,5-Triazin-2(1H)-one, 4-amino-1-(2-deoxy-β-D-erythro-pentofuranosyl)-[CAS] | 23339-46-0 2353-33-5 | | | Anticancer, antimetabolite | Myelo-dysplastic syndrome |
| declopramide | Benzamide, 4-amino-3-chloro-N-(2-(diethylamino)ethyl)-[CAS] | 891-60-1 | WO | 9732582 | Anticancer, other | Cancer, colorectal |
| Deferiprone | | 30652-11-0 | | | | |
| Deferoxamine | | 70-51-9 | | | | |

TABLE IV-continued

| API Generic Name | API Chemical Name | CAS No. | Patent Reference | | Example of Therapeutic Use | Example of Indication |
|---|---|---|---|---|---|---|
| deflazacort | 5H-Pregna-1,4-dieno[17,16]oxazole-3,20-dione, 21-(acetyloxy)-11-hydroxy-2'-methyl-, (11β,16β)-[CAS] | 14484-47-0 74712-90-6 | GB | 1077393 | Hormone | Asthma |
| Defosfamide | | 3733-81-1 | | | | |
| degarelix | N-acetyl-3-(naphtalen-2-yl)-D-alanyl-4-chloro-D-phenylalanyl-3-(pyridin-3-yl)-D-alanyl-L-seryl-4-[[[(4S)-2,6-dioxohexahydropyrimidin-4-yl]carbonyl]amino]-L-phenylalanyl-4-(carbamoylamino)-D-phenylalanyl-L-leucyl-N6-(1-methylethyl)-L-lysyl-L-prolyl-D-alaninamide | 214766-78-6 | | | Anticancer, hormonal | Cancer, prostate |
| dehydroascorbic acid | L-threo-2,3-Hexodiulosonic acid gamma-lactone | 490-83-5 | | | Cognition enhancer | Alzheimer's disease |
| Dehyrdocholic Acid | | 81-23-2 | | | | |
| Dehydroemetine | | 4914-30-1 | | | | |
| delapril | Glycine, N-(2,3-dihydro-1H-inden-2-yl)-N-[N-[1-(ethoxycarbonyl)-3-phenylpropyl]-L-alanyl]-, (S)-[CAS] | 83435-66-9 83435-67-0 | EP | 51391 | Antihypertensive, renin system | Hypertension, general |
| delapri + manidipine | Glycine, N-(2,3-dihydro-1H-inden-2-yl)-N-[N-[1-(ethoxycarbonyl)-3-phenylpropyl]-L-alanyl]-, (S)-3,5-Pyridinedicarboxylic acid, 1,4-dihydro-2,6-dimethyl-4-(3-nitrophenyl)-, 2-[4-(diphenylmethyl)-1-piperazinyl]ethyl methyl ester [CAS] | | FR | 2733911 | Formulation, fixed-dose combinations | Hypertension, general |
| delavirdine | Piperazine, 1-[3-[(1-methylethyl)amino]-2-pyridinyl]-4-[[5-(methylsulfonyl)amino]-1H-indol-2-yl]carbonyl]-[CAS] | 136817-59-9 | WO | 9109849 | Antiviral, anti-HIV | Infection, HIV/AIDS |
| Delmadinone | | 13698-49-2 | | | | |
| Delmopinol | | 79874-76-3 | | | | |
| delorazepam | 2H-1,4-Benzodiazepin-2-one, 7-chloro-5-(2-chlorophenyl)-1,3-dihydro-[CAS] | 2894-67-9 | CH | 408029 | Anxiolytic | |
| delucemine | 3,3-Bis-(m-fluorophenyl)-N-methylpropylamine [CAS] | 186495-99-8 | | | Neuroprotective | Ischaemia, cerebral |
| Demanyl | | 6909-62-2 | | | | |
| Demecarium | | 56-94-0 | | | | |
| demeclocycline | 2-Naphthacenecarboxamide, 7-chloro-4-(dimethylamino)-1,4,4a,5,5a,6,11,12a-octahydro-3,6,10,12,12a-pentahydroxy-1,11-dioxo-, [4S-(4Alpha,4aAlpha,5aAlpha,6β,12Alpha)]-[CAS] | 127-33-3 | | | Formulation, modified-release, <=24 hr | Infection, general |
| Demecolcine | | 477-30-5 | | | | |
| Demegestone | | 10116-22-0 | | | | |
| Demexiptilline | | 24701-51-7 | | | | |
| denaverine | Benzeneacetic acid, Alpha-(2-ethylbutoxy)-Alpha-phenyl-, 2-(dimethylamino)ethyl ester, [CAS] | 3321-06-0 | DE | 4133785 | Analgesic, NSAID | Pain, musculoskeletal |
| Denileukin Diftitox | | 173146-27-5 | | | | |
| Denopamine | | 71771-90-9 | | | | |

TABLE IV-continued

| API Generic Name | API Chemical Name | CAS No. | Patent Reference | | Example of Therapeutic Use | Example of Indication |
|---|---|---|---|---|---|---|
| Denopterin | | 22006-84-4 | | | | |
| Deoxycholic Acid | | 83-44-3 | | | | |
| Deoxycorticosterone | | 64-85-7 | | | | |
| Deoxydihydro-streptomycin | | 26086-49-7 | | | | |
| Deoxyepinephrine | | 501-15-5 | | | | |
| Depreotide | | 161982-62-3 | | | | |
| depsipeptide | L-Valine, N-[(3S,4E)-3-hydroxy-7-mercapto-1-oxo-4-heptenyl]-D-valyl-D-cysteinyl-(2Z)-2-amino-2-butenoyl-, (4-1)-lactone, cyclic (1-2)-disulfide [CAS] | 128517-07-7 | EP | 352646 | Anticancer, antibiotic | Cancer, general |
| Deptropine | | 604-51-3 | | | | |
| Dequalinium | | 522-51-0 | | | | |
| dersalazine | Benzoic acid, 2-hydroxy-5-[[4-[3-[4-(2-methyl-1H-imidazol[4,5-c]pyridin-1-yl]methyl]-1-piperidinyl]-3-oxo-1-phenyl-1-propenyl]phenyl]azo] (Z) [CAS] | 188913-57-7 188913-58-8 | U.S. | 5,747,477 | Anti-inflammatory | Colitis, ulcerative |
| Deserpidine | | 131-01-1 | | | | |
| desferrioxamine | Butanediamide, N-[5-[[4-[[5-(acetylhydroxyamino)pentyl]amino]-1,4-dioxobutyl]hydroxyamino]pentyl]-N-(5-aminopentyl)-N-hydroxy-[CAS] | 70-51-9 | | | Antidote | Poisoning, metal |
| Desflurane | | 57041-67-5 | | | | |
| Desipramine | | 50-47-5 | | | | |
| Deslanoside | | 17598-65-1 | | | | |
| desloratadine | 5H-Benzo(5,6)cyclohepta(1,2-b)pyridine, 8-chloro-6,11-dihydro-11-(4-piperidinylidene)-[CAS] | 100643-71-8 | U.S. | 5,595,997 | Antiallergic, non-asthma | Rhinitis, allergic, perennial |
| deslorelin | Luteinizing hormone-releaseing factor (pig), 6-D-tryptophan-9-(N-ethyl-L-prolinamide)-10-deglycinamide-[CAS] | 57773-65-6 | U.S. | 4,034,082 | Releasing hormones | Cancer, prostate |
| desmopressin | Vasopressin, 1-(3-mercaptopropanoic acid)-8-D-arginine-[CAS] | 16679-58-6 | DE | 2948345 | Hormone | Enuresis |
| Desogestrel | | 54024-22-5 | | | | |
| desogestrel + estradiol | Estra-1,3,5(10)-triene-3,17-diol (17β)-, mixt. with (17Alpha)-13-ethyl-11-methylene-18,19-dinopregn-4-en-20-yn-17-ol [CAS] | 122364-17-4 | | | Menopausal disorders | Hormone replacement therapy |
| desogestrel, Akzo Nobel | 18,19-Dinopregn-4-en-20-yn-17-ol, 13-ethyl-11-methylene-, (17Alpha)-[CAS] | 54024-55-5 | | | Formulation, oral, other | Contraceptive, female |
| desogestrel + ethinylestrad (1) | 18,19-Dinopregn-4-en-20-yn-17-ol, 13-ethyl-11-methylene-, (17Alpha)-[CAS] | 54024-22-5 71138-35-7 | U.S. | 3,927,046 | Formulation, oral, other | Contraceptive, female |
| Desomorphine | | 427-00-9 | | | | |
| Desonide | | 638-94-8 | | | | |
| Desoximetasone | | 382-67-2 | | | | |
| Detaxtran | | 9015-73-0 | | | | |
| Devacade | | 50-02-2 | | | | |
| dexamethasone | Pregna-1,4-diene-3,20-dione, 9-fluoro-11,17,21-trihydroxy-16-methyl-, (11β,16Alpha)-[CAS] | 2392-39-4 312-93-6 | WO | 9308176 | Analgesic, other Formulation, other | Pain, general Inflammation, ocular |

TABLE IV-continued

| API Generic Name | API Chemical Name | CAS No. | Patent Reference | Example of Therapeutic Use | Example of Indication |
|---|---|---|---|---|---|
| dexanabinol | 6H-Dibenzo[b,d]pyran-9-methanol, 3-(1,1-dimethylheptyl)-6a,7,10,10a-tetrahydro-1-hydroxy-6,6-dimethyl-, (6aS-trans)-[CAS] | 112924-45-5 | EP 427518 | Neuroprotective | Head trauma |
| dexecadotril | Glycine, N-[2-[(acetylthio)methyl]-1-oxo-3-phenylpropyl]-, phenylmethyl ester, (R)-[CAS] | 112573-72-5 | EP 318377 | Alimentary/Metabolic, other | Unspecified |
| dexefaroxan | 1H-Imidazole, 2-(2-ethyl-2,3-dihydro-2-benzofuranyl)-4,5-dihydro-[CAS] | 89197-00-2 89197-32-0 | EP 71368 | Cognition enhancer | Alzheimer's disease |
| Dexetimide | | 21888-98-2 | | | |
| dexibuprofen | Benzeneacetic acid, Alpha-methyl-4-(2-methylpropyl)-, (AlphaS)-[CAS] | 51146-56-6 | | Analgesic, NSAID | Pain, general |
| dexketoprofen | Benzeneacetic acid, 3-benzoyl-Alpha-methyl-, (S)-[CAS] | 22161-81-5 | | Anti-inflammatory | Inflammation, general |
| dexloxiglumide | Pentanoic acid, 4-[(3,4-dichlorobenzoyl)amino]-5-[(3-methoxypropyl)pentylamino]-5-oxo-, (R)-[CAS] | 119817-90-2 | EP 0344184 | GI inflammatory/bowel disorders | Irritable bowel syndrome |
| dexmedetomidine | 1H-Imidazole, 4-[1-(2,3-dimethylphenyl)ethyl]-, (R)-[CAS] | 113775-47-6 86347-15-1 19262-68-1 | EP 187471 | Hypnotic/Sedative | Anaesthesia |
| dexmethylphenidate | 2-Piperidineacetic acid, Alpha-phenyl-, methyl ester, (AlphaR,2R)- | 6700-34-1 125-71-3 | | Psychostimulant | Attention deficit disorder |
| Dexpanthenol | | 81-13-0 | | | |
| dexrazoxane | 2,6-Piperazinedione, 4,4'-(1-methyl-1,2-ethanediyl)bis-, (S)-[CAS] | 24584-09-6 | DE 1910283 | Radio/chemoprotective | Chemotherapy-induced injury, general |
| Dextran-1 | Dextran [CAS] | 9004-54-0 56087-11-7 | | Plasma substitute | |
| Dextranomer | | 51-64-9 | | | |
| Dextroamphetamine | | | | | |
| dextromethorphan | Morphinan, 3-methoxy-17-methyl-, (9Alpha, 13Alpha, 14Alpha)-, | 6700-34-1 125-71-3 | U.S. 4,221,788 | Formulation, oral, other | Cough, Emotional lability |
| Dextromoramide | | 357-56-2 | | | |
| dextropropoxyphene | Benzeneethanol, Alpha-[2-(dimethylamino)-1-methylethyl]-Alpha-phenyl-, propanoate (ester), [S-(R*,S*)]-[CAS] | 469-62-5 | | Formulation, modified-release, other | Pain, general |
| Dezocine | | 53648-55-8 | | | |
| DF-1012 | N-Tropyl 7-azaindol-3-ylcarboxamide | 163220-65-3 | WO 9504742 | Respiratory | Respiratory disease, general |
| DFA-IV | di-D-fructofuranose 2,6':6,2' dianhydride | | U.S. 5,700,832 | Antianaemic | Anaemia, aplastic |
| d-Fenchone | | 4695-62-9 | | | |
| D-Glucuronolactone | | 32449-92-6 | | | |
| Diab II | Diab II | 309956-85-2 | U.S. 6,153,632 | Antidiabetic | Diabetes, Type II |
| diacerein | 2-Anthracenecarboxylic acid, 4,5-bis(acetyloxy)-9,10-dihydro-9,10-dioxo-[CAS] | 13739-02-1 | U.S. 4,244,968 | Antiarthritic, other | Arthritis, rheumatoid |
| Diampromide | | 552-25-0 | | | |
| Diamthazole | | 136-96-9 | | | |

TABLE IV-continued

| API Generic Name | API Chemical Name | CAS No. | Patent Reference | Example of Therapeutic Use | Example of Indication |
|---|---|---|---|---|---|
| Diathymosulfone | | 5964-62-5 | | | |
| Diatrizoate | | 737-31-5 | | | |
| diazepam | 2H-1,4-Benzodiazepin-2-one, 7-chloro-1,3-dihydro-1-methyl-5-phenyl-[CAS] | 439-14-5 | | Formulation, transmucosal, systemic | Anxiety, epilepsy, general |
| Diaziquone | | 57998-68-2 | | | |
| Diazoxide | | 364-98-7 | | | |
| dibekacin | D-Streptamine, O-3-amino-3-deoxy-Alpha-D-glucopyranosyl-(1-6)-O-[2,6-diamino-2,3,4,6-tetradeoxy-Alpha-D-erythro-hexopyranosyl-(1-4)]-2-deoxy-, sulfate (salt)[CAS] | 34493-98-6 58580-55-5 | GB 1349302 | Aminoglycoside antibiotic | Infection, general |
| Dibenzepin | | 4498-32-2 | | | |
| Dibromopropamidine | | 496-00-4 | | | |
| Dibucaine | | 61-12-1 | | | |
| Dichloralphenazone | | 480-30-8 | | | |
| Dichloramine T | | 473-34-7 | | | |
| Dichlorisone | | 7008-26-6 | | | |
| Dichlorobenzyl Alcohol | | 1777-82-8 | | | |
| Dichlorophen | | 97-23-4 | | | |
| Dichlorophenarsine | | 536-29-8 | | | |
| Dichlorphenamide | | 120-97-8 | | | |
| diclofenac + HA | Hyaluronic acid + benzeneacetic acid, 2-[(2,6-dichlorophenyl)amino]-[CAS] | | | Formulation, transdermal, systemic | Keratosis |
| diclofenac | Benzeneacetic acid, 2-[(2,6-dichlorophenyl)amino]-, [CAS] | 15307-79-6 15307-86-5 15307-81-0 | | Formulation, modified-release, <=24 hr | Pain, general |
| Dicloxacillin | | 3116-76-5 | | | |
| Dicumarol | | 66-76-2 | | | |
| Dicyclomine | | 77-19-0 | | | |
| didanosine | Inosine, 2',3'-dideoxy-[CAS] | 69655-05-6 | U.S. 4,861,759 | Antiviral, anti-HIV | Infection, HIV/AIDS |
| Dideoxyadenosine | | 4097-22-7 | | | |
| didox | Benzamide, N,3,4-trihydroxy-[CAS] | 69839-83-4 | U.S. 4,263,322 | Anticancer, antimetabolite | Cancer, general |
| Dienestrol | | 84-17-3 | | | |
| dienogest | 19-Norpregna-4,9-diene-21-nitrile, 17-hydroxy-3-oxo-, (17Alpha)-[CAS] | 65928-58-7 | GB 1524917 | Menstruation disorders | Endometriosis |
| dienogest + estradiol | 19-Norpregna-4,9-diene-21-nitrile, 17-hydroxy-3-oxo-, (17Alpha) + Estra-1,3,5(10)-triene-3,17-diol(17β) | | | Formulation, fixed-dose combinations | Contraceptive, female |
| Diethadione | | 702-54-5 | | | |
| Diethazine | | 60-91-3 | | | |
| Diethylbromo-acetamide | | 511-70-6 | | | |
| Diethylcarbamazine | | 90-89-1 | | | |
| diethylpropion | 1-Propanone, 2-(diethylamino)-1-phenyl-[CAS] | 90-84-6 | | Formulation, modified-release, <=24 hr | Obesity |
| Diethylstilbestrol | | 56-53-1 | | | |
| Difemerine | | 80387-96-8 | | | |

TABLE IV-continued

| API Generic Name | API Chemical Name | CAS No. | Patent Reference | Example of Therapeutic Use | Example of Indication |
|---|---|---|---|---|---|
| Difenamizole | | 20170-20-1 | | | |
| Difenoxin | | 28782-42-5 | | | |
| Difenpiramide | | 51481-40-3 | | | |
| diflomotecan | (5R)-5-Ethyl-9,10-difluoro-1,4,5,13-tetrahydro-5-hydroxy-3H,15H-oxepino[3',4':6,indolizino[1,2-b]quinoline-3,15-dione | 220997-97-7 | | Anticancer, other | Cancer, general |
| diflorasone | Pregna-1,4-diene-3,20-dione, 17,21-bist(acetyloxy)-6,9-difluoro-11-hydroxy-16-methyl-, (6Alpha,11β,16β)-[CAS] | 33564-31-7<br>2557-49-5 | U.S. 3,980,778 | Antipsoriasis | |
| Difloxacin | | 98106-17-3 | | | |
| Diflucortolone | | 2607-6-9 | | | |
| diflunisal | 2',4'-difluoro-4-hydroxy[1,1'-biphenyl]-3-carboxylic acid | 23674-86-4<br>22494-42-4 | GB 1175212 | Analgesic, NSAID | Pain, post-operative |
| Difluprednate | | 23674-86-4 | | | |
| Digitalin | | 752-61-4 | | | |
| Digitoxin | | 71-63-6 | | | |
| digoxin | Card-20(22)-enolide, 3-[(O-2,6-dideoxy-β-D-ribo-hexopyranosyl-(1-4)-O-2,6-dideoxy-β-D-ribo-hexopyranosyl-(1-4)-2,6-dideoxy-β-D-ribo-hexopyranosyl)oxy]-12,14-dihydroxy-, (3β,5β,12β)-[CAS] | 20830-75-5 | U.S. 4,088,750 | Formulation, oral, enteric-coated | Heart failure |
| Dihexyverine | | 561-77-3 | | | |
| Dihydralazine | | 484-23-1 | | | |
| Dihydrocodeine | | 125-28-0 | | | |
| Dihydrocodeinone Enol | | 466-90-0 | | | |
| dihydroergocryptine | Ergocryptine, dihydro-[CAS] | 25447-66-9 | | Formulation, other | Depression, general |
| dihydroergotamine | Ergotaman-3',6,18-trione, 9,10-dihydro-12'-hydroxy-2'-methyl-5'-(phenylmethyl)-, (5'Alpha,10Alpha)-[CAS] | 511-12-6 | 6495535 | Formulation, modified-release, other | Migraine |
| Dihydromorphine | | 509-60-4 | | | |
| Dihydrostreptomycin | | 128-46-1 | | | |
| Dihydrotachysterol | | 67-96-9 | | | |
| Dihydroxyaluminum | | 13682-92-3<br>539-68-4 | | | |
| Diisopromine | | 5966-41-6 | | | |
| Diisopropyl Paraoxon | | 3254-66-8 | | | |
| Diisopropylamine | | 660-27-5 | | | |
| dilazep | Benzoic acid, 3,4,5-trimethoxy-, (tetrahydro-1H-1,4-diazepine-1,4(5H)-diyl)di-3,1-propanediyl ester [CAS] | 35898-87-4 | JP 51095086 | Vasodilator, coronary | |
| Dilevalol | | 75659-07-3 | | | |
| diloxanide | 2-Furancarboxylic acid, 4-[(dichloroacetyl)methylamino]phenyl ester [CAS] | 3736-81-0<br>579-38-4 | | Amoebicide | |

TABLE IV-continued

| API Generic Name | API Chemical Name | CAS No. | | Patent Reference | Example of Therapeutic Use | Example of Indication |
|---|---|---|---|---|---|---|
| diltiazem | 1,5-Benzothiazepin-4(5H)-one, 3-(acetyloxy)-5-[2-(dimethylamino)ethyl]-2,3-dihydro-2-(4-methoxyphenyl)-, (2S-cis)-[CAS] | 33286-22-5 42399-41-7 | U.S. U.S. EP | 4,721,619 5,529,791 322277 | Antianginal | Angina, hypertension, general |
| Dimecrotic Acid | | 7706-67-4 | | | | |
| Dimefline | | 1165-48-6 | | | | |
| Dimemorfan | | 36309-01-0 | | | | |
| Dimenhydrinate | | 523-87-5 | | | | |
| Dimenoxadol | | 509-78-4 | | | | |
| Dimepheptanol | | 545-90-4 | | | | |
| Dimercaprol | | 59-52-9 | | | | |
| Dimetacrine | | 4757-55-5 | | | | |
| Dimethadione | | 695-53-4 | | | | |
| Dimethazan | | 519-30-2 | | | | |
| Dimethindene | | 5636-83-9 | | | | |
| Dimethisoquin | | 86-80-6 | | | | |
| Dimethisterone | | 79-64-1 | | | | |
| Dimethocaine | | 94-15-5 | | | | |
| Dimethoxanate | | 477-93-0 | | | | |
| Dimethyl Sulfoxide | | 67-68-5 | | | | |
| Dimethylthiambutene | | 524-84-5 | | | | |
| Dimetofrine | | 22950-29-4 | | | | |
| Dimorpholamine | | 119-48-2 | | | | |
| dinoprostone | Prosta-5,13-dien-1-oic acid, 11,15-dihydroxy-9-oxo-, (5Z,11Alpha,13E,15S)-[CAS] | 363-24-6 | | | Formulation, modified-release, <=24 hr | Labour, induction |
| diosmectite | Smecta-[CAS] | 110070-78-5 | FR | 2770778 | Antidiarrhoeal | Diarrhoea, general |
| diosmin | 4H-1-Benzopyran-4-one, 7-[[6-O-(6-deoxy-Alpha-L-mannopyranosyl)-beta,-D-glucopyranosyl]oxy]-5-hydroxy-2-(3-hydroxy-4-methoxyphenyl)-[CAS] | 520-27-4 | DE | 2602314 | Vasoprotective, systemic | |
| Dioxadrol | | 6495-46-1 | | | | |
| Dioxaphetyl | | 467-86-7 | | | | |
| Dioxethedrine | | 497-75-6 | | | | |
| Dioxybenzone | | 131-53-3 | | | | |
| Diphemanil | | 62-97-5 | | | | |
| Diphenadione | | 82-66-6 | | | | |
| Diphencyprone | | 886-38-4 | | | | |
| Diphenhydramine | | 58-73-1 | | | | |
| Diphenidol | | 972-02-1 | | | | |
| Diphenoxylate | | 915-30-0 | | | | |
| Diphenylpyraline | | 147-20-6 | | | | |
| Diphetarsone | | 515-76-4 | | | | |
| Diphtheria & Tetanus Toxoids And Acellular Pertussis Vaccine Adsorbed | | | | | | |

TABLE IV-continued

| API Generic Name | API Chemical Name | CAS No. | Patent Reference | | Example of Therapeutic Use | Example of Indication |
|---|---|---|---|---|---|---|
| Dipipanone dipivefrin | Propanoic acid, 2,2-dimethyl-, 4-[1-hydroxy-2-(methylamino)ethyl]-1,2-phenylene ester, (+/−)-[CAS] | 467-83-4 52365-63-6 | U.S. | 3,809,714 | Antiglaucoma | Glaucoma |
| Dipyridamole Dipyrocetyl Dipyrone diquafosol | Uridine 5′-(pentahydrogen tetraphosphate)-5′-ester with uridine, [CAS] | 58-32-2 486-79-3 5907-38-0 211427-08-6 | | | Ophthalmological | Dry eye syndrome |
| dirithromycin | Erythromycin, 9-deoxo-11-deoxy-9,11-[imino[2-(2-methoxyethoxy)ethylidene]oxy]-, [9S(R)]-[CAS] | 62013-04-1 | DE | 2515075 | Macrolide antibiotic | Tonsillitis |
| disodium pamidronate | Phosphonic acid, (3-amino-1-hydroxypropylidene)bis-, disodium salt [CAS] | 57248-88-1 | EP | 177443 | Osteoporosis treatment | Hypercalcaemia of malignancy |
| Disofenin disopyramide | 2-Pyridineacetamide, Alpha-[2-[bis(1-methylethyl)amino]ethyl]-Alpha-phenyl-[CAS] | 65717-97-7 3737-09-5 | | | Formulation, modified-release, <=24 hr | Arrhythmia, general |
| Distigmine Disulfamide Disulfiram Ditazol Dithiazanine dithranol | 9(10H)-Anthracenone, 1,8-dihydroxy- [CAS] | 15879-67-2 671-88-5 97-77-8 18471-20-0 514-73-8 1143-38-0 | | | Formulation, dermal, topical | Psoriasis |
| Ditiocarb Dixanthogen Dixyrazine DJ-927 | | 148-18-5 502-55-6 2470-73-7 | WO | 01027115 | Anticancer, other | Cancer, general |
| DK-507k | (−)-7-[(7S)-7-Amino-5-azaspiro[2,4]heptan-5-yl]-6-fluoro-1-[(1R,2S)-2-fluoro-1-cyclopropyl]-1,4-dihydro-8-methoxy-4-oxo-3-quinolinecarboxylic acid hydrochloride monohydrate | | | | Quinolone antibacterial | Infection, general |
| <i>DL</i>-Lactic Acid DMDC | Cytidine, 2′-deoxy-2′-methylene-, monohydrochloride [CAS] | 598-82-3 113648-25-2 | WO | 8807049 | Anticancer, antimetabolite | Cancer, general |
| DMXAA | 5,6-dimethylxanthenone-4-acetic acid | | | | Anticancer, other | Cancer, lung, general |
| DNA Stealth Nucleosides Dobesilate | | | U.S. | 6,132,776 | Antiviral, anti-HIV | Infection, HIV/AIDS |
| dobutamine | 1,2-Benzenediol, 4-[2-[[3-(4-hydroxyphenyl)-1-methylpropyl]amino]ethyl]-, (+/−)-[CAS] | 20123-80-2 34368-04-2 49745-95-1 | U.S. | 3,987,200 | Cardiostimulant | |

TABLE IV-continued

| API Generic Name | API Chemical Name | CAS No. | Patent Reference | Example of Therapeutic Use | Example of Indication |
|---|---|---|---|---|---|
| Docarpamine | | 74639-40-0 | | | |
| docetaxel | (2R,3S)-N-Carboxy-3-phenylisoserine, N-tert-butyl ester, 13-ester with 5β,20-epoxy-1,2Alpha,4,7β,10β,13Alpha-hexahydroxytax-11-en-9-one 4-acetate 2-benzoate-[CAS] | 114977-28-5 14808-66-6 | EP 253738 | Anticancer, other | Cancer, breast |
| docosahexaenoic acid | | | EP 707487 | Hypolipidaemic/Antiatherosclerosis | Hyperlipidaemia, general |
| docosanol | 1-Docosanol [CAS] | 661-19-8 | EP 469064 | Antiviral, other | Infection, herpes simplex virus |
| docusate | | 128-49-4 577-11-7 | U.S. 4,752,617 | Formulation, dermal, topical | Infection, herpes simplex virus prophylaxis |
| dofetilide | Methanesulfonamide, N-[4-[2-[methyl[2-[4-[(methylsulfonyl)amino]phenoxy]ethyl]amino]ethyl]phenyl]-[CAS] | 115256-11-6 | EP 245997 | Antiarrhythmic | Fibrillation, atrial |
| dolasetron mesilate | 1H-Indole-3-carboxylic acid, octahydro-3-oxo-2,6-methano-2H-quinolizin-8-yl ester, (2Alpha,6Alpha,8Alpha,9Alphaβ)-, monomethanesulfonate-[CAS] | 115956-13-3 115956-12-2 | EP 266730 | Antiemetic | Chemotherapy-induced nausea and vomiting |
| Domiodol | | 61869-07-6 | | | |
| Domiphen | | 538-71-6 | | | |
| Domitroban | | 112966-96-8 | | | |
| domperidone | 2H-Benzimidazol-2-one, 5-chloro-1-[1-[3-(2,3-dihydro-2-oxo-1H-benzimidazol-1-yl)propyl]-4-piperidinyl]-1,3-dihydro-[CAS] | 57808-66-9 | U.S. 4,066,772 | Antiemetic | |
| donepezil | 1H-Inden-1-one, 2,3-dihydro-5,6-dimethoxy-2-((1-(phenylmethyl)-4-piperidinyl)methyl)-, [CAS] | 120011-70-3 120014-06-4 | EP 296560 | Cognition enhancer | Alzheimer's disease |
| donitriptan | Piperazine, 1-(((3-(2-aminoethyl)-1H-indol-5-yl)oxy)acetyl)-4-(4-cyanophenyl)-[CAS] | 170912-52-4 | | Antimigraine | Migraine |
| Dopamine | | 51-61-6 | | | |
| Dopexamine | | 86197-47-9 | | | |
| doramapimod | urea, N-[3-(1,1-dimethylethyl)-1H-pyrazol-5-yl]-N-[4-[2-(4-morpholinyl)ethoxy)-1-naphthalenyl]- | 285983-48-4 | | Antiarthritic, immunological | Arthritis, rheumatoid |
| doranidazole | (±)-1,2,4-Butanetriol, 3-((2-nitro-1H-imidazol-1-yl)methoxy)-[CAS] | 137339-64-1 | WO 9414778 | Radio/chemosensitizer | Surgery adjunct |
| doripenem | (1R,5S,6S)-2-[(3S,5S)-5-(sulfamoylaminomethyl)pyrrolidin-3-yl]thio-6-[(1R)-1-hydroxyethyl]-1-methylcarbapen-2-em-3-carboxylic acid | 148016-81-3 | EP 528678 | Beta-lactam antibiotic | Infection, urinary tract |
| dorzolamide | 4H-Thieno(2,3-b)thiopyran-2-sulfonamide, 4-(ethylamino)-5,6-dihydro-6-methyl-,7,7-dioxide (4S-trans)-[CAS] | 120279-96-1 | EP 296879 | Antiglaucoma | Glaucoma |

TABLE IV-continued

| API Generic Name | API Chemical Name | CAS No. | Patent Reference | | Example of Therapeutic Use | Example of Indication |
|---|---|---|---|---|---|---|
| dorzolamide + timolol | 4H-Thieno(2,3-b)thiopyran-2-sulfonamide, 4-(ethylamino)-5,6-dihydro-6-methyl-7,7-dioxide (4S-trans) + ethyl 2-propanol, 1-[[(1,1-dimethyl)amino]-3-[[4-(4-morpholinyl)-1,2,5-thiadiazol-3-yl]oxy]-, (S), (Z)-2-butenedioate (1:1) (salt) [CAS] | 120279-96-1 26839-75-8 26921-17-5 | | | Formulation, fixed-dose combinations | Glaucoma |
| dosmalfate | Aluminium, (μ7-(7-((6-O-(6-deoxy-2,3,4-tri-O-sulfo-Alpha-L-mannosylpyranosyl)-2,3,4-tri-O-sulfo-β-D-glucopyranosyl)oxy)-5-hydroxy-2-(4-methoxy-3-(sulfooxyphenyl)-4H-1-benzopyran-4-onato(7-))tetradeca-μ-hydroxyheneicosahydroxytetradeca-μ-hydroxyheneicosahydroxytetradeca-[CAS] | 122312-55-4 | | | Antiulcer | Ulcer, gastric |
| dosulepine | 1-Propanamine, 3-dibenzo[b,e]thiepin-11(6H)-ylidene-N,N-dimethyl-[CAS] | 113-53-1 | | | Antidepressant | |
| Dotarizine | | 84625-59-2 | | | | |
| Dothiepin | | 113-53-1 | | | | |
| Doxacurium | | 106819-53-8 | | | | |
| Doxapran | | 309-29-5 | | | | |
| doxazosin | Piperazine, 1-(4-amino-6,7-dimethoxy-2-quinazolinyl)-4-[(2,3-dihydro-1,4-benzodioxin-2-yl)carbonyl-[CAS] | 74191-85-8 | GB | 2007656 | Antihypertensive, adrenergic | Hypertension, general |
| Doxefazepam | | 40762-15-0 | | | | |
| Doxenitoin | | 3254-93-1 | | | | |
| doxepin | 1-Propanamine, 3-dibenz[b,e]oxepin-11(6H)ylidene-N,N-dimethyl- | 1668-19-5 | | | Formulation, dermal, topical | Pruritus |
| doxercalciferol | 9,10-secoergosta-5,7,10(19),22-tetraene-1,3-diol (1Alpha, 3β, 5Z, 7E, 22E) [CAS] | 54573-75-0 | U.S. | 5,104,854 | Hormone | Hyperparathyroidism |
| doxifluridine | Uridine, 5'-deoxy-5-fluoro-[CAS] | 3094-09-5 | U.S. | 4,071,680 | Anticancer, antimetabolite | Cancer, colorectal |
| doxofylline | 1H-Purine-2,6-dione, 7-(1,3-dioxolan-2-ylmethyl)-3,7-dihydro-1,3-dimethyl-[CAS] | 69975-86-6 | U.S. | 4,187,308 | Antiasthma | Asthma |
| doxorubicin | 5,12-Naphthacenedione, 10-[(3-amino-2,3,6-trideoxy-Alpha-L-lyxo-hexopyranosyl)oxy]-7,8,9,10-tetrahydro-6,8,11-trihydroxy-8-(hydroxyacetyl)-1-methoxy-, (8S-cis)-[CAS] | 23214-92-8 | EP | 191824 | Formulation, optimized, liposomes | Cancer, general |
| doxycycline | 2-Naphthacenecarboxamine, 4-(dimethyl)amino)-1,4,4a,5,5a,6,11,12a-octahydro-3,5,10,12,12a-pentahydroxy-6-methyl-1,11-dioxo-[4S-(4Alpha,4aAlpha,5Alpha,5aAlpha,6Alpha,12aAlpha)]-[CAS] | 564-25-0 17086-28-1 | | | Formulation, modified-release, immediate | Periodontitis |
| doxylamine | N,N-Dimethyl-2-[1-phenyl-1-(2-pyridinyl)ethoxy]ethanamine | 469-21-4 | | | Formulation, transmucosal, systemic | Rhinitis, allergic, general |
| DPC-817 | β-D-2',3'-didehydro-2',3'-dideoxy-5-fluorocytidine | | | | Antiviral, anti-HIV | Infection, HIV/AIDS |

TABLE IV-continued

| API Generic Name | API Chemical Name | CAS No. | Patent Reference | | Example of Therapeutic Use | Example of Indication |
|---|---|---|---|---|---|---|
| DPI-3290 | | | | | | |
| DQ-113 | 5-Amino-7-[(3S,4R)-(1-aminocyclopropyl)-3-fluoropyrrolidin-1-yl]-1-[(1R,2S)-2-fluoro-1-cyclopropyl]-1,4-dihydro-8-methyl-4-oxo-3-quinolinecarboxylic acid | | U.S. | 5,681,830 | Analgesic, other Quinolone antibacterial | Pain, general Infection, general |
| Drofenine | | 1679-76-1 | | | | |
| Droloxifene | | 82413-20-5 | | | | |
| Drometrizole | | 2440-22-4 | | | | |
| Dromostanolone | | 58-19-5 | | | | |
| dronabinol | 6H-Dibenzo[b,d]pyran-1-ol, 6a,7,8,10a-tetrahydro-6,6,9-trimethyl-3-pentyl-, (6aR-trans)-[CAS] | 1972-08-3 | | | Antiemetic | Chemotherapy-induced nausea and vomiting |
| dronedarone | 2-n-Butyl 3-[4-(3-di-n-butylamino-propoxy)benzoyl]5-methylsulfonamidobenzofuran | | | | Antiarrhythmic | Arrhythmia, general |
| Droperidol | | 548-73-2 | | | | |
| Droprenilamine | | 57653-27-7 | | | | |
| Dropropizine | | 17692-31-8 | | | | |
| Drospirenone | | 67392-87-4 | | | | |
| Drotaverine | | 14009-24-6 | | | | |
| Drotebanol | | 03/02/3176 | | | | |
| droxicam | 2H,5H-1,3-Oxazino[5,6-c][1,2]benzothiazine-2,4(3H)-dione, 5-methyl-3-(2-pyridinyl)-, 6,6-dioxide [CAS] | 90101-16-9 | EP | 99770 | Anti-inflammatory | Inflammation, general |
| droxidopa | L-Tyrosine, β,3-dihydroxy-, threo-[CAS] | 23651-95-8 | EP | 128684 | Antiparkinsonian | Parkinson's disease |
| Droxidopa | | 23651-95-8 | | | | |
| DU-125530 | 1,2-Benzisothiazol-3(2H)-one, 2-[4-[4-(7-chloro-2,3-dihydro-1,4-benzodioxin-5-yl)-1-piperazinyl]butyl]-, 1,1-dioxide [CAS] | 161611-99-0 | EP | 633260 | Anxiolytic | Anxiety, general |
| duloxetine | 2-Thiophenepropanamine, N-methyl-Gamma-(1-naphthalenyloxy)-, hydrochloride, (S)-[CAS] | 136434-34-9 116539-59-4 | U.S. | 5,362,886 | Antidepressant | Depression, general |
| duramycin | | 1306-06-5 | WO | 9428726 | Formulation, inhalable, solution | Cystic fibrosis |
| Durapatite | | | | | | |
| dutasteride | 4-Azaandrost-1-ene-17-carboxamide, N-(2,5-bis(trifluoromethyl)phenyl)-3-oxo-, (5Alpha,17β)-[CAS] | 164656-23-9 | U.S. | 5,565,467 | Prostate disorders | Benign prostatic hyperplasia |
| DW-1141 | N,N-diisopropyl-4-[4-(3-aminobenzo[d]isoxazol-6-yloxy)butoxy]-3-methoxybenzamide | | | | Osteoporosis treatment | Osteoporosis |
| DW-286a | (R)-(−)-7-(4-aminomethyl-4-methyl-3-(Z)-methyloxyimino)pyrrolidin-1-yl)-1-cyclopropyl-6-fluoro-4-oxo-1,4-dihydro[1,8]naphthyridine-3-carboxylic acid | | | | Quinolone antibacterial | Infection, general |
| DW-471 | | | U.S. | 5,922,871 | Antiviral, other | Infection, hepatitis-B virus |

TABLE IV-continued

| API Generic Name | API Chemical Name | CAS No. | Patent Reference | Example of Therapeutic Use | Example of Indication |
|---|---|---|---|---|---|
| DX-9065a | 2-Naphthalenepropanoic acid, 7-(aminoiminomethyl)-Alpha-[4-[[1-(1-iminoethyl)-3-pyrrolidinyl]oxy]phenyl]-, monohydrochloride, pentahydrate, [S-(R*,R*)]-[CAS] | 155204-81-2 | | Antithrombotic | Thrombosis, general |
| DY-9760e | 1H-Indazole, 3-[2-[4-(3-chloro-2-methylphenyl)-1-piperazinyl]ethyl]-1-(1H-imidazol-4-ylmethyl)-5,6-dimethoxy-[CAS] | 160522-00-9 | U.S. 5,681,954 | Neuroprotective | Ischaemia, cerebral |
| Dyclonine | | 586-60-7 | | | |
| Dydrogesterone | | 152-62-5 | | | |
| Dymanthine | | 124-28-7 | | | |
| Dyphyllin | | 479-18-5 | | | |
| E-1010 | 1-Azabicyclo[3.2.0]hept-2-ene-2-carboxylic acid, 6-[(1R)-1-hydroxyethyl]-3-[[(3S,5S)-5-[(R)-hydroxy(3R)-3-pyrrolidinylmethyl]-3-pyrrolidinyl]thio]-4-methyl-7-oxo-, monohydrochloride, (4R,5S,6S)-[CAS] | 186319-97-1 | | Beta-lactam antibiotic | Infection, general |
| E-2101 | N-Ethyl-1-(1-(2-fluorophenethyl)piperidin-4-yl]-1H-indol-6-yl]acetamide | | | Muscle relaxant | Muscle spasm, general |
| E2F antagonists | | | WO 9606943 | Anticancer, other | Cancer, general |
| E-3620 | Benzamide, 4-amino-5-chloro-N-(8-methyl-8-azabicyclo[3.2.1]oct-3-yl)-2-[(1-methyl-2-butynyl)oxy]-, monohydrochloride, [3(S)-endo]-[CAS] | 151213-86-4 | EP 554794 | Antacid/ Antiflatulent | Dyspepsia |
| E-5564 | Alpha-D-Glucopyranose, 3-O-decyl-2-deoxy-6-O-(2-deoxy-3-O-(3R)-3-methoxydecyl)-6-O-methyl-2-(((11Z)-1-oxo-11-octadecenyl)amino)-4-O-phosphono-β-D-glucopyranosyl)-2-((1,3-dioxotetradecyl)amino)-1-(dihydrogen phosphate), tetrasodium salt [CAS] | 185954-98-7 | EP 536969 | Septic shock treatment | Sepsis |
| E-5842 | Pyridine, 4-(4-fluorophenyl)-1,2,3,6-tetrahydro-1-[4-(1H-1,3,4-triazol-1-yl)butyl]-, 2-hydroxy-1,2,3-propanetricarboxylate (1:1)[CAS] | 220120-14-9 | | Neuroleptic | Schizophrenia |
| E-6259 | 1-(4-Aminosulfonylphenyl)-5-(2,4-difluorophenyl)-4,5-dihydro-3-trifluoromethyl-1-H-pyrazole | | | Antiarthritic, other | Unspecified |
| EAA-90 | 1H-Imidazole, [2-(8,9-Dioxo-2,6-diazabicyclo[5.2.0]non-1(7)-en-2-yl)-ethyl]phosphonic acid | 57-08-9 | | Analgesic, other | Pain, neuropathic |
| ε-Acetamidocaproic Acid | | 60-32-2 | | | |
| ε-Aminocaproic Acid | | | | | |
| ebastine | 1-Butanone, 1-[4-(1,1-dimethylethyl)phenyl]-4-[4-(diphenylmethoxy)-1-piperidinyl]-[CAS] | 90729-43-4 | EP 134124 | Antiallergic, non-asthma | Rhinitis, allergic, seasonal |
| eberconazole | 1H-Imidazole, 1-(2,4-dichloro-10,11-dihydro-5H-dibenzo[a,d]cyclohepten-5-yl)-[CAS] | 128326-82-9 130104-32-4 | ES 2012297 | Antifungal | Infection, dermatological |

TABLE IV-continued

| API Generic Name | API Chemical Name | CAS No. | Patent Reference | Example of Therapeutic Use | Example of Indication |
|---|---|---|---|---|---|
| ebrotidine | Benzenesulfonamide, N-[[[2-[[[2-[(aminoiminomethyl)amino]-4-thiazolyl]methyl]thio]ethyl]amino]methylene]-4-bromo-[CAS] | 100981-43-9 | EP 159012 | Antiulcer | Ulcer, duodenal |
| ebselen | 1,2-Benzisoselenazol-3(2H)-one, 2-phenyl-[CAS] | 60940-34-3 | EP 44971 | Neuroprotective | Haemorrhage, subarachnoid |
| Eburnamonine | | 474-00-0 | | | |
| Ecabapide | | 104775-36-2 | | | |
| ecabet | 1-Phenanthrenecarboxylic acid, 1,2,3,4,4a,9,10,10a-octahydro-1,4a-dimethyl-7-(1-methylethyl)-6-sulfo-, [1R-(1Alpha,4aβ,10aAlpha)]-[CAS] | 33159-27-2<br>86408-72-2 | DE 3239172 | Antiulcer | Ulcer, gastric |
| ecadotril | Glycine, N-[2-[(acetylthio)methyl]-1-oxo-3-phenylpropyl]-,phenylmethyl ester, (S)-[CAS] | 112573-73-6 | EP 318377 | Antihypertensive, other | Hypertension, general |
| Ecgonidine | | 484-93-5 | | | |
| Ecgonine | | 481-37-8 | | | |
| Echothiophate | | 513-10-0 | | | |
| Econazole | | 27220-47-9 | | | |
| ecopipam | 5H-Benzo[d]naphth[2,1-b]azepin-12-ol, 11-chloro-6,6a,7,8,9,13b-hexahydro-7-methyl-, (6aS-trans)-[CAS] | 112108-01-7 | EP 230270 | Anorectic/Antiobesity | Obesity |
| ecraprost | Prosta-8,13-dien-1-oic acid, 11,15-dihydroxy-9-(1-oxobutoxy)-, butyl ester, (11Alpha,13E,15S)-[CAS] | 136892-64-3 | EP 423697 | Vasodilator, peripheral | Peripheral vascular disease |
| Ectylurea | | 95-04-5 | | | |
| ED-71 | 9,10-Secocholesta-5,7,10(19)-triene-1,3,25-triol, 2-(3-hydroxypropoxy)-, (1Alpha,2β,3β,5Z,7E)-[CAS] | 104121-92-8 | EP 184206 | Osteoporosis treatment | Osteoporosis |
| edaravone | 3H-Pyrazol-3-one, 2,4-dihydro-5-methyl-2-phenyl-[CAS] | 89-25-8 | JP 62108814 | Neuroprotective | Infarction, cerebral |
| Edatrexate | | 80576-83-6 | | | |
| Edetate Calcium Disodium | | 62-33-9 | | | |
| Edetate Disodium | | 139-33-3 | | | |
| Edetate Sodium | | 64-02-8 | | | |
| Edetate Trisodium | | 150-38-9 | | | |
| edonentan | Butanamide,N-[[2'-[[4,5-dimethyl-3-isoxazoyl)amino]sulfonyl]-4-(2-oxazolyl)[1,1'-biphenyl]-2-yl]methyl]-N,3,3-trimethyl-, monohydrate | 210891-04-6 | U.S. 6,183,721 | Cardiostimulant | Heart failure |
| edotreotide | [N-[2-[4,7-Bis[(carboxy-kappaO)methyl]-10-(carboxymethyl)-1,4,7,10-tetraazacyclododec-1-yl-kappaN1,kappaN4,kappaN10]acetyl]-D-phenylalanyl-L-cysteinyl-L-tyrosyl-D-tryptophyl-L-lysyl-L-threanyl-L-cysteinyl-L-threoninol cyclic (2-7)-disulfidato(3-)]yttrium | 204318-14-9 | | Anticancer, hormonal | Cancer, lung, small cell |

TABLE IV-continued

| API Generic Name | API Chemical Name | CAS No. | Patent Reference | Example of Therapeutic Use | Example of Indication |
|---|---|---|---|---|---|
| edoxudine | Uridine, 2'-deoxy-5-ethyl-[CAS] | 15176-29-1 | GB 1170565 | Antiviral, other | Infection, herpes virus, general |
| Edrecolomab | | 156586-89-9 | | | |
| Edrophonium | | 116-38-1 | | | |
| Efalith | Butanedioic acid, lithium salt [CAS] | 16090-09-8 | | Antipruritic/inflamm, allergic | Eczema, seborrhoeic |
| efaproxiral | Propanoic acid, 2-[4-[2-[(3,5-dimethylphenyl)amino]-2-oxoethyl]phenoxy]-2-methyl-[CAS] | 131179-95-8 | U.S. 5,705,521 | Radio/chemosensitizer | Cancer, brain |
| efavirenz | 2H-3,1-Benzoxazin-2-one, 6-chloro-4-(cyclopropylethynyl)-1,4-dihydro-4-(trifluoromethyl)-, (S)-[CAS] | 154598-52-4 | WO 9403440 | Antiviral, anti-HIV | Infection, HIV/AIDS |
| efletirizine | [2-[4-[Bis(p-fluorophenyl)methyl]-1-piperazinyl]ethoxy]acetic acid | 150756-35-7 | GB 2311940 | Antiallergic, non-asthma | Allergy, general |
| eflornithine | DL-Ornithine, 2-(difluoromethyl)-[CAS] | 70052-12-9 67037-37-0 | U.S. 4,413,141 | Protozoacide, dermal, topical | Infection, trypanosomiasis, African, Hirsutism |
| Efloxate | | 119-41-5 | | | |
| eflucimibe | Benzeneacetamide, Alpha-(dodecylthio)-N-(4-hydroxy-2,3,5-trimethylphenyl)-(S)-[CAS] | 202340-45-2 | | Hypolipidaemic/Antiatherosclerosis | Hyperlipidaemia, general |
| efonidipine | 3-pyridinecarboxylic acid, 5-(5,5-dimethyl-1,3,2-dioxaphosphorinan-2-yl)-1,4-dihydro-2,6-dimethyl-4-(3-nitrophenyl)-, 2-phenyl(phenylmethyl)amino)ethyl ester, P-oxide [CAS] | 111011-53-1 111011-63-3 111011-76-8 | EP 230944 | Antihypertensive, other | Hypertension, general |
| EGIS-7229 | 5-Chloro-4-[3-[N-[2-(3,4-dimethoxyphenyl)ethyl]-N-methylamino]propylamino]-3(2H)-pyridazinone fumarate [CAS] | 150800-12-7 190333-92-7 | DE 4243381 | Antiarrhythmic | Arrhythmia, general |
| eglumegad | Bicyclo[3.1.0]hexane-2,6-dicarboxylic acid, 2-amino-, (1S,2S,5R,6S)-[CAS] | 176199-48-7 209216-09-1 | | Anxiolytic | Anxiety, general |
| egualen | 1-Azulenesulfonic acid, 3-ethyl-7-(1-methylethyl)-, | 97683-31-3 99287-30-6 10417-94-4 | EP 147915 | Antiulcer | Ulcer, gastric |
| Eicosapentaenoic Acid | | | | | |
| elarofiban | 3-Pyridinepropanoic acid, β-[[(3R)-1-[1-oxo-3-(4-piperidinyl)propyl]-3-piperidinyl]carbonyl]amino]-, (βS)-[CAS] | 198958-88-2 | WO 9741102 | Antithrombotic | Thrombosis, general |
| Elcatonin | | 60731-46-6 | | | |
| Eledoisin | | 69-25-0 | | | |
| eletriptan | 1H-Indole, 3-((1-methyl-2-pyrrolidinyl)methyl)-5-(2-(phenylsulfonyl)ethyl)-(R)-[CAS] | 143322-58-1 | U.S. 5,607,951 | Antimigraine | Migraine |
| Elgodipine | | 119413-55-7 | | | |
| Ellagic Acid | | 476-66-4 | | | |
| Elliptinium | | 58337-35-2 | | | |
| Eltoprazine | | 98224-03-4 | | | |

TABLE IV-continued

| API Generic Name | API Chemical Name | CAS No. | Patent Reference | Example of Therapeutic Use | Example of Indication |
|---|---|---|---|---|---|
| elvucitabine | β-L-2',3'-Didehydro-2',3'-dideoxy-5-fluorocytidine | 181785-84-2 | | Antiviral, other | Infection, hepatitis-B virus |
| elzasonan | (2Z)-4-(3,4-dichlorophenyl)-2-[2-(4-methylpiperazin-1-yl)benzylidene]thiomorpholin-3-one monohydrochloride-[CAS] | 220322-05-4 361343-20-6 | | Antidepressant | Depression, general |
| Embelin | | 550-24-3 | | | |
| Embramine | | 3565-72-8 | | | |
| emedastine | 1H-Benzimidazole, 1-(2-ethoxyethyl)-2-(hexahydro-4-methyl-1H-1,4-diazepin-1-yl)-, (E)-2-butenedioate (1:2) [CAS] | 87233-61-2 87233-62-3 | EP 79545 | Antiallergic, non-asthma | Rhinitis, allergic, general |
| Emepronium | | 3614-30-0 | | | |
| Emetine | | 483-18-1 | | | |
| Emitefur | | 110690-43-2 | | | |
| EMM-210525 | 17Alpha-Acetoxy-6Alpha-methyl-19-nor-1β,2β-dihydrocyclopropa[1,2']pregn-4-ene-3,20-dione + Estra-1,3,5(10)-triene-3,17-diol(17β) | | | Formulation, fixed-dose combinations | Hormone replacement therapy |
| Emodin | | 518-82-1 | | | |
| emorfazone | 3(2H)-Pyridazinone, 4-ethoxy-2-methyl-5-(4-morpholinyl)-[CAS] | 38957-41-4 | JP 7224030 | Anti-inflammatory | |
| EMR-62203 | | | WO 9806722 | Male sexual dysfunction | Impotence |
| emtricitabine | 2(1H)-Pyrimidinone, 4-amino-5-fluoro-1-(2-(hydroxymethyl)-1,3-oxathiolan-5-yl)-, (2R-cis)-[CAS] | 143491-57-0 | WO 9214743 | Antiviral, anti-HIV | Infection, HIV/AIDS |
| Emylcamate | | 78-28-4 | | | |
| enalapril | L-Proline, 1-[N-[1-(ethoxycarbonyl)-3-phenylpropyl]-L-alanyl]-, (S)-, (Z)-2-butenedioate [CAS] | 76095-16-4 | U.S. 4,374,829 | Antihypertensive, renin system | |
| Enalaprilat | | 76420-72-9 | | | |
| Enallylpropymal | | 1861-21-8 | | | |
| Encainide | | 66778-36-7 | | | |
| Enciprazine | | 68576-86-3 | | | |
| Endralazine | | 39715-02-1 | | | |
| enfenamic acid | Benzoic acid, 2-[(2-phenylethyl)amino]-[CAS] | 23049-93-6 | IN 103066 | Anti-inflammatory | |
| enflurane | Ethane, 2-chloro-1-(difluoromethoxy)-1,1,2-trifluoro-[CAS] | 13838-16-9 | U.S. 3,469,011 | Anaesthetic, inhalation | Anaesthesia |
| Enilconazole | | 35554-44-0 | | | |
| Eniluracil | | 59989-18-3 | | | |
| ENMD-0995 | S-3-amino-phthalidoglutarimide | | U.S. 5,712,291 | Anticancer, other | Cancer, myeloma |
| Enocitabine | | 55726-47-1 | | | |
| Enol-3-IPA | 1H-Indole-3-propanoic acid, Alpha-oxo-[CAS] | 392-12-1 | EP 106813 | Hypnotic/Sedative | Insomnia |
| enoxacin | 1,8-Naphthyridine-3-carboxylic acid, 1-ethyl-6-fluoro-1,4-dihydro-4-oxo-7-(1-piperazinyl)-[CAS] | 74011-58-8 | U.S. 4,359,578 | Quinolone antibacterial | Infection, general |

TABLE IV-continued

| API Generic Name | API Chemical Name | CAS No. | Patent Reference | | Example of Therapeutic Use | Example of Indication |
|---|---|---|---|---|---|---|
| enoxaparin | Heparin, [CAS] | 9005-49-6 9041-08-1 | EP | 40144 | Antithrombotic | Thrombosis, venous |
| enoximone | 2H-Imidazol-2-one, 1,3-dihydro-4-methyl-5-[4-(methylthio)benzoyl]-[CAS] | 77671-31-9 | EP | 59948 | Cardiostimulant | Heart failure |
| Enoxolone enprostil | 4,5-Heptadienoic acid, 7-[3-hydroxy-2-(3-hydroxy-4-phenoxy-1-butenyl)-5-oxocyclopentyl]-, methyl ester, [1Alpha,2β(1E,3R*),3Alpha]-[CAS] | 471-53-4 73121-56-9 | GB | 2025431 | Protaglandin | Ulcer, duodenal |
| enrasentan | 1H-Indene-2-carboxylic acid, 1-(1,3-benzodioxol-5-yl)-2,3-dihydro-3-(2-(2-hydroxyethoxy)-4-methoxyphenyl)-5-propoxy-, (1S-(1Alpha,2β,3Alpha))-[CAS] | 167256-08-8 | U.S. | 5,817,693 | Antihypertensive, other | Hypertension, pulmonary |
| entacapone | 2-Propenamide, 2-cyano-3-(4,5-dihydroxy-3-nitrophenyl)-N,N-diethyl-[CAS] | 130929-57-6 | EP | 426468 | Antiparkinsonian | Parkinson's disease |
| entecavir | 6H-Purin-6-one, 2-amino-1,9-dihydro-9-(((1S,3R,4S)-4-hydroxy-3-(hydroxymethyl)-2-methylenecyclopentyl]-[CAS] | 142217-69-4 | EP | 481754 | Antiviral, other | Infection, hepatitis-B virus |
| Enviomycin epalrestat | 3-Thiazolidineacetic acid, 5-(2-methyl-3-phenyl-2-propenylidene)-4-oxo-2-thioxo-, (E,E)-[CAS] | 33103-22-9 82159-09-9 | EP | 47109 | Symptomatic antidiabetic | Neuropathy, diabetic |
| Epavir | L-lysine-cis-5,8,11,14,17-eicosapentanoate with L-lysine-cis-4,7,10,13,16,19-doahexanoate | | | | Antiviral, other | Infection, herpes simplex virus |
| EPC-K1 | L-ascorbic acid 2-[3,4-dihydro-2,5,7,8-tetramethyl-2-(4,8,12-trimethyltridecyl)-2H-1-benzopyran-6-yl-hydrogen phosphate]potassium-[CAS] | 127061-56-7 | EP | 127471 | Neuroprotective | Infarction, cerebral |
| eperisone | 1-Propanone, 1-(4-ethylphenyl)-2-methyl-3-(1-piperidinyl)-[CAS] | 64840-90-0 | U.S. | 3,995,047 | Muscle relaxant | Spastic paralysis |
| epervudine | Uridine, 2'-deoxy-5-(1-methylethyl)-[CAS] | 60136-25-6 | DE | 2918260 | Antiviral, other | Infection, herpes simplex virus |
| Ephedrine Epicillin Epimestrol epinastine | 1H-Dibenz[c,f]imidazo[1,5-a]azepin-3-amine, 9,13b-dihydro-[CAS] | 299-42-3 26774-90-3 7004-98-0 80012-43-7 | DE | 3008944 | Antiasthma | Asthma |
| eoinephrine | (R)-4-[1-hydroxy-2-(methylamino)-ethyl]-1,2-benzenediol | 51-43-4 | | | Formulation, inhalable, dry powder | Anaphylaxis |
| Epirizole epirubicin | 5,12-Naphthacenedione, 10-[(3-amino-2,3,6-trideoxy-Alpha-L-arabino-hexopyranosyl)oxy]-7,8,9,10-tetrahydro-6,8,11-trihydroxy-8-(hydroxyacetyl)-1-methoxy-, (8S-cis)-[CAS] | 18694-40-1 56390-09-1 56420-45-2 | GB | 1457632 | Anticancer, antibiotic | |

TABLE IV-continued

| API Generic Name | API Chemical Name | CAS No. | Patent Reference | Example of Therapeutic Use | Example of Indication |
|---|---|---|---|---|---|
| Epitiostanol | | 2363-58-8 | | | |
| eplerenone | Pregn-4-ene-7,21-dicarboxylic acid, 9,11-epoxy-17-hydroxy-3-oxo-, Gamma-lactone, methyl ester (7Alpha, 11Alpha, 17Alpha)-[CAS] | 107724-20-9 | EP 122232 | Antihypertensive, diuretic | Hypertension, general |
| eplivanserin | 1-Propanone, 1-(2-fluorophenyl)-3-(4-hydroxyphenyl)-, O-(2-(dimethylamino)ethyl)oxime, (Z)-, (E)-2-butenedioate (2:1) (salt) [CAS] | 130580-02-8 | EP 373998 | Anxiolytic | Schizophrenia |
| epoprostenol | Prosta-5,13-dien-1-oic acid, 6,9-epoxy-11,15-dihydroxy-, (5Z,9Alpha,11Alpha,13E,15S)-[CAS] | 35121-78-9 61849-14-7 | DE 2720999 | Prostaglandin | Hypertension, pulmonary |
| Epostane | | 80471-63-2 | | | |
| Eprazinone | | 10402-90-1 | | | |
| Epristeride | | 119169-78-7 | | | |
| eprosartan | 3-[2-Butyl-1-(4-carboxybenzyl)-1H-imidazol-5-yl]-2-(2-thienylmethyl)-2-(E)-propenoic acid | 133040-01-4 | EP 403159 | Antihypertensive, renin system | Hypertension, general |
| Eprozinol | | 32665-36-4 | | | |
| eptapirone | 4-methyl-2-[4-(4-(pyrimidin-2-yl)-piperazino)-butyl]-2H,4H-1,2,4-triazin-3,5-dione | 179756-85-5 | | Antidepressant | Depression, general |
| eptaplatin | Platinum, [(4R,5R)-2-(1-methylethyl)-1,3-dioxolane-4,5-dimethanamine-kappaN4,kappaN5][propanedioato(2-)-kappaO1,kappaO3]-, (SP-4-2)-[CAS] | 146665-77-2 | WO 9216539 | Anticancer, alkylating | Cancer, lung, small cell |
| Eptastigmine | | 101246-68-8 | | | |
| eptazocine | 1,6-Methano-1H-4-benzazonin-10-ol, 2,3,4,5,6,7-hexahydro-1,4-dimethyl-, (1S)-[CAS] | 72522-13-5 | U.S. 4,082,744 | Analgesic, other | |
| Eptifibatide | | 188627-80-7 | | | |
| Equilenin | | 517-09-9 | | | |
| Equilin | | 474-86-2 | | | |
| ERA-923 | ERA 923 [CAS] | 352233-89-7 | EP 802183 | Female contraceptive | Contraceptive, female |
| erdosteine | Acetic acid, [[2-oxo-2-[(tetrahydro-2-oxo-3-thienyl)amino]ethyl]thio]-[CAS] | 84611-23-4 | EP 61386 | Respiratory | Respiratory disease, general |
| Ergocornine | | 564-36-3 | | | |
| Ergocorninine | | 564-37-4 | | | |
| Ergoloid Mesylates | | 8067-24-1 | | | |
| Ergonovine | | 60-79-7 | | | |
| Ergosterol | | 57-87-4 | | | |
| ergotamine | (5'Alpha)-12'-Hydroxy-2'methyl-(phenylmethyl)ergotaman-3',6',18-trione | 113-15-5 | | Formulation, inhalable, systemic | Migraine |
| Eritadenine | | 23918-98-1 | | | |
| erlotinib | 4-Quinazolinamine, N-(3-ethynylphenoxy)-6,7-bis(2-methoxyethoxy)-, monohydrochloride [CAS] | 183319-69-9 | WO 9630347 | Anticancer, other | Cancer, lung, non-small cell |

TABLE IV-continued

| API Generic Name | API Chemical Name | CAS No. | Patent Reference | Example of Therapeutic Use | Example of Indication |
|---|---|---|---|---|---|
| ertapenem | 1-Azabicyclo[3.2.0]hept-2-ene-2-carboxylic acid, 3-[[(3S,5S)-5-[[(3-carboxyphenyl)amino]carbonyl]-3-pyrrolidinyl]thio]-6-[(1R)-1-hydroxyethyl]-4-methyl-7-oxo-, [CAS] | 153773-82-1 153832-46-3 | WO 9315078 | Beta-lactam antibiotic | Infection, GI tract |
| Erythrityl Tetranitrate | | 7297-25-8 | | | |
| Erythrocentaurin | | 50276-98-7 | | | |
| erythromycin acistrate | Erythromycin, 2'-acetate, octadecanoate (salt) [CAS] | 96128-89-1 | U.S. 4,599,326 | Macrolide antibiotic | Infection, general |
| Erythromycin Estolate | | 3521-62-8 | | | |
| Erythromycin Glucoheptonate | | 23067-13-2 | | | |
| Erythromycin Lactobionate | | 3847-29-8 | | | |
| Erythromycin Propionate | | 134-36-1 | | | |
| Erythromycin Stearate | | 643-22-1 | | | |
| erythromycin stinoprate | Erythromycin, 2'-propanoate, compd. with N-acetyl-L-cysteine (1:1) [CAS] | 84252-03-9 | EP 57489 | Macrolide antibiotic | Infection, respiratory tract, lower |
| erythromycin | Erythromycin [CAS] | 114-07-8 | | Formulation, dermal, topical | Acne |
| Erythrophleine | | 36150-73-9 | | | |
| Esaprazole | | 64204-55-3 | | | |
| escitalopram | 5-Isobenzofurancarbonitrile, 1-[3-(dimethylamino)propyl]-1-(4-fluorophenyl)-1,3-dihydro-, (S)-[CAS] | 128196-01-0 | EP 347066 | Antidepressant | Depression, general |
| Esculin | | 531-75-9 | | | |
| Eseridine | | 25573-43-7 | | | |
| esmolol | Benzenepropanoic acid, 4-[2-hydroxy-3-[(1-methylethyl)amino]propoxy]-, methyl ester, (+/-)-[CAS] | 81147-92-4 | U.S. 4,387,103 | Antihypertensive, adrenergic | Tachycardia, supraventricular |
| esomeprazole | bis (5-methoxy-2-(((4-methoxy-3,5-dimethyl-2-pyridinyl)methyl)sulfinyl)-1H-benzimidazolato) | 161973-10-0 | U.S. 5,877,192 | Antispasmodic | Gastro-oesophageal reflux |
| estazolam | 4H-[1,2,4]Triazolo[4,3-a][1,4]benzodiazepine, 8-chloro-6-phenyl- [CAS] | 29975-16-4 | U.S. 3,987,052 | Hypnotic/Sedative | |
| estradiol | Androst-4-en-3-one, 17-hydroxy-, (17β)- [CAS] | 58-22-0 | U.S. 5,460,820 | Formulation, transdermal, patch | Sexual dysfunction, female |
| estradiol | Estra-1,2,5(10)-triene-3,17-diol (17β) [CAS] | 50-28-2 | EP 430491 | Formulation, transdermal, systemic | Menopausal symptoms, general |
| estramustine | Estra-1,3,5(10)-triene-3,17-diol (17β)-, 3-[bis(2-chloroethyl)carbamate] 17-[CAS] | 2998-57-4 4891-15-0 52205-73-9 | | Anticancer, alkylating | Cancer, prostate |
| Estriol | | 50-27-1 | | | |

TABLE IV-continued

| API Generic Name | API Chemical Name | CAS No. | Patent Reference | Example of Therapeutic Use | Example of Indication |
|---|---|---|---|---|---|
| estrogen | | 53-16-7 | WO 9924041 | Menopausal disorders | Menopausal symptoms, general |
| Estrone | | | | | |
| eszopiclone | 1-Piperazinecarboxylic acid, 4-methyl-6-(5-chloro-2-pyridinyl)-6,7-dihydro-7-oxo-5H-pyrrolo(3,4-b)pyrazin-5-yl ester (S)-[CAS] | 138729-47-2 | U.S. 5,786,357 | Hypnotic/Sedative | Insomnia |
| Etafedrine | | 7681-79-0 | | | |
| Etafenone | | 90-54-0 | | | |
| Etamiphyllin | | 314-35-2 | | | |
| Etanercept | | 185243-69-0 | | | |
| Etanidazole | | 22668-01-5 | | | |
| Etaqualone | | 7432-25-9 | | | |
| Eterobarb | | 27511-99-5 | | | |
| Ethacridine | | 442-16-0 | | | |
| Ethacrynic Acid | | 58-54-8 | | | |
| Ethadion | | 520-77-4 | | | |
| Ethambutol | | 74-55-5 | | | |
| Ethamivan | | 304-84-7 | | | |
| Ethamsylate | | 2624-44-4 | | | |
| Ethanolamine | | 141-43-5 | | | |
| Ethaverine | | 486-47-5 | | | |
| Ethchlorvynol | | 113-18-8 | | | |
| Ethenzamide | | 938-73-8 | | | |
| Ethiazide | | 1824-58-4 | | | |
| Ethinamate | | 126-52-3 | | | |
| Ethinyl Estradiol | | 57-63-6 | | | |
| ethinyl estradiol | 19-Norpregna-1,3,5(10)-trien-20-yne-3,17-diol, 3-(2-propanesulfonate), (17Alpha)-[CAS] | 28913-23-7 | DE 1949095 | Formulation, modified-release, >24 hr | Cancer, prostate |
| Ethionamide | | 536-33-4 | | | |
| Ethisterone | | 434-03-7 | | | |
| Ethoheptazine | | 77-15-6 | | | |
| Ethopropazine | | 522-00-9 | | | |
| Ethosuximide | | 77-67-8 | | | |
| Ethotoin | | 86-35-1 | | | |
| Ethoxzolamide | | 452-35-7 | | | |
| Ethybenztropine | | 524-83-4 | | | |
| Ethyl Alcohol | | 64-17-5 | | | |
| Ethyl Biscoumacetate | | 548-00-5 | | | |
| Ethyl Chloride | | 75-00-3 | | | |
| Ethyl Dibunate | | 5560-69-0 | | | |
| Ethyl Ether | | 60-29-7 | | | |
| ethyl icosapentate | 5,8,11,14,17-Eicosapentaenoic acid, ethyl ester, (all-Z)-[CAS] | 86227-47-6 | JP 61043143 | Antithrombotic | Peripheral vascular disease |
| ethyl loflazepate | 1H-1,4-Benzodiazepine-3-carboxylic acid, 7-chloro-5-(2-fluorophenyl)-2,3-dihydro-2-oxo-, ethyl ester [CAS] | 29177-84-2 | U.S. 3,657,223 | Anxiolytic | Anxiety, general |
| Ethyl Loflazepate | | 29177-84-2 | | | |

TABLE IV-continued

| API Generic Name | API Chemical Name | CAS No. | Patent Reference | Example of Therapeutic Use | Example of Indication |
|---|---|---|---|---|---|
| Ethylamine | | 75-04-7 | | | |
| Ethylene | | 74-85-1 | | | |
| Ethylestrenol | | 965-90-2 | | | |
| Ethylidene Dicoumarol | | 1821-16-5 | | | |
| Ethylmethyl-thiambutene | | 441-61-2 | | | |
| Ethylmorphine | | 76-58-4 | | | |
| Ethylnorepinephrine | | 536-24-3 | | | |
| Ethynodiol | | 1231-93-2 | | | |
| ethynylcytidine | Uridine, 3'-C-ethynyl-[CAS] | 180300-49-6 | WO 9618636 | Anticancer, antimetabolite | Cancer, general |
| Etidronate | Phosphonic acid, (1-hydroxyethylidene)bis-, [CAS] | 36637-18-0 2809-21-4 7414-83-7 | U.S. 4,137,309 | Osteoporosis treatment | Osteoporosis |
| Etidronic Acid | | 2809-21-4 | | | |
| Etifelmin | | 341-00-4 | | | |
| etifoxine | 4H-3,1-Benzoxazin-2-amine, 6-chloro-N-ethyl-4-methyl-4-phenyl-[CAS] | 21715-46-8 | U.S. 3,725,404 | Anxiolytic | |
| Etilefrin | | 709-55-7 | | | |
| etilevodopa | L-Tyrosine, 3-hydroxy-, ethyl ester [CAS] | 37178-37-3 | U.S. 5,354,885 | Antiparkinsonian | Parkinson's disease |
| etiprednol | androsta-1,4-diene-17-carboxylic acid, 17-[(dichloroacetyl)oxy]-11-hydroxy-3-oxo-, ethyl ester, (11β,17Alpha)- | 199331-40-3 | | GI inflammatory/ bowel disorders | Crohn's disease |
| Etiroxate | | 17365-01-4 | | | |
| Etizolam | | 40054-69-1 | | | |
| etodolac | Pyrano[3,4-b]indole-1-acetic acid, 1,8-diethyl-1,3,4,9-tetrahydro-[CAS] | 41340-25-4 | U.S. 3,939,178 | Antiarthritic, other | Arthritis, osteo |
| Etodroxizine | | 17692-34-1 | | | |
| etofenamate | Benzoic acid, 2-[[3-(trifluoromethyl)phenyl]amino]-, 2-(2-hydroxyethoxy)ethyl ester [CAS] | 30544-47-9 | GB 1285400 | Anti-inflammatory, topical | Inflammation, general |
| etofibrate | 3-Pyridinecarboxylic acid, 2-[2-(4-chlorophenoxy)-2-methyl-1-oxopropoxy]ethyl ester [CAS] | 31637-97-5 | U.S. 3,723,446 | Hypolipaemic/ Antiatherosclerosis | |
| Etofylline | | 519-37-9 | | | |
| etofylline clofibrate | Propanoin acid, 2-(4-chlorophenoxy)-2-methyl-, 2-(1,2,3,6-tetrahydro-1,3-dimethyl-2,6-dioxo-7H-purin-7-yl)ethyl ester [CAS] | 54504-70-0 | DE 2308826 | Hypolipaemic/ Antiatherosclerosis | |
| Etofylline Nicotinate | | 13425-39-3 | | | |
| Etoglucid | | 1954-28-5 | | | |
| Etomidate | | 33125-97-2 | | | |
| Etomidoline | | 21590-92-1 | | | |
| Etonitazene | | 911-65-9 | | | |
| etonogestrel | 18,19-Dinorpregn-4-en-20-yn-3-one, 13-ethyl-17-hydroxy-11-methylene, (17Alpha)-[CAS] | 54048-10-1 | | Formulation, implant | Contraceptive, female |

TABLE IV-continued

| API Generic Name | API Chemical Name | CAS No. | Patent Reference | | Example of Therapeutic Use | Example of Indication |
|---|---|---|---|---|---|---|
| Etoperidone | | 52942-31-1 | | | | |
| etoposide | Furo[3',4':6,7]naphtho[2,3-d]-1,3-dioxol-6(5aH)-one, 9-[(4,6-O-ethylidene-β-D-glucopyranosyl)oxy]-5,8,8a,9-tetrahydro-5-(4-hydroxy-3,5-dimethoxyphenyl)-, [5R-[5Alpha,5aβ,8aAlpha,9β(R*)]]-[CAS] | 33419-42-0 | GB | 1205966 | Anticancer, other | Cancer, testicular |
| etoposide phosphate | Furo[3',4':6,7]naphtho[2,3-d]-1,3-dioxol-6(5aH)-one, 9-[(3,5-dimethoxy-4-(phosphonooxy)phenyl]-9-[(4,6-O-ethylidene-β-D-glucopyranosyl)oxy]-5,8,8a,9-tetrahydro-, [5R-[5Alpha,5aβ,8aAlpha,9β(R*)]]-[CAS] | 117091-64-2 | EP | 302473 | Anticancer, other | Cancer, testicular |
| etoricoxib | 2,3-Bipyridine, 5-chloro-6'-methyl-3-(4-(methylsulfonyl)phenyl) [CAS] | 202409-33-4 | WO | 9803484 | Antiarthritic, other | Arthritis, osteo |
| Etoxadrol | | 28189-85-7 | | | | |
| Etozolin | | 73-09-6 | | | | |
| etretinate | 2,4,6,8-Nonatetraenoic acid, 9-(4-methoxy-2,3,6-trimethylphenyl)-3,7-dimethyl-, ethyl ester, (all-E)-[CAS] | 54350-48-0 | U.S. | 4,215,215 | Antipsoriasis | |
| Etryptamine | | 2235-90-7 | | | | |
| Etymemazine | | 523-54-6 | | | | |
| Eucatropine | | 100-91-4 | | | | |
| Eugenol | | 97-53-0 | | | | |
| EUK-134 | Manganese, chloro[2,2'-[1,2-ethanediylbis[(nitrilo-kappaN)methylidyne]]bis(6-methoxyphenolato-kappaO]]]-, (SP-5-13)-[CAS] | 81065-76-1 | U.S. | 6,046,188 | Cardiovascular | Unspecified |
| EUK-189 | | | U.S. | 6,046,188 | Radio/chemoprotective | Chemotherapy-induced injury, general |
| Evans Blue | | 314-13-6 | | | | |
| everolimus | Rapamycin, 42-O-(2-hydroxyethyl)-[CAS] | 159351-69-6 | WO | 9409010 | Immunosuppressant | Transplant rejection, general |
| exalamide | Benzamide, 2-(hexyloxy)-[CAS] | 53370-90-4 | GB | 726786 | Antifungal | Infection, fungal, general |
| Exametazime | | 105613-48-7 | | | | |
| exatecan | 10H,13H-Benzo[de]pyrano[3',4':6,7]indolizino[1,2-b]quinoline-10,13-dione, 1-amino-9-ethyl-5-fluoro-1,2,3,9,12,15-hexahydro-9-hydroxy-4-methyl-, (1A,9S)-, [CAS] | 171335-80-1 | | | Anticancer, other | Cancer, pancreatic |
| exemestane | Androsta-1,4-diene-3,17-dione, 6-methylene-[CAS] | 107868-30-4 | DE | 3622841 | Anticancer, hormonal | Cancer, breast |
| Exifone | | 52479-85-3 | | | | |
| exisulind | 1H-Indene-3-acetic acid 5-fluoro-2-methyl-1-((4-(methylsulfonyl)phenyl)methylene)-, (Z)-[CAS] | 59973-80-7 | | | Anticancer, other | Polyp |

TABLE IV-continued

| API Generic Name | API Chemical Name | CAS No. | Patent Reference | | Example of Therapeutic Use | Example of Indication |
|---|---|---|---|---|---|---|
| Exosurf ® ezetimibe | 2-Azetidinone, 1-(4-fluorophenyl)-3-[(3S)-3-(4-fluorophenyl)-3-hydroxypropyl]-4-(4-hydroxyphenyl)-, (3R,4S)-[CAS] | 99732-49-7 163222-33-1 | U.S. | 5,846,966 | Hypolipaemic/Antiatherosclerosis | Hypercholesterolaemia |
| Factor IX | | 9001-28-9 | | | | |
| Factor VIII | | 9001-27-8 | | | | |
| Factor XIII | | 9013-56-3 | | | | |
| fadolmidine | 1H-Inden-5-ol, 2,3-dihydro-3-(1H-imidazol-4-ylmethyl), monohydrochloride [CAS] | 189353-32-0 | WO | 9712874 | Analgesic, other | Pain, general |
| Fadrozole | | 102676-47-1 | | | | |
| falecalcitriol | 9,10-Secocholesta-5,7,10(19)-triene-1,3,25-triol, 26,26,26,27,27,27-hexafluoro-, (1Alpha,3β,5Z,7E)-[CAS] | 83805-11-2 | JP | 03099022 | Osteoporosis treatment | Hyperparathyroidism |
| famciclovir | 1,3-Propanediol, 2-[2-(2-amino-9H-purin-9-yl)ethyl]-, diacetate (ester)-[CAS] | 104227-87-4 | JP | 61085388 | Antiviral, other | Infection, gynaecological |
| famotidine | Propanimidamide, 3-[[[2-[(aminoiminomethyl)amino]-4-thiazolyl]methyl]thio]-N-(aminosulfonyl)-[CAS] | 76824-35-6 | U.S. | 4,283,408 | Antiulcer | Ulcer, duodenal |
| fampridine | 4-pyridamine | 504-24-5 | | | Neuroprotective | Spinal cord injury |
| fandofloxacin | 3-Quinolinecarboxylic acid, 6-fluoro-1-(5-fluoro-2-pyridinyl)-1,4-dihydro-7-(4-methyl-1-piperazinyl)-4-oxo, [CAS] | 164150-85-0 164150-99-6 | U.S. | 5,496,947 | Quinolone antibacterial | Infection, urinary tract |
| Fantofarone faropenem daloxate | (5R,6S)-6-[1(R)-Hydroxyethyl]-2-[2(R)-tetrahydrofuryl]-2-penem-3-carboxylic acid-5-methyl-2-oxo-1,3-dioxol-4-ylmethyl ester | 114432-13-2 | | | Beta-lactam antibiotic | Infection, general |
| faropenem | 4-Thia-1-azabicyclo[3.2.0]hept-2-ene-2-carboxylic acid, 6-(1-hydroxyethyl)-7-oxo-3-(tetrahydro-2-furanyl)-, [5R-[3(R*),5Alpha,6Alpha(R*)]]-[CAS] | 122547-49-3 | EP | 410727 | Beta-lactam antibiotic | Infection, ocular |
| fasidotril | L-Alanine, N-[(2S)-3-(acetylthio)-2-(1,3-benzodioxol-5-ylmethyl)-1-oxopropyl]-, phenylmethyl ester [CAS] | 135038-57-2 | EP | 419327 | Antihypertensive, renin system | Hypertension, general |
| fasudil | 1H-1,4-Diazepine, hexahydro-1-(5-isoquinolinylsulfonyl)-[CAS] | 103745-39-7 105628-07-7 | EP | 187371 | Neuroprotective | Vasospasm, general |
| Fazadinium Bromide febarbamate | 2,4,6(1H,3H,5H)-Prrimidinetrione, 1-[2-[(aminocarbonyl)oxy]-3-butoxypropyl]-5-ethyl-5-phenyl-[CAS] | 49564-56-9 13246-02-1 | U.S. | 3,075,983 | Psychostimulant | |
| Febuprol | | 3102-00-9 | | | | |
| febuxostat | 5-Thiazolecarboxylic acid, 2-[3-cyano-4-(2-methylpropoxy)phenyl]-4-methyl-[CAS] | 144060-53-7 | WO | 9209279 | Antigout | Hyperuricaemia |
| Fedotozine felbamate | 1,3-Propanediol, 2-phenyl-, dicarbamate [CAS] | 123618-00-8 25451-15-4 | U.S. | 4,868,327 | Antiepileptic | Epilepsy, general |
| felbinac | [1,1'-Biphenyl]-4-acetic acid [CAS] | 5728-52-9 | EP | 127840 | Anti-inflammatory, topical | |

TABLE IV-continued

| API Generic Name | API Chemical Name | CAS No. | Patent Reference | | Example of Therapeutic Use | Example of Indication |
|---|---|---|---|---|---|---|
| felodipine | 3,5-Pyridinedicarboxylic acid, 4-(2,3-dichlorophenyl)-1,4-dihydro-2,6-dimethyl-, ethyl methyl ester [CAS] | 72509-76-3 | U.S. | 4,264,611 | Antihypertensive, other | Hypertension, general |
| Felypressin | | 56-59-7 | | | | |
| Femoxetine | | 59859-58-4 | | | | |
| Fenbenicillin | | 1926-48-3 | | | | |
| fenbufen | [1,1'-Biphenyl]-4-butanoic acid, Gamma-oxo-[CAS] | 36330-85-5 | U.S. | 3,784,701 | Anti-inflammatory | |
| Fenbutrazate | | 4378-36-3 | | | | |
| Fencamfamine | | 1209-98-9 | | | | |
| Fencamine | | 28947-50-4 | | | | |
| Fenclozic Acid | | 17969-20-9 | | | | |
| Fendiline | | 13042-18-7 | | | | |
| Fendosal | | 53597-27-6 | | | | |
| Fenethylline | | 3736081 | | | | |
| Fenfluramine | | 458-24-2 | | | | |
| Fenipentol | | 583-03-9 | | | | |
| fenofibrate | Propanoic acid, 2-[4-(4-chlorobenzoyl)phenoxy]-2-methyl-, 1-methylethyl ester [CAS] | 26129-32-8 49562-28-9 | | | Formulation, modified-release, <=24 hr | Hyper-lipidaemia, general |
| fenoldopam | 1H-3-Benzazepine-7,8-diol, 6-chloro-2,3,4,5-tetrahydro-1-(4-hydroxyphenyl)-[CAS] | 67227-56-9 67227-57-0 | EP | 22330 | Antihypertensive, other | Hypertension, general |
| Fenoprofen | | 31879-05-7 | | | | |
| Fenoterol | | 13392-18-2 | | | | |
| fenoverine | 10H-Phenothiazine, 10-[[4-(1,3-benzodioxol-5-ylmethyl)-1-piperazinyl]acetyl]-[CAS] | 37561-27-6 | FR | 2092639 | Antispasmodic | |
| Fenoxazoline | | 4846-91-7 | | | | |
| Fenoxedil | | 54063-40-0 | | | | |
| Fenozolone | | 15302-16-6 | | | | |
| Fenpentadiol | | 15687-18-0 | | | | |
| Fenpiprane | | 3540-95-2 | | | | |
| Fenpiverinium Bromide | | 125-60-0 | | | | |
| Fenproporex | | 15686-61-0 | | | | |
| Fenquizone | | 20287-37-0 | | | | |
| fenretinide | Retinamide, N-(4-hydroxyphenyl)-[CAS] | 65646-68-6 5053066 | BE | 847942 | Anticancer, other | Cancer, breast |
| Fenspiride | | | | | | |
| fentanyl | Propanamide, N-phenyl-N-[1-(2-phenylethyl)-4-piperidinyl]-[CAS] | 437-38-7 | | | Formulation, transmucosal, systemic | Anaesthesia, adjunct |
| Fentiazac | | 18046-21-4 | | | | |
| Fenticlor | | 97-24-5 | | | | |
| fenticonazole | 1H-Imidazole, 1-[2-(2,4-dichlorophenyl)-2-[[4-(phenylthio)phenyl]methoxy]ethyl]-[CAS] | 72479-26-6 73151-29-8 | U.S. | 4,221,803 | Antifungal | Infection, gynaecological |

TABLE IV-continued

| API Generic Name | API Chemical Name | CAS No. | Patent Reference | Example of Therapeutic Use | Example of Indication |
|---|---|---|---|---|---|
| Fentonium Bromide | | 5868064 | | | |
| fepradinol | Benzenemethanol, Alpha[[(2-hydroxy-1,1-dimethylethyl)amino]methyl]-, (+−)-[CAS] | 36981-91-6 67704-50-1 63075-57-8 | | Anti-inflammatory, topical | |
| Feprazone | | 30748-29-9 | | | |
| Ferric Sodium Edetate | | 15708-41-5 | | | |
| ferrioxamine B | | | WO 9426263 | Septic shock treatment | Respiratory distress syndrome, adult |
| Ferrocholinate | | 1336-80-7 | | | |
| Ferrous Gluconate | | 299-29-6 | | | |
| ferumoxytol | Polyglucose sorbitol carboxymethyl ether-coated non-stoichiometric magnetite | | | Imaging agent | Diagnosis, cancer |
| fesoterodine | 2-((1R)-3-(bis(1-methylethyl)amino)-1-phenylpropyl)-4-(hydroxymethyl)Phenyl ester, (2E)-2-butenedioate (1:1) (Salt) [CAS] | 286930-03-8 | | Urological | Incontinence |
| fexofenadine | Benzeneacetic acid, 4-[1-hydroxy-4-[4(hydroxydiphenylmethyl)-1-piperidinyl]butyl]-Alpha,Alpha-dimethyl-, [CAS] | 153439-40-8 83799-24-0 138452-21-8 | U.S. 5,345,693 | Antiallergic, non-asthma | Rhinitis, allergic, seasonal |
| Fibrostat | | | CA 2132416 | Vulnerary | Wound healing |
| fidarestat | Spiro(4H-1-benzopyran-4,4'-imidazolidine)-2-carboxamide, 6-fluoro-2,3-dihydro-2',5'-dioxo-, (2S-cis)-, [CAS] | 136087-85-9 | EP 418834 | Symptomatic antidiabetic | Neuropathy, diabetic |
| fiduxosin | 8-Phenyl-3-[4-[(3aR,9bR)-1,3a,4,9b-1] tetrahydro-9-methoxy[1]benzopyrano[3,4-c]pyrrol-2(3H)-yl]butyl]pyrazino[2',3':4,5]thieno[3,2-d]pyrimidine-2,4(1H,3H)-dione | 208993-54-8 | | Prostate disorders | Benign prostatic hyperplasia |
| finasteride | 4-Azaandrost-1-ene-17-carboxamide, N-(1,1-dimethylethyl)-3-oxo-, (5Alpha,17β)- [CAS] | 98319-26-7 | EP 155096 | Prostate disorders | Benign prostatic hyperplasia |
| finrozole | Benzonitrile, 4-(3-(4-fluorophenyl)-2-hydroxy-1-(1H-1,2,4-triazol-1-yl)-propyl)- [CAS] | 160146-16-7 | EP 476944 | Urological | Urinary retention |
| Fipexide | | 34161-24-5 | | | |
| FK-960 | N-(4-Acetyl-1-piperazinyl)-4-fluorobenzamide monohydrate-[CAS] | 133920-70-4 | WO 9101979 | Cognition enhancer | Alzheimer's disease |
| Flavopiridol | | 146426-40-6 | | | |
| flavoxate | 4H-1-Benzopyran-8-carboxylic acid, 3-methyl-4-oxo-2-phenyl-, 2-(1-piperidinyl)ethyl ester [CAS] | 15301-69-6 3717-88-2 | U.S. 2,921,070 | Urological | |
| flecainide | Benzamide, N-(2-piperidinylmethyl)-2,5-bis(2,2,2-trifluoroethoxy)-, [CAS] | 54143-55-4 54143-56-5 | | Formulation, modified-release, <=24 hr | Fibrillation, atrial |
| fleroxacin | 3-Quinolinecarboxylic acid, 6,8-difluoro-1-(2-fluoroethyl)-1,4-dihydro-7-(4-methyl-1-piperazinyl)-4-oxo-[CAS] | 79660-53-0 79660-72-3 | U.S. 4,398,029 | Quinolone antibacterial | Infection, general |
| Flesinoxan | | 98206-10-1 | | | |

TABLE IV-continued

| API Generic Name | API Chemical Name | CAS No. | Patent Reference | Example of Therapeutic Use | Example of Indication |
|---|---|---|---|---|---|
| flibanserin | 2H-Benzimidazol-2-one, 1,3-dihydro-2-(2-(4-(3-(trifluoromethyl)phenyl)-1-piperazinyl)ethyl)-[CAS] | 167933-07-5 | | Reproductive/gonadal, general | Sexual dysfunction, female |
| floctafenine | Benzoic acid, 2-[[8-(trifluoromethyl)-4-quinolinyl]amino]-, 2,3-dihydroxypropyl ester [CAS] | 23779-99-9 | U.S. 3,644,368 | Analgesic, NSAID | |
| flomoxef | 5-Oxa-1-azabicyclo[4.2.0]oct-2-ene-2-carboxylic acid, 7-[[[(difluoromethyl)thio]acetyl]amino]-3-[[(1-(2-hydroxyethyl)-1H-tetrazol-5-yl]thio]methyl]-7-methoxy-8-oxo-, (6R-cis)-[CAS] | 92823-03-5<br>99665-00-6 | EP 128536 | Cephalosporin, injectable | Infection, general |
| Flopropione | | 2295-58-1 | | | |
| Florantyrone | | 519-95-9 | | | |
| Flosequinan | | 76568-02-0 | | | |
| Floxacillin | | 5250-39-5 | | | |
| Floxuridine | | 50-91-9 | | | |
| Fluacizine | | 30223-48-4 | | | |
| Fluanisone | | 1480-19-9 | | | |
| fluasterone | Androst-5-en-17-one, 16-fluoro-, (16Alpha)-[CAS] | 112859-71-9 | EP 246650 | Cardiovascular | Keratosis |
| fluazacort | 5'H-Pregna-1,4-dieno[17,16-d]oxazole-3,20-dione, 21-(acetyloxy)-9-fluoro-11-hydroxy-2'-methyl-, (11β,16β)-[CAS] | 19888-56-3 | U.S. 3,461,119 | Antipruritic/inflamm, non-allergic | |
| Flucloronide | | 3693-39-8 | | Formulation, other | |
| flucloxacillin | | 1847-24-1 | | | |
| Fluconazole | 1H-1,2,4-Triazole-1-ethanol, Alpha-(2,4-difluorophenyl)-Alpha-(1H-1,2,4-triazol-1-ylmethyl)-[CAS] | 342214-51-2<br>86386-73-4 | EP 96569 | Antifungal | Infection, general<br>Infection, dermatological |
| Flucytosine | | 2022-85-7 | | | |
| fludarabine | 9H-Purin-6-amine, 2-fluoro-9-(5-O-phosphono-β-D-arabinofuranosyl)-[CAS] | 75607-67-9<br>21679-14-1 | U.S. 4,357,324 | Anticancer, antimetabolite | Cancer, leukaemia, chronic lymphocytic |
| Fludeoxyglucose F18 | | 105851-17-0 | | | |
| Fludiazepam | | 3900-31-0 | | | |
| Fludrocortisone | | 127-31-1 | | | |
| Flufenamic Acid | | 530-78-9 | | | |
| Fluindione | | 957-56-2 | | | |
| flumazenil | 4H-Imidazo[1,5-a][1,4]benzodiazepine-3-carboxylic acid, 8-fluoro-5,6-dihydro-5-methyl-6-oxo-, ethyl ester [CAS] | 78755-81-4 | EP 27214 | Neurological | |
| Flumecinol | | 56430-99-0 | | | |
| Flumequine | | 42835-25-6 | | | |
| Flumethasone | | 2135-17-3 | | | |
| Flumethiazide | | 148-56-1 | | | |
| flunarizine | Piperazine, 1-[bis(4-fluorophenyl)methyl]-4-(3-phenyl-2-propenyl)-, (E)-[CAS] | 30484-77-6<br>52468-60-7<br>27848-84-6 | GB 1268710 | Antimigraine | |

TABLE IV-continued

| API Generic Name | API Chemical Name | CAS No. | Patent Reference | Example of Therapeutic Use | Example of Indication |
|---|---|---|---|---|---|
| flunisolide | Pregna-1,4-diene-3,20-dione, 6-fluoro-11,21-dihydroxy-16,17-[(1-methylethylidene)bis(oxy)]-, (6Alpha,11β,16Alpha)-[CAS] | 3385-03-3 | U.S. 3,124,571 | Antiasthma | Rhinitis, allergic, general |
| flunitrazepam | 2H-1,4-Benzodiazepin-2-one, 5-(2-fluorophenyl)-1,3-dihydro-1-methyl-7-nitro-[CAS] | 1622-62-4 | U.S. 3,116,203 | Hypnotic/Sedative | |
| Flunoxaprofen | | 66934-18-7 | | | |
| Fluocinolone Acetonide | | 67-73-2 | | | |
| Fluocinonide | | 356-12-7 | | | |
| Fluocortin Butyl | | 41767-29-7 | | | |
| Fluocortolone | | 152-97-6 | | | |
| Fluorescein | | 2321-07-5 | | | |
| Fluoresone | | 2924-67-6 | | | |
| Fluorometholone | | 426-13-1 | | | |
| Fluorosalan | | 4776061 | | | |
| fluorouracil | 2,4(1H,3H)-Pyrimidinedione, 5-fluoro-[CAS] | 51-21-8 | | Formulation, transdermal, enhanced | Keratosis |
| fluoxetine | Benzenepropanamine, N-methyl-Gamma-[4-(trifluoromethyl)phenoxy]-, (+/-)-[CAS] | 54910-89-3 | U.S. 4,314,081 | Antidepressant | Depression, general |
| Fluoxymesterone | | 56296-78-7 | | | |
| Flupentixol | | 76-43-7 | | | |
| Fluperolone | | 2709-56-0 | | | |
| Fluphenazine | | 2119-75-7 | | | |
| | | 69-23-8 | | | |
| flupirtine | Carbamic acid, [2-amino-6-[[(4-fluorophenyl)methyl]amino]-3-pyridinyl]-, ethyl ester [CAS] | 33400-45-2 | U.S. 4,481,205 | Analgesic, other | Pain, post-operative |
| Fluprednidene Acetate | | 56995-20-1 | | | |
| Fluprednisolone | | 75507-68-5 | | | |
| Fluproquazone | | 1255-35-2 | | | |
| Flurandrenolide | | 53-34-9 | | | |
| Flurazepam | | 40507-23-1 | | | |
| | | 1524-88-5 | | | |
| flurbiprofen | [1,1'-Biphenyl]-4-acetic acid, 2-fluoro-Alpha-methyl-[CAS] | 17617-23-1 | U.S. 3,793,457 | Anti-inflammatory | |
| | | 5104-49-4 | | | |
| flurithromycin | Erythromycin, 8-fluoro-mono(ethyl butanedioate) (ester)-[CAS] | 82730-23-2 | EP 56291 | Macrolide antibiotic | Infection, respiratory tract, lower |
| Flurogestone | | 2529-45-5 | | | |
| Flurothyl | | 333-36-8 | | | |
| Fluroxen | | 406-90-6 | | | |
| Fluspirilene | | 1841-19-6 | | | |
| flutamide | Propanamide, 2-methyl-N-[4-nitro-3-(trifluoromethyl)phenyl]-[CAS] | 13311-84-7 | U.S. 4,329,364 | Anticancer, hormonal | |
| flutazolam | Oxazolo[3,2-d][1,4]benzodiazepin-6(5H)-one, 10-chloro-11b-(2-fluorophenyl)-2,3,7,11b-tetrahydro-7-(2-hydroxyethyl)-[CAS] | 27060-91-9 | U.S. 3,905,956 | Anxiolytic | |

TABLE IV-continued

| API Generic Name | API Chemical Name | CAS No. | Patent Reference | | Example of Therapeutic Use | Example of Indication |
|---|---|---|---|---|---|---|
| fluticasone | Androsta-1,4-diene-17-carbothioic acid, 6,9-difluoro-11,17-dihydroxy-16-methyl-3-oxo-, S-(fluoromethyl) ester, (6Alpha,11β,16Alpha,17Alpha)-[CAS] | 80474-14-2 90566-53-3 | | | Formulation, inhalable, solution | Asthma |
| flutoprazepam | 2H-1,4-Benzodiazepin-2-one, 7-chloro-1-(cyclopropylmethyl)-5-(2-fluorophenyl)-1,3-dihydro-[CAS] | 25967-29-7 | GB | 1253368 | Anxiolytic | Psychosis, general |
| flutrimazole | 1H-Imidazole, 1-[(2-fluorophenyl)(4-fluorophenyl)phenylmethyl]-[CAS] | 119006-77-8 | EP | 352352 | Antifungal | Infection, dermatological |
| Flutropium Bromide | | 63516-07-4 | | | | |
| fluvastatin | 6-Heptenoic acid, 7-[3-(4-fluorophenyl)-1-(1-methylethyl)-1H-indol-2-yl]-3,5-dihydroxy-, monosodium salt, [R*,S*-(E)]-(±)-[CAS] | 93957-55-2 93957-54-1 | EP | 114027 | Hypolipaemic/Antiatherosclerosis | Hypercholest-erolaemia |
| fluvoxamine | 1-Pentanone, 5-methoxy-1-[4-(trifluoromethyl)phenyl]-O-(2-aminoethyl)oxime, (E)-[CAS] | 54739-18-3 61718-82-9 | GB | 1535226 | Antidepressant | Depression, general, Obsessive-compulsive disorder |
| Folic Acid | | 59-30-3 | | | | |
| Folinic Acid | | 58-05-9 | | | | |
| Fomepizole | | 7554-65-6 | | | | |
| fominoben | Benzamide, N-[3-chloro-2-[[methyl[2-(4-morpholinyl)-2-oxoethyl]amino]methyl]phenyl]-[CAS] | 18053-31-1 24600-36-0 | U.S. | 3,661,903 | Respiratory stimulant | Eczema, general |
| Fomivirsen | | 144245-52-3 | | | | |
| Fomocaine | | 17692-39-6 | | | | |
| Fonazine | | 7456-24-8 | | | | |
| fondaparinux | Alpha-D-Glucopyranoside, methyl O-2-deoxy-6-O-sulfo-2-(sulfamino)-Alpha-D-glucopyranosyl-(1-4)-O-β-D-glucopyranuronosyl-(1-4)-O-2-deoxy-3,6-di-O-sulfo-2-(sulfoamino)-Alpha-D-glucopyranosyl-(1-4)-O-2-O-sulfo-Alpha-L-idopyranuronosyl-(1-4)-2-deoxy-2-(sulfoamino)-6-(hydrogen sulfate) [CAS] | 104993-28-4 114870-03-0 | | | Anticoagulant | Thrombosis, venous |
| Formebolone | | 2454117 | | | | |
| formestane | Androst-4-ene-3,17-dione, 4-hydroxy-[CAS] | 566-48-3 | EP | 346953 | Anticancer, hormonal | Cancer, breast |
| Formocortal | | 2825-60-7 | | | | |
| formoterol | Formamide, N-[2-hydroxy-5-[1-hydroxy-2-[[2-(4-methoxyphenyl)-1-methylethyl]amino]ethyl]phenyl]-, (R*,R*)-(+/−)-[CAS] | 43229-80-7 73573-87-2 | GB | 1415256 | Antiasthma | Asthma |
| fosamprenavir | Carbamic acid, ((1S,2R)-3-(((4-aminophenyl)sulfonyl)(2-methylpropyl)amino)-1-(phenylmethyl)-2-(phosphonooxy)propyl)-C-((3S)-tetrahydro-3-furanyl ester, [CAS] | 226700-81-8 | | | Antiviral, anti-HIV | Infection, HIV/AIDS |

TABLE IV-continued

| API Generic Name | API Chemical Name | CAS No. | Patent Reference | Example of Therapeutic Use | Example of Indication |
|---|---|---|---|---|---|
| foscarnet | Phosphinecarboxylic acid, dihydroxy-, oxide, trisodium salt [CAS] | 34156-56-4 4428-95-9 | U.S. 4,839,445 | Antiviral, other | Infection, cytomegalovirus |
| Fosfestrol | | 63585-09-1 522-40-7 | | | |
| fosfluconazole | 2,4-difluoro-Alpha,Alpha-bis(1H-1,2,4-triazol-1-ylmethyl)benzyl alcohol, dihydrogen phosphate (ester) | 194798-83-9 | | Antifungal | Infection, fungal, general |
| fosfomycin | Phosphonic acid, (3-methyloxiranyl)-, (2R-cis)-[CAS] | 23155-02-4 26016-98-8 | GB 1223923 | Antibiotic, other | Infection, general |
| fosfomycin trometamol | Phosphonic acid, (3-methyloxiranyl)-, (2R-cis)-, compd. with 2-amino-2-(hydroxymethyl)-1,3-propanediol (1:1)-[CAS] | 78964-85-9 | EP 27597 | Antibiotic, other | Infection, urinary tract |
| Fosfosal | | 6064-83-1 | | | |
| fosinopril | L-Proline, 4-cyclohexyl-1-[[[2-methyl-1-(1-oxopropoxy)propoxy](4-phenylbutyl)phosphinyl]acetyl]-, (2Alpha,4β)-[CAS] | 88889-14-9 98048-97-6 | EP 63896 | Antihypertensive, renin system | Hypertension, general |
| fosphenytoin | 2,4-Imidazolidinedione, 5,5-diphenyl-3-[(phosphonooxy)methyl]-[CAS] | 92134-98-0 93390-81-9 | U.S. 4,260,769 | Antiepileptic | Epilepsy, generalized, tonic-clonic |
| fotemustine | Phosphonic acid, [1-[[[(2-chloroethyl)nitrosoamino]carbonyl]amino]ethyl]-, diethyl ester [CAS] | 92118-27-9 | EP 117959 | Anticancer, alkylating | Cancer, melanoma |
| Fropenem | | 106560-14-9 | | | |
| frovatriptan | 1H-Carbazole-6-carboxamide, 2,3,4,9-tetrahydro-3-(methylamino)-, (R)-[CAS] | 158747-02-5 | WO 9922730 | Antimigraine | Migraine |
| Fructose | | 57-48-7 | | | |
| Fructose-1,6-diphosphate | | 488-69-7 | | | |
| FTC | | | | Antiviral, anti-HIV | Infection, HIV/AIDS |
| FTY-720 | 2(1H)-Pyrimidinone, 4-amino-5-fluoro-1-(2-(hydroxymethyl)-1,3-oxathiolan-5-yl)-(4R) 1,3-Propanediol, 2-amino-2-(2-(4-octylphenyl)ethyl)-, hydrochloride [CAS] | 162359-56-0 | WO 9408943 | Immunosuppressant | Transplant rejection, general |
| fudosteine | Alanine, 3-((3-hydroxypropyl)thio)-[CAS] | 13189-98-5 | U.S. 5,047,428 | Antitussive | Cough |
| fulvestrant | Estra-1,3,5(10)-triene-3,17-diol, 7-[9-[4,4,5,5,5-pentafluoropentyl)sulfinyl]nonyl]-, (7Alpha,17β)-[CAS] | 129453-61-8 | EP 346014 | Anticancer, hormonal | Cancer, breast |
| fumagiline | 2,4,6,8-Decatetraenedioic acid, mono[5-methoxy-4-[2-methyl-3-(3-methyl-2-butenyl)oxiranyl]-1-oxaspiro[2.5]oct-6-yl] ester, [3R-[3Alpha,4Alpha(2R*,3R*),5β,6β(all-E)]]-[CAS] | 23110-15-8 | | Protozoacide | Infection, GI tract |
| Fumagillin | | 23110-15-8 | | | |
| Furaltadone | | 139-91-3 | | | |
| Furazabol | | 1239-29-8 | | | |
| Furazolidone | | 67-45-8 | | | |

TABLE IV-continued

| API Generic Name | API Chemical Name | CAS No. | Patent Reference | Example of Therapeutic Use | Example of Indication |
|---|---|---|---|---|---|
| Furazolium Chloride | | 5118-17-2 | | | |
| Furonazide | | 3460-67-1 | | | |
| furosemide | Benzoic acid, 5-(aminosulfonyl)-4-chloro-2-[(2-furanylmethyl)amino]-[CAS] | 54-31-9 | | Formulation, modified-release, other | Hypertension, general |
| Fursultiamine | | 804-30-8 | | | |
| Furtrethonium | | 7618-86-2 | | | |
| Fusidic Acid | | 06/03/6990 | | | |
| G1, YM BioSciences | 1-(5-bromofur-2-yl)-2-bromo-2-nitroethene | | | Antifungal | Infection, gynaecological |
| G25 | | | WO 9804252 | Antimalarial | Infection, malaria |
| GABA-A Alpha5 inverse agonist, Mer | | | WO 0206285 | Cognition enhancer | Alzheimer's disease |
| gabapentin | Cyclohexaneacetic acid, 1-(aminomethyl)-[CAS] | 60142-96-3 | U.S. 4,152,326 | Antiepileptic | Epilepsy, general |
| gabexate | Benzoic acid, 4-[[6-[(aminoiminomethyl)amino]-1-oxohexyl]oxy]-, ethyl ester, mononethanesulfonate [CAS] | 39492-01-8 56974-61-9 | U.S. 3,751,447 | GI inflammatory/bowel disorders | Pancreatitis |
| gaboxadol | Isoxazolo[5,4-c]pyridin-3(2H)-one, 4,5,6,7-tetrahydro-[CAS] | 64603-91-4 | CA 1125288 | Hypnotic/Sedative | Sleep disorder, general |
| Gadobenat Dimeglumine | | 127000-20-8 | | | |
| Gadobutrol | | 138071-82-6 | | | |
| Gadodiamide | | 131410-48-5 | | | |
| Gadopentetic Acid | | 80529-93-7 | | | |
| Gadoteridol | | 120066-54-8 | | | |
| Gadoversetamide | | 131069-91-5 | | | |
| Gadoxetic Acid | | 135326-11-3 | | | |
| galantamine | (4aS,6R,8aS)-6-Hydroxy-3-methoxy-11-methyl-5,6,9,10,11,12-hexahydro-4aH-benzofuro[3a,3,2-e,f][2]benzazepine | 357-70-0 | | Formulation, modified-release, other | Alzheimer's disease |
| Galanthamine | β-Alanine, 2-[4-[(2,6-dideoxy-2-fluoro-Alpha-L-talopyranosyl)oxy]-1,2,3,4,6,11-hexahydro-2,5,12-trihydroxy-7-methoxy-6,11-dioxo-2-naphthacenyl]-2-oxoethyl ester, [CAS] | 140637-82-7 140637-86-1 | EP 424899 | Anticancer, antibiotic | Cancer, breast |
| galarubicin | | | | | |
| Gallamine Triethiodide | | 65-29-2 | | | |
| Gallic Acid | | 149-91-7 | | | |
| gallium maltolate | 4H-Pyran-4-one, 3-hydroxy-2-methyl-, gallium complex | | | Anticancer, other | Cancer, myeloma |
| gallium nitrate | Nitric acid, gallium salt [CAS] | 13494-90-1 | U.S. 4,529,593 | Osteoporosis treatment | Hypercalcaemia of malignancy |
| gallopamil | Benzeneacetonitrile, Alpha-[3-[[2-(3,4-dimethoxyphenyl)ethyl]methylamino]propyl]-3,4,5-trimethoxy-Alpha-(1-methylethyl)-[CAS] | 16662-47-8 | GB 1367677 | Antianginal | Angina, general |
| γ-Aminobutyric Acid | | 56-12-2 | | | |
| Ganaxolone | | 38398-32-2 | | | |

TABLE IV-continued

| API Generic Name | API Chemical Name | CAS No. | Patent Reference | | Example of Therapeutic Use | Example of Indication |
|---|---|---|---|---|---|---|
| ganciclovir | 6H-Purin-6-one, 2-amino-1,9-dihydro-9-[[2-hydroxy-1-(hydroxymethyl)ethoxy]methyl]-[CAS] | 107910-75-8 82410-32-0 | EP | 49072 | Antiviral, other | Infection, cytomegalovirus |
| ganirelix | [N-Ac-D-Nal,D-pCl-Phe,D-Pal,D-hArg(Et)2,hArg(Et)2,D-Ala]GnRH-[CAS] | 124904-93-4 | EP | 312052 | Releasing hormones | Infertility, female |
| ganstigmine | Carbamic acid, (2-ethylphenyl)-, (3aS,8aS)-1,2,3,3a,8,8a-hexahydro-1,3a,8-trimethylpyrrolo[2,3-b]indol-5-yl ester, | 223585-99-7 | EP | 1023297 | Cognition enhancer | Alzheimer's disease |
| gantofiban | 1-Piperazineacetic acid, 4-[[(5R)-3-[4-[imino(methoxycarbonyl)amino]methyl]-phenyl]-2-oxo-5-oxazolidinyl]methyl]-, ethylester [CAS] | 183547-57-1 | EP | 741133 | Antithrombotic | Thrombosis, general |
| garenoxacin | 3-Quinolinecarboxylic acid, 1-cyclopropyl-8-(difluoromethoxy)-7-((1R)-2,3-dihydro-1-methyl-1H-isoindol-5-yl)-1,4-dihydro-4-oxo-monomethanesulfonate [CAS] | 223652-82-2 | | | Quinolone antibacterial | Infection, respiratory tract, lower |
| garnocestim | 5-73-macrophage inflammatory protein 2Alpha (human gene gro2)-[CAS] | 246861-96-1 | | | Radio/ chemoprotective | Chemotherapy-induced injury, bone marrow, neutropenia |
| gatifloxacin | 3-Quinolinecarboxylic acid, 1-cyclopropyl-6-fluoro-1,4-dihydro-8-methoxy-7-(3-methyl-1-piperazinyl)-4-oxo-, (+/-)-[CAS] | 112811-59-3 | EP | 230295 | Quinolone antibacterial | Infection, respiratory tract, general |
| Gefarnate | | 51-77-4 | | | | |
| gefitinib | 4-Quinazolinamine, N-(3-chloro-4-fluorophenyl)-7-methoxy-6-(3-(4-morpholinyl)propoxy) [CAS] | 184475-35-2 | WO | 9633980 | Anticancer, other | Cancer, lung, non-small cell |
| gemcabene | 6,6'-oxybis(2,2-dimethylhexanoate) | 209789-08-2 | | | Hypolipaemic/ Antiatherosclerosis | Hyperlipidaemia, general |
| gemcitabine | Cytidine, 2'-deoxy-2',2'-difluoro-, [CAS] | 122111-03-9 95058-81-4 | GB | 2136425 | Anticancer, antimetabolite | Cancer, pancreatic |
| gemeprost | Prosta-2,13-dien-1-oic acid, 11,15-dihydroxy-16,16-dimethyl-9-oxo-, methyl ester, (2E,11Alpha,13E,15R)-[CAS] | 64318-79-2 | GB | 1540427 | Prostaglandin | |
| gemfibrozil | Pentanoic acid, 5-(2,5-dimethylphenoxy)-2,2-dimethyl-[CAS] | 25812-30-0 | U.S. | 3,674,836 | Hypolipaemic/ Antiatherosclerosis | Hyper-lipidaemia, general |
| gemifloxacin | 1,8-Naphthyridine-3-carboxylic acid, 7-(3-(aminomethyl)-4-(methoxyimino)-1-pyrrolidinyl)-1-cyclopropyl-6-fluoro-1,4-dihydro-4-oxo-[CAS] | 175463-14-6 | U.S. | 5,869,670 | Quinolone antibacterial | Infection, respiratory tract, general |
| gentamicin | Gentamicin [CAS] | 1403-66-3 | | | Formulation, implant | Infection, general |
| Gentian Violet | | 548-62-9 | | | | |
| Gentiopicrin | | 20831-76-9 | | | | |
| Gentisic Acid | | 490-79-9 | | | | |
| Gepefrine | | 18840-47-6 | | | | |

TABLE IV-continued

| API Generic Name | API Chemical Name | CAS No. | Patent Reference | Example of Therapeutic Use | Example of Indication |
|---|---|---|---|---|---|
| gepirone | 2,6-Piperidinedione, 4,4-dimethyl-1-[4-[4-(2-pyrimidinyl)-1-piperazinyl]butyl]-[CAS] | | | Formulation, modified-release, other | Depression, general |
| gestodene | 18,19-Dinorpregna-4,15-dien-20-yn-3-one, 13-ethyl-17-hydroxy-, (17Alpha)-[CAS] | 109852-02-0 60282-87-3 | GB 1569135 | Formulation, fixed-dose combinations | Contraceptive, female |
| gestodene + ethinylest | 18,19-Dinopregna-4,15-dien-20-yn-3-one, 13-ethyl-17-hydroxy-, (17Alpha) mixt with 19-Norpregna-1,3,5(10)-trien-20-yne-13,17-diol (17Alpha) | | | Formulation, modified-release, >24 hr | Contraceptive, female |
| Gestonorone Caproate | | 1253-28-7 | | | |
| Gestrinone | | 16320-04-0 | | | |
| γ-Hydroxybutyrate | | 591-81-1 | | | |
| gimatecan | (4S)-11-[(E)-[(1,1-dimethylethoxy)imino]methyl]-4-ethyl-4-hydroxy-1-12-dihydro-14H-pyrano[3',4':6,7]indolizino[1,2-b]quinoline-3,14(4H)-dione | 292618-32-7 | | Anticancer, other | Cancer, brain |
| Giractide | | 24870-04-0 | | | |
| Gitoxin | | 4562-36-1 | | | |
| GL-406349 | | | | | |
| | N,N'-Bis[2-[N-[2-(N2,N5-dimethyl-DL-lysylamino)ethyl]carbamoyl]1H-indol-6-yl]-1H-indole-2,5-dicarboxamide | 3820-67-5 | | Antifungal | Infection, fungal, general |
| Glafenine | | 147245-92-9 | | | |
| glatiramer | L-Glutamic acid, polymer with L-alanine, L-lysine and L-tyrosine, [CAS] | 28704-27-0 | WO 5800808 | Multiple sclerosis treatment | Multiple sclerosis, relapsing-remitting |
| Glibornuride | | 26944-48-9 | | | |
| gliclazide | Benzenesulfonamide, N-[[(hexahydrocyclopenta[c]pyrrol-2(1H)-yl)amino]carbonyl]-4-methyl-[CAS] | 21187-98-4 | GB 1153982 | Antidiabetic | Diabetes, Type II |
| glimepiride | 1H-Pyrrole-1-carboxamide, 3-ethyl-2,5-dihydro-4-methyl-N-[2-[4-[[[[(4-methylcyclohexyl)amino]carbonyl]amino]sulfonyl]phenyl]ethyl]-2-oxo-[CAS] | 93479-97-1 | WO 9303724 | Antidiabetic | Diabetes, Type II |
| γ-Linolenic Acid | | 506-26-3 | | | |
| glipizide | Pyrazinecarboxamide, N-[2-[4-[[[(cyclohexylamino)carbonyl]amino]sulfonyl]-phenyl]ethyl]-5-methyl-[CAS] | 29094-61-9 | U.S. 3,669,966 | Antidiabetic | |
| gliquidone | Benzenesulfonamide, N-[(cyclohexylamino)carbonyl]-4-[2-(3,4-dihydro-7-methoxy-4,4-dimethyl-1,3-dioxo-]2(1H)-isoquinolinyl)ethyl]-[CAS] | 33342-05-1 | GB 1277847 | Antidiabetic | Diabetes, general |
| glisolamide | 3-Isoxazolecarboxamide, N-[2-[4-[[[(cyclohexylamino)carbonyl]amino]sulfonyl]phenyl]ethyl]-5-methyl-[CAS] | 24477-37-0 | | Antidiabetic | Diabetes, general |
| Glisoxepid | | 25046-79-1 | | | |
| Glucametacin | | 52443-21-7 | | | |
| Glucoheptonic Acid | | 87-74-1 | | | |

TABLE IV-continued

| API Generic Name | API Chemical Name | CAS No. | Patent Reference | | Example of Therapeutic Use | Example of Indication |
|---|---|---|---|---|---|---|
| Gluconic Acid glucosamine | D-Glucose, 2-amino-2-deoxy-, [CAS] | 526-95-4 29031-19-4 3416-24-8 | DE | 1953689 | Antiarthritic, other | Arthritis, osteo |
| Glucosulfone glufosfamide | β-D-Glucopyranose, 1-(N,N'-bis(2-chloroethyl)pheophorodiamidate)-[CAS] | 554-18-7 132682-98-5 | DE | 3835772 | Anticancer, alkylating | Cancer, general |
| Glutamic Acid | | 56-86-0 | | | | |
| Glutaraldehyde | | 111-30-8 | | | | |
| Glutethimide | | 77-21-4 | | | | |
| Glyburide | | 10238-21-8 | | | | |
| Glybuthiazol(e) | | 535-65-9 | | | | |
| Glybuzole | | 1492-02-0 | | | | |
| Glycerol | | 56-81-5 | | | | |
| Glycocyamine | | 352-97-6 | | | | |
| Glycol Salicylate | | 87-28-5 | | | | |
| Glyconiazide | | 3691-74-5 | | | | |
| Glycopyrrolate | | 596-51-0 | | | | |
| Glyhexamide | | 451-71-8 | | | | |
| Glymidine | | 339-44-6 | | | | |
| Glypinamide | | 1228-19-9 | | | | |
| GMDP | N-acetylglucosaminyl-N-acetylmuramyl dipeptide | | | | Anti-infective, other | Infection, general |
| Gold Sodium Thiemalat | | 12244-57-4 | | | | |
| Gold Sodium Thiosulfate | | 10233-88-2 | | | | |
| goserelin | Luteinizing hormone-releasing factor (pig), 6-[O-(1,1-dimethylethyl)-D-serine]-10-deglycinamide-, 2-(aminocarbony)hydrazide [CAS] | 65807-02-5 | U.S. | 4,100,274 | Releasing hormones | Cancer, prostate |
| GPI-1485 | L-Proline, 1-(3,3-dimethyl-1,2-dioxopentyl)-, 3-(3-pyridinyl)propyl ester [CAS] | 186452-09-5 | | | Antiparkinsonian | Parkinson's disease |
| GPI-5693 | 2-(Phosphonomethyl)pentanedioic acid | | U.S. | 5,672,592 | Analgesic, other | Pain, neuropathic |
| Grafiskin granisetron | 1H-Indazole-3-carboxamide, 1-methyl-N-(9-methyl-9-azabicyclo[3.3.1]non-3-yl)-, endo-[CAS] | 107007-99-8 109889-09-0 | EP | 200444 | Antiemetic | Chemotherapy-induced nausea and vomiting |
| Grepafloxacin griseofulvin | Spiro[benzofuran-2(3H),1'-[2]cyclohexane]-3,4'-dione, 7-chloro-2',4,6-trimeth-oxy-6'methyl-, (1'S-trans)-[CAS] | 119914-60-2 126-07-8 | | | Formulation, dermal, topical | Infection, dermatological |
| Guaiacol | | 90-05-1 | | | | |
| Guaiapate | | 852-42-6 | | | | |
| Guaiazulene | | 489-84-9 | | | | |
| Guaifenesin | | 93-14-1 | | | | |
| guaimesal | 4H-1,3-Benzodioxin-4-one, 2-(2-methoxyphenoxy)-2-methyl-[CAS] | 81674-79-5 | GB | 2098201 | Anti-inflammatory | |
| Guamecycline | | 16545-11-2 | | | | |
| Guanabenz | | 5051-62-7 | | | | |

TABLE IV-continued

| API Generic Name | API Chemical Name | CAS No. | Patent Reference | Example of Therapeutic Use | Example of Indication |
|---|---|---|---|---|---|
| Guanadrel | | 40580-59-4 | | | |
| Guanethidine | | 55-65-2 | | | |
| Guanfacine | | 29110-47-2 | | | |
| Guanoxabenz | | 24047-25-4 | | | |
| Guanoxan | | 2165-19-7 | | | |
| gugulipid | Pregna-4,17(20)-diene-3,16-dione [CAS] | 95975-55-6 | EP 447706 | Hypolipaemic/Antiatherosclerosis | |
| Gusperimus | | 104317-84-2 | | Muscle relaxant | Anaesthesia, adjunct |
| GW-280430A | (Z)-2-Chlorofumaric acid 1-[3-[-[6,7-dimethoxy-2(S)-methyl-1(R)-(3,4,5-trimethoxybenzyl)-1,2,3,4-tetrahydroisoquinolinium-2-yl]propyl] | | | | |
| GW-320659 | [2S,3S,5R]-2-[3,5-difluorophenyl]-3,5-dimethyl-2-morpholinol | | | Anorectic/Antiobesity | Obesity |
| GYKI-16084 | (+)-R-2-[3-[N-(2-Benzo[1,4]dioxanylmethyl)amino]-1-propyl)-3(2H)-pyridazinone hydrochloride | | U.S. 6,194,411 | Prostate disorders | Benign prostatic hyperplasia |
| Hachimycin | | 1394-02-1 | | | |
| Halazepam | | 23092-17-3 | | | |
| Halcinonide | | 3093-35-4 | | | |
| halobetasol | Pregna-1,4-diene-3,20-dioe, 21-chloro-6,9-difluoro-11-hydroxy-16-methyl-17-(1-oxopropoxy)-, (6Alpha,11β,16-[CAS] | 66852-54-8 | U.S. 4,619,921 | Antipsoriasis | Psoriasis |
| halofantrine | 9-Phenanthrenemethanol, 1,3-dichloro-Alpha-[2-(dibutylamino)ethyl]-6-(trifluoromethyl)-[CAS] | 36167-63-2 69756-53-2 | EP 138374 | Antimalrial | Infection, malaria |
| halometasone | Pregna-1,4-diene-3,20-dione, 2-chloro-6,9-difluoro-11,17,21-trihydroxy-16-methyl-, (6Alpha,11β,16Alpha)-[CAS] | 50629-82-8 | U.S. 4,076,737 | Antipruritic/inflamm, allergic | |
| Haloperidol | | 52-86-8 | | | |
| Halopredone | | 57781-14-3 | | | |
| Haloprogin | | 777-11-7 | | | |
| Halopropane | | 679-84-5 | | | |
| Halothane | | 151-67-7 | | | |
| Haloxazolam | | 59128-97-1 | | | |
| harkoseride | 2(R)-Acetamido-N-benzyl-3-methoxypropionamide | | WO 9733861 | Antiepileptic | Epilepsy, general |
| HE-2000 | 16Alpha-Bromo-3β-hydroxy-5Alpha-androstane-17-one | | | Antiviral, anti-HIV | Infection, HIV/AIDS |
| Healos | | | WO 9714376 | Musculoskeletal | Regeneration, bone |
| Hematoporphyrin | | 14459-29-1 | | | |
| Hepronicate | | 7237-81-2 | | | |
| Heptabarbital | | 509-86-4 | | | |
| Heptaminol | | 372-66-7 | | | |
| Hetacillin | | 3511-16-8 | | | |
| Hetastarch | | 9004-62-0 | | | |
| Hexachlorophene | | 70-30-4 | | | |
| Hexadimethrine Bromide | | 28728-55-4 | | | |

TABLE IV-continued

| API Generic Name | API Chemical Name | CAS No. | Patent Reference | | Example of Therapeutic Use | Example of Indication |
|---|---|---|---|---|---|---|
| Hexafluorenium Bromide | | 317-52-2 | | | | |
| Hexamethonium | | 60-26-4 | | | | |
| Hexamidine | | 3811-75-4 | | | | |
| Hexapropymate | | 358-52-1 | | | | |
| Hexedine | | 5980-31-4 | | | | |
| Hexestrol | | 84-16-2 | | | | |
| Hexestrol Bis(β-diethylaminoethyl ether) | | 2691-45-4 | | | | |
| Hexethal | | 144-00-3 | | | | |
| Hexetidine | | 141-94-6 | | | | |
| Hexobarbital | | 56-29-1 | | | | |
| Hexobendine | | 54-03-5 | | | | |
| Hexocyclium Methyl Sulfate | | 115-63-9 | | | | |
| Hexoprenaline | | 3215-70-1 | | | | |
| Hextend | Hextend [CAS] | 235746-51-7 | U.S. | 5,407,428 | Plasma substitute | Surgery adjunct |
| Hexylcaine | | 532-76-3 | | | | |
| HF-0299 | 11b-hydroxy androstenedione | | | | Osteoporosis treatment | Osteoporosis |
| HGP-2 | Benzeneacetic acid, 4-[2-hydroxy-3-[(1-methylethyl)amino]propoxy]-, 2-tricyclo[3.3.1.13.7]dec-1-ylethyl ester, (2Z)-2-butenedioate (1:1) (salt) [CAS] | 121009-31-2 | | | Antiglaucoma | Glaucoma |
| HGP-64 | 8-Azoniabicyclo[3.2.1]octane, 3-(3-ethoxy-1,3-dioxo-2-phenylpropoxy)-8,8-dimethyl-, (3-endo)-, methyl sulfate [CAS] | 113932-41-5 | | | Antiepileptic | Epilepsy, general |
| hidrosmin | Hydrosmin-[CAS] | 120250-44-4 | | | Vasoprotective, systemic | |
| histamine | histamine | 51-45-6 | EP | 0493468 | Anticancer, immunological | Cancer, melanoma |
| Histapyrrodine | | 493-80-1 | | | | |
| histrelin | Luteinizing hormone-releasing factor (pig), 6-[1-(phenylmethyl)-D-histidine]-9-(N-ethyl-L-prolinamide)-10-deglycinamide-[CAS] | 76712-82-8 | EP | 217659 | Releasing hormones | Precocious puberty |
| HM-101 | HM 101 [CAS] | 217311-70-1 | | | Osteoporosis treatment | Osteoporosis |
| HMN-214 | (E)-4-[2-(p-methoxybenzenesulfonamide)-phenyl]ethenyl]pyridine-1-oxide | | | | Anticancer, other | Cancer, general |
| Homatropine | | 87-00-3 | | | | |
| Homocamfin | | 535-86-4 | | | | |
| Homochlorcyclizine | | 848-53-3 | | | | |
| Hopantenic Acid | | 18679-90-8 | | | | |
| HP-228 | Glycinamide, N-acetyl-L-norleucyl-L-glutaminyl-L-histidyl-D-phenylalanyl-L-arginyl-D-tryptophyl-[CAS] | 172617-89-9 | EP | 759770 | Analgesic, other | Pain, post-operative |
| Huperzine A | | 102518-79-6 | | | | |

TABLE IV-continued

| API Generic Name | API Chemical Name | CAS No. | Patent Reference | | Example of Therapeutic Use | Example of Indication |
|---|---|---|---|---|---|---|
| hyaluronan | Hyaluronic acid [CAS] | 9004-61-9 | | | Formulation, other | Restenosis |
| Hycanthone | | 3105-97-3 | | | | |
| Hydocarpic Acid | | 459-67-6 | | | | |
| Hydralazine | | 86-54-4 | | | | |
| Hydrastine | | 118-08-1 | | | | |
| Hydrastinine | | 6592-85-4 | | | | |
| Hydrochlorothiazide | | 58-93-5 | | | | |
| hydrocodone | Morphinan-6-one, 4,5-epoxy-3-hydroxy-17-methyl-,(5Alpha)-[CAS] | 466-99-9 125-29-1 | | | Formulation, modified-release, other | Pain, general |
| Hydrocortamate | | 76-47-1 | | | | |
| hydrocortisone | Pregn-4-ene-3,20-dione, 21-(acetyloxy)-11-hydroxy-17-(1-oxopropoxy)-, (11β)-[CAS] | 74050-20-7 50-23-7 | DE | 2826257 | Dermatological | Unspecified |
| hydrocortisone butyrate propio | Pregn-4-ene-3,20-dione, 11-hydroxy-17-(1-oxobutoxy)-21-(1-oxopropoxy)-, (11β)-[CAS] | 72590-77-3 | DE | 2910899 | Antipruritic/inflamm, allergic | |
| Hydroflumethiazide | | 135-09-1 | | | | |
| hydromorphone | Morphinan-6-one,4,5-epoxy-3-hydroxy-17-methyl-,(5Alpha)-, mixt with acetamide, N-(4-hydroxyphenyl)-, mixt with morphinan-6-one, 17-(cyclopropylmethyl)-4,5-epoxy-3,14-dihydroxy-, (5Alpha)- | 103-90-2 16590-41-3 466-99-9 | | | Formulation, fixed-dose combinations | Pain, general |
| Hydroquinidine | | 1435-55-8 | | | | |
| Hydroquinine | | 522-66-7 | | | | |
| Hydroquinone | | 123-31-9 | | | | |
| Hydroxocobalamin | | 13422-51-0 | | | | |
| Hydroxyamphetamine | | 1518-86-1 | | | | |
| Hydroxychloroquine | | 118-42-3 | | | | |
| Hydroxydione | | 53-10-1 | | | | |
| Hydroxypethidine | | 468-56-4 | | | | |
| Hydroxyphenamate | | 50-19-1 | | | | |
| Hydroxypropyl Cellulose | | 9004-64-2 | | | | |
| Hydroxystilbamidine | | 495-99-8 | | | | |
| Hydroxytetracaine | | 490-98-2 | | | | |
| Hydroxyzine | | 68-88-2 | | | | |
| Hylan G-F 20 | | | | | | |
| Hymecromone | | 90-33-5 | | | | |
| hyoscyamine | benzeneacetic acid, Alpha(hydroxymethyl)-, 8-methyl-8-azabicyclo [3.2.1.]oct-3-yl ester, [3(S)-endo]- | 101-31-5 | | | Formulation, oral, orally-disintegrating | Ulcer, GI, general |
| hypericin | Phenanthro[1,10,9,8-opqra]perylene-7,14-dione, 1,3,4,6,8,13-hexahydroxy-10,11-dimethyl-[CAS] | 548-04-9 | | | Anticancer, other | Cancer, brain |
| IACFT | | 180468-34-2 | | | | |
| ibandronic acid | Phosphonic acid, [1-hydroxy-3-(methylpentylamino)propylidene]bis-[CAS] | 114084-78-5 | EP | 252504 | Osteoporosis treatment | Hypercalcaemia of malignancy |

TABLE IV-continued

| API Generic Name | API Chemical Name | CAS No. | Patent Reference | | Example of Therapeutic Use | Example of Indication |
|---|---|---|---|---|---|---|
| ibopamine | Propanoic acid, 2-methyl-, 4-[2-(methylamino)ethyl]-1,2-phenylene ester-[CAS] | 66195-31-1 | GB | 1551661 | Cardiostimulant | Heart failure |
| ibopamine | Propanoic acid, 2-methyl-, 4-[2-(methylamino)ethyl]-1,2-phenylene ester-[CAS] | 66195-31-1 | | | Formulation, mucosal, topical | Surgery adjunct |
| Ibritumomab Tiuxetan | | 206181-63-7 | | | | |
| ibrolipim | Phosphonic acid, [[4-[[(4-bromo-2-cyanophenyl)amino]carbonyl]phenyl]methyl]-, diethyl ester [CAS] | 133208-93-2 | EP | 402033 | Hypolipaemic/Antiatherosclerosis | Hypertri-glyceridaemia |
| ibudilast | 1-Propanone, 2-methyl-1-[2-(1-methylethyl)pyrazolo[1,5-a]pyridin-3-yl]-[CAS] | 50847-11-5 | EP | 215438 | Antiasthma | Asthma |
| Ibufenac | | 1553-60-2 | | | | |
| ibuprofen piconol | Benzeneacetic acid, Alpha-methyl-4-(2-methylpropyl)-, 2-pyridinylmethyl ester [CAS] | 64622-45-3 | DE | 2658610 | Antipruritic/inflamm, non-allergic | Eczema, contact |
| ibuprofen | Benzeneacetic acid, Alpha-methyl-4-(2-methylpropyl)-[CAS] | 15687-27-1 | | | Formulation, modified-release, other | Inflammation, general |
| Ibuproxam | | 53648-05-8 | | | | |
| ibutilide | Methanesulfonamide, N-[4-[4-(ethylheptylamino)-1-hydroxybutyl]phenyl]-, (+/-), [CAS] | 122647-31-8 122647-32-9 | JP | 60239458 | Antiarrhythmic | Fibrillation, atrial |
| ICA-17043 | | | U.S. | 6,288,122 | Antisickling | Anaemia, sickle cell |
| icodextrin | Dextrin-[CAS] | 9004-53-9 | | | Urological | Renal failure |
| idarubicin | 5,12-Naphthacenedione, 9-acetyl-7-[(3-amino-2,3,6-trideoxy-Alpha-L-lyxo-hexopyranosyl)oxy]-7,8,9,10-tetrahydro-6,9,11-trihydroxy-, (7S-cis)-[CAS] | 58957-92-9 86189-66-4 | U.S. | 4,471,052 | Anticancer, antibiotic | Cancer, leukaemia, acute lymphocytic |
| Idazoxan | | 79944-58-4 | | | | |
| IdB-1016 | 2-(2,3-dihydro-2-(4-hydroxy-3-methoxyphenyl)-3-(hydroxymethyl)-1,4-benzodioxin-6-yl)-2,3-dihydro-3,5,7-trihydroxy-4H-1-benzopyran-4-one phosphatidylcholine complex | 134499-06-2 | EP | 209038 | Anticancer, hormonal | Cancer, ovarian |
| idebenone | 2,5-Cyclohexadiene-1,4-dione, 2-(10-hydroxydecyl)-5,6-dimethoxy-3-methyl-[CAS] | 58186-27-9 | EP | 58057 | Neuroprotective | Ischaemia, cerebral |
| IDN-5109 | 4-Hexenoic acid, 3-[[(1,1-dimethylethoxy)carbonyl]amino]-2-hydroxy-5-methyl-, (3aS,4R,7R,8aS,9S,10aR,12aS,12bR,13S,13aS)-7,12a-bis(acetyloxy)-13-(benzoyloxy)-3a,4,7,8,8a,9,10,10a,12,12a,12b,13-dodecahydro-9-hydroxy-5,8a,14,14-tetramethyl-2,8-dioxo-6,13a-methano- | 186348-05-0 | U.S. | 5,264,591 | Anticancer, other | Cancer, colorectal |

TABLE IV-continued

| API Generic Name | API Chemical Name | CAS No. | Patent Reference | Example of Therapeutic Use | Example of Indication |
|---|---|---|---|---|---|
| Idoxifen | 13aH-oxeto [2″,3″:5′,6′] benzo[1,2,4,5] cyclodeca [1,2-d] dioxyl-4-yl ester, 2R,3S) [CAS] | 116057-75-1 | | | |
| idraparinux | Alpha-D-Glucopyranoside, methyl O-2,3,4-tri-O-methyl-6-O-sulfo-Alpha-D-glucopyranosyl-(1,4)-O-2,3-di-O-methyl-β-D-glucopyranuronosyl-(1,4)-O-2,3,6-tri-O-sulfo-Alpha-D-glucopyranosyl-(1,4)-O-2,3-di-O-methyl-Alpha-L-idopyranuronosyl-(1,4)-, tris(hydrogen sulfate) nonasodium salt [CAS] | 149920-56-9 | AU 698456 | Antithrombotic | Thrombosis, venous |
| idrocilamide | 2-Propenamide, N-(2-hydroxyethyl)-3-phenyl-[CAS] | 6961-46-2 | U.S. 3,659,014 | Anti-inflammatory, topical | |
| ifenprodil | (7)-2-(4-benzyl piperidino)-1-p-hydroxyphenylpropanol tartrate | 23210-58-4 23210-56-2 | U.S. 3,509,164 | Neuroprotective | |
| ifosfamide | 2H-1,3,2-Oxazaphosphorin-2-amine, N,3-bist(2-chloroethyl)tetrahydro-2-oxide [CAS] | 3778-73-2 | U.S. 3,732,340 | Anticancer, alkylating | Cancer, lung, general |
| iguratimod | N-[3-(Formylamino)-4-oxo-6-phenoxy-4H-chromen-7-yl] methanesulfonamide | 123663-49-0 | DE 3834204 | Antiarthritic, other | Arthritis, rheumatoid |
| ilaprazole | 1H-Benzimidazole, 2-(((4-methoxy-3-methyl-2-pyridinyl) methyl)sulfinyl)-5-(1H-pyrrol-1-yl)-[CAS] | 172152-36-2 | U.S. 5,703,097 | Antiulcer | Ulcer, GI, general |
| ilomastat | Butanediamide, N4-hydroxy-N1-(1-(1H-indol-3-ylmethyl)-2-(methylamino)-2-oxoethyl)-2-(2-methylpropyl)-, (S-(R*,S*))-[CAS] | 142880-36-2 | U.S. 5,892,112 | COPD treatment | Emphysema, smoking-related |
| iloperidone | Ethanone, 1-[4-[3-[4-(6-fluoro-1,2-benzisoxazol-3-yl)-1-piperidinyl]propoxy]-3-methoxyphenyl]-[CAS] | 133454-47-4 | U.S. 5,776,963 | Neuroleptic | Schizophrenia |
| iloprost trometamol | Pentanoic acid, 5-[hexahydro-5-hydroxy-4-(3-hydroxy-4-methyl-1-octen-6-ynyl)-2(1H)-pentalenylidene]-[CAS] | 78919-13-8 | DE 3417638 | Prostaglandin | Peripheral vascular disease |
| ILX23-7553 | 1Alpha,25-Hydroxy-16-yne vitamin D3 | | | Anticancer, other | Cancer, general |
| imatinib | 4-((Methyl-1-piperazinyl)methyl)-N-[4-methyl-3-[[4-(3-pyridinyl)-2-pyrimidinyl]amino]-phenyl]benzamide methanesulfonate | 152459-95-5 | U.S. 5,521,184 | Anticancer, other | Cancer, leukaemia, chronic myelogenous |
| imidapril | 4-Imidazolidinecarboxylic acid, 3-[2-[[(1-(ethoxycarbonyl)-3-phenylpropyl]amino]-1-oxopropyl]-1-methyl-2-oxo-, [4S-[3[R*(R*)],4R*]]-[CAS] | 89371-37-9 89396-94-1 | EP 95163 | Antihypertensive, renin system, Musculoskeletal | Hypertension, general, Cachexia |
| imidazole salicylate | Benzoic acid, 2-hydroxy-, compd. with 1H-imidazole (1:1) [CAS] | 36364-49-5 | U.S. 4,329,340 | Anti-inflammatory | Pain, general |
| imipenem | 1-Azabicyclo[3.2.0]hept-2-ene-2-carboxylic acid, 6-(1-hydroxyethyl)-3-[[2-[(iminomethyl)amino]ethyl]thio]-7-oxo-, [5R-[5Alpha,6Alpha(R*)]]-[CAS] | 64221-86-9 74431-23-5 81129-83-1 | GB 1570990 | Beta-lactam antibiotic | Infection, general |
| Imipramine | | 50-49-7 | | | |

TABLE IV-continued

| API Generic Name | API Chemical Name | CAS No. | Patent Reference | Example of Therapeutic Use | Example of Indication |
|---|---|---|---|---|---|
| Imipramine N-Oxide | | 6929-98-7 | | | |
| imiquimod | 1H-Imidazo[4,5-c]quinolin-4-amine, 1-(2-methylpropyl)-[CAS] | 99011-02-6 | EP 145340 | Antiviral, other | Infection, human papilloma virus |
| Imolamine | | 318-23-0 | | | |
| implitapide | Benzeneacetamide, Alpha-cyclopentyl-4-((2,4-dimethyl-9H-pyrido(2,3-b)indol-9-yl)methyl)-N-((1R)-2-hydroxy-1-phenylethyl)-(AlphaS)-[CAS] | 177469-96-4 | EP 705831 | Hypolipaemic/Antiatherosclerosis | Atherosclerosis |
| Improsulfan | | 13425-98-4 | | | |
| Inaperisone | | 99323-21-4 | | | |
| incadronate | Phosphonic acid, [(cycloheptyl)amino)methylene]bis-, [CAS] | 138330-18-4 | | Musculoskeletal | Hypercalcaemia of malignancy |
| Incadronic Acid | | 124351-85-5 | | | |
| Indalpine | | 63758-79-2 | | | |
| Indanazoline | | 40507-78-6 | | | |
| indapamide | 4-chloro-N-(2-methylindolin-1-yl)-3-sulfamoylbenzamide | 26807-65-8 | GB 1203691 | Antihypertensive, diuretic | Hypertension, general |
| Indecainid | | 74517-78-5 | | | |
| indeloxazine | Morpholine, 2-[(1H-inden-7-yloxy)methyl]-[CAS] | 60929-23-9 65043-22-3 65043-22-3 | JP 52083773 | Cognition enhancer | Alzheimer's disease |
| Indeloxazine | | | | | |
| indenolol | 2-Propanol, 1-[1H-inden-4(or 7)-yloxy]-3-[(1-methylethyl)amino]-[CAS] | 30190-87-5 60607-68-3 68906-88-7 | GB 1290343 | Antihypertensive, adrenergic | |
| indinavir | D-erthro-Pentonamide, 2,3,5-trideoxy-N-(2,3-dihydro-2-hydroxy-1H-inden-1-yl)-5-(2-(((1,1-dimethylethyl)amino)carbonyl)-4-(3-pyridinylmethyl)-1-piperazinyl)-2-(phenylmethyl), [1S-[1Alpha(R*),2Alpha]]-, [CAS] | 150378-17-9 157810-81-6 | EP 0541168 | Antiviral, anti-HIV | Infection, HIV/AIDS |
| indiplon | Acetamide, N-methyl-N-(3-(3-(2-thienylcarbonyl)pyrazolo(1,5-a) pyrimidin-7-yl)phenyl)-[CAS] | 325715-02-4 | U.S. 6,399,621 | Hypnotic/Sedative | Insomnia |
| indisetron | 1H-Indazole-3-carboxamide, N-(3,9-dimethyl-3,9-diazabicyclo(3.3.1)non-7-yl)-, diendo-[CAS] | 160472-97-9 | | Antiemetic | Nausea and vomiting, general |
| indisulam | 1,4-Benzenedisulfonamide, N-(3-chloro-1H-indol-7-yl)-[CAS] | 165668-41-7 | | AAnticancer, other | Cancer, lung, non-small cell |
| Indobufen | | 63610-08-2 | | | |
| Indocyanine Green | | 3599-32-4 | | | |
| indometacin | 1H-Indole-3-acetic acid, 1-(4-chlorobenzoyl)-5-methoxy-2-methyl-[CAS] | 53-86-1 | | Formulation, modified-release, other | Inflammation, general |
| Indoprofen | | 31842-01-0 | | | |
| indoramin | Benzamide, N-[1-[2-(1H-indol-3-yl)ethyl]-4-piperidinyl]-[CAS] | 26844-12-2 38821-52-2 | GB 1218570 | Antihypertensive, adrenergic | |
| Induclem | | | U.S. 5,993,810 | Labour inducer | Labour, induction |

TABLE IV-continued

| API Generic Name | API Chemical Name | CAS No. | Patent Reference | Example of Therapeutic Use | Example of Indication |
|---|---|---|---|---|---|
| Infliximab | | 170277-31-3 | | | |
| Inosine Pranobex | | 36703-88-5 | | | |
| Inositol | | 87-89-8 | | | |
| Inositol Niacinate | | 6556112 | | | |
| Iobenguane | | 80663-95-2 | | | |
| Iobenzamic Acid | | 3115057 | | | |
| Iobitridol | | 136949-58-1 | | | |
| Iocarmic Acid | | 10397-75-8 | | | |
| Iocetamic Acid | | 16034-77-8 | | | |
| Iodamide | | 440-58-4 | | | |
| iodine | Iodine [CAS] | 7553-56-2 | | Formulation, oral, other | Fibrocystic breast disorder |
| Iodipamide | | 606-17-7 | | | |
| Iodixanol | | 92339-11-2 | | | |
| Iodoalphionic Acid | | 577-91-3 | | | |
| iodochlorhydroxyquin | 5-Chloro-7-iodo-8-quinolinol | 130-26-7 | | Cognition enhancer | Alzheimer's disease |
| Iodoform | | 75-47-8 | | | |
| Iodopyracet | | 300-37-8 | | | |
| Iodopyrrole | | 87-58-1 | | | |
| Iodoquinol | | 83-73-8 | | | |
| Iofetamine 123I | | 75917-92-9 | | | |
| Ioglycamic Acid | | 2618-25-9 | | | |
| Iohexol | | 66108-95-0 | | | |
| Iomeglamic Acid | | 25827-76-3 | | | |
| Iomeprol | | 78649-41-9 | | | |
| Iopamidol | | 60166-93-0 | | | |
| Iopanoic Acid | | 96-83-3 | | | |
| Iopentol | | 89797-00-2 | | | |
| Iophendylate | | 99-79-6 | | | |
| Iophenoxic Acid | | 96-84-4 | | | |
| Iopromide | | 73334-07-3 | | | |
| Iopronic Acid | | 41473-08-9 | | | |
| Iopydol | | 5579-92-0 | | | |
| Iopydone | | 5579-93-1 | | | |
| Iothalamic Acid | | 2276-90-6 | | | |
| Iotrolan | | 79770-24-4 | | | |
| Ioversol | | 87771-40-2 | | | |
| Ioxaglic Acid | | 59017-64-0 | | | |
| Ioxilan | | 107793-72-6 | | | |
| IP-751 | (3R,4R)-(delta6)-THC-DMH-11-oic acid | | WO 9401429 | Analgesic, other | Pain, neuropathic |
| Ipidacrine | | 62732-44-9 | | | |
| IPL-576092 | Stigmastan-15-one, 22,29-epoxy-3,4,6,7,29-pentahydroxy-, (3Alpha,4β,5Alpha,6Alpha,7β,14β,22S)-[CAS] | 137571-30-3 | U.S. 6,046,185 | Antiasthma | Asthma |

TABLE IV-continued

| API Generic Name | API Chemical Name | CAS No. | Patent Reference | Example of Therapeutic Use | Example of Indication |
|---|---|---|---|---|---|
| Ipodate ipratropium bromide | | 5587-89-3 66985-17-9 22254-24-6 | | Formulation, inhalable, solution | Chronic obstructive pulmonary disease |
| ipratpopium | (endo,syn)-(±)-3-(3-Hydroxy-1-oxo-2-phenylpropoxy)-8-methyl-8-(1-methylethyl)-8-azoniabicyclo[3.2.1]octane | | | Formulation, inhalable, topical | Asthma |
| ipratropium | (endo,syn)-(±)-3-(3-Hydroxy-1-oxo-2-phenylpropoxy)-8-methyl-8-(1-methylethyl)-8-azoniabicyclo[3.2.1]octane | | | Formulation, inhalable, topical | Asthma |
| iprazochrome | Hydrazinecarboxamide, 2-[1,2,3,6-tetrahydro-3-hydroxy-1-(1-methylethyl)-6-oxo-5H-indol-5-ylidene]-[CAS] | 7248-21-7 | | Haemostatic | |
| ipriflavone | 4H-1-Benzopyran-4-one, 7-(1-methylethoxy)-3-phenyl-[CAS] | 35212-22-7 | EP 214647 | Osteoporosis treatment | Osteoporosis |
| Iprindole Iproclozid Iponiazid Ipsapiron | | 5560-72-5 3544-35-2 54-92-2 95847-70-4 | | | |
| irbesartan | 2-n-butyl-4-spirocyclopentane-1-[((2'-tetrazol-5-yl)biphenyl-4-yl)methyl]-2-imidazolin-5-one | 138402-11-6 | WO 9114679 | Antihypertensive, renin system | Hypertension, general |
| IRFI-042 | Butanedioic acid, mono[2-[2-(acetylthio)ethyl]-2,3-dihydro-4,6,7-trimethyl-5-benzofuranyl] ester, (+/-)-[CAS] | 134867-62-2 | U.S. 5,114,966 | Cardiovascular | Atherosclerosis |
| IRFI-165 | N-Cyclopentyl-1-methylimidazo[1,2-a]quinoxalin-4-amine | 191349-26-5 | EP 865442 | Antidepressant | Depression, general |
| Iridomyrmecin irindalone | -Imidazolidinone, 1-[2-[4-[3-(4-fluorophenyl)-2,3-dihydro-1H-inden-1-yl]-1-piperazinyl]ethyl]-, (1R-trans)-[CAS] | 485-43-8 104113-57-7 96478-43-2 | EP 183349 | Antidepressant | Depression, general |
| Irinotecan irofulven | Spiro[cyclopropane-1,5'-[5H]inden]-7'(6H)-one, 6'-hydroxy-2',4',6'-trimethyl-, (R)-[CAS] | 97682-44-5 125392-76-9 | U.S. 5,563,176 | Anticancer, other | Cancer, prostate |
| Iron Sorbitex isogladine | 1,3,5-Triazine-2,4-diamine, 6-(2,5-dichlorophenyl)-[CAS] | 1338-16-5 57381-26-7 57381-28-9 57381-33-6 | U.S. 4,657,907 | Antihypertensive, diuretic | Hypertension, general |
| IS-741 | Cyclohexanecarboxamide, N-[2-[(ethylsulfonyl)amino]-5-(trifluoromethyl)-3-pyridinyl]-[CAS] | 141283-87-6 | EP 465913 | GI inflammatory/bowel disorders | Pancreatitis |
| isaglitazone | 2,4-Thiazolidinedione, 5-[[6-[(2-fluorophenyl)methoxy]-2-naphthalenyl]methyl]-[CAS] | 161600-01-7 | U.S. 5,594,016 | Antidiabetic | Diabetes, Type II |
| ISAtx-247 | | | NZ 502362 | Immunosuppressant | Transplant rejection, general |

TABLE IV-continued

| API Generic Name | API Chemical Name | CAS No. | Patent Reference | | Example of Therapeutic Use | Example of Indication |
|---|---|---|---|---|---|---|
| Isbogrel | | 89667-40-3 | | | | |
| isepamicin | D-Streptamine, O-6-amino-6-deoxy-Alpha-D-glucopyranosyl-(1-4)-O-[3-deoxy-4-C-methyl-3-(methylamino)-β-L-arabinopyranosyl-(1-6)]-N1-(3-amino-2-hydroxy-1-oxopropyl)-2-deoxy-, (S)-[CAS] | 58152-01-5 58152-03-7 | U.S. | 4,029,882 | Aminoglycoside antibiotic | Infection, dermatological |
| Isoaminile | | 77-51-0 | | | | |
| Isobutyl p-Aminobenzoate | | 94-14-4 | | | | |
| Asocarboxazid | | 59-63-2 | | | | |
| isoconazole | 1-[2-[2-6-dichlorobenzyloxy)-2-(2,4-dichlorophenyl)ethyl] | 24168-96-5 27523-40-6 | GB | 1244530 | Antifungal | Infection, fungal, general |
| Isoetharine | | 530-08-5 | | | | |
| isofloxythepin | 1-Piperazineethanol, 4-[3-fluoro-10,11-dihydro-8-(1-methylethyl)dibenzo[b,f]thiepin-10-yl]-[CAS] | 106819-39-0 106819-41-4 70931-18-9 | GB | 2010843 | Neuroleptic | |
| isoflurane | Ethane, 2-chloro-2-(difluoromethoxy)-1,1,1-trifluoro-[CAS] | 26675-46-7 | U.S. | 3,535,388 | Anaesthetic, inhalation | Anaesthesia |
| Isoflurophate | | 55-91-4 | | | | |
| Isoladol | | 530-34-7 | | | | |
| Isomethadone | | 466-40-0 | | | | |
| Isometheptene | | 503-01-5 | | | | |
| Isoniazid | | 54-85-3 | | | | |
| Isonixin | | 57021-61-1 | | | | |
| Isopromethazine | | 303-14-0 | | | | |
| Isopropamide Iodide | | 71-81-8 | | | | |
| Isopropyl Alcohol | | 67-63-0 | | | | |
| isopropyl unoprostone | 5-Heptenoic acid, 7-(3,5-dihydroxy-2-(3-oxodecyl)cyclopentyl)-, 1-methylethylester, (1R-(1Alpha(Z), 2β,3Alpha,5Alpha))-[CAS] | 120373-24-2 | EP | 289349 | Prostaglandin | Glaucoma |
| Isoproterenol | | 7683-59-2 | | | | |
| Isosorbide | | 652-67-5 | | | | |
| isosorbide dinitrate | D-Glucitol, 1,4:3,6-dianhydro-, dinitrate [CAS] | 87-33-2 | | | Formulation, modified-release, other | Angina, general |
| isosorbide mononitrate | D-Glucitol, 1,4:3,6-dianhydro-, 5-nitrate [CAS] | 16051-77-7 | | | Formulation, modified-release, other | Angina, general |
| Isothipendyl | | 482-15-5 | | | | |
| isotretinoin | Retinoic acid, 13-cis-[CAS] | 4759-48-2 | U.S. | 4,843,096 | Antiacne | Acne |
| Isovaleryl Diethylamide | | 533-32-4 | | | | |
| Isoxepac | | 55453-87-7 | | | | |
| Isoxicam | | 34552-84-6 | | | | |
| Isoxsuprine | | 395-28-8 | | | | |

TABLE IV-continued

| API Generic Name | API Chemical Name | CAS No. | Patent Reference | | Example of Therapeutic Use | Example of Indication |
|---|---|---|---|---|---|---|
| isradipine | 3,5-Pyridinedicarboxylic acid, 4-(4-benzofurazanyl)-1,4-dihydro-2,6-dimethyl-, methyl 1-methylethyl ester [CAS] | 75695-93-1 | GB | 2037766 | Antihypertensive, other | Hypertension, general |
| israpafant | 6H-Thieno[3,2-f][1,2,4]triazolo[4,3-a][1,4]diazepine, 4-(2-chlorophenyl)-6,9-dimethyl-2-[2-[4-(2-methylpropyl)phenyl]ethyl]-[CAS] | 117279-73-9 | EP | 268242 | Antiasthma | Asthma |
| ISV-403 | | | U.S. | 5,447,926 | Formulation, mucosal, topical | Conjunctivitis |
| Itasetron | | 123258-84-4 | | | | |
| ITF-282 | ITF 282 [CAS] | 93615-44-2 | GB | 2115821 | Antianaemic | Anaemia, general |
| itopride | Benzamide, N-[4-[2-(dimethylamino)ethoxy]phenyl]methyl]-3,4-dimethoxy-, monohydrochloride [CAS] | 122892-31-3 | EP | 306827 | Gastroprokinetic | Gastritis |
| itraconazole | 3H-1,2,4-Triazol-3-one, 4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-[CAS] | 84625-61-8 | EP | 6711 | Antifungal | Infection, fungal, general |
| Itramin | | 13445-63-1 | | | | |
| itriglumide | 1-Naphthalenepropanoic acid, β-[2-[(8-azaspiro[4.5]dec-8-ylcarbonyl)-4,6-dimethylphenyl]amino]-2-oxoethyl]-, (βR)-[CAS] | 201605-51-8 | WO | 9800404 | Anxiolytic | Anxiety, general |
| iturelix | D-Alaninamide N-acetyl-3-(2-naphthalenyl) D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-prolyl-[CAS] | 112568-12-4 | WO | 8901944 | Fertility enhancer | Infertility, female |
| ivabradine | 7,8-dimethoxy-3-{3-[[(1S)(4,5-dimethoxybenzocyclobutan-1-yl)methyl]methylamino]propyl}-1,3,4,5-tetrahydro-2H-benzazepin-2-one | | | | Antianginal | Angina, general |
| ixabepilone | 17-Oxa-4-azabicyclo(14.1.0)heptadecane-5,9-dione, 7,11-dihydroxy-8,8,10,12,16-pentamethyl-3-(1-methyl-2-(2-methyl-4-thiazolyl)ethenyl, (1R,3S,7S,10R,11S,12S,16R) [CAS] | 219989-84-1 | | | Anticancer, other | Cancer, breast |
| J-104132 | 5H-Cyclopenta[b]pyridine-6-carboxylic acid, 5-(1,3-benzodioxol-5-yl)-2-butyl-7-[2[(2S)-2-carboxypropyl]-4-methoxyphenyl]-6,7-dihydro-, (5S,6R,7R)-[CAS] | 198279-45-7 | WO | 9737665 | Antihypertensive, other | Heart failure |
| J-107088 | 5H-Indole(2,3-a)pyrrolo(3,4-c)carbazole-5,7(6H)-dione, 12-β-D-glucopyranosyl-12,13-dihydroxy-2,10-dihydroxy-6-((2-hydroxy-1-(hydroxymethyl)ethyl)amino-[CAS] | 174402-32-5 | | | Anticancer, other | Cancer, bladder |

TABLE IV-continued

| API Generic Name | API Chemical Name | CAS No. | Patent Reference | | Example of Therapeutic Use | Example of Indication |
|---|---|---|---|---|---|---|
| J-113397 | 1-[(3R,4R)-1-Cyclooctylmethyl-3-hydroxymethyl-4-piperidyl]-3-ethyl-1,3-dihydro-2H-benzimidazole-2-one | | | | Analgesic, other | Pain, general |
| Janex-1 | Phenol, 4-[(6,7-dimethoxy-4-quinazolinyl)amino]-[CAS] | 202475-60-3 | | | Anticancer, other | Cancer, leukaemia, general |
| josamycin | Leucomycin V, 3-acetate 4B-(3-methylbutanoate) [CAS] | 16846-24-5 | JP | 41021759 | Macrolide antibiotic | Infection, general |
| JTV-519 | 1,4-Benzothiazepine, 2,3,4,5-tetrahydro-7-methoxy-4-[1-oxo-3-[4-(phenylmethyl)-1-piperidinyl]propyl]-[CAS] | 145903-06-6 | WO | 9212148 | Cardiovascular | Infarction, myocardial |
| K-777 | | | U.S. | 6,287,840 | Protozoacide | Infection, trypanosomiasis, American |
| Kainic Acid Kalimate Kallidin | Kalimate-[CAS] | 487-79-6 92354-70-6 342-10-9 | | | Urological | |
| KB-130015 | Acetic acid (2,6-diodo-4-((2-methyl-3-benzofuranyl)methyl)phenoxy)-[CAS] | 147030-48-6 | | | Antiarrhythmic | Arrhythmia, general |
| KCB-328 | Methanesulfonamide, N-[3-amino-4-[2-[[2-(3,4-dimethoxyphenyl)ethyl]methylamino]ethoxy]phenyl]-, monohydrochloride [CAS] | 177596-55-3 | WO | 9604231 | Antiarrhythmic | Arrhythmia, general |
| Kebuzone ketamine | 2-(2-Chlorophenyl)-2-(methylamino)-cyclohexanone hydrochloride | 853-34-9 6740-88-1 | | | Formulation, transmucosal, nasal | Pain, post-operative |
| ketanserin | 2,4(1H,3H)-Quinazolinedione, 3-[2-[4-(4-fluorobenzoyl)-1-piperidinyl]ethyl]-[CAS] | 74050-98-9 83846-83-7 | EP | 13612 | Antihypertensive, other | Hypertension, general |
| ketazolam | 4H-[1,3]Oxazino[3,2-d][1,4]benzodiazepine-4,7(6H)-dione, 11-chloro-8,12b-dihydro-2,8-dimethyl-12b-phenyl-[CAS] | 27223-35-4 | GB | 1222294 | Anxiolytic | |
| Kethoxal Ketobemidone ketoconazole | Piperazine, 1-acetyl-4-[4-[[2-(2,4-dichlorophenyl)-2-(1H-imidazol-1-ylmethyl)-1,3-dioxolan-4-yl]methoxy]phenyl]-, cis-[CAS] | 27762-78-3 469-79-4 65277-42-1 | U.S. | 4,335,125 | Antifungal | Infection, fungal, general |
| ketoprofen | mono(3-benzoyl-Alpha-methylbenzeneacetate) [CAS] | 173011-11-5 | EP | 502502 | Formulation, transdermal, systemic | Pain, general |
| ketorolac | 1H-Pyrrolizine-1-carboxylic acid, 5-benzoyl-2,3-dihydro-, (+/-)-[CAS] | 74103-06-3 74103-07-4 | EP | 53021 | Analgesic, NSAID | |
| Ketorolac Tromethamine ketotifen | 10-H-Benzo[4,5]cyclohepta[1,2-b]thiophen-10-one, 4,9-dihydro-4-(1-methyl-4-piperidinylidene)-, (E)-2-butenedioate (1:1)-[CAS] | 34580-13-7 34580-14-8 | GB | 1355539 | Antiasthma | Asthma |

TABLE IV-continued

| API Generic Name | API Chemical Name | CAS No. | Patent Reference | Example of Therapeutic Use | Example of Indication |
|---|---|---|---|---|---|
| Khellin | | 82-02-0 | | | |
| kinetin | | 9001-29-0 | | Dermatological | Photodamage |
| KNI-272 | 4-Thiazolidinecarboxamide, N-(1,1-dimethylethyl)-3-[2-hydroxy-3-[[(5-isoquinolinyloxy)acetyl]amino]-3-(methylthio)-1-oxopropyl]amino]-3-phenylbutyl]-, [4R-[3[2S*,3S*(R*)],4R*]]-[CAS] | 147318-81-8 | U.S. 5,466,028 | Antiviral, anti-HIV | Infection, HIV/AIDS |
| KP-103 | (R,R)-2-(2,4-Difluorophenyl)-3-(4-methylenepiperidin-1-yl)-1-(1,2,4-triazol-1-yl)-2-butanol | | | Antifungal | Infection, general |
| KP-157 | | | U.S. 6,110,961 | Antidepressant | Depression, general |
| KP-544 | | 151276-95-8 | WO 9919305 | Cognition enhancer | Unspecified |
| KRN-5500 | L-glycero-β-L-manno-Heptopyranosylamine, 4-deoxy-4-[[[[(2E,4E)-1-oxo-2,4-tetradecadienyl]amino]acetyl]amino]-N-1H-purin-6-yl-[CAS] | | WO 9015811 | Anticancer, antibiotic | Cancer, colorectal |
| KT-136 | Alpha-D-Glucopyranoside, β-D-fructofuranosyl, mixt. with 1-ethenyl-2-pyrrolidinone homopolymer compd. with iodine [CAS] | 121602-88-8 | | Formulation, dermal, topical | Ulcer, decubitus |
| KUL-7211 | (–)-2-[(2S)-1,2,3,4-tetrahydro-2-[[(2R)-2-hydroxy-2-(4-hydroxphenyl)ethyl]amino]naphthalen-7-yloxy]-N,N-dimethylacetamide hydrochloride monohydrate | | | Urological | Urinary calculus |
| KW-2170 | 6H-Pyrazolo[4,5,1-de]acridin-6-one,5-[(3-aminopropyl)amino]-7,10-dihydroxy-2-[[(2-hydroxyethyl)amino]methyl]-, dihydrochloride [CAS] | 207862-44-0 | | Anticancer, alkylating | Cancer, lung, non-small cell |
| KW-6002 | 1H-Purine-2,6-dione, 8-(2-(3,4-dimethoxyphenyl)ethenyl)-1,3-diethyl-3,7-dihydro-7-methyl-(E)-[CAS] | 155270-99-8 | | Antiparkinsonian | Parkinson's disease |
| KW-7158 | 3,3,3-Trifluoro-2-hydroxy-2-methyl-N-(10-oxo-4,10-dihydrothieno[3,2-C][1]benzothiepin-9-yl)propanamide 5,5 dioxide | | | Urological | Incontinence |
| L-365260 | Urea, N-(2,3-dihydro-1-methyl-2-oxo-5-phenyl-1H-1,4-benzodiazepin-3-yl)-N'-(3-methylphenyl)-, (R)-[CAS] | 1118101-09-0 | EP 284256 | Anticancer, other | Cancer, general |
| L-5-hydroxy-tryptophan | L-Tryptophan, 5-hydroxy-[CAS] | 4350-09-8 | | Metabolic and enzyme disorders | Unspecified |
| L-745337 | Methanesulfonamide, N-[6-[(2,4-difluorophenyl)thio]-2,3-dihydro-1-oxo-1H-inden-5-yl]-[CAS] | 158205-05-1 | WO 9413635 | Analgesic, NSAID | Pain, general |
| L-758298 | Phosphonic acid, [3-[[(2R,3S)-2-.((1R)-1-[3,5-bis(trifluoromethyl)phenyl]ethoxy]-3-(4-fluorophenyl)-4-morpholinyl]methyl]-2,5-dihydro-5-oxo-1H-1,2,4-triazol-1-yl]-[CAS] | 172673-20-0 | WO 9523798 | Antimetic | Chemotherapy-induced nausea and vomiting |

TABLE IV-continued

| API Generic Name | API Chemical Name | CAS No. | Patent Reference | | Example of Therapeutic Use | Example of Indication |
|---|---|---|---|---|---|---|
| L-826141 | | | | | | Unspecified |
| labetalol | 5-[1-hydroxy-2-[(1-methyl-3-phenylpropyl)amino]ethyl]salicylamide HCl | 32780-64-6 36894-69-6 | WO U.S. | 9722585 4,012,444 | Antiasthma Antihypertensive, adrenergic | Unspecified |
| lacidipine | 3,5-Pyridinedicarboxylic acid, 4-[2-[3-(1,1-dimethylethoxy)-3-oxo-1-propenyl]phenyl]-1,4-dihydro-2,6-dimethyl-, diethyl ester, (E) [CAS] | 103890-78-4 | GB | 2164336 | Antihypertensive, other | Hypertension, general |
| Lactic Acid | | | | | | |
| lactitol | D-Glucitol, 4-O-β-D-galactopyranosyl- [CAS] | 585-86-4 | | | Hepatoprotective | Infection, neurological |
| Lactulose | | 4618-18-2 | | | | |
| lafutidine | Acetamide, 2-[(2-furanylmethyl)sulfinyl]-N-[4-[[4-(1-piperidinylmethyl)-2-pyridinyl]oxy]-2-butenyl]-, (Z)-[CAS] | 118288-08-7 169899-19-8 | EP | 282077 | Antiulcer | Ulcer, gastric |
| Lamifiban | | 144412-49-7 | | | | |
| lamivudine | 2(1H)-Pyrimidinone, 4-amino-1-[2-(hydroxymethyl)-1,3-oxathiolan-5-yl]-, (2R-cis)-[CAS] | 134678-17-4 | EP | 51397 | Antiviral, anti-HIV | Infection, HIV/AIDS |
| lamotrigine | 1,2,4-Triazine-3,5-diamine, 6-(2,3-dichlorophenyl)-[CAS] | 84057-84-1 | EP | 21121 | Antiepileptic | Epilepsy, partial (focal, local) |
| landiolol | Benzenepropanoic acid, 4-[2-hydroxy-3-[[2-(4-morpholinylcarbonyl)amino]ethyl]amino]-propoxy]-, (2,2-dimethyl-1,3-dioxolan-4-yl)methyl ester, [S-(R*,R*)]-HCL | 133242-30-5 | EP | 397031 | Antiarrhythmic | Tachycardia, general |
| lanicemine | (S)-Alpha-phenyl-2-pyridine ethanamine dihydrochloride | 153322-05-5 | | | Neurological | Unspecified |
| laniquidar | Methyl 6,11-dihydro-11-[1-[2-[4-(-2-quinolylmethoxy)phenyl]ethyl]-4-piperidinylidene]-5H-imidazo[2,1-b][3]benzazepine-3-carboxylate | 197509-46-9 | WO | 9734897 | Radio/chemosensitizer | Cancer, general |
| lanoconazole | 1H-Imidazole-1-acetonitrile, Alpha-[4-(2-chlorophenyl)-1,3-dithiolan-2-ylidene]-, (E)-(±)-[CAS] | 101530-10-3 | U.S. | 4,738,976 | Antifungal | Infection, fungal, general |
| Lanoteplase | | 171870-23-8 | | | | |
| Lanreotide | | 108736-35-2 | | | | |
| lansoprazole | 1H-Benzimidazole, 2-[[(3-methyl-4-(2,2,2-trifluoroethoxy)-2-pyridyl]methyl]sulfinyl]- [CAS] | 103577-45-3 | EP | 174726 | Antiulcer | Ulcer, duodenal |
| lanthanum carbonate | Carbonic acid, lanthanum(3+) salt (3:2)[CAS] | 587-26-8 | U.S. | 5,968,976 | Urological | Hyperphosphataemia |
| lapatinib | 4-Quinazolinamine, N-[3-chloro-4-[(3-fluorobenzyl)methoxy phenyl]-6-[5-[[[2-[methylsulfonyl]ethyl]amino]methyl]furan-2-yl] | 388082-78-8 | | | Anticancer, other | Cancer, breast |
| laquinimod | | 248281-84-7 | | | Multiple sclerosis treatment | Multiple sclerosis, general |

TABLE IV-continued

| API Generic Name | API Chemical Name | CAS No. | Patent Reference | | Example of Therapeutic Use | Example of Indication |
|---|---|---|---|---|---|---|
| lasofoxifene | 2-Naphthalenol, 5,6,7,8-tetrahydro-6-phenyl-5-(4-(2-(1-pyrrolidinyl)ethoxy)phenyl-(5R-cis)-, (S-(R*,R*))-2,3-dihydroxybutanedioate [CAS] | 190791-29-8 | WO | 9716434 | Menopausal disorders | Hormone replacement therapy |
| latamoxef | 5-Oxa-1-azabicyclo[4.2.0]oct-2-ene-2-carboxylic acid, 7-[[carboxy(4-hydroxyphenyl)acetyl]amino]-7-methoxy-3-[[(1-methyl-1H-tetrazol-5-yl)thio]methyl]-8-oxo-[CAS] | 64952-97-2<br>64953-12-4 | GB | 1547351 | Beta-lactam antibiotic | Infection, general |
| latanoprost | 5-Heptenoic acid, 7-(3,5-dihydroxy-2-(3-hydroxy-5-phenylpentyl)cyclopentyl)-, 1-methylethyl ester, (1R-(1Alpha(Z),2β(R*),3Alpha,5Alpha))-[CAS] | 130209-82-4 | WO | 9002553 | Prostaglandin | Glaucoma |
| Lauroguadine | | | | | | |
| Laurolinium Acetate | | | | | | |
| Lawsone | | 135-43-3<br>146-37-2<br>83-72-7 | | | | |
| LAX-111 | | | | | Neuroleptic | Schizophrenia |
| | 1-(Z,Z,Z,Z,Z-eicosa-5,8,11,14,17-pentaenoyloxy)-3-(Z,Z,Z,Z,Z-eicosa-5,8,11,14,17-pentaenoyloxy)-propane | | | | | |
| Lazabemide | | | | | | |
| LB-30057 | Benzenecarboximidic acid, 4-[(2S)-3-(cyclopentylmethyl)amino)-2-[(2-naphthalenylsulfonyl)amino]-3-oxopropyl]-, hydrazide [CAS] | 103878-84-8 | WO | 9749673 | Antithrombotic | Thrombosis, venous |
| L-Cystine | | 7262-75-1 | | | | |
| Lefetamine | | | | | | |
| leflunomide | 4-Isoxazolecarboxamide, 5-methyl-N-[4-(trifluoromethyl)phenyl]-[CAS] | 75706-12-6 | EP | 13376 | Antiarthritic, immunological | Arthritis, rheumatoid |
| leflunomide | 4-Isoxazolecarboxamide, 5-methyl-N-[4-(trifluoromethyl)phenyl]-[CAS] | 104981-93-3<br>75706-12-6 | U.S. | 5,610,173 | Anticancer, other | Cancer, ovarian |
| Leiopyrrole | | 5633-16-9 | | | | |
| lenampicillin | 4-Thia-1-azabicyclo[3.2.0]heptane-2-carboxylic acid, 6-[(aminophenylacetyl)amino]-3,3-dimethyl-7-oxo-, (5-methyl-2-oxo-1,3-dioxol-4-yl)methyl ester, [2S-[2Alpha,5Alpha,6β(S*)]]-[CAS] | 80734-02-7<br>86273-18-9 | EP | 61206 | Penicillin, oral | Infection, general |
| lentinan | Lentinan [CAS] | 37339-90-5 | | | Anticancer, immunological | Cancer, stomach |
| Lepirudin | | | | | | |
| lercanidipine | 3,5-Pyridinedicarboxylic acid, 1,4-dihydro-2,6-dimethyl-4-(3-nitrophenyl)-, 2-[(3,3-diphenylpropyl)methylamino]-1,1-dimethylethyl methyl ester-, hydrochloride [CAS] | 100427-26-7<br>132866-11-6 | U.S. | 4,705,797 | Antihypertenzive, other | Hypertension, general |
| lerisetron | 1H-Benzimidazole, 1-(phenylmethyl)-2-(1-piperazinyl)-[CAS] | 143257-98-1 | U.S. | 5,256,665 | Antimetic | Nausea and vomiting, general |

TABLE IV-continued

| API Generic Name | API Chemical Name | CAS No. | Patent Reference | | Example of Therapeutic Use | Example of Indication |
|---|---|---|---|---|---|---|
| Lesopitron | | 132449-46-8 | | | | |
| leteprinim | Benzoic acid, 4-((3-(1,6-dihydro-6-oxo-9H-purin-9-yl)-1-oxopropyl)amino)-, monopotassium salt [CAS] | 138117-50-7 | U.S. | 6,338,963 | Antiparkinsonian | Parkinson's disease |
| letosteine | 4-Thiazolidinecarboxylic acid, 2-[2-(2-ethoxy-2-oxoethyl)thio]ethyl]-[CAS] | 53943-88-7 | U.S. | 4,032,534 | COPD treatment | Bronchitis, chronic |
| letrozole | Benzonitrile, 4,4'-(1H-1,2,4-triazol-1-ylmethylene)bis-[CAS] | 112809-51-5 | EP | 236940 | Anticancer, hormonal | Cancer, breast |
| Leucocyanidin | | 480-17-1 | | | | |
| Leuprolide | | 53714-56-0 | | | | |
| leuprolide acetate | Luteinizing hormone-releasing factor (pig), 6-D-leucine-9-(N-ethyl-L-prolinamide)-10-deglycinamide-, monoacetate (salt) [CAS] | 53714-56-0 74381-53-6 | | | Formulation, implant | Cancer, prostate |
| leuprorelin | Luteinizing hormone-releasing factor (pig), 6-D-leucine-9-(N-ethyl-L-prolinamide)-10-deglycinamide-, [CAS] | 53714-56-0 | | | Formulation, implant | Cancer, prostate |
| Levallorphan | | 152-02-3 | | | | |
| levamisole | Imidazo[2,1-b]thiazole, 2,3,5,6-tetrahydro-6-phenyl-, (S)-[CAS] | 14769-73-4 16895-80-5 | U.S. | 4,584,305 | Anthelmintic | Infection, helminth, general |
| Levcromakalim | | 94535-50-9 | | | | |
| levetiracetam | 1-Pyrrolidineacetamide, Alpha-ethyl-2-oxo-, (S)-[CAS] | 102767-28-2 | EP | 162036 | Antiepileptic | Epilepsy, general |
| levobetaxolol | 2-Propanol, 1-(4-(2-(cyclopropylmethoxy)ethyl)phenoxy)-3-((1-methylethyl)amino) hydrochloride [CAS] | 116209-55-3 | | | Formulation, mucosal, topical | Glaucoma |
| levobunolol | 1(2H)-Naphthalenone, 5-[3-[(1,1-dimethylethyl)amino]-2-hydroxypropoxy]-3,4-dihydro-, (S)-[CAS] | 279112-14-7 47141-42-4 | U.S. | 3,641,152 | Formulation, mucosal, topical | Glaucoma |
| levobupivacaine | 2-Piperidinecarboxamide, 1-butyl-N-(2,6-dimethylphenyl)-, (S)-[CAS] | 27262-47-1 | WO | 9510276 | Anaesthetic, injectable | Anaesthesia |
| levocabastine | 4-Piperidinecarboxylic acid, 1-[4-cyano-4-(4-fluorophenyl)cyclohexyl]-3-methyl-4-phenyl-, [3S-[1(cis),3Alpha,4β]]-[CAS] | 79449-98-2 79516-68-0 79547-78-7 | U.S. | 4,369,184 | Antiallergic, non-asthma | Rhinitis, allergic, general |
| levocetirizine | Acetic acid, (2-(4-((4-chlorophenyl)phenylmethyl)-1-piperazinyl)ethoxy)-, (R)-[CAS] | 130018-77-8 | WO | 9406429 | Antiallergic, non-asthma | Allergy, general |
| Levodopa | | 59-92-7 | | | | |
| levodropropizine | 1,2-Propanediol, 3-(4-phenyl-1-piperazinyl)-, (S)-[CAS] | 99291-25-5 | EP | 147847 | Antitussive | Cough |
| levofloxacin | 7H-Pyrido[1,2,3-de]-1,4-benzoxazine-6-carboxylic acid, 9-fluoro-2,3-dihydro-3-methyl-10-(4-methyl-1-piperazinyl)-7-oxo-, (S)-[CAS] | 100986-85-4 138199-71-0 | EP | 206283 | Quinolone antibacterial | Infection, respiratory tract, lower |
| Levomethadyl Acetate | | 1477-40-3 | | | | |
| levomoprolol | 2-Propanol, 1-(2-methoxyphenoxy)-3-((1-methylethyl)amino]-, (S)-[CAS] | 27058-84-0 5741-22-0 | EP | 15418 | Antihypertensive, adrenergic | |
| levonorgestrel | 18,19-Dinopregn-4-en-20-yn-3-one, 13-ethyl-17-hydroxy-, (17Alpha)-[CAS] | 77164-20-6 797-63-7 | | | Formulation, implant | Contraceptive, female |

TABLE IV-continued

| API Generic Name | API Chemical Name | CAS No. | Patent Reference | Example of Therapeutic Use | Example of Indication |
|---|---|---|---|---|---|
| Levophacetoperane | | | | | |
| Levopropoxyphene | | | | | |
| Levorphanol | | 24558-01-8 | | | |
| | | 2338-37-6 | | | |
| | | 77-07-6 | | | |
| levosimendan | Propanedinitrile, [[4-(1,4,5,6-tetrahydro-4-methyl-6-oxo-3-pyridazinyl)phenyl]hydrazono]-, (R)-[CAS] | 131741-08-7 141505-33-1 | EP 383449 | Cardiostimulant | Heart failure |
| levosulpride | Benzamide, 5-(aminosulfonyl)-N-[(1-ethyl-2-pyrrolidinyl)methyl]-2-methoxy-, (S)-[CAS] | 23672-07-3 | GB 2014990 | Antiemetic | Dyspepsia |
| Levothyroxine | | | | | |
| levovirin | 1-β-L-ribofuranosyl-1,2,4-triazole-3-carboxamide | | | Antiviral, other | Infection, hepatitis-C virus |
| lexipafant | L-Leucine, N-methyl-N-[[4-[(2-methyl-1H-imidazo[4,5-c]pyridin-1-yl)methyl]phenyl]sulfonyl]-, ethyl ester-[CAS] | 139133-26-9 | WO 9203423 | Neurological | Dementia, AIDS-related |
| LF-15-0195 | | | WO 9624579 | Immunosuppressant | Lupus erythematosus, general |
| LF-16-0687 | 2-Pyrrolidinecarboxamide, N-[3-[[4-(aminoiminomethyl)benzoyl]amino]propyl]-1-[[(2,4-dichloro-3-[[(2,4-dimethyl-8-quinolinyl)oxy]methyl]phenyl]sulfonyl]-, (2S)-[CAS] | 209733-45-9 | FR 2756562 | Neuroprotective | Head trauma |
| LGD-1550 | 2,4,6-Octatrienoic acid, 7-(3,5-bis(1,1-dimethylethyl)phenyl)-3-methyl-(2E,4E,6E)-[CAS] | 178600-20-9 | | Anticancer, other | Cancer, cervical |
| LH | | 902-67-9 | | | |
| LH-RH | | 934-40-6 | | | |
| liarozote | 1H-Benzimidazole, 5-[(3-chlorophenyl)-1H-imidazol-1-ylmethyl]-[CAS] | 115575-11-6 | | Formulation, other | Psoriasis |
| licofelone | 1H-Pyrrolizine-5-acetic acid, 6-(4-chlorophenyl)-2,3-dihydro-2,2-dimethyl-7-phenyl-[CAS] | 156897-06-2 | | Antiarthritic, other | Arthritis, osteo |
| Licostinel | | 153504-81-5 | | | |
| lidadronate | Phosphonic acid, [1-amino-3-(dimethylamino)propylidene]bis-[CAS] | 63132-38-7 | WO 9702827 | Urological | Unspecified |
| Lidamidine | | 66871-56-5 | | | |
| lidocaine | Acetamide, 2-(diethylamino)-N-(2,6-dimethylphenyl)-[CAS] | 137-58-6 | | Formulation, transdermal, patch | Pain, post-herpetic |
| Lidofenin | | 59160-29-1 | | | |
| Lidoflazine | | 3416-26-0 | | | |
| limaprost | Prosta-2,13-dien-1-oic acid, 11,15-dihydroxy-17,20-dimethyl-9-oxo-,(2E,11Alpha,13E,15S,17S)-,[CAS] | 74397-12-9 | GB 2041368 | Prostaglandin | Buerger's syndrome |
| Lincomycin | | 154-21-2 | | | |
| Lindan | | 58-89-9 | | | |

TABLE IV-continued

| API Generic Name | API Chemical Name | CAS No. | Patent Reference | | Example of Therapeutic Use | Example of Indication |
|---|---|---|---|---|---|---|
| linezolid | Acetamide, N-((3-(3-fluoro-4-(4-morpholinyl)phenyl)-2-oxo-5-oxazolidinyl)methyl)-, (S)-[CAS] | 165800-03-3 | WO | 9507271 | Antibiotic, other | Infection, dermatological |
| Linoleic Acid | | 60-33-3 | | | | |
| Linolenic Acid | | 463-40-1 | | | | |
| Liothyronine | | 6893023 | | | | |
| Lipase | | 9001-62-1 | | | | |
| Lipo-dexamethasone | Pregna-1,4-diene-3,20-dione, 9-fluoro-11,17-dihydroxy-16-methyl-21-[(1-oxohexadecyl)oxy]-, (11β,16Alpha)-[CAS] | 14899-36-6 | | | Formulation, optimized, microemulsion | Arthritis, rheumatoid |
| lipo-flurbiprofen | [1,1'-Biphenyl]-4-acetic acid, 2-fluoro-Alpha-methyl-, 1-(acetyloxy)ethyl ester [CAS] | 91503-79-6 | JP | 60208910 | Formulation, optimized, microemulsion | Pain, cancer |
| Lipogel HA | | | EP | 525655 | Formulation, optimized, liposomes | Unspecified |
| LiquiVent | perfluorooctylbromide | 423-55-2 | U.S. | 5,437,272 | Lung Surfactant | Respiratory distress syndrome, adult |
| liranaftate | Carbamothioic acid, (6-methoxy-2-pyridinyl)methyl-, O-(5,6,7,8-tetrahydro-2-naphthalenyl) ester [CAS] | 88678-31-3 | GB | 2124617 | Antifungal | Infection, dermatological |
| lisinopril | L-Proline, 1-[N2-(1-carboxy-3-phenylpropyl)-L-lysyl]-, (S)-[CAS] | 76547-98-3 83915-83-7 100324-81-0 | EP | 12401 | Antihypertensive, renin system | Hypertension, general |
| Lisofylline | | | | | | |
| lisuride | Urea, N'-[(8Alpha)-9,10-didehydro-6-methylergolin-8-yl]-N,N-diethyl-, [CAS] | 19875-60-8 305-13-5 18016-80-3 | | | Antiprolactin | Acromegaly |
| Lithium Citrate lithium | Carbonic acid, dilithium salt [CAS] | 919-16-4 554-13-2 | | | Formulation, modified-release, <=24 hr | Depression, bipolar |
| lixivaptan | Benzamide, N-[3-chloro-4-(5H-pyrrolo[2,1-c][1,4]benzodiazepin-10(11H)-ylcarbonyl)phenyl]-5-fluoro-2-methyl-[CAS] | 168079-32-1 | U.S. | 5,736,540 | Cardiovascular | Heart failure |
| LJP-1082 | | | U.S. | 6,207,160 | Immunosuppressant | Thrombosis, venous |
| LLUAlpha | | | | | Antihypertensive, other | Hypertension, general |
| LMP-160 | | | U.S. | 5,643,893 | Antiasthma | Asthma |
| LMP-420 | | | U.S. | 5,643,893 | Antiarthritic, other | Arthritis, |
| lobaplatin | Platinum, (1,2-cyclobutanedimethanamine-N,N')[2-hydroxypropanoato(2-)-O1,O2]-, [SP-4-3-(S)(trans)]-[CAS] | 135558-11-1 | DE | 4115559 | Anticancer, alkylating | Cancer, lung, small cell |
| Lobeline | | 90-69-7 | | | | |
| Lobenzarit | | 63329-53-3 | | | | |

TABLE IV-continued

| API Generic Name | API Chemical Name | CAS No. | Patent Reference | | Example of Therapeutic Use | Example of Indication |
|---|---|---|---|---|---|---|
| Iodoxamide | 2,2'-((2-chloro-5-cyano-1,3-phenylene)diimino)bis(2-oxoacetate)-2-amino-2-(hydroxymethyl)-1,3-propanediol (1:2) | 63610-09-3 53882-12-5 | U.S. | 4,439,445 | Antiasthma | Asthma |
| Lofentanil | | 61380-40-3 | | | | |
| lofepramine | Ethanone, 1-(4-chlorophenyl)-2-[[3-(10,11-dihydro-5H-dibenz[b,f]azepin-5-yl)propyl]methylamino]-[CAS] | 23047-25-8 26786-32-3 | GB | 1177525 | Antidepressant | |
| lofexidine | 1H-Imidazole, 2-[1-(2,6-dichlorophenoxy)ethyl]-4,5-dihydro-[CAS] | 31036-80-3 | GB | 1181356 | Antihypertensive, adrenergic | Hypertension, general |
| Loflucarban | | 790-69-2 | | | | |
| lomefloxacin | 3-Quinolinecarboxylic acid, 1-ethyl-6,8-difluoro-1,4-dihydro-7-(3-methyl-1-piperazinyl)-4-oxo-[CAS] | 98079-51-7 98079-52-8 | EP | 140116 | Quinolone antibacterial | Infection, respiratory tract, lower |
| lomerizine | Piperazine, 1-[bis(4-fluorophenyl)methyl]-4-[(2,3,4-trimethoxyphenyl)methyl]-, [CAS] | 101477-54-7 101477-55-8 | EP | 159566 | Antimigraine | Migraine |
| lomifylline | 7-(5-oxohexyl)theophylline | 10226-54-7 | DE | 2207860 | Neurological | |
| lomustine | Urea, N-(2-chloroethyl)-N'-cyclohexyl-N-nitroso-[CAS] | 13010-47-4 | JP | 48075526 | Anticancer, alkylating | |
| lonafarnib | 1-Piperidinecarboxamide, 4-[2-[4-[(11R)-3,10-dibromo-8-chloro-6,11-dihydro-5H-benzo[5,6]cyclohepta[1,2-b]pyridin-11-yl]-1-piperidinyl]-2-oxoethyl]-[CAS] | 193275-84-2 | U.S. | 5,874,442 | Anticancer, other | Cancer, lung, non-small cell |
| Lonapalene | | 91431-42-4 | | | | |
| Lonazolac | | 53808-88-1 | | | | |
| lonidamine | 1H-Indazole-3-carboxylic acid, 1-[(2,4-dichlorophenyl)methyl]-[CAS] | 50264-69-2 | DE | 2310031 | Radio/chemosensitizer | Cancer, breast |
| loperamide | 4-(p-chlorophenyl)-4-hydroxy-N,N-dimethyl-Alpha,Alpha-diphenyl-1-piperidine butyramide HCl | 34552-83-5 53179-11-6 | U.S. | 3,714,159 | Antidiarrhoeal | Diarrhoea, general |
| loperamide oxide | 1-Piperidinebutanamide, 4-(4-chlorophenyl)-4-hydroxy-N,N-dimethyl-Alpha,Alpha-diphenyl-, 1-oxide, trans-[CAS] | 106900-12-3 | EP | 219898 | Antidiarrhoeal | Diarrhoea, general |
| loprazolam | 1H-Imidazo[1,2-a][1,4]benzodiazepin-1-one, 6-(2-chlorophenyl)-2,4-dihydro-2-[(4-methyl-1-piperazinyl)methylene]-8-nitro-[CAS] | 61197-73-7 61197-93-1 70111-54-5 | GB | 1496426 | Hypnotic/Sedative | |
| Loprinone loracarbef | 1-Azabicyclo[4.2.0]oct-2-ene-2-carboxylic acid, 7-[(aminophenylacetyl)amino]-3-chloro-8-oxo-, [6R-[6Alpha,7β(R*)]]-[CAS] | 106730-54-5 76470-66-1 121961-22-6 | EP | 14475 | Cephalosporin, oral | Infection, respiratory tract, lower |
| Lorajmine loratadine | 1-Piperidinecarboxylic acid, 4-(8-chloro-5,6-dihydro-11H-benzo[5,6]cyclohepta[1,2-b]pyridin-11-ylidene)-, ethyl ester-[CAS] | 47562-08-3 79794-75-5 | EP | 42544 | Antiallergic, non-asthma | Rhinitis, allergic, general |
| lorazepam | 2H-1,4-Benzodiazepin-2-one, 7-chloro-5-(2-chlorophenyl)-1,3-dihydro-3-hydroxy- | 846-49-1 | | | Formulation, oral, orally-disintegrating | Epilepsy, general |
| lorcainide | Benzeneacetamide, N-(4-chlorophenyl)-N-[1-(1-methylethyl)-4-piperidinyl]-[CAS] | 58934-46-6 59729-31-6 | DE | 2642856 | Antiarrhythmic | |

TABLE IV-continued

| API Generic Name | API Chemical Name | CAS No. | Patent Reference | | Example of Therapeutic Use | Example of Indication |
|---|---|---|---|---|---|---|
| lormetazepam | 2H-1,4-Benzodiazepin-2-one, 7-chloro-5-(2-chlorophenyl)-1,3-dihydro-3-hydroxy-1-methyl-[CAS] | 848-75-9 | U.S. | 3,296,249 | Hypnotic/Sedative | Insomnia |
| lornoxicam | 2H-Thieno[2,3-e]-1,2-thiazine-3-carboxamide, 6-chloro-4-hydroxy-2-methyl-N-2-pyridinyl-, 1,1-dioxide-[CAS] | 70374-39-9 | EP | 313935 | Analgesic, NSAID | Pain, post-operative |
| losartan | 1H-Imidazole-5-methanol, 2-butyl-4-chloro-1-[[2'-(1H-tetrazol-5-yl)[1,1'-biphenyl]-4-yl]methyl]-, [CAS] | 124750-99-8 114798-26-4 | EP | 253310 | Antihypertensive, renin system | Hypertension, general |
| loteprednol | Androsta-1,4-diene-17-carboxylic acid, 17-[(ethoxycarbonyl)oxy]-11-hydroxy-3-oxo-, chloromethyl ester, (11β,17Alpha)-[CAS] | 82034-46-6 | GB | 2079755 | Anti-inflammatory, topical | Uveitis |
| Lotrafiban Lovastatin Loxapine | | 171049-14-2 75330-75-5 10/02/1977 | | | | |
| loxiglumide | Pentanoic acid, 4-[(3,4-dichlorobenzoyl)amino]-[(3-methoxypropyl)pentylamino]-5-oxo-, (±)-[CAS] | 107097-80-3 | WO | 8703869 | GI inflammatory/bowel disorders | Pancreatitis |
| loxoprofen | Benzeneacetic acid, Alpha-methyl-4-[(2-oxocyclopentyl)methyl]-[CAS] | 68767-14-6 80382-23-6 87828-36-2 | EP | 55588 | Antiarthritic, other | Arthritis, rheumatoid |
| Lu-35-138 | 1-[3[[2-[5-chloro-1-(4-fluorophenyl)-3-1H-indolyl]ethyl]methylamino]propyl]-2-imidazolidinone hydrochloride | | WO | 9516684 | Neuroleptic | Psychosis, general |
| Lubeluzole lubiprostone | (−)-7-[(2R,4aR,5R,7aR)-2-(1,1-difluoropentyl)-2-hydroxy-6-oxooctahydrocyclopenta[b]pyran-5-yl]heptanoic acid | 144665-07-6 136790-76-6 | | | Laxative | Constipation |
| lucanthone | Thioxanthen-9-one, 1-((2-(diethylamino)ethyl)amino)-4-methyl-[CAS] | 479-50-5 | | | Radio/chemosensitizer | Cancer, brain |
| Lucanthone Lumefantrine lumiracoxib | Benzeneacetic acid, 2-((2-chloro-6-fluorophenyl)amino)-5-methyl-[CAS] | 548-57-2 82186-77-4 220991-20-8 | | | Analgesic, NSAID | Pain, general |
| lurtotecan | 11H-1,4-Dioxino[2,3-g]pyrano[3',4':6,7]indolizino[1,2-b]quinoline 9,12-[8H,14H]-dione, 8-ethyl-2,3-dihydro-8-hydroxy-15-[[4-methyl-1-piperazinyl]methyl]-, [CAS] | 155773-58-3 | | | Formulation, optimized, lipocomes | Cancer, ovarian |
| lutetium texaphyrin | Lutetium, bis(acetato-O)[9,10-diethyl-20,21-bis-[2-[2-methoxyethoxy)ethoxy]-4,15-dimethyl-8,11-imino-3,6,16,13-dinitrilo-1,18-benzodiazacycloeicosine-5,14-dipropanolato-N1,N18,N23,N24,N25]-, (PB 7-11-23324)-[CAS] | 156436-90-7 | WO | 9906411 | Radio/chemosensitizer | Athero-sclerosis |
| IV-216 | Zinc[2-(2,6-dichloroanilinophenyl]acetate | | | | Anti-inflammatory | Arthritis, rheumatoid |

TABLE IV-continued

| API Generic Name | API Chemical Name | CAS No. | Patent Reference | Example of Therapeutic Use | Example of Indication |
|---|---|---|---|---|---|
| LX-104 | Hexadecanamide, N-[4-[[2-[2-[[O-(N-acetyl-Alpha-neuraminosyl)-(2-3)-O-β-D-galactopyranosyl-(1-4)-O-[6-deoxy-Alpha-L-galactopyranosyl]oxy]ethoxy]ethoxy]methyl]phenyl]-2-tetradecyl-[CAS] | 158792-45-1 | | Cognition enhancer | Dementia, senile, general |
| LY-156735 | β-methyl-6-chloromelatonin | | EP 655243 | Hypnotic/Sedative | Sleep disorder, general |
| LY-293111 | Benzoic acid, 2-[3-[3-[(5-ethyl-4'-fluoro-2-hydroxy[1,1'-biphenyl]-4-yl)oxy]propoxy]-2-propylphenoxy]-[CAS] | 161172-51-6 | | Anticancer, other | Cancer, melanoma |
| LY-293558 | 3-Isoquinolinecarboxylic acid, decahydro-6-[2-(1H-tetrazol-5-yl)ethyl]-, [3S-(3Alpha.,4aAlpha.6β,8aAlpha.)]-[CAS] | 154652-83-2 | | Anticancer, other | Pain, neuropathic |
| LY-355703 | 1,4-Dioxa-8,11-diazacyclohexadec-13-ene-2,5,9,12-tetrone, 10-[(3-chloro-4-methoxyphenyl)methyl]-6,6-dimethyl-3-(2-methylpropyl)-16-[(1S)-1-[(2S,3R)-3-phenyloxiranyl]ethyl]-, (3S,10R,13E,16S)-[CAS] | 18256-67-7 | WO 9707798 | Anticancer, other | Cancer, lung, non-small cell |
| Lyapolate | | 25053-27-4 | | | |
| Lymecycline | | 992-21-2 | | | |
| Lynestrenol | | 52-76-6 | | | |
| Lypressin | | 50-57-7 | | | |
| Lysine Acetylsalicylate | | 62952-06-1 | WO 9624331 | Analgesic, NSAID | Diagnostic, cancer |
| lysine salicylate | L-Lysine, 2-hydroxybenzoate [CAS] | 59535-08-9 | WO 9843093 | Diagnostic | |
| lysophospholipids | | | | | |
| M-40403 | Dichloro[(4aR,13aR,17aR,21aR)-1,2,3,4,4a,5,6,12,13a,14,15,16,17,17a,18,19,20,21,21a-eicosahydro-1,7-nitrilo-7H-dibenzo[b,h][1,4,7,10]tetraazacyclo-heptadecine-kappaN5,kappaN13,kappaN18,kappaN21,kappaN22]manganese | | U.S. 6,180,620 | Anticancer, other | Unspecified |
| mabuprofen | Benzeneacetamide, N-(2-hydroxyethyl)-Alpha-methyl-4-(2-methylpropyl)-, (+/-)-[CAS] | 82821-47-4 | DE 3121595 | Anti-inflammatory | |
| Mabuterol | | 56341-08-3 | | | |
| Macrophage Colony-Stimulating Factor | | 81627-83-0 | | | |
| MADU | | 840-50-6 | | | |
| mafenide | Benzenesulfonamide, 4-(aminomethyl)-monoacetate [CAS] | 13009-99-9 138-39-6 | | Vulnerary | Burns |
| mafosfamide | Ethanesulfonic acid, 2-[[2-[bis(2-chloroethyl)amino]tetrahydro-2H-1,3,2-oxazaphosphorin-4-yl]thio]-, P-oxide, cis-(±)-[CAS] | 88859-04-5 98845-64-8 | EP 393575 | Anticancer, alkylating | Cancer, renal |
| magaldrate | Aluminum magnesium hydroxide sulfate (Al5Mg10(OH)31(SO4)2), hydrate [CAS] | 74978-16-8 | U.S. 2,923,660 | Antacid/Antiflatulent | |
| Magenta I | | 632-99-5 | | | |

TABLE IV-continued

| API Generic Name | API Chemical Name | CAS No. | Patent Reference | Example of Therapeutic Use | Example of Indication |
|---|---|---|---|---|---|
| Magnesium Acetylsalicylate | | 132-49-0 | | | |
| Magnesium Carbonate Hydroxid | | 39409-82-0 | | | |
| magnesium chloride | Magnesium chloride (MgCl2) [CAS] | 7786-30-3 | | Formulation, oral, enteric-coated | Nutrition |
| Magnesium Citrate | | 3344-18-1 | | | |
| magnesium gluconate | D-Gluconic acid, magnesium salt (2:1) [CAS] | 3632-91-5 | | Formulation, other | Hypertension, general |
| Magnesium Lactate | | 18917-93-6 | | | |
| Magnesium Salicylate | | 18917-89-0 | | | |
| Malathion | | 121-75-5 | | | |
| Malotilate | | 59937-28-9 | | | |
| Mandelic Acid | | 90-64-2 | | | |
| Mandelic Acid Isoamyl Ester | | 5421045 | | | |
| Mangafodipir | | 118248-94-5 (free acid); 155319-91-8 (hexa-hydrogen) | | | |
| manidipine | 3,5-Pyridinedicarboxylic acid, 1,4-dihydro-2,6-dimethyl-4-(3-nitrophenyl)-, 2-[4-(diphenylmethyl)-1-piperazinyl]ethyl methyl ester [CAS] | 89226-50-6 89226-75-5 | EP 94159 | Antihypertensive, other | Hypertension, general |
| Mannomustine | | | | | |
| mannose-6-phosphate | mannose-6-phosphate | 551-74-6 | | Vulnerary | Wound healing |
| Maprotilline | | | | | |
| maribavir | 1H-Benzimidazol-2-amine, 5,6-dichloro-N-(1-methylethyl)-1-β-L-ribofuranosyl-[CAS] | 10262-69-8 176161-24-3 | | Antiviral, other | Infection, cytomegalo-virus |
| marimastat | N-[2,2-Dimethyl-α(S)-(N-methylcarbamoyl)propyl]-N,3(S)-dihydroxy-2(R)-isobutylsuccinamide | 154039-60-8 | WO 9402447 | Anticancer, other | Cancer, pancreatic |
| maxacalcitol | 1,3-Cyclohexanediol, 4-methylene-5-(2-(octahydro-1-(1-(3-hydroxy-3-methylbutoxy)ethyl)-7a-methyl-4H-inden-4-ylidene)ethylidene)-, (1S-(1Alpha(R*),3aβ,4E(1S*,3R*,5Z),7aAlpha))-[CAS] | 103909-75-7 | U.S. 4,891,364 | Hormone | Hyperpara-thyroidism |
| mazindol | 3H-Imidazo[2,1-a]isoindol-5-ol, 5-(4-chlorophenyl)-2,5-dihydro-[CAS] | 22232-71-9 | U.S. 3,763,178 | Anorectic/Antiobesity | Obesity |
| Mazipredone | | | | | |
| MCC-5723 | | 13085-08-0 | | | |
| MCC-478 | (2-amino-6-(4-methoxyphenylthio)-9-[2-(phosphonomethoxy)ethyl]purine bis(2,2,2-trifluoroethyl)ester) | | U.S. 6,043,259 | Cardiovascular Antiviral, other | Unspecified Infection, hepatitis-B virus |
| MCI-154 | 3(2H)-Pyridazinone, 4,5-dihydro-6-[4-(4-pyridinylamino)phenyl]-, monohydrochloride [CAS] | 98326-32-0 98326-33-1 | EP 145019 | Cardiostimulant | Heart failure |

TABLE IV-continued

| API Generic Name | API Chemical Name | CAS No. | Patent Reference | Example of Therapeutic Use | Example of Indication |
|---|---|---|---|---|---|
| m-Cresyl Acetate | | 122-46-3 | | | |
| MDAM | Gamma-Methylene-10-deazaaminopterin | | | Anticancer, antimetabolite | Cancer, general |
| MDI-101 | | 403849-94-5 | U.S. 4,885,311 | Antiacne | Acne |
| MDI-403 | | 139290-65-6 | U.S. 4,677,120 | Antiacne | Acne |
| MDL-100907 | 4-Piperidinemethanol, Alpha-(2,3-dimethoxyphenyl)-1-(2-(4-fluorophenyl)ethyl)-, (R)-[CAS] | | | Hypnotic/Sedative | Sleep disorder, general |
| mebendazole | methyl-5-benzoylbenzimidazole-2-carbamate | 31431-39-7 | GB 1307306 | Anthelmintic | |
| mebeverine | Benzoic acid, 3,4-dimethoxy-, 4-[ethyl[2-(4-methoxyphenyl)-1-methylethyl]amino]butyl ester [CAS] | 3625-06-7 | | Antispasmodic | Irritable bowel syndrome |
| Mebhydroline | | 524-81-2 | | | |
| Mebrofenin | | 78266-06-5 | | | |
| Mebutamate | | 64-55-1 | | | |
| mecamylamine | Bicyclo(2.2.1)heptan-2-amine, N,2,3,3-tetramethyl-[CAS] | 60-40-2 | | Neurological | Unspecified |
| Mechlorethamine | | 51-75-2 | | | |
| Mechlorethamine Oxide | | 302-70-5 | | | |
| mecillinam | 4-Thia-1-azabicyclo[3.2.0]heptane-2-carboxylic acid, 6-[[(hexahydro-1H-azepin-1-yl)methylene]amino]-3,3-dimethyl-7-oxo-, [2S-(2Alpha,5Alpha,6.beta.)]-[CAS] | 32887-01-7 32887-03-9 | GB 1293590 | Penicillin, injectable | Infection, general |
| Meclizine | | 569-65-3 | | | |
| Meclocycline | | 2013-58-3 | | | |
| Mecloqualone | | 6385-02-0 | | | |
| meclofenamate | Benzoic acid, 2-[(2,6-dichloro-3-methylphenyl)amino]-, monosodium salt [CAS] | 644-62-2 | | Antiarthritic, other | Arthritis, osteo |
| Meclofenamic Acid | | 644-62-2 | | | |
| Meclofenoxate | | 51-68-3 | | | |
| Mecloqualone | | 340-57-8 | | | |
| Mecysteine | | 18598-63-5 | | | |
| Medazepam | | 12/06/2898 | | | |
| medifoxamine | Ethanamine, N,N-dimethyl-2,2-diphenoxy-[CAS] | 32359-34-5 | FR M5498 | Antidepressant | |
| Medrogestone | | 977-79-7 | | | |
| Medronic Acid | | 1984-15-2 | | | |
| medroxyprogesterone | Pregn-4-ene-3,20-dione, 17-(acetyloxy)-6-methyl-,(6Alpha) | 71-58-9 | | Formulation, fixed-dose combinations | Contraceptive, female |
| Medrysone | | 520-85-4 | | | |
| Mefenamic Acid | | 2668-66-8 | | | |
| Mefenorex | | 61-68-7 | | | |
| Mefexamide | | 17243-57-1 | | | |
| mefloquine | 4-Quinolinemethanol, Alpha-2-piperidinyl-2,8-bis(trifluoromethyl)-, (R*,S*)-(±)-[CAS] | 1227-61-8 51773-92-3 53230-10-7 69191-18-0 | GB 1594282 | Antimalarial | |
| Mefruside | | 7195-27-9 | | | |
| Megestrol | | 595-33-5 | | | |

TABLE IV-continued

| API Generic Name | API Chemical Name | CAS No. | Patent Reference | | Example of Therapeutic Use | Example of Indication |
|---|---|---|---|---|---|---|
| Meglumin | | 22154-43-4 131-49-7 | | | | |
| meglutol | 2-hydroxy-2-methyl-1,3-propandicarboxylic acid | 503-49-1 | U.S. | 3,629,449 | Hypolipaemic/ Antiatherosclerosis | Hyper-lipidaemia, general |
| melagatran | Glycine, N-[(1R)-2-[(2S)-2-[[[[4-(aminoiminomethyl)phenyl]methyl]amino]carbonyl]-1-azetidinyl]-1-cyclohexyl-2-oxoethyl]-[CAS] | 159776-70-2 | WO | 9616671 | Antithrombotic | Thrombosis, general |
| melanocortin-4 agonist | N-[(3R)-1,2,3,4-Tetrahydroisoquinolinium-3-ylcarbonyl]-(1R)-1-(4-chlorobenzyl)-2-[4-cyclohexyl-4-(1H-1,2,4-triazol-1-ylmethyl)piperidin-1-yl]-2-oxoethylamine(1) | | | | Anorectic/ Antiobesity | Obesity |
| Melarsoprol | | 494-79-1 | | | | |
| Melengestrol | | 5633-18-1 | | | | |
| melevodopa | Alanine, 3-(3,4-dihydroxyphenyl)-methylester [CAS] | 7101-51-1 | EP | 252290 | Antiparkinsonian | Parkinson's disease |
| Melinamide | | 14417-88-0 | | | | |
| Melitracen | | 5118-29-6 | | | | |
| meloxicam | 2H-1,2-Benzothiazine-3-carboxamide, 4-hydroxy-2-methyl-N-(5-methyl-2-thiazolyl)-, 1,1-dioxide-[CAS] | 71125-38-7 | U.S. | 4,233,299 | Antiarthritic, other | Arthritis, rheumatoid |
| melperone | 1-Butanone, 1-(4-fluorophenyl)-4-(4-methyl-1-piperidinyl)-[CAS] | 1622-79-3 3575-80-2 | BE | 651144 | Neuroleptic | |
| Melphalan | | 148-82-3 | | | | |
| meluadrine | Benzenemethanol, 2-chloro-Alpha-(((1,1-dimethylethyl)amino)methyl)-4-hydroxy-, (R)-, (R*, R*»)-2,3-dihydroxybutanedioate (1:1) (salt) [CAS] | 134865-37-5 | EP | 420120 | Labour inhibitor | Labour, preterm |
| memantine | Tricyclo[3.3.1.13,7]decan-1-amine, 3,5-dimethyl [CAS] | 41100-52-1 19982-08-2 | EP | 392059 | Cognition enhancer | Dementia, AIDS-related |
| MEN-10700 | Acetamide, 2-[[[(5R,6S)-6-[(1R)-1-hydroxyethyl]-2-methyl-7-oxo-4-thia-1-azabicyclo[3.2.0]hept-2-en-3-yl]methyl]methylamino]-[CAS] | 195874-55-6 | WO | 9406803 | Beta-lactam antibiotic | Infection, general |
| MEN-10755 | 5,12-Naphthacenedione, 7-[[4-O-(3-amino-2,3,6-trideoxy-Alpha-L-lyxo-hexopyranosyl)-2,6-dideoxy-Alpha-L-lyxo-hexopyranosyl]oxy]-7,8,9,10-tetrahydro-6,9,11-trihydroxy-9-(hydroxyacetyl)-, hydrochloride, (7S,9S)-[CAS] | 169317-77-5 | WO | 9509173 | Anticancer, antibiotic | Cancer, breast |
| Menadiol | | 481-85-6 | | | | |
| Menadione | | 58-27-5 | | | | |
| Menadoxime | | 573-01-3 | | | | |
| Menbutone | | 3562-99-0 | | | | |
| Menogaril | | 71628-96-1 | | | | |
| MENT | 7Alpha-Methyl-19-nortestosterone | | | | Formulation, transdermal, systemic | Contraceptive, male |
| menthol | Cyclohexanol, 5-methyl-2-(1-methlethyl)-[CAS] | 1490-04-6 89-78-1 | | | Formulation, dermal, topical | Pruritus |

TABLE IV-continued

| API Generic Name | API Chemical Name | CAS No. | Patent Reference | | Example of Therapeutic Use | Example of Indication |
|---|---|---|---|---|---|---|
| Menthyl Valerate | | 89-47-4 | | | | |
| Meobentine | | 46464-11-3 | | | | |
| Meparfynol | | 77-75-8 | | | | |
| mepartricin | Partricin, methyl ester [CAS] | 11121-32-7 | U.S. | 3,780,173 | Antifungal | Infection, Candida, general |
| Mepazine | | 60-89-9 | | | | |
| Mepenzolate Bromide | | 76-90-4 | | | | |
| Meperidine | | 57-42-1 | | | | |
| Mephenesin | | 59-47-2 | | | | |
| Mephenoxalone | | 70-07-5 | | | | |
| Mephentermine | | 100-92-5 | | | | |
| Mephenytoin | | 50-12-4 | | | | |
| Mephobarbital | | 115-38-8 | | | | |
| Mepindolol | | 23694-81-7 | | | | |
| Mepitiostane | | 21362-69-6 | | | | |
| mepivacaine | N-(2,6-Dimethylphenyl)-1-methyl-2-piperidinecarboxamide | 96-88-8 | | | Formulation, modified-release, >24 hr | Pain, post-operative |
| Mepixanox | | 17854-59-0 | | | | |
| Meprednisone | | 1247-42-3 | | | | |
| Meprobamate | | 57-53-4 | | | | |
| meproscillarin | Bufa-4,20,22-trienolide, 3-[(6-deoxy-4-O-methyl-Alpha-L-mannopyranosyl)oxy]-14-hydroxy-, (3β)-[CAS] | 33396-37-1 | DE | 1910207 | Cardiostimulant | Heart failure |
| meptazinol | Phenol, 3-(3-ethylhexahydro-1-methyl-1H-azepin-3-yl) [CAS] | 54340-58-8 59263-76-2 | GB | 1285025 | Analgesic, other | Pain, general |
| mequitazine | 10H-Phenothiazine, 10-(1-azabicyclo[2.2.2]oct-3-ylmethyl)-[CAS] | 29216-28-2 | GB | 1250534 | Antiallergic, non-asthma | |
| Meralein | | 4386-35-0 | | | | |
| Meralluride | | 8069-64-5 | | | | |
| Merbromin | | 129-16-8 | | | | |
| Mercaptomerin | | 21259-76-7 | | | | |
| Mercumallylic Acid | | 86-36-2 | | | | |
| Mercuric Chloride, Ammoniated | | 10124-48-8 | | | | |
| Mercuric Oleate | | 1191-80-6 | | | | |
| Mercuric Oxycyanide | | 1335-31-5 | | | | |
| merimepodib | Carbamic acid, ((3-(((3-methoxy-4-(5-oxazolyl)phenyl)amino)carbonyl)amino)-phenyl)methyl)-(3S)-tetrahydro-3-furanyl ester [CAS] | 198821-22-6 | U.S. | 5,807,878 | Antiviral, other | Infection, hepatitis-C virus |
| meropenem | 1-Azabicyclo[3.2.0]hept-2-ene-2-carboxylic acid, 3-[[5-[(dimethylamino)carbonyl]-3-pyrrolidinyl]thio]-6-(1-hydroxyethyl)-4-methyl-7-oxo-, [4R-[3(3S*,5S*),4Alpha,5β,6β(R*)]]-[CAS] | 96036-03-2 | EP | 126587 | Beta-lactam antibiotic | Infection, respiratory tract, lower |
| Mersalyl | | 492-18-2 | | | | |
| Mesalamine | | 89-57-6 | | | | |

TABLE IV-continued

| API Generic Name | API Chemical Name | CAS No. | Patent Reference | | Example of Therapeutic Use | Example of Indication |
|---|---|---|---|---|---|---|
| mesalazine | Benzoic acid, 5-amino-2-hydroxy-[CAS] | 89-57-6 | WO | 5541170 | Formulation, oral, other | Colitis, ulcerative |
| Mesna | | 19767-45-4 | | | | |
| Mesoridazine | | 5588-33-0 | | | | |
| Mestanolone | | 521-11-9 | | | | |
| Mesterolone | | 1424-00-6 | | | | |
| Mestranol | | 72-33-3 | | | | |
| Mesulfen | | 135-58-0 | | | | |
| Metaclazepam | | 84031-17-4 | | | | |
| Metampicillin | | 6489-97-0 | | | | |
| Metapramine | | 21730-16-5 | | | | |
| Metaproterenol | | 586-06-1 | | | | |
| Metaraminol | | 54-49-9 | | | | |
| Metazocine | | 3734-52-9 | | | | |
| metergoline | Carbamic acid, [[(8β)-1,6-dimethylergolin-8-yl]methyl]-, phenylmethyl ester [CAS] | 17692-51-2 21631-37-8 | GB | 1401935 | Antiprolactin | Amenorrhoea |
| metformin | Imidodicarbonimidic diamide, N,N-dimethyl [CAS] | 2706-42-5 657-24-9 | | | Formulation, modified-release, <=24 hr | Diabetes, Type II |
| Methacholine | | 62-51-1 | | | | |
| Methacycline | | 914-00-1 | | | | |
| Methadone | | 76-99-3 | | | | |
| Methafurylene | | 531-06-6 | | | | |
| Methamphetamine | | 537-46-2 | | | | |
| Methandriol | | 521-10-8 | | | | |
| Methandrostenolone | | 72-63-9 | | | | |
| Methantheline | | 53-46-3 | | | | |
| Methapyrilene | | 91-80-5 | | | | |
| Methaqualone | | 72-44-6 | | | | |
| Metharbital | | 50-11-3 | | | | |
| Methazolamide | | 554-57-4 | | | | |
| Methdilazine | | 1982-37-2 | | | | |
| Methenamine | | 100-97-0 | | | | |
| Methenolone | | 153-00-4 | | | | |
| Methestrol | | 130-73-4 | | | | |
| Methetoin | | 5696-06-0 | | | | |
| Methicillin | | 132-92-3 | | | | |
| Methimazole | | 60-56-0 | | | | |
| Methiodal | | 126-31-8 | | | | |
| Methionic Acid | | 503-40-2 | | | | |
| Methionine | | 63-68-3 | | | | |
| Methisazone | | 1910-68-5 | | | | |
| Methithural | | 467-43-6 | | | | |
| Methixene | | 02/02/4969 | | | | |
| Methocarbamol | | 532-03-6 | | | | |
| Methohexital | | 22151-68-4 | | | | |
| methotrexate | L-Glutamic acid, N-[4-[[(2,4-diamino-6-pteridinyl)methyl]methylamino]benzoyl]-[CAS] | 59-05-2 | U.S. | 2,512,572 | Anticancer, antimetabolite | Cancer, general |

TABLE IV-continued

| API Generic Name | API Chemical Name | CAS No. | Patent Reference | Example of Therapeutic Use | Example of Indication |
|---|---|---|---|---|---|
| Methotrimeprazine | | 60-99-1 | | | |
| Methoxamine | | 390-28-3 | | | |
| Methoxsalen | | 298-81-7 | | | |
| Methoxyflurane | | 76-38-0 | | | |
| Methoxyphenamine | | 93-30-1 | | | |
| Methoxypromazine | | 61-01-8 | | | |
| Methscopolamine | | 155-41-9 | | | |
| Methsuximide | | 77-41-8 | | | |
| Methyclothiazide | | 135-07-9 | | | |
| Methyl Blue | | 28983-56-4 | | | |
| Methyl Nicotinate | | 93-60-7 | | | |
| Methyl Propyl Ether | | 557-17-5 | | | |
| Methyl Salicylate | | 119-36-8 | | | |
| Methyl tert-Butyl Ether | | 1634-04-4 | | | |
| Methylbenzethonium Chloride | | 25155-18-4 | | | |
| Methylcobalamin | | 13422-55-4 | | | |
| methyldopa | L-Tyrosine, 3-hydroxy-Alpha-methyl-[CAS] | 555-30-6 | | Formulation, modified-release, <=24 hr | Hypertension, general |
| Methylene Blue | | 61-73-4 | | | |
| Methylergonovine | | 113-42-8 | | | |
| Methylhexaneamide | | 105-41-9 | | | |
| methylphenidate | 2-Piperidineacetic acid, Alpha-phenyl-, methyl ester [CAS] | 113-45-1 298-59-9 | | Formulation, modified-release, multi | Attention deficit disorder |
| Methylprednisolone | | 83-43-2 | | | |
| methylprednisolone aceponate | Pregna-1,4-diene-3,20-dione, 21-(acetyloxy)-11-hydroxy-6-methyl-17-(1-oxopropoxy)-, (6Alpha,11β)-[CAS] | 86401-95-8 | EP 72247 | Antipruritic/inflamm, allergic | Pruritus |
| methylprednisolone suleptanate | Pregna-1,4-diene-3,20-dione, 11,17-dihydroxy-6-methyl-21-[[8-[methyl(2-sulfoethyl)amino]-1,8-dioxooctyl]oxy]-, monosodium salt, (6Alpha,11β)-[CAS] | 90350-40-6 | JP 59137500 | Antiasthma | Asthma |
| Methylthiouracil | | 56-04-2 | | | |
| Methyltrienolone | | 965-93-5 | | | |
| Methyprylon | | 125-64-4 | | | |
| Methysergide | | 361-37-5 | | | |
| Metiazinic Acid | | 13993-65-2 | | | |
| metipranolol | Phenol, 4-[2-hydroxy-3-[(1-methylethyl)amino]propoxy]-2,3,6-trimethyl-, 1-acetate [CAS] | 22664-55-7 | GB 1206148 | Antihypertensive, adrenergic | |
| metoclopramide | Benzamide, 4-amino-5-chloro-N-[2-(diethylamino)ethyl]-2-methoxy-[CAS] | 364-62-5 | | Formulation, modified-release, <=24 hr | Gastro-oesophageal reflux |
| Metocurine Iodide | | 7601-55-0 | | | |
| Metofenazate | | 388-51-2 | | | |

TABLE IV-continued

| API Generic Name | API Chemical Name | CAS No. | Patent Reference | | Example of Therapeutic Use | Example of Indication |
|---|---|---|---|---|---|---|
| metolazone | 6-Quinazolinesulfonamide, 7-chloro-1,2,3,4-tetrahydro-2-methyl-3-(2-methylphenyl)-4-oxo-[CAS] | 17560-51-9 | U.S. | 4,517,179 | Antihypertensive, diuretic | |
| Metopimazine | | 14008-44-7 | | | | |
| Metopon | | 143-52-2 | | | | |
| metoprolol | 2-Propanol, 1-[4-(2-methoxyethyl)phenoxy]-3-[(1-methylethyl)amino]-, (+/−)-[CAS] | 51384-51-1<br>56392-17-7<br>37350-58-6 | | | Formulation, modified-release, other | Hypertension, general |
| Metralindole | | 54188-38-4 | | | | |
| Metrizamide | | 31112-62-6 | | | | |
| Metrizoic Acid | | 1949-45-7 | | | | |
| Metron S | | 13946-02-6 | | | | |
| Metyrapone | | 54-36-4 | | | | |
| Metyrosine | | 672-87-7 | | | | |
| Mexazolam | | 31868-18-5 | | | | |
| Mexenone | | 1641-17-4 | | | | |
| Mexiletine | | 31828-71-4 | | | | |
| mezlocillin | 4-Thia-1-azabicyclo[3.2.0]heptane-2-carboxylic acid, 3,3-dimethyl-6-[[[[3-(methylsulfonyl)-2-oxo-1-imidazolidinyl]carbonyl]amino]-phenylacetyl]amino]-7-oxo-, [2S-[2Alpha,5Alpha,6β(S*)]]-[CAS] | 42057-22-7<br>51481-65-3<br>72539-76-5 | GB | 1301961 | Penicillin, injectable | Infection, general |
| MFH-244 | Benzenecarboximidic acid, 3,4,5-trihydroxy-, ethyl ester, hydrochloride | 95933-76-9 | U.S. | 4,623,659 | Cardiovascular | Reperfusion injury |
| mianserin | Dibenzo[c,f]pyrazino[1,2-a]azepine, 1,2,3,4,10,14b-hexahydro-2-methyl-[CAS] | 21535-47-7<br>24219-97-4<br>116644-53-2<br>103775-75-3 | GB | 1173783 | Antidepressant | Depression, general |
| Mibefradil | | 116644-53-2 | | | | |
| Miboplatin | | 235114-32-6 | | | | |
| Micafungin | | | | | | |
| miconazole | 1H-Imidazole, 1-(2,4-dichlorophenyl)-2[2,4-dichlorophenyl)methoxy]ethyl] | 22916-47-8 | | | Formulation, modified-release, other | Infection, Candida, general |
| Micronomicin | | 52093-21-7 | | | | |
| midaxifyline | 1H-Purine-2,6-dione-8-(1-aminocyclopentyl)-3,7-dihydro-1,3-dipropyl-[CAS] | 151159-23-8 | U.S. | 5,378,844 | Cardiovascular | Unspecified |
| midazolam | 4H-Imidazo[1,5-a][1,4]benzodiazepine, 8-chloro-6-(2-fluorophenyl)-1-methyl-[CAS] | 59467-70-8<br>59467-94-6 | U.S. | 4,280,957 | Anaesthetic, injectable | Infection, general |
| midecamycin | Leucomycin V, 3,4B-dipropanoate [CAS] | 35457-80-8 | U.S. | 3,761,588 | Macrolide antibiotic | Infection, general |
| midecamycin acetate | Leucomycin V, 3B,9-diacetate 3,4B-dipropanoate [CAS] | 55881-07-7 | JP | 49124087 | Macrolide antibiotic | Infection, general |
| midesteine | 2-Thiophenecarbothioic acid, S-[1-methyl-2-oxo-2-[(tetrahydro-2-oxo-3-thienyl)amino]ethyl] ester [CAS] | 94149-41-4 | EP | 120534 | COPD treatment | Emphysema, general |
| midodrine | Acetamide, 2-amino-N-[2-(2,5-dimethoxyphenyl)-2-hydroxyethyl]-[CAS] | 42318-56-0<br>42794-76-3 | EP | 164571 | Urological | Incontinence |

TABLE IV-continued

| API Generic Name | API Chemical Name | CAS No. | Patent Reference | Example of Therapeutic Use | Example of Indication |
|---|---|---|---|---|---|
| midostaurin | Benzamide, N-(2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl-, (9Alpha,10β,11β,13Alpha)- [CAS] | 120685-11-2 | EP 296110 | Anticancer, other | Cancer, leukaemia, acute myelogenous |
| mifepristone | Estra-4,9-dien-3-one, 11-[4-(dimethylamino)phenyl]-17-hydroxy-17-(1-propynyl)-, (11β,17β)-[CAS] | 84371-65-3 | EP 57115 | Abortifacient | Abortion |
| miglitol | 3,4,5-Piperidinetriol, 1-(2-hydroxyethyl)-2-(hydroxymethyl)-, [2R-(2Alpha,3β,4Alpha,5β)]-[CAS] | 72432-03-2 | EP 55431 | Antidiabetic | Diabetes, Type I |
| miglustat | 3,4,5-Piperidinetriol, 1-butyl-2-(hydroxymethyl)-(2R-(2Alpha, 3β, 4Alpha, 5β) [CAS] | 72599-27-0 | DE 2758025 | Metabolic and enzyme disorders | Gaucher's disease |
| mildronate | Hydrazinium, 2-(2-carboxyethyl)-1,1,1-trimethyl), inner salt-[CAS] | 76144-81-5 | WO 8001068 | Cardiostimulant | Heart failure |
| milnacipran | Cyclopropanecarboxamide, 2-(aminomethyl)-N,N-diethyl-1-phenyl-, cis-(±)-[CAS] | 101152-94-7 92623-85-3 | U.S. 4,478,836 | Antidepressant | Depression, general |
| Miloxacin milrinone | [3,4'-Bipyridine]-5-carbonitrile, 1,6-dihydro-2-methyl-6-oxo-[CAS] | 37065-29-5 78415-72-2 | U.S. 4,313,951 | Cardiostimulant | Heart failure |
| iltefosine | Ethanaminium, 2-[[(hexadecyloxy)hydroxyphosphinyl]oxy]-N,N,N-trimethyl-, hydroxide, inner salt [CAS] | 53949-20-5 58066-85-6 | EP 225608 | Anticancer, other | Cancer, skin, general |
| minaprine | 4-Morpholineethanamine, N-(4-methyl-6-phenyl-3-pyridazinyl)-[CAS] | 25905-77-5 25953-17-7 | GB 1345880 | Antidepressant | Depression, general |
| minocycline | 2-Naphthacenecarboxamide, 4,7-bist(dimethylamino)-1,4,4a,5,5a,6,11,12a-octahydro-3,10,12,12a-tetrahydroxy-1,11-dioxo-, [4S-(4Alpha,4aAlpha,5a.alpha,12aAlpha)]- [CAS] | 10118-90-8 | | Formulation, optimized, microparticles | Infection, oral |
| minodronic acid | Phosphonic acid, (1-hydroxy-2-imidazo(1,2-a)pyridin-3-ylethylidene)bis-, [CAS] | 180064-38-4 | EP 354806 | Anticancer, other | Cancer, myeloma |
| minoxidil | 2,4-Pyrimidinediamine, 6-(1-piperidinyl)-, 3-oxide [CAS] | 38304-91-5 | U.S. 4,139,619 | Vasodilator, peripheral | Hypertension, general |
| Miokamycin mirtazapine | Pyrazino[2,1-a]pyrido[2,3-c][2]benzazepine, 1,2,3,4,10,14b-hexahydro-2-methyl-[CAS] | 55881-07-7 85650-52-8 61337-67-5 | GB 1543171 | Antidepressant | Depression, general |
| misoprostol | Prost-13-en-1-oic acid, 11,16-dihydroxy-16-methyl-9-oxo-, methyl ester, (11Alpha,13E)-(±)-[CAS] | 59122-46-2 59122-48-4 | U.S. 4,301,146 | Prostaglandin | Ulcer, gastric |

TABLE IV-continued

| API Generic Name | API Chemical Name | CAS No. | Patent Reference | Example of Therapeutic Use | Example of Indication |
|---|---|---|---|---|---|
| mitemcinal | Erythromycin, 8,9-didehydro-N-demethyl-9-deoxo-6,11-dideoxy-6,9-epoxy-12-O-methyl-N-(1-methylethyl)-11-oxo-, (2E)-2-butenedioate (2:1) [CAS] | 154802-96-7 | WO 9324509 | Gastroprokinetic | Gastro-oesophageal reflux |
| mitiglinide | Calcium (2S)-2-benzyl-3-(cis-hexahydro-2-isoindolinylcarbonyl)propionate, dihydrate-[CAS] | 145525-41-3 | EP 507534 | Antidiabetic | Diabetes, Type II |
| Mitobronitol Mitoguazone | | 488-41-5 459-86-9 | | | |
| mitolactol | Galactitol, 1,6-dibromo-1,6-dideoxy-[CAS] | 10318-26-0 | U.S. 3,993,781 | Anticancer, alkylating | Cancer, cervical |
| mitomycin | Azino[2',3':3,4]pyrrolo[1,2-a]indole-4,7-dione, 5-amino-8-[[(aminocarbonyl)oxy]methyl]-1,1a,2,8,8a,8b-hexahydro-8a-methoxy-5-methyl-, [1aS-(1aAlpha,8β,8aAlpha,8bAlpha)]-[CAS] | 50-07-7 | | Formulation, parenteral, other | Cancer, stomach |
| Mitotane | | 53-19-0 | | | |
| mitoxantrone | 9,10-Anthracenedione, 1,4-dihydroxy-5,8-bis[[2-[(2-hydroxyethyl)amino]ethyl]amino]-[CAS] | 65271-80-9 70476-82-3 | U.S. 4,197,249 | Anticancer, other | Cancer, breast |
| mitoxantrone | 9,10-Anthracenedione, 1,4-dihydroxy-5,8-bis[[2-[(2-hydroxyethyl)amino]ethyl]amino]-[CAS] | 65271-80-9 70476-82-9 | | Formulation, optimized, liposomes | Cancer, general |
| MIV-210 | (3'-Fluoro-2',3'-dideoxy guanosine) | | | Antiviral, other | Infection, hepatitis-B virus |
| mivacurium | Isoquinolinium, 2,2'-[(1,8-dioxo-4-octene-1,8-diyl)bis(oxy-3,1-propanediyl)bis[1,2,3,4-tetrahydro-6,7-dimethoxy-2-methyl-1-[(3,4,5-trimethoxyphenyl)methyl]-, dichloride, [R-[R*,R*-(E)]]]-[CAS] | 106861-44-3 | EP 181055 | Muscle relaxant | Anaesthesia, adjunct |
| Mivazerol | | 125472-02-8 | | | |
| mizolastine | 4(1H)-Pyrimidinone, 2-[[1-[1-[(4-fluorophenyl)methyl]-1H-benzimidazol-2-yl]-4-piperidinyl]methylamino]-[CAS] | 108612-45-9 | EP 217700 | Antiallergic, non-asthma | Rhinitis, allergic, general |
| Mizoribine | | 50924-49-7 | | | |
| MKC-733 | (R)-N-(3-quinuclidinyl)-7-oxo-4,7-dihydrothieno[3,2-b]pyridine-6-carboxamide hydrochloride | 194093-42-0 | JP 09216888 | Gastroprokinetic | Gastro-oesophageal reflux |
| MLN-519 | 6-Oxa-2-azabicyclo[3.2.0]heptane-3,7-dione, 1-[(1S)-1-hydroxy-2-methylpropyl]-4-propyl-, (1R,4R,5S)-[CAS] | 211866-70-5 | WO 9915183 | Neuroprotective | Ischaemia, cerebral |
| MLN-576 | 4-Methoxy-benzo[a]phenazine-11-carboxylic acid (2-dimethylamino)-1-(R)-methylethyl)-amide | | | Anticancer, other | Cancer, general |
| moclobemide | Benzamide, 4-chloro-N-[2-(4-morpholinyl)ethyl]-[CAS] | 71320-77-9 | EP 326023 | Antidepressant | Depression, general |

TABLE IV-continued

| API Generic Name | API Chemical Name | CAS No. | Patent Reference | | Example of Therapeutic Use | Example of Indication |
|---|---|---|---|---|---|---|
| modafinil | Acetamide, 2-[(diphenylmethyl)sulfinyl]-[CAS] | 68693-11-8 | DE | 2809625 | Psychostimulant | Narcolepsy |
| moexipril | 3-Isoquinolinecarboxylic acid, 2-[2-[[1-(ethoxycarbonyl)-3-phenylpropyl]amino]-1-oxopropyl]-1,2,3,4-tetrahydro-6,7-dimethoxy-(3S-(2(R*(R*)),3R*))-[CAS] | 103775-10-6 103775-14-0 | U.S. | 4,344,949 | Antihypertensive, renin system | Hypertension, general |
| Mofarotene | | 125533-88-2 | | | | |
| Mofebutazone | | 2210-63-1 | | | | |
| Mofegiline | | 119386-96-8 | | | | |
| mofezolac | 5-Isoxazoleacetic acid, 3,4-bis(4-methoxyphenyl)-[CAS] | 78967-07-4 | EP | 26928 | Analgesic, NSAID | Pain, post-operative |
| MOL-6131 | N-[4-(aminomethyl)benzyl]-8(S)-[1-[4-[2-(4-aminophenyl)-acetamido]butyryl]piperidin-4-yl]-2-(naphthalen-1-ylmethyl)-1,3-dioxo-2,3,5,8-tetrahydro-1H-[1,2,4]triazolo[1,2-a]-pyridazine-5(R)-carboxamide | | | | | Asthma |
| Molindone | | 7416-34-4 | | | | |
| molsidomine | Sydnone imine, N-(ethoxycarbonyl)-3-(4-morpholinyl)-[CAS] | 25717-80-0 | U.S. | 3,769,283 | Vasodilator, coronary | |
| mometasone | Pregna-1,4-diene-3,20-dione, 9,21-dichloro-11,17-dihydroxy-16-methyl-, (11β,16Alpha)-[CAS] | 105102-22-5 83919-23-7 | EP | 57401 | Antipruritic/inflamm, allergic | Psoriasis |
| Monatepil | | 103377-41-9 103-16-2 | | | | |
| Monobenzone | | | | | | |
| monolaurin | Dodecanoic acid, monoester with 1,2,3-propanetriol [CAS] | 27215-38-9 | U.S. | 4,885,282 | Dermatological | Ichthyosis |
| montelukast | Cyclopropaneacetic acid, 1-[[[1-[3-[2-(7-Chloro-2-quinolinyl)ethenyl]phenyl]-3-[2-(1-hydroxy-1-methylethyl)phenyl]propyl]thio]methyl]-, [CAS] | 151767-02-1 158966-92-8 | | | Antiasthma | Asthma |
| Monteplase | | 122007-85-6 | | | | |
| Moperone | | 1050-79-9 | | | | |
| Mopidamol | | 13665-88-8 | | | | |
| Moprolol | | 5741-22-0 | | | | |
| moracizine | Carbamic acid, [10-[3-(4-morpholinyl)-1-oxopropyl]-10H-phenothiazin-2-yl]-, ethyl ester [CAS] | 29560-58-5 31883-05-3 | U.S. | 3,864,487 | Antiarrhythmic | Tachycardia, ventricular |
| Morazone | | 6536-18-1 | | | | |
| Moricizine | | 31883-05-3 | | | | |
| Moroxydine | | 3731-59-7 | | | | |
| Morphazinamide | | 952-54-5 | | | | |
| morphine | Morphine-3,6-diol, 7,8-didehydro-4,5-epoxy-17-methyl-(5Alpha,6Alpha)-, [CAS] | 57-27-2 6055-06-7 | | | Formulation, parenteral, other | Pain, cancer |
| morphine-6-glucuronide | morphine-6-glucuronide | 64-31-3 | | | Formulation, inhalable, systemic | Pain, general |

TABLE IV-continued

| API Generic Name | API Chemical Name | CAS No. | Patent Reference | Example of Therapeutic Use | Example of Indication |
|---|---|---|---|---|---|
| mosapramine | Spiro[imidazo[1,2-a]pyridine-3(2H),4'-piperidin]-2-one, 1'-[3-(3-chloro-10,11-dihydro-5H-dibenz[b,f]azepin-5-yl)propyl]hexahydro-, (+/-)-[CAS] | 89419-40-9 98043-60-8 | U.S. 4,337,260 | Neuroleptic | |
| mosapride | Benzamide, 4-amino-5-chloro-2-ethoxy-N-[(4-((4-fluorophenyl)methyl)-2-morpholinyl)methyl]-[CAS] | 112885-41-3 112885-42-4 | EP 243959 | GI inflammatory/bowel disorders | Gastritis |
| motexafin gadolinium | Gadolinium, bis(acetato-kappaO)(9,10-diethyl-20,21-bis(2-(2-(2-methoxyethoxy)ethoxy)-4,15-dimethyl-8,11-imino-3,16:16,13-dinitrilo-1,18-benzodiazacycloeicosine-5,14-dipropanalato-kappaN1,kappaN18,kappaN23,kappaN24,kappaN25), (PB-7-11-233224) [CAS] | 246252-06-2 | | Radio/chemosensitizer | Cancer, brain |
| Motretinide | | 56281-36-8 | | | |
| Moveltipril | | 85856-54-8 | | | |
| Moxalactam | | 64952-97-2 | | | |
| Moxastine | | 3572-74-5 | | | |
| Moxaverine | | 10539-19-2 | | | |
| Moxestrol | | 34816-55-2 | | | |
| moxifloxacin | 3-Quinolinecarboxylic acid, 1-cyclopropyl-6-fluoro-1,4-dihydro-8-methoxy-7-(octahydro-6H-pyrrolo(3,4-b)pyridin-6-yl)-4-oxo-, hydrochloride (4aS-cis)-[CAS] | 186826-86-8 151096-09-2 | DE 19546249 | Quinolone antibacterial | Infection, respiratory tract, general |
| moxisylyte | Phenol, 4-[2-(dimethylamino)ethoxy]-2-methyl-5-(1-methylethyl)-, acetate (ester), [CAS] | 964-52-3 54-32-0 | | Male sexual dysfunction | Impotence |
| moxonidine | 5-Pyrimidinamine, 4-chloro-N-(4,5-dihydro-1H-imidazol-2-yl)-6-methoxy-2-methyl-[CAS] | 75438-57-2 | DE 2849537 | Antihypertensive, other | Hypertension, general |
| M-PGA | (-)-(S)-2-Methyl-2-(1-oxo-2,3-dihydro-1H-isoindol-2-yl)pentanedioic acid | | U.S. 5,712,291 | Anticancer, other | Cancer, general |
| MPI-5010 | Platinum diamminedichloro-, (SP-4-2) + (R)-4-[1-hydroxy-2-(methylamino)-ethyl]-1,2-benzenediol | | U.S. 6,224,883 | Formulation, parenteral, other | Cancer, head and neck |
| MPI-5020 | 2,4(1H,3H)-Pyrimidinedione, 5-fluoro-[CAS] | 51-21-8 | U.S. 5,750,146 | Formulation, parenteral, other | Cancer, breast |
| MPL | | 198076-81-2 | | Immunostimulant, other | Vaccine adjunct |
| MRS-1754 | | | | | Antiasthma |
| MS-209 | 1-Piperazineethanol, 4-(diphenylacetyl)-Alpha-[(5-quinolinyloxy)methyl]-, (2E)-2-butenedioate(2:3) (salt) [CAS] | 158681-49-3 | U.S. 6,060,481 | Radio/chemosensitizer | Cancer, breast |
| MS-275 | N-(2-Aminophenyl)-4-[N-(pyridin-3-yl-methoxycarbonyl)aminomethyl]benzamide | 201688-00-8 | | Anticancer, antimetabolite | Cancer, lung, general |
| MS-325 | | | EP 839805 | | |
| MS-377 | | 12650-69-0 | | Neuroleptic | Schizophrenia |
| Mupirocin | | 300-54-9 | | | |
| Muscarin | | | | | |

TABLE IV-continued

| API Generic Name | API Chemical Name | CAS No. | Patent Reference | | Example of Therapeutic Use | Example of Indication |
|---|---|---|---|---|---|---|
| Muzolimine | | 55294-15-0 | | | | |
| MX-1013 | | | | | | |
| mycophenolate mofetil | 4-Hexenoic acid, 6-(1,3-dihydro-4-hydroxy-6-methoxy-7-methyl-3-oxo-5-isobenzofuranyl)-4-methyl-, 2-(4-morpholinyl)ethyl ester, (E)-[CAS] | 116680-01-4 128794-94-5 | U.S. WO | 6,153,591 9119498 | Hepatoprotective Immunosuppressant | Unspecified Transplant rejection, general |
| mycophenolic acid | 4-hexanoic acid, 6-(1,3-dihydro-4-hydroxy-6-methoxy-7-methyl-3-oxo-5-isobenzofuranyl)-4-methyl-, | 37415-62-6 24280-93-1 | | | Formulation, oral, enteric-coated | Transplant rejection, general |
| Myrophine | | 467-18-5 | | | | |
| N-(Hydroxymethyl)-nicotinamide | | 3569-99-1 | | | | |
| N,N,N',N'-Tetraethylphthalamide | | 83-81-8 | | | | |
| N₂-Formyl-sulfisomidine | | 795-13-1 | | | | |
| N₄-β-D-Glucosylsulfanilamide | | 53274-53-6 | | | | |
| N₄-Sulfanilylsulfanilamide | | 547-52-4 | | | | |
| Nabilone | | | | | | |
| nabumetone | 2-Butanone, 4-(6-methoxy-2-naphthalenyl)-[CAS] | 51022-71-0 42924-53-8 | GB | 1476721 | Anti-inflammatory | Arthritis, osteo |
| N-acetylcysteine | L-Cysteine, N-acetyl-[CAS] | 616-91-1 | | | Anticancer, other | Cancer, general |
| N-Acetylmethionine | | 65-82-7 | | | | |
| nadifloxacin | 1H,5H-Benzo[ij]quinolizine-2-carboxylic acid, 9-fluoro-6,7-dihydro-8-(4-hydroxy-1-piperidinyl)-5-methyl-1-oxo-, (+/−)-[CAS] | 124858-35-1 | U.S. | 4,399,134 | Quinolone antibacterial | Acne |
| nadolol | 2,3-Naphthalenediol, 5-[3-[(1,1-dimethylethyl)amino]-2-hydroxypropoxy]-1,2,3,4-tetrahydro-[CAS] | 42200-33-9 | U.S. | 4,346,106 | Antihypertensive, adrenergic | |
| Nadoxolol | | 54063-51-3 | | | | |
| nafamostat | Benzoic acid, 4-[(aminoiminomethyl)amino]-, 6-(aminoiminomethyl)-2-naphthalenyl ester-[CAS] | 80251-32-7 81525-10-2 82956-11-4 | EP | 450232 | GI inflammatory/bowel disorders | Pancreatitis |
| nafarelin | Luteinizing hormone-releasing factor (pig), 6-[3-(2-naphthalenyl)-D-alanine]-[CAS] | 76932-56-4 86220-42-0 147-52-4 | EP | 21234 | Releasing hormones | Endometriosis |
| Nafcillin | | 31329-57-4 | | | | |
| Nafronyl | | | | | | |
| naftidofuryl | 2-Furanpropanoic acid, tetrahydro-Alpha-(1-naphthalenylmethyl)-, 2-(diethylamino)ethyl ester | 31329-57-4 | | | Formulation, modified-release, other | Unspecified |
| naftifine | 1-Naphthalenemethanamine, N-methyl-N-(3-phenyl-2-propenyl)-, (E)-[CAS] | 65472-88-0 65473-14-5 | U.S. | 4,282,251 | Antifungal | Infection, dermatological |
| naftopidil | 1-Piperazineethanol, 4-(2-methoxyphenyl)-Alpha-[(1-naphthalenyloxy)methyl]-[CAS] | 57149-07-2 | U.S. | 3,997,666 | Antihypertensive, adrenergic | Hypertension, general |

TABLE IV-continued

| API Generic Name | API Chemical Name | CAS No. | Patent Reference | Example of Therapeutic Use | Example of Indication |
|---|---|---|---|---|---|
| nalbuphine | Morphinan-3,6,14-triol, 17-(cyclobutylmethyl)-4,5-epoxy-, (5Alpha,6Alpha)-[CAS] | 20594-83-6 23277-43-2 | U.S. 3,393,197 | Analgesic, other | Pain, general |
| Nalidixic Acid | | 389-08-2 | | | |
| nalmefene | Morphinan-3,14-diol, 17-(cyclopropylmethyl)-4,5-epoxy-6-methylene-,(5Alpha)-[CAS] | 55096-26-9 | JP 56167687 | Dependence treatment | Poisoning, drug |
| Nalorphine | | 62-67-9 | | | |
| naloxone | Morphinan-6-one, 17-allyl-4,5Alpha-epoxy-3,14-dihydroxy-, hydrochloride [CAS] | 357-08-4 465-65-6 | | Septic shock treatment | |
| naltrexone | Morphinan-6-one, 17-(cyclopropylmethyl)-4,5-epoxy-3,14-dihydroxy-, (5Alpha)-[CAS] | 16590-41-3 16676-29-2 | U.S. 3,332,950 | Dependence treatment | Addiction, narcotic/opiate |
| NAMI | Imidazolium trans(imidazole)(dimethylsulfoxide)-tetrachlororuthenate (III) | | | Anticancer, other | Cancer, general |
| naminidil | Guanidine, N-cyano-N'-(4-cyanophenyl)-N"-[(1R)-1,2,2-trimethylpropyl]-[CAS] | 220641-11-2 | | Dermatological | Alopecia, general |
| Nandrolone | | 434-22-0 | | | |
| Naphazoline | | 835-31-4 | | | |
| Naphthalene | | 91-20-3 | | | |
| naproxen betainate | Methanaminium, 1-carboxy-N,N,N-trimethyl-salt with (R)-6-methoxy-Alpha-methyl-2-naphthaleneacetic acid (1:1), sodium salt [CAS] | 104124-26-7 | U.S. 4,672,077 | Antiarthritic, other | Arthritis, rheumatoid |
| naproxen | 2-Naphthaleneacetic acid, 6-methoxy-Alpha-methyl-, [CAS] | 26159-34-2 22204-53-1 | GB 1211134 | Analgesic, NSAID | Pain, general |
| naratriptan | 1H-Indole-5-ethanesulfonamide, N-methyl-3-(1-methyl-4-piperidinyl)-[CAS] | 121679-13-8 | EP 303507 | Antimigraine | Migraine |
| Narceine | | 131-28-2 | | | |
| Narcobarbital | | 125-55-3 | | | |
| Natamycin | | 7681-93-8 | | | |
| nateglinide | D-phenylalanine, N-((4-(1-methylethyl)cyclohexyl)carbonyl)-, trans- [CAS] | 105816-04-4 | EP 196222 | Antidiabetic | Diabetes, Type II |
| N-Butyldeoxy-nojirimycin | | 72599-27-0 | | | |
| N-Butylscopol-ammonium Bromide | | 149-64-4 | | | |
| NC-503 | | | U.S. 5,643,562 | Anti-inflammatory | Amyloidosis |
| NC-531 | | | U.S. 5,643,562 | Cognition enhancer | Alzheimer's disease |
| NCX-1000 | | | WO 0061604 | Hepatoprotective | Cirrhosis, hepatic |
| NCX-4016 | Benzoic acid, 2-(acetyloxy)-, 2-((nitrooxy)methyl)phenyl ester [CAS] | 175033-36-0 | WO 9716405 | Symptomatic antidiabetic | Insulin-related metabolic syndrome |
| NCX-456 | Benzoic acid, 5-amino-2-hydroxy-, 4-(nitrooxy)butyl ester [CAS] | 256499-26-0 | | GI inflammatory/ bowel disorders | Inflammatory bowel disease |

TABLE IV-continued

| API Generic Name | API Chemical Name | CAS No. | Patent Reference | Example of Therapeutic Use | Example of Indication |
|---|---|---|---|---|---|
| NCX-950 | Alpha'-[[(1,1-dimethylethyl)amino]methyl]-4-hydroxy-1,3-benzenedimethanol nitrate | | | Antiasthma | Asthma |
| n-Docosanol | | 661-19-8 | | | |
| NE-100 | Benzeneethanamine, 4-methoxy-3-(2-phenylethoxy)-N,N-dipropyl-, hydrochloride [CAS] | 149409-57-4 | WO 9307113 | Neuroleptic | Schizophrenia |
| Nealbarbital | | 561-83-1 | | | |
| nebivolol | 2H-1-Benzopyran-2-methanol, Alpha,Alpha'-[iminobis(methylene)]bis[6-fluoro-3,4-dihydro]-, (2R*(R*(R*(S*)))-(1+)- [CAS] | 118457-14-0 99200-09-6 | EP 145067 | Antihypertensive, adrenergic | Hypertension, general |
| nebostinel | N1-(4,4-Dimethylcyclohexyl)-L-isoglutamine | 163000-63-3 | EP 0688312 | Cognition enhancer | Unspecified |
| Nebracetam | | 97205-34-0 | | | |
| nedaplatin | Platinum, diammine[hydroxyacetato(2-)-O1,O2]-, (SP-4-3)-[CAS] | 95734-82-0 | EP 216362 | Anticancer, alkylating | |
| nedocromil | 4H-Pyrano[3,2-g]quinoline-2,8-dicarboxylic acid, 9-ethyl-6,9-dihydro-4,6-dioxo-10-propyl-[CAS] | 69049-73-6 69049-74-7 | EP 555718 | Antiasthma, Ophthalmological | Rhinitis, allergic, general, Ocular disorder, general |
| nefazodone | 3H-1,2,4-Triazol-3-one, 2-[3-[4-(3-chlorophenyl)-1-piperazinyl]propyl]-5-ethyl-2,4-dihydro-4-(2-phenoxyethyl)-, [CAS] | 82752-99-6 83366-66-9 | U.S. 4,338,317 | Antidepressant | Depression, general |
| nefiracetam | 1-Pyrrolidineacetamide, N-(2,6-dimethylphenyl)-2-oxo-[CAS] | 77191-36-7 | U.S. 4,341,790 | Cognition enhancer | Dementia, senile, general |
| nefopam | 1H-2,5-Benzoxazocine, 3,4,5,6-tetrahydro-5-methyl-1-phenyl-[CAS] | 13669-70-0 23327-57-3 33404-78-3 | U.S. 3,487,153 | Analgesic, NSAID | |
| Negamycin | | | | | |
| nelfinavir | 3-Isoquinolinecarboxamide, N-(1,1-dimethylethyl)decahydro-2-(2-hydroxy-3-(((3-hydroxy-2-methylbenzoyl)amino)-4-(phenylthio)butyl)-, (3S-(2(2S*,3S*),3Alpha,4aβ,8aβ))-, [CAS] | 159989-65-8 159989-64-7 | | Antiviral, anti-HIV | Infection, HIV/AIDS |
| Nemonapride | | 75272-39-8 | | | |
| Neostigmine | | 59-99-4 | | | |
| nepadutant | Cyclo[3-amino-L-alanyl-L-leucyl-N-[2-(acetylamino)-2-deoxy-β-D-glucopyranosyl]-L-asparaginyl-L-Alpha-aspartyl-L-tryptophyl-L-phenylalanyl], (4-1)-lactam [CAS] | 183747-35-5 | WO 9628467 | Antiasthma | Asthma |
| neramexane | 1,3,3,5,5-pentamethylcyclohexylamine | 202807-80-5 219810-59-0 | | Dependence treatment | Addiction, alcohol |
| neridronic acid | Phosphonic acid, (6-amino-1-hydroxyhexylidene)bis-[CAS] | 79778-41-9 | | Musculoskeletal | Osteogenesis imperfecta |
| Neriifolin | | 466-07-9 | | | |
| N-Ethylamphetamine | | 457-87-4 | | | |
| neticonazole | 1H-Imidazole, 1-[2-(methylthio)-1-[2-(pentyloxy)phenyl]ethenyl]-, monohydrochloride, (E)-[CAS] | 130773-02-3 130726-68-0 | EP 445540 | Antifungal | Infection, Candida, general |

TABLE IV-continued

| API Generic Name | API Chemical Name | CAS No. | Patent Reference | | Example of Therapeutic Use | Example of Indication |
|---|---|---|---|---|---|---|
| netilmicin | D-Streptamine, O-3-deoxy-4-C-methyl-3-(methylamino)-β-L-arabinopyranosyl-(1-6)-O-[2,6-diamino-2,3,4,6-tetradeoxy-Alpha-D-glycero-hex-4-enopyranosyl-(1-4)]-2-deoxy-N1-ethyl-[CAS] | 56391-56-1 56391-57-2 | GB | 1473733 | Aminoglycoside antibiotic | Infection, general |
| nevirapine | 6H-Dipyrido[3,2-b:2',3'-e][1,4]diazepin-6-one, 11-cyclopropyl-5,11-dihtdro-4-methyl-[CAS] | 129618-40-2 | EP | 429987 | Antiviral, anti-HIV | Infection, HIV/AIDS |
| NGD-98-2 | | | WO | 9635689 | Anxiolytic | Anxiety, general |
| Nialamide | | 51-12-7 | | | | |
| Niaprazine | | 27367-90-4 | | | | |
| Nicametate | | 3099-52-3 | | | | |
| nicaraven | 3-Pyridinecarboxamide, N,N'-(1-methyl-1,2-ethanediyl)bis-[CAS] | 79455-30-4 | EP | 29602 | Neuroprotective | Haemorrhage, subarachnoid |
| nicardipine | 3,5-Pyridinedicarboxylic acid, 1,4-dihydro-2,6-dimethyl-4-(3-nitrophenyl)-, methyl 2-[methyl(phenylmethyl)amino]ethyl ester [CAS] | 54527-84-3 55985-32-5 | U.S. | 3,985,758 | Neuroprotective | Hypertension, general |
| nicergoline | Ergoline-8-methanol, 10-methoxy-1,6-dimethyl-, (8/b)-, 5-bromo-3-pyridinecarboxylate(ester) | 27848-84-6 | | | Formulation, modified-release, other | Unspecified |
| Niceritrol | | 5868053 | | | | |
| Niclosamide | | 50-65-7 | | | | |
| Nicoclonate | | 10571-59-2 | | | | |
| Nicofuranose | | 15351-13-0 | | | | |
| Nicomol | | 27959-26-8 | | | | |
| Nicomorphine | | 639-48-5 | | | | |
| nicorandil | 3-Pyridinecarboxamide, N-[2-(nitrooxy)ethyl]-[CAS] | 65141-46-0 | U.S. | 4,792,564 | Vasodilator, coronary | Hypertension, general |
| Nicotinamide | | 98-92-0 | | | | |
| nicotine | Pyridine, 3-(1-methyl-2-pyrrolidinyl)-, (S)-[CAS] | 54-11-5 | | | Formulation, inhalable, other | Addiction, nicotine |
| Nicotinic Acid | | 59-67-6 | | | | |
| Nicotinic Acid Benzyl Ester | | 94-44-0 | | | | |
| Nicotinyl Alcohol | | 100-55-0 | | | | |
| nifedipine | 4-(2'-nitrophenyl)-2,6-dimethyl-3,5-dicarbomethoxy-1,4-dihydropyridine | 21829-25-4 | GB | 1173862 | Vasodilator, coronary | Hypertension, general |
| nifekalant | 2,4(1H,3H)-Pyrimidinedione, 6-[[2-[(2-hydroxyethyl)[3-(4-nitrophenyl)propyl]amino]ethyl]amino]-1,3-dimethyl-, [CAS] | 130636-43-0 130656-51-8 | EP | 369627 | Antiarrhythmic | Arrhythmia, general |
| Nifenalol | | 7413-36-7 | | | | |
| Niflumic Acid | | 4394-00-7 | | | | |
| Nifuratel | | 4936-47-4 | | | | |
| Nifurfoline | | 3363-58-4 | | | | |
| Nifuroxazide | | 965-52-6 | | | | |
| Nifuroxime | | 6236051 | | | | |
| Nifurpirinol | | 13411-16-0 | | | | |

TABLE IV-continued

| API Generic Name | API Chemical Name | CAS No. | Patent Reference | | Example of Therapeutic Use | Example of Indication |
|---|---|---|---|---|---|---|
| Nifurprazine | | 1614-20-6 | | | | |
| Nifurtimox | | 23256-30-6 | | | | |
| Nifurtoinol | | 1088-92-2 | | | | |
| nifurzide | 2-Thiophenecarboxylic acid, 5-nitro-, [3-(5-nitro-2-furanyl)-2-propenylidene]hydrazide [CAS] | 39978-42-2 | U.S. | 3,847,911 | Antidiarrhoeal | Infection, GI tract |
| NIK-254 | Gentamicin, sulfate (salt) [CAS] | 1405-41-0 | | | Formulation, other | Infection, general |
| Nikethamide | | 59-26-7 | | | | |
| nilutamide | 2,4-Imidazolidinedione, 5,5-dimethyl-3-[4-nitro-3-(trifluoromethyl)phenyl]-[CAS] | 63612-50-0 | U.S. | 4,472,382 | Anticancer, hormonal | Cancer, prostate |
| nilvadipine | 3,5-Pyridinedicarboxylic acid, 2-cyano-1,4-dihydro-6-methyl-4-(3-nitrophenyl)-, 3-methyl 5-(1-methylethyl) ester [CAS] | 75530-68-6 | U.S. | 4,338,322 | Antihypertensive, other | Hypertension, general |
| nimesulide | Methanesulfonamide, N-(4-nitro-2-phenoxyphenyl)-[CAS] | 51803-78-2 | U.S. | 3,840,597 | Anti-inflammatory | Pain, general |
| Nimetazepam | | 2011-67-8 | | | | |
| nimodipine | 3,5-Pyridinedicarboxylic acid, 1,4-dihydro-2,6-dimethyl-4-(3-nitrophenyl)-, 2-methoxyethyl 1-methylethyl ester [CAS] | 66085-59-4 | EP | 533014 | Neuroprotective | |
| Nimorazole | | 6506-37-2 | | | | |
| nimustine | Urea, N'-[(4-amino-2-methyl-5-pyrimidinyl)methyl]-N-(2-chloroethyl)-N-nitroso-[CAS] | 103745-00-2 42471-28-3 55661-38-6 | GB | 1374344 | Anticancer, alkylating | Cancer, brain |
| Ninopterin | | 2179-16-0 | | | | |
| NIP-142 | N-[4(S)-(Cyclopropylamino)-3-(R)-hydroxy-2,2-dimethyl-7-nitro-3,4-dihydro-2H-1-benzopyran-6-yl]-4-methoxybenzeneacetamide | | WO | 9804542 | Antiarrhythmic | Fibrillation, atrial |
| NIP-531 | N'-[3,5-Bis(trifluoromethyl)benzyl]-N-[3-[N-[1-(4-fluorobenzyl)benzimidazol-2-yl]-amino]propyl-N-methylurea hydrochloride | | | | Antipruritic/inflamm, allergic | Eczema, atopic |
| niperotidine | N-[2-[[5-[(dimethylamino)methyl](furfuryl)thio]ethyl]-2-nitro-N'-piperonyl-1,1-ethenediamine | 84845-75-0 | GB | 2104071 | Antiulcer | Ulcer, GI, general |
| nipradilol | 2H-1-Benzopyran-3-ol, 3,4-dihydro-8-[2-hydroxy-3-[(1-methylethyl)amino]propoxy]-, 3-nitrate [CAS] | 81486-22-8 86247-86-1 | EP | 42299 | Formulation, mucosal, topical | Glaucoma |
| Niridazole | | 61-57-4 | | | | |
| nisoldipine | 3,5-Pyridinedicarboxylic acid, 1,4-dihydro-2,6-dimethyl-4-(2-nitrophenyl)-, methyl 2-methylpropyl ester-[CAS] | 63675-72-9 | GB | 1516793 | Antihypertensive, other | Hypertension, general |
| nitazoxanide | Benzamide, 2-(acetyloxy)-N-(5-nitro-2-thiazolyl)-[CAS] | 55981-09-4 | U.S. | 5,387,598 | Protozoacide | Infection, GI tract |
| nitisinone | 1,3-Cyclohexanedione, 2-[2-nitro-4-(trifluoromethyl)benzoyl]-[CAS] | 104206-65-7 | EP | 186118 | Metabolic and enzyme disorders | Cirrhosis, hepatic |
| nitracrine | 1,3-Propanediamine, N,N-dimethyl-N'-(1-nitro-9-acridinyl)-[CAS] | 4533-39-5 6514-85-8 146-22-5 | FR | 1458183 | Anticancer, other | Cancer, ovarian |
| Nitrazepam | | | | | | |

TABLE IV-continued

| API Generic Name | API Chemical Name | CAS No. | Patent Reference | | Example of Therapeutic Use | Example of Indication |
|---|---|---|---|---|---|---|
| nitrendipine | 3,5-Pyridinedicarboxylic acid, 1,4-dihydro-2,6-dimethyl-4-(3-nitrophenyl)-, ethyl methyl ester-[CAS] | 39562-70-4 | GB | 1358951 | Antihypertensive, other | Hypertension, general |
| nitroflurbiprofen | (1,1'-Biphenyl)-4-acetic acid, 2-fluoro-Alpha-methyl-, 4-(nitrooxy)butyl ester [CAS] | 158836-71-6 | EP | 670825 | Urological | Incontinence |
| Nitrofurantoin | | 67-20-9 | | | | |
| Nitrofurazone | | 59-87-0 | | | | |
| nitroglycerin | 1,2,3-Propanetriol, trinitrate [CAS] | 55-63-0 | | | Formulation, transdermal, patch | Angina, general |
| Nitromersol | | 133-58-4 | | | | |
| nitronaproxen | 2-Naphthaleneacetic acid, 6-methoxy-Alpha-methyl 4-(nitrooxy)butyl ester (AlphaS)-[CAS] | 163133-43-5 | WO | 9509831 | Analgesic, NSAID | Pain, post-operative |
| nitroxazepine | Dibenz[b,f][1,4]oxazepin-11(10H)-one, 10-[3-(dimethylamino)propyl]-2-nitro-, monohydrochloride [CAS] | 16398-39-3 | NL | 6608671 | Antidepressant | |
| Nitroxoline | | 4008-48-4 | | | | |
| nizatidine | 1,1-Ethenediamine, N-[2-[[[2-[(dimethylamino)methyl]-4-thiazolyl]methyl]thio]ethyl]-N'-methyl-2-nitro-[CAS] | 76963-41-2 | EP | 49618 | Antiulcer | Ulcer, duodenal |
| Nizofenone | | 54533-85-6 | | | | |
| NM-3 | 3-(2-methylcarboxymethyl)-6-methoxy-8-hydroxy-isocoumarin | | JP | 08176138 | Anticancer, other | Cancer, general |
| NM-702 | 4-Bromo-5-(3-pyridylmethylamino)-6-[3-(4-chlorophenyl)propoxy]-3(2H)pyridazinone hydrochloride | | | | Antithrombotic | Peripheral vascular disease |
| N-Methylephedrine | | 552-79-4 | | | | |
| N-Methylepinephrine | | 554-99-4 | | | | |
| N-Methylglucamine | | 6284-40-8 | | | | |
| NN-414 | 6-chloro-3-(1-methylcyclopropylamino)-4H-thieno[3,2-e]-[1,2,4]thiadiazine-1,1-dioxide | | | | Antidiabetic | Diabetes, Type II |
| NNC-05-1869 | (R)-1-(3-(10,11-dihydro-5H-dibenzo[a,d]cyclohepten-5-ylidene)-1-propyl)-3-piperidine carboxylic acid | | | | Symptomatic antidiabetic | Neuropathy, diabetic |
| Nogalamycin | | 1404-15-5 | | | | |
| nolatrexed | 4(1H)-Quinazolinone, 2-amino-6-methyl-5-(4-pyridinylthio)-, [CAS] | 152946-68-4 | WO | 9320055 | Anticancer, antimetabolite | Cancer, liver |
| nolomirole | Propanoic acid, 2-methyl-, 5,6,7,8-tetrahydro-6-(methylamino)-1,2-naphthalenediyl ester, hydrochloride, (+/-)-[CAS] | 147149-76-6 138531-51-8 | WO | 9529147 | Cardiostimulant | Heart failure |
| nolpitantium | 1-Azoniabicyclo[2.2.2]octane, 1-[2-[3-(3,4-dichlorophenyl)-1-[[3-(1-methylethoxy)phenyl]acetyl]-3-piperidinyl]ethyl]-4-phenyl-, chloride, (S)-[CAS] | 153050-21-6 | EP | 591040 | GI inflammatory/bowel disorders | Inflammatory bowel disease |

TABLE IV-continued

| API Generic Name | API Chemical Name | CAS No. | Patent Reference | Example of Therapeutic Use | Example of Indication |
|---|---|---|---|---|---|
| nomegestrol | 19-Norpregna-4,6-diene-3,20-dione, 17-(acetyloxy)-6-methyl-[CAS] | 58652-20-3 | DE 2522533 | Menstruation disorders | Menstrual disorder, general |
| Nomifensine | | 24526-64-5 | | | |
| Noprylsulfamide | | 576-97-6 | | | |
| Norbolethone | | 1235-15-0 | | | |
| Nordazepam | | 1088-11-5 | | | |
| Nordefrin | | 6539-57-7 (unspecified); 74812-63-8 (R*,S*)-(±)-form | | | |
| Nordihydroguaiaretic Acid | | 27686-84-6 (meso-form); 500-38-9 (unspecified) | | | |
| Norelgestromin, Ethinyl Estradiol | | | | | |
| Norepinephrine | | 51-41-2 | | | |
| Norethandrolone | | 52-78-8 | | | |
| Norethindrone | | 68-22-4 | | | |
| Norethynodrel | | 68-23-5 | | | |
| Norfenefrine | | 536-21-0 | | | |
| norfloxacin | 3-Quinolinecarboxylic acid, 1-ethyl-6-fluoro-1,4-dihydro-4-oxo-7-(1-piperazinyl)-[CAS] | 68077-27-0 | U.S. 4,146,719 | Quinolone antibacterial | Infection, general |
| Norgesterone | | 70458-96-7 | | | |
| Norgestimate | | 13563-60-5 | | | |
| Norgestrel | | 35189-28-7 | | | |
| Norgestrienone | | 6533-00-2 | | | |
| Norlevorphanol | | 848-21-5 | | | |
| Normethadone | | 1531-12-0 | | | |
| Normethandrone | | 467-85-6 | | | |
| Nomorphine | | 514-61-4 | | | |
| Norphenazone | | 466-97-7 | | | |
| Norpipanone | | 89-25-8 | | | |
| Norpseudoephedrine | | 561-48-8 | | | |
| Nortriptyline | | 492-39-7 | | | |
| Norvinisterone | | 72-69-5 | | | |
| Noscapine | | 6795-60-4 | | | |
| Novembichin | | 128-62-1 | | | |
| Novobiocin | | 1936-40-9 | | | |
| Noxiptilin | | 303-81-1 | | | |
| Noxythiolin | | 3362-45-6 | | | |
| NS-1209 | Butanoic acid, 2-[[[5-[4-[(dimethylamino)sulfonyl]phenyl]-1,2,6,7,8,9-hexahydro-8-methyl-2-oxo-3H-pyrrolo[3,2-h]isoquinolin-3-ylidene]amino]oxy]-3-hydroxy-[CAS] | 15599-39-0 254751-28-5 | WO 9426747 | Antiepileptic | Epilepsy, general |

TABLE IV-continued

| API Generic Name | API Chemical Name | CAS No. | Patent Reference | Example of Therapeutic Use | Example of Indication |
|---|---|---|---|---|---|
| NS-1231 | 5-(4-chlorophenyl)-6,7,8,9-tetrahydro-1H-pyrolo-(3,2-h)naphthalene-2,3-dione-3-oxime | | | Neuroprotective | Ischaemia, cerebral |
| NS-126 | | | U.S. 5,063,222 | Antiallergic, non-asthma | Rhinitis, allergic, general |
| NS-220 | 2-Methyl-c-5-[4-[5-methyl-2-(4-methylphenyl)-4-oxazolyl]butyl]-1,3-dioxane-r-2-carboxylic acid | | | Hypolipaemic/Antiatherosclerosis | Atherosclerosis |
| NS-2330 | NS 2330 [CAS] | 402856-42-2 | | Cognition enhancer | Alzheimer's disease |
| NS5A inhibitors | | | U.S. 6,030,785 | Antiviral, other | Infection, hepatitis-C virus |
| NS-7 | Pyrimidine, 4-(4-fluorophenyl)-2-methyl-6-[[5-(1-piperidinyl)pentyl]oxy]-, monohydrochloride [CAS] | 178429-67-9 | WO 9607641 | Neuroprotective | Ischaemia, cerebral |
| NS-8 | 2-Amino-5-(2-fluorophenyl)-4-methyl-1H-pyrrole-3-carbonitrile | | | Urological | Incontinence |
| NSC-330507 | 17-Allylaminogeldanamycin | | | Anticancer, antibiotic | Cancer, general |
| NSC-619534 | 2-chloroethyl phenyl selenone | | | Anticancer, alkylating | Cancer, general |
| NSC-697726 | 2,5-diazinidinyl-3-[hydroxymethyl]6-methyl-1,4-benzoquinone | 120-34-3 | | Anticancer, antibiotic | Cancer, general |
| N-Sulfanilyl-3,4-xylamide | | | | | |
| NU-6027 | 2,4-Pyrimidinediamine, 6-(cyclohexylmethoxy)-5-nitroso-[CAS] | 220036-08-8 | | Anticancer, other | Cancer, general |
| NV-07 | 2,4,6(1H,3H,5H)-Pyrimidinetrione, 5-ethyl-5-sec-pentyl-, 2-oxime [CAS] | 53745-16-7 | U.S. 6,455,032 | Antipruritic/inflamm, non-allergic | Keratosis |
| NVP-SRA880 | ([3R,4aR,10aR]-1,2,3,4,4a,5,10,10a-Octahydro-6-methoxy-1-methyl-benz[g]quinoline-3-carboxylic acid-4-(4-nitrophenyl)piperazine amide, hydrogen maleate | | | Neurological | Unspecified |
| NW-1029 | (S)(+)-2-[4-(2-fluorobenzyloxy)benzylamino]propanamide methansulfonate | | | Analgesic, other | Pain, general |
| NXY-059 | CPI 22 [CAS] | 168021-79-2 | U.S. 5,780,510 | Neuroprotective | Ischaemia, cerebral |
| Nylidrin | | 447-41-6 | | | |
| NZ-314 | 1-Imidazolidineacetic acid, 3-[(3-nitrophenyl)methyl]-2,4,5-trioxo-[CAS] | 128043-99-2 | EP 353198 | Symptomatic antidiabetic | Neuropathy, diabetic |
| NZ-419 | 5-hydroxy-1-methylimidazolidine-2,4-dione | 114-90-9 | EP 412940 | Urological | Renal failure |
| Obidoxime Chloride | | | | | |
| OC-108 | OC 108 [CAS] | 162602-62-2 | | Vasoprotective, topical | Venous insufficiency |

TABLE IV-continued

| API Generic Name | API Chemical Name | CAS No. | Patent Reference | Example of Therapeutic Use | Example of Indication |
|---|---|---|---|---|---|
| ocinaplon | Methanone, 2-pyridinyl[7-(4-pyridinyl)pyrazolo[1,5-a]pyrimidin-3-yl]-[CAS] | 96604-21-6 | EP 129847 | Anxiolytic | Generalized anxiety disorder |
| Octabenzone | | 1843-05-6 | | | |
| Octacaine | | 13912-77-1 | | | |
| Octamoxin | | 4684-87-1 | | | |
| Octaverine | | 549-68-8 | | | |
| octenidine | 1-Octanamine, N,N'-(1,10-decanediyldi-1(4H)-pyridinyl-4-ylidene)bis-[CAS] | 70775-75-6 71251-02-0 86767-75-1 | WO 8705501 | Stomatological | Periodontitis |
| Octodrine | | 543-82-8 | | | |
| Octopamine | | 104-14-3 | | | |
| Octotiamine | | 137-86-0 | | | |
| octreotide | L-Cysteinamide, D-phenylalanyl-L-cysteinyl-L-phenylalanyl-D-tryptophy-L-lysyl-L-threonyl-N-[2-hydroxy-1-(hydroxymethyl)propyl]-, cyclic (2-7)-disulfide, [R-(R*,R*)]-[CAS] | 83150-76-9 | | Formulation, fixed-dose combinations | Cancer, general |
| Octyl Methoxycinnamate | | 5466-77-3 | | | |
| ofloxacin | 7H-Pyrido[1,2,3-de]-1,4-benzoxazine-6-carboxylic acid, 9-fluoro-2,3-dihydro-3-methyl-10-(4-methyl-1-piperazinyl)-7-oxo-, (+/-)-[CAS] | 82419-36-1 | EP 47005 | Quinolone antibacterial | |
| o-Iodohippurate | | 133-17-5 | | | |
| loanzapine | 10H-Thieno(2,3-b)(1,5)benzodiazepine, 2-methyl-4-(4-methyl-1-piperazinyl)-[CAS] | 132539-06-1 | EP 454436 | Neuroleptic | Schizophrenia |
| Oleandrin | | 465-16-7 | | | |
| Oleic Acid | | 112-80-1 | | | |
| olmesartan - medoxomil | 1H-Imidazole-5-carboxylic acid, 4-(1-hydroxy-1-methylethyl)-2-propyl-1-((2'-(1H-tetrazol-5-yl)(1,1'-biphenyl)-4-yl)methyl)-, (5-methyl-2-oxo-1,3-dioxol-4-yl) methyl ester [CAS] | 144689-63-4 | EP 503785 | Antihypertensive, renin system | Hypertension, general |
| olopatadine | 11-[(Z)-3-(Dimethylamino)propylidene]-6,11-dihydrodibenz[b,e]oxepin-2-acetic acid, monohydrochloride | 113806-05-6 140462-76-6 | EP 235796 | Ophthalmological | Conjunctivitis |
| olpadronic acid | Monosodium 3-dimethylamino-1-(hydroxypropylidene)-1,1-bisphosphonate | 63132-39-8 | WO 9619998 | Osteoporosis treatment | Osteoporosis |
| olsalazine | Benzoic acid, 3,3'-azobis[6-hydroxy-[CAS] | 15722-48-2 53200-51-4 | U.S. 4,559,330 | GI inflammatory/ bowel disorders | Colitis, ulcerative |
| olipraz | 3H-1,2-Dithiole-3-thione, 4-methyl-5-pyrazinyl-[CAS] | 64224-21-1 | DE 2705641 | Anticancer, other | Cancer, general |
| OM-294DP | 2-[3(R)-(Dodecanoyloxytetradecanamido]-N-[4-[3(R)-hydroxytetradecanamido]-5-(phosphonooxy)pentyl]-4-(phosphonooxy)butyramide | | | Anticancer, immunological | Unspecified |

TABLE IV-continued

| API Generic Name | API Chemical Name | CAS No. | Patent Reference | Example of Therapeutic Use | Example of Indication |
|---|---|---|---|---|---|
| Omacor | ethyl (5Z,8Z,11Z,14Z,17Z)-eicosa-5,8,11,14,17-pentaenoate + ethyl (4Z,7Z,10Z,13Z,16Z,19Z)-docosa-4,7,10,13,16,19-hexaenoate | 81926-94-5 86227-47-6 | | Hypolipaemic/ Antiatherosclerosis | Hypertrigly-ceridaemia |
| omapatrilat | 7H-Pyrido(2,1-b)(1,3)thiazepine-7-carboxylic acid, octahydro-4-((2-mercapto-1-oxo-3-phenylpropyl)amino)-5-oxo, (4S-(4Alpha(R*),7Alpha,10aß))-[CAS] | 167305-00-2 | U.S. 5,508,272 | Antihypertensive, renin system | Hypertension, general |
| omeprazole | 1H-Benzimidazole, 5-methoxy-2-[[(4-methoxy-3,5-dimethyl-2-pyridinyl)methyl]sulfinyl]-[CAS] | 73590-58-6 | U.S. 4,255,431 | Antiulcer | Ulcer, GI, general |
| omiloxetine | Ethanone, 2-[(3R,4S)-3-[(1,3-benzodioxol-5-yloxy)methyl]-4-(4-fluorophenyl)-1-piperidinyl]-1-(4-fluorophenyl)-, rel-[CAS] | 176894-09-0 | | Antidepressant | Depression, general |
| omoconazole | 1H-Imidazole, 1-[2-[2-(4-chlorophenoxy)ethoxy]-2-(2,4-dichlorophenyl)-1-methylethenyl]-, (Z)-[CAS] | 74512-12-2 | EP 8804 | Antifungal | Infection, dermatological |
| Onapristone ondansetron | 4H-Carbazol-4-one, 1,2,3,9-tetrahydro-9-methyl-3-[(2-methyl-1H-imidazol-1-yl)methyl]-[CAS] | 96346-61-1 99614-01-4 99614-02-5 | U.S. 4,847,281 | Antiemetic | Chemotherapy-induced nausea and vomiting |
| ONO-3403 | Benzoic acid, 4-[(1E)-3-[(2-ethoxy-2-oxoethyl)-2-propenylamino]-2-methyl-3-oxo-1-propenyl]-, 4-(aminoiminomethyl)phenyl ester, monomethanesulfonate [CAS] | 181586-07-2 | | GI inflammatory/ bowel disorders | Unspecified |
| ONO-4128 | 1,4,9-Triazaspiro(5.5)undecane-2,5-dione, 1-butyl-3-(cyclohexylmethyl)-9-(2,3-dihydro-1,4-benzodioxin-6-yl)methyl- [CAS] | 342394-93-8 | | Antiviral, anti-HIV | Infection, HIV/AIDS |
| ONO-8815 Ly | L-lysine (Z)-7-[(1R,2R,3R,5R)-5-chloro-3-hydroxy-2-[(E)-(S)-4-(1-ethylcyclobutyl)-4-hydroxy-1-butenyl]cyclopentyl]-5-heptenoate | | | Labour inhibitor | Labour, preterm |
| ONT-093 | | | U.S. 5,756,527 | Radio/ chemosensitizer | Cancer, general |
| OPC-14523 | 2(1H)-Quinolinone, 1-[3-[4-(3-chlorophenyl)-1-piperazinyl]propyl]-3,4-dihydro-5-methoxy-[CAS] | 145969-30-8 | EP 512525 | Antidepressant | Depression, general |
| OPC-31260 | Benzamide, N-[4-[[5-(dimethylamino)-2,3,4,5-tetrahydro-1H-1-benzazepin-1-yl]carbonyl]phenyl]-2-methyl-(5R)-2-[1-(2-chloro-4-(1- | 137975-06-5 | WO 9105549 | Urological | Unspecified |
| OPC-51803 | pyrolidinyl)benzoyl)-2,3,4,5-tetrahydro-1H-1-benzazepin-5-yl]-N-isopropylacetamide | | | Antidiabetic | Diabetes, insipidus |
| OPC-6535 | 2-Pyridinecarboxylic acid, 6-[2-(3,4-diethoxyphenyl)-4-thiazolyl]-[CAS] | 145739-56-6 | WO 9209586 | GI inflammatory/ bowel disorders | Inflammatory bowel disease |
| Opiniazide | | 2779-55-7 | | | |

TABLE IV-continued

| API Generic Name | API Chemical Name | CAS No. | Patent Reference | Example of Therapeutic Use | Example of Indication |
|---|---|---|---|---|---|
| opioid analgesics | 2-(4-trifluoromethylphenyl)-N-methyl-[1-phenyl-2-(1-pyrolidinyl)ethyl]acetamide] | 315-72-0 | | Analgesic, other | Pain, general |
| Opipramol | | 2574-78-9 | | | |
| Orazamide | | | | | |
| orazipone | 2,4-Pentanedione, 3-((4-methylsulfonyl)phenyl)methylene)-[CAS] | 137109-78-5 | EP 440324 | Antiasthma | Unspecified |
| Org-12962 | Piperazine, 1-[6-chloro-5-(trifluoromethyl)-2-pyridinyl]-, monohydrochloride [CAS] | 210821-63-9 | | Antidepressant | Depression, general |
| Org-24448 | | | U.S. 6,166,008 | Neuroleptic | Schizophrenia |
| oritavancin | Vancomycin, 22-O-(3-amino-2,3,6-trideoxy-3-C-methyl-Alpha-L-arabino-hexopyranosyl)-N3''-[(4''-chloro[1,1'-biphenyl]-4-yl)methyl]-,(4''R)-[CAS] | 171099-57-3 | U.S. 5,840,684 | Peptide antibiotic | Infection, dermatological |
| orlistat | L-Leucine, N-formyl-, 1-(3-hexyl-4-oxo-2-oxetanyl)methyl]dodecyl ester, [2S-[2Alpha(R*),3β]]-[CAS] | 96829-58-2 | EP 129748 | Anorectic/Antiobesity | Obesity |
| ormeloxifene | Pyrrolidine, 1-[2-(p-(7-methoxy-2,2-dimethyl-3-phenyl-4-chromanyl)phenoxy)ethyl]-, trans-[CAS] | 31477-60-8 | DE 2329201 | Female contraceptive | Contraceptive, female |
| Ormidazole | | 16773-42-5 | | | |
| Ornipressin | | 3397-23-7 | | | |
| Ornithine | | 70-26-8 | | | |
| ornoprostil | Prost-13-en-1-oic acid, 11,15-dihydroxy-17,20-dimethyl-6,9-dioxo-, methyl ester, (11Alpha,13E,15S,17S)-[CAS] | 70667-26-4 | U.S. 4,278,688 | Prostaglandin | Ulcer, gastric |
| Orotic Acid | | 65-86-1 | | | |
| Orphenadrine | | 83-98-7 | | | |
| Orthocaine | | 536-25-4 | | | |
| Osalmid | | 526-18-1 | | | |
| osanetant | Acetamide, N-[1-[3-[(3R)-1-benzoyl-3-(3,4-dichlorophenyl)-3-piperidinyl]propyl]-4-phenyl-4-piperidinyl]-N-methyl-[CAS] | 160492-56-8 | EP 673928 | Neuroleptic | Schizophrenia |
| osaterone | 2-Oxapregna-4,6-diene-3,20-dione, 17-(acetyloxy)-6-chloro-[CAS] | 105149-00-6 | EP 193871 | Prostate disorders | Benign prostatic hyperplasia |
| oseltamivir | 1-Cyclohexene-1-carboxylic acid, 4-(acetylamino)5-amino-3-(1-ethylpropoxy)-, ethyl ester, (3R-(3Alpha,(4β,5Alpha))-[CAS] | 196618-13-0 | WO 9626933 | Antiviral, other | Infection, influenza virus |
| OSI-7836 | 4'-Thio-β-D-arabinofuranosylcytosine | | | Anticancer, antimetabolite | Cancer, general |
| OSI-7904 | Pentanedioic acid, 2-[5-[[(1,2-dihydro-3-methyl-1-oxobenzo[f]quinazolin-9-yl)methyl]amino]-1,3-dihydro-1-oxo-2H-isoindol-2-yl]-, (S)-[CAS] | 139987-54-5 | WO 9119700 | Formulation, optimized, liposomes | Cancer, general |
| ospemifene | Ethanol, 2-[4-[(1Z)-4-chloro-1,2-diphenyl-1-butenyl]phenoxy]-[CAS] | 128607-22-7 | WO 9607402 | Menopausal disorders | Osteoporosis |
| otilonium bromide | Ethanaminium, N,N-diethyl-N-methyl-2-[4-[[2-(octyloxy)benzoyl]amino]benzoyl]oxy]-, bromide [CAS] | 26095-59-0 | GB 1181406 | Antispasmodic | Irritable bowel syndrome |
| Ouabain | | 630-60-4 | | | |

TABLE IV-continued

| API Generic Name | API Chemical Name | CAS No. | Patent Reference | Example of Therapeutic Use | Example of Indication |
|---|---|---|---|---|---|
| Oxaceprol | | 33966-33-7 | | | |
| Oxacillin | | 66-79-5 | | | |
| Oxaflozane | | 26629-87-8 | | | |
| oxaliplatin | Platinum, (1,2-cyclohexanediamine-N,N')[ethanedioato(2-)-O,O']-, [SP-4-2-(1R-trans)]-[CAS] | 61825-94-3 | EP 393575 | Anticancer, alkylating | Cancer, colorectal |
| Oxalyt-C | 1,2,3-Propanetricarboxylic acid, 2-hydroxy-, potassium sodium salt [CAS] | 28060-67-5 | DE 2249274 | Urological | |
| Oxamarin | | 15301-80-1 | | | |
| Oxametacine | | 27035-30-9 | | | |
| Oxamniquine | | 21738-42-1 | | | |
| oxandrolone | 2-Oxaandrostan-3-one, 17-hydroxy-17-methyl-, (5Alpha,17β)-[CAS] | 53-39-4 | U.S. 3,128,283 | Reproductive/gonadal, general | Sex-chromosome abnormality, Turner's syndrome |
| Oxantel | | 36531-26-7 | | | |
| Oxapropanium | | 541-66-2 | | | |
| oxaprozin | 2-Oxazolepropanoic acid, 4,5-diphenyl-[CAS] | 21256-18-8 | GB 1206403 | Antiarthritic, other | Arthritis, osteo |
| oxatomide | 2H-Benzimidazol-2-one, 1-[3-[4-(diphenylmethyl)-1-piperazinyl]propyl]-1,3-dihydro-[CAS] | 60607-34-3 | GB 1579365 | Antiallergic, non-asthma | Rhinitis, allergic, general |
| oxazepam | 7-Chloro-1,3-dihydro-3-hydroxy-5-phenyl-2H-1,4-benzodiazepin-2-one | 604-75-1 | | Formulation, oral, orally-disintegrating | Anxiety, general |
| oxazolam | Oxazolo[3,2-d][1,4]benzodiazepin-6(5H)-one, 10-chloro-2,3,7,11b-tetrahydro-2-methyl-11b-phenyl-[CAS] | 27167-30-2 | U.S. 3,772,371 | Anxiolytic | |
| oxcarbazepine | 5H-Dibenz[b,f]azepine-5-carboxamide, 10,11-dihydro-10-oxo-[CAS] | 28721-07-5 29331-92-8 | DE 2011087 | Antiepileptic | Epilepsy, general |
| Oxeladin | | 468-61-1 | | | |
| Oxendolone | | 33765-68-3 | | | |
| Oxethazaine | | 126-27-2 | | | |
| Oxetoron | | 26020-55-3 | | | |
| oxiconazole | Ethanone, 1-(2,4-dichlorophenyl)-2-(1H-imidazol-1-yl)-, O-[(2,4-dichlorophenyl)methyl]oxime, (Z)-[CAS] | 64211-45-6 | GB 1514870 | Antifungal | Infection, fungal, general |
| Oxidronic Acid | | 15468-10-7 | | | |
| Oxiniacic Acid | | 2398-81-4 | | | |
| Oxiracetam | | 62613-82-5 | | | |
| oxitropium | 3-Oxa-9-azoniatricyclo[3.3.1.02,4]nonane, 9-ethyl-7-(3-hydroxy-1-oxo-2-phenylpropoxy)-9-methyl-, bromide, [(7S)-(1Alpha,2β,4β,5Alpha,7β)]-[CAS] | 30286-75-0 | GB 1178305 | Antiasthma | |
| Oxolamin | | 959-14-8 | | | |
| Oxolinix Acid | | 14698-29-4 | | | |
| Oxophenarsine | | 538-03-4 | | | |
| Oxprenolol | | 6452-71-7 | | | |
| Oxybenzone | | 131-57-7 | | | |

TABLE IV-continued

| API Generic Name | API Chemical Name | CAS No. | Patent Reference | | Example of Therapeutic Use | Example of Indication |
|---|---|---|---|---|---|---|
| oxybutynin | Benzeneacetic acid, Alpha-cyclohexyl-Alpha-hydroxy-, 4-(diethylamino)-2-butynyl ester-[CAS] | 5633-20-5 | | | Formulation, modified-release, other | Incontinence |
| Oxycinchophen | | 485-89-2 | | | | |
| oxycodone | Morphinan-6-one, 4,5-epoxy-14-hydroxy-3-methoxy-17-methyl-, (5Alpha)- | 76-42-6 | | | Formulation, transmucosal, nasal | Pain, general |
| Oxytedrine | | 15687-41-9 | | | | |
| Oxygent | Octane, 1-bromo-1,1,2,2,3,3,4,4,5,5,6,6,7,7,8,8,8-heptadecfluoro-[CAS] | 423-55-2 | | | Haematological | Surgery adjunct |
| Oxymesterone | | 145-12-0 | | | | |
| Oxymetazoline | | 1491-59-4 | | | | |
| oxymetholone | Androstan-3-one, 17-hydroxy-2-(hydroxymethylene)-17-methyl-, (5Alpha,17β)-[CAS] | 434-07-1 | | | Hormone | Anaemia, general |
| Oxymethurea | | 140-95-4 | | | | |
| oxymorphone | (5Alpha)-4,5-Epoxy-3,14-dihydroxy-17-methylmorphinan-6-one [CAS] | 76-41-5 | | | Formulation, modified-release, immediate | Pain, general |
| Oxypendyl | | 5585-93-3 | | | | |
| Oxypertine | | 153-87-7 | | | | |
| Oxyphenbutazone | | 129-20-4 | | | | |
| Oxyphencyclimine | | 125-53-1 | | | | |
| Oxyphenisatin | | 115-33-3 | | | | |
| Oxyphenonium | | 50-10-2 | | | | |
| Oxypinocamphone | | 10136-65-9 | | | | |
| oxypurinol | 1H-Pyrazolo[3,4-d]pyrimidine-4,6(5H,7H)-dione [CAS] | 2465-59-0 | | | Antigout | Hyper-uricaemia |
| Oxytetracycline | | 79-57-2 | | | | |
| ozagrel | 2-Propenoic acid, 3-[4-(1H-imidazol-1-ylmethyl)phenyl]-, (E)-[CAS] | 78712-43-3 82571-53-7 536-95-8 | GB | 2025946 | Antithrombotic | Vasospasm, cerebral |
| p-(Benzyl-sulfonamido)-benzoic Acid | | | | | | |
| P-100 | | | U.S. | 6,313,777 | Antiviral, anti-HIV | Infection, HIV/AIDS |
| P-1202 | Pentanoic acid, 5-amino-4-oxo, methyl ester, hydrochloride [CAS] | 79416-27-6 | U.S. | 6,034,267 | Dermatological | Keratosis |
| P32/98 | Di-(3N-[(2S,3S)-2-amino-3-methyl-pentanoyl]-1,3-thiazolidine)fumarate | | | | Antidiabetic | Diabetes, Type II |
| PA-824 | | | WO | 9701562 | Antimycobacterial | Infection, tuberculosis |
| PACAP 38 | Pituitary adenylate cyclase-activating peptide-38 [CAS] | 128606-20-2 | U.S. | 5,128,242 | Neuroprotective | Nerve injury, general |
| pactitaxel | 5β,20-Epoxy-1,2Alpha,4,7β,10β,13Alpha-hexahydroxytax-11-en-9-one-4,10-diacetate-2-benzoate-13-(Alpha-phenylhippurate) | 33069-62-4 | | | Formulation, optimized, nanoparticles | Cancer, breast |
| PADRE | | | U.S. | 6,413,935 | Immunostimulant, other | Vaccine adjunct |

TABLE IV-continued

| API Generic Name | API Chemical Name | CAS No. | Patent Reference | | Example of Therapeutic Use | Example of Indication |
|---|---|---|---|---|---|---|
| pagoclone | 1H-Isoindol-1-one, 2-(7-chloro-1,8-naphthyridin-2-yl)-2,3-dihydro-3-(5-methyl-2-oxohexyl)-(R)-[CAS] | 133737-32-3 | U.S. | 4,960,779 | Anxiolytic | Panic disorder |
| PAI inhibs | | | WO | 9404512 | Antithrombotic | Thrombosis, venous |
| palindore | | | | | | |
| Palivizumab | 8H-1,4-dioxino[2,3-e]indol-8-one,2,3,7,9-tetrahydro-2-[(phenylmethyl)amino]methyl]-, 2(S)-, (2E)-2-butendioate (1:1) | 189681-71-8 | | | Neuroleptic | Schizophrenia |
| palonosetron | | 188039-54-5 | | | | |
| | 3aS-2-[(S)-1-Azabicyclo[2.2.2]oct-3-yl]-2,3,3a4,5,6-hexahydro-1-oxo-1H-benz[de]isoquinoline hydrochloride | 135729-62-3 | U.S. | 5,202,333 | Antiemetic | Chemotherapy-induced nausea and vomiting |
| Panabrom | | 606-04-2 | | | | |
| Pamaquine | | 491-92-9 | | | | |
| pamicogral | 1H-Pyrrole-1-acetic acid, 2-[4,5-bis(4-methoxyphenyl)-2-thiazolyl]-, ethyl ester [CAS] | 101001-34-7 | EP | 159677 | Antithrombotic | Thrombosis, cerebral |
| pamidronate | (3-Amino-1-hydroxypropylidene)diphosphonic acid-[CAS] | 40391-99-9 | | | Formulation, implant | Hypercalcaemia of malignancy |
| p-Aminobenzoic Acid | | 150-13-0 | | | | |
| p-Aminohippuric Acid | | 61-78-9 | | | | |
| p-Aminopropiophenone | | 70-69-9 | | | | |
| p-Aminosalicylic Acid | | 65-49-6 | | | | |
| Panavir | 4,4'-isopropylidenedithiobis-2,6-di-t-butylphenol | | | | Neuroprotective | Vasospasm, cerebral |
| Pancuronium | | 15500-66-0 | | | | |
| Panipenem | | 87726-17-8 | | | | |
| Pantethine | | 16816-67-4 | | | | |
| pantoprazole | 1H-Benzimidazole, 5-(difluoromethoxy)-2-[[(3,4-dimethyloxy-2-pyridinyl)methyl]-sulfinyl]-[CAS] | 102625-70-7 | EP | 166287 | Antiulcer | Ulcer, duodenal |
| Pantothenic Acid | | 79-83-4 | | | | |
| Papain | | 58-74-2 | | | | |
| Papaverine | | | | | | |
| paracetamol | Acetamide, N-(4-hydroxyphenyl)-[CAS] | 103-90-2 | | | Formulation, oral, other, modified-release | Pain, general |
| Paraflutizide | | 1580-83-2 | | | | |
| Paraldehyde | | 123-63-7 | | | | |
| Paramethadione | | 115-67-3 | | | | |
| Paramethasone | | 53-33-8 | | | | |
| Paranyline | | 1729-61-9 | | | | |
| Parathyroid Hormone | | 9002-64-6 | | | | |
| parecoxib | Propanamide, N-(4-(5-methyl-3-phenyl-4-isoxazolyl)phenyl)sulfonyl)-, sodium salt [CAS] | 198470-85-8 | WO | 9738986 | Analgesic, NSAID | Pain, post-operative |

TABLE IV-continued

| API Generic Name | API Chemical Name | CAS No. | Patent Reference | | Example of Therapeutic Use | Example of Indication |
|---|---|---|---|---|---|---|
| Parethoxycaine | | 94-23-5 | | | | |
| Pargyline | | 555-57-7 | | | | |
| paricalcitol | 19-Nor-9,10-secoergosta-5,7,22-triene-1,3,25-triol, (1Alpha,3β,7E,22E)-[CAS] | 131918-61-1 | EP | 387077 | Hormone | Hyperparathy-roidsm |
| paromomycin | O-2-Amino-2-deoxy-Alpha-D-glucopyranosyl-(1-4)-O-[O-2,6-diamino-2,6-dideoxy-β-L-idopyranosyl-(1-3)-β-D-ribofuranosyl-(1-5)]-2-deoxy-D-streptamine | 7542-37-2 | | | Protozoacide | Infection, leishmaniasis |
| paroxetine | Piperidine, 3-[(1,3-benzodioxol-5-yloxy)methyl]-4-(4-fluorophenyl)-, (3S-trans)-[CAS] | 61869-08-7 | EP | 223403 | Antidepressant, formulation, oral, orally-disintegrating | Depression, general |
| Paroxypropione | | 70-70-2 | | | | |
| Parsalmide | | 30653-83-9 | | | | |
| PaTrin-2 | 4-Bromothenylguanine | | | | Radio/chemosensitizer | Cancer, melanoma |
| Pazinaclone | | 103255-66-9 | | | | |
| pazufloxacin | 7H-Pyrido[1,2,3-de]-1,4-benzoxazine-6-carboxylic acid, 10-(1-aminocyclopropyl)-9-fluoro-2,3-dihydro-3-methyl-7-oxo-, (S)-[CAS] | 127045-41-4 127046-45-1 136905-87-8 | DE | 3913245 | Quinolone antibacterial | Infection, general |
| p-Bromoacetanilide | | 103-88-8 | | | | |
| PC-NSAIDs | | | U.S. | 4,918,063 | Formulation, other | Arthritis, general |
| PD-0166285 | 6-(2,6-Dichlorophenyl)-2-[4-(diethylamino-ethoxy)-phenylamino]-8-pyrido[2,3-D]pyrimidine-7-one | | | | Anticancer, other | Cancer, general |
| Pecilocin | | 19504-77-9 | | | | |
| pefloxacin | 3-Quinolinecarboxylic acid, 1-ethyl-6-fluoro-1,4-dihydro-7-(4-methyl-1-piperazinyl)-4-oxo-[CAS] | 70458-92-3 | GB | 1598915 | Quinolone antibacterial | Infection, urinary tract |
| pegvisomant | Somatotropin (18-aspartic acid, 21-asparagine, 120-lysine, 167-asparagine, 168-alanine, 171-serine, 172-arginine, 174-serine, 179-threonine (human), pegylated [CAS] | 218620-50-9 | | | Somatostatin | Acromegaly |
| Pelletierine | | 4396-1-4 | | | | |
| pemetrexed | L-Glutamic acid, N-[4-[2-(2-amino-4,7-dihydro-4-oxo-1H-pyrrolo[2,3-d]pyrimidin-5-yl)ethyl]benzoyl]-, disodium salt [CAS] | 137281-23-3 150399-23-8 | U.S. | 5,248,775 | Anticancer, antimetabolite | Cancer, mesothel-ioma |
| pemirolast | 4H-Pyrido[1,2-a]pyrimidin-4-one, 9-methyl-3-(1H-tetrazol-5-yl)-[CAS] | 100299-08-9 69372-19-6 | U.S. | 4,457,932 | Antiasthma | Asthma |
| Pemoline | | 2152-34-3 | | | | |
| Pempidine | | 79-55-0 | | | | |
| PEN-203 | | | U.S. | 5,955,446 | Antiviral, other | Infection, human papilloma virus |

TABLE IV-continued

| API Generic Name | API Chemical Name | CAS No. | Patent Reference | | Example of Therapeutic Use | Example of Indication |
|---|---|---|---|---|---|---|
| Penamecillin | | 983-85-7 | | | | |
| penbutolol | 2-Propanol, 1-(2-cyclopentylphenoxy)-3-[(1,1-dimethylethyl)amino]-, (S)-, sulfate (2:1) (salt) [CAS] | 38363-32-5 38363-40-5 | GB | 1215751 | Antihypertensive, adrenergic | |
| penciclovir | 6H-Purin-6-one, 2-amino-1,9-dihydro-9-[4-hydroxy-3-(hydroxymethyl)butyl]-[CAS] | 39809-25-1 | JP | 60058982 | Antiviral, other | Infection, herpes simplex virus |
| Penethamate | | 808-71-9 | | | | |
| penfluridol | 4-Piperidinol, 1-[4,4-bis(4-fluorophenyl)butyl]-4-[4-chloro-3-(trifluoromethyl)phenyl]-[CAS] | 26864-56-2 | DE | 2040231 | Neuroleptic | |
| Penicillamine | | 52-67-5 | | | | |
| Penicillin G | | 61-33-6 | | | | |
| Penicillin G Benzathine | | 1538-09-6 | | | | |
| Penicillin G Procaine | | 6130-64-9 | | | | |
| Penicillin N | | 525-94-0 | | | | |
| Penicillin O | | 87-09-2 | | | | |
| Penicillin V | | 87-08-1 | | | | |
| Penimepicycline | | 4599-60-4 | | | | |
| Penntuss | | 78-12-6 | U.S. | 4,221,778 | Formulation, modified-release, other | Rhinitis, allergic, general |
| Pentaerythritol Chloral | | 2209-86-1 | | | | |
| Pentaerythritol Dichlorohydrin | | 597-71-7 | | | | |
| Pentaerythritol | | 5534-95-2 | | | | |
| Pentagastrin | | 7001-56-1 | | | | |
| Pentagestrone | | 9005-27-0 | | | | |
| PentaLyte | Starch, 2-hydroxyethyl ether [CAS] | 541-20-8 | U.S. | 5,407,428 | Plasma substitute | Surgery adjunct |
| Pentam thionium | | | | | | |
| pentamidine | Benzenecarboximidamide, 4,4'-[1,5-pentanediylbis(oxy)]bis-[CAS] | 100-33-4 | | | Formulation, inhalable, systemic | Infection, *Pneumocystis jiroveci* prophylaxis |
| Pentazocine | | 359-83-1 | | | | |
| Pentetate | | 121111-24-9 | | | | |
| Pentetic Acid | | 67-43-6 | | | | |
| Pentetreotide | | 138661-02-6 | | | | |
| Penthienate | | 60-44-6 | | | | |
| Pentifylline | | 1028-33-7 | | | | |
| Pentigetide | | 62087-72-3 | | | | |
| Pentisomide | | 78833-03-1 | | | | |
| Pentobarbital | | 76-74-4 | | | | |
| Pentolinium | | 52-62-0 | | | | |
| Pentorex | | 434-43-5 | | | | |
| pentosan | Xylan, [CAS] | 373319-17-8 | U.S. | 5,180,715 | Urological | Inflammation, urinary tract |

TABLE IV-continued

| API Generic Name | API Chemical Name | CAS No. | Patent Reference | | Example of Therapeutic Use | Example of Indication |
|---|---|---|---|---|---|---|
| pentostatin | Imidazo[4,5-d][1,3]diazepin-8-ol, 3-(2-deoxy-β-D-erythro-pentofuranosyl)-3,6,7,8-tetrahydro-, (R)-[CAS] | 53910-25-1 | U.S. | 3,923,785 | Anticancer, antimetabolite | Cancer, leukaemia, hairy cell |
| pentoxifylline | 1H-Purine-2,6-dione, 3,7-dihydro-3,7-dimethyl-1-(5-oxohexyl)-[CAS] | | | | Neuroprotective | Amyotrophic lateral sclerosis |
| Pentoxyl | | 147-61-5 | | | | |
| Pentrinitrol | | 1607-17-6 | | | | |
| Pentylenetetrazole | | 54-95-5 | | | | |
| peplomycin | Bleomycinamide, N1-[3-[(1-phenylethyl)amino]propyl]-, (S)-[CAS] | 68247-85-8 | U.S. | 4,195,018 | Anticancer, antibiotic | |
| Perazine | | 84-97-9 | | | | |
| Perflubron | | 423-55-2 | | | | |
| Perfosfamide | | 62435-42-1; 39800-16-3 (unspecified) | | | | |
| pergolide | Ergoline, 8-[(methylthio)methyl]-6-propyl-, (8β)-, monomethanesulfonate-[CAS] | 66104-22-1 66104-23-2 | U.S. | 4,797,405 | Antiparkinsonian | Parkinson's disease |
| Perhexiline | | 6621-47-2 | | | | |
| Pericyazine | | 2622-26-6 | | | | |
| perifosine | Piperidinium, 4-[[hydroxy(octadecyloxy)phosphinyl]oxy]-1,1-dimethyl-, inner salt [CAS] | 157716-52-4 | EP | 594999 | Anticancer, other | Cancer, prostate |
| perillyl alcohol | 1-Cyclohexene-1-methanol, 4-(1-methylethenyl)-[CAS] | 536-59-4 | U.S. | 5,110,832 | Anticancer, other | Cancer, breast |
| Perimethazine | | 13093-88-4 | | | | |
| perindopril | 1H-Indole-2-carboxylic acid, 1-[2-[[1-(ethoxycarbonyl)butyl],amino]-1-oxopropyl]octahydro-, [2S-[1-[R*(R*)],2Alpha,3aβ,7aβ]]-, compd. with 2-methyl-2-propanamine (1:1) [CAS] | 107133-36-8 82834-16-0 95153-31-4 | EP | 49658 | Antihypertensive, renin system | Hypertension, general |
| Periodyl | | 53586-99-5 | | | | |
| perisoxal | 1-Piperidineethanol, Alpha-(5-phenyl-3-isoxazolyl)-, 2-hydroxy-1,2,3-propanetricarboxylate (2:1) (salt) [CAS] | 2139-25-5 2055-44-9 | JP | 04217925 | Anti-inflammatory | |
| Perlapine | | 1977-11-3 | | | | |
| Permethrin | | 52645-53-1 | | | | |
| perospirone | 1H-Isoindole-1,3(2H)-dione, 2-[4-[4-(1,2-benzisothiazol-3-yl)-1-piperazinyl]butyl]hexahydro-, cis-[CAS] | 129273-38-7 150915-41-6 | CA | 2167004 | Neuroleptic | Schizophrenia |
| Perphenazine | | 58-39-9 | | | | |
| Petroleum Benzin | | 8030-30-6 | | | | |
| PH-10 | | | | | | |
| Phanquinone | | 84-12-8 | | | | |
| Pharmaprojects No. 4994 | | | U.S. | 6,331,286 | Antipsoriasis | Psoriasis |
| Pharmaprojects No. 5325 | | | WO | 9638482 | Immunological | Unspecified |
| Pharmaprojects No. 5972 | | | WO | 9703986 | Neuroleptic | Schizophrenia |
| Pharmaprojects No. | | | WO | 0204426 | Antiasthma | Asthma |
| Pharmaprojects No. | | | U.S. | 6,057,346 | Antiviral, anti-HIV | Infection, |

TABLE IV-continued

| API Generic Name | API Chemical Name | CAS No. | Patent Reference | Example of Therapeutic Use | Example of Indication |
|---|---|---|---|---|---|
| Pharmaprojects No. 6362 | | | | | HIV/AIDS |
| Pharmaprojects No. 6446 | (R)-N-[4-[2-[[2-Hydroxy-2-(3-pyridinyl)ethyl]amino]ethyl]phenyl]-4-[4-(trifluoromethyl)phenyl]thiazo-2-yl]-benzenesulfonamide | | | Anorectic/Antiobesity | Obesity |
| Pharmaprojects No. 6590 | | | WO 0206223 | Psychostimulant | Attention deficit disorder |
| Pharmaprojects No. 6656 | | | U.S. 6,455,026 | Genomics-based drug discovery | Cancer, brain |
| Pharmaprojects No. 6691 | | | U.S. 6,299,900 | Formulation, other | Pain, general |
| Pharmaprojects No. 6743 | 3-(6-Aminopyridin-3-yl)-N-methyl-N-[(1-methyl-1H-indol-2-yl)methyl]acrylamide | | | Antibacterial, other | Infection, general |
| Pharmaprojects No. 6748 | 1,2,3,4,10,14b-Hexahydro-6-methoxy-2-methyldibenzo[c,f]pyrazino[1,2-a]azepin | | | Antidepressant | Depression, general |
| Phenacaine | | 620-99-5 | | | |
| Phenacemide | | 63-98-9 | | | |
| Phenacetin | | 62-44-2 | | | |
| Phenadoxone | | 467-84-5 | | | |
| Phenallymal | | 115-43-5 | | | |
| Phenamet | | 3819-34-9 | | | |
| Phenazocine | | 127-35-5 | | | |
| Phenazopyridine | | 136-40-3 | | | |
| Phenbutamide | | 3149-00-6 | | | |
| Phencyclidine | | 77-10-1 | | | |
| Phendimetrazine | | 634-03-7 | | | |
| Phenelzine | | 51-71-8 | | | |
| Phenesterine | | 3546-10-9 | | | |
| Phenetharbital | | 357-67-5 | | | |
| Phenethicillin | | 132-93-4 | | | |
| Pheneturide | | 90-49-3 | | | |
| Phenformin | | 114-86-3 | | | |
| Phenglutarimide | | 1156-05-4 | | | |
| Phenindamine | | 82-88-2 | | | |
| Phenindione | | 83-12-5 | | | |
| Pheniprazine | | 55-52-7 | | | |
| Pheniramine | | 86-21-5 | | | |
| Phenmetrazine | | 134-49-6 | | | |
| Phenobarbital | | 50-06-6 | | | |
| Phenobutiodil | | 554-24-5 | | | |
| Phenocoll | | 103-97-9 | | | |
| Phenoctide | | 78-05-7 | | | |
| Phenolphthalein | | 77-09-8 | | | |
| Phenolphthalol | | 81-92-5 | | | |
| Phenolsulfonphthalein | | 143-74-8 | | | |
| Phenol-tetrachlorophthalein | | 639-44-1 | | | |
| Phenoperidine | | 562-26-5 | | | |
| Phenosulfazole | | 515-54-8 | | | |

TABLE IV-continued

| API Generic Name | API Chemical Name | CAS No. | Patent Reference | Example of Therapeutic Use | Example of Indication |
|---|---|---|---|---|---|
| Phenoxybenzamine | | 59-96-1 | | | |
| Phenoxypropazine | | 3818-37-9 | | | |
| Phenprobamate | | 673-31-4 | | | |
| Phenprocoumon | | 435-97-2 | | | |
| phenserine | Pyrrolo(2,3-b)indol-5-ol, 1,2,3,3a,8,8a-hexahydro-1,3a,8-trimethyl-phenylcarbamate (ester), (3aS-cis)-[CAS] | 101246-66-6 | | Cognition enhancer | Alzheimer's disease |
| Phensuximide | | 86-34-0 | | | |
| Phentermine | | 122-09-8 | | | |
| Phentetiothalein | | 18265-54-8 | | | |
| phentolamine | Phenol, 3-((4,5-dihydro-1H-imidazol-2-yl)methyl)(4-methylphenyl)amino)-, monomethanesulfonate (salt) [CAS] | 65-28-1 50-60-2 | | Formulation, oral, other | Impotence |
| Phenyl Acetylsalicylate | | 134-55-4 | | | |
| Phenyl Aminosalicylate | | 133-11-9 | | | |
| Phenyl Salicylate | | 118-55-8 | | | |
| Phenylbutazone | | 50-33-9 | | | |
| Phenylephrine | | 61-76-7 | | | |
| Phenylethanolamine | | 7568-93-6 | | | |
| Phenylmercury | | 102-98-7 | | | |
| Phenylmethylbarbituric Acid | | 76-94-8 | | | |
| phenylpropanolamine | Benzenemethanol, Alpha-(1-aminoethyl)-, (R*,S*)-(+/-)-[CAS] | 14838-15-4 | | Anorectic/Antiobesity, formulation, optimized, microparticles | |
| Phenylpropyl-methylamine | | 93-88-9 | | | |
| Phenyltoloxamine | | 92-12-6 | | | |
| Phenyramidol | | 553-69-5 | | | |
| phenytoin | 2,4-Imidazolidinedione, 5,5-diphenyl-[CAS] | 57-41-0 | | Formulation, oral, other | Epilepsy, general |
| Phethenylate | | 510-34-9 | | | |
| Phloroglucinol | | 108-73-6 | | | |
| Pholcodine | | 509-67-1 | | | |
| Pholedrine | | 370-14-9 | | | |
| Phosphocreatine | | 67-07-2 | | | |
| Phosphocysteamine | | 5746-40-7 | | | |
| Phosphorylcholine | | 107-73-3 | | | |
| Phthalylsulfacetamide | | 131-69-1 | | | |
| Phthalylsulfathiazole | | 85-73-4 | | | |
| p-Hydroxyephedrine | | 365-26-4 | | | |
| Phylloquinone | | 84-80-0 | | | |
| Physostigmine | | 57-47-6 | | | |
| Phytic Acid | | 83-86-3 | | | |

TABLE IV-continued

| API Generic Name | API Chemical Name | CAS No. | Patent Reference | | Example of Therapeutic Use | Example of Indication |
|---|---|---|---|---|---|---|
| PI-88 | D-Mannose, O-6-O-phosphono-Alpha-D-mannopyranosyl-(1-3)-O-Alpha-D-mannopyranosyl-(1-3)-O-Alpha-D-mannopyranosyl-(1-3)-O-Alpha-D-mannopyranosyl-(1-2)-hydrogen sulphate [CAS] | 185077-23-0 | | | Anticancer, other | Cancer, melanoma |
| Piberaline | | 39640-15-8 | | | | |
| piboserod | 2H-(1,3)Oxazino(3,2-a)indole-10-carboxamide, N-(1-butyl-4-piperidinyl)methyl)-3,4-dihydro-[CAS] | 152811-62-6 | WO | 9318036 | Antiarrhythmic | Fibrillation, atrial |
| Picilorex | | 62510-56-9 | | | | |
| Picloxydine | | 5636-92-0 | | | | |
| Picoperine | | 21755-66-8 | | | | |
| Picosulfate | | 10040-45-6 | | | | |
| Picotamide | | 32828-81-2 | | | | |
| Picumast | | 39577-19-0 | | | | |
| pidotimod | 4-Thiazolidinecarboxylic acid, 3-[(5-oxo-2-pyrrolidinyl)carbonyl]-[CAS] | 121808-62-6 | EP | 276752 | Immunomodulator, anti-infective | Infection, respiratory tract, lower |
| Pifarnine | | 56208-01-6 | | | | |
| piketoprofen | Benzeneacetamide, 3-benzoyl-Alpha-methyl-N-(4-methyl-2-pyridinyl)-[CAS] | 60576-13-8 | GB | 1436502 | Anti-inflammatory, topical | |
| Pildralazine | | 64000-73-3 | | | | |
| pilocarpine | 2(3H)-Furanone, 3-ethyldihydro-4-[(1-methyl-1H-imidazol-5-yl)methyl]-, (3S-cis)-[CAS] | 92-13-7 | | | Formulation, implant, Stomatological | |
| Piloplex | 2-Propenoic acid, 2-methyl-, dodecyl ester, polymer with 2-propenoicacid, compd. with (3S-cis)-3-ethyldihydro-4-[(1-methyl-1H-imidazol-5-yl)methyl]-2(3H)-furanone [CAS] | 62783-28-2 | DE | 2636559 | Formulation, mucosal, topical | Glaucome |
| pilsicainide | 1H-Pyrrolizine-7a(5H)-acetamide, N-(2,6-dimethylphenyl)tetrahydro-, monohydrochloride [CAS] | 88069-49-2 88069-67-4 | U.S. | 4,564,624 | Antiarrhythmic | Arrhythmia, general |
| Pimeclone | | 534-84-9 | | | | |
| pimecrolimus | 15,19-Epoxy-3H-pyrido(2,1-c)(1,4)oxaazacyclotricosine-1,7,20,21(4H,23H)-tetrone, 3-(2-(4-chloro-3-methoxycyclohexyl)-1-methyletheny)-8-ethyl-5,6,8,11,12,13,14,15,16,17,18,19,24,25,26,26a-hexadecahydro-5,19-dihydroxy-14,16-dimethoxy-4,10,12,18-tetramethyl-(3S-(3R*E(1S*,3S*,4R*)),4S*,5R*,8S*,9E*,12R*,14R*,5S*,16R*,18S,19S*,26aR*))-[CAS] | 137071-32-0 | EP | 626385 | Antipruritic/inflamm, allergic | Eczema, atopic |

TABLE IV-continued

| API Generic Name | API Chemical Name | CAS No. | Patent Reference | Example of Therapeutic Use | Example of Indication |
|---|---|---|---|---|---|
| Pimefylline | | 10001-43-1 | | | |
| pimilprost | Acetic acid, [2-[octahydro-5-hydroxy-6-(3-hydroxy-5-methyl-1-nonenyl)-2-pentalenyl]ethoxy]-, methyl ester, [2R-[2Alpha,3Alpha,4Alpha(1E,3S*,5S*),5β,6a Alpha]]-[CAS] | 139403-31-9 | | Dermatological | Ulcer, general |
| Piminodine | | 13495-09-5 | | | |
| Pimobendan | | 74150-27-9 | | | |
| pimozide | 2H-Benzimidazol-2-one, 1-[1-[4,4-bis(4-fluorophenyl)butyl]-4-piperidinyl]-1,3-dihydro-[CAS] | 2062-78-4 | FR M3695 | Neuroleptic | |
| Pinacidil | | 85371-64-8 | | | |
| pinaverium | Morpholinium, 4-[(2-bromo-4,5-dimethoxyphenyl)methyl]-4-[2-[2-(6,6-dimethylbicyclo[3.1.1]hept-2-yl)ethoxy]ethyl]-, [CAS] | 53251-94-8 59995-65-2 | EP 406743 | Antispasmodic | Irritable bowel syndrome |
| pinazepam | 2H-1,4-Benzodiazepin-2-one, 7-chloro-1,3-dihydro-5-phenyl-1-(2-propynyl)-[CAS] | 52463-83-9 | DE 2339790 | Anxiolytic | |
| Pindolol | | 13523-86-9 | | | |
| pioglitazone | 2,4-Thiazolidinedione, 5-[[4-[2-(5-ethyl-2-pyridinyl)ethoxy]phenyl]methyl]-, monohydrochloride (+/−)-[CAS] | 11025-46-8 112529-15-4 | EP 193256 | Antidiabetic | Diabetes, Type II |
| Pipacycline | | 1110-80-1 | | | |
| Pipamazine | | 84-04-8 | | | |
| Pipamperone | | 1893-33-0 | | | |
| Pipazethate | | 2167-85-3 | | | |
| Pipebuzone | | 27315-91-9 | | | |
| Pipecurium | | 52212-02-9 | | | |
| pipecuronium | Piperazinium, 4,4'-[(2β,3Alpha,5Alpha,16β,17β)-3,17-bis(acetyloxy)androstane-2,16-diyl]bis[1,1]-dimethyl-, [CAS] | 52212-02-9 68399-57-5 | GB 1398050 | Muscle relaxant | Anaesthesia, adjunct |
| pipemidic acid | Pyrido[2,3-d]pyrimidine-6-carboxylic acid, 8-ethyl-5,8-dihydro-5-oxo-2-(1-piperazinyl)-[CAS] | 51940-44-4 | GB 1451911 | Antibacterial, other | Infection, urinary tract |
| Pipenzolate Bromide | | 125-51-9 | | | |
| Piperacetazine | | 3819-00-9 | | | |
| piperacillin | 4-Thia-1-azabicyclo[3.2.0]heptane-2-carboxylic acid, 6-[[[[(4-ethyl-2,3-dioxo-1-piperazinyl)carbonyl]amino]phenylacetyl]-amino]-3,3-dimethyl-7-oxo-,[2S-[2Alpha,5Alpha,6β(S*)]]-[CAS] | 59703-84-3 61477-96-1 | GB 1508062 | Penicillin, injectable | Infection, general |
| Piperazine Adipate | | 142-88-1 | | | |
| Piperidione | | 77-03-2 | | | |
| Piperidolate | | 82-98-4 | | | |
| Piperilate | | 4546-39-8 | | | |
| piperine analogues | | | WO 002544 | Dermatological | Vitiligo |
| Piperocaine | | 136-82-3 | | | |
| Piperonal | | 120-57-0 | | | |
| Piperoxan | | 59-39-2 | | | |

TABLE IV-continued

| API Generic Name | API Chemical Name | CAS No. | Patent Reference | Example of Therapeutic Use | Example of Indication |
|---|---|---|---|---|---|
| Piperylone | | 2531-4-6 | | | |
| Pipobroman | | 54-91-1 | | | |
| Piposulfan | | 2608-24-4 | | | |
| pipotiazine | Hexadecanoic acid, 2-[1-[3-[2-[(dimethylamino)sulfonyl]-10H-phenothiazin-10-yl]propyl]-4-piperidinyl]ethyl ester [CAS] | 37517-26-3 39860-99-6 | U.S. 4,782,077 | Neuroleptic | |
| Pipoxolan | | 18174-58-8 | | | |
| Pipradrol | | 467-60-7 | | | |
| piprozolin | Acetic acid, [3-ethyl-4-oxo-5-(1-piperidinyl)-2-thiazolidinylidene]-, ethyl ester [CAS] | 17243-64-0 | U.S. 3,971,794 | GI inflammatory/bowel disorders | Motility dysfunction, GI, general |
| Piracetam | | 7491-74-9 | | | |
| pirarubicin | 5,12-Naphthacenedione, 10-[[3-amino-2,3,6-trideoxy-4-O-(tetrahydro-2H-pyran-2-yl)-Alpha-L-lyxo-hexopyranosyl]oxy]-7,8,9,10-tetrahydro-6,8,11-trihydroxy-8-(hydroxyacetyl)-1-methoxy-, [8S-[8Alpha,10Alpha(S*)]]-[CAS] | 72496-41-4 | U.S. 4,303,785 | Anticancer, antibiotic | Cancer, breast |
| Pirazolac | | 71002-09-0 | | | |
| pirbuterol | 2,6-Pyridinedimethanol, Alpha6-[[(1,1-dimethylethyl)amino]methyl]-3-hydroxy-, monoacetate (salt) [CAS] | 38029-10-6 38677-81-5 65652-44-0 1043-21-6 | U.S. 3,786,160 | Antiasthma | Asthma |
| Pirenoxine | | | | | |
| pirenzepine | 6H-Pyrido[2,3-b][1,4]benzodiazepin-6-one, 5,11-dihydro-11-[(4-methyl-1-piperazinyl)acetyl]-[CAS] | 28797-61-7 29868-97-1 | FR 1505795 | Antiulcer | |
| piretanide | Benzoic acid, 3-(aminosulfonyl)-4-phenoxy-5-(1-pyrrolidinyl)-[CAS] | 55837-27-9 | U.S. 4,010,273 | Antihypertensive, diuretic | Hypertension, general |
| pirfenidone | 2(1H)-Pyridinone, 5-methyl-1-phenyl-[CAS] | 53179-13-8 | | Respiratory | Fibrosis, pulmonary |
| piribedil | Pyrimidine, 2-[4-(1,3-benzodioxol-5-ylmethyl)-1-piperazinyl]-[CAS] | 3605-01-4 | U.S. 3,299,067 | Vasodilator, peripheral | Parkinson's disease |
| Piridocaine | | 87-21-8 | | | |
| Pirifibrate | | 55285-45-5 | | | |
| Piritramide | | 302-41-0 | | | |
| Piritrexim | | 72732-56-0 | | | |
| pirlindole | 1H-Pyrazine[3,2,1-jk]carbazole, 2,3,3a4,5,6-hexahydro-8-methyl-[CAS] | 16154-78-2 60762-57-4 | SU 276060 | Antidepressant | Depression, general |
| pimenol | 2-Pyridinemethanol, Alpha-[3-(2,6-dimethyl-1-piperidinyl)propyl]-Alpha,phenyl-, cis-(+)-[CAS] | 61477-94-9 68252-19-7 | U.S. 4,112,103 | Antiarrhythmic | Tachycardia, supraventricular |
| Piroctone | | 50650-76-5 | | | |
| Piroheptine | | 16378-21-5 | | | |
| Piromidic Acid | | 19562-30-2 | | | |
| piroxicam | 2H-1,2-Benzothiazine-3-carboxamide, 4-hydroxy-2-methyl-N-2-pyridinyl-, 1,1-dioxide [CAS] | 36322-90-4 | U.S. 3,862,319 | Anti-inflammatory | |

TABLE IV-continued

| API Generic Name | API Chemical Name | CAS No. | Patent Reference | Example of Therapeutic Use | Example of Indication |
|---|---|---|---|---|---|
| piroxicam betadex | β-Cyclodextrin, compd. with 4-hydroxy-2-methyl-N-2-pyridinyl-2H-1,2-benzothiazine-3-carboxamide 1,1-dioxide-[CAS] | 121696-62-6 96684-39-8 | EP 153998 | Formulation, other | Pain, musculo-skeletal |
| piroxicam cinnamate | 2-Propenoic acid, 3-phenyl-, 2-methyl-3-[(2-pyridinylamino)carbonyl]-2H-1,2-benzothiazin-4-yl ester, S,S-dioxide [CAS] | 87234-24-0 | EP 79639 | Antiarthritic, other | Inflammation, general |
| Pirozadil | | 54110-25-7 | | | |
| Pirprofen | | 31793-07-4 | | | |
| pitavastatin | 6-Heptenoic acid, 7-[2-cyclopropyl-4-(4-fluorophenyl)-3-quinolinyl]-3,5-dihydroxy-, calcium salt (2:1), [S-[R*,S*-(E)]]-[CAS] | 147526-32-7 | EP 304063 | Hypolipaemic/Antiatherosclerosis | Hyper-lipidaemia, general |
| pivagabine | N-trimethylacetyl-4-aminobutyric acid | 69542-93-4 | | Neurological | Anxiety, general |
| pivaloyloxymethyl | Butanoic acid, (2,2-dimethyl-1-oxopropoxy)methyl ester [CAS] | 122110-53-6 | EP 302349 | Anticancer, other | Cancer, lung, non-small cell |
| Pivalylbenzhydrazine | | 306-19-4 | | | |
| Pivampicillin | | 33817-20-8 | | | |
| pivampicillin/pivmecillinam | | 98445-47-7 | | Penicillin, oral | Infection, general |
| Pivcefalexin | | 63836-75-9 | | | |
| pivmecillinam | 4-Thia-1-azabicyclo[3.2.0]heptane-2-carboxylic acid, 6-[[(hexahydro-1H-azepin-1-yl)methylene]amino]-3,3-dimethyl-7-oxo-, (2,2-dimethyl-1-oxopropoxy)methyl ester, [2S-(2Alpha,5Alpha,6β)]-[CAS] | 32886-97-8 | GB 1293590 | Penicillin, oral | Infection, general |
| pixantrone | Benz[g]isoquinoline-5,10-dione, 6,9-bis[(2-aminoethyl)amino]-, (2Z)-2-butenedioate(1:2) [CAS] | 144675-97-8 | EP 503537 | Anticancer, other | Cancer, lymphoma, non-Hodgkin's |
| pizotifen | 4-(9,10-dihydro-4H-benzo[4,5]cyclohepta[1,2-b]thien-4-ylidene)-1-methylpiperidine | 15574-96-6 | DE 2346747 | Antimigraine | |
| Pizotyline | | 15574-96-6 | | | |
| PKI-166 | Phenol, 4-(4-(((1R)-1-phenylethyl)amino)-1H-pyrrolo(2,3-d)pyrimidin-6-yl)-[CAS] | 187724-61-4 | | Anticancer, other | Cancer, general |
| p-Lactophenetide | | 539-08-2 | | | |
| Plafibride | | 63394-05-8 | | | |
| plasminogen activator | Plasminogen activator [CAS] | 105913-11-9 | EP 151996 | Fibrinolytic | Infarction, myocardial |
| Plasmocid | | 551-01-9 | | | |
| Platonin | | 3571-88-8 | | | |
| Plaunotol | | 64218-02-6 | | | |
| PLD-118 | Cyclopentanecarboxylic acid, 2-amino-4-methylene-, (1R,2S)-[CAS] | 198022-65-0 | EP 805145 | Antifungal | Infection, Candida, general |
| PLD-147 | (OC-6-43)-Bis(acetato)(1-adamantylamine)ammine-dichloro-platinum (IV) | | | Anticancer, alkylating | Cancer, general |
| pleconaril | 1,2,4-Oxadiazole, 3-(3,5-dimethyl-4-(3-(3-methyl-5-isoxazolyl)propoxy)phenyl)-5-(trifluoromethyl)-[CAS] | 153168-05-9 | U.S. 5,464,848 | Antiviral, other | Infection, respiratory tract, general |

TABLE IV-continued

| API Generic Name | API Chemical Name | CAS No. | Patent Reference | Example of Therapeutic Use | Example of Indication |
|---|---|---|---|---|---|
| Plicamycin | | 18379-89-7 | | | |
| p-Methyldiphen-hydramine | | 19804-27-4 | | | |
| PMS-601 | | | WO 0001677 | Antiviral, Anti-HIV | Infection, HIV/AIDS |
| Pneumococcal Vaccine, Diphtheria Conjugate | | | | | |
| Pneumococcal Vaccine, Polyvalent | | | | | |
| PNU-288034 | N-[[(5s)-3[4[(1,1-dioxido-4-thiomorpholinyl)3,5-difluorophenyl]-2-oxo-5-oxazolidinyl]methyl]acetamide] | | | Antibiotic, other | Infection, general |
| Podophyllotoxin | | 518-28-5 | | | |
| polaprezinc | Zinc, bis(N-β-alanyl-L-histidinato-N3,OAlpha)-, (T-4)-[CAS] | 107667-60-7 | EP 303380 | Antiulcer | Ulcer, duodenal |
| Poldine Methylsulfate | | 545-80-2 | | | |
| Policresulen | | 9011-2-3 | | | |
| Polidexide | | 9064-92-0 | | | |
| polidocanol | | 3055-99-0 | | Vasoprotective, systemic | Venous insufficiency |
| Polyethylene glycol monododecyl ether | | 9002-92-0 | | | |
| Poliovirus Vaccine Inactivated | | | | | |
| poly-ADPRT inhibitors | | | WO 9845253 | Anticancer, other | Cancer, general |
| Polyestradiol Phosphate | | 28014-46-2 | | | |
| Polyphenon E | Polyphenon E [CAS] | 188265-33-0 | | Antiviral, other | Infection, human papilloma virus |
| Polythiazide | | 346-18-9 | | | |
| porfimer | Photofrin [CAS] | 87806-31-3 | U.S. 4,882,234 | Anticancer, other | Cancer, lung, non-small cell |
| Perfiromycin | | 801-52-5 | | | |
| posaconazole | D-threo-Pentitol, 2,5-anhydro-1,3,4-trideoxy-2-C-(2,4-difluorophenyl)-4-((4-(4-(4-((1S,2S)-1-ethyl-2-hydroxypropyl)-1,5-dihydro-5-oxo-4H-1,2,4-triazol-4-yl)phenyl)-1-piperazinyl)phenoxy)methyl)-1-(1H-1,2,4-triazol-1-yl)-[CAS] | 171228-49-2 | U.S. 5,714,490 | Antifungal | Infection, fungal, general |
| Posatirelin | | 7866473-0 | | | |
| potassium chloride | Potassium chloride (KCl) [CAS] | 7447-40-7 | | Formulation, oral, enteric-coated | |
| Potassium Gluconate | | 299-27-4 | | | |
| Potassium Gualacolsulfonate | | 1321-14-8 | | | |
| Potassium p-Aminobenzoate | | 138-84-1 | | | |

TABLE IV-continued

| API Generic Name | API Chemical Name | CAS No. | Patent Reference | | Example of Therapeutic Use | Example of Indication |
|---|---|---|---|---|---|---|
| Potassium Permanganate | | 7722-64-7 | | | | |
| Povidone | | 9003-39-8 | | | | |
| Povidone-Iodine | | 25655-41-8 | | | | |
| PP-117 | 3-Pyridinemethanol, hydrofluoride [CAS] | 62756-44-9 | DE | 2633028 | Formulation, oral, other | Unspecified |
| PR-2699 | (−)-(E)-[4-(2,4-dichlorophenyl)-1,3-dithiolan-2-ylidene]-1-imidazolylacetonitrile | | | | Antifungal | Infection, fungal, general |
| PR-608 | (S)-(−)-1-[4,4-bis(4-fluorophenyl)butyl]-4-(2-hydroxy-3-phenylaminopropyl)piperazine trihydrochloride | | | | Antiparkinsonian | Parkinson's disease |
| Practolol | | 6673-35-4 | | | | |
| Prajmaline | | 35080-11-6 | | | | |
| Pralidoxime | | 51-15-0 | | | | |
| pralnacasan | 6H-Pyridazino[1,2-a][1,2]diazepine-1-carboxamide, N-((2R,3S)-2-ethoxytetrahydro-5-oxo-3-furanyl)octahydro-9-((1-isoquinolinyl)carbonyl)amino)-6,10-dioxo-, (1S,9S)-[CAS] | 192755-52-5 | | | Antiarthritic, immunological | Arthritis, rheumatoid |
| pramipexole | 2,6-Benzothiazolediamine, 4,5,6,7-tetrahydro-N6-propyl-, (S)-[CAS] | 104632-26-0 | EP | 186087 | Antiparkinsonian | Parkinson's disease |
| pramiracetam | 1-Pyrrolidineacetamide, N-[2-[bis(1-methylethyl)amino]ethyl]-2-oxo-, monohydrochloride [CAS] | 68497-62-1 72869-16-0 75733-50-5 | U.S. | 4,145,347 | Cognition enhancer | Amnesia |
| Pramiverin | | 14334-40-8 | | | | |
| pramlintide | 1,2-Dithia-5,8,11,14,17-pentaazacycloeicosane, cyclic peptide deriv. [CAS] | 151126-32-8 | U.S. | 5,124,314 | Antidiabetic | Diabetes, Type I |
| Pramoxine | | 140-65-8 | | | | |
| pranidipine | 3,5-Pyridinedicarboxylic acid, 1,4-dihydro-2,6-dimethyl-4-(3-nitrophenyl)-, methyl 3-phenyl-2-propenyl ester, (E)-[CAS] | 99522-79-9 | EP | 173126 | Antihypertensive, other | Hypertension, general |
| Pranlukast | | 103177-37-3 | | | | |
| pranoprofen | 5H-[1]Benzopyrano[2,3-b]pyridine-7-acetic acid, Alpha-methyl-[CAS] | 52549-17-4 | | | Formulation, mucosal, topical | Ocular disorder, general |
| prasterone | Androst-5-en-17-one, 3-hydroxy-, (3β)-[CAS] | 53-43-0 | | | Labour inducer | |
| pratosartan | 4(3H)-Cycloheptimidazolone, 5,6,7,8-tetrahydro-2-propyl-3-[[2′-(1H-tetrazol-5-yl)[1,1′-biphenyl]-4-yl]methyl]-[CAS] | 153804-05-8 | U.S. | 5,409,947 | Antihypertensive, renin system | Hypertension, general |
| pravastatin | 1-Naphthaleneheptanoic acid, 1,2,6,7,8,8a-hexahydro-β,delta,6-trihydroxy-2-methyl-8-(2-methyl-1-oxobutoxy)-, monosodium salt, [1S-[1Alpha(βS*,deltaS*),2Alpha,6Alpha,8β(R*),8aAlpha]]-[CAS] | 81093-37-0 81131-70-6 | U.S. | 4,346,227 | Hypolipaemic/ Antiatherosclerosis | Atherosclerosis |
| Prazepam | | 2955-38-6 | | | | |

TABLE IV-continued

| API Generic Name | API Chemical Name | CAS No. | Patent Reference | Example of Therapeutic Use | Example of Indication |
|---|---|---|---|---|---|
| praziquantel | 4H-Pyrazino[2,1-a]isoquinolin-4-one, 2-(cyclohexylcarbonyl)-1,2,3,6,7,11b-hexahydro-[CAS] | 55268-74-1 | U.S. 4,001,411 | Schistosomicide | |
| prazosin | Piperazine, 1-(4-amino-6,7-dimethoxy-2-quinazolinyl)-4-(2-furanylcarbonyl)-[CAS] | 19216-56-9 19237-84-4 73771-04-7 | U.S. 4,092,315 | Antihypertensive, adrenergic | Hypertension, general |
| Predicarbate | | | | | |
| predinimustine | Pregna-1,4-diene-3,20-dione, 21-[4-[4-[bis(2-chloroethyl)amino]phenyl]-1-oxobutoxy]-11,17-dihydroxy-, (11β)-[CAS] | 29069-24-7 | GB 1272841 | Anticancer, alkylating | |
| Prednisolone | | 50-24-8 | | | |
| Prednisolone 21-Diethylaminoacetate | | 5626-34-6 | | | |
| prednisolone farnesil | Pregna-1,4-diene-3,20-dione, 11,17-dihydroxy-21-[(3,7,11-trimethyl-1-oxo-2,6,10-dodecatrienyl)oxy]-, [11β,21(2E,6E)]-[CAS] | 118244-44-3 | EP 332143 | Antiarthritic, other | Arthritis, rheumatoid |
| Prednisolone Sodium Phosphate | | 125-02-0 | | | |
| Prednisone | | 53-03-2 | | | |
| Predrival | | 15180-00-4 | | | |
| Prednylidene | | 599-33-7 | | | |
| pregabalin | Hexanoic acid, 3-(aminomethyl)-5-methyl-, (S)-[CAS] | 148553-50-8 | | Antiepileptic | Epilepsy, general |
| Pregnan-3α-ol-20-one | | 128-20-1 | | | |
| Premarin + trimegestone | Estra-4,9-dien-3-one, 17-(2-hydroxy-1-oxopropyl)-17-methyl-, [17β(S)]-[CAS] | 74513-62-5 | | Menopausal disorders | Hormone replacement therapy |
| prenalterol | Phenol, 4-[2-hydroxy-3-[(1-methylethyl)amino]propoxy]-, hydrochloride, (S)-[CAS] | 57526-81-5 61260-05-7 | GB 1470039 | Cardiostimulant | |
| Prenoxdiazine | | 982-43-4 | | | |
| Prenylamine | | 390-64-7 | | | |
| prezatide | Cuprate(1-), (N2-(N-glycyl-L-histidyl)-L-lysinato(N2-(N-glycyl-L-histidyl)-L-lysinato(2-))-, hydrogen, [CAS] | 130120-57-9 | | Vulnerary | Wound healing |
| Pridinol | | 511-45-5 | | | |
| Prifinium | | 4630-95-9 | | | |
| Prilocaine | | 721-50-6 | | | |
| Primaquine | | 90-34-6 | | | |
| Primidone | | 125-33-7 | | | |
| Prinomastat | | 192329-42-3 | | | |
| PRO-2000 | | | U.S. 5,614,599 | Antiviral, anti-HIV | Infection, HIV prophylaxis |
| Probenecid | | 57-66-9 | | | |
| Probucol | | 23288-49-5 | | | |
| procainamide | Benzamide, 4-amino-N-[2-(diethylamino)ethyl]-[CAS] | 51-06-9 | | Formulation, other | Arrhythmia, general |
| | | 614-39-1 | | | |
| Procaine | | 59-46-1 | | | |
| Procarbazine | | 671-16-9 | | | |

TABLE IV-continued

| API Generic Name | API Chemical Name | CAS No. | Patent Reference | | Example of Therapeutic Use | Example of Indication |
|---|---|---|---|---|---|---|
| procaterol | 2(1H)-Quinolinone, 8-hydroxy-5-[1-hydroxy-2-[(1-methylethyl)amino]butyl]-monohydrochloride [CAS] | 59828-07-8 60443-17-6 72332-33-3 | GB | 1496766 | Antiasthma | |
| prochlorperazine | 10H-Phenothiazine,2-chloro-10-[3-(4-methyl-1-piperazinyl)propyl]-, (Z)-2-butenedioate | 58-38-8 84-02-6 | | | Formulation, oral, other | Nausea and vomiting, general |
| procodazol | 1H-Benzimidazole-2-propanoic acid [CAS] | 23249-97-0 | ES | 407882 | Anticancer, immunological | Cancer, general |
| Procyclidine | | 77-37-2 | | | | |
| Procymate | | 13931-64-1 | | | | |
| Prodipine | | 31314-38-2 | | | | |
| Proflavine | | 92-62-6 | | | | |
| Progabide | | 62666-20-0 | | | | |
| progesterone | Prefn-4-ene-3,20-dione [CAS] | 57-83-0 | | | Formulation, transmucosal, systemic | Amenorrhoea |
| proglumetacin | 1H-Indole-3-acetic acid, 1-(4-chlorobenzoyl)-5-methoxy-2-methyl-, 2-(4-(3-((4-(benzoylamino)-5-(dipropylamino)-1,5-dioxopentyl)oxy)propyl)-1-piperazinyl)ethylester, (+/-)-[CAS] | 57132-53-3 59209-40-4 | GB | 1467568 | Anti-inflammatory | Inflammation, general |
| proglumide | Pentanoic acid, 4-(benzoylamino)-5-(dipropylamino)-5-oxo-, (+/-)-[CAS] | 6620-60-6 | DE | 1518125 | Antiulcer | Ulcer, gastric |
| Proheptazine | | 77-14-5 | | | | |
| Prolactin | | 9002-62-4 | | | | |
| Prolintane | | 493-92-5 | | | | |
| Prolonium | | 123-47-7 | | | | |
| Promazine | | 58-40-2 | | | | |
| Promedol | | 64-39-1 | | | | |
| Promegestone | | 34184-77-5 | | | | |
| promestriene | Estra-1,3,5(10)-triene, 17-methoxy-3-propoxy-, (17β)-[CAS] | 39219-28-8 | GB | 1337198 | Reproductive/gonadal, general | Acne |
| Promethazine | | 60-87-7 | | | | |
| Pronethalol | | 54-80-8 | | | | |
| propacetamol | Glycine, N,N-diethyl-, 4-(acetylamino)phenyl ester [CAS] | 66532-85-2 66532-86-3 | U.S. | 4,127,671 | Formulation, parenteral, other | |
| propafenone | 1-Propanone, 1-[2-[2-hydroxy-3-(propylamino)propoxy]phenyl]-3-phenyl-[CAS] | 54063-53-5 | GB | 1307455 | Antiarrhythmic | Fibrillation, ventricular |
| Propagermanium | | 12758-40-6 | | | | |
| Propallylonal | | 545-93-7 | | | | |
| Propamidine | | 104-32-5 | | | | |
| propane-1,2-diol | 1,2-propanediol | 57-55-6 | | | Formulation, dermal, topical | Infection, fungal, general |
| Propanidid | | 1421-14-3 | | | | |
| Propantheline | | 50-34-0 | | | | |
| Proparacaine | | 499-67-2 | | | | |
| Propatyl | | 2921-92-8 | | | | |

TABLE IV-continued

| API Generic Name | API Chemical Name | CAS No. | Patent Reference | | Example of Therapeutic Use | Example of Indication |
|---|---|---|---|---|---|---|
| propenidazole | ethyl trans-Alpha-acetyl-1-methyl-5-nitroimidazole-2-acrylate | 76448-31-2 | | | Antifungal | Infection, trichomoniasis |
| propentofylline | 1H-Purine-2,6-dione, 3,7-dihydro-3-methyl-1-(5-oxohexyl)-7-propyl-[CAS] | 55242-55-2 | GB | 1470220 | Neuroprotective | Ischaemia, cerebral |
| Propicillin | | 551-27-9 | | | | |
| Propiomazine | | 362-29-8 | | | | |
| Propionic Acid | | 79-09-4 | | | | |
| propionyl L-carnitine | 1-Propanaminium, 3-carboxy-N,N,N-trimethyl-2-(1-oxopropoxy)-, chloride, (R)-[CAS] | 119793-66-7 20084-19-1 | GB | 2008578 | Vasodilator, peripheral | Peripheral vascular disease |
| Propipocaine | | 3670-68-6 | | | | |
| Propipram | | 15686-91-6 | | | | |
| propiverine | 2,2-diphenyl-2-(1-propoxy)acetic acid (1-methylpiperid-4-yl) ester hydrochloride | 54556-98-8 60569-19-9 10321-12-7 | | | Urological | Incontinence |
| Propizepine | | 2078-54-8 | | | | |
| propofol | Phenol, 2,6-bis(1-methylethyl)-[CAS] | 2078-54-8 | U.S. | 4,056,635 | Anaesthetic, injectable | Anaesthesia |
| Propoxycaine | | 550-83-4 | | | | |
| Propoxyphene | | 469-62-5 | | | | |
| propranolol | 2-Propanol, 1-[(1-methylethyl)amino]-3-(1-naphthalenyloxy)-[CAS] | 318-98-9 525-66-6 | | | Formulation, modified-release, <=24 hr | Hypertension, general |
| Propylhexedrine | | 101-40-6 | | | | |
| Propyliodone | | 587-61-1 | | | | |
| Propylthiouracil | | 51-25-5 | | | | |
| Propyphenazone | | 479-92-5 | | | | |
| Proquazone | | 22760-18-5 | | | | |
| Proscillaridin | | 466-06-8 | | | | |
| Prostacyclin | | 35121-78-9 | | | | |
| Prostaglandin E$_1$ | | 745-65-3 | | | | |
| Prostaglandin E$_2$ | | 363-24-6 | | | | |
| Prostaglandin F$_{2\alpha}$ | | 551-11-1 | | | | |
| Prosultiamine | | 59-58-5 | | | | |
| Protein C | | 60202-16-6 | | | | |
| Protheobromine | | 50-39-5 | | | | |
| Prothipendyl | | 303-69-5 | | | | |
| Protiofate | | 58416-00-5 | | | | |
| Protionamide | | 14222-60-7 | | | | |
| protizinic acid | 10H-Phenothiazine-2-acetic acid, 7-methoxy-Alpha,10-dimethyl-, (+/-)-[CAS] | 13799-03-6 | U.S. | 3,450,698 | Anti-inflammatory | |
| Protoanemonin | | 108-28-1 | | | | |
| Protokol | | 136-70-9 | | | | |
| Protoporphyrin IX | | 553-12-8 | | | | |
| Protriptyline | | 438-60-8 | | | | |
| Pro-Urokinase | | 82657-92-9 | | | | |
| Proxazole | | 5696-9-3 | | | | |
| Proxibarbal | | 2537-29-3 | | | | |
| proxigermanium | Propanoic acid, 3,3'-(1,3-dioxo-1,3-digermoxanediyl)bis-[CAS] | 12758-40-6 | FR | 2005110 | Antiviral, other | Infection, hepatitis-B virus |

TABLE IV-continued

| API Generic Name | API Chemical Name | CAS No. | Patent Reference | Example of Therapeutic Use | Example of Indication |
|---|---|---|---|---|---|
| Proxyphylline | | 603-00-9 | | | |
| Prozapine | | 3426-8-2 | | | |
| Prucalopride | | 179474-81-8 | | | |
| prulifloxacin | 1H,4H-[1,3]Thiazeto[3,2-a]quinoline-3-carboxylic acid, 6-fluoro-1-methyl-7-[4-[(5-methyl-2-oxo-1,3-dioxol-4-yl)methyl]-1-piperazinyl]-4-oxo-[CAS] | 123447-62-1 | EP 315828 | Quinolone antibacterial | Infection, respiratory tract, general |
| Pseudococaine | | 478-73-9 | | | |
| pseudoephedrine + triprolidine | Benzenemethanol, Alpha-[1-(methylaminoethyl]-, hydrochloride, [S-(R*,R*)]-, mixt. with (E)-2-[1-(4-methylphenyl)-3-(1-pyrrolidinyl)-1-propenyl]pyridine monohydrochloride [CAS] | | | Formulation, modified-release, other | Rhinitis, allergic, general |
| pseudoephedrine | Benzenemethanol, Alpha-[1-(methylaminoethyl]-, [S-(R*,R*)]-[CAS] | 90-82-4, 8054-27-1, 345-78-8 | | Formulation, oral, other | Infection, respiratory tract, general |
| Psilocybin | | 520-52-5 | | | |
| PSK-3841 | Benzonitrile, 4-[3-(4-hydroxybutyl)-4,4-dimethyl-2,5-dioxo-1-imidazolidinyl]-2-(trifluoromethyl)-[CAS] | 154992-24-2 | | Dermatological | Alopecia, general |
| p-Sulfanilyl-benzylamine | | 4393-19-5 | | | |
| PT-141 | | | U.S. 6,051,555 | Male sexual dysfunction | Impotence |
| Pteropterin | | 89-38-3 | | | |
| Puromycin | | 53-79-2 | | | |
| PX-12 | 1-Methylpropyl 2-mercaptoimidazolyl disulfide | | | Anticancer, other | Cancer, general |
| Pyrantel | | 15686-83-6 | | | |
| Pyrazinamide | | 98-96-4 | | | |
| Pyridinol Carbamate | | 1882-26-4 | | | |
| Pyridostigmine Bromide | | 101-26-8 | | | |
| Pyridoxal 5-Phosphate | | 54-47-7 | | | |
| Pyridoxine | | 58-56-0 | | | |
| Pyrilamine | | 91-84-9 | | | |
| Pyrimethamine | | 58-14-0 | | | |
| Pyrinoline | | 1740-22-3 | | | |
| Pyrisuccideanol | | 33605-94-6 | | | |
| Pyrithione | | 1121-30-8 | | | |
| Pyrithyldione | | 77-04-3 | | | |
| Pyritinol | | 1098-97-1 | | | |
| Pyrocatechol | | 120-80-9 | | | |
| Pyrogallol | | 87-66-1 | | | |
| Pyronaridine | | 74847-35-1 | | | |
| Pyrovalerone | | 3563-49-3 | | | |
| Pyroxylin | | 9004-70-0 | | | |
| Pyrrobutamine | | 91-82-7 | | | |
| Pyrrocaine | | 2210-77-7 | | | |

TABLE IV-continued

| API Generic Name | API Chemical Name | CAS No. | Patent Reference | Example of Therapeutic Use | Example of Indication |
|---|---|---|---|---|---|
| Pyrrolnitrin | | 1018-71-9 | | | |
| Pyrvinium Pamoate | | 3546-41-6 | | | |
| quazepam | 2H-1,4-Benzodiazepine-2-thione, 7-chloro-5-(2-fluorophenyl)-1,3-dihydro-1-(2,2,2-trifluoroethyl)-[CAS] | 36735-22-5 | U.S. 3,845,039 | Hypnotic/Sedative | Insomnia |
| Quercetin | | 117-39-5 | | | |
| quetiapine | Ethanol, 2-[2-(4-dibenzo[b,f][1,4]thiazepin-11-yl-1-piperazinyl)ethoxy]-, (E)-2-butenedioate (2:1) (salt) [CAS] | 111974-69-7 111974-72-2 | EP 240228 | Neuroleptic | Schizophrenia |
| Quinacillin | | 1596-63-0 | | | |
| quinacrine | N-(6-Chloro-2-methoxy-9-acridinyl)-N,N-diethyl-1,4-pentanediamine + 10H-Phenothiazine-10-propanamine, 2-chloro-N,N-dimethyl | 83-89-6 | | Neurological | Creutzfeldt-Jakob disease |
| quinagolide | Sulfamide, N,N-diethyl-N'-(1,2,3,4,4a,5,10,10a-octahydro-6-hydroxy-1-propylbenzo[g]quinolin-3-yl)-, (3Alpha,4aAlpha,10aβ)-(+/-)-[CAS] | 87056-78-8 94424-50-7 97805-49-7 | EP 77754 | Antiprolactin | Hyperprolactin-aemia |
| quinapril | 3-Isoquinolinecarboxylic acid, 2-[2-[[1-(ethoxycarbonyl)-3-phenylpropyl]amino]-1-oxopropyl]-1,2,3,4-tetrahydro-, [3S-[2[R*(R*)],3R*]]-[CAS] | 82586-55-8 85441-61-8 90243-99-5 | EP 49605 | Antihypertensive, renin system | Hypertension, general |
| quinaprilat | 3-Isoquinolinecarboxylic acid, 2-[2-[(1-carboxy-3-phenylpropyl)amino]-1-oxopropyl]-1,2,3,4-tetrahydro-, [3S-[2[R*(R*)],3R*]]-[CAS] | 82768-85-2 | EP 46953 | Antihypertensive, renin system | Hypertension, general |
| Quinapyramine | | 20493-41-8 | | | |
| Quinbolone | | 2487-63-0 | | | |
| Quinestradiol | | 1169-79-5 | | | |
| Quinestrol | | 152-43-2 | | | |
| Quinethazone | | 73-49-4 | | | |
| quinfamide | 2-Furancarboxylic acid, 1-(dichloroacetyl)-1,2,3,4-tetrahydro-6-quinolinyl ester [CAS] | 62265-68-3 | U.S. 3,997,542 | Amoebicide | |
| quinidine | Cinchonan-9-ol, 6-methoxy-, (9S)-, sulfate (1:1) (salt) [CAS] | 747-45-5 56-54-2 | | Formulation, modified-release, other | Arrhythmia, general |
| Quinine | | 130-95-0 | | | |
| Quinocide | | 525-61-1 | | | |
| Quinupramine | | 31721-17-2 | | | |
| Quinupristin | | 120138-50-3 | | | |
| R-107500 | cis-2,3,3a,8-tetrahydro-N,N-dimethyldibenz[c,f]isoxazolo[2,3-a]azepine-2-methanamine | | WO 9614320 | Anxiolytic | Anxiety, general |
| R-667 | | | WO 0204439 | COPD treatment | Emphysema, general |
| rabeprazole | 1H-Benzimidazole, 2-[[[4-(3-methoxypropoxy)-3-methyl-2-pyridinyl]methyl]sulfinyl]-, sodium salt- [CAS] | 117976-89-3 117976-90-6 | EP 268956 | Antiulcer | Ulcer, gastric |

TABLE IV-continued

| API Generic Name | API Chemical Name | CAS No. | Patent Reference | | Example of Therapeutic Use | Example of Indication |
|---|---|---|---|---|---|---|
| racecadotril | Glycine, N-[2-[(acetylthio)methyl]-1-oxo-3-phenylpropyl]-, phenylmethyl ester, (+/-)-[CAS] | 112573-72-5 81110-73-8 | EP | 38758 | Antidiarrhoeal | Diarrhoea, general |
| Racemethorphan | | 510-53-2 | | | | |
| raloxifene | Methanone, [6-hydroxy-2-(4-hydroxyphenyl)benzo[b]thien-3-yl][4-[2-(1-piperidinyl)ethoxy]phenyl]-, hydrochloride [CAS] | 82640-04-8 84449-90-1 | EP | 62503 | Osteoporosis treatment | Osteoporosis |
| raltitrexed | L-glutamic acid, N-[[5-[[(1,4-dihydro-2-methyl-4-oxo-6-quinazolinyl)methyl]methylamino]-2-thienyl]carbonyl]-[CAS] | 112887-68-0 | EP | 239362 | Anticancer, antimetabolite | Cancer, colorectal |
| ramatroban | 9H-Carbazole-9-propanoic acid, 3-[[(4-fluorophenyl)sulfonyl]amino]-1,2,3,4-tetrahydro-, (R)-[CAS] | 116649-85-5 | EP | 242518 | Antiallergic, non-asthma | Rhinitis, allergic, perennial |
| Ramifenazone | | 3615-24-5 | | | | |
| ramipril | Cyclopenta[b]pyrrole-2-carboxylic acid, 1-[2-[[1-(ethoxycarbonyl)-3-phenylpropyl]amino]-1-oxopropyl]octahydro-, [2S-[1[R*(R*)],2Alpha,3aβ,6aβ]]-[CAS] | 87269-97-4 87333-19-5 | EP | 79022 | Antihypertensive, renin system | Heart failure |
| ramosetron | Methanone, (1-methyl-1H-indol-3-yl)(4,5,6,7-tetrahydro-1H-benzimidazol-5-yl)-, monohydrochloride, (R)-[CAS] | 132907-72-3 132036-88-5 | EP | 381422 | Antiemetic | Nausea and vomiting, general |
| Ramot project No. 1097 | | 58994-96-0 | U.S. | 5,730,992 | Dermatological | Unspecified |
| Ranimustine | | | | | | |
| ranitidine | 1,1-Ethenediamine, N-[2-[[[5-[(dimethylamino)methyl]-2-furanyl]methyl]thio]ethyl]-N'-methyl-2-nitro-[CAS] | 66357-35-5 | U.S. | 4,128,658 | Antiulcer | Ulcer, duodenal |
| ranitidine bismuth citrate | 1,2,3-Propanetricarboxylic acid, 2-hydroxy-bismuth(3+) salt (1:1), compd. with N-(2-(((5-((dimethylamino)methyl)-2-furanyl)methyl)thio)ethyl)-N'-methyl-2-nil-ethenediamine (1:1)-[CAS] | 128345-62-0 | EP | 533281 | Antiulcer | Ulcer, duodenal |
| ranolazine | 1-Piperazineacetamide, N-(2,6-dimethylphenyl)-4-[2-hydroxy-3-(2-methoxyphenoxy)propyl]-, (+/-)-[CAS] | 95635-55-5 95635-56-6 | EP | 126449 | Antianginal | Angina, general |
| Ranpirnase Rapacuronium | | 133737-96-9 156137-99-4 | | | | |
| rasagiline | 1H-Inden-1-amine, 2,3-dihydro-N-2-propynyl-, (R)-, [CAS] | 161735-79-1 | U.S. | 5,457,133 | Antiparkinsonian | Parkinson's disease |
| Raubasine | | 483-04-5 | | | | |
| ravuconazole | Benzonitrile, 4-[2-[(1R,2R)-2-(2,4-difluorophenyl)-2-hydroxy-1-methyl-3-(1H-1,2,4-triazol-1-yl)propyl]-4-thiazolyl]-[CAS] | 182760-06-1 | | | Antifungal | Infection, meningitis, general |
| raxofelast | 2-Benzofuranacetic acid, 5-(acetyloxy)-2,3-dihydro-4,6,7-trimethyl-, (+)-[CAS] | 128232-14-4 | U.S. | 4,999,350 | Symptomatic antidiabetic | Nephropathy, diabetic |

TABLE IV-continued

| API Generic Name | API Chemical Name | CAS No. | Patent Reference | Example of Therapeutic Use | Example of Indication |
|---|---|---|---|---|---|
| razoxane | 2,6-Piperazinedione, 4,4'-(1-methyl-1,2-ethanediyl)bis-[CAS] | 21416-67-1, 21416-87-5 | GB 1234935 | Anticancer, other | Cancer, general |
| RC-529 | Tetradecanoic acid (1R)-1-(2-((2-deoxy 3-O-((3R)-1-oxo-3-(((1-oxotetradecyl)oxy)tetradecyl)amino-4-O-phosphono-β-D-glucopyranosyl)oxy)ethyl)amino)-2-oxoethyl)dodecyl ester; compd. with N,N-diethylethanamine (1:1) [CAS] | 216014-46-9 | | Immunostimulant, other | Vaccine adjunct |
| rebamipide | 4-Quinolinepropanoic acid, Alpha-[(4-chlorobenzoyl)amino]-1,2-dihydro-2-oxo-[CAS] | 90098-04-7 | DE 3324034 | Antiulcer | |
| rebimastat | L-Valinamide, N-((2S)-2-mercapto-1-oxo-4-(3,4,4-trimethyl-2,5-dioxo-1-imidazolidinyl)butyl)-L-leucyl-N,3-dimethyl-[CAS] | 259188-38-0 | | Anticancer, other | Cancer, lung, non-small cell |
| reboxetine | Morpholine, 2-[(2-ethoxyphenoxy)phenylmethyl]-, (R*,S*)-[CAS] | 71620-89-8, 98769-81-4 | U.S. 4,229,449 | Antidepressant | Depression, general |
| Remacemide remifentanil | 1-Piperidinepropanoic acid, 4-(methoxycarbonyl)-4-((1-oxopropyl)phenylamino)-methyl ester [CAS] | 128298-28-2 132539-07-2, 132875-61-7 | EP 383579 | Analgesic, other | Pain, general |
| reminetant | Tricyclo[3.3.1.13,7]decane-2-carboxylic acid, 2-[[[1-(7-chloro-4-quinolinyl)-5-(2,6-dimethoxyphenyl)-1H-pyrazol-3-yl]carbonyl]amino]-[CAS] | 146362-70-1 | EP 699438 | Neuroleptic | Schizophrenia |
| Remoxipride renzapride | Benzamide, 4-amino-N-1-azabicyclo[3.3.1]non-4-yl-5-chloro-2-methoxy-[CAS] | 80125-14-0 109872-41-5 88721-77-1 | JP 58188885 | Gastroprokinetic | Irritable bowel syndrome |
| repaglinide | Benzoic acid, 2-ethoxy-4-[2-[[3-methyl-1-[2-(1-piperidinyl)phenyl]butyl]amino]-2-oxoethyl]-, (S)-[CAS] | 135062-02-1 | WO 9300337 | Antidiabetic | Diabetes, Type II |
| repertaxin L-lysine salt | 2(R)-4-Isobutylphenylpropionyl methanesulfonamide L-lysine salt | | WO 0024710 | Cardiovascular | Reperfusion injury |
| repinotan | 1,2-Benzisothiazol-3(2H)-one, 2-(4-(((3,4-dihydro-2H-1-benzopyran-2-yl)methyl)amino)butyl)-, 1,1-dioxide, monohydrochloride [CAS] | 144980-29-0 144980-77-8 | U.S. 5,137,901 | Neuroprotective | Ischaemia, cerebral |
| repirinast | 4H-Pyrano[3,2-c]quinoline-2-carboxylic acid, 5,6-dihydro-7,8-dimethyl-4,5-dioxo-, 3-methylbutyl ester [CAS] | 73080-51-0 | U.S. 4,298,610 | Antiasthma | |
| Reposal reproterol | 1H-Purine-2,6-dione, 7-[3-[[2-(3,5-dihydroxyethyl)amino]propyl]-3,7-dihydro-1,3-dimethyl-[CAS] | 3625-25-0 13055-82-8 54063-54-6 | FR M5969 | Antiasthma | Asthma |
| Rescimetol Rescinnamine | | 73573-42-9 24815-24-5 | | | |

TABLE IV-continued

| API Generic Name | API Chemical Name | CAS No. | Patent Reference | Example of Therapeutic Use | Example of Indication |
|---|---|---|---|---|---|
| Reserpiline | | 131-02-2 | | | |
| Reserpine | | 50-55-5 | | | |
| Resibufogenin | | 465-39-4 | | | |
| resiquimod | 1H-Imidazo(4,5-c)quinoline-1-ethanol(ethoxymethyl)-Alpha, Alpha-dimethyl-[CAS] | 144875-48-9 | U.S. 5,389,640 | Antiviral, other | Infection, hepatitis-C virus |
| Resorcinol | | 108-46-3 | | | |
| Reteplase | | 133652-38-7 | | | |
| retigabine | Carbamic acid, (2-amino-4-((4-fluorophenyl)methyl)aminophenyl)-, ethyl ester [CAS] | 150812-12-7 | DE 4200259 | Antiepileptic | Epilepsy, general |
| retinoic acid | Retinoic acid [CAS] | 302-79-4 | | Formulation, parenteral, other | Cancer, leukaemia, acute myelogenous |
| Revimid | | | U.S. 6,281,230 | Anticancer, other | Cancer, myelome |
| R-flurbiprofen | [1,1'-Biphenyl]-4-acetic acid, 2-fluoro-Alpha-methyl | 5104-49-4 | | Anticancer, other | Cancer, prostate |
| Rho (D) Immune Globulin (Human) | | | | | |
| Rho-kinase inhibitors | | | WO 0156988 | Antiasthma | Unspecified |
| ribavirin | 1H-1,2,4-Triazole-3-carboxamide, 1-β-D-ribofuranosyl-[CAS] | 36791-04-5 | U.S. 4,122,771 | Antiviral, other | Infection, haemorrhagic fever |
| Riboflavin | | 146-17-8 | | | |
| ribostamycin | D-Streptamine, O-2,6-diamono-2,6-dideoxy-Alpha-D-glucopyranosyl-(1-4)-O-[β-D-ribofuranosyl-(1-5)]-2-deoxy-[CAS] | 25546-65-0 | GB 1254883 | Aminoglycoside antibiotic | Infection, general |
| Ricinoleic Acid | | 141-22-0 | | | |
| Ridogrel | | 110140-89-1 | | | |
| rifabutin | Rifamycin XIV, 1',4-didehydro-1-deoxy-1,4-dihydro-5'-(2-methylpropyl)-1-oxo-[CAS] | 72559-06-9 | U.S. 4,219,478 | Antimycobacterial | Infection, Mycobacterium avium complex |
| rifalazil | Rifamycin VIII, 1',4-didehydro-1-deoxy-1,4-dihydro-3'-hydroxy-5'-[4-(2-methylpropyl)-1-piperazinyl]-1-oxo-[CAS] | 129791-92-0 129791-94-2 133633-12-2 | EP 366914 | Antimycobacterial | Infection, tuberculosis |
| rifametane | Rifamycin, 3-[[[1-(diethylamino)ethylidene]hydrazono]methyl]-[CAS] | 94168-98-6 | EP 119571 | Antimycobacterial | Infection, general |
| Rifamide | | 2750-76-7 | | | |
| rifampicin + trimethoprim | Rifamycin, 3-[[(4-methyl-1-piperazinyl)imino]methyl]-, mixt. with 5-[(3,4,5-trimethoxyphenyl)methyl]-2,4-pyrimidinediamine [CAS] | 61498-94-0 | | Formulation, fixed-dose combinations | |
| Rifampin | | 13292-46-1 | | | |
| Rifamycin SV | | 6998-60-3 | | | |
| rifapentine | Rifamycin, 3-[[(4-cyclopentyl-1-piperazinyl)imino]methyl]-[CAS] | 61379-65-5 | DE 2608218 | Antibiotic, other | Infection, tuberculosis |

TABLE IV-continued

| API Generic Name | API Chemical Name | CAS No. | Patent Reference | | Example of Therapeutic Use | Example of Indication |
|---|---|---|---|---|---|---|
| rifaximin | Epoxypentadeca[1,11,13]trieniminobenzofuro[4,5-e]pyrido[1,2-a]benzimidazole-1,15(2H)-dione, 25-(acetyloxy)-5,6,21,23-tetrahydroxy-27-methoxy-2,4,11,16,20,22,25,26-octamethyl-, [2S-(2R*,16Z,18E,20R*,22S*,23S*,24S*,25R*,26S*,27R*,28E)] | 80621-81-4 | GB | 2079270 | Antibiotic, other | Infection, GI tract |
| rifaximine cream | 4-deoxy-4'-methylpyrido[1,2-1,2]imidoazo[5,4-c]rifamycin SV | 80621-81-4 | BE | 888895 | Formulation, dermal, topical | Infection, dermatological |
| Rilmazafone rilmenidine | 2-Oxazolamine, N-(dicyclopropylmethyl)-4,5-dihydro-[CAS] | 99593-25-6 54187-04-1 54249-57-9 | DE | 2362754 | Antihypertensive, adrenergic | Hypertension, general |
| riluzole | 2-Benzothiazolamine, 6-(trifluoromethoxy)-[CAS] | 1744-22-5 | EP | 50551 | Neuroprotective | Amyotrophic lateral sclerosis |
| Rimantadine rimazolium | 4H-Pyridol[1,2-a]pyrimidinium, 3-(ethoxycarbonyl)-6,7,8,9-tetrahydro-1,6-dimethyl-4-oxo-, [CAS] | 13392-28-4 28610-84-6 35615-72-6 | DE | 2461349 | Analgesic, NSAID | |
| rimexolone | Androsta-1,4-dien-3-one, 11-hydroxy-16,17-dimethyl-17-(1-oxopropyl)-, (11β,16Alpha,17β)-[CAS] | 49697-38-3 | DE | 2301317 | Ophthalmological | Inflammation, ocular |
| Rimiterol rimonabant | 1H-Pyrazole-3-carboxamide, 5-(4-chlorophenyl)-1-(2,4-dichlorophenyl)-4-methyl-N-1-piperidinyl-, monohydrochloride [CAS] | 32953-89-2 158681-13-1 | U.S. | 5,624,941 | Anorectic/Antiobesity | Obesity |
| riodoxol Rioprostil risedronate | 1,3-Benzenediol, 2,4,6-triiodo-[CAS] Phosphonic acid, (1-hydroxy-2-(3-pyridinyl)ethylidene)bis-, monosodium salt | 19403-92-0 77287-05-9 115436-72-1 | U.S. EP | 3,755,251 304961 | Antiviral, other Osteoporosis treatment | Pagets disease |
| Risedronic Acid risperidone | 4H-Pyridol[1,2-a]pyrimidin-4-one, 3-[2-[4-(6-fluoro-1,2-benzisoxazol-3-yl)-1-piperidinyl]ethyl]-6,7,8,9-tetrahydro-2-methyl-[CAS] | 105492-24-6 106266-06-2 | EP | 196132 | Neuroleptic, formulation, optimized, microencapsulate | Schizophrenia |
| Ritanserin Ritipenem ritodrine | Benzenemethanol, 4-hydroxy-Alpha-[1-[[2-(4-hydroxyphenyl)ethyl]amino]ethyl]-, (R*,S*)-[CAS] | 87051-43-2 84845-57-8 23239-51-2 26652-09-5 | U.S. | 3,410,944 | Labour inhibitor | Labour, preterm |
| ritonavir | 2,4,7,12-Tetraazatridecan-13-oic acid, 10-hydroxy-2-methyl-5-(1-methylethyl)-1-(2-(1-methylethyl)-4-thiazolyl)-3,6-dioxo-8,11-bis(phenylmethyl)-, 5-thiazolyl-methyl ester, (5S-(5R*,8R*,10R*,11R*))-[CAS] | 155213-67-5 | WO | 9414436 | Antiviral, anti-HIV | Infection, HIV/AIDS |
| Rituximab rivastigmine | Carbamic acid, ethylmethyl-, 3[1-(dimethylamino)ethyl]phenyl ester, (S)-[CAS] | 174722-31-7 123441-03-2 129101-54-8 | DE | 3805744 | Cognition enhancer | Alzheimer's disease |

TABLE IV-continued

| API Generic Name | API Chemical Name | CAS No. | Patent Reference | Example of Therapeutic Use | Example of Indication |
|---|---|---|---|---|---|
| rizatriptan | 1H-Indole-3-ethanamine, N,N-dimethyl-5-(1H-1,2,4-triazol-1-ylmethyl)-, [CAS] | 145202-66-0 159776-67-7 144034-80-0 | EP 497512 | Antimigraine | Migraine |
| RJR-2403 | 3-Buten-1-amine, N-methyl-4-(3-pyridinyl)-, (3E)-, (2E)-2-butenedioate (1:1) [CAS] | 183288-99-5 | | Cognition enhancer | Alzheimer's disease |
| RNA Stealth Nucleosides | 5-Formyluridine | | | Antiviral, other | Infection, hepatitis-C virus |
| Ro-0094889 | 2′,3′-Di-O-acetyl-5′-vinylcytidine | | | Anticancer, antimetabolite | Cancer, general |
| Ro-61-1790 | 2-Pyridinesulfonamide, N-[6-(2-hydroxyethoxy)-5-(2-methoxyphenoxy)-2-[2-(1H-tetrazol-5-yl)-4-pyridinyl]-4-pyrimidinyl]-5-methyl-[CAS] | 180384-56-9 | WO 9619459 | Cardiovascular | Haemorrhage, subarachnoid |
| Rociverine | | 53716-44-2 | | | |
| rocuronium | Pyrrolidinium, 1-[(2β,3Alpha,5Alpha,16β,17β)-17-(acetyloxy)-3-hydroxy-2-(4-morpholinyl)androstan-16-yl]-1-(2-propenyl)-, bromide-[CAS] | 104855-17-6 104884-91-5 119302-91-9 143558-00-3 | EP 287150 | Muscle relaxant | Muscle spasm, general |
| rofecoxib | 2(5H)-Furanone, 4-(4-(methylsulfonyl)phenyl)-3-phenyl-[CAS] | 162011-90-7 | U.S. 5,474,995 | Analgesic, NSAID | Arthritis, osteo |
| roflumilast | Benzamide, 3-(cyclopropylmethoxy)-N-(3,5-dichloro-4-pyridinyl)-4-(difluoromethoxy)-[CAS] | 162401-32-3 | WO 9501338 | COPD treatment | Chronic obstructive pulmonary disease |
| rokitamycin | Leucomycin V, 4B-butanoate 3B-propanoate [CAS] | 74014-51-0 | U.S. 4,242,504 | Macrolide antibiotic | Infection, general |
| Rolipram | | 61413-54-5 | | | |
| Rolitetracycline | | 751-97-3 | | | |
| Romurtide | | 78113-36-7 | | | |
| Ronifibrate | | 42597-57-9 | | | |
| ropinirole | 2H-Indol-2-one, 4-[2-(dipropylamino)ethyl]-1,3-dihydro-, monohydrochloride-[CAS] | 91374-20-8 91374-21-9 | EP 266033 | Antiparkinsonian | Parkinson's disease |
| ropivacaine | 2-Piperidinecarboxamide, N-(2,6-dimethylphenyl)-1-propyl-, (S)-[CAS] | 84057-95-4 98717-15-8 | EP 239710 | Anaesthetic, local | Anaesthesia |
| Roquinimex | | 84088-42-6 | | | |
| rosaprostol | Cyclopentaneheptanoic acid, 2-hexyl-5-hydroxy-[CAS] | 56695-65-9 | GB 1523355 | Prostaglandin | |
| Rosaramicin | | 35834-26-5 | | | |
| Rose Bengal | | 632-68-8 | | | |
| rosiglitazone | 2,4-Thiazolidinedione, 5-((4-(2-methyl-2-pyridinylamino)ethoxy)phenyl)methyl)-, (Z)-2-butenedioate (1:1) [CAS] | 122320-73-4 155141-29-0 | U.S. 5,002,953 | Antidiabetic | Diabetes, Type II |
| rosoxacin | 3-Quinolinecarboxylic acid, 1-ethyl-1,4-dihydro-4-oxo-7-(4-pyridinyl)-[CAS] | 40034-42-2 | U.S. 3,753,993 | Quinolone antibacterial | Infection, gonorrhoea |

TABLE IV-continued

| API Generic Name | API Chemical Name | CAS No. | Patent Reference | Example of Therapeutic Use | Example of Indication |
|---|---|---|---|---|---|
| rostaporfin | Tin, dichloro[ethyl 3,4,10,21-tetrahydro-4,9,14,19-tetraethyl-18,19-dihydro-3,8,13,18-tetramethyl-20-phorbinecarboxylato(2-)-kappaN23,kappaN24,kappaN25,kappaN26]-, (OC-6-13)-[CAS] | 114494-17-6 | | Ophthalmological | Macular degeneration |
| rosuvastatin | 6-Heptenoic acid, 7-(4-(4-fluorophenyl)-6-(1-methylethyl)-2-(methyl(methylsulfonyl)amino)-5-pyrimidinyl)-3,5-dihydroxy- (S-(R*,S*-(E))) [CAS] | 147098-20-2 | JP 2648897 | Hypolipaemic/ Antitherosclerosis | Hyperlipidaemia, general |
| rotigotine | 1-Naphthalenol, 5,6,7,8-tetrahydro-6-[propyl[2-(2-thienyl)ethyl]amino]-, (S)- [CAS] | 99755-59-6 | U.S. 4,564,628 | Antiparkinsonian | Parkinson's disease |
| Rotraxate | | 92071-51-7 | | | |
| Roxarsone | | 121-19-7 | | | |
| roxatidine | Acetamide, 2-(acetyloxy)-N-[3-(1-piperidinylmethyl)phenoxy]propyl]-, [CAS] | 78628-28-1 93793-83-0 | EP 24510 | Antiulcer | Ulcer, gastric |
| roxifiban | L-Alanine, 3-(((3-(4-(aminoiminomethyl)phenyl)-4,5-dihydro-5-isoxazolyl)acetyl)amino)-N-(butoxycarbonyl)-, methyl ester, (R)-, [CAS] | 176022-59-6 | U.S. 5,849,736 | Antithrombotic | Thrombosis, general |
| Roxindol | | 112192-04-8 | | | |
| roxithromycin | Erythromycin, 9-[O-[(2-methoxyethoxy)methyl]oxime][CAS] | 80214-83-1 80214-86-4 | | Macrolide antibiotic | Infection, general |
| RPR-109881A | Benzenepropanoic acid, β-((1,1-dimethylethoxy)carbonyl)amino)-Alpha-hydroxy-(1S,2S,4S,7R,8aR,9aS,10aR,12aS,12bR)-7,12a-bis(acetyloxy)-1-(benzoyloxy)-1,3,47,8,9,9a,10,10a,12,12a,12b-dodecahydro-2-hydroxy-5,13,13-trimethyl-8-oxo-2,6-methano-2H-cyclodeca(3,4) cyclopropa (4,5) benz (1,2-b) oxet-4-yl ester, dihydrate Alpha R, betaS [CAS] | 192573-38-9 | | Anticancer, other | Cancer, lung, general |
| RPR-130401 | 4,9-Ethano-3aH-benz[f]isoindole-3a-carboxylicacid, 1,2,3,4,9,9a-hexahydro-2-[2-(2-methoxyphenyl)-1-oxo-2-propenyl]-9-(4-methylphenyl)-, (3aR,4S,9S,9aR)-rel- [CAS] | 210282-69-2 | WO 9829390 | Anticancer, other | Cancer, general |
| R-roscovitine | | | U.S. 6,316,456 | Anticancer, other | Cancer, lung, non-small cell |
| RS-0406 | N'N'-bis(3-hydroxyphenyl)pyridazine-3,6-diamine | 131179-95-8 | | Neuroprotective | Alzheimer's disease |
| RSR-13 | | 79-58-3 | | | |
| Rubijervine nubitecan | 1H-Pyrano(3',4':6,7)indolizino(1,2-b)quinoline-3,14(4H,12H)-dione, 4-ethyl-4-hydroxy-10-nitro-, (S)-[CAS] | 91421-42-0 | U.S. 6,485,514 | Anticancer, other | Cancer, pancreatic |

TABLE IV-continued

| API Generic Name | API Chemical Name | CAS No. | Patent Reference | Example of Therapeutic Use | Example of Indication |
|---|---|---|---|---|---|
| ruboxistaurin | 9H,18H-5,21:12,17-Dimethenodibenzo(e,k)pyrrolo(3,4-h)(1,4,13)oxadiazacyclohexadecine-18,20(19H)-dione,9-(((dimethylamino)methyl)-6,7,10,11-tetrahydro-, (S)-[CAS] | 169939-94-0 | | Symptomatic antidiabetic | Retinopathy, diabetic |
| Rufinamide | | 106308-44-5 | | | |
| rufloxacin | 7H-Pyrido[1,2,3-de]-1,4-benzothiazine-6-carboxylic acid, 9-fluoro-2,3-dihydro-10-(4-methyl-1-piperazinyl)-7-oxo-[CAS] | 101363-10-4 102052-47-1 106017-08-7 | EP 165375 | Quinolone antibacterial | Infection, general |
| rupatadine | 5H-Benzo[5,6]cyclohepta[1,2-b]pyridine, 8-chloro-6,11-dihydro-11-[1-[(5-methyl-3-pyridinyl)methyl]-4-piperidinylidene]-, trihydrochloride-[CAS] | 156611-76-6 | EP 0577957 | Antiallergic, non-asthma | Rhinitis, allergic, seasonal |
| Rutin | | 153-18-4 | | | |
| RWJ-54428 | 5-Thia-1-azabicyclo[4.2.0]oct-2-ene-2-carboxylic acid, 7-[[(2Z)-(2-amino-5-chloro-4-thiazolyl)(hydroxyimino)acetyl]amino]-3-[[3-[[(2-aminoethyl)thio]methyl]-4-pyridinyl]thio]methyl]-8-oxo-, (6R,7R)-[CAS] | 189448-35-9 | WO 3713772 | Cephalosporin, injectable | Infection, beta-lactamase resistant |
| S-0139 | Olean-12-en-28-oic acid, 27-[[3-[5-hydroxy-2-[(4-methoxy-1,4-dioxo-2-butenyl)amino]phenyl]-1-oxo-2-propenyl]oxy]-3-oxo-[CAS] | 193969-54-9 | WO 9727314 | Cardiovascular | Ischaemia, cerebral |
| S-15535 | Piperazine, 1-(2,3-dihydro-1,4-benzodioxin-5-yl)-4-(2,3-dihydro-1H-inden-2-yl)-[CAS] | 146998-34-7 | | Cognition enhancer | Cognitive disorder, general |
| S-18886 | 1-Naphthalenepropanoic acid, 6-(((4-chlorophenyl)sulfonyl)amino)-5,6,7,8-tetrahydro-2-methyl [CAS] | 165537-73-5 | | Antithrombotic | Thrombosis, general |
| S-34730 | 7-chloro-6-sulfamoyl-2-(1H)-quinoleinone-3-phosphonic acid | | | Neuroprotective | Unspecified |
| S-3578 | 7β-[2-(5-amino-1,2,4-thiadiazol-3-yl)-2(Z)-ethoxyiminoacetamido]-3-(1-(N-methylaminopropyl)-1H-imidazo[4,5-b]pyridinium-4-methyl-3-cephem-4-carboxylate monosulfate | | | Cephalosporin, injectable | Infection, general |
| S-36496 | 2-[N-[4-(4-Chlorophenylsulfonylamino)butyl]-N-[3-[(4-isopropylthiazol-2-yl)methyloxy]benzyl]sulfamoyl]benzoic acid | | | Antiasthma | Asthma |
| S-36527 | 2-[N-[4-(4-Chlorophenylsulfonylamino)butyl]-N-[3-[(4-(4-cyclobutylthiazol-2-yl)ethyl]benzyl]sulfamoyl]benzoic acid | | | Antiasthma | Asthma |

TABLE IV-continued

| API Generic Name | API Chemical Name | CAS No. | Patent Reference | Example of Therapeutic Use | Example of Indication |
|---|---|---|---|---|---|
| S-5751 | (1R,2R,3S,5S)-7-[2-(5-Hydroxybenzothiophen-3-ylcarboxamido)-6,6-dimethylbicyclo[3.1.1]hept-3yl]-5(Z)-heptenoic acid | | | Antiallergic, non-asthma | Allergy, general |
| S-8510 | Imidazo[4,5-d]pyrano[4,3-b]pyridine, 1,6,7,9-tetrahydro-2-(3-isoxazolyl)-, phosphate (1:1) [CAS] | 151466-23-8 | EP 556008 | Cognition enhancer | Alzheimer's disease |
| S-8921 | 2-Naphthalenecarboxylis acid, 1-(3,4-dimethoxyphenyl)-3-(3-ethyl-1-oxopentyl)-4-hydroxy-6,7,8-trimethoxy-, methyl ester [CAS] | 151165-96-7 | WO 9308155 | Hypolipaemic/ Antiatherosclerosis | Hypercholest-erolaemia |
| Sabcomeline | | 159912-53-5 | | | |
| Sabeluzole | | 104383-17-7 | | | |
| S-Adenosylmethionine | | 29908-03-0 | | | |
| safinamide | (S)(+)-2-[4-(3-fluorobenzyloxy)benzylamino]propanamide methansulfonate | 133865-89-1 | AU 711309 | Antiepileptic | Epilepsy, general |
| Salacetamide | | 487-48-9 | | | |
| Salazosulfadimidine | | 2315-8-4 | | | |
| salbutamol | 1,3-Benzenedimethanol,Alpha1-[[(1,1-dimethylethyl)amino]methyl]-4-hydroxy- [CAS] | 18559-94-9 | EP 451745 | Formulation, inhalable, topical, dry powder | Asthma |
| Salicin | | 138-52-3 | | | |
| Salicyl Alcohol | | 90-01-7 | | | |
| Salicylamide | | 65-45-2 | | | |
| Salicylamide O-Acetic Acid | | 25395-22-6 | | | |
| Salicylanilide | | 87-17-2 | | | |
| Salicylic Acid | | 69-72-7 | | | |
| Salicylsilfuric Acid | | 89-45-2 | | | |
| Salinazid | | 495-84-1 | | | |
| salmeterol | 1,3-Benzenedimethanol, 4-hydroxy-Alpha1-[[[6-(4-phenylbutoxy)hexyl]amino]methyl]-, (±)-1-hydroxy-2-naphthalenecarboxylate [CAS] | 89365-50-4 94749-08-3 | WO 9006775 | Antiasthma | Asthma |
| Salsalate | | 552-94-3 | | | |
| Salverine | | 6376-26-7 | | | |
| Samarium 153Sm Lexidronam | | 154427-83-5 | | | |
| sampatrilat | L-Tyrosine, N2-(methylsulfonyl)-L-lysyl-1-[(2S)-3-amino-2-carboxypropyl]cyclopentanecarbonyl- [CAS] | 129981-36-8 | EP 358398 | Antihypertensive, renin system | Hypertension, general |
| Sancycline | | 808-26-4 | | | |
| Saperconazole | | 110588-57-3 | | | |
| sapropterin | 4(1H)-Pteridinone, 2-amino-6-(1,2-dihydroxypropyl)-5,6,7,8-tetrahydro-, dihydrochloride, [6R-[6R*,(1R*,2S)]]- [CAS] | 69056-38-8 62989-33-7 | EP 191335 | Antidepressant | Hyperphenyl-alaninaemia |

TABLE IV-continued

| API Generic Name | API Chemical Name | CAS No. | Patent Reference | Example of Therapeutic Use | Example of Indication |
|---|---|---|---|---|---|
| saquinavir | Butanediamide, N1-[3-[[(1,1-dimethylethyl)amino]carbonyl]octahydro-2(1H)-isoquinolinyl]-2-hydroxy-1-(phenylmethyl)propyl]-2-[(2-quinolinylcarbonyl)amino]-, [3S-[2[1R*(R*),2S*],3Alpha,4aβ,8aβ]]-[CAS] | 127779-20-8 | EP 432695 | Antiviral, anti-HIV | Infection, HIV/AIDS |
| Saralasin | | 34273-10-4 | | | |
| saredutant | Benzamide, N-[4-[4-(acetylamino)-4-phenyl-1-piperidinyl]-2-(3,4-dichloropenyl)butyl]-N-methyl-, (S)-[CAS] | 142001-63-6 | EP 474561 | Antiasthma | Asthma |
| sarizotan | 3-Pyridinemethanamine, N-((3,4-dihydro-2H-1-benzopyran-2-yl)methyl)-5-(4-fluorophenyl)-[CAS] | 177975-08-5 | EP | Antiparkinsonian | Parkinson's disease |
| sarpogrelate | Butanedioic acid, mono[2-(dimethylamino)-1-[[2-[2-(3-methoxyphenyl)ethyl]phenoxy]methyl]ethyl] ester [CAS] | 125926-17-2 | EP 398326 | Antithrombotic | |
| Satigrel | | 111753-73-2 | | | |
| satraplatin | Platinum, bis(acetato-O)amminedichloro(cyclohexanamine)-, (OC-6-43)-[CAS] | 129580-63-8 | EP 328274 | Anticancer, alkylating | Cancer, prostate |
| Satumomab | | 144058-40-2 | | | |
| SB-237376 | | | | Antiarrhythmic | Fibrillation, atrial |
| SB-238039 | N-[3-[[2-(3,4-dimethoxyphenyl)ethyl]amino]propyl]-4-nitrobenzamide, HCl | | | Anticancer, other | Cancer, general |
| SB-277011 | (5-(2-phenylamino-4-pyrimidinyl)-4-)(4-fluorophenyl)-1-(4-piperidinyl)imidazole trans-N-[4-[2-(Cyano-1,2,3,4-tetrahydroisoquinolin-2-yl)ethyl]cyclohexyl]-4-quinolinecarboxamide | | | Neuroleptic | Schizophrenia |
| Scarlet Red | | 85-83-6 | | | |
| SCH-00013 | Benzonitrile, 4-[2-[3,6-dihydro-4-(1,4,5,6-tetrahydro-6-oxo-3-pyridazinyl)-1(2H)-pyridinyl]-1-hydroxyethyl]-[CAS] | 217963-18-3 | EP 618204 | Cardiostimulant | Heart failure |
| Sch-23863 | (2-[10,11-Dihydro-5-ethoxy-5H-dibenzo[a,d]cyclohepten-S-yl]-N,N-dimethyl-ethanamine | | | Immunosuppressant | Inflammation, general |
| saredutant | Benzamide, N-[4-[4-(acetylamino)-4-phenyl-1-piperidinyl]-2-(3,4-dichlorophenyl)butyl]-N-methyl-, (S)-[CAS] | 142001-63-6 | EP 474561 | Antiasthma | Asthma |
| sarizotan | 3-Pyridinemethanamine, N-((3,4-dihydro-2H-1-benzopyran-2-yl)methyl)-5-(4-fluorophenyl)-[CAS] | 177975-08-5 | EP | Antiparkinsonian | Parkinson's disease |
| sarpogrelate | Butanedioic acid, mono[2-(dimethylamino)-1-[[2-[2-(3-methoxyphenyl)ethyl]phenoxy]methyl]ethyl] ester [CAS] | 125926-17-2 | EP 398326 | Antithrombotic | |
| Satigrel | | 111753-73-2 | | | |

TABLE IV-continued

| API Generic Name | API Chemical Name | CAS No. | Patent Reference | | Example of Therapeutic Use | Example of Indication |
|---|---|---|---|---|---|---|
| satraplatin | Platinum, bis(acetato-O)amminedichloro(cyclohexanamine)-, (OC-6-43)-[CAS] | 129580-63-8 | EP | 328274 | Anticancer, alkylating | Cancer, prostate |
| Satumomab | | | | | | |
| SB-237376 | N-[3-[[2-(3,4-dimethoxyphenyl)ethyl]amino]propyl]-4-nitrobenzamide, HCl | 144058-40-2 | | | Antiarrhythmic | Fibrillation, atrial |
| SB-238039 | (5-(2-phenylamino-4-pyrimidinyl)-4-)(4-fluorophenyl)-1-(4-piperidinyl)imidazole | | | | Anticancer, other | Cancer, general |
| SB-277011 | trans-N-[4-[2-(6-Cyano-1,2,3,4-tetrahydroisoquinolin-2-yl)ethyl]cyclohexyl]-4-quinolinecarboxamide | | | | Neuroleptic | Schizophrenia |
| Scarlet Red | | 85-83-6 | | | | |
| SCH-00013 | Benzonitrile, 4-[2-[3,6-dihydro-4-(1,4,5,6-tetrahydro-6-oxo-3-pyridazinyl)-1(2H)-pyridinyl]-1-hydroxyethyl]-[CAS] | 217963-18-3 | EP | 618204 | Cardiostimulant | Heart failure |
| Sch-23863 | (2-[10,11-Dihydro-5-ethoxy-5H-dibenzo[a,d]cyclohepten-S-yl]-N,N-dimethyl-ethanamine | | | | Immunosuppressant | Inflammation, general |
| sertaconazole | 1H-Imidazole, 1-[2-[(7-chlorobenzo[b]thien-3-yl)methoxy]-2-(2,4-dichlorophenyl)ethyl]-[CAS] | 99592-32-2 | EP | 151477 | Antifungal | Infection, dermatological |
| sertindole | 2-Imidazolidinone, 1-[2-[4-[5-chloro-1-(4-fluorophenyl)-1H-indol-3-yl]-1-piperidinyl]ethyl]-[CAS] | 106516-24-9 | EP | 392959 | Neuroleptic | Schizophrenia |
| sertraline | 1-Naphthalenamine, 4-(3,4-dichlorophenyl)-1,2,3,4-tetrahydro-N-methyl-, (1S-cis)-[CAS] | 79559-97-0 79617-96-2 79617-97-3 64294-95-7 | EP | 30081 | Antidepressant | Depression, general |
| Setastine | | | | | | |
| sevelamer | 2-Propen-1-amine polymer with (chloromethyl)oxirane, hydrochloride [CAS] | 152751-57-0 52757-95-6 | U.S. | 5,496,545 | Urological | Renal failure |
| sevoflurane | Propane, 1,1,1,3,3,3-hexafluoro-2-(fluoromethoxy)-[CAS] | 28523-86-6 | DE | 1954268 | Anaesthetic, inhalation | Anaesthesia |
| SG-210 | 2H-1,4-Benzothiazine-2-acetic acid, 3,4-dihydro-3-oxo-4-((4,5,7-trifluoro-2-benzothiazolyl)methyl)-[CAS] | 143162-65-6 | | | Symptomatic antidiabetic | Neuropathy, diabetic |
| sibutramine | Cyclobutanemethanamine, 1-(4-chlorophenyl)-N,N-dimethyl-Alpha-(2-methylpropyl)-[CAS] | 106650-56-0 84485-00-7 | GB | 2098602 | Anorectic/ Antiobesity | Obesity |
| siccanin | (4aS-(4aAlpha,6aAlpha,11bAlpha,13aR*,13bAlpha))-1,2,3,4,4a,5,6a,11b,13b-decahydro-4,4,6a,9-tetramethyl-13H-benzo[a]furo[2,3,4-mn]xanthen-11-ol | 22733-60-4 | JP | 37003548 | Antifungal | |
| sildenafil | Piperazine, 1-((3-(4,7-dihydro-1-methyl-7-oxo-3-propyl-1H-pyrazolo(4,3-d)pyrimidin-5-yl)-4-ethoxyphenyl)sulfonyl)-4-methyl, 2-hydroxy-1,2,3-propanetricarboxylate-(1:1) [CAS] | 171599-83-0 139755-83-2 | WO | 9428902 | Male sexual dysfunction | Impotence |

TABLE IV-continued

| API Generic Name | API Chemical Name | CAS No. | Patent Reference | | Example of Therapeutic Use | Example of Indication |
|---|---|---|---|---|---|---|
| silodosin | 1H-Indole-7-carboxamide, 2,3-dihydro-1-(3-hydroxypropyl)-5-[(2R)-2-[[2-[2-(2,2,2-trifluoroethoxy)phenoxy]ethyl]amino]propyl]-[CAS] | 160970-54-7 | EP | 600675 | Urological | Dysuria |
| Silver Lactate | | 128-00-7 | | | | |
| Sch-57790 | 1-Piperazineacetonitrile, 4-cyclohexyl-alpha-[4-[(S)-(4-methoxyphenyl)sulfinyl]phenyl]-[CAS] | 221660-80-6 | | | Cognition enhancer | Alzheimer's disease |
| Sch-63390 | 7H-Pyrazolo[4,3-e][1,2,4]triazolo[1,5-c]pyrimidin-5-amine, 2-(2-furanyl)-7-(3-phenylpropyl)-[CAS] | 174648-45-4 | | | Antiparkinsonian | Parkinson's disease |
| Scillarenin | | 465-22-5 | | | | |
| Scopolamine | | 51-34-3 | | | | |
| Scopolamine N-Oxide | | 97-75-6 | | | | |
| scopolamine | Benzeneacetic acid, Alpha-(hydroxymethyl)-, 9-methyl-3-oxa-9-azatricyclo[3.3.1.02,4]non-7-yl ester, [7(S)-(1Alpha,2β,4β,5Alpha,7β)]-[CAS] | 51-34-3 | U.S. | 4,262,003 | Formulation, transdermal, other | Nausea and vomiting, general |
| SCS technology | | | | | | Unspecified |
| secalciferol | 9,10-Secocholesta-5,7,10(19)-triene-3,24,25-triol, (3β,5Z,7E,24R)-[CAS] | 55721-11-4 | U.S. EP | 6,046,188 301167 | Antiasthma Osteoporosis treatment | Osteo-dystrophy |
| secnidazole | 1H-Imidazole-1-ethanol, Alpha,2-dimethyl 5-nitro-[CAS] | 3366-95-8 | FR | M3270 | Protozoacide | Infection, trichomoniasis |
| Secobarbital | | 309-43-3 | | | | |
| selegiline | Benzeneethanamine, N,Alpha-dimethyl-N-2-propynyl, (R)-[CAS] | 14611-51-9 | GB | 1153578 | Antiparkinsonian | |
| Selenomethionine | | 1464-42-2 | | | | |
| Sematilide | | 101526-83-4 | | | | |
| Semotiadil | | 116476-13-2 | | | | |
| seocalcitol | 1,3-Cyclohexanediol, 5-((1-(6-ethyl-6-hydroxy-1-methyl-2,4-octadienyl)octahydro-7a-methyl-4H-inden-4-ylidene)ethylidene)-4-methylene-, (1R-(1Alpha(1R*,2E,4E),3aβ,4E(1R*,3S*,5Z),7aAlpha))-[CAS] | 134404-52-7 | WO | 9100855 | Anticancer, other | Cancer, liver |
| Sepimostat | | 103926-64-3 | | | | |
| seratrodast | Benzeneheptanoic acid, zeta-(2,4,5-trimethyl-3,6-dioxo-1,4-cyclohexadien-1-yl)-, (+/-)-[CAS] | 103187-07-1 112665-43-7 | EP | 232089 | Antiasthma | Asthma |
| sertaconazole | 1H-Imidazole, 1-[2-[(7-chlorobenzo[b]thien-3-yl)methoxy]-2-(2,4-dichlorophenyl)ethyl]-[CAS] | 99592-32-2 | EP | 151477 | Antifungal | Infection, dermatological |
| sertindole | 2-Imidazolidinone, 1-[2-[4-[5-chloro-1-(4-fluorophenyl)-1H-indol-3-yl]-1-piperidinyl]ethyl]-[CAS] | 106516-24-9 | EP | 392959 | Neuroleptic | Schizophrenia |
| sertraline | 1-Naphthalenamine, 4-(3,4-dichlorophenyl)-1,2,3,4-tetrahydro-N-methyl-, (1S-cis)-[CAS] | 79559-97-0 79617-96-2 79617-97-3 | EP | 30081 | Antidepressant | Depression, general |
| Setastine | | 64294-95-7 | | | | |

TABLE IV-continued

| API Generic Name | API Chemical Name | CAS No. | Patent Reference | | Example of Therapeutic Use | Example of Indication |
|---|---|---|---|---|---|---|
| sevelamer | 2-Propen-1-amine polymer with (chloromethyl)oxirane, hydrochloride [CAS] | 152751-57-0 52757-95-6 | U.S. | 5,496,545 | Urological | Renal failure |
| sevoflurane | Propane, 1,1,1,3,3,3-hexafluoro-2-(fluoromethoxy)-[CAS] | 28523-86-6 | DE | 1954268 | Anaesthetic, inhalation | Anaesthesia |
| SG-210 | 2H-1,4-Benzothiazine-2-acetic acid, 3,4-dihydro-3-oxo-4-((4,5,7-trifluoro-2-benzothiazolyl)methyl)-[CAS] | 143162-65-6 | | | Symptomatic antidiabetic | Neuropathy, diabetic |
| sibutramine | Cyclobutanemethanamine, 1-(4-chlorophenyl)-N,N-dimethyl-Alpha-(2-methylpropyl)-[CAS] | 106650-56-0 84485-00-7 | GB | 2098602 | Anorectic/Antiobesity | Obesity |
| siccanin | (4aS-(4aAlpha,6aAlpha,11bAlpha,13aR*,13bAlpha))-1,2,3,4,4a,5,6a,11b,13b-decahydro-4,4,6a,9-tetramethyl-13H-benzo[a]furo[2,3,4-mn]xanthen-11-ol | 22733-60-4 | JP | 37003548 | Antifungal | |
| sildenafil | Piperazine, 1-((3-(4,7-dihydro-1-methyl-7-oxo-3-propyl-1H-pyrazolo(4,3-d)pyrimidin-5-yl)-4-ethoxyphenyl)sulfonyl)-4-methyl, 2-hydroxy-1,2,3-propanetricarboxylate-(1:1) [CAS] | 171599-83-0 139755-83-2 | WO | 9428902 | Male sexual dysfunction | Impotence |
| silodosin | 1H-Indole-7-carboxamide, 2,3-dihydro-1-(3-hydroxypropyl)-5-[(2R)-2-[[2-(2,2,2-trifluoroethoxy)phenoxy]ethyl]amino]-propyl]-[CAS] | 160970-54-7 | EP | 600675 | Urological | Dysuria |
| Silver Lactate | | 128-00-7 | | | | |
| Silver Picrate | | 146-84-9 | | | | |
| silver sulfadiazine | N'-2-pyrimidinylsulfanilamide monosilver salt | 22199-08-2 68-35-9 | | | Anti-infective, other | Infection, general |
| Simetride | | 154-82-5 | | | | |
| Simfibrate | | 14929-11-4 | | | | |
| simvastatin | Butanoic acid, 2,2-dimethyl-, 1,2,3,7,8,8a-hexahydro-3,7-dimethyl-8-[2-(tetrahydro-4-hydroxy-6-oxo-2H-pyran-2-yl)ethyl]-1-naphthalenyl ester, [1S-[1Alpha,3Alpha,7β,8β(2S*,4S*),8aβ]]-[CAS] | 79902-63-9 | U.S. | 4,444,784 | Hypolipaemic/Antiatherosclerosis | Hyperlipidaemia, general |
| Sincalide | | 25126-32-3 | | | | |
| Sintropium Bromide | | 79467-19-9 | | | | |
| Sisomicin | | 32385-11-8 | | | | |
| sitafloxacin | 3-Quinolinecarboxylic acid, 7-(7-amino-5-azaspiro[2.4]hept-5-yl)-8-chloro-6-fluoro-1-(2-fluorocyclopropyl)-1,4-dihydro-4-oxo-, [1R-[1Alpha(S*),2Alpha]]-, hydrate | 127254-12-0 | EP | 341493 | Quinolone antibacterial | Infection, general |
| sitamaquine | 1,6-Hexanediamine, N,N-diethyl-N'-(6-methoxy-4-methyl-8-quinolinyl)-[CAS] | 5330-29-0 57695-04-2 | | | Protozoacide | Infection, leishmaniasis |
| sitaxsentan | N-(4-Chloro-3-methyl-5-isoxazolyl)-2-[[4,5-(methylenedioxy)-o-tolyl]acetyl]-3-thiophenesulfonamide | 184036-34-8 | U.S. | 5,464,853 | Antihypertensive, other | Hypertension, pulmonary |

TABLE IV-continued

| API Generic Name | API Chemical Name | CAS No. | Patent Reference | Example of Therapeutic Use | Example of Indication |
|---|---|---|---|---|---|
| sivelestat | Glycine, N-[2-[[[4-(2,2-dimethyl-1-oxopropoxy)phenyl]sulfonyl]amino]benzoyl]-[CAS] | 127373-66-4 | EP 347168 | Respiratory | Systemic inflammatory response syndrome |
| SJA-6017 | Butanamide, 2-[[(4-fluorophenyl)sulfonyl]amino]-N-((1S)-1-formyl-3-methylbutyl),-3-methyl-, (2S)-[CAS] | 190274-53-4 | EP 771565 | Ophthalmological | Cataract |
| SL-65-1498 | 6-Fluoro-9-methyl-2-phenyl-4-pyrrolidin-1-ylcarbonyl)-2,9-dihydro-1H-pyrido[3,4-b]indole-1-one | | EP 607076 | Anxiolytic | Anxiety, general |
| SLV-306 | (3S,2R)-3-[1-[2'-(Ethoxycarbonyl)-4'-phenyl-butyl-]cyclopentan-1-carbonylamino]-2,3,4,5-tetra-hydro-2-oxo-1H-benzazepin-1-acetic acid | | | Antihypertensive, diuretic | Hypertension, general |
| SLV-308 | 2(3H)-Benzoxazolone, 7-(4-methyl-1-piperaziniyl)-, monohydrochloride | 269718-83-4 | | Antiparkinsonian | Parkinson's disease |
| Sm153 lexidronam | Samarate(5-)-153Sm, (((1,2-ethanediylbis(nitrilobis(methylene)))-tetrakis(phosphonato))(8-)-N,N',OP,OP',OP''',OP'''')-, pentasodium, (OC-6-21)-[CAS] | 160369-78-8 | | Analgesic, other | Pain, cancer |
| S-Methylmethionine | | 4727-40-6 | | | |
| SMP-300 | N-(Aminoiminomethyl)-11-chloro-5,6,7,8-tetrahydro-8-oxo-4H-pyrrolo[3,2,1-k][1]benzazocine-2-carboxamide monomethanesulfonate monohydrate | | | Antianginal | Angina, general |
| SN-38 | (4S)-4,7,11-triethyl-3,4,12,14-tetrahydro-4,10-dihydroxy-3,14-dioxo-1H-pyrano[3',4':6,7]indolizino[1,2-b]quindin-9-yl | 100286-90-6 | | Formulation, optimized, liposomes | Cancer, colorectal |
| SNAP-7941 | ((+)-methyl (4S)-3-[[(3-(4-[3-(acetylamino)phenyl]-1-piperidinyl)propyl)amino]carbonyl]-4-(3,4-difluorophenyl)-6-(methoxymethyl)-2-oxo-1,2,3,4-tetrahydro-5-pyrimidinecarboxylate hydrochloride | | | Anxiolytic | Anxiety, general |
| SOA-132 | 2-Naphthalenecarboxamide, N-[2-[4-(diphenylmethoxy)-1-piperidinyl]ethyl]-3-hydroxy-5-(3-pyridinylmethoxy)-[CAS] | 143964-80-1 | | Formulation, inhalable, topical | Asthma |
| soblidotin | L-valinamide, N,N-dimethyl-L-valyl-N-[2-methoxy-4-[2-[1-methoxy-2-methyl-2-oxo-3-(2-phenylethyl)amino]propyl]-1-pyrrolidinyl]-1-(2-methylpropyl)-4-oxobutyl]-N-methyl-, [2S-[1[1R*(R*),2S*],2R*(1S*,2S*)]]-[CAS] | 149606-27-0 | WO 9303054 | Anticancer, other | Cancer, lung, non-small cell |
| Sobrerol | | 498-71-5 | | | |
| sobuzoxane | Carbonic acid, 1,2-ethanediylbis[(2,6-dioxo 4,1-piperazinediyl)methylene]bis(2-methylpropyl) ester [CAS] | 98631-95-9 | EP 140327 | Anticancer, other | Cancer, lymphoma, T-cell |

TABLE IV-continued

| API Generic Name | API Chemical Name | CAS No. | Patent Reference | Example of Therapeutic Use | Example of Indication |
|---|---|---|---|---|---|
| Sodium Arsanilate | | 127-85-5 | | | |
| Sodium Arsphenamine | | 1936-28-3 | | | |
| Sodium Chloride | | 14992-59-7 | | | |
| Sodium Dibunate | | 6484-89-5 | | | |
| Sodium Folate | | 149-44-0 | | | |
| Sodium Formaldehy desulfoxylate Sodium Glycerophosphate | | 1334-74-3 | | | |
| Sodium Hyaluronate | | | | | |
| Sodium Iodomethamate | | 519-26-6 | | | |
| Sodium Nitrite | | 7632-00-0 | | | |
| Sodium Nitroprusside | | 14402-89-2 | | | |
| sodium oxybate | Butyric acid, 4-hydroxy monosodium salt [CAS] | 502-85-2 | | Psychostimulant | Narcolepsy |
| Sodium Phenol-sulfonate | | 1300-51-2 | | | |
| sodium phenylbutyrate | Butyric acid, 4-phenyl-, sodium salt-[CAS] | 1716-12-7 | | Formulation, oral, other | Hyper-ammonaemia |
| sodium phosphate | Sodium phosphate monobasic monohydrate + sodium phosphate dibasic anhydrous | | U.S. 6,162,464 | Formulation, oral, other | Surgery adjunct |
| sodium prasterone sulfate | 3β-hydroxy-5-androsten-17-one(sodium sulfate dihydrate) | 137-40-6 | EP 380036 | Formulation, mucosal, topical | Labour, induction |
| Sodium Propionate | | | | | |
| sodium salicylate | Benzoic acid, 2-hydroxy-, monosodium salt [CAS] | 54-21-7 | | Formulation, oral, solubility-enhanced | Pain, general |
| Sodium Tetradecyl Sulfate | | 139-88-8 | | | |
| sofalcone | Acetic acid, [5-[(3-methyl-2-butenyl)oxy]-2-[3-[4-[(3-methyl-2-butenyl)oxy]phenyl]-1-oxo-2-propenyl]phenoxy]-[CAS] | 64506-49-6 | GB 1523241 | Antiulcer | |
| Solasulfone | | 133-65-3 | | | |
| solifenacin | Butanedioic acid compd with (1S)-(3R)-1-azabicyclo(2.2.2)oct-3-yl 3,4-dihydro-1-phenyl-2(1H)-isoquinolinecarboxylate (1:1) [CAS] | 242478-38-2 | | Urological | Overactive bladder |
| Sorbinicate | D-Glucitol, hexa-3-ptridinecarboxylate [CAS] | 6184-06-1 | BE 883352 | Hypolipaemic/ Antiatherosclerosis | |
| Sorbitol | | 50-70-4 | | | |
| Sorivudine | | 77181-69-2 | | | |
| sotalol | Methanesulfonamide, N-[4-[1-hydroxy-2-[(1-methylethyl)amino]ethyl]phenyl]-[CAS] | 3930-20-9 959-24-0 13642-52-9 554-71-2 | | Antiarrhythmic | |
| Soterenol | | | | | |
| Sozoiodolic Acid | | | | | |
| spaglumic acid | L-Glutamic acid, N-(N-acetyl-L-Alpha-aspartyl)-[CAS] | 3106-85-2 80619-64-3 | | Formulation, mucosal, topical | Conjunctivitis |
| sparfloxacin | 3-Quinolinecarboxylic acid, 5-amino-1-cyclopropyl-7-(3,5-dimethyl-1-piperazinyl)-6,8-difluoro-1,4-dihydro-4-oxo-, cis-[CAS] | 110871-86-8 | EP 221463 | Quinolone antibacterial | Infection, respiratory tract, general |

TABLE IV-continued

| API Generic Name | API Chemical Name | CAS No. | Patent Reference | | Example of Therapeutic Use | Example of Indication |
|---|---|---|---|---|---|---|
| Sparteine SPA-S-843 | Candicin D, 18-decarboxy-40-demethyl-3,7-dideoxo-N3'-((dimethylamino)acetyl)-18-((2-(dimethylamino)ethyl)aminocarbonyl)-3,7-dihydroxy-N47-methyl-5-oxo cyclic 15,19-hemiacetal, comp with L-ascorbic acid (1:2) [CAS] | 90-39-1 202748-83-2 | U.S. | 5,298,495 | Antifungal | Infection, fungal, general |
| Spasmolytol SPD-754 | 2(1H)-Pyrimidinone, 4-amino-1-(2-(hydroxymethyl)-1,3-oxathiolan-4-yl-(2R-cis)- | 25333-96-4 160707-69-7 | U.S. | 6,228,860 | Antiviral, anti-HIV | Infection, HIV/AIDS |
| Spectinomycin SPI-339 | 4-[3(4-Oxo-4,5,6,7-tetrahydroindol-yl)propionylamino]benzoic acid ethyl ester | 1695-77-8 | | | Cognition enhancer | Alzheimer's disease |
| Spiperone spirapril | 1,4-Dithia-7-azaspiro[4.4]nonane-8-carboxylic acid, 7-[2-[1-(ethoxycarbonyl)-3-phenylpropyl]amino]-1-oxopropyl]-, [8S-[7[R*(R*)],8R*]]-[CAS] | 749-02-0 83647-97-6 | EP | 50800 | Antihypertensive, renin system | Hypertension, general |
| Spirogermanium spironolactone | Pregn-4-ene-21-carboxylic acid, 7-(acetylthio)-17-hydroxy-3-oxo-, Gamma-lactone,(7Alpha,17Alpha)-[CAS] | 41992-23-8 52-01-7 | EP | 124147 | Formulation, dermal, topical | Acne |
| SR-121463 | Benzamide, N-(1,1-dimethylethyl)-4-[[cis-5'-ethoxy-4-[2-(4-morpholinyl)ethoxy]-2'-oxospiro[cyclohexane-1,3'-[3H]indol]-1'(2'H)-yl]sulfonyl]-3-methoxy-[CAS] | 185913-78-4 | WO | 9715556 | Cardiostimulant | Heart failure |
| SR-144190 | Morpholine, 4-benzoyl-2-(3,4-difluorophenyl)-2-[2-[4-[[(dimethylamino)carbonyl][amino]-4-phenyl-1-piperidinyl]ethyl]-, (2R)-[CAS] | 201152-86-5 | WO | 9623787 | Anxiolytic | Anxiety, general |
| SR-146131 | 1H-Indole-1-acetic acid, 2-[[[4-(4-chloro-2,5-dimethoxyphenyl)-5-(2-cyclohexylethyl)-2-thiazolyl]amino]carbonyl]-5,7-dimethyl-[CAS] | 221671-61-0 | WO | 9915525 | Anorectic/Antiobesity | Obesity |
| SR-271425 | N-[1-[2-(diethylamino)ethylamino]-7-methoxy-9-oxo-9H-thioxanthen-4-ylmethyl]formamide | | | | Anticancer, alkylating | Cancer, general |
| SR-27897 | 1H-Indole-1-acetic acid, 2-[[[4-(2-chlorophenyl)-2-thiazolyl]amino]carbonyl]-[CAS] | 136381-85-6 | EP | 432040 | Anticancer, other | Cancer, pancreatic |
| SR-31747 | Cyclohexanamine, N-(3-chloro-4-cyclohexylphenyl)-2-propenyl)-N-ethyl-, hydrochloride, (Z)-[CAS] | 132173-07-0 | EP | 376850 | Anticancer, other | Cancer, myeloma |
| SR-58611 | Acetic acid, [[(7S)-7-[[(2R)-2-(3-chlorophenyl)-2-hydroxyethyl]amino]-5,6,7,8-tetrahydro-2-naphthalenyl]oxy]-, ethyl ester, hydrochloride [CAS] | 121524-09-2 | EP | 303546 | GI inflammatory/ bowel disorders | Irritable bowel syndrome |

TABLE IV-continued

| API Generic Name | API Chemical Name | CAS No. | Patent Reference | Example of Therapeutic Use | Example of Indication |
|---|---|---|---|---|---|
| SS732 | | | U.S. 5,385,900 | Formulation, mucosal, topical | Infection, ocular |
| SS-750 | (R)-(−)-2-(2,4-difluorophenyl)-1-(ethylsulfonyl)-1,1-difluoro-3-(1H-1,2,4-triazol-1-yl)-2-propanol | | U.S. 6,083,968 | Antifungal | Infection, fungal, general |
| β-alethine | Propanamide, N,N'(dithiodi-2,1-ethanediyl)bis(3-amino)-[CAS] | 646-08-2 | | Anticancer, immunological | Cancer, myeloma |
| SSR-149415 | (2S,4R)-1-[5-chloro-1-[(2,4-dimethoxyphenyl)sulfonyl]-3-(2-methoxyphenyl)-2-oxo-2,3-dihydro-1H-indol-3-yl]-4-hydroxy-N,N-dimethyl-2-pyrrolidone carboxamide | | WO 0155130 | Antidepressant | Depression, general |
| SSR-180575 | 2-(7-chloro-5-methyl-4-oxo-3-phenyl-4,5-dihydro-3H-pyridazino[4,5-6]indol-1-yl)-N,N-dimethylacetamide | | | Neuroprotective | Unspecified |
| SSR-181507 | (3-Exo)-8-benzoyl-N-[(2S)-7-chloro-2,3-dihydro-1,4-benzodioxin-2-yl]methyl]-8-azabicyclo[3.2.1]octane-3-methanamine HCl | | U.S. 6,221,879 | Neuroleptic | Schizophrenia |
| SSR-591813 | (5aS,8S,10aR)-5a,6,9,10-tetrahydro, 7H,11H-8,10a-methanopyrido[2',3':5,6]pyrano[2,3-d]azepine | | | Dependence treatment | Addiction, nicotine |
| SST-101 | D-Glucitol, 1,4:3,6-dianhydro-, dinitrate [CAS] | 87-33-2 | | Formulation, transdermal, other | Angina, general |
| SSY-726 | (−)-(R)-3-Methyl-2-(methylsulfonyl)-1-(1,2,4-triazol-1-yl)-2-[4-(trifluoromethyl)-phenyl]-2-butanol | | U.S. 5,147,886 | Antifungal | Infection, fungal, general |
| ST-200 | 1-Propanaminium, 2-(acetyloxy)-3-carboxy-N,N,N-trimethyl-, chloride, (R)-[CAS] | 5080-50-2 | DE 3015635 | Cognition enhancer | Dementia, senile, general |
| stachyfilin | | | WO 9711947 | Antiviral, other | Infection, influenza virus |
| Stallimycin | | | | | |
| Stampidine | | 636-47-5 | U.S. 6,350,736 | Antiviral, anti-HIV | Infection, HIV/AIDS |
| Stannous Pyrophosphate | | 15578-26-4 | | | |
| stannsoporfin | (OC-6-13)-Dihydrogen dichloro[7,12-diethyl-3,8,13,17-tetramethyl-21H,23H-porphine-2,18-dipropanoato(4-)-N21,N22,N23,N24]stannate(2-) | 106344-20-1 | | Hepatoprotective | Hyperbilirubinaemia |
| Stanolone Stanozolol | | 521-18-6 10418-03-8 (2H form); 302-96-5 (1H form) | | | |
| Staph aureus ther | | | U.S. 6,376,652 | Genomics-based drug discovery | Infection, MRSA |

TABLE IV-continued

| API Generic Name | API Chemical Name | CAS No. | Patent Reference | Example of Therapeutic Use | Example of Indication |
|---|---|---|---|---|---|
| STAT4 inhibitors | | | WO 9629341 | Immunosuppressant | Unspecified |
| stavudine | Thymidine, 2',3'-didehydro-3'-deoxy-[CAS] | 3056-17-5 | EP 501511 | Antiviral, anti-HIV | Infection, HIV/AIDS |
| Stenbolone | | 5197-58-0 | | | |
| stepronin | Glycine, N-[1-oxo-2-[(2-thienylcarbonyl)thio]propyl]-[CAS] | 72324-18-6 | U.S. 4,242,354 | Antitussive | Cough |
| Stibocaptate | | 27279-76-1 | | | |
| Stibophen | | 15489-16-4 | | | |
| Stilbamidine | | 122-06-5 | | | |
| stiripentol | 1-Penten-3-ol, 1-(1,3-benzodioxol-5-yl)-4,4-dimethyl-[CAS] | 49763-96-4 | | Antiepileptic | Epilepsy, general |
| Streptodornase | | 37340-82-2 | | | |
| Streptomycin | | 57-92-1 | | | |
| Streptonicozid | | 5667-71-0 | | | |
| Streptonigrin | | 3930-19-6 | | | |
| Streptozocin | | 18883-66-4 | | | |
| strontium ranelate | 3-Thiopheneacetic acid, 5-[bis(carboxymethyl)amino]-2-carboxy-4-cyano-, strontium salt (1:2)-[CAS] | 135459-87-9 | EP 415850 | Osteoporosis treatment | Osteoporosis |
| strontium-89 chloride | Strontium chloride (89SrCl2) [CAS] | 38270-90-5 | | Analgesic, other | Pain, cancer |
| Succimer | | 304-55-2 | | | |
| Succinimide | | 123-56-8 | | | |
| Succinylcholine | | 55-94-7 | | | |
| Succinylcholine | | 71-27-2 | | | |
| Succinylsulfathiazole | | 116-43-8 | | | |
| Succisulfone | | 5934-14-5 | | | |
| suclofenide | | 302279-49-3 | | | |
| sucralfate | Aluminium, hexadeca-μ-hydroxytetracosahydroxy(μ8-(1,3,4,6-tetra-O-sulfo-β-D-fructofuranosyl-Alpha-D-glucopyranoside tetrakis(hydrogen sulfato)(8-))hexadeca-[CAS] | 54182-58-0 | JP 58208233 | Antiulcer, Formulation, oral, other | Ulcer, general |
| sufentanil | Propanamide, N-[4-(methoxymethyl)-1-[2-(2-thienyl)ethyl]-4-piperidinyl]-N-phenyl-[CAS] | 56030-54-7 | U.S. 3,998,834 | Analgesic, other, formulation implant | Pain, general |
| sulbactam | 4-Thia-1-azabicyclo[3.2.0]heptane-2-carboxylic acid, 3,3-dimethyl-7-oxo-, 4,4-dioxide, (2S-cis)-[CAS] | 68373-14-8 | GB 2000138 | Antibiotic, other | Infection, general |
| sulbactam + ampicillin | | 117060-71-6 | U.S. 4,234,579 | Antibiotic, other | Infection, general |
| sulbenicillin | 4-Thia-1-azabicyclo[3.2.0]heptane-2-carboxylic acid, 3,3-dimethyl-7-oxo-6-[(phenylsulfoacetyl)amino]-, [2S-[2Alpha,5Alpha,6β(S*)]]-[CAS] | 28002-18-8 41744-40-5 | GB 1289358 | Penicillin, injectable | Infection, pseudomonal |
| Sulbentine | | 350-12-9 | | | |
| sulbutiamine | Propanoic acid, 2-methyl-, dithiobis[3-[1-[[(4-amino-2-methyl-5-pyrimidinyl)methyl]formylamino]-ethylidene]-3,1-propanediyl] ester [CAS] | 3286-46-2 67-16-3 | | Neurological | Unspecified |

TABLE IV-continued

| API Generic Name | API Chemical Name | CAS No. | Patent Reference | Example of Therapeutic Use | Example of Indication |
|---|---|---|---|---|---|
| sulconazole | 1H-Imidazole, 1-[2-[[(4-chlorophenyl)methyl]thio]-2-(2,4-dichlorophenyl)ethyl]-, (+/-)-[CAS] | 61318-90-9 61318-91-0 | U.S. 4,055,652 | Antifungal | Infection, fungal, general |
| Sulesomab | | 167747-19-5 | | | |
| Sulfabenzamide | | 127-71-9 | | | |
| Sulfacetamide | | 144-80-9 | | | |
| Sulfachlorpyridazine | | 80-32-0 | | | |
| Sulfachrysoidine | | 485-41-6 | | | |
| Sulfacytine | | 17784-12-2 | | | |
| Sulfadiazine | | 68-35-9 | | | |
| Sulfadicramide | | 115-68-4 | | | |
| Sulfadimethoxine | | 122-11-2 | | | |
| Sulfadoxine | | 2447-57-6 | | | |
| Sulfaethidole | | 94-19-9 | | | |
| Sulfaguanidine | | 57-67-0 | | | |
| Sulfaguanole | | 27031-08-9 | | | |
| Sulfalene | | 152-47-6 | | | |
| Sulfaloxic Acid | | 14376-16-0 | | | |
| Sulfamerazine | | 127-79-7 | | | |
| Sulfameter | | 651-06-9 | | | |
| Sulfamethazine | | 57-68-1 | | | |
| Sulfamethizole | | 144-82-1 | | | |
| Sulfamethomidine | | 3772-76-7 | | | |
| Sulfamethoxazole | | 723-46-6 | | | |
| Sulfamethoxypyridazine | | 80-35-3 | | | |
| Sulfametrole | | 32909-92-5 | | | |
| Sulfamidochrysoidine | | 103-12-8 | | | |
| Sulfamoxole | | 729-99-7 | | | |
| Sulfanilamide | | 63-74-1 | | | |
| Sulfanilic Acid | | 121-57-3 | | | |
| Sulfanilylurea | | 547-44-4 | | | |
| Sulfaperine | | 599-88-2 | | | |
| Sulfaphenazole | | 526-08-9 | | | |
| Sulfaproxyline | | 116-42-7 | | | |
| Sulfapyrazine | | 116-44-9 | | | |
| Sulfapyridine | | 144-83-2 | | | |
| Sulfarside | | 1134-98-1 | | | |
| Sulfarsphenamine | | 618-82-6 | | | |
| sulfasalazine | Benzoic acid, 2-hydroxy-5-[[4-[(2-pyridinylamino)sulfonyl]phenyl]azo]-[CAS] | 599-79-1 | | Formulation, oral, enteric-coated | Arthritis, rheumatoid |
| Sulfasomizole | | 632-00-8 | | | |
| Sulfasymazine | | 1984-94-7 | | | |
| Sulfathiazole | | 72-14-0 | | | |
| Sulfathiourea | | 515-49-1 | | | |
| Sulfinalol | | 66264-77-5 | | | |
| Sulfinpyrazone | | 57-96-5 | | | |
| Sulfiram | | 95-05-6 | | | |
| Sulfisomidine | | 515-64-0 | | | |
| Sulfisoxazole | | 127-69-5 | | | |

TABLE IV-continued

| API Generic Name | API Chemical Name | CAS No. | Patent Reference | Example of Therapeutic Use | Example of Indication |
|---|---|---|---|---|---|
| Sulfobromophthalein | | 71-67-0 | | | |
| Sulfonethylmethane | | 76-20-0 | | | |
| Sulfoniazide | | 3691-81-4 | | | |
| Sulfonmethane | | 115-24-2 | | | |
| Sulforidazine | | 14759-06-9 | | | |
| Sulfoxone | | 144-75-2 | | | |
| sulindac | cis-5-fluoro-2-methyl-1-[(p-methylsulfinyl)benzylidene]indene-3-acetic acid | 38194-50-2 | U.S. 3,725,548 | Anti-inflammatory | Inflammation, general |
| Sulisatin | | 54935-03-4 | | | |
| Sulisobenzone | | 4065-45-6 | | | |
| Sulmarin | | 29334-07-4 | | | |
| Sulmazole | | 73384-60-8 | | | |
| Suloctidil | | 54063-56-8 | | | |
| Sulphan Blue | | 129-17-9 | | | |
| sulpiride | Benzamide, 5-(aminosulfonyl)-N-[(1-ethyl-2-pyrrolidinyl)methyl]-2-methoxy-[CAS] | 15676-16-1 | | Alimentary/Metabolic, other | |
| sulprostone | 5-Heptenamide, 7-[3-hydroxy-2-(3-hydroxy-4-phenoxy-1-butenyl)-5-oxocyclopentyl]-N-(methylsulfonyl)-, [1R-[1Alpha(Z),2β(1E,3R*),3Alpha]]-[CAS] | 60325-46-4 | U.S. 4,024,179 | Prostaglandin | Abortion |
| sultamicillin | 4-Thia-1-azabicyclo(3.2.0)heptane-2-carboxylic acid, 6-((aminophenylacetyl)amino)-3,3-dimethyl-7-oxo-, (((3,3-dimethyl-7-oxo-4-thia-1-azabicyclo(3.2.0)hept-2-yl)carbonyl)oxy)methyl ester, S, S-dioxide, (2S-(2.alpha.(2R*,5S*),5,alpha.,6.beta.(S*)))-[CAS] | 117060-71-6 76497-13-7 | GB 2044255 | Penicillin, oral | Infection, general |
| Sulthiame | | 61-56-3 | | | |
| sultopride | Benzamide, N-[(1-ethyl-2-pyrrolidinyl)methyl]-5-(ethylsulfonyl)-2-methoxy-[CAS] | 53583-79-2 | FR M5916 | Neuroleptic | Psychosis, general |
| Sultosilic Acid | | 57775-26-5 | | | |
| sumanirole | 4H-Imidazo[4,5,1-ij]quinolin-2(1H)-one, 5,6-dihydro-5-(methylamino)-, (5R)-, (2Z)-2-butenedioate (1:1) [CAS] | 179386-44-8 | WO 9514020 | Antiparkinsonian | Parkinson's disease |
| sumatriptan | 1H-Indole-5-methanesulfonamide, 3-[2-(dimethylamino)ethyl]-N-methyl-, butanedioate (1:1)-[CAS] | 103628-46-2 103628-48-4 | EP 147107 | Antimigraine | Migraine |
| SUN-N8075 | | | | Neuroprotective | Infarction, cerebral |
| suplatast | 1-(4-amino-2,3,5-trimethylphenoxy)-3-(4-[4-(4-fluorobenzyl)phenyl]piperazin-1-yl)propan-2(s)-ol dimethanesulfonate Sulfonium, [3-[[4-(3-ethoxy-2-hydroxypropoxy)phenyl]amino]-3-oxopropyl]dimethyl-, [CAS] | 94055-76-2 | JP 59167564 | Antiasthma | Asthma |
| Suprofen | | 40828-46-4 | | | |
| Suramin | | 129-46-4 | | | |

TABLE IV-continued

| API Generic Name | API Chemical Name | CAS No. | Patent Reference | Example of Therapeutic Use | Example of Indication |
|---|---|---|---|---|---|
| surfactant TA | Beractant [CAS] | 108778-82-1 | WO 9117766 | Lung Surfactant | Respiratory distress syndrome, general |
| Suriclone | | 53813-83-5 | | | |
| Suxibuzone | | 27470-51-5 | | | |
| SYM-1010 | | | U.S. 5,830,998 | Antiapileptic | Epilepsy, general |
| SYM-2081 | L-Glutamic acid, 4-methyl-, (4R)-[CAS] | 31137-74-3 | | Analgesic, other | Pain, general |
| SYM-2207 | 4-(Aminophenyl)-1-methyl-6,7-(methylenedioxy)-N-butyl-1,2-dihydrophthalazine-2-carboxamide | | | Neuroprotective | Ischaemia, cerebral |
| Symclosene | | 87-90-1 | | | |
| Syn-1253 | 1-cyclopropyl-6-fluoro-8-methoxy-7-[3-(4-methyl-1,2,3-triazol-1-yl)pyrrolidin-1-yl]-4-oxo-1,4-dihydroquinoline 3-carboxylic acid | | | Quinolone antibacterial | Infection, peritoneum |
| Syn-2190 | 1-Azetidinesulfonic acid, 3-[[(2E)-[(1,4-dihydro-1,5-dihydroxy-4-oxo-2-pyridinyl)methoxy]imino]-2-thienylacetyl]amino]-2-methyl-4-oxo, (2S,3S)-[CAS] | 214963-75-4 | WO 9847895 | Antibacterial, other | Infection, general |
| Syn-2869 | 3H-1,2,4-Triazol-3-one, 4-(4-(4-((1R,2R)-2-(2,4-difluorophenyl)-2-hydroxy-1-methyl-3-(1H-1,2,4-triazol-1-yl)propyl)-1-piperazinyl)phenyl)-2,4-dihydro-2((4-(trifluoromethoxy)phenyl)methyl)-[CAS] | 210562-98-4 | U.S. 6,153,616 | Antifungal | Infection, Aspergillus |
| Synephrine | | 94-07-5 | | | |
| Syrosingopine | | 84-36-6 | | | |
| T-1095 | 1-Propanone, 3-(5-benzofuranyl)-1-(2-hydroxy-6-((6-O-methoxycarbonyl)-β-D-glucopyranosyl)oxy)-4-methylphenyl)-[CAS] | 209746-59-8 | EP 850948 | Antidiabetic | Diabetes, general |
| T-1249 | L-Phenylalaninamide, N-acetyl-L-tryptophyl-L-glutaminyl-L-Alpha-glutamyl-L-tryptophyl-L-Alpha-glutamyl-L-glutaminyl-L-lysyl-L-isoleucyl-L-threonyl-L-alanyl-L-leucyl-L-leucyl-L-Alpha-glutaminyl-L-glutaminyl-L-alanyl-L-glutaminyl-L-isoleucyl-L-glutaminyl-L-glutaminyl-L-Alpha-glutamyl-L-lysyl-L-Alpha-glutamyl-asparaginyl-L-tyrosyl-L-Alpha-glutamyl-L-leucyl-L-glutaminyl-L-lysyl-L-leucyl-L-Alpha-aspartyl-L-lysyl-l-trytophyl-L-ananyl-L-seryl-L-leucyl-L-trytophyl-L-Alpha-glutamyl-L-tryptophyl-[CAS] | 251562-00-2 | WO 9959615 | Antiviral, anti-HIV | Infection, HIV/AIDS |
| T-3912 | 1-cyclopropyl-8-methyl-7-[5-methyl-6-(methylamino)-3-pyridinyl]-4-oxo-1,4-dihydro-3-quinolinecarboxylic acid | | | Quinolone antibacterial | Infection, dermatological |

TABLE IV-continued

| API Generic Name | API Chemical Name | CAS No. | Patent Reference | | Example of Therapeutic Use | Example of Indication |
|---|---|---|---|---|---|---|
| T-588 | Benzo(b)thiophene-5-methanol, Alpha-((2-(diethylamino)ethoxy)methyl)-, hydrochloride, (R)-[CAS] | 142935-03-3 | EP | 565965 | Cognition enhancer | Alzheimer's disease |
| T-67 | Benzenesulfonamide, 2,3,4,5,6-pentafluoro-N-(3-fluoro-4-methoxyphenyl)-[CAS] | 195533-53-0 | | | Anticancer, other | Cancer, liver |
| T-82 | | | U.S. | 5,190,951 | Cognition enhancer | Alzheimer's disease |
| TA-2005 | 2(1H)-Quinolinone, 8-hydroxy-5-[1-hydroxy 2-[[2-(4-methoxyphenyl)-1-methylethyl]amino]ethyl]-, monohydrochloride, [R-(R*,R*)]-[CAS] | 137888-11-0 | U.S. | 4,579,854 | Antiasthma | Asthma |
| TA-2005 | 2(1H)-Quinolinone, 8-hydroxy-5-[1-hydroxy 2-[[2-(4-methoxyphenyl)-1-methylethyl]amino]ethyl]-, monohydrochloride, [R-(R*,R*)]-[CAS] | | WO | 189480 | Formulation, inhalable, solution | Asthma |
| TA-993 | 1,5-Benzothiazepin-4(5H)-one, 3-(acetyloxy)-5-[2-(dimethylamino)ethyl]-2,3-dihydro-8-methyl-2-(4-methylphenyl)-, (2R,3R)-rel-(−)-, (2Z)-2-butenedioate [CAS] | 122024-98-0 | JP | 01045376 | Antithrombotic | Peripheral vascular disease |
| tabimorelin | (R)-Alpha-[(E)-5-Amino-N,5-dimethyl-2-hexenamido]-N-methyl-N-[(R)-Alpha-(methylcarbamoyl)phenethyl]-2-napthalenepropionamide | 170851-70-4 193079-69-5 | | | Releasing hormones | Growth hormone deficiency |
| tacalcitol | 9,10-Secocholesta-5,7,10(19)-triene-1,3,24-triol, (1Alpha,3β,5Z,7E,24R)-[CAS] | 57333-96-7 93129-94-3 | EP | 129003 | Antipsoriasis | Keratosis |
| tacedinaline | Benzamide, 4-(acetylamino)-N-(2-aminophenyl)-[CAS] | 112522-64-2 | DE | 3613571 | Anticancer, other | Cancer, pancreatic |
| tacrine | 9-Acridinamine, 1,2,3,4-tetrahydro-[CAS] | 1684-40-8 321-64-2 | EP | 332147 | Cognition enhancer | Alzheimer's disease |
| Tacrolimus | | 104987-11-3 | | | | |
| tadalafil | Pyrazino(1',2':1,6)pyrido(3,4-b)indole 1,4-dione, 6-(1,3-benzodioxol-5-yl)-2,3,6,7,12,12a-hexahydro-2-methyl-, (6R-trans) [CAS] | 171596-29-5 | U.S. | 6,143,746 | Male sexual dysfunction | Impotence |
| tafenoquine | 1,4-Pentanediamine, N4-[2,6-dimethoxy-4-methyl-5-[3-(trifluoromethyl)phenoxy]-8-quinolinyl]-[CAS] | 106635-80-7 106635-81-8 80065-55-0 | U.S. | 4,617,394 | Antimalarial | Infection, malaria |
| tafluposide | | 179067-42-6 | WO | 9612727 | Anticancer, other | Cancer, general |
| TAK-375 | (S)-N-[2-(1,6,7,8-Tetrahydro-2H-indeno[5,4-b]furan-8-yl)]propionamide | | | | Hypnotic/Sedative | Insomnia |
| TAK-427 | 2-[6-[[3-[4-(Diphenylmethoxy)piperidino]imidazo[1,2-b]pyridazin-2-yl-2-methylpropionic acid dihydrate | | | | Antipruritic/allergic | Eczema, atopic |
| TAK-559 | (E)-4-[4-[5-Methyl-2-phenyl-1,3-oxazol-4-yl)methoxy]benzyloxyimino]-4-phenylbutyric acid | | | | Antidiabetic | Diabetes, general |

TABLE IV-continued

| API Generic Name | API Chemical Name | CAS No. | Patent Reference | | Example of Therapeutic Use | Example of Indication |
|---|---|---|---|---|---|---|
| Taka-Diastase | | 9001-19-8 | | | | |
| talampanel | 7H-1,3-Dioxolo[4,5-h][2,3]benzodiazepine,7-acetyl-5-(4-aminophenyl)-8,9-dihydro-8-methyl-,(8R)-[CAS] | 161832-65-1 | U.S. | 5,639,751 | Antiepileptic | Epilepsy, general |
| Talampicillin | | 47747-56-8 | | | | |
| talaporfin | N-[(2S,3S)-18-Carboxy-2-(2-carboxyethyl)-13-ethyl-2,3-dihydro-3,7,12,17-tetramethyl-8-vinyl porphyrin-20-yl]acetyl]-L-aspartic acid | 220201-34-3 | | | Radio/chemosensitizer | Cancer, lung, general |
| Talastine | | 16188-61-7 | | | | |
| Talbutal | | 115-44-6 | | | | |
| Talinolol | | 57460-41-0 | | | | |
| talipexole | 4H-Thiazolo[4,5-d]azepin-2-amine, 5,6,7,8-tetrahydro-6-(2-propenyl)-[CAS] | 101626-70-4 36085-73-1 | DE | 3503963 | Antiparkinsonian | Schizophrenia |
| talnetant | 4-Quinolinecarboxamide, 3-hydroxy-2-phenyl-N-[(1S)-1-phenylpropyl]-[CAS] | 174636-32-9 | WO | 9532948 | GI inflammatory/bowel disorders | Irritable bowel syndrome |
| talniflumate | 3-Pyridinecarboxylic acid, 2-[[3-(trifluoromethyl)phenyl]amino]-, 1,3-dihydro-3-oxo-1-isobenzofuranyl ester [CAS] | 66898-62-2 | BE | 858864 | Anti-inflammatory | Inflammation, ocular |
| taltirelin | L-Prolinamide, N-[(hexahydro-1-methyl-2,6-dioxo-4-pyrimidinyl)carbonyl]-L-histidyl-, (S)-[CAS] | 103300-74-9 | JP | 61033197 | Neurological | Dyskinesia, general |
| tamoxifen | Ethanamine, 2-[4-(1,2-diphenyl-1-butenyl)phenoxy]-N,N-dimethyl-, (Z)-[CAS] | 10540-29-1 | U.S. | 4,536,516 | Anticancer, hormonal | |
| tamsulosin | Benzenesulfonamide, 5-[2-[[2-(2-ethoxyphenoxy)ethyl]amino]propyl]-2-methoxy-, (R)-[CAS] | 106133-20-4 80223-99-0 | EP | 34432 | Prostate disorders | Benign prostatic hyperplasia |
| tandospirone | 4,7-Methano-1H-isoindole-1,3(2H)-dione, hexahydro-2-[4-[4-(2-pyrimidinyl)-1-piperazinyl]butyl]-, (3aAlpha,4β,7β,7aAlpha)-, 2-hydroxy-1,2,3-propanetricarboxylate (1:1) [CAS] | 112457-95-1 87760-53-0 | EP | 82402 | Anxiolytic | Anxiety, general |
| Tannoform | | 9010-29-1 | | | | |
| Taprostene | | 108945-35-3 | | | | |
| tariquidar | 3-Quinolinecarboxamide, N-[2-[[[4-[2-(3,4-dihydro-6,7-dimethoxy-2(1H)-isoquinolinyl)ethyl]phenyl]amino]carbonyl]-4,5-dimethoxyphenyl]-[CAS] | 206873-63-4 | WO | 9817648 | Radio/chemosensitizer | Cancer, lung, non-small cell |
| TAS-103 | 6-[[2-(Dimethylamino)ethyl]amino]-3-hydroxy-7H-indeno[2,1-c]quinolin-7-one dihydrochloride | 174634-09-4 | WO | 9532187 | Anticancer, other | Cancer, lung, non-small cell |
| Tasosartan | | 145733-36-4 | | | | |
| Taurocholic Acid | | 81-24-3 | | | | |
| Taurolidine | | 19388-87-5 | | | | |
| tazanolast | Acetic acid, oxo[[3-(1H-tetrazol-5-yl)phenyl]amino]-, butyl ester [CAS] | 82989-25-1 | U.S. | 4,778,816 | Antiasthma | |

TABLE IV-continued

| API Generic Name | API Chemical Name | CAS No. | Patent Reference | Example of Therapeutic Use | Example of Indication |
|---|---|---|---|---|---|
| tazarotene | 3-Pyridinecarboxylic acid, 6-[(3,4-dihydro-4,4-dimethyl-2H-1-benzothiopyran-6-yl)ethynyl]-, ethyl ester [CAS] | 118292-40-3 | EP 284288 | Antipsoriasis | Psoriasis |
| Tazobactam |  |  |  |  |  |
| tazobactam + piperacillin |  | 89786-04-9 |  | Antibiotic, other | Infection, general |
| TBC-3711 |  |  |  |  |  |
| TCH-346 | N-Methyl-N-propargyl-10-aminomethyl-dibenzo(b,f)oxepin | 374680-51-0 | JP 58225091 | Cardiovascular Neuroprotective | Heart failure Amyotrophic lateral sclerosis |
| tebipenem | 5-Hexenoic acid, 4-hydroxy-, polymer with 4-ethenyl-1H-imidazole [CAS] | 82200-24-6 |  | Beta-lactam antibiotic | Infection, streptococcal |
| tecadenoson | Adenosine, N-[(3R)-tetrahydro-3-furanyl]-[CAS] | 204512-90-3 | WO 9808855 | Antiarrhythmic | Tachycardia, supraventricular |
| tecastemizole | 1H-Benzimidazol-2-amine, 1-((4-fluorophenyl)methyl)-N-4-piperidinyl-[CAS] | 75970-99-9 | U.S. 4,219,559 | Antiallergic, non-asthma | Rhinitis, allergic, seasonal |
| Technetium 99mTc Bicisate |  | 121281-41-2 |  |  |  |
| Technetium 99mTc Mertiatide |  | 125224-05-7; 104348-91-6 109581-73-9 |  |  |  |
| Technetium 99mTc Sestamibi |  |  |  |  |  |
| Technetium 99mTc Teboroxime |  | 104716-22-5 |  |  |  |
| Teclothiazide |  | 4267-5-4 5560-78-1 |  |  |  |
| Teclozan |  |  |  |  |  |
| tedisamil | Spiro[cyclopentane-1,9'-[3,7]diazabicyclo[3.3.1]nonane], 3',7'-bis(cyclopropylmethyl)-[CAS] | 90961-53-8 | EP 102833 | Antiarrhythmic | Fibrillation, atrial |
| Tefurane |  | 124-72-1 |  |  |  |
| tegafur | 2,4(1H,3H)-Pyrimidinedione, 5-fluoro-1-(tetrahydro-2-furanyl)-[CAS] | 17902-23-7 | GB 1168391 | Anticancer, antimetabolite | Cancer, general |
| tegafur + uracil | 2,4(1H,3H)-Pyrimidinedione, 5-fluoro-1-(tetrahydro-2-furanyl)-, mixt. with 2,4(1H,3H)-pyrimidinedione-[CAS] | 74578-38-4 | EP 224885 | Anticancer, antimetabolite | Cancer, breast |
| tegaserod | Hydrazinecarboximidamide, 2-((5-methoxy-1H-indol-3-yl)methylene)-N-pentyl-, (Z)-2-butenedioate [CAS] | 189188-57-6 145158-71-0 |  | GI inflammatory/bowel disorders | Irritable bowel syndrome |
| Teicoplanin |  | 61036-64-4 |  |  |  |
| telbivudine | β-L-2'-deoxythymidine | 3424-98-4 |  | Antiviral, other | Infection, hepatitis-B virus |
| Telenzepine |  | 80880-90-6 |  |  |  |
| telithromycin | 3-De((2,6-dideoxy-3-C-methyl-3-O-methyl-Alpha-L-ribo-hexopyranosyl)oxy)-11,12-dideoxy-6-O-methyl-3-oxo-12,11-(oxycarbonyl((4-(4-(3-pyridinyl)-1H-imidazol-1-yl)butyl)imino))-[CAS] | 191114-48-4 | EP 680967 | Macrolide antibiotic | Infection, respiratory tract, general |

TABLE IV-continued

| API Generic Name | API Chemical Name | CAS No. | Patent Reference | | Example of Therapeutic Use | Example of Indication |
|---|---|---|---|---|---|---|
| telmesteine | 3,4-Thiazolidinedicarboxylic acid, 3-ethyl ester, (R)-[CAS] | 122946-43-4 | | | COPD treatment | Bronchitis, chronic |
| telmisartan | (1,1'-Biphenyl)-2-carboxylic acid, 4'-((1,4-dimethyl-2'-propyl(2,6'-bi-1H-benzimidazol)-1'-yl)methyl)-[CAS] | 144701-48-4 | EP | 502314 | Antihypertensive, renin system | Hypertension, general |
| telomerase inhibs | | | WO | 9941261 | Anticancer, other | Cancer, general |
| temazepam | 7-chloro-1,3-dihydro-3-hydroxy-1-methyl-5-phenyl-2H-1,4-benzodiazepin-2-one | 846-50-4 | U.S. | 3,197,467 | Hypnotic/Sedative | Insomnia |
| temiverine | Benzeneacetic acid, Alpha-cyclohexyl-Alpha-hydroxy-, 4-(diethylamino)-1,1-dimethyl-2-butynyl ester, [CAS] | 129927-33-9 | GB | 2222828 | Urological | Pollakisuria |
| temocapril | 1,4-Thiazepine-4(5H)-acetic acid, 6-[[1-(ethoxycarbonyl)-3-phenylpropyl]amino]tetrahydro-5-oxo-2-(2-thienyl)-, [2S-[2Alpha,6β(R*)]]-[CAS] | 102090-90-4 110221-44-8 111902-57-9 | U.S. | 4,495,188 | Antihypertensive, renin system | Hypertension, general |
| Temocillin | | 66148-78-5 | | | | |
| temoporfin | Phenol, 3,3',3'',3'''-(2,3-dihydro-21H,23H-porphine-5,10,15,20-tetrayl)tetrakis-[CAS] | 122341-38-2 | EP | 337601 | Radio/chemosensitizer | Cancer, head and neck |
| temozolomide | Imidazo[5,1-d]-1,2,3,5-tetrazine-8-carboxamide, 3,4-dihydro-3-methyl-4-oxo-[CAS] | 85622-93-1 | DE | 3231255 | Anticancer, alkylating | Cancer, brain, general |
| tenatoprazole | 1H-Imidazo(4,5-b)pyridine, 5-methoxy-2-(((4-methoxy-3,5-dimethyl-2-pyridinyl)methyl)sulfinyl)-[CAS] | 113712-98-4 | U.S. | 4,808,596 | Antiulcer | Ulcer, gastric |
| Tenecteplase | | 191588-94-0 120210-48-2 | | | | |
| Tenidap | | | | | | |
| teniposide | Furo[3':4'.6,7]naphtho[2,3-d]-1,3-dioxol-6(5aH)-one, 5,8,8a,9-tetrahydro-5-(4-hydroxy-3,5-dimethoxyphenyl)-9-[[4,6-O-(2-thienylmethylene)-β-D-glucopyranosyl]oxy]-, [5R-[5Alpha,5aβ,8aAlpha,9β(R*)]]-[CAS] | 29767-20-2 | U.S. | 3,524,844 | Anticancer, other | Cancer, lymphoma, non-Hodgkin's |
| tenofovir | Phosphonic acid, (((1R)-2-(6-amino-9H-purin-9-yl)-1-methylethoxy)methyl)-[CAS] | 147127-20-6 | | | Antiviral, anti-HIV | Infection, HIV/AIDS |
| tenofovir disoproxil | 2,4,6,8-tetraoxa-5-phosphanonanedioic acid, 5-(2-(6-amino-9H-purin-9-yl)-1-methylethoxymethyl) bis(1-methylethyl)ester, 5-oxide (R)-, (E)-2-butenedioate | 202138-50-9 | | | Antiviral, anti-HIV | Infection, HIV/AIDS |
| Tenonitrozole | | 3810-35-3 | | | | |
| tenoxicam | 2H-Thieno[2,3-e]-1,2-thiazine-3-carboxamide, 4-hydroxy-2-methyl-N-2-pyridinyl-, 1,1-dioxide [CAS] | 59804-37-4 | GB | 1519811 | Antiarthritic, other | |
| Tenuazonic Acid | | 610-88-8 | | | | |
| teprenone | 5,9,13,17-Nonadecatetraen-2-one, 6,10,14,18-tetramethyl-[CAS] | 3796-63-2 6809-52-5 | | | Antiulcer | |
| terazosin | Piperazine, 1-(4-amino-6,7-dimethoxy-2-quinazolinyl)-4-[(tetrahydro-2-furanyl)carbonyl]-[CAS] | 63074-08-8 63590-64-7 70024-40-7 | U.S. | 4,112,097 | Antihypertensive, adrenergic | Hypertension, general |

TABLE IV-continued

| API Generic Name | API Chemical Name | CAS No. | Patent Reference | Example of Therapeutic Use | Example of Indication |
|---|---|---|---|---|---|
| terbinafine | 1-Naphthalenemethanamine, N-(6,6-dimethyl-2-hepten-4-ynyl)-N-methyl-, (E)-[CAS] | 78628-80-5 91191-71-6 | EP 24587 | Antifungal | Infection, dermatological |
| terbutaline | 1,3-Benzenediol, 5-[2-[(1,1-dimethylethyl)amino]-1-hydroxyethyl]-[CAS] | 23031-25-6 | | Formulation, mucosal, topical | Dysmenorrhoea |
| terconazole | Piperazine, 1-[4-[[2-(2,4-dichlorophenyl)-2-(1H-1,2,4-triazol-1-ylmethyl)-1,3-dioxolan-4-yl]methoxy]phenyl]-4-(1-methylethyl)-, cis-[CAS] | 67915-31-5 | U.S. 4,358,449 | Antifungal | Vaginitis |
| terfenadine | 1-Piperidinebutanol, Alpha-[4-(1,1-dimethylethyl)phenyl]-4-(hydroxydiphenylmethyl)-[CAS] | 50679-08-8 | U.S. 3,878,217 | Antiallergic, non-asthma | |
| terguride | Urea, N,N-diethyl-N'-[(8Alpha)-6-methylergolin-8-yl]-[CAS] | 37686-84-3 | EP 159522 | Antiprolactin | Hyperprolactinaemia |
| Terlipressin | | 14636-12-5 | | | |
| Terodiline | | 15793-40-5 | | | |
| Terofenamate | | 29098-15-5 | | | |
| Terpin | | 80-53-5 | | | |
| tertalolol | 2-Propanol, 1-[(3,4-dihydro-2H-1-benzothiopyran-8-yl)oxy]-3-[(1,1-dimethylethyl)amino]-, hydrochloride, (+/-)-[CAS] | 33580-30-2 83688-84-0 34784-64-0 | GB 1308191 | Antihypertensive, adrenergic | Hypertension, general |
| tert-Pentyl Alcohol | | 75-85-4 | | | |
| tesaglitazar | (2S)-2-ethoxy-3-[4-[2-[4-[(methylsulfonyl)oxy]phenyl]ethoxy]phenyl]propanoic acid | | | Antidiabetic | Diabetes, Type II |
| tesmilifene | Ethanamine, N,N-Diethyl-2-(4-(phenylmethyl)phenoxy)-[CAS] | 92981-78-7 | | Radio/chemosensitizer | Cancer, breast |
| Testolactone | | 968-93-4 | | | |
| Testosterone | androst-4-en-3-one, 17-hydroxy-, (17β)-[CAS] | 58-22-0 5949-44-0 | | Formulation, transdermal, systemic | Hormone replacement therapy |
| tetrabamate | | 60763-47-5 | DE 2748794 | Anxiolytic | Addiction, alcohol |
| Tetrabarbital | | 76-23-3 | | | |
| Tetrabenazine | | 58-46-8 | | | |
| Tetracaine | | 136-47-0 | | | |
| Tetrachloroethylene | | 127-18-4 | | | |
| tetracine | Benzoic acid, 4-(butylamino)-, 2-(dimethylamino)ethyl ester [CAS] | 94-24-6 | | Formulation, transdermal, systemic | Pain, general |
| tetracycline | 2-Naphthacenecarboxamide, 4-(dimethylamino)-1,4,4a,5,5a,6,11,12a-octahydro-3,6,10,112,12a-pentahydroxy-6-methyl-1,11-dioxo-, [4S-(4Alpha,4aAlpha,5aAlpha,6β,12aAlpha)]-[CAS] | 60-54-8 | | Formulation, oral, other | Infection, oral |
| Tetrahydrozoline | | 84-22-0 | | | |
| Tetrandrine | | 518-34-3 | | | |

TABLE IV-continued

| API Generic Name | API Chemical Name | CAS No. | Patent Reference | Example of Therapeutic Use | Example of Indication |
|---|---|---|---|---|---|
| Tetrantoin | | 52094-70-9 | | | |
| Tetrazepam | | 10379-14-3 | | | |
| Tetrofosmin | | 127502-06-1 | | | |
| tetroxoprim | 2,4-Pyrimidinediamine, 5-[[3,5-dimethoxy-4-(2-methoxyethoxy)phenyl]methyl]-[CAS] | 53808-87-0 74515-38-1 | U.S. 3,992,379 | Trimethoprim and analogues | Infection, general |
| Tevenel ® | | 4302-95-8 | | | |
| tezacitabine | Cylidine, 2'-deoxy-2'-(fluoromethylene)-, (2E)-[CAS] | 130306-02-4 | U.S. 5,616,702 | Anticancer, antimetabolite | Cancer, colorectal |
| tezosentan | 2-Pyridinesulfonamide, N-(6-(2-hydroxyethanoxy)-5-(2-methoxyphenoxy)-2-(2-(1H-tetrazol-5-yl)-4-pyridinyl)-4-pyrimidinyl)-5-(1-methylethyl)-[CAS] | 180384-57-0 | | Cardiostimulant | Oedema, general |
| thalidomide | 1H-Isoindole-1,3(2H)-dione, 2-(2,6-dioxo-3-piperidinyl)-[CAS] | 50-35-1 | | Dermatological | Infection, dermatological |
| Thenaldine | | 86-12-4 | | | |
| Thenyldiamine | | 91-79-2 | | | |
| Theobromine | | 83-67-0 | | | |
| Theofibrate | | 54504-70-0 | | | |
| theophylline | 1H-Purine-2,6-dione, 3,7-dihydro-1,3-dimethyl-[CAS] | 58-55-9 5967-84-0 | | Formulation, modified-release, other | Asthma |
| Thiabendazole | | 148-79-8 | | | |
| Thiacetazone | | 104-06-3 | | | |
| thiacymserine | Carbamic acid, [4-(1-methylethyl)phenyl]-, (3aS,8aS)-3,3a,8,8a-tetrahydro-3a,8-dimethyl-2H-thieno[2,3-b]indol-5-yl ester [CAS] | 145209-51-4 | | Cognition enhancer | Alzheimer's disease |
| Thialbarbital | | 467-36-7 | | | |
| Thiamine | | 59-43-8 | | | |
| Thiamine | | 154-87-0 | | | |
| Thiamine | | 67-16-3 | | | |
| Thiamiprine | | 5581-52-2 | | | |
| Thiamphenicol | | 15318-45-3 | | | |
| Thiamylal | | 77-27-0 | | | |
| Thiazesim | | 5845-26-1 | | | |
| Thiazinamium | | 58-34-4 | | | |
| Thiazolinobutazone | | 54749-86-9 | | | |
| Thiazolsulfone | | 473-30-3 | | | |
| Thibenzazoline | | 6028-35-9 | | | |
| Thiethylperazine | | 1420-55-9 | | | |
| Thimerfonate | | 5964-24-9 | | | |
| Thimerosal | | 54-64-8 | | | |
| Thiobarbital | | 77-32-7 | | | |
| Thiobutabarbital | | 2095-57-0 | | | |
| Thiocarbamizine | | 91-71-4 | | | |
| Thiocarbarsone | | 120-02-5 | | | |
| Thiocolchicine | | 2730-71-4 | | | |
| Thiocresol | | 26445-03-4 | | | |
| Thioctic Acid | | 62-46-4 | | | |

TABLE IV-continued

| API Generic Name | API Chemical Name | CAS No. | Patent Reference | Example of Therapeutic Use | Example of Indication |
|---|---|---|---|---|---|
| Thioglycerol | | 96-27-5 | | | |
| Thioguanine | | 154-42-7 | | Anticancer, immunological | Cancer, general |
| Thioinrag | L-Thiolyrosinyl-glycinyl-glycine | | | | |
| Thiopental | | 71-73-8 | | | |
| Thiopropazate | | 84-06-0 | | | |
| Thioproperazine | | 316-81-4 | | | |
| Thioridazine | | 50-52-2 | | | |
| Thiothixene | | 5591-45-7 | | | |
| Thiovir | Thiophosphonoformic acid | | | Antiviral, anti-HIV | Infection, HIV/AIDS |
| Thiphenamil | | 82-99-5 | | | |
| Thiram | | 137-26-8 | | | |
| Thonzylamine | | 63-56-9 | | | |
| Thozalinone | | 655-05-0 | | | |
| Thromboplastin | | 9035-58-9 | | | |
| Thurfyl Nicotinate | | 70-19-9 | | | |
| thymectacin | | | U.S. 6,245,750 | Anticancer, other | Cancer, colorectal |
| Thymol | | 89-83-8 | | | |
| Thymopentin | | 69558-55-0 | | | |
| Thynyl N-Isoamylcarbamate | | 578-20-1 | | | |
| Thyropropic Acid | | 51-26-3 | | | |
| Thyroxine | | 51-48-9 | | | |
| Tiadenol | | 6964-20-1 | | | |
| tiagabine | 3-Piperidinecarboxylic acid, 1-[4,4-bis(3-methyl-2-thienyl)-3-butenyl]-, (R)-[CAS] | 115103-54-3 | WO 8700171 | Antiepileptic | Epilepsy, general |
| Tiamenidine | | 31428-61-2 | | | |
| tianeptine | Heptanoic acid, 7-[(3-chloro-6,11-dihydro-6-methyldibenzo[c,f][1,2]thiazepin-11-yl)amino]-, S,S-dioxide [CAS] | 72797-41-2 66981-73-5 | GB 1269551 | Antidepressant | Depression, general |
| tiapride | Benzamide, N-[2-(diethylamino)ethyl]-2-methoxy-5-(methylsulfonyl)-[CAS] | 51012-32-9 | GB 1394563 | Neuroleptic | |
| tiaprofenic acid | 2-Thiopheneacetic acid, 5-benzoyl-Alpha-methyl-[CAS] | 33005-95-7 | GB 1331505 | Antiarthritic, other | |
| Tiaramide | | 32527-55-2 | | | |
| tiazofurin | 4-Thiazolecarboxamide, 2-β-D-ribofuranosyl-[CAS] | 60084-10-8 | EP 54432 | Anticancer, antimetabolite | Cancer, leukaemia, chronic myelogenous |
| Tibezonium | | 54663-47-7 | | | |
| tibolone | 19-Norpregn-5(10)-en-20-yn-3-one, 17-hydroxy-7-methyl-, (7Alpha,17Alpha)-[CAS] | 5630-53-5 | EP 389035 | Menopausal disorders | Hormone replacement therapy |
| Ticarcillin | | 34787-01-4 | | | |
| ticlopidine | Thieno[3,2-c]pyridine, 5-[(2-chlorophenyl)methyl]-4,5,6,7-tetrahydro-[CAS] | 53885-35-1 55142-85-3 | GB 1554424 | Antithrombotic | |
| Ticrynafen | | 40180-04-9 | | | |

TABLE IV-continued

| API Generic Name | API Chemical Name | CAS No. | Patent Reference | Example of Therapeutic Use | Example of Indication |
|---|---|---|---|---|---|
| tiemonium | 4-(3-hydroxy-3-phenyl-3-thien-2-yl-propyl)-4-methylmorpholinium | 6252-92-2 144-12-7 | | Antispasmodic | |
| tigecycline | 2-Naphthacenecarboxamide, 4,7-bis(dimethylamino)-9-[[[(1,1-dimethylethyl)amino]acetyl]amino]-1,4,4a,5,5a,6,11,12a-octahydro-3,10,12,12a-tetrahydroxy-1,11-dioxo-, (4S,4aS,5aR,12aS)-[CAS] | 220620-09-7 | EP 582829 | Tetracycline | Infection, general |
| Tigemonam | | 102507-71-1 | | | |
| Tigloidine | | 495-83-0 | | | |
| Tilidine | | 20380-58-9 | | | |
| Tilisolol | | 85136-71-6 | | | |
| tilmacoxib | Benzenesulfonamide, 4-(4-cyclohexyl-2-methyl-5-oxazolyl)-2-fluoro-[CAS] | 180200-68-4 | WO 9619463 | Alimentary/Metabolic, other | Polyp |
| tiludronic acid | Phosphonic acid, [[(4-chlorophenyl)thio]methylene]bis-[CAS] | 89987-06-4 | EP 100718 | Osteoporosis treatment | Paget's disease |
| Timentin | | 86482-18-0 | | Antibiotic, other | Infection, general |
| timepidium | Piperidinium, 3-(di-2-thienylmethylene)-5-methoxy-1,1-dimethyl-, [CAS] | 35035-05-3 | GB 1358446 | Antispasmodic | |
| Timiperone | | 57648-21-2 | | | |
| timolol | (−)-1-(t-butyl)amino-3-[(4-morpholino-1,2,5-thiadiazol-3-yl)oxy]-2-propanolmaleate (1:1) salt | 26839-75-8 26921-17-5 | GB 1253709 | Antihypertensive, adrenergic, antiglaucoma | |
| Timonacic | | 444-27-9 | | | |
| Tin Ethyl Etiopurpurin | | 113471-15-1 | | | |
| tinazoline | 1H-Indole, 3-[(4,5-dihydro-1H-imidazol-2-yl)thio]-[CAS] | 62882-99-9 | U.S. 3,376,311 | Vasodilator, peripheral | |
| Tinidazole | | 19387-91-8 | | | |
| Tinoridine | | 24237-54-5 | | | |
| Tiocarlide | | 910-86-1 | | | |
| Tioclomarol | | 22619-35-8 | | | |
| tioconazole | 1H-Imidazole, 1-[2-[(2-chloro-3-thienyl)methoxy]-2-(2,4-dichlorophenyl)ethyl]-[CAS] | 61675-64-7 65899-73-2 | U.S. 4,062,966 | Antifungal | Infection, fungal, general |
| tiopronin | Glycine, N-(2-mercapto-1-oxopropyl)-[CAS] | 1953-02-2 | U.S. 3,246,025 | Urological | Homocystinuria |
| tiotropium | 3-Oxa-9-azoniatricyclo(3.3.1.02,4)nonane, 7-((hydroxydi-2-thienylacetyl)oxy)-9,9-dimethyl-, [CAS] | 136310-93-5 | EP 418716 | COPD treatment | Chronic obstructive pulmonary disease |
| Tioxolone | | 4991-65-5 | | | |
| Tipepidine | | 5169-78-8 | | | |
| tipifarnib | 2(1H)-Quinolone, 6-(amino(4-chlorophenyl)(1-methyl-1H-imidazol-5-yl)methyl)-4-(3-chlorophenyl)-1-methyl [CAS] | 192185-68-5 192185-72-1 | WO 9716443 | Anticancer, other | Cancer, breast |

TABLE IV-continued

| API Generic Name | API Chemical Name | CAS No. | Patent Reference | Example of Therapeutic Use | Example of Indication |
|---|---|---|---|---|---|
| tipranavir | N-[3-[(R)-[4-Hydroxy-2-oxo-6(R)-(2-phenylethyl)-6-propyl-5,6-dihydro-2H-pyran-3-yl]propyl]phenyl]-5-(trifluoromethyl)pyridine-2-sulfonamide | 174484-41-4 | | Antiviral, anti-HIV | Infection, HIV/AIDS |
| tiquizium | 2H-Quinolizinium, 3-(di-2-thienylmethylene)octahydro-5-methyl-, [CAS] | 71731-58-3 | U.S. 4,205,074 | Antispasmodic | |
| tirapazamine | 1,2,4-Benzotriazin-3-amine, 1,4-dioxide- [CAS] | 20028-80-2 27314-97-2 5424-06-6 | DE 2204574 | Radio/chemosensitizer | Cancer, lung, non-small cell |
| Tiratricol | | 51-24-1 | | | |
| tirilazad | Pregna-1,4,9(11)-triene-3,20-dione, 21-[4-(2,6-di-1-pyrrolidinyl-4-pyrimidinyl)-1-piperazinyl]-16-methyl-, (16Alpha)-, [CAS] | 110101-65-0 110101-67-2 110101-66-1 | WO 8701706 | Neuroprotective | Haemorrhage, subarachnoid |
| tirofiban | L-Tyrosine, N-(butylsulfonyl)-O-[4-(4-piperidinyl)butyl]-, [CAS] | 142373-60-2 144494-65-5 | EP 478363 | Antithrombotic | Infarction, myocardial |
| tiropramide | Benzenepropanamide, Alpha-(benzoylamino)-4-[2-(diethylamino)ethoxy]-N,N-dipropyl-, (+/-)-[CAS] | 55837-29-1 | DE 2503992 | Antispasmodic | Muscle spasm, general |
| Titanium Sulfate | | 13825-74-6 55560-96-8 | | | |
| tixocortol | Pregn-4-ene-3,20-dione, 21-[(2,2-dimethyl-1-oxopropyl)thio]-11,17-dihydroxy-, (11β)- [CAS] | 61951-99-3 | GB 1475795 | Antiallergic, non-asthma, mucosal, topical | Rhinitis, allergic, general |
| tizanidine | 2,1,3-Benzothiadiazol-4-amine, 5-chloro-N-(4,5-dihydro-1H-imidazol-2-yl)-[CAS] | 51322-75-9 | GB 1429926 | Muscle relaxant | Spastic paralysis |
| TLK-199 | Glycine, L-Gamma-glutamyl-S-(phenylmethyl)-L-cysteinyl-2-phenyl-, diethyl ester, (2R)-[CAS] | 168682-53-9 | U.S. 5,679,643 | Immunostimulant, other | Myelo-dysplastic syndrome |
| TLK-286 | Glycine, L-Gamma-glutamyl-3-[[2-[[bis[bis(2-chloroethyl)amino]phosphinyl]oxy]ethyl]sulfonyl]-L-alanyl-2-phenyl-, (2R)-[CAS] | 158382-37-7 | U.S. 5,545,621 | Anticancer, other | Cancer, ovarian |
| TNF-β analogue | | | RU 2035185 | Anticancer, immunological | Cancer, general |
| TNP-470 | | 129298-91-5 | | | |
| TO-186 | | 5534-02-1 | | Antipruritic/inflamm, allergic | |
| tobramycin | Pregna-1,4-diene-3,20-dione, 9-fluoro-11β,17,21-trihydroxy-16,beta.-methyl-, 17-butyrate 21-propionate [CAS] O-3-amino-3-deoxy-Alpha-D-glucopyranosyl-(1,6)-O-(2,6-diamino-2,3,6-trideoxy-Alpha-D-ribo-hexopyranosyl-(1-4)-2-deoxy-[CAS] | 32986-56-4 | | Formulation, inhalable, topical | Infection, respiratory tract, general |
| tocainide | Propanamide, 2-amino-N-(2,6-dimethylphenyl)-[CAS] | 41708-72-9 | U.S. 4,218,477 | Antiarrythmic | Fibrilation, ventricular |
| Tocamphyl | | 5634-42-4 | | | |
| tocladesine | 8-Chloroadenosine 3'5'-cyclic phosphate | 41941-56-4 | | Anticancer, other | Cancer, colorectal |
| Tocoretinate | | 40516-48-1 | | | |
| Todralazine | | 14679-73-3 | | | |

TABLE IV-continued

| API Generic Name | API Chemical Name | CAS No. | Patent Reference | | Example of Therapeutic Use | Example of Indication |
|---|---|---|---|---|---|---|
| Tofenacin | | 15301-93-6 | | | | |
| tofimilast | 5H-Pyrazolo[3,4-c]-1,2,4-triazolo[4,3-a]pyridine,9-cyclopentyl-7-ethyl-6,9-dihydro-3-(2-thienyl)- | 185954-27-2 | | | Antiasthma | Asthma |
| tofisopam | 5H-2,3-Benzodiazepine, 1-(3,4-dimethoxyphenyl)-5-ethyl-7,8-dimethoxy-4-methyl-[CAS] | 22345-47-7 | GB | 1334271 | Anxiolytic | Anxiety, general |
| Tolazamid | | 1156-19-0 | | | | |
| Tolazolin | | 59-98-3 | | | | |
| Tolbutamide | | 64-77-7 | | | | |
| tolcapone | Methanone, (3,4-dihydroxy-5-nitrophenyl)(4-methylphenyl)-[CAS] | 134308-13-7 | EP | 237929 | Antiparkinsonian | Parkinson's disease |
| tolciclate | Carbamothioic acid, methyl(3-methylphenyl)-, O-(1,2,3,4-tetrahydro-1,4-methanonaphthalen-6-yl) ester [CAS] | 50838-36-3 | GB | 1364407 | Antifungal | Infection, dermatological |
| Tolcyclamide | | 664-95-9 | | | | |
| tolevamer | Benzenesulfonic acid, 4-ethenyl-, homopolymer. | 28038-50-8 | | | Antibacterial, other | Infection, Clostridium, general |
| tolfenamic acid | Benzoic acid, 2[(3-chloro-2-methylphenyl)amino]-[CAS] | 137110-19-5 | DE | 1543295 | Anti-inflammatory | Inflammation, general |
| Tolindate | | 27877-51-6 | | | | |
| Toliprolol | | 2933-94-0 | | | | |
| Tolmetin | | 26171-23-3 | | | | |
| Tolnaftate | | 2398-96-1 | | | | |
| Tolonidine | | 4201-22-3 | | | | |
| Tolonium | | 92-31-9 | | | | |
| toloxatone | 2-Oxazolidinone, 5-(hydroxymethyl)-3-(3-methylphenyl)-[CAS] | 29218-27-7 | GB | 1250538 | Antidepressant | |
| Tolperisone | | 728-88-1 | | | | |
| Tolpropamine | | 5632-44-0 | | | | |
| Tolrestat | | 82964-04-3 | | | | |
| tolserine | Carbamic acid, (2-methylphenyl)-, (3aS,8aR)-1,2,3,3a,8,8a-hexahydro-1,3a,8-trimethylpyrrolo[2,3-b]indol-5-yl ester [CAS] | 145209-30-9 | | | Cognition enhancer | Alzheimer's disease |
| tolterodine | Phenol, 2-(3-(bis(1-methylethyl)amino)-1-phenylpropyl)-4-methyl-, (R)-[CAS] | 124937-51-5 | EP | 325571 | Urological | Incontinence |
| tolvaptan | Benzamide, N-[4-[(7-chloro-2,3,4,5-tetrahydro-5-hydroxy-1H-1-benzazepin-1-yl)carbonyl]-3-methylphenyl]-2-methyl-[CAS] | 150683-30-0 | EP | 450097 | Cardiovascular | Heart failure |
| Tolycaine | | 3686-58-6 | | | | |
| Topiramate | Beta-D-Fructopyranose, 2,3:4,5-bis-O-(1-methylethylidene)-, sulfamate [CAS] | 97240-79-4 | EP | 533483 | Antiepileptic | Epilepsy, generalized, tonic-clonic |
| topoisomerase inhibitors | | | U.S. | 5,733,880 | Anticancer, other | Cancer, general |

TABLE IV-continued

| API Generic Name | API Chemical Name | CAS No. | Patent Reference | Example of Therapeutic Use | Example of Indication |
|---|---|---|---|---|---|
| topotecan | 1H-Pyrano[3',4':6,7]indolizino[1,2-b]quinoline-3,14(4H,12H)-dione, 9-[(dimethylamino)methyl]-4-ethyl-4,10-dihydroxy-, (S)-[CAS] | 123948-87-8 | EP 231122 | Anticancer, other | Cancer, ovarian |
| torasemide | 3-Pyridinesulfonamide, N-[[(1-methylethyl)amino]carbonyl]-4-[(3-methylphenyl)amino]-[CAS] | 56211-40-6 | U.S. 4,018,929 | Antihypertensive, diuretic | Hypertension, general |
| torcetapib | ethyl (2R,4S)-4-[[3,5-bis(trifluoromethyl)benzyl](methoxycarbonyl)amino]-2-ethyl-6-(trifluoromethyl)-3,4-dihydroquinoline-1(2H)-carboxylate | 262352-17-0 | | Hypolipaemic/Antiatherosclerosis | Athero-sclerosis |
| torcitabine | β-L-2'Deoxycytidine | | | Antiviral, other | Infection, hepatitis-B virus |
| toremifene | Ethanamine, 2-[4-(4-chloro-1,2-diphenyl-1-butenyl)phenoxy]-N,N-dimethyl-, (Z)-[CAS] | 89778-26-7 89778-27-8 56211-40-6 | EP 95875 | Anticancer, hormonal | Cancer, breast |
| Torsemide | | | | | |
| Tositumomab | | | | | |
| tosulfloxacin | 1,8-Naphthyridine-3-carboxylic acid, 7-(3-amino-1-pyrrolidinyl)-1-(2,4-difluorophenyl)-6-fluoro-1,4-dihydro-4-oxo-, [CAS] | 100490-36-6 115964-29-9 208921-02-2 | U.S. 4,704,459 | Quinolone antibacterial | Infection, urinary tract |
| tramadol | Cyclohexanol, 2-[(dimethylamino)methyl]-1-(3-methoxyphenyl)-, cis-(+/-)-[CAS] | 27203-92-5 36282-47-0 1082-57-1 | | Analgesic, other | Pain, general |
| Tramazoline | | | | | |
| trandolapril | 1H-Indole-2-carboxylic acid, 1-[2-[(1-carboxy-3-phenylpropyl)amino]-1-oxopropyl]octahydro-, [2S-[1[R*(R*)],2Alpha,3aAlpha,7aβ]]-[CAS] | 87679-71-8 87679-37-6 52-53-9 | DE 3151690 | Antihypertensive, renin system | Hypertension, general |
| tranexamic acid | Cyclohexanecarboxylic acid, 4-(aminomethyl)-, trans-[CAS] | 1197-18-8 | U.S. 3,950,405 | Antifibrinolytic | Menstrual disorder, general |
| tranilast | Benzoic acid, 2-[[3-(3,4-dimethoxyphenyl)-1-oxo-2-propenyl]amino]-[CAS] | 53902-12-8 | U.S. 3,940,422 | Vulnerary | Wound healing |
| trans-retinoic acid | Retinoic acid [CAS] | 302-79-4 | | Anticancer, other | Cancer, general |
| Tranylcypromine | | | | | |
| trapidil | [1,2,4]Triazolo[1,5-a]pyrimidin-7-amine, N,N-diethyl-5-methyl-[CAS] | 155-09-9 15421-84-8 | DD 55956 | Vasodilator, coronary | |
| Trastuzumab | | 180288-69-1 | | | |
| travoprost | 5-Heptenoic acid, 7-(3,5-dihydroxy-2-(3-hydroxy-4-(3-(trifluoromethyl)phenoxy)-1-butenyl)cyclopentyl)-, 1-methylethyl ester (1R(1Alpha(Z),2β(1E,3R*),3Alpha,5Alpha) [CAS] | 157283-68-6 | | Formulation, mucosal, topical | Glaucoma |
| Traxanox | | | | | |
| traxoprodil | 1-Piperidineethanol, 4-hydroxy-Alpha-(4-hydroxyphenyl)-β-methyl-4-phenyl-, (AlphaS,βS)-[CAS] | 58712-69-9 134234-12-1 188591-67-5 | | Analgesic, other | Pain, general |

TABLE IV-continued

| API Generic Name | API Chemical Name | CAS No. | Patent Reference | Example of Therapeutic Use | Example of Indication |
|---|---|---|---|---|---|
| trazodone | 1,2,4-Triazolo[4,3-a]pyridin-3(2H)-one, 2-[3-[4-(3-chlorophenyl)-1-piperazinyl]propyl]-[CAS] | 19794-93-5 25332-39-2 | U.S. 4,215,104 | Antidepressant | |
| Tremacamra | | 155576-45-7 | | | |
| Trenbolone | | 10161-33-8 | | | |
| Trengestone | | 5192-84-7 | | | |
| treosulfan | 1,2,3,4-Butanetetrol, 1,4-dimethanesulfonate, [S-(R*,R*)]-[CAS] | 299-75-2 | WO 8401506 | Anticancer, alkylating | |
| trepibutone | Benzenebutanoic acid, 2,4,5-triethoxy-Gamma-oxo-[CAS] | 41826-92-0 | GB 1387733 | Antispasmodic | |
| treprostinil | Prosta-5,13-dien-1-oic acid, 6,9-epoxy-11,15-dihydroxy-, [5Z,9Alpha,11Alpha,13E,15S]-[CAS] | 35121-78-9 61849-14-7 | U.S. 6,054,486 | Formulation, parenteral, other | Hypertension, pulmonary |
| tretinoin | Retinoic acid [CAS] | 302-79-4 | | Formulation, dermal, topical | Acne |
| tretoquinol | 6,7-Isoquinolinediol, 1,2,3,4-tetrahydro-1-[(3,4,5-trimethoxyphenyl)methyl]-, (S)-[CAS] | 18559-59-8 30418-38-3 21650-42-0 24305-27-9 | ZA 6802416 | Antiasthma | |
| TRH | | | | | |
| TRI 50b | TRI 50b [CAS] | 226214-49-9 | | Antithrombotic | Thrombosis, general |
| Triacetin | | 102-76-1 | | | |
| Triamcinolone Acetonide | | 76-25-5 | | | |
| Triamcinolone Benetonide | | 31002-79-6 | | | |
| Triamcinolone Hexacetonide | | 5611-51-8 | | | |
| triamcinolone | Pregna-1,4-diene-3,20-dione, 9-fluoro-11,21-dihydroxy-16,17-[(1-methylethylidene)bis(oxy)]-, (11β,16Alpha)-[CAS] | 76-25-5 124-94-7 | | Formulation, inhalable, topical | Asthma |
| Triamterene | | 396-01-0 | | | |
| triapine | Triapine [CAS] | 236392-56-5 | U.S. 6,458,816 | Anticancer, antimetabolite | Cancer, leukaemia, general |
| Triaziquone | | 68-76-8 | | | |
| triazolam | 8-chloro-6-(2-chlorophenyl)-1-methyl-4H-[1,2,4]-triazolo[4,3-a][1,4]benzodiazepine | 28911-01-5 | U.S. 3,980,790 | Hypnotic/Sedative | Insomnia |
| Tribenoside | | 10310-32-4 | | | |
| Trichlorfon | | 52-68-6 | | | |
| Trichlormethiazide | | 133-67-5 | | | |
| Trichlormethine | | 555-77-1 | | | |
| Trichloroethylene | | 79-01-6 | | | |
| Triclobisonium | | 79-90-3 | | | |
| Triclocarban | | 101-20-2 | | | |
| Triclofenol Piperazine | | 5714-82-9 | | | |
| Triclofos | | 306-52-5 | | | |
| Triclosan | | 3380-34-5 | | | |
| Tricromyl | | 85-90-5 | | | |

TABLE IV-continued

| API Generic Name | API Chemical Name | CAS No. | Patent Reference | Example of Therapeutic Use | Example of Indication |
|---|---|---|---|---|---|
| Tridihexethyl Iodide | | 125-99-5 | | | |
| trientine | 1,2-Ethanediamine, N,N2-bis(2aminoethyl)-, [CAS] | 38260-01-4 112-24-3 | | Metabolic and enzyme disorders | Wilson's disease |
| Triethanolamine | | 102-71-6 | | | |
| Triethylenemelamine | | 51-18-3 | | | |
| Triethylenephos-phoramide | | 545-55-1 | | | |
| Triethylene-thiophosphoramide | | 52-24-4 | | | |
| Trifluoperazine | | 117-89-5 | | | |
| Trifluperidol | | 749-13-3 | | | |
| Triflupromazine | | 146-54-3 | | | |
| trifluridine | Thymidine, Alpha,Alpha,Alpha-trifluoro-[CAS] | 70-00-8 | U.S. 3,201,387 | Antiviral, other | Infection, herpes virus, general |
| triflusal | Benzoic acid, 2-(acetyloxy)-4-(trifluoromethyl)-[CAS] | 322-79-2 | U.S. 4,096,252 | Antithrombotic | Thrombosis, general |
| Trihexyphenidyl | | 52-49-3 | | | |
| triolstane | Androst-2-ene-2-carbonitrile, 4,5-epoxy-3,17-dihydroxy-, (4Alpha,5Alpha,17β)-[CAS] | 13647-35-3 | U.S. 3,296,255 | Anticancer, hormonal | Cancer, breast |
| Trimazosin | | 35795-16-5 | | | |
| trimebutine | Benzoic acid, 3,4,5-trimethoxy-, 2-(dimethylamino)-2-phenylbutyl ester, (Z)-2-butenedioate (1:1) [CAS] | 34140-59-5 39133-31-8 | DE 2151716 | Antispasmodic | |
| Trimecaine | | 616-68-2 | | | |
| Trimeprazine | | 84-96-8 | | | |
| Trimetazidine | | 5011-34-7 | | | |
| Trimethadione | | 127-48-0 | | | |
| Trimethaphan | | 68-91-7 | | | |
| Trimethobenzamide | | 138-56-7 | | | |
| Trimethoprim | | 738-70-5 | | | |
| Trimetozine | | 635-41-6 | | | |
| trimetrexate | 2,4-Quinazolinediamine, 5-methyl-6-[[(3,4,5-trimethoxyphenyl)amino]methyl]-[CAS] | 52128-35-5 82952-64-5 | U.S. 4,391,809 | Antifungal | Infection, Pneumocystis jiroveci |
| trimipramine | 5H-Dibenz[b,f]azepine-5-propanamine, 10,11-dihydro-N,N,β-trimethyl-, (Z)-2-butenedioate (1:1) [CAS] | 521-78-8 739-71-9 | | Antidepressant | |
| Trimoprostil | | 69900-72-7 | | | |
| Trioxsalen | | 3902-71-4 | | | |
| tripamide | Benzamide, 3-(aminosulfonyl)-4-chloro-N-(octahydro-4,7-methano-2H-isoindol-2-yl)-, (3aAlpha,4Alpha,7Alpha,7aAlpha)-[CAS] | 73803-48-2 | JP 7305585 | Antihypertensive, diuretic | Hypertension, general |
| Triparanol | | 78-41-1 | | | |
| Tripelennamine | | 91-81-6 | | | |
| Triprolidine | | 486-12-4 | | | |
| triptorelin | Luteinizing hormone-releasing factor (pig), 6-D-tryptophan-[CAS] | 124508-66-3 57773-63-4 | U.S. 4,010,125 | Releasing hormones | Cancer, prostate |

TABLE IV-continued

| API Generic Name | API Chemical Name | CAS No. | Patent Reference | Example of Therapeutic Use | Example of Indication |
|---|---|---|---|---|---|
| tritiozine | Morpholine, 4-[thioxo(3,4,5-trimethoxyphenyl)methyl]-[CAS] | 35619-65-9 | U.S. 3,862,138 | Antiulcer | |
| Tritoqualine | | 14504-73-5 | | | |
| TRK-530 | Phosphonic acid, [[[4-(methylthio)phenyl]thio]methylene]bis-, disodium salt [CAS] | 151425-92-2 | WO 9410181 | Antiarthritic, other | Arthritis, rheumatoid |
| TRK-820 | 2-Propenamide, N-[(5Alpha,6β)-17-(cyclopropylmethyl)-4,5-epoxy-3,14-dihydroxymorphinan-6-yl]-3-(3-furanyl)-N-methyl-, monohydrochloride, (2E)-[CAS] | 152658-17-8 | WO 9315081 | Antipruritic/inflamm, non-allergic | Pruritus |
| Troclosene | | 2244-21-5 | | | |
| trofosfamide | 3-2-(chloroethyl)-2-[bis(2-chloroethyl)amino]tetrahydro-2H-1,3,2-oxazaphosphorin 2-oxide | 22089-22-1 | GB 1188159 | Anticancer, alkylating | |
| Troglitazone | | 97322-87-7 | | | |
| Troleandomycin | | 2751-9-9 | | | |
| Trolnitrate | | 588-42-1 | | | |
| tromantadine | N-(1-adamantyl)-2-(2-dimethylamine ethoxy)acetamide | 53783-83-8 | DE 1941218 | Antiviral, other | Infection, herpes simplex virus |
| Tromethamine | | 77-86-1 | | | |
| Tropacine | | 6878-98-4 | | | |
| Tropesin | | 65189-78-8 | | | |
| Tropicamide | | 1508-75-4 | | | |
| tropine | 1H-Indole-3-acetic acid, 1-(4-chlorobenzoyl)-5-methoxy-2-methyl-, carboxy-2-phenylethyl ester, (+/−)[CAS] | 65189-78-8 | | Antiarthritic, other | |
| tropisetron | 1H-Indole-3-carboxylic acid, 8-methyl-8-azabicyclo[3.2.1]oct-3-yl ester, endo-[CAS] | 89565-68-4 | GB 2125398 | Antiemetic | Chemotherapy-induced nausea and vomiting |
| Trospectomycin | | 88669-04-9 | | | |
| trospium | 3Alpha-Hydroxyspiro[1AlphaH,5AlphaH-nortropane-8,1'-pyrrolidinium] benzilate | 10405-02-4 | | Urological | Pollakisuria |
| trovafloxacin | 1,8-Naphthyridine-3-carboxylic acid, 7-(6-amino-3-azabicyclo[3.1.0]hex-3-yl)-1-(2,4-difluorophenyl)-6-fluoro-1,4-dihydro-4-oxo-, (1Alpha,5Alpha,6Alpha)-, [CAS] | 147059-72-1 147059-75-4 | U.S. 5,164,402 | Quinolone antibacterial | Infection, respiratory tract, general |
| troxacitabine | 2(1H)-Pyrimidinone, 4-amino-1-(2-(hydroxymethyl)-1,3-dioxolan-4-yl)-, (2S-cis)-[CAS] | 145918-75-8 | | Anticancer, other | Cancer, leukaemia, acute myelogenous |
| Troxerutin | | 7085-55-4 | | | |
| troxipide | Benzamde, 3,4,5-trimethoxy-N-3-piperidinyl-, (+/−)[CAS] | 30751-05-4 | U.S. 3,647,805 | Antiulcer | Ulcer, gastric |
| Trypan Red | | 99777-81-8 | | | |
| Tryparsamide | | 574-64-1 | | | |
| Tryptophan | | 554-72-3 | | | |
| TSH | | 73-22-3 | | | |
| | | 9002-71-5 | | | |

TABLE IV-continued

| API Generic Name | API Chemical Name | CAS No. | Patent Reference | Example of Therapeutic Use | Example of Indication |
|---|---|---|---|---|---|
| TSN-09 | 6,14-Ethenomorphinan-7-methanol, 17-(cyclopropylmethyl)-Alpha-(1,1-dimethylethyl)-, 5-epoxy-18,19-dihydro-3-hydroxy-6-methoxy-Alpha-methyl-, [5Alpha,7Alpha,(S)]-[CAS] | 52485-79-7 | | Formulation, transdermal, patch | Pain, cancer |
| TU-2100 | Nonanedioic acid, bis[2-(ethoxycarbonyl)phenyl] ester | 123-82-0 | U.S. 6,180,669 | Antiacne | Acne |
| Tuaminoheptane | | 69-33-0 | | | |
| Tubercidin | | 57-94-3 | | | |
| Tubocurarine Chloride | | | | | |
| tulobuterol | Benzenemethanol, 2-chloro-Alpha-[[(1,1-dimethylethyl)amino]methyl]-[CAS] | 41570-61-0 | DE 2244737 | Antiasthma | Asthma |
| TV-3326 | N-(Propargyl-(3R)aminoindan-5-yl)-ethyl methyl carbamate | | | Cognition enhancer | Alzheimer's disease |
| TY-11223 | Acetic acid, [2-[2,3,3a,6,7,7a-hexahydro-2-hydroxy-1-(3-hydroxy-4,4-dimethyl-1,6-nonadiynyl)-1H-inden-5-yl]ethoxy]-, [1S-[1Alpha(R*),2β,3aAlpha,7aAlpha]]-[CAS] | 140694-43-5 | U.S. 4,837,342 | Antithrombotic | Unspecified |
| TY-12533 | 6,7,8,9-Tetrahydro-2-methyl-5H-cyclohepta[b]pyridine-3-carbonylguanidine maleate | | U.S. 6,258,829 | Antiarrhythmic | Unspecified |
| TYB-3215 | D-Glucitol, 1,4:3,6-dianhydro-, dinitrate [CAS] | 87-33-2 | | Formulation, modified-release, other | Angina, general |
| Tybamate | | 4268-36-4 | | | |
| tyloxapol | 4-(1,1,3,3-Tetramethylbutyl)phenol polymer with formaldehyde and oxirane [CAS] | 25301-02-4 | | Formulation, inhalable, topical | Cystic fibrosis |
| Tymazoline | | 24243-97-8 | | | |
| Tyramine | | 51-67-2 | | | |
| Tyropanoate | | 7246-21-1 | | | |
| Ubenimex | | 58970-76-6 | | | |
| ufenamate | Benzoic acid, 2-[[3-(trifluoromethyl)phenyl]amino]-, butyl ester [CAS] | 67330-25-0 | BE 861852 | Antipruritic/inflamm, non-allergic | |
| Undecylenic Acid | | 112-38-9 | | | |
| Unoprostone | | 12037-36-6 | | | |
| UR-8880 | 4-[4-Chloro-5-(3-fluoro-4-methoxyphenyl)imidazol-1-imidazol-1-yl]benzenesulfonamide-[CAS] | | | Anti-inflammatory | Inflammation, general |
| Uracil Mustard | | 66-75-1 | | | |
| Uralyt-U | 1,2,3-Propanetricarboxylic acid, 2-hydroxy-, potassium sodium salt (5:6:6), hydrate [CAS] | 55049-48-4 | U.S. 4,400,535 | Urological | |
| urapidil | 2,4(1H,3H)-Pyrimidinedione, 6-[[3-[4-(2-methoxyphenyl)-1-piperazinyl]propyl]amino]-1,3-dimethyl-[CAS] | 34661-75-1 | GB 1309324 | Antihypertensive, adreergic | Hypertension, general |
| urea | Urea [CAS] | 57-13-6 | | | |
| Uredepa | | 302-49-8 | | Antipsoriasis | |

TABLE IV-continued

| API Generic Name | API Chemical Name | CAS No. | Patent Reference | Example of Therapeutic Use | Example of Indication |
|---|---|---|---|---|---|
| Urethan | | 51-79-6 | | | |
| Uridine 5'-Triphosphate | | 63-39-8 | | | |
| Urinastatin | | | | | |
| ursodeoxycholic acid | 3Alpha,7β-dihydroxy-5β-cholan-24-oic acid [CAS] | 80449-31-6 128-13-2 | | Formulation, other; Cirrhosis, primary biliary; hepatic dysfunction, biliary calculus | Cirrhosis, primary biliary |
| Ursodiol | | 128-13-2 | | | |
| Ushercell | | | U.S. 6,063,773 | Formulation, mucosal, topical | Contraceptive, female |
| Uzarin | | 20231-81-6 | | | |
| valaciclovir | L-Valine, 2-[(2-amino-1,6-dihydro-6-oxo-9H-purin-9-yl)methoxy]ethyl ester [CAS] | 124832-26-4 | EP 308065 | Antiviral, other | Infection, herpes simplex virus |
| Valacyclovir | | 124832-26-4 | | | |
| valdecoxib | Benzenesulfonamide, 4-(5-methyl-3-phenyl-4-isoxazolyl)- [CAS] | 181695-72-7 | U.S. 5,859,257 | Antiarthritic, other | Arthritis, rheumatoid |
| Valdetamide | | 512-48-1 | | | |
| Valethamate | | 90-22-2 | | | |
| valganciclovir | L-Valine, 2-[(2-amino-1,6-dihydro-6-oxo-9H-purin-9-yl)methoxy]-3-hydroxypropyl ester [CAS] | 175865-59-5 175865-60-8 | EP 694547 | Antiviral, other | Infection, cytomegalovirus |
| Valnoctamide | | 4171-13-5 | | | |
| valomaciclovir | L-Valine (3R)-3-((2-amino-1,6-dihydro-6-oxo-9H-purin-9-yl)methyl)-4-((1-oxooctadecyl)oxy)butyl ester [CAS] | 195156-77-5 | | Antiviral, other | Infection, herpes simplex virus |
| valproate | Pentanoic acid, 2-propyl-, [CAS] | 76584-70-8 1069-66-5 | U.S. 4,988,731 | Antiepileptic | Epilepsy, generalized, tonic-clonic |
| Valproic Acid | | 99-66-1 | | | |
| Valpromide | | 2430-27-5 | | | |
| valrocemide | Pentanamide, N-(2-amino-2-oxoethyl)-2-propyl- [CAS] | 92262-58-3 | U.S. 5,585,358 | Antiepileptic | Epilepsy, general |
| valrubicin | Pentanoic acid, 2-(1,2,3,4,6,11-hexahydro-2,5,12-trihydroxy-7-methoxy-6,11-dioxo-4-((2,3,6-trideoxy-3-((trifluoroacetyl)amino)-Alpha-L-lyxo-hexopyranosyl)oxy)-2-naphthacenyl)-2-oxoethyl ester (2S-cis)- [CAS] | 56124-62-0 | U.S. 4,035,566 | Anticancer, antibiotic | Cancer, bladder |
| valsartan | L-Valine, N-(1-oxopentyl)-N-[[2'-(1H-tetrazol-5-yl)[1,1'-biphenyl]-4-yl]methyl]- [CAS] | 137862-53-4 | EP 443983 | Antihypertensive, renin system | Hypertension, general |
| Valspodar | | 121584-18-7 | | | |
| vardenafil | Piperazine, 1-(3-(1,4-dihydro-5-methyl(4-oxo-7-propylimidazo(5,1-f)(1,2,4)-triazin-2-yl)-4-ethoxyphenyl)sulfonyl)-4-ethyl-[CAS] | 224785-90-4 | | Male sexual dysfunction | Sexual dysfunction, male, general |

TABLE IV-continued

| API Generic Name | API Chemical Name | CAS No. | Patent Reference | Example of Therapeutic Use | Example of Indication |
|---|---|---|---|---|---|
| varespladib | Acetic acid, ((3-(aminooxoacetyl)-2-ethyl-1-(phenylmethyl)-1H-indol-4-yl)oxy)-[CAS] | 172732-68-2 172733-42-5 | EP 675110 | Septic shock treatment | Sepsis |
| Varicella Virus Vaccine | | | | | |
| vatanidipine | 3,5-Pyridinedicarboxylic acid, 1,4-dihydro-2,6-dimethyl-4-(3-nitrophenyl)-, 2-[4-[4-(diphenylmethyl)-1-piperazinyl]phenyl]ethyl methyl ester, [CAS] | 116308-55-5 133743-71-2 | EP 257616 | Neuroprotective | Hypertension, general |
| VEA | | | U.S. 6,007,817 | Radio/chemosensitizer | Cancer, general |
| vecuronium | Piperidinium, 1-[(2β,3Alpha,5Alpha,16β,17β)-3,17-bis(acetyloxy)-2-(1-piperidinyl)androstan-16-yl]-1-methyl-, [CAS] | 50700-72-6 | U.S. 4,237,126 | Muscle relaxant | Anaesthesia, adjunct |
| Velnacrine | | 104675-29-8 | | | |
| venlafaxine | Cyclohexanol, 1-[2-(dimethylamino)-1-(4-methoxyphenyl)ethyl]-, [CAS] | 93413-69-5 99300-78-4 66644-81-3 | GB 2227743 | Antidepressant | Depression, general |
| Veralipride | | 52-53-9 | | Formulation, modified-release, other | |
| verapamil | Benzeneacetonitrile, Alpha-[3-[[2-(3,4-dimethoxyphenyl)ethyl]methylamino]propyl]-3,4-dimethoxy-Alpha-(1-methylethyl)-[CAS] | | | | Hypertension, general |
| verteporfin | 23H,25H-Benzo[b]porphine-9,13-dipropanoic acid, 18-ethenyl-4,4a-dihydro-3,4-bis(methoxycarbonyl)-4a,8,14,19-tetramethyl-, monomethyl ester, trans-[CAS] | 129497-78-5 | U.S. 5,238,940 | Ophthalmological | Macular degeneration |
| vesnarinone | Piperazine, 1-(3,4-dimethoxybenzoyl)-4-(1,2,3,4-tetrahydro-2-oxo-6-quinolinyl)-[CAS] | 81840-15-5 | GB 2086896 | Cardiostimulant | Heart failure |
| Vetrabutine | | 3735-45-3 | | | |
| VF-233 | Benzene carboximidamide, N,3,4,5-tetrahydroxy-[CAS] | 95933-74-7 | U.S. 4,623,659 | Cardiovascular | Reperfusion, injury |
| VI-0134 | | | U.S. 6,403,597 | Male sexual dysfunction | Premature ejaculation |
| vidarabine | 9H-Purin-6-amine, 9-β-D-arabinofuranosyl-[CAS] | 24356-66-9 5536-17-4 | GB 1159290 | Antiviral, other | Infection, herpes virus, general |
| vigabatrin | 5-Hexenoic acid, 4-amino-[CAS] | 68506-86-5 60643-86-9 | GB 1472525 | Antiepileptic | Epilepsy, partial (focal, local) |
| vilazodone | 2-Benzofurancarboxamide, 5-[4-[4-(5-cyano-1H-indol-3-yl)butyl]-1-piperazinyl]-[CAS] | 163521-12-8 | EP 648767 | Antidepressant | Depression, general |
| Viloxazine | | 46817-91-8 | | | |
| Viminol | | 21363-18-8 | | | |
| Vinbarbital | | 125-44-0 865-21-4 | | | |
| vinblastine | | 474-00-0 4880-88-0 | | | |
| vinburnine | Eburnamenin-14(15H)-one, (3Alpha,16Alpha)-[CAS] | | DE 1932245 | Cognition enhancer | |

TABLE IV-continued

| API Generic Name | API Chemical Name | CAS No. | Patent Reference | Example of Therapeutic Use | Example of Indication |
|---|---|---|---|---|---|
| Vincamine | | 1617-90-9 | | | |
| Vinconate | | 70704-03-9 | | | |
| vincristine | Vincaleukoblastine, 22-oxo-, sulfate (1:1) (salt) [CAS] | 2068-78-2 57-22-7 | EP 207831 | Formulation, parenteral, other | Cancer, general |
| vindesine | Vincaleukoblastine, 3-(aminocarbonyl)-O4-deacetyl-3-de(methoxycarbonyl)- [CAS] | 53643-48-4 59917-39-4 | GB 1463575 | Anticancer, other | Cancer, leulaemia, acute lymphocytic |
| vinflunine | Aspidospermidine-3-carboxylic acid, 4-(acetyloxy)-6,7-didehydro-15-[(2R,4R,6S,8S)-4-(1,1-difluoroethyl)-1,3,4,5,6,7,8,9-octahydro-8-(methoxycarbonyl)-2,6-methano-2H-azecino[4,3-b]indol-8-yl]-3-hydroxy-16-methoxy-1-methyl-, methyl ester, (2β,3β,4β,5Alpha,12β,19Alpha)- [CAS] | 162652-95-1 | FR 2707988 | Anticancer, other | Cancer, general |
| vinorelbine | C'-Norvincaleukoblastine, 3',4'-didehydro-4'-deoxy- [CAS] | 71486-22-1 | EP 10458 | Anticancer, other | Cancer, lung, non-small cell |
| vinpocetine | Eburnamenine-14-carboxylic acid, ethyl ester, (3Alpha,16Alpha)- [CAS] | 42971-09-5 | GB 1405127 | Cognition enhancer | Cognitive disorder, general |
| Vinyl Ether | | 109-93-3 | | | |
| Vinylbital | | 2430-49-1 | | | |
| Viquidil | | 84-55-9 | | | |
| Viridin | | 3306-52-3 | | | |
| Visnadine | | 477-32-7 | | | |
| Vitamin A | | 68-26-8 | | | |
| vitamin B12 | Vitamin B12 [CAS] | 68-19-9 | | Formulation, transmucosal, nasal | Anaemia, general |
| vitamin C | L-Ascorbic acid [CAS] | 50-81-7 | | Formulation, modified-release, <=24 hr | Nutrition |
| Vitamin D$_2$ | | 50-14-6 | | | |
| Vitamin D$_3$ | | 67-97-0 | | | |
| Vitamin K$_5$ | | 83-70-5 | | | |
| Vitamins, Prenatal | | | | | |
| VLA-4 antagonists | ((R,S)-4-(4-(Amino-imino-methyl)-phenyl)-3-((4-biphenylyl)-methyl)-4-methyl-2,5-dioxoimidazolidin-1-yl)-acetyl-L-N-methyl-aspartyl-L-phenylglycine | | EP 842943 | Antiasthma | Asthma |
| VNP-4010M | 1,2-Bis(methylsulfonyl)-1-(2-chloroethyl)-2-(methylamino)carbonylhydrazine | | U.S. 6,040,338 | Anticancer, alkylating | Cancer, general |
| voglibose | D-epi-Inositol, 3,4-dideoxy-4-[[2-hydroxy-1-(hydroxymethyl)ethyl]amino]-2-C-(hydroxymethyl)- [CAS] | 83480-29-9 | EP 56194 | Antidiabetic | Diabetes, Type II |
| voriconazole | 4-Pyrimidineethanol, Alpha-(2,4-difluorophenyl)-5-fluoro-β-methyl-Alpha-(1H-1,2,4-triazol-1-ylmethyl)-, (R-(R*,S*))- [CAS] | 137234-62-9 | EP 440372 | Antifungal | Infection, fungal, general |

TABLE IV-continued

| API Generic Name | API Chemical Name | CAS No. | Patent Reference | Example of Therapeutic Use | Example of Indication |
|---|---|---|---|---|---|
| Vorozole VUF-K-8788 | 7-[3-[4-(2-Quinolinylmethyl)-1-piperazinyl]propoxy]-3,4-dihydro-2H-1,4-benzothiazine-3-one | 129731-10-8 | | Antiasthma | Asthma |
| Warfarin WF-10 | Tetrachlorodecaoxide [CAS] | 81-81-2 92047-76-2 | | Radio/chemoprotective | Chemotherapy-induced injury, bone marrow, general |
| WMC-79 | 2-(3-[4-[3-(6-oxo-6H-2,10b-diaza-aceanthrenylen-5-ylamino)propyl]-piperazin-1-yl]propyl)-5-nitro-2-aza-phenalene-1,3-dione | | | Anticancer, other | Cancer, colorectal |
| wound healing matrix | | | U.S. 5,897,880 | Formulation, transdermal, patch | Ulcer, diabetic |
| WP-170 | | | U.S. 6,531,121 | Cytokine | Unspecified |
| xaliproden | Pyridine, 1,2,3,6-tetrahydro-1-[2-(2-naphthalenyl)ethyl]-4-[3-(trifluoromethyl)phenyl]-, [CAS] | 90494-79-4 135354-020-8 | EP 101381 | Neuroprotective | Amyotrophic lateral sclerosis |
| xamoterol | 4-Morpholinecarboxamide, N-[2-[[2-hydroxy-3-(4-hydroxyphenoxy)propyl]amino]ethyl]-, (+/-)- [CAS] | 73210-73-8 81801-12-9 | GB 2002748 | Cardiostimulant | Heart failure |
| Xanomeline Xanthinol Niacinate Xemilofiban Xenbucin Xibenolol | | 131986-45-3 437-74-1 149820-74-6 959-10-4 81584-06-7 | | | |
| xibornol | Phenol, 4,5-dimethyl-2-(1,7,7-trimethylbicyclo[2.2.1]hept-2-yl)-, exo- [CAS] | 13741-18-9 | GB 1206774 | Antibacterial, other | Infection, general |
| ximelagatran | Glycine, N-((R)-cyclohexyl-2-((2S)-2-((((4-(hydroxyamino)iminomethyl)phenyl)methyl)-aminocarbonyl)-1-azetidinyl)2-oxoethyl ethyl ester [CAS] | 192939-46-1 | | Antithrombotic | Thrombosis, venous |
| Ximoprofen xipamide | Benzamide, 5-(aminosulfonyl)-4-chloro-N-(2,6-dimethylphenyl)-2-hydroxy-[CAS] | 56187-89-4 14293-44-8 | U.S. 3,567,777 | Antihypertensive, diuretic | |
| xorphanol | Morphinan-3-ol, 17-(cyclobutylmethyl)-8-methyl-6-methylene-, (8β)-[CAS] | 77287-89-9 | | Analgesic, other | Pain, cancer |
| XR-5118 | 2,5-Piperazinedione, 3-[[5-[[2-(dimethylamino)ethyl]thio]-2-thienyl]methylene]-6-(phenylmethylene)-, monohydrochloride, (3Z,6Z)-[CAS] | 174766-49-5 | WO 9532190 | Anticancer, other | Cancer, general |
| XR-5944 | N,N'-(1,2-Ethanediyl)bis(imino-2,1-ethanediyl)bis(9-methylphenazine-1-carboxamide) | | EP 934278 | Anticancer, other | Cancer, general |
| Xylometazoline Xylose | | 526-36-3 58-86-6 | | | |

TABLE IV-continued

| API Generic Name | API Chemical Name | CAS No. | Patent Reference | | Example of Therapeutic Use | Example of Indication |
|---|---|---|---|---|---|---|
| YH-1885 | 2-Pyrimidinamine, 4-(3,4-dihydro-1-methyl-2(1H)-isoquinolinyl)-N-(4-fluorophenyl)-5,6-dimethyl-, monohydrochloride [CAS] | 178307-42-1 | WO | 9605177 | Antiulcer | Ulcer, GI, general |
| YM-511 | Benzonitrile, 4-[[(4-bromophenyl)methyl]-4H-1,2,4-triazol-4-ylamino]-[CAS] | 148869-05-0 | WO | 9305027 | Anticancer, hormonal | Cancer, breast |
| YM-598 | potassium(E)-N-[6-methoxy-5-(2-methoxyphenoxy)-2-(pyrimidin-2-yl)pyrimidin-4-yl]-2-phenylethenesulfonamidate | | | | Anticancer, other | Cancer, prostate |
| Yohimbine | | 146-48-5 | | | | |
| YT-146 | Adenosine, 2-(1-octynyl)-[CAS] | 90596-75-1 | U.S. | 5,270,304 | Anti-inflammatory | Inflammation, general |
| Z-321 | Thiazolidine, 3-((2,3-dihydro-1H-inden-2-yl)acetyl)-4-(1-pyrrolidinylcarbonyl)-, (R)-[CAS] | 130849-58-0 | EP | 372484 | Cognition enhancer | Dementia, senile, general |
| Z-335 | (1H-Indene-5-acetic acid, 2[[[(4-chlorophenyl)sulfonyl]amino]methyl]-2,3-dihydro-Alpha-methyl-10-oxo-[CAS] | 146731-14-8 | JP | 92506077 | Antithrombotic | Peripheral vascular disease |
| zafirlukast | Carbamin acid, [3-[[2-methoxy-4-[[[(2-methylphenyl)sulfonyl]amino]carbonyl]phenyl]methyl]-1-methyl-1H-indol-5-yl]-, cyclopentyl ester [CAS] | 107753-78-6 | EP | 199543 | Antiasthma | Asthma |
| zalcitabine | Cytidine, 2',3'-dideoxy-[CAS] | 7481-89-2 | U.S. | 4,879,277 | Antiviral, anti-HIV | Infection, HIV/AIDS |
| Zaldaride | | 109826-26-8 | | | | |
| zaleplon | Acetamide, N-[3-(3-cyanopyrazolo[1,5-a]pyrimidin-7-yl)phenyl]-N-ethyl-[CAS] | 151319-34-5 | EP | 776898 | Hypnotic/Sedative | Insomnia |
| zaltoprofen | Dibenzo[b,f]thiepin-2-acetic acid, 10,11-dihydro-Alpha-methyl-10-oxo-[CAS] | 74711-43-6 | JP | 55053282 | Anti-inflammatory | |
| zanamivir | 5-Acetamido-2,6-anhydro-3,4,5-trideoxy-4-guanidino-D-glycero-D-galacto-non-2-enonic acid [CAS] | 139110-80-8 | WO | 9116320 | Antiviral, other | Infection, influenza virus |
| zanapezil | 1-Propanone, 3-(1-(phenylmethyl)-4-piperidinyl)-1-(2,3,4,5-tetrahydro-1H-1-benzazepin-8-yl)-[CAS] | 142852-50-4 | EP | 487071 | Cognition enhancer | Alzheimer's disease |
| Zatebradine | | 85175-67-3 | | | | |
| ZD-0473 | Platinum, amminedichloro(2-methylpyridine)-(SP-4-3)-[CAS] | 181630-15-9 | EP | 727430 | Anticancer, alkylating | Cancer, ovarian |
| ZD-0947 | | | WO | 9528388 | Urological | Overactive bladder |
| ZD-6126 | N-acetylcolchinol-O-phosphate | | | | Anticancer, other | Cancer, general |
| ZD-9331 | 1H-Tetrazole-5-butanoic acid, Alpha-((((1,4-dihydro-2,7-dimethyl-4-oxo-6-quinazolinyl)methyl)-2-propynylamino)-2-fluorobenzoyl)amino) (S)-[CAS] | 153537-73-6 | GB | 2264946 | Anticancer, antimetabolite | Cancer, pancreatic |
| zebularine | 2(1H)-Pyrimidinone, 1-β-D-ribofuranosyl-[CAS] | 3690-10-6 | | | Anticancer, other | Cancer, general |

TABLE IV-continued

| API Generic Name | API Chemical Name | CAS No. | Patent Reference | Example of Therapeutic Use | Example of Indication |
|---|---|---|---|---|---|
| zelandopam | 7,8-Isoquinolinediol, 4-(3,4-dihydroxyphenyl)-1,2,3,4-tetrahydro-, [CAS] | 138086-00-7 | JP 03190818 | Vasodilator, renal | Hypertension, general |
| Zenarestat | | 112733-06-9 | | | |
| Ziconotide | | 107452-89-1 | | | |
| zidovudine | Thymidine, 3'-azido-3'-deoxy-[CAS] | 30516-87-1 | U.S. 4,724,232 | Antiviral, anti-HIV | Infection, HIV/AIDS |
| zileuton | Urea, N-(1-benzo[b]thien-2-yl)ethyl)-N-hydroxy-[CAS] | 111406-87-2 | EP 279263 | Antiasthma | Asthma |
| Zimeldine | | 56775-88-3 | | | |
| zinc acetate | hexakis(\m-acetato)-\m4-oxotetrazinc | 12129-82-7 | | Antiviral, other | Infection, herpes simplex virus prophylaxis |
| zinc acexamate | Hexanoic acid, 6-(acetylamino)-, zinc salt (2:1)-[CAS] | 70020-71-2 | EP 369088 | Antiulcer | Ulcer, duodenal |
| zinc ibuprofenate | | 78416-80-5 | | Anti-inflammatory, topical | Inflammation, dermal |
| Zinc p-Phenolsulfonate | | 127-82-2 | | | |
| Zinc Salicylate | | 16283-36-6 | | | |
| Zinostatin | | 9014-2-2 | | | |
| zinostatin stimalamer | | 123760-07-6 | EP 136791 | Anticancer, antibiotic | Cancer, liver |
| Zipeprol | | 34758-83-3 | | | |
| ziprasidone | 2H-Indol-2-one, 5-(2-(4-(1,2-benzisothiazol-3-yl)-1-piperazinyl)ethyl)-6-chloro-1,3-dihydro-[CAS] | 122883-93-6 146939-27-7 | EP 281309 | Neuroleptic | Schizophrenia |
| zofenopril | L-Proline, 1-[3-(benzoylthio)-2-methyl-1-oxopropyl]-4-(phenylthio)-, [1(R*),2Alpha,4Alpha]-[CAS] | 75176-37-3 81872-10-8 81972-10-8 81938-43-4 | GB 2028327 | Antihypertensive, renin system | Hypertension, general |
| zofenpril + HCTZ | L-Proline, 1-[3-(benzoylthio)-2-methyl-1-oxopropyl]-4-(phenylthio)-, [1(R*),2Alpha,4Alpha]- + 6-Chloro-3,4-dihydro-2H-1,2,4-benzothiazide-7-sulfonamide 1,1-dioxide [CAS] | | | Formulation, fixed-dose combinations | Hypertension, general |
| zoledronic acid | Phosphonic acid, [1-hydroxy-2-(1H-imidazol-1-yl)ethylidene]bis-[CAS] | 118072-93-8 165800-06-6 | EP 531253 | Osteoporosis treatment | Hypercalcaemia of malignancy |
| zolimidine | 2-(p-methylsulfonylphenyl)imidazo[1,2-a]pyridine | 1222-57-7 | U.S. 3,318,880 | Antiulcer | Gastritis |
| zolmitriptan | 2-Oxazokidinone, 4-((3-(2-(dimethylamino)ethyl)-1H-indol-5-yl)methyl)-, (S)-[CAS] | 139264-17-8 | WO 9118897 | Antimigraine | Migraine |
| zolpidem | Imidazol[1,2-a]pyridine-3-acetamide, N,N,6-trimethyl-2-(4-methylphenyl)-(R-(R*,R*))-2,3-dihydroxybutanediotade (2:1) [CAS] | 99294-93-6 82626-48-0 | EP 50563 | Hypnotic/Sedative | Insomnia |

TABLE IV-continued

| API Generic Name | API Chemical Name | CAS No. | Patent Reference | Example of Therapeutic Use | Example of Indication |
| --- | --- | --- | --- | --- | --- |
| Zomepirac | | | | | |
| zonampanel | 1(2H)-Quinoxalineacetic acid, 3,4-dihydro-7-(1H-imidazol-1-yl)-6-nitro-2,3-dioxo-[CAS] | 33369-31-2 210245-80-0 | | Neuroprotective | Ischaemia, cerebral |
| zoniporide | 1H-pyrazole-4-carboxamide,N-(aminoimino methyl)-5-cyclopropyl-1-(5-quinolinyl)-, | 249296-45-5 | | Cardiovascular | Unspecified |
| zonisamide | 1,2-Benzisoxazole-3-methanesulfonamide [CAS] | 68291-97-4 68291-98-5 | GB 2025931 | Antiepileptic | Epilepsy, generalized, tonic-clonic |
| zopiclone | 1-Piperazinecarboxylic acid, 4-methyl-, 6-(5-chloro-2-pyridinyl)-6,7-dihydro-7-oxo-5H-pyrrolo[3,4-b]pyrazin-5-yl ester [CAS] | 43200-80-2 | GB 1358680 | Hypnotic/Sedative | Insomnia |
| Zopolrestat | | 110703-94-1 | | | |
| Zorubicin | | 54083-22-6 | | | |
| zosuquidar | 1-Piperazineethanol, 4-(1,1-difluoro-1,1a,6,10b-tetrahydrodibenzo[a,e]cyclopropa[c]cyclo-hepten-6-yl)-Alpha-[(5-quinolinyloxy)methyl]-,[6(R)-(1aAlpha,6Alpha,10bAlpha)]-[CAS] | 167465-36-3 | | Radio/chemosensitizer | Cancer, leukaemia, acute myelogenous |
| zotepine | Ethanamine, 2-[(8-chlorodibenzo[b,f]thiepin-10-yl)oxy]-N,N-dimethyl-[CAS] | 26615-21-4 | GB 1247067 | Neuroleptic | Schizophrenia |
| ZP-123 | | | WO 0162775 | Antiarrhythmic | Arrhythmia, general |
| Z-tamoxifen | Ethanamine, 2-[4-(1,2-diphenyl-1-butenyl)phenoxy]-N,N-dimethyl-, (Z)-[CAS] | 10540-29-1 | | Anticancer, hormonal | Cancer, colorectal |
| zuclopenthixol | 1-Piperazineethanol, 4-[3-(2-chloro-9H-thioxanthen-9-ylidene)propyl]-, (Z)-[CAS] | 53772-83-1 982-24-1 85721-05-7 64053-00-5 | EP 27082 | Neuroleptic | Psychosis, general |

The invention claimed is:

1. A co-crystal comprising an API and a co-crystal former selected from:
   (a) carbamazepine and saccharin;
   (b) carbamazepine and nicotinamide;
   (c) carbamazepine and trimesic acid;
   (d) celecoxib and nicotinamide;
   (e) celecoxib and 18-crown-6;
   (f) 5-fluorouracil and urea;
   (g) acetaminophen and 4,4'-bipyridine;
   (h) phenytoin and pyridone;
   (i) aspirin and 4,4'-bipyridine;
   (j) ibuprofen and 4,4'-bipyridine;
   (k) flurbiprofen and 4,4'-bipyridine;
   (l) flurbiprofen and trans-1,2-bis(4-pyridyl) ethylene;
   (m) carbamazepine and p-phthalaldehyde;
   (n) carbamazepine and 2,6-pyridinecarboxylic acid;
   (o) carbamazepine and 5-nitroisoplithalic acid;
   (p) carbamazepine and 1,3,5,7-adamantane tetracarboxylic acid; or
   (q) carbamazepine and benzoquinone, wherein the API and co-crystal former are hydrogen bonded to each other.

2. The co-crystal according to claim 1, wherein said co-crystal comprises carbamazepine and saccharin.

3. The co-crystal according to claim 1, wherein said co-crystal comprises carbamazepine and nicotinamide.

4. The co-crystal according to claim 1, wherein said co-crystal comprises carbamazepine and trimesic acid.

5. The co-crystal according to claim 1, wherein said co-crystal comprises celecoxib and nicotinamide.

6. The co-crystal according to claim 1, wherein said co-crystal comprises celecoxib and 18-crown-6.

7. The co-crystal according to claim 1, wherein said co-crystal comprises 5-fluorouracil and urea.

8. The co-crystal according to claim 1, wherein said co-crystal comprises acetaminophen and 4,4'-bipyridine.

9. The co-crystal according to claim 1, wherein said co-crystal comprises phenytoin and pyridine.

10. The co-crystal according to claim 1, wherein said co-crystal comprises aspirin and 4,4'-bipyridine.

11. The co-crystal according to claim 1, wherein said co-crystal comprises ibuprofen and 4,4'-bipyridine.

12. The co-crystal according to claim 1, wherein said co-crystal comprises flurbiprofen and 4,4'-bipyridine.

13. The co-crystal according to claim 1, wherein said co-crystal comprises flurbiprofen and trans-1,2-bis(4-pyridyl) ethylene.

14. The co-crystal according to claim 1, wherein said co-crystal comprises carbamazepine and p-phthalaldehyde.

15. The co-crystal according to claim 1, wherein said co-crystal comprises carbamazepine and 2,6-pyridinecarboxylic acid.

16. The co-crystal according to claim 1, wherein said co-crystal comprises carbamazepine and 5-nitroisophthalic acid.

17. The co-crystal according to claim 1, wherein said co-crystal comprises carbamazepine and 1,3,5,7-adamantane tetracarboxylic acid.

18. The co-crystal according to claim 1, wherein said co-crystal comprises carbamazepine and benzoquinone.

19. A pharmaceutical composition comprising a pharmaceutically acceptable diluent, excipient, or carrier and a co-crystal comprising an API and a co-crystal former selected from:
   (a) carbamazepine and saccharin;
   (b) carbamazepine and nicotinamide;
   (c) carbamazepine and trimesic acid;
   (d) celecoxib and nicotinamide;
   (e) celecoxib and 18-crown-6;
   (f) 5-fluorouracil and urea;
   (g) acetaminophen and 4,4'-bipyridine;
   (h) phenytoin and pyridone;
   (i) aspirin and 4,4'-bipyridine;
   (j) ibuprofen and 4,4'-bipyridine;
   (k) flurbiprofen and 4,4'-bipyridine;
   (l) flurbiprofen and trans-1,2-bis(4-pyridyl)ethylene;
   (m) carbamazepine and p-phthalaldehyde;
   (n) carbamazepine and 2,6-pyridinecarboxylic acid;
   (o) carbamazepine and 5-nitroisophthalic acid;
   (p) carbamazepine and 1,3,5,7-adamantane tetracarboxylic acid; or
   (q) carbamazepine and benzoquinone, wherein the API and co-crystal former hydrogen bonded to each other.

20. The pharmaceutical composition according to claim 19, wherein said co-crystal comprises carbamazepine and saccharin.

21. The pharmaceutical composition according to claim 19, wherein said co-crystal comprises carbamazepine and nicotinamide.

22. The pharmaceutical composition according to claim 19, wherein said co-crystal comprises carbamazepine and trimesic acid.

23. The pharmaceutical composition according to claim 19, wherein said co-crystal comprises celecoxib and nicotinamide.

24. The pharmaceutical composition according to claim 19, wherein said co-crystal comprises celecoxib and 18-crown-6.

25. The pharmaceutical composition according to claim 19, wherein said co-crystal comprises 5-fluorouracil and urea.

26. The pharmaceutical composition according to claim 19, wherein said co-crystal comprises acetaminophen and 4,4'-bipyridine.

27. The pharmaceutical composition according to claim 19, wherein said co-crystal comprises phenytoin and pyridine.

28. The pharmaceutical composition according to claim 19, wherein said co-crystal comprises aspirin and 4,4'-bipyridine.

29. The pharmaceutical composition according to claim 19, wherein said co-crystal comprises ibuprofen and 4,4'-bipyridine.

30. The pharmaceutical composition according to claim 19, wherein said co-crystal comprises flurbiprofen and 4,4'-bipyridine.

31. The pharmaceutical composition according to claim 19, wherein said co-crystal comprises flurbiprofen and trans-1,2-bis(4-pyridyl)ethylene.

32. The pharmaceutical composition according to claim 19, wherein said co-crystal comprises carbamazepine and p-phthalaldehyde.

33. The pharmaceutical composition according to claim 19, wherein said co-crystal comprises carbamazepine and 2,6-pyridinecarboxylic acid.

34. The pharmaceutical composition according to claim 19, wherein said co-crystal comprises carbamazepine and 5-nitroisophthalic acid.

35. The pharmaceutical composition according to claim 19, wherein said co-crystal comprises carbamazepine and 1,3,5,7-adamantane tetracarboxylic acid.

36. The pharmaceutical composition according to claim 19, wherein said co-crystal comprises carbamazepine and benzoquinone.

* * * * *

UNITED STATES PATENT AND TRADEMARK OFFICE
CERTIFICATE OF CORRECTION

| | |
|---|---|
| PATENT NO. | : 7,927,613 B2 |
| APPLICATION NO. | : 10/660202 |
| DATED | : April 19, 2011 |
| INVENTOR(S) | : Orn Almarsson et al. |

It is certified that error appears in the above-identified patent and that said Letters Patent is hereby corrected as shown below:

<u>Column 6,</u>
Lines 18-19, "Pure phenyloin and a co-crystal with phenyloin" should read
--Pure phenytoin and a co-crystal with phenytoin--.

<u>Column 12,</u>
Line 32, "200 150 100," should read --200, 150, 100,--.
Line 34, "200 150, 100 90," should read --200, 150, 100, 90,--.

<u>Column 14,</u>
Line 33, "Cmax" should read --$C_{max}$--.

<u>Column 20,</u>
Line 23, "$AgF_{3\,CSO3}$" should read --$AgF_3CSO_3$--.

<u>Column 30,</u>
Line 6, "+/- 10 degrees" should read --+/- 1.0 degrees--.
Line 11, "(82001 TA" should read --($^8$2001 TA--.

<u>Column 37,</u>
Line 7, "β80.291(2)," should read --β=80.291(2),--.
Line 16, "by π-υ" should read --by π- π--.
Line 27, "Phenyloin:" should read --Phenytoin:--.
Line 28, "phenyloin and" should read --phenytoin and--.
Line 31, "phenyloin/" should read --phenytoin/--.
Line 46, "phenyloin-phenyloin" should read --phenytoin-phenytoin--.
Lines 56-57, "(phenyloin" should read --(phenytoin--.
Line 66, "0.02= 2θ" should read --0.02° 2θ--.

Signed and Sealed this
Twenty-second Day of May, 2012

David J. Kappos
*Director of the United States Patent and Trademark Office*

CERTIFICATE OF CORRECTION (continued)
U.S. Pat. No. 7,927,613 B2

Column 38,
Lines 59-60, "λ=200 (2) K" should read --T=200 (2) K--.

Column 40,
Line 23, "I>2θ (I)," should read --I>2σ (I),--.

Column 41,
Line 52, "$2\theta_{max} = 56.600°$," should read --$2\theta_{max} = 56.60°$--.

Column 42,
Line 17, "(22.)" should read --(22.0)--.
Line 26, "cocrystal" should read --co-crystal--.

Column 51, Table 1,
Column "MP", Row "Adenine"
    "200 (sub.)" should read --220 (sub.)--.

Column 58, Table 1,
Column "Molecular Structure", Row "Lactobionic acid"

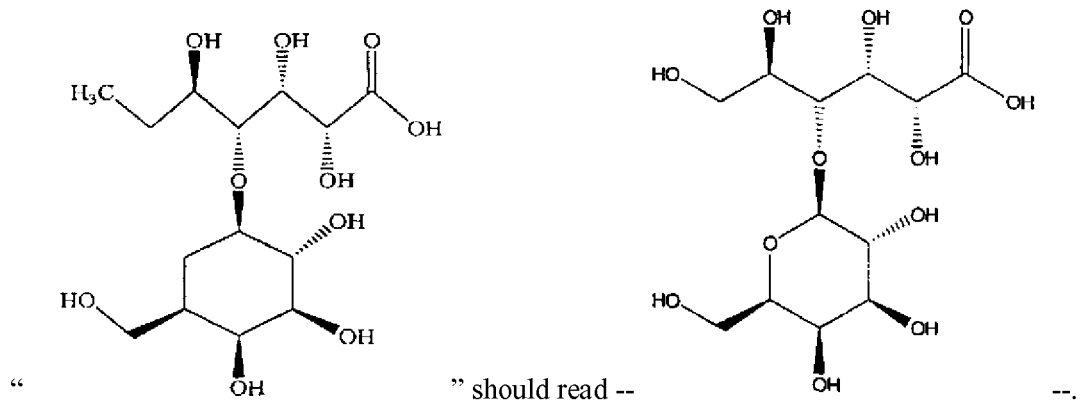

Column 62, Table 1,
Column "Molecular Structure", Row "Pyridoxine"

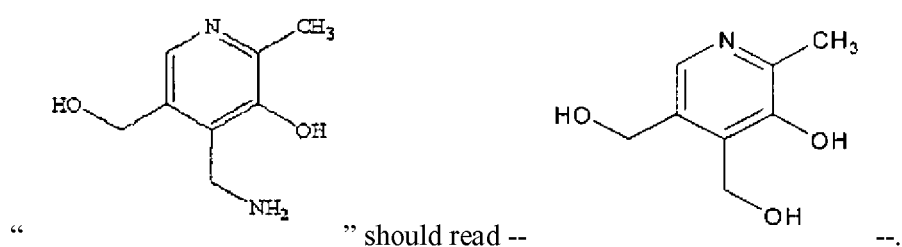

Column 104, Table III, Column "Functional Group":
"pyridine thiol n-heterocyclic ring thionedisulfide pyrrolidindione iodine hydrazone thiocyanate *bromine aromatic"

should read:
--pyridine *chlorine alkyne thiol n-heterocyclic ring thionedisulfide pyrrolidindione iodine hydrazone--.

Column 105, Table III,
Column "Functional Group"
    "thio ster" should read --thioester--.

Column 107, Table III,
Column "Functional Group"
    "nitrate est r alcohol ether acetate" should read
    --nitrate ester bromine alcohol ether acetate--.

Column 108, Table III,
Column "Functional Group"
    "nitrat ester" should read --nitrate ester--.
    "st r-O" should read --ester-O--.

Column 110, Table III,
Column "Functional Group"
    "Amin t rtiary" should read --Amine tertiary--.

Column 119, Table IV,
Column "API Chemical Name", Row "(R)-salbutamol"
    "1,3-Benzenedimethanol, Alpha1-(((1,1-dimethylethyl)amino)methyl)-4-hydroxy-[CAS]"
    should read
    --1,3-Benzenedimethanol, Alpha1-(((1,1-dimithylethyl)amino)methyl)-4-hydroxy-[CAS]--.

Column 125, Table IV,
Column "API Chemical Name", Row "aceglutamide"
    "Aluminum, pentakis(N2-acetyl-L-glutaminoato)tetrahydroxytri- [CAS]"
    should read
    --Aluminum, pentakis(N2-acetyl-L-glutaminato)tetrahydroxytri- [CAS]--.

Column 127, Table IV,
Column "CAS No.", Row "ACTH"
    "900-60-2" should read --9002-60-2--.

Column 130, Table IV,
Column "API Chemical Name", Row "albaconazole"
    "4(3H)-Quinazolinone, 7-chloro-3-[(1R,2R)-2-(2,4-difluorophenyl)-2-hydroxy-1-methyl-3-(1H01,2,4-triazol-1-yl)propyl]- [CAS]"
    should read --4(3H)-Quinazolinone, 7-chloro-3-[(1R,2R)-2-(2,4-difluorophenyl)-2-hydroxy-1-methyl-3-(1H-1,2,4-triazol-1-yl)propyl]- [CAS]--.

Column 134, Table IV,
Column "API Chemical Name", Row "alsactide"
"Alpha1-17-Carticotropin, 1-β-alanine-17-[N-(4-aminobutyl)-L-lysinamide]-[CAS]"
should read
--Alpha1-17-Corticotropin, l-β-alanine-17-[N-(4-aminobutyl)-L-lysinamide]-[CAS]--.
Column "API Generic Name"
"Althiazid" should read --Althiazide--.

Column 136, Table IV,
Column "API Generic Name"
"Ambazon" should read --Ambazone--.
"Ambusid" should read --Ambuside--.

Column 141, Table IV,
Column "API Generic Name"
"amrinose" should read --amrinone--.
Column "Example of Indication", Row "amtolmetin guacil"
"rheumatiod" should read --rheumatoid--.

Column 144, Table IV,
Column "Patent Reference Row", Row "Antiprogestin"
"19703061" should read --19706061--.

Column 148, Table IV,
Column "API Generic Name"
"Aesthinol" should read --Arsthinol--.

Column 149, Table IV,
Column "CAS No.", Row "asoprisnil"
"199396-76-1" should read --199396-76-4--.

Column 151, Table IV,
Column "CAS No.", Row "atomoxetine"
"83015-36-3" should read --83015-26-3--.

Column 153, Table IV,
Column "API Generic Name"
"azasertron" should read --azasetron--.
"azathipprine" should read --azathioprine--.

Column 162, Table IV,
Column "API Chemical Name", Row "bexarotene"
"Benzoic acid, 4-(1-(5,6,7,8-tetrahydro-3,5,5,8,8-pentamethyl-2-naphthalenyl)-[CAS]" should read
--Benzoic acid, 4-(1-(5,6,7,8-tetrahydro-3,5,5,8,8-pentamethyl-2-naphthalenyl)ethenyl)- [CAS]--.

Column 164, Table IV,
Column "API Generic Name"
"birlcodar" should read --biricodar--.

Column 166, Table IV,
Column "API Generic Name"
"Bitoscanat" should read --Bitoscanate--.

Column 168, Table IV,
Column "API Generic Name"
"Brozuridine" should read --Broxuridine--.

Column 176, Table IV,
Column "CAS No.", Row "calcium polycarbophil"
"9003-97-9" should read --9003-97-8--.

Column 180, Table IV,
Column "API Chemical Name", Row "carboplatin"
"Platinum, diammine[1,1-cyclobutanedicarboxylate(2-)]-, (SP-4-2)- [CAS]" should read
--Platinum, diammine[1,1-cyclobutanedicarboxylato(2-)]-, (SP-4-2)- [CAS]--.

Column 187, Table IV,
Column "API Generic Name"
"cefotazime" should read --cefotaxime--.

Column 189, Table IV.
Column "API Chemical Name", Row "cefprozil"
"5-Thio-1-azabicyclo[4.2.0]oct-2-ene-2-carboxylic acid, 7-[[amino(4-hydroxyphenyl)acetyl]amino]-8-oxo-3-(1-propenyl)-, [6R-[6Alpha,7β(R*)]]-[CAS"
should read
--5-Thia-1-azabicyclo[4.2.0]oct-2-ene-2-carboxylic acid, 7-[[amino(4-hydroxyphenyl)acetyl]amino]-8-oxo-3-(1-propenyl)-, [6R-[6Alpha,7β(R*)]]-[CAS--.

CERTIFICATE OF CORRECTION (continued)
U.S. Pat. No. 7,927,613 B2

Column 189, Table IV,
Column "CAS No.", Row "cefprozil"
"92665-29-7" should read --92665-29-7
121123-17-9--.
Column "Patent Reference", Row "cefsulodin"
"GB" should read --GB 1387656--.

Column 190, Table IV,
Column "Patent Reference", Row "ceftibuten"
"EP" should read --EP 136721--.

Column 191, Table IV,
Row "Cefuzonam"

| "Patent Reference | Example of Therapeutic Use | Example of Indication |
|---|---|---|
| U.S. 5,760,068 | Antiarthritic, other | Arthritis rheumatoid" | should read

| --Patent Reference | Example of Therapeutic Use | Example of Indication--. |
|---|---|---|

Column 191, Table IV,
Row "celecoxib"

| "Patent Reference | Example of Therapeutic Use | Example of Indication" |
|---|---|---| should read

| --Patent Reference | Example of Therapeutic Use | Example of Indication |
|---|---|---|
| U.S. 5,760,068 | Antiarthritic, other | Arthritis Rheumatoid--. |

Row "Cellulose Ethyl Hydroxyethyl Ether"

| "API Generic Name | API Chemical Name | CAS No. |
|---|---|---|
| Cellulose Ethyl Hydroxyethyl Ether" | | | should read

| --API Generic Name | API Chemical Name | CAS No. |
|---|---|---|
| Cellulose Ethyl Hydroxyethyl Ether | | 9004-58-4--. |

Column 191, Table IV,

"API API Patent Example of Example of
Generic Name Chemical Name CAS No. Reference Therapeutic Use Indication Cellulose Ethyl
Hydroxyethyl Ether
CEP-1347 9,12-Epoxy-1H- 156177-65-0 WO 9731002 Antiparkinsonian Parkinson's
diindolo[1,2,3-fg:3',2',1'- disease"

should read

--API API Patent Example of Example of
Generic Name Chemical Name CAS No. Reference Therapeutic Use Indication Cellulose Ethyl 9004-58-4
Hydroxyethyl Ether
Centchroman 31477-60-8
CEP-1347 9,12-Epoxy-1H- 156177-65-0 WO 9731002 Antiparkinsonian Parkinson's
diindolo[1,2,3-fg:3',2',1'- disease--.

Column 193, Table IV,
Column "API Chemical Name", Row "cethromycin"
"2H-Oxacyclotetradecino(4,3-d)oxazole-2,6,8,14(1H,7H,9H)-tetrone 4-ethyloctahydro-3a,7,9,11,13,15-hexamethyl-11-((3-(3-quinolinyl)-2-propenyl)oxy)-10-((33.4.6-trideoxy-3-(dimethylamino)-β-D-xylo-hexapyranosyl)oxy)-,(3aS,4R,7R,9R,10R,11R,13R,15R,15aR)- [CAS]"
should read
--2H-Oxacyclotetradecino(4,3-d)oxazole-2,6,8,14(1H,7H,9H)-tetrone 4-ethyloctahydro-3a,7,9,11,13,15-hexamethyl-11-((3-(3-quinolinyl)-2-propenyl)oxy)-10-((3,4,6-trideoxy-3-(dimethylamino)-β-D-xylo-hexapyranosyl)oxy)-,(3aS,4R,7R,9R,10R,11R,13R,15R,15aR)- [CAS]--.

Column 195, Table IV,
Column "API Generic Name",
"Chloriazepoxide" should read --Chlordiazepoxide--.

Column 197, Table IV,
Column "API Generic Name",
"Chlorthenoxazine(e)" should read --Chlorthenoxazin(e)--.

Column 203, Table IV,
Column "API Generic Name",
"Clemizol" should read --Clemizole--.

CERTIFICATE OF CORRECTION (continued)
U.S. Pat. No. 7,927,613 B2

Column 205, Table IV,
Column "API Generic Name",
    "Clofibrat" should read --Clofibrate--.

Column 207, Table IV,
Column "Patent Reference", Row "cloxazolam"
    "3,442,371" should read --3,772,371--.

Column 214, Table IV,
Column "API Generic Name",
    "Cycloniumelodide" should read --Cyclonium Iodide--.

Column 218, Table IV,
Column "API Generic Name",
    "DAX<SciClone" should read --DAX, SciClone--.
    "d-Camphocarboxylic" should read --d-Camphocarboxylic Acid--.

Column 221, Table IV,
Column CAS No.", Row "Deoxycorticosterone"
    "64-85-7" should read --64-58-7
                        56-47-3--.

Column 236, Table IV,
Column CAS No.", Row "doxylamine"
    "469-21-4" should read --469-21-6--.

Column 239, Table IV,
Column "API Generic Name",
    "Dyphyllin" should read --Dyphylline--.

Column 248, Table IV,
Column "API Generic Name",
    "eoinephrine" should read --epinephrine--.

Column 253, Table IV,
Column "API Generic Name",
    "Ethadion" should read --Ethadione--.

Column 263, Table IV,
Column "CAS No.", Row "fepradinol"
    "36981-91-6
    67704-50-1
    63075-57-8" should read --36981-91-6
                            67704-50-1
                            63075-47-8--.

Column "Patent Reference", Row "fexofenadine"
"5,345,693" should read --5,375,693--.

Column 268, Table IV,
Column "API Generic Name",
"Fluroxen" should read --Fluroxene--.

Column 273, Table IV,
Column "API Generic Name",
"Gadobenat
Dimeglumine" should read --Gadobenate
Dimeglumine--.

Column 279, Table IV,
Column "API Generic Name",
"Gold Sodium
Thiemalat" should read --Gold Sodium
Thiomalate--.

Column 291, Table IV,
Column "API Generic Name",
"Indecainid" should read --Indecainide--.

Column 292, Table IV,
Column "API Generic Name",
"Induclem" should read --Inducterm--.

Column 295, Table IV,
Column "API Generic Name",
"Iproclozid" should read --Iproclozide--.

Column 295, Table IV,
Column "API Generic Name",
"Ipsapiron" should read --Ipsapirone--.

Column 297, Table IV,
Column "API Generic Name",
"Asocarboxazid" should read --Isocarboxazid--.

Column 299, Table IV,
Column "CAS No.", Row "itraconazole"
"84625-61-8" should read --84625-61-6--.

Column 303, Table IV,
Column "Patent Reference", Row "KNI-272"
"5,466,028" should read --5,644,028--.

Column 304, Table IV,
Column "Example of Therapeutic Use", Row "L-758298"
"Antimetic" should read --Antiemetic--.

Column 312, Table IV,
Column "CAS No.", Row "LH"
"902-67-9" should read --9002-67-9--.
Column "CAS No.", Row "LH-RH"
"934-40-6" should read --9034-40-6--.

Column 312, Table IV,
Column "API Generic Name",
"liarozote" should read --liarozole--.
"Lindan" should read --Lindane--.

Column 313, Table IV,
Column "API Generic Name",
"Lipo-dexamethasone" should read --Lipo-dexamethasone palmitate--.
"Lisofyllin" should read --Lisofylline--.

Column 325, Table IV,
Column "API Generic Name",
"Meglumin" should read --Meglumine--.

Column 328, Table IV,
Column "Patent Reference", Row "merimepodib"
"5,807,878" should read --5,807,876--.

Column 331, Table IV,
Column "API Generic Name"
"Methylhexaneamide" should read --Methylhexaneamine--.

Column 336, Table IV,
Column "API Generic Name"
",iltefosine" should read --miltefosine--.

Column 342, Table IV,
Column "API Generic Name",
"Muscarin" should read --Muscarine--.

CERTIFICATE OF CORRECTION (continued)
U.S. Pat. No. 7,927,613 B2

Column 360, Table IV,
Column "API Generic Name",
    "loanzapine" should read --olanzapine--.

Column 366, Table IV,
Column "API Generic Name",
    "Oxetoron" should read --Oxetorone--.
    "Oxolamin" should read --Oxolamine--.
    "Oxolinix Acid" should read --Oxolinic Acid--.

Column 368, Table IV,
Column "API Generic Name",
    "pactitaxel" should read --paclitaxel--.

Column 369, Table IV,
Column "API Generic Name"
    "pamicogral" should read --pamicogrel--.

Column 374, Table IV,
Column "API Generic Name"
    "Pentam thonium" should read --Pentamethonium--.

Column 407, Table IV,
Column "Patent Reference", Row "ribavirin"
    "4,122,771" should read --4,211,771--.

Column 410, Table IV,
Column "Cas No.", Row "Risedronic Acid"
    "105492-24-6" should read --105462-24-6--.

Column 413, Table IV,
Column "API Generic Name",
    "Roxindol" should read --Roxindole--.

Column 415, Table IV,
Column "API Chemical Name", Row "RWJ-54428"
    "5-Thia-1-azabicyclo[4.2.0]oct-2-ene-2-carboxylic acid, 7-[[(2Z)-(2-amino-5-chloro-4-thiazolyl)(hydroxyimino)acetyl]amino]-3-[(3-[[(2-aminoethyl)thio]methyl]-4-pyridinyl]thio]-methyl]-4-pyridinyl]thio]-8-oxo-, (6R,7R)-[CAS]"
should read
--5-Thia-1-azabicyclo[4.2.0]oct-2-ene-2-carboxylic acid, 7-[[(2Z)-(2-amino-5-chloro-4-thiazolyl)(hydroxyimino)acetyl]amino]-3-[(3-[[(2-aminoethyl)thio]methyl]-4-pyridinyl]thio]-8-oxo-, (6R,7R)- [CAS]--.

CERTIFICATE OF CORRECTION (continued)
U.S. Pat. No. 7,927,613 B2

Column "Patent Reference", Row "RWJ-54428"
"3,713,772" should read --9,713,772--.

Column 418, Table IV,
Column "API Generic Name"
"Salicylsilfuric Acid" should read --Salicylsulfuric Acid--.

Column 435, Table IV,
Column "API Generic Name",
"stepronim" should read --stepronin--.

Column 439, Table IV,
Column "API Generic Name",
"silprostone" should read --sulprostone--.

Column 451, Table IV,
Column "Cas No.", Row "terbinafine"
"91191-71-6" should read --91161-71-6--.

Column 455, Table IV,
Column "API Generic Name",
"Thioimrag" should read --Thioimreg--.
Column "API Chemical Name", Row "Thioimrag"
"L-Thiolyrosinyl-glycinyl-glycine" should read
--L-Thiotyrosinyl-glycinyl-glycine--.

Column 461, Table IV,
Column "API Generic Name",
"Tolazamid" should read --Tolazamide--.

Column 461, Table IV,
Column "API Generic Name"
"Tolazolin" should read --Tolazoline--.

Column 463, Table IV,
Column "Patent Reference", Row "topotecan"
"231122" should read --321122--.

Column 465, Table IV,
Column "Cas No.", Row "tretoquinol"
"18559-59-8" should read --18559-59-6--.

Column 466, Table IV,
Column "Cas No.", Row "triapine"
"236392-56-5" should read --236392-56-6--.

CERTIFICATE OF CORRECTION (continued)
U.S. Pat. No. 7,927,613 B2

<u>Column 484, Table IV,</u>
Column "Cas No.", Row "zofenopril"
"75176-37-3
81872-10-8
81972-10-8
81938-43-4"
should read
--75176-37-3
81872-10-8
81938-43-4--.

<u>Column 486, Table IV,</u>
Column "Patent Reference", Row "zuclopenthixol"
"27082" should read --270282--.